(12) United States Patent
Bhamidipati et al.

(10) Patent No.: US 9,145,433 B2
(45) Date of Patent: Sep. 29, 2015

(54) GDF-8 INHIBITORS

(71) Applicants: Somasekhar Bhamidipati, Foster City, CA (US); Marina Gelman, San Francisco, CA (US); Pingyu Ding, Foster City, CA (US); Rajinder Singh, Belmont, CA (US); Jeffrey Clough, Redwood City, CA (US); Todd Kinsella, Redwood City, CA (US); Donald Payan, Hillsborough, CA (US)

(72) Inventors: Somasekhar Bhamidipati, Foster City, CA (US); Marina Gelman, San Francisco, CA (US); Pingyu Ding, Foster City, CA (US); Rajinder Singh, Belmont, CA (US); Jeffrey Clough, Redwood City, CA (US); Todd Kinsella, Redwood City, CA (US); Donald Payan, Hillsborough, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/046,834

(22) Filed: Oct. 4, 2013

(65) Prior Publication Data

US 2014/0107073 A1    Apr. 17, 2014

Related U.S. Application Data

(60) Provisional application No. 61/710,449, filed on Oct. 5, 2012.

(51) Int. Cl.

| | | |
|---|---|---|
| *C07D 513/04* | (2006.01) | |
| *C07D 405/04* | (2006.01) | |
| *C07D 487/04* | (2006.01) | |
| *C07D 401/04* | (2006.01) | |
| *C07F 9/6503* | (2006.01) | |
| *C07D 417/04* | (2006.01) | |
| *C07D 471/04* | (2006.01) | |
| *C07D 405/14* | (2006.01) | |
| *C07D 401/14* | (2006.01) | |
| *C07D 213/26* | (2006.01) | |
| *C07D 498/04* | (2006.01) | |
| *C07D 413/04* | (2006.01) | |
| *C07D 417/14* | (2006.01) | |
| *C07D 453/02* | (2006.01) | |

(52) U.S. Cl.
CPC .......... *C07F 9/65038* (2013.01); *C07D 213/26* (2013.01); *C07D 401/04* (2013.01); *C07D 401/14* (2013.01); *C07D 405/04* (2013.01); *C07D 405/14* (2013.01); *C07D 413/04* (2013.01); *C07D 417/04* (2013.01); *C07D 417/14* (2013.01); *C07D 453/02* (2013.01); *C07D 471/04* (2013.01); *C07D 487/04* (2013.01); *C07D 498/04* (2013.01); *C07D 513/04* (2013.01)

(58) Field of Classification Search
CPC .. C07D 514/04; C07D 405/04; C07D 487/04; C07D 453/02; C07D 417/14; C07D 413/04

USPC ........ 546/121, 275.7, 270.1, 139, 273.4, 119, 546/346, 22; 514/300, 307
See application file for complete search history.

(56) References Cited

U.S. PATENT DOCUMENTS

| 7,345,059 B2 | 3/2008 | Barth et al. |
| 7,470,807 B2 | 12/2008 | Shoda et al. |
| 8,653,276 B2 | 2/2014 | Altenburger et al. |

FOREIGN PATENT DOCUMENTS

| EP | 1 308 441 | 5/2003 |
| WO | WO 00/40243 | 7/2000 |
| WO | WO 01/57040 | 8/2001 |
| WO | WO 03/082191 | 10/2003 |
| WO | WO 2005/000817 | 1/2005 |
| WO | 2005/085227 | 9/2005 |
| WO | WO 2005/100353 | 10/2005 |
| WO | WO 2008/006583 | 1/2008 |
| WO | WO 2008/052734 | 5/2008 |
| WO | WO 2008/080461 | 7/2008 |
| WO | 2008131000 | * 10/2008 |
| WO | WO 2009/013335 | 1/2009 |
| WO | WO 2009/032653 | 3/2009 |

(Continued)

OTHER PUBLICATIONS

Lin et al., "2,3,5-Trisubstituted pyridines as selective AKT inhibitors@?Part I: Substitution at 2-position of the core pyridine for ROCK1 selectivity," Bioorganic & Medicinal Chemistry Letters, vol. 20, No. 2, Jan. 15, 2010, pp. 673-678.
Dombroski , et al., "Benzimidazolone p38 inhibitors," Bioorganic & Medicinal Chemistry Letters, vol. 14, No. 4, Feb. 23, 2004, pp. 919-923.
Database CA [Online] Chemistry Abstract Service, Columbus, Ohio, US; Yamashita et al: "Preparation of pyridine derivatives as akt kinase inhibitors," retrieved from STN Database accession No. 2005:1004732; Sep. 15, 2005, pp. 1-34.

(Continued)

*Primary Examiner* — Niloofar Rahmani
(74) *Attorney, Agent, or Firm* — Travis Young; McDonnell Boehnen Hulbert & Berghoff LLP

(57) ABSTRACT

Described are GCF-8 inhibitors of the formula (I),

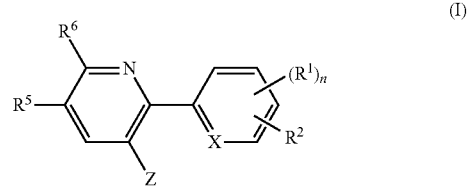

and pharmaceutically acceptable salts thereof, wherein n, $R^1$, $R^2$, $R^5$, $R^6$, X and Z are defined herein. Also provided are pharmaceutical compositions comprising the same. Such compounds and compositions are useful in methods for inhibiting GDF-8 in a cell and methods for treating a patient suffering from a disease or disorder, wherein the patient would therapeutically benefit from an increase in mass or strength of muscle tissue.

21 Claims, No Drawings

(56) References Cited

FOREIGN PATENT DOCUMENTS

WO   WO 2009/115665      9/2009
WO      2011095196    * 11/2011

OTHER PUBLICATIONS

International Search Report and Written Opinion of PCT Application Serial No. PCT/US2013/063585 filed Oct. 4, 2013.

* cited by examiner

GDF-8 INHIBITORS

CROSS-REFERENCE TO RELATED APPLICATIONS

This application claims the benefit of priority of U.S. Provisional Patent Application Ser. No. 61/710,449, filed Oct. 5, 2012, which is hereby incorporated herein by reference in its entirety.

BACKGROUND OF THE DISCLOSURE

1. Field of the Disclosure

This disclosure relates to pharmaceutically active compounds and methods for their use. In particular the disclosure relates to kinase inhibitors. In one aspect the compounds also inhibit the signaling of cytokines such as TGF-β1, Growth Differentiation Factor-8 (GDF-8) and other members of the TGF-βs, activins, inhibins, bone morphogenetic proteins and Mullerian-inhibiting substance, that signal through a family of transmembrane kinase receptors. The inhibitors are useful for treating inflammatory disorders, such as inflammatory or obstructive airway diseases, such as pulmonary hypertension, pulmonary fibrosis, liver fibrosis; and cancer. The inhibitors are particularly useful for diagnosing, preventing, or treating human or animal disorders in which an increase in muscle tissue would be therapeutically beneficial. Exemplary disorders include neuromuscular disorders (e.g., muscular dystrophy and muscle atrophy), congestive obstructive pulmonary disease, muscle wasting syndrome, sarcopenia, and cachexia; adipose tissue disorders (such as obesity); type 2 diabetes; and bone degenerative disease (such as osteoporosis).

2. Summary of the Related Art

Growth and Differentiation Factor-8 (GDF-8), also known as myostatin, and TGF-β1 are a members of the Transforming Growth Factor-beta (TGF-β) superfamily of structurally related growth factors, all of which possess physiologically important growth-regulatory and morphogenetic properties (Kingsley et al. (1994) Genes Dev., 8: 133-46; Hoodless et al. (1998) Curr. Topics Microbiol. Immunol., 228: 235-72). For example, activation of TGF-β1 signaling and expansion of extracellular matrix are early and persistent contributors to the development and progression of fibrotic disorders, such as involved in chronic renal disease and vascular disease. Border W. A., et al, N. Engl. J. Med., 1994; 331(19), 1286-92. GDF-8 is a negative regulator of skeletal muscle mass, and there is considerable interest in identifying factors which regulate its biological activity. For example, GDF-8 is highly expressed in the developing and adult skeletal muscle. The GDF-8 null mutation in transgenic mice is characterized by a marked hypertrophy and hyperplasia of the skeletal muscle (McPherson et al. (1997) Nature, 387: 83-90). Similar increases in skeletal muscle mass are evident in naturally occurring mutations of GDF-8 in cattle (Ashmore et al. (1974) Growth, 38: 501 507; Swatland and Kieffer (1994) J. Anim. Sci., 38: 752-757; McPherron and Lee (1997) Proc. Natl. Acad. Sci. USA, 94: 12457-12461; and Kambadur et al. (1997) Genome Res., 7: 910-915). Since GDF-8 is expressed in both developing and adult muscles, it is not clear whether it regulates muscle mass during development or in adults. Thus, the question of whether or not GDF-8 regulates muscle mass in adults is important from a scientific and therapeutic perspective. Recent studies have also shown that muscle wasting associated with HIV-infection in humans is accompanied by increases in GDF-8 protein expression (Gonzalez-Cadavid et al. (1998) PNAS, 95: 14938-43). In addition, GDF-8 can modulate the production of muscle-specific enzymes (e.g., creatine kinase) and modulate myoblast cell proliferation (WO 00/43781).

A number of human and animal disorders are associated with loss or functional impairment of muscle tissue, including muscular dystrophy, muscle atrophy, congestive obstructive pulmonary disease, muscle wasting syndrome, sarcopenia, and cachexia. To date, very few reliable or effective therapies exist for these disorders. However, the terrible symptoms associated with these disorders may be substantially reduced by employing therapies that increase the amount of muscle tissue in patients suffering from the disorders. While not curing the conditions, such therapies would significantly improve the quality of life for these patients and could ameliorate some of the effects of these diseases. Thus, there is a need in the art to identify new therapies that may contribute to an overall increase in muscle tissue in patients suffering from these disorders.

In addition to its growth-regulatory and morphogenetic properties in skeletal muscle, GDF-8 may also be involved in a number of other physiological processes, including glucose homeostasis in the development of type 2 diabetes and adipose tissue disorders, such as obesity. For example, GDF-8 modulates pre-adipocyte differentiation to adipocytes (Kim et al. (2001) BBRC, 281: 902-906).

There are also a number of conditions associated with a loss of bone, including osteoporosis, especially in the elderly and/or postmenopausal women. Currently available therapies for these conditions work by inhibiting bone resorption. A therapy that promotes new bone formation would be a desirable alternative to or addition to, these therapies.

Like TGF-β-1, -2, and -3, the GDF-8 protein is synthesized as a precursor protein consisting of an amino-terminal propeptide and a carboxy-terminal mature domain (McPherron and Lee, (1997) Proc. Natl. Acad. Sci. USA, 94: 12457-12461). Before cleavage, the precursor GDF-8 protein forms a homodimer. The amino-terminal propeptide is then cleaved from the mature domain. The cleaved propeptide may remain noncovalently bound to the mature domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). It is believed that two GDF-8 propeptides bind to the GDF-8 mature dimer (Thies et al. (2001) Growth Factors, 18: 251-259). Due to this inactivating property, the propeptide is known as the "latency-associated peptide" (LAP), and the complex of mature domain and propeptide is commonly referred to as the "small latent complex" (Gentry and Nash (1990) Biochemistry, 29: 6851-6857; Derynck et al. (1995) Nature, 316: 701-705; and Massague (1990) Ann. Rev. Cell Biol., 12: 597-641). Other proteins are also known to bind to GDF-8 or structurally related proteins and inhibit their biological activity. Such inhibitory proteins include follistatin, and potentially, follistatin-related proteins (Gamer et al. (1999) Dev. Biol., 208: 222-232). The mature domain is believed to be active as a homodimer when the propeptide is removed.

GDF-8 is highly conserved in sequence and in function across species. The amino acid sequence of murine and human GDF-8 is identical, as is the pattern of mRNA expression (McPherron et al. (1997) Nature 387: 83-90; Gonzalez-Cadavid et al. (1998) Proc. Natl. Acad. Sci. USA 95: 14938-14943). This conservation of sequence and function suggests that inhibition of GDF-8 in humans is likely to have a similar effect to inhibition of GDF-8 in mice.

GDF-8 is involved in the regulation of many critical biological processes. Due to its key function in these processes, GDF-8 may be a desirable target for therapeutic intervention.

For example, U.S. Pat. No. 7,320,789, shows that GDF-8 antibodies in mouse models canincrease muscle strength (e.g., for treating sarcopenia). increase muscle mass and strength in dystrophic muscle (e.g., for treating Duchenne's muscular dystrophy), increase bone mass and bone density (e.g., for prevention and treatment of osteoporosis), augment bone healing (e.g., for treating an established muscle or bone degenerative disease (e.g., fracture repair and spine fusion, preventing the decline in bone mass, microarchitecture and strength associated with estrogen deficiency, increasing trabecular bone density), and are useful for treatment of metabolic disorders such as type 2 diabetes, impaired glucose tolerance, metabolic syndrome (e.g., syndrome X), insulin resistance induced by trauma (e.g., burns), and adipose tissue disorders (e.g., obesity).

In particular, therapeutic agents that inhibit the activity of GDF-8 may be used to treat human or animal disorders in which an increase in muscle tissue would be therapeutically beneficial, particularly muscle and adipose tissue disorders, bone degenerative diseases, neuromuscular disorders, and diabetes, as discussed above.

SUMMARY OF THE DISCLOSURE

In one aspect, the present disclosure relates to compounds of the formula (I),

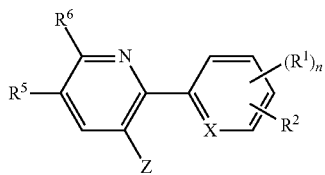

and pharmaceutically acceptable salts thereof, wherein n, $R^1$, $R^2$, $R^5$, $R^6$, X and Z are defined herein.

In another aspect, disclosed are pharmaceutical compositions comprising a compound or pharmaceutically acceptable salt of a compound according to formula (I) and a pharmaceutically acceptable carrier, excipient, or diluent.

In another aspect, disclosed are methods for inhibiting GDF-8 in a cell comprising contacting the cell with an effective amount of a compound or pharmaceutically acceptable salt of a compound according to formula (I) or a pharmaceutical composition comprising a compound or pharmaceutically acceptable salt of a compound according to formula (I) and a pharmaceutically acceptable carrier, excipient, or diluent.

In another aspect, disclosed are methods for treating a patient suffering from a disease or disorder, wherein the patient would therapeutically benefit from an increase in mass or strength of muscle tissue, comprising administering to a patient a therapeutically effective amount of a compound or pharmaceutically acceptable salt of a compound according to formula (I) or a pharmaceutical composition comprising a compound or pharmaceutically acceptable salt of a compound according to formula (I) and a pharmaceutically acceptable carrier, excipient, or diluent.

In another aspect, disclosed are methods for increasing muscle mass in a mammal comprising administering a therapeutically effective amount of a compound or pharmaceutically acceptable salt of a compound according to formula (I) or a pharmaceutical composition comprising a compound or pharmaceutically acceptable salt of a compound according to formula (I) and a pharmaceutically acceptable carrier, excipient, or diluent.

In another aspect, disclosed are methods for increasing muscle strength in a mammal comprising administering a therapeutically effective amount of a compound or pharmaceutically acceptable salt according to formula (I) or a pharmaceutical composition comprising a compound or pharmaceutically acceptable salt according to formula (I) and a pharmaceutically acceptable carrier, excipient, or diluent.

In another aspect, disclosed are methods for increasing trabecular bone density in a patient in need thereof, comprising administering a therapeutically effective amount of a compound or pharmaceutically acceptable salt according to formula (I) or a pharmaceutical composition comprising a compound or pharmaceutically acceptable salt according to formula (I) and a pharmaceutically acceptable carrier, excipient, or diluent.

DETAILED DESCRIPTION OF THE DISCLOSURE

In one aspect, the disclosure comprises pharmaceutical compounds of formula (I),

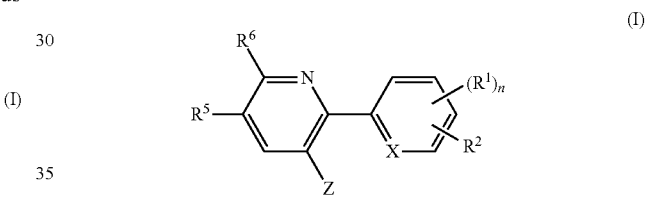

and pharmaceutically acceptable salts thereof, wherein
X is C(H) or N;
$R^1$ and $R^2$ are each independently hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^{10}$, or —$C_{1-6}$alkyl-$R^{10}$, wherein $R^{10}$ is —OR, —SR, —$NR^aR^a$, —C(O)R, —C(O)OR, —C(O)$NR^aR^a$, —S(O)$_2NR^aR^a$, —OC(O)R, —N(R)C(O)R, —OC(O)OR, —O(CH$_2$)$_m$C(O)$NR^aR^a$, —N(R)C(O)OR, —N(R)C(O)$NR^aR^a$, —N(R)S(O)$_2NR^aR^a$ or —N(R)S(O)$_2$R;
or when $R^1$ and $R^2$ are attached to adjacent carbon atoms they are optionally taken together with the atoms to which they are attached to form a 5- or 6-membered ring optionally substituted with one or two groups that are each independently halogen, oxo, oxime, imino, $C_{1-6}$alkyl, $C_{1-6}$haloalkyl, or —$R^{10}$;
each $R^a$ is independently R or, two $R^a$ together with the nitrogen atom to which they are attached form a 3-8 membered heterocyclyl group, optionally including 1-4 additional heteroatoms selected from O, N and S and optionally substituted with 1-4 R groups;
each $R^b$ is independently halogen, cyano, oxo, $C_{1-6}$alkyl, $C_{1-6}$haloalkyl, or —OR;
m is 0, 1 or 2;
n is 1, 2, 3 or 4;
$R^5$ and $R^6$ are each independently hydrogen, halogen, $C_{1-6}$alkyl optionally substituted with 1-3 $R^b$, $C_{1-6}$haloalkyl, $C_{3-8}$cycloalkyl optionally substituted with one or two $R^b$, heteroaryl optionally substituted with one or two $R^b$, aryl optionally substituted with one or two $R^b$, heterocyclyl($C_{1-6}$alkyl) optionally substituted with one or two $R^b$, —OR, —SR, —NR$^a$R$^a$, —OC(O)R, —C(O)NR$^a$R$^a$, —OC(O)NR$^a$R$^a$, —C(O)OR, —N(R)C(O)R, —N(R)S(O)$_2$R, or $R^5$ and $R^6$ are optionally taken together with the atoms to which they are attached to form a 5- or 6-membered ring optionally including 1-3 additional heteroatoms selected from O, N and S and optionally substituted with 1-4 $R^b$;

Z is (a) a fused bicyclic ring of the formula,

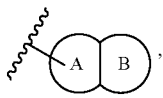

wherein ring A is a phenyl or 5- or 6-membered heteroaryl, ring B is a 5- or 6-membered heterocyclyl or 5- or 6-membered heteroaryl;

or (b) pyridinyl or pyrimidinyl, wherein

Z is optionally substituted by one or two groups that are each independently halogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl($C_{1-6}$alkyl), —$R^Z$, or —$C_{1-6}$alkyl-$R^Z$, wherein the $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), and heteroaryl($C_{1-6}$alkyl) are each optionally substituted by one or two groups that are each independently halogen, $C_{1-6}$alkyl, or —$R^Z$;

and $R^Z$ is cyano, —CF$_3$, —OR, —SR, —NR$^a$R$^a$, —C(O)R, —C(O)OR, —C(O)NR$^a$R$^a$, —S(O)$_2$NR$^a$R$^a$, —S(O)$_2$R$^o$, —OC(O)R, —N(R)C(O)R, —OC(O)OR, —OC(O)NR$^a$R$^a$, —N(R)C(O)OR, —N(R)C(O)NR$^a$R$^a$, —N(R)S(O)$_2$R, or —OP(O)(OR)$_2$;

or Z is (c) phenyl substituted with 1, 2, 3, 4, or 5 groups that are each independently a halogen;

wherein each R is independently hydrogen, $C_{1-6}$alkyl, $C_{1-6}$haloalkyl, $C_{3-8}$cycloalkyl, heterocyclyl, aryl, heteroaryl, heteroaryl(heteroaryl)-, heterocyclyl(aryl)-, heteroaryl(heterocyclyl)-, $C_{3-8}$cycloalkyl($C_{1-6}$alkyl), heterocyclyl($C_{1-6}$alkyl), aryl($C_{1-6}$alkyl), or heteroaryl($C_{1-6}$alkyl), each optionally substituted by 1-5 groups that are each independently $R^b$, —OR$^o$, —SR$^o$, —N(R$^o$)$_2$, —C(O)R$^o$, —C(O)OR$^o$, —C(O)N(R$^o$)$_2$, —S(O)$_2$N(R$^o$)$_2$, —OC(O)R$^o$, —N(R$^o$)C(O)R$^o$, —OC(O)OR$^o$, —O(CH$_2$)$_m$C(O)N(R$^o$)$_2$, —N(R$^o$)C(O)OR$^o$, —N(R$^o$)C(O)N(R$^o$)$_2$, or —N(R$^o$)S(O)$_2$R$^o$;

and each R$^o$ is independently hydrogen, $C_{1-6}$haloalkyl, $C_{1-6}$alkyl optionally substituted with 1-3 $R^b$, $C_{3-8}$cycloalkyl optionally substituted with one or two $R^b$ or, alternatively two R$^o$ together with a nitrogen atom to which they are bound (for example when R is —C(O)N(R$^o$)$_2$) form a 3-8 membered heterocyclyl group, optionally including 1-4 additional heteroatoms selected from O, N and S and optionally substituted with 0-3 $R^b$ and R groups.

For example, in one embodiment, the disclosure provides pharmaceutically active compounds and pharmaceutically acceptable salts thereof as described above, in which n is 1;

X is C(H) or N;

$R^1$ and $R^2$ are each independently hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —R$^{10}$, or —$C_{1-6}$alkyl-R$^{10}$, wherein R$^{10}$ is —OR, —SR, —NR$^a$R$^a$, —C(O)R, —C(O)OR, —C(O)NR$^a$R$^a$, —S(O)$_2$NR$^a$R$^a$, —OC(O)R, —N(R)C(O)R, —OC(O)OR, —OC(O)NR$^a$R$^a$, —N(R)C(O)OR, —N(R)C(O)NR$^a$R$^a$, or —N(R)S(O)$_2$R;

or when $R^1$ and $R^2$ are attached to adjacent carbon atoms they are optionally taken together with the atoms to which they are attached to form a 5- or 6-membered heteroaryl group optionally substituted with one or two groups that are each independently halogen, $C_{1-6}$alkyl, $C_{1-6}$haloalkyl, or —R$^{10}$;

each R$^a$ is independently R or, two R$^a$ together with the nitrogen atom to which they are attached form a 3-8 membered heterocyclyl group, optionally including 1-4 additional heteroatoms selected from O, N and S and optionally substituted with 1-4 R groups;

$R^5$ and $R^6$ are each independently hydrogen, halogen, $C_{1-6}$alkyl, $C_{1-6}$haloalkyl, $C_{3-8}$cycloalkyl, —OR, —SR, —NR$^a$R$^a$, —OC(O)R, —N(R)C(O)R, or —N(R)S(O)$_2$R;

Z is (a) a fused bicyclic ring of the formula,

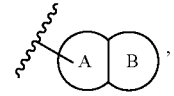

wherein ring A is a phenyl or 5- or 6-membered heteroaryl, ring B is a 5- or 6-membered heterocyclyl or 5- or 6-membered heteroaryl, and wherein Z is optionally substituted by one or two groups that are each independently halogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl($C_{1-6}$alkyl), —$R^Z$, or —$C_{1-6}$alkyl-$R^Z$, wherein the $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), and heteroaryl($C_{1-6}$alkyl) are each optionally substituted by one or two groups that are each independently halogen, $C_{1-6}$alkyl, or —$R^Z$;

and $R^Z$ is —OR, —SR, —NR$^a$R$^a$, —C(O)R, —C(O)OR, —C(O)NR$^a$R$^a$, —S(O)$_2$NR$^a$R$^a$, —OC(O)R, —N(R)C(O)R, —OC(O)OR, —OC(O)NR$^a$R$^a$, —N(R)C(O)OR, —N(R)C(O)NR$^a$R$^a$, —N(R)S(O)$_2$R, or —OP(O)(OR)$_2$;

or (b) phenyl substituted with 1, 2, 3, 4, or 5 groups that are each independently a halogen;

and each R is independently hydrogen or $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), or heteroaryl($C_{1-6}$alkyl), each optionally substituted by one or two groups that are each independently —OR$^o$, —SR$^o$, —N(R$^o$)$_2$, —C(O)R$^o$, —C(O)OR$^o$, —C(O)N(R$^o$)$_2$, —S(O)$_2$N(R$^o$)$_2$, —OC(O)R$^o$, —N(R$^o$)C(O)R$^o$, —OC(O)OR$^o$, —OC(O)N(R$^o$)$_2$, —N(R$^o$)C(O)OR$^o$, —N(R$^o$)C(O)N(R$^o$)$_2$, or —N(R$^o$)S(O)$_2$R$^o$, wherein each R$^o$ is independently hydrogen or $C_{1-6}$alkyl.

The disclosure further comprises subgenera of formula (I) in which the substituents are selected as any and all combinations of one or more of structural formula (I), n, $R^1$, $R^2$, $R^5$, $R^6$, X, Z, $R^a$, $R^b$, $R^Z$ R and $R^0$ as defined herein, including without limitation, the following:
Structural Formula I is One of Formulae (Ia)-(Ih):
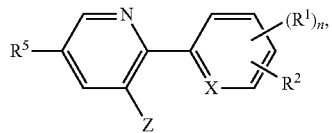
(Ia)
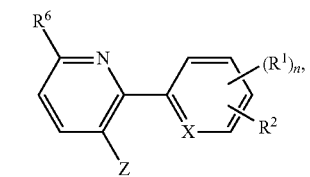
(Ib)
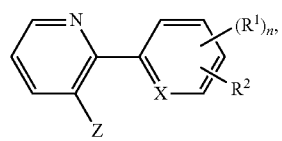
(Ic)
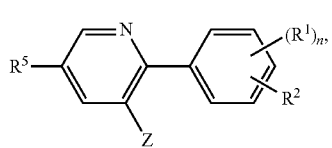
(Id)
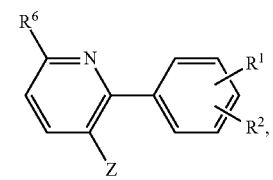
(Ie)
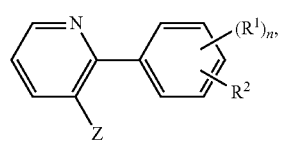
(If)
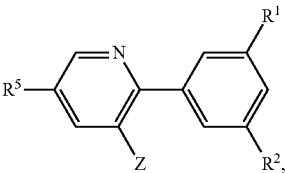
(Ig)
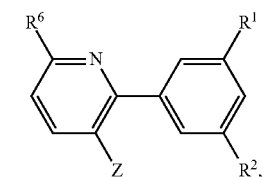
(Ih)
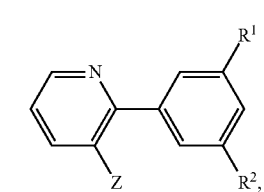
(Ii)
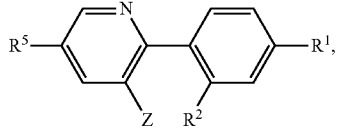
(Ij)
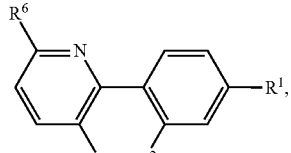
(Ik)
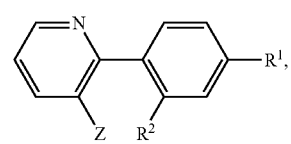
(Il)
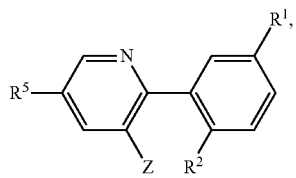
(Im)
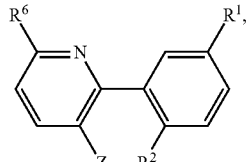
(In)
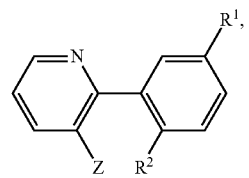
(Io)
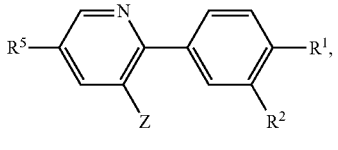
(Ip)
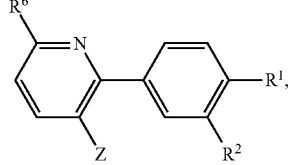
(Iq)
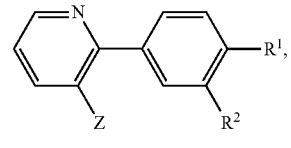
(Ir)

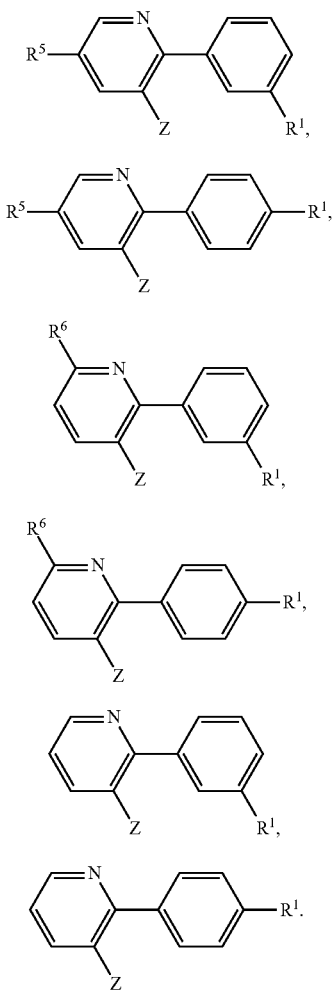

X in any of Formulae (I), (Ia), and (Ib) is Selected from One of the Following Groups (1a)-(1b):
  (1a) X is C(H).
  (1b) X is N.

$R^1$ in any of Formulae (I) and (Ia)-(Ix) is Selected from One of the Following Groups (2a)-(2m):
  (2a) $R^1$ is hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, each optionally substituted with one two or three R, —$R^{10}$, or —$C_{1-6}$alkyl-$R^{10}$, wherein $R^{10}$ is —OR, —SR, —$NR_2$, —C(O)R, —C(O)OR, —C(O)$NR_2$, —S(O)$_2NR_2$, —OC(O)R, —N(R)C(O)R, —OC(O)OR, —OC(O)$NR_2$, —N(R)C(O)OR, —N(R)C(O)$NR_2$, or —N(R)S(O)$_2$R.
  (2b) $R^1$ is hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —OR, —SR, —$NR_2$, —C(O)R, —C(O)OR, —C(O)$NR_2$, —S(O)$_2NR_2$, —OC(O)R, —N(R)C(O)R, or —N(R)S(O)$_2$R.
  (2c) $R^1$ is hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —$OR^1$, —$N(R^{11})_2$, —$C(O)N(R^{11})_2$, —$S(O)_2N(R^{11})_2$, or —$N(R^{11})S(O)_2R^{11}$, wherein each $R^{11}$ is hydrogen or $C_{1-6}$alkyl.
  (2d) $R^1$ is hydrogen, halogen, cyano, $C_{1-4}$alkyl, $C_{1-4}$haloalkyl, $C_{3-6}$cycloalkyl, $C_{3-6}$cycloalkenyl, —$C_{1-6}$alkyl-$OR^{11}$, —$OR^{11}$, —$N(R^{11})_2$, —$S(O)_2N(R^{11})_2$, or —$N(R^{11})S(O)_2R^{11}$, wherein each $R^{11}$ is hydrogen or $C_{1-6}$alkyl.
  (2e) $R^1$ is fluoro, cyano, methyl, ethyl, isopropyl, t-butyl, trifluoromethyl, hydroxy, methoxy, isopropoxy, benzyloxy, cyclopropyl, cyclopentyl, cyclopentenyl, phenyl, amino, dimethylamino, methylsulfonylamino, aminocarbonyl, dimethylaminocarbonyl, n-propylaminocarbonyl, aminosulfonyl, or hydroxymethyl.
  (2f) $R^1$ is halogen or $C_{1-6}$alkyl.
  (2 g) $R^1$ is halogen or $C_{1-4}$alkyl.
  (2h) $R^1$ is halogen or methyl.
  (2i) $R^1$ is fluoro or methyl.
  (2j) $R^1$ is fluoro.
  (2k) $R^1$ is methyl.
  (2l) $R^1$ is hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^{10}$, or —$C_{1-6}$alkyl-$R^{10}$, wherein $R^{10}$ is —OR, —SR, —$NR_2$, —C(O)R, —C(O)OR, —C(O)$NR_2$, —S(O)$_2NR_2$, —OC(O)R, —N(R)C(O)R, —OC(O)OR, —OC(O)$NR_2$, —N(R)C(O)OR, —N(R)C(O)$NR_2$, or —N(R)S(O)$_2$R.
  (2m) any one of (2a)-(2d) and (2l), where $R^1$ is not hydrogen.

$R^2$ in any of Formulae (I) and (Ia)-(Ir) is Selected from One of the Following Groups (3a)-(3m):
  (3a) $R^2$ is hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^{10}$, or —$C_{1-6}$alkyl-$R^{10}$, wherein $R^{10}$ is —OR, —SR, —$NR_2$, —C(O)R, —C(O)OR, —C(O)$NR_2$, —S(O)$_2NR_2$, —OC(O)R, —N(R)C(O)R, —OC(O)OR, —OC(O)$NR_2$, —N(R)C(O)OR, —N(R)C(O)$NR_2$, or —N(R)S(O)$_2$R.
  (3b) $R^2$ is hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —OR, —SR, —$NR_2$, —C(O)R, —C(O)OR, —C(O)$NR_2$, —S(O)$_2NR_2$, —OC(O)R, —N(R)C(O)R, or —N(R)S(O)$_2$R.
  (3c) $R^2$ is hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —$OR^{11}$, —$N(R^{11})_2$, —$C(O)N(R^{11})_2$, —$S(O)_2N(R^{11})_2$, or —$N(R^{11})S(O)_2R^{11}$, wherein each $R^{11}$ is hydrogen or $C_{1-6}$alkyl
  (3d) $R^2$ is hydrogen, halogen, cyano, $C_{1-4}$alkyl, $C_{1-4}$haloalkyl, $C_{3-6}$cycloalkyl, $C_{3-6}$cycloalkenyl, —$C_{1-6}$alkyl-$OR^{11}$, —$OR^{11}$, —$N(R^{11})_2$, —$S(O)_2N(R^{11})_2$, or —$N(R^{11})S(O)_2R^{11}$, wherein each $R^{11}$ is hydrogen or $C_{1-6}$alkyl.
  (3e) $R^2$ is fluoro, cyano, methyl, ethyl, isopropyl, t-butyl, trifluoromethyl, hydroxy, methoxy, isopropoxy, benzyloxy, cyclopropyl, cyclopentyl, cyclopentenyl, phenyl, amino, dimethylamino, methylsulfonylamino, aminocarbonyl, dimethylaminocarbonyl, n-propylaminocarbonyl, aminosulfonyl, or hydroxymethyl.
  (3f) $R^2$ is halogen or $C_{1-6}$alkyl.
  (3g) $R^2$ is halogen or $C_{1-4}$alkyl.
  (3h) $R^2$ is halogen or methyl.
  (3i) $R^2$ is fluoro or methyl.
  (3j) $R^2$ is fluoro.
  (3k) $R^2$ is methyl.
  (3l) $R^2$ is hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^{10}$, or —$C_{1-6}$alkyl-$R^{10}$, wherein $R^{10}$ is —OR, —SR, —$NR_2$, —C(O)R, —C(O)OR, —C(O)$NR_2$, —S(O)$_2NR_2$, —OC(O)R, —N(R)C(O)R, —OC(O)OR, —OC(O)$NR_2$, —N(R)C(O)OR, —N(R)C(O)$NR_2$, or —N(R)S(O)$_2$R.

(3m) any one of (3a)-(3d) and (3l) where $R^2$ is not hydrogen.

$R^1$ and $R^2$ in any of Formulae (I) and (Ia)-(Ir) are Selected from One of the Following Groups (4a)-(4j):

(4a) $R^1$ and $R^2$ are each independently hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^{10}$, or —$C_{1-6}$alkyl-$R^{10}$, wherein $R^{10}$ is —OR, —SR, —$NR_2$, —C(O)R, —C(O)OR, —C(O)$NR_2$, —S(O)$_2$$NR_2$, —OC(O)R, —N(R)C(O)R, —OC(O)OR, —OC(O)$NR_2$, —N(R)C(O)OR, —N(R)C(O)$NR_2$, or —N(R)S(O)$_2$R.

(4b) $R^1$ and $R^2$ are each independently hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —OR, —SR, —$NR_2$, —C(O)R, —C(O)OR, —C(O)$NR_2$, —S(O)$_2$$NR_2$, —OC(O)R, —N(R)C(O)R, or —N(R)S(O)$_2$R.

(4c) $R^1$ and $R^2$ are each independently hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —$OR^{11}$, —$N(R^{11})_2$, —$C(O)N(R^{11})_2$, —$S(O)_2N(R^{11})_2$, or —$N(R^{11})S(O)_2R^{11}$, wherein each $R^{11}$ is hydrogen or $C_{1-6}$alkyl.

(4d) $R^1$ and $R^2$ are each independently hydrogen, halogen, cyano, $C_{1-4}$alkyl, $C_{3-6}$cycloalkyl, $C_{3-6}$cycloalkenyl, —$C_{1-6}$alkyl-$OR^{11}$, —$OR^{11}$, —$N(R^{11})_2$, —$C(O)N(R^{11})_2$, —$S(O)_2N(R^{11})_2$, or —$N(R^{11})S(O)_2R^{11}$, wherein each $R^{11}$ is hydrogen or $C_{1-6}$alkyl.

(4e) $R^1$ and $R^2$ are each independently hydrogen, fluoro, cyano, methyl, ethyl, isopropyl, t-butyl, trifluoromethyl, hydroxy, methoxy, isopropoxy, benzyloxy, cyclopropyl, cyclopentyl, cyclopentenyl, phenyl, amino, dimethylamino, methylsulfonylamino, aminocarbonyl, dimethylaminocarbonyl, n-propylaminocarbonyl, aminosulfonyl, or hydroxymethyl.

(4f) $R^1$ and $R^2$ are each independently hydrogen, halogen, or $C_{1-6}$alkyl.

(4g) $R^1$ is fluoro and $R^2$ is methyl.

(4h) any one of (4a)-(4f), where $R^1$ is not hydrogen.

(4i) any one of (4a)-(4f), where $R^2$ is not hydrogen.

(4j) any one of (4a)-(4f), where neither $R^1$ nor $R^2$ is hydrogen.

$R^5$ in any of Formulae (I) and (Ia)-(Ix) is Selected from One of the Following Groups (5a)-(5r):

(5a) $R^5$ is hydrogen, halogen, $C_{1-6}$alkyl, —OR, —$NR^aR^a$, —N(R)C(O)R, or —N(R)S(O)$_2$R.

(5b) $R^5$ is hydrogen, halogen, $C_{1-6}$alkyl, —$OR^{50}$, —$NR^{50}R^{50}$, —$N(R^{50})C(O)R^{50}$, or —$N(R^{50})S(O)_2R^{50}$, wherein each $R^{50}$ is independently hydrogen or $C_{1-6}$alkyl.

(5c) $R^5$ is hydrogen, halogen, $C_{1-4}$alkyl, —$OR^{50}$, —$NR^{50}R^{50}$, —$N(R^{50})C(O)R^{50}$, or —$N(R^{50})S(O)_2R^{50}$, wherein each $R^{50}$ is independently hydrogen or $C_{1-4}$alkyl.

(5d) $R^5$ is hydrogen, fluoro, chloro, methyl, methoxy, ethoxy, amino, acetylamino, or methylsulfonylamino (5e) $R^5$ is fluoro or chloro.

(5f) $R^5$ is fluoro.

(5g) $R^5$ is chloro.

(5h) $R^5$ is methyl.

(5i) $R^5$ is methoxy or ethoxy.

(5j) $R^5$ is amino, acetylamino, or methylsulfonylamino.

(5k) $R^5$ is hydrogen.

(5l) $R^5$ is —$NR^aR^a$.

(5m) $R^5$ is —N(R)CO(R).

(5n) $R^5$ is heteroaryl optionally substituted with one or two $R^b$ or aryl optionally substituted with one or two $R^b$.

(5o) $R^5$ is $C_{3-8}$cycloalkyl optionally substituted with one or two $R^b$ or heterocyclyl($C_{1-6}$alkyl) optionally substituted with one or two $R^b$.

(5p) $R^5$ is hydrogen, halogen, $C_{1-6}$alkyl, $C_{1-6}$haloalkyl, $C_{3-8}$cycloalkyl, —OR, —SR, —$NR^aR^a$, —OC(O)R, —N(R)C(O)R, or —N(R)S(O)$_2$R.

(5q) $R^5$ is hydrogen, halogen, $C_{1-6}$alkyl optionally substituted with 1-3 $R^b$, $C_{1-6}$haloalkyl, $C_{3-8}$cycloalkyl optionally substituted with one or two $R^b$, heteroaryl optionally substituted with one or two $R^b$, —OR, —SR, —$NR^aR^a$, —OC(O)R, —C(O)$NR^aR^a$, —OC(O)$NR^aR^a$, —C(O)OR, —N(R)C(O)R, —N(R)S(O)$_2$R.

(5r) any one of (5a)-(5d), (5p) and (5q), where $R^5$ is not hydrogen.

$R^6$ in any of Formulae (I) and (Ia)-(Ix) is Selected from One of the Following Groups (6a)-(6n):

(6a) $R^6$ is hydrogen, halogen, $C_{1-6}$alkyl, —OR, —$NR^aR^a$, —N(R)C(O)R, or —N(R)S(O)$_2$R.

(6b) $R^6$ is hydrogen, halogen, $C_{1-6}$alkyl, —$OR^{60}$, —$NR^{60}R^{60}$, —$N(R^{60})C(O)R^{60}$, or —$N(R^{60})S(O)_2R^{60}$, wherein each $R^{60}$ is independently hydrogen or $C_{1-6}$alkyl.

(6c) $R^6$ is hydrogen, halogen, $C_{1-4}$alkyl, —$OR^{60}$, —$NR^{60}R^{60}$, —$N(R^{60})C(O)R^{60}$, or —$N(R^{60})S(O)_2R^{60}$, wherein each $R^{60}$ is independently hydrogen or $C_{1-4}$alkyl.

(6d) $R^6$ is hydrogen, fluoro, chloro, methyl, methoxy, ethoxy, amino, acetylamino, or methylsulfonylamino (6e) $R^6$ is fluoro or chloro.

(6f) $R^6$ is fluoro.

(6g) $R^6$ is chloro.

(6h) $R^6$ is methyl.

(6i) $R^6$ is methoxy or ethoxy.

(6j) $R^6$ is amino, acetylamino, or methylsulfonylamino.

(6k) $R^6$ is hydrogen.

(6l) $R^6$ is hydrogen, halogen, $C_{1-6}$alkyl, $C_{1-6}$haloalkyl, $C_{3-8}$cycloalkyl, —OR, —SR, —$NR^aR^a$, —OC(O)R, —N(R)C(O)R, or —N(R)S(O)$_2$R.

(6m) $R^6$ is hydrogen, halogen, $C_{1-6}$alkyl optionally substituted with 1-3 $R^b$, $C_{1-6}$haloalkyl, $C_{3-8}$cycloalkyl optionally substituted with one or two $R^b$, heteroaryl optionally substituted with one or two $R^b$, —OR, —SR, —$NR^aR^a$, —OC(O)R, —C(O)$NR^aR^a$, —OC(O)$NR^aR^a$, —C(O)OR, —N(R)C(O)R, —N(R)S(O)$_2$R.

(6n) any one of (6a)-(6d), (6l) and (6m), where $R^6$ is not hydrogen.

$R^5$ and $R^6$ in any of Formulae (I) and (Ia)-(Ix) are Selected from One of the Following Groups (7a)-(7u):

(7a) $R^5$ and $R^6$ are each independently hydrogen, halogen, $C_{1-6}$alkyl, —OR, —$NR^aR^a$, —N(R)C(O)R, or —N(R)S(O)$_2$R.

(7b) one of $R^5$ and $R^6$ is hydrogen, and the other is halogen, $C_{1-6}$alkyl, —OR, —$NR^aR^a$, —N(R)C(O)R, or —N(R)S(O)$_2$R.

(7c) $R^5$ and $R^6$ are each independently hydrogen, halogen, $C_{1-6}$alkyl, —$OR^7$, —$NR^7R^7$, —$N(R^7)C(O)R^7$, or —$N(R^7)S(O)_2R^7$, wherein each $R^7$ is independently hydrogen or $C_{1-6}$alkyl.

(7d) one of $R^5$ and $R^6$ is hydrogen, and the other is halogen, $C_{1-6}$alkyl, —$OR^7$, —$NR^7R^7$, —$N(R^7)C(O)R^7$, or —$N(R^7)S(O)_2R^7$, wherein each $R^7$ is independently hydrogen or $C_{1-6}$alkyl.

(7e) $R^5$ and $R^6$ are each independently hydrogen, halogen, $C_{1-4}$alkyl, —$OR^7$, —$NR^7R^7$, —$N(R^7)C(O)R^7$, or —$N(R^7)S(O)_2R^7$, wherein each $R^7$ is independently hydrogen or $C_{1-4}$alkyl.

(7f) one of $R^5$ and $R^6$ is hydrogen, and the other is halogen, $C_{1-4}$alkyl, —$OR^7$, —$NR^7R^7$, —$N(R^7)C(O)R^7$, or —$N(R^7)S(O)_2R^7$, wherein each $R^7$ is independently hydrogen or $C_{1-4}$alkyl.

(7g) $R^5$ and $R^6$ are each independently hydrogen, fluoro, chloro, methyl, methoxy, ethoxy, amino, acetylamino, or methylsulfonylamino (7h) one of $R^5$ and $R^6$ is hydrogen, and the other is fluoro, chloro, methyl, methoxy, ethoxy, amino, acetylamino, or methylsulfonylamino.

(7i) any one of (7a)-(7h), where one of $R^5$ and $R^6$ is not hydrogen.

(7j) $R^5$ and $R^6$ are each hydrogen.

(7k) one of $R^5$ and $R^6$ is hydrogen, and the other is fluoro, or chloro.

(7l) one of $R^5$ and $R^6$ is hydrogen, and the other is methyl.

(7m) one of $R^5$ and $R^6$ is hydrogen, and the other is methoxy or ethoxy.

(7n) one of $R^5$ and $R^6$ is hydrogen, and the other is amino, acetylamino, or methylsulfonylamino (7o) one of $R^5$ and $R^6$ is hydrogen, and the other is amino.

(7p) one of $R^5$ and $R^6$ is hydrogen, and the other is acetylamino (7q) one of $R^5$ and $R^6$ is hydrogen, and the other is methylsulfonylamino (7r) $R^5$ and $R^6$ are each independently hydrogen, halogen, $C_{1-6}$alkyl optionally substituted with 1-3 $R^b$, $C_{1-6}$haloalkyl, $C_{3-8}$cycloalkyl optionally substituted with one or two $R^b$, heteroaryl optionally substituted with one or two $R^b$, —OR, —SR, —$NR^aR^a$, —OC(O)R, —C(O)$NR^aR^a$, —OC(O)$NR^aR^a$, —C(O)OR, —N(R)C(O)R, —N(R)S(O)$_2$R, or $R^5$ and $R^6$ are optionally taken together with the atoms to which they are attached to form a 5- or 6-membered ring optionally including 1-3 additional heteroatoms selected from O, N and S and optionally substituted with 1-4 $R^b$.

(7s) $R^5$ and $R^6$ are taken together with the atoms to which they are attached to form a 5- or 6-membered ring optionally including 1-3 additional heteroatoms selected from O, N and S and optionally substituted with 1-4 $R^b$.

(7t) $R^5$ and $R^6$ are each independently hydrogen, halogen, $C_{1-6}$alkyl, $C_{1-6}$haloalkyl, $C_{3-8}$cycloalkyl, —OR, —SR, —$NR^aR^a$, —OC(O)R, —N(R)C(O)R, or —N(R)S(O)$_2$R.

(7u) any one of (7r) and (7t), where one of $R^5$ and $R^6$ is not hydrogen.

Z in any of Formulae (I) and (Ia)-(Ix) is Selected from One of the Following Groups (8a)-(8tt):

(8a) Z is a fused bicyclic ring of the formula,

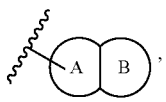

wherein ring A is a phenyl or pyridyl ring; and ring B is a 5- or 6-membered heterocyclyl or 5- or 6-membered heteroaryl, wherein Z is optionally substituted as in formula (I).

(8b) Z is as in (8a), wherein ring B is a 5- or 6-membered heterocyclyl.

(8c) Z is as in (8a), wherein ring B is a 5-membered heterocyclyl.

(8d) Z is as in (8a), wherein ring B is a 6-membered heterocyclyl.

(8e) Z is as in (8a), wherein ring B is a 5- or 6-membered heteroaryl.

(8f) Z is as in (8a), wherein ring B is a 5-membered heteroaryl.

(8g) Z is as in (8a), wherein ring B is a thienyl, pyrrolyl, furanyl, imidazolyl, pyrazolyl, thiazolyl, or oxazolyl ring.

(8h) Z is as in (8a), wherein ring B is a 6-membered heteroaryl.

(8i) Z is as in (8a), wherein ring B is a pyridyl, pyrimidinyl, or pyrazinyl ring.

(8j) Z is as in any one of (8a)-(8i), wherein ring A is a phenyl ring.

(8k) Z is as in any one of (8a)-(8i), wherein ring A is a pyridyl ring.

(8l) Z is of the formula,

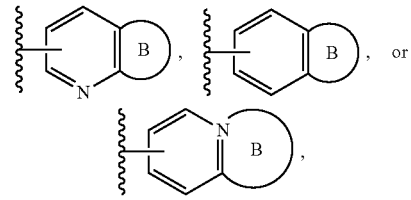

wherein each is optionally substituted by one or two groups that are each independently halogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl($C_{1-6}$alkyl), —$R^Z$, or —$C_{1-6}$alkyl-$R^Z$, wherein the $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl ($C_{1-6}$ alkyl), and heteroaryl($C_{1-6}$alkyl) are each optionally substituted by one to four groups that are each independently $C_{1-6}$alkyl or —$R^Z$.

(8m) Z is of the formula,

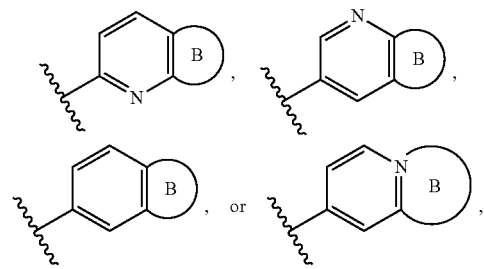

wherein each is optionally substituted by one or two groups that are each independently halogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl($C_{1-6}$alkyl), —$R^Z$, or —$C_{1-6}$alkyl-$R^Z$, wherein the $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl ($C_{1-6}$ alkyl), and heteroaryl($C_{1-6}$alkyl) are each optionally substituted by one to four groups that are each independently $C_{1-6}$alkyl or —$R^Z$.

(8n) Z is of the formula,

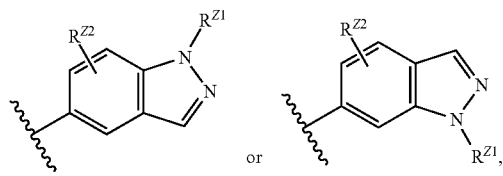

wherein $R^{Z1}$ is hydrogen, $C_{1-6}$alkyl, $C_{1-6}$haloalkyl, $C_{3-8}$cycloalkyl or —$C_{1-6}$alkyl-$R^Z$; and $R^{Z2}$ is hydrogen, halogen, $C_{1-6}$haloalkyl, $C_{3-8}$cycloalkyl or $C_{1-6}$alkyl, wherein the $C_{3-8}$cycloalkyl for $R^{Z1}$ and $R^{Z2}$ are optionally substituted with one or two halogen, $C_{1-6}$alkyl, or —$R^Z$.

(8o) Z is of the formula,

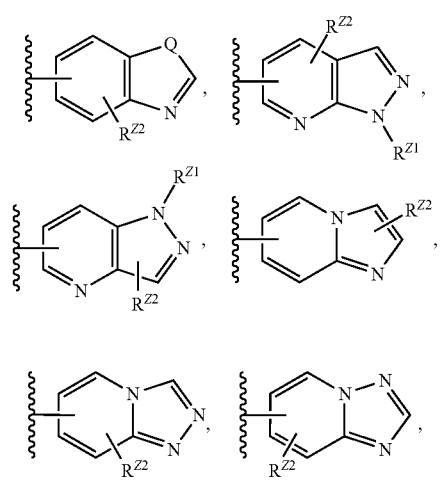

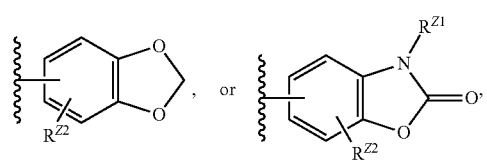

wherein

Q is —O—, —S—, or —N($R^{Z1}$)—; and $R^{Z1}$ is hydrogen, $C_{1-6}$alkyl, $C_{1-6}$haloalkyl, or —$C_{1-6}$alkyl-$R^Z$; and $R^{Z2}$ is hydrogen, halogen, or $C_{1-6}$alkyl.

(8p) As in (8o), where Z is of the formula,

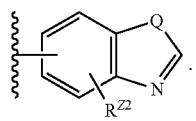

(8q) As in (8o), where Z is of the formula,

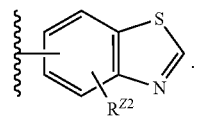

(8r) As in (8o), where Z is of the formula,

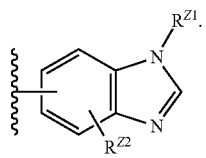

(8s) As in (8o), where Z is of the formula,

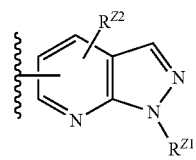

(8t) As in (8o), where Z is of the formula,

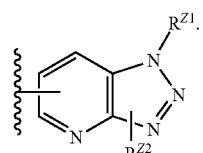

(8u) As in (8o), where Z is of the formula,

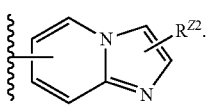

(8v) As in (8o), where Z is of the formula,

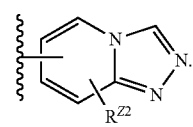

(8w) As in (8o), where Z is of the formula,

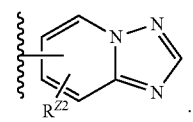

(8x) As in (8o), where Z is of the formula,

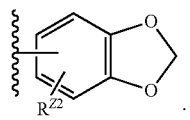

(8y) As in (8o), where Z is of the formula,

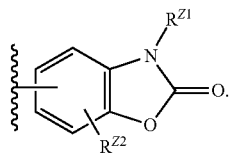

(8z) As in any one of (8n), (8r)-(8t), and (8y), where $R^{Z1}$ is hydrogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl ($C_{1-6}$ alkyl), $-R^{Z3}$, $-C_{1-6}$alkyl-$R^{Z3}$, or $-C_{1-6}$alkyl-$R^{Z4}$, wherein $R^{Z3}$ is $-C(O)R$, $-C(O)OR$, $-C(O)NR_2$, or $-S(O)_2NR_2$; and $R^{Z4}$ is $-OR$, $-SR$, $-NR_2$, $-OC(O)R$, $-N(R)C(O)R$, $-OC(O)OR$, $-OC(O)NR_2$, $-N(R)C(O)OR$, $-N(R)C(O)NR_2$, $-N(R)S(O)_2R$, or $-OP(O)(OR)_2$.

(8aa) As in any one of (8n), (8r)-(8t), and (8y), where $R^{Z1}$ is hydrogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl($C_{1-6}$alkyl), $-R^{Z3}$, $-C_{1-6}$alkyl-$R^{Z3}$, or $-C_{1-6}$alkyl-$R^{Z4}$, wherein $R^{Z3}$ is $-C(O)R^{Z6}$, $-C(O)OR^{Z6}$, $-C(O)NR^{Z6}{}_2$, or $-S(O)_2NR^{Z5}{}_2$; and $R^{Z4}$ is $-OR^{Z5}$, $-SR^{Z5}$, $-NR^{Z5}{}_2$, $-OC(O)R^{Z5}$, $-N(R^{Z5})C(O)R^{Z5}$, $-OC(O)OR^{Z5}$, $-OC(O)NR^{Z5}{}_2$, $-N(R^{Z5})C(O)OR^{Z5}$, $-N(R^{Z5})C(O)NR^{Z5}{}_2$, $-N(R^{Z5})S(O)_2R^{Z5}$, or $-OP(O)(OR^{Z5})_2$, and wherein each $R^{Z5}$ is independently hydrogen or $C_{1-6}$alkyl; and each $R^{Z6}$ is independently hydrogen or $C_{1-6}$alkyl, $C_{3-8}$cycloalkyl($C_{1-6}$alkyl), heterocyclyl($C_{1-6}$alkyl), aryl($C_{1-6}$alkyl), or heteroaryl($C_{1-6}$alkyl), each optionally substituted by one or two groups that are each independently $-OR^0$, $-SR^0$, $-N(R^0)_2$, $-C(O)R^0$, $-C(O)OR^0$, $-C(O)N(R^0)_2$, $-S(O)_2N(R^0)_2$, $-OC(O)R^0$, $-N(R^0)C(O)R^0$, $-OC(O)OR^0$, $-OC(O)N(R^0)_2$, $-N(R^0)C(O)OR^0$, $-N(R^0)C(O)N(R^0)_2$, or $-N(R^0)S(O)_2R^0$, wherein each $R^0$ is independently hydrogen or $C_{1-6}$alkyl.

(8bb) As in any one of (8n), (8r)-(8t), and (8y), where $R^{Z1}$ is hydrogen, $C_{1-6}$alkyl, heterocyclyl, heterocyclyl($C_{1-6}$alkyl), $-C_{1-6}$alkyl$-R^{Z4}$, or $-C(O)OR^{Z6}$, wherein $R^{Z4}$ is $-OR^{Z5}$, $-SR^{Z5}$, $-NR^{Z5}{}_2$, $-OC(O)R^{Z5}$, $N(R^{Z5})C(O)R^{Z5}$, $-OC(O)OR^{Z5}$, $-OC(O)NR^{Z5}{}_2$, $-N(R^{Z5})C(O)OR^{Z5}$, $-N(R^{Z5})C(O)NR^{Z5}{}_2$, $N(R^{Z5})S(O)_2R^{Z5}$, or $-OP(O)(OR^{Z5})_2$, wherein the heterocyclyl and heterocyclyl($C_{1-6}$alkyl) are each optionally substituted by one or two groups that are each independently halogen or $C_{1-6}$alkyl; and wherein each $R^{Z5}$ is independently hydrogen or $C_{1-6}$alkyl; and each $R^{Z6}$ is independently hydrogen or $C_{1-6}$alkyl, $C_{3-8}$cycloalkyl($C_{1-6}$alkyl), heterocyclyl($C_{1-6}$alkyl), aryl($C_{1-6}$alkyl), or heteroaryl($C_{1-6}$alkyl), each optionally substituted by $-OR^0$, $-SR^0$, $-N(R^0)_2$, $-C(O)R^0$, $-C(O)OR^0$, or $-C(O)N(R^0)_2$, wherein each $R^0$ is independently hydrogen or $C_{1-6}$alkyl.

(8cc) As in any one of (8n), (8r)-(8t), and (8y), where $R^{Z1}$ is hydrogen, $C_{1-6}$alkyl, heterocyclyl, heterocyclyl($C_{1-6}$ alkyl), $-C_{1-6}$alkyl-$OR^{Z5}$, $-C_{1-6}$alkyl-$OP(O)(OR^{Z5})_2$, or $-C(O)OR^{Z6}$, wherein the heterocyclyl and heterocyclyl($C_{1-6}$alkyl) are each optionally substituted by one or two $C_{1-6}$alkyl groups; and wherein each $R^{Z5}$ is independently hydrogen or $C_{1-6}$alkyl; each $R^{Z6}$ is independently hydrogen or $C_{1-6}$alkyl or heteroaryl($C_{1-6}$alkyl), each optionally substituted by $-OR^0$, or $-N(R^0)_2$, wherein each $R^0$ is independently hydrogen or $C_{1-6}$alkyl.

(8dd) As in any one of (8n), (8r)-(8t), and (8y), where $R^{Z1}$ is hydrogen, methyl, ethyl, isopropyl, 2-(morpholin-4-yl)ethyl, 2-(4-methylpiperazin-1-yl)ethyl, 3-hydroxypropyl, 3-ethoxypropyl, 4-tetrahydropyranyl, N-methylpiperidin-4-yl, $-CH_2-OP(O)(OH)_2$, or 3-(indol-3-yl)-2-aminopropyloxycarbonyl.

(8ee) As in any one of (8n)-(8dd), where $R^{Z2}$ is hydrogen or halogen.

(8ff) As in any one of (8n)-(8dd), where $R^{Z2}$ is hydrogen or $C_{1-6}$alkyl.

(8gg) As in any one of (8n)-(8dd), where $R^{Z2}$ is hydrogen or methyl.

(8hh) As in any one of (8n)-(8dd), where $R^{Z2}$ is hydrogen.

(8ii) Z is halophenyl (e.g., 4-halophenyl).

(8jj) Z is dihalophenyl.

(8kk) Z is fluorophenyl.

(8ll) Z is 4-fluorophenyl.

(8 mm) Z is

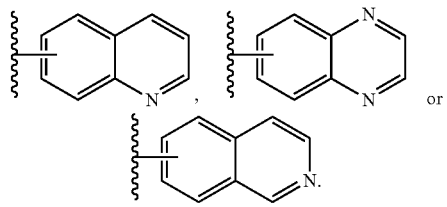

(8nn) Z is

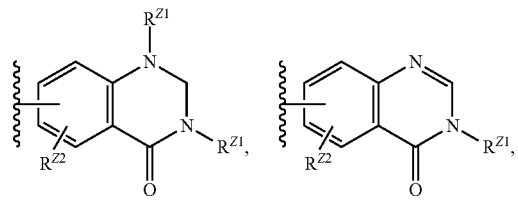

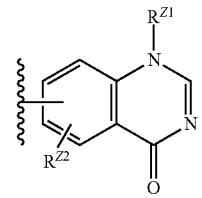

Z is

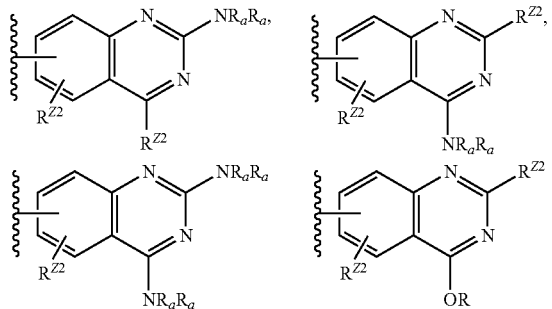

(8oo) In any one of (8nn) and (8oo), independently is for each occurrence hydrogen, $C_{1-6}$alkyl, $C_{1-6}$haloalkyl, $C_{3-8}$cycloalkyl or —$C_{1-6}$alkyl-$R^Z$, wherein the $C_{3-8}$cycloalkyl are optionally substituted by one or two halogen, $C_{1-6}$alkyl, or —$R^Z$.

(8pp) In any one of (8nn)-(8 pp), $R^{Z2}$ independently is for each occurrence hydrogen, halogen, $C_{1-6}$alkyl, $C_{1-6}$haloalkyl, $C_{3-8}$cycloalkyl, —$R^Z$, or —$C_{1-6}$alkyl-$R^Z$, wherein the $C_{3-8}$cycloalkyl are optionally substituted by one or two halogen, $C_{1-6}$alkyl, or —$R^Z$.

(8qq) Z is of the formula,

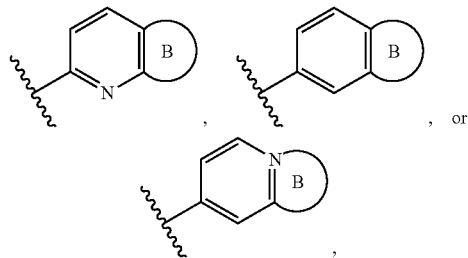

wherein each is optionally substituted by one or two groups that are each independently halogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl($C_{1-6}$alkyl), —$R^Z$, or —$C_{1-6}$alkyl-$R^Z$, wherein the $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl ($C_{1-6}$ alkyl), and heteroaryl($C_{1-6}$alkyl) are each optionally substituted by one to four groups that are each independently $C_{1-6}$alkyl or —$R^Z$.

(8rr) Z is of the formula,

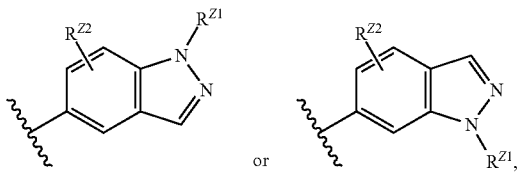

wherein $R^{Z1}$ is hydrogen, $C_{1-6}$alkyl, $C_{1-6}$haloalkyl, or —$C_{1-6}$alkyl-$R^Z$; and $R^{Z2}$ is hydrogen, halogen, or $C_{1-6}$alkyl.

(8ss) Z is pyridinyl.
(8tt) Z is pyrimidinyl, optionally substituted by one or two groups that are each independently halogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl($C_{1-6}$alkyl), —$R^Z$, or —$C_{1-6}$alkyl-$R^Z$, wherein the $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), and heteroaryl($C_{1-6}$alkyl) are each optionally substituted by one or two groups that are each independently halogen, $C_{1-6}$alkyl, or —$R^Z$; and $R^Z$ is cyano, —$CF_3$, —OR, —SR, —$NR^aR^a$, —C(O)R, —C(O)OR, —C(O)$NR^aR^a$, —S(O)$_2NR^aR^a$, —S(O)$_2R^0$, —OC(O)R, —N(R)C(O)R, —OC(O)OR, —OC(O)$NR^aR^a$, —N(R)C(O)OR, —N(R)C(O)$NR^aR^a$, —N(R)S(O)$_2$R, or —OP(O)(OR)$_2$.

In any of Formulae (I) and (Ia)-If) is Selected from One of the Following Definitions (9a)-(9c):
(9a) n is 1.
(9b) n is 1, 2 or 3.
(9c) n is 1 or 2.

The compounds of formulae (I) and (Ia)-(Ix) described above are useful as kinase inhibitors and/or inhibitors of cytokine signaling. Exemplary kinases inhibited by the presently disclosed compounds formulae I and (Ia)-(Ix) include, without limitation, ACVR1; ACVR1B (ALK-4); ACVR1c; ACVR2A; ACVR2B; ACVRL1; BMPR1A; BMPR1B; BMPR2; TGFBR1 (ALK-5), PI3K and MAP4K4 (HGK). Exemplary cytokines, the signaling of which is inhibited by the present compounds of formulae (I), include, without limitation, TGF-β superfamily, including TGF-β1 and GDF-8. In one aspect the present compounds are selective for one or more kinase and/or cytokine signaling pathway. For example, exemplary compounds inhibit TGF-β1 signaling, GDF-8 signaling, or both. In one aspect the present compounds inhibit GDF-8 signaling preferentially to TGF-β1 signaling, such that GDF8 signaling is inhibited at least about 1.5-fold more potently or from about 1.1-fold to about 25-fold more potently. In one embodiment certain compounds inhibit GDF8 signaling at least about 5-fold more potently, such as from about 8-fold to about 50-fold, or at least about 10-fold more potently, such as from about 15-fold to about 300-fold more potently.

Exemplary compounds of formulae I and (Ia-Ix) (e.g., Compounds 63, 389, 448, 456, 460, 494 and 818) inhibit MAP4K4 with an IC50 of less than about 500 nM. Such compounds are particularly useful in muscle disorders, such as cachexia and sarcopenia as MAP4K4 acts as a suppressor of skeletal muscle differentiation. See, Wang M, Amano S U, Flach R J, Chawla A, Aouadi M, Czech P. Molecular and cellular biology. 2013 February; 33(4): 678-87.

In particular the present compounds can be use to treat disorders, such as pulmonary hypertension, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, atherosclerosis, peritoneal and sub-dermal adhesion, kidney fibrosis, lung fibrosis, including idiopathic pulmonary fibrosis, and liver fibrosis, hepatitis B, hepatitis C, alcohol-induced hepatitis, cancer, haemochromatosis, primary biliary cirrhosis, restenosis, retroperitoneal fibrosis, mesenteric fibrosis, endometriosis, keloids, cancer, abnormal bone function, inflammatory disorders, scarring and photaging of the skin.

Particular proliferative diseases that can be treated with the present compounds include those selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, melanoma, psoriasis, prostate hyperplasia, a neoplasia, a neoplasia of epithelial character, leukemias and lymphomas, a mammary carcinoma or a leukemia. Other diseases include Cowden syndrome, Lhermitte-Dudos disease and Bannayan-Zonana syndrome, or diseases in which the PI3K/PKB pathway is aberrantly activated.

The compounds of Formula (I) described herein also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, $^{18}$F etc. Thus, the disclosed compounds may be enriched in one or more of these isotopes relative to the natural abundance of such isotope. As is known to those of skill in the art, such isotopically enriched compounds are useful for a variety of purposes. For example, substitution with heavier isotopes such as deuterium ($^2$H) may afford certain therapeutic advantages that result from greater metabolic stability. Substitution with positron emitting isotopes, such as 18F can be useful in Positron Emission Tomography (PET) studies. By way of example, deuterium ($^2$H) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

Particular embodiments of this aspect of the disclosure include compounds of any one of the Formula (I), each as defined in each of the following rows, wherein each entry is a group number as defined above (e.g., (1b) refers to X is N), and a dash "—" indicates that the variable is as defined for formula (I) or defined according to any one of the applicable variable definitions (1a)-(8ll) [e.g., when X is a dash, it can be either as defined for Formula (I) or any one of definitions (1a)-(1b)]:

| Formula (I) | R$^1$ & R$^2$ | R$^5$ & R$^6$ | Z |
|---|---|---|---|
| (Id) | (4a) | (7a) | (8a) |
| (Id) | (4a) | (7a) | (8n) |
| (Id) | (4a) | (7a) | (8rr) |
| (Id) | (4a) | (7a) | (8o) |
| (Id) | (4a) | (7g) | (8a) |
| (Id) | (4a) | (7g) | (8n) |
| (Id) | (4a) | (7g) | (8rr) |
| (Id) | (4a) | (7g) | (8o) |
| (Id) | (4a) | (7i) | (8a) |
| (Id) | (4a) | (7i) | (8n) |
| (Id) | (4a) | (7i) | (8rr) |
| (Id) | (4a) | (7i) | (8o) |
| (Id) | (4d) | (7a) | (8a) |
| (Id) | (4d) | (7a) | (8n) |
| (Id) | (4d) | (7a) | (8rr) |
| (Id) | (4d) | (7a) | (8o) |
| (Id) | (4d) | (7g) | (8a) |
| (Id) | (4d) | (7g) | (8n) |
| (Id) | (4d) | (7g) | (8rr) |
| (Id) | (4d) | (7g) | (8o) |
| (Id) | (4d) | (7i) | (8a) |
| (Id) | (4d) | (7i) | (8n) |
| (Id) | (4d) | (7i) | (8rr) |
| (Id) | (4d) | (7i) | (8o) |
| (Id) | (4e) | (7a) | (8a) |
| (Id) | (4e) | (7a) | (8n) |
| (Id) | (4e) | (7a) | (8rr) |
| (Id) | (4e) | (7a) | (8o) |
| (Id) | (4e) | (7g) | (8a) |
| (Id) | (4e) | (7g) | (8n) |
| (Id) | (4e) | (7g) | (8rr) |
| (Id) | (4e) | (7g) | (8o) |
| (Id) | (4e) | (7i) | (8a) |
| (Id) | (4e) | (7i) | (8n) |
| (Id) | (4e) | (7i) | (8rr) |
| (Id) | (4e) | (7i) | (8o) |
| (Id) | (4f) | (7a) | (8a) |
| (Id) | (4f) | (7a) | (8n) |
| (Id) | (4f) | (7a) | (8rr) |
| (Id) | (4f) | (7a) | (8o) |
| (Id) | (4f) | (7g) | (8a) |
| (Id) | (4f) | (7g) | (8n) |
| (Id) | (4f) | (7g) | (8rr) |
| (Id) | (4f) | (7g) | (8o) |
| (Id) | (4f) | (7i) | (8a) |
| (Id) | (4f) | (7i) | (8n) |
| (Id) | (4f) | (7i) | (8rr) |
| (Id) | (4f) | (7i) | (8o) |
| (Id) | (4g) | (7a) | (8a) |
| (Id) | (4g) | (7a) | (8n) |
| (Id) | (4g) | (7a) | (8rr) |
| (Id) | (4g) | (7a) | (8o) |
| (Id) | (4g) | (7g) | (8a) |
| (Id) | (4g) | (7g) | (8n) |
| (Id) | (4g) | (7g) | (8rr) |
| (Id) | (4g) | (7g) | (8o) |
| (Id) | (4g) | (7i) | (8a) |
| (Id) | (4g) | (7i) | (8n) |
| (Id) | (4g) | (7i) | (8rr) |
| (Id) | (4g) | (7i) | (8o) |
| (Id) | (2j), (3k) | (7a) | (8a) |
| (Id) | (2j), (3k) | (7a) | (8n) |
| (Id) | (2j), (3k) | (7a) | (8rr) |
| (Id) | (2j), (3k) | (7a) | (8o) |
| (Id) | (2j), (3k) | (7g) | (8a) |
| (Id) | (2j), (3k) | (7g) | (8n) |
| (Id) | (2j), (3k) | (7g) | (8rr) |
| (Id) | (2j), (3k) | (7g) | (8o) |
| (Id) | (2j), (3k) | (7i) | (8a) |
| (Id) | (2j), (3k) | (7i) | (8n) |
| (Id) | (2j), (3k) | (7i) | (8rr) |
| (Id) | (2j), (3k) | (7i) | (8o) |
| (Ie) | (4a) | (7a) | (8a) |
| (Ie) | (4a) | (7a) | (8n) |
| (Ie) | (4a) | (7a) | (8rr) |
| (Ie) | (4a) | (7a) | (8o) |
| (Ie) | (4a) | (7g) | (8a) |
| (Ie) | (4a) | (7g) | (8n) |
| (Ie) | (4a) | (7g) | (8rr) |
| (Ie) | (4a) | (7g) | (8o) |
| (Ie) | (4a) | (7i) | (8a) |
| (Ie) | (4a) | (7i) | (8n) |
| (Ie) | (4a) | (7i) | (8rr) |
| (Ie) | (4a) | (7i) | (8o) |
| (Ie) | (4d) | (7a) | (8a) |
| (Ie) | (4d) | (7a) | (8n) |
| (Ie) | (4d) | (7a) | (8rr) |
| (Ie) | (4d) | (7a) | (8o) |
| (Ie) | (4d) | (7g) | (8a) |
| (Ie) | (4d) | (7g) | (8n) |
| (Ie) | (4d) | (7g) | (8rr) |
| (Ie) | (4d) | (7g) | (8o) |
| (Ie) | (4d) | (7i) | (8a) |
| (Ie) | (4d) | (7i) | (8n) |
| (Ie) | (4d) | (7i) | (8rr) |
| (Ie) | (4d) | (7i) | (8o) |
| (Ie) | (4e) | (7a) | (8a) |
| (Ie) | (4e) | (7a) | (8n) |
| (Ie) | (4e) | (7a) | (8rr) |
| (Ie) | (4e) | (7a) | (8o) |

| Formula (I) | R¹& R² | R⁵& R⁶ | Z |
|---|---|---|---|
| (Ie) | (4e) | (7g) | (8a) |
| (Ie) | (4e) | (7g) | (8n) |
| (Ie) | (4e) | (7g) | (8rr) |
| (Ie) | (4e) | (7g) | (8o) |
| (Ie) | (4e) | (7i) | (8a) |
| (Ie) | (4e) | (7i) | (8n) |
| (Ie) | (4e) | (7i) | (8rr) |
| (Ie) | (4e) | (7i) | (8o) |
| (Ie) | (4f) | (7a) | (8a) |
| (Ie) | (4f) | (7a) | (8n) |
| (Ie) | (4f) | (7a) | (8rr) |
| (Ie) | (4f) | (7a) | (8o) |
| (Ie) | (4f) | (7g) | (8a) |
| (Ie) | (4f) | (7g) | (8n) |
| (Ie) | (4f) | (7g) | (8rr) |
| (Ie) | (4f) | (7g) | (8o) |
| (Ie) | (4f) | (7i) | (8a) |
| (Ie) | (4f) | (7i) | (8n) |
| (Ie) | (4f) | (7i) | (8rr) |
| (Ie) | (4f) | (7i) | (8o) |
| (Ie) | (4g) | (7a) | (8a) |
| (Ie) | (4g) | (7a) | (8n) |
| (Ie) | (4g) | (7a) | (8rr) |
| (Ie) | (4g) | (7a) | (8o) |
| (Ie) | (4g) | (7g) | (8a) |
| (Ie) | (4g) | (7g) | (8n) |
| (Ie) | (4g) | (7g) | (8rr) |
| (Ie) | (4g) | (7g) | (8o) |
| (Ie) | (4g) | (7i) | (8a) |
| (Ie) | (4g) | (7i) | (8n) |
| (Ie) | (4g) | (7i) | (8rr) |
| (Ie) | (4g) | (7i) | (8o) |
| (Ie) | (2j), (3k) | (7a) | (8a) |
| (Ie) | (2j), (3k) | (7a) | (8n) |
| (Ie) | (2j), (3k) | (7a) | (8rr) |
| (Ie) | (2j), (3k) | (7a) | (8o) |
| (Ie) | (2j), (3k) | (7g) | (8a) |
| (Ie) | (2j), (3k) | (7g) | (8n) |
| (Ie) | (2j), (3k) | (7g) | (8rr) |
| (Ie) | (2j), (3k) | (7g) | (8o) |
| (Ie) | (2j), (3k) | (7i) | (8a) |
| (Ie) | (2j), (3k) | (7i) | (8n) |
| (Ie) | (2j), (3k) | (7i) | (8rr) |
| (Ie) | (2j), (3k) | (7i) | (8o) |
| (If) | (4a) | — | (8a) |
| (If) | (4a) | — | (8n) |
| (If) | (4a) | — | (8rr) |
| (If) | (4a) | — | (8o) |
| (If) | (4d) | — | (8a) |
| (If) | (4d) | — | (8n) |
| (If) | (4d) | — | (8rr) |
| (If) | (4d) | — | (8o) |
| (If) | (4e) | — | (8a) |
| (If) | (4e) | — | (8n) |
| (If) | (4e) | — | (8rr) |
| (If) | (4e) | — | (8o) |
| (If) | (4f) | — | (8a) |
| (If) | (4f) | — | (8n) |
| (If) | (4f) | — | (8rr) |
| (If) | (4f) | — | (8o) |
| (If) | (4g) | — | (8a) |
| (If) | (4g) | — | (8n) |
| (If) | (4g) | — | (8rr) |
| (If) | (4g) | — | (8o) |
| (If) | (2j), (3k) | — | (8a) |
| (If) | (2j), (3k) | — | (8n) |
| (If) | (2j), (3k) | — | (8rr) |
| (If) | (2j), (3k) | — | (8o) |
| (Ir) | (4a) | — | (8a) |
| (Ir) | (4a) | — | (8n) |
| (Ir) | (4a) | — | (8rr) |
| (Ir) | (4a) | — | (8o) |
| (Ir) | (4d) | — | (8a) |
| (Ir) | (4d) | — | (8n) |
| (Ir) | (4d) | — | (8rr) |
| (Ir) | (4d) | — | (8o) |
| (Ir) | (4e) | — | (8a) |
| (Ir) | (4e) | — | (8n) |
| (Ir) | (4e) | — | (8rr) |
| (Ir) | (4e) | — | (8o) |
| (Ir) | (4f) | — | (8a) |
| (Ir) | (4f) | — | (8n) |
| (Ir) | (4f) | — | (8rr) |
| (Ir) | (4f) | — | (8o) |
| (Ir) | (4g) | — | (8a) |
| (Ir) | (4g) | — | (8n) |
| (Ir) | (4g) | — | (8rr) |
| (Ir) | (4g) | — | (8o) |
| (Ir) | (2j), (3k) | — | (8a) |
| (Ir) | (2j), (3k) | — | (8n) |
| (Ir) | (2j), (3k) | — | (8rr) |
| (Ir) | (2j), (3k) | — | (8o) |

In certain such embodiments, n is 1.

In one particular embodiment, the compound of formula (I) is according to the formula,

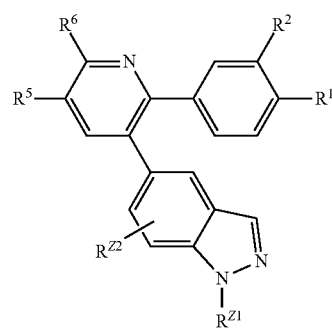

(II)

or pharmaceutically acceptable salts thereof, wherein $R^1$ and $R^2$ are each independently hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^{10}$, or —$C_{1-6}$alkyl-$R^{10}$, wherein $R^{10}$ is —OR, —SR, —NR$_2$, —C(O)R, —C(O)OR, —C(O)NR$_2$, —S(O)$_2$NR$_2$, —OC(O)R, —N(R)C(O)R, —OC(O)OR, —OC(O)NR$_2$, —N(R)C(O)OR, —N(R)C(O)NR$_2$, or —N(R)S(O)$_2$R;

$R^5$ and $R^6$ are each independently hydrogen, halogen, $C_{1-6}$alkyl, $C_{1-6}$haloalkyl, $C_{3-8}$cycloalkyl, —OR, —SR, —NR$_2$, —OC(O)R, —N(R)C(O)R, or —N(R)S(O)$_2$R;

$R^{Z1}$ is hydrogen, $C_{1-6}$alkyl, $C_{1-6}$haloalkyl, $C_{3-8}$cycloalkyl, heterocyclyl, aryl, heteroaryl, $C_{3-8}$ cycloalkyl($C_{1-6}$ alkyl), heterocyclyl($C_{1-6}$ alkyl), aryl($C_{1-6}$ alkyl), heteroaryl($C_{1-6}$ alkyl), —$R^{Z3}$, —$C_{1-6}$ alkyl-$R^{Z3}$, or —$C_{1-6}$ alkyl-$R^{Z4}$, wherein the $C_{3-8}$cycloalkyl, heterocyclyl, aryl, heteroaryl, $C_{3-8}$cycloalkyl($C_{1-6}$alkyl), heterocyclyl($C_{1-6}$ alkyl), aryl($C_{1-6}$ alkyl), and heteroaryl($C_{1-6}$ alkyl) are each optionally substituted by one or two groups that are each independently halogen, $C_{1-6}$alkyl, —$R^{Z3}$, or —$R^{Z4}$, wherein $R^{Z3}$ is —C(O)R, —C(O)OR, —C(O)NR$_2$, or —S(O)$_2$NR$_2$; and $R^{Z4}$ is —OR, —SR, —NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, or —OP(O)(OR)$_2$;

$R^{Z2}$ is hydrogen, halogen, or $C_{1-6}$alkyl;

and each R is independently hydrogen or $C_{1-6}$alkyl, $C_{1-6}$haloalkyl, $C_{3-8}$cycloalkyl, heterocyclyl, aryl, heteroaryl, $C_{3-8}$ cycloalkyl($C_{1-6}$ alkyl), heterocyclyl($C_{1-6}$ alkyl), aryl($C_{1-6}$alkyl), or heteroaryl($C_{1-6}$alkyl), each optionally substituted by one or two groups that are each independently —$OR^0$, —$SR^0$, —$N(R^0)_2$, —$C(O)R^0$, —$C(O)OR^0$, —$C(O)N(R^0)_2$, —$S(O)_2N(R^0)_2$, —$OC(O)R^0$, —$N(R^0)C(O)R^0$, —$OC(O)OR^0$, —$OC(O)N(R^0)_2$, —$N(R^0)C(O)OR^0$, —$N(R^0)C(O)N(R^0)_2$, or —$N(R^0)S(O)_2R^0$, wherein each $R^0$ is independently hydrogen or $C_{1-6}$alkyl.

The disclosure further comprises subgenera of formula (II) in which the substituents are selected as any and all combinations of one or more of $R^1$, $R^2$, $R^5$, $R^6$, $R^{Z1}$, and $R^{Z2}$ as defined herein, including without limitation, the following:

$R^1$ is Selected from One of the Following Groups (9a)-(9k):

(9a) $R^1$ is hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —OR, —SR, —$NR_2$, —C(O)R, —C(O)OR, —$C(O)NR_2$, —$S(O)_2NR_2$, —OC(O)R, —N(R)C(O)R, or —$N(R)S(O)_2R$.

(9b) $R^1$ is hydrogen, halogen, cyano, $C_{1-6}$alkyl, $C_{1-6}$haloalkyl, $C_{3-8}$cycloalkyl, $C_{3-8}$cycloalkenyl —$R^{10}$, or —$C_{1-6}$alkyl-$R^{10}$, wherein $R^{10}$, is —$OR^{11}$, —$N(R^{11})_2$, —$C(O)N(R^{11})_2$, —$S(O)_2N(R^{11})_2$, or —$N(R^{11})S(O)_2R^{11}$, wherein each $R^{11}$ is hydrogen or $C_{1-6}$alkyl.

(9c) $R^1$ is hydrogen, halogen, cyano, $C_{1-4}$alkyl, $C_{1-4}$haloalkyl, $C_{3-6}$cycloalkyl, $C_{3-6}$cycloalkenyl, —$C_{1-6}$alkyl-$OR^{11}$, —$OR^{11}$, —$N(R^{11})_2$, —$C(O)N(R^{11})_2$, —$S(O)_2N(R^{11})_2$, or —$N(R^{11})S(O)_2R^{11}$, wherein each $R^{11}$ is hydrogen or $C_{1-6}$alkyl.

(9d) $R^1$ is fluoro, cyano, methyl, ethyl, isopropyl, t-butyl, trifluoromethyl, hydroxy, methoxy, isopropoxy, benzyloxy, cyclopropyl, cyclopentyl, cyclopentenyl, phenyl, amino, dimethylamino, methylsulfonylamino, aminocarbonyl, dimethylaminocarbonyl, n-propylaminocarbonyl, aminosulfonyl, or hydroxymethyl.

(9e) $R^1$ is halogen or $C_{1-6}$alkyl.

(9f) $R^1$ is halogen or $C_{1-4}$alkyl.

(9g) $R^1$ is halogen or methyl.

(9h) $R^1$ is fluoro or methyl.

(9i) $R^1$ is fluoro.

(9j) $R^1$ is methyl.

(9k) any one of (9a)-(9c), where $R^1$ is not hydrogen.

$R^2$ is Selected from One of the Following Groups (10a)-(10k):

(10a) $R^2$ is hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —OR, —SR, —$NR_2$, —C(O)R, —C(O)OR, —$C(O)NR_2$, —$S(O)_2NR_2$, —OC(O)R, —N(R)C(O)R, or —$N(R)S(O)_2R$.

(10b) $R^2$ is hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —$OR^{11}$, $N(R^{11})_2$, —$C(O)N(R^{11})_2$, —$S(O)_2N(R^{11})_2$, or —$N(R^{11})S(O)_2R^{11}$, wherein each $R^{11}$ is hydrogen or $C_{1-6}$alkyl.

(10c) $R^2$ is hydrogen, halogen, cyano, $C_{3-6}$alkyl, $C_{3-6}$haloalkyl, $C_{3-6}$cycloalkyl, $C_{3-6}$cycloalkenyl, —$C_{1-6}$alkyl-$OR^{11}$, —$OR^{11}$, —$N(R^{11})_2$, —$C(O)N(R^{11})_2$, —$S(O)_2N(R^{11})_2$, or —$N(R^{11})S(O)_2R^{11}$, wherein each $R^{11}$ is hydrogen or $C_{1-6}$alkyl.

(10d) $R^2$ is fluoro, cyano, methyl, ethyl, isopropyl, t-butyl, trifluoromethyl, hydroxy, methoxy, isopropoxy, benzyloxy, cyclopropyl, cyclopentyl, cyclopentenyl, phenyl, amino, dimethylamino, methylsulfonylamino, aminocarbonyl, dimethylaminocarbonyl, n-propylaminocarbonyl, aminosulfonyl, or hydroxymethyl.

(10e) $R^2$ is halogen or $C_{1-6}$alkyl.

(10f) $R^2$ is halogen or $C_{1-4}$alkyl.

(10g) $R^2$ is halogen or methyl.

(10h) $R^2$ is fluoro or methyl.

(10i) $R^2$ is fluoro.

(10j) $R^2$ is methyl.

(10k) As in any of (10a)-(10c), in which $R^2$ is not hydrogen.

$R^1$ and $R^2$ are Selected from One of the Following Groups (11a)-(11i):

(11a) $R^1$ and $R^2$ are each independently hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —OR, —SR, —$NR_2$, —C(O)R, —C(O)OR, —$C(O)NR_2$, —$S(O)_2NR_2$, —OC(O)R, —N(R)C(O)R, or —$N(R)S(O)_2R$.

(11b) $R^1$ and $R^2$ are each independently hydrogen, halogen, cyano, $C_{1-6}$alkyl, $C_{1-6}$haloalkyl, $C_{3-8}$cycloalkyl, $C_{3-8}$cycloalkenyl, —$R^{10}$, or —$C_{1-6}$alkyl-$R^{10}$, wherein $R^{10}$ is —$OR^{11}$, —$N(R^{11})_2$, —$C(O)N(R^{11})_2$, —$S(O)_2N(R^{11})_2$, or —$N(R^{11})S(O)_2R^{11}$, wherein each $R^{11}$ is hydrogen or $C_{1-6}$alkyl.

(11c) $R^1$ and $R^2$ are each independently hydrogen, halogen, cyano, $C_{1-4}$alkyl, $C_{1-4}$haloalkyl, $C_{3-6}$cycloalkyl, $C_{3-6}$cycloalkenyl, —$C_{1-6}$alkyl-$OR^{11}$, —$OR^{11}$, —$N(R^{11})_2$, —$C(O)N(R^{11})_2$, —$S(O)_2N(R^{11})_2$, or —$N(R^{11})S(O)_2R^{11}$, wherein each $R^{11}$ is hydrogen or $C_{1-6}$alkyl.

(11d) $R^1$ and $R^2$ are each independently hydrogen, fluoro, cyano, methyl, ethyl, isopropyl, t-butyl, trifluoromethyl, hydroxy, methoxy, isopropoxy, benzyloxy, cyclopropyl, cyclopentyl, cyclopentenyl, phenyl, amino, dimethylamino, methylsulfonylamino, aminocarbonyl, dimethylaminocarbonyl, n-propylaminocarbonyl, aminosulfonyl, or hydroxymethyl.

(11e) $R^1$ and $R^2$ are each independently hydrogen, halogen, or $C_{1-6}$alkyl.

(11f) $R^1$ is fluoro and $R^2$ is methyl.

(11g) any one of (11a)-(11e), where $R^1$ is not hydrogen.

(11h) any one of (11a)-(11e), where $R^2$ is not hydrogen.

(11i) any one of (11a)-(11e), where neither $R^1$ nor $R^2$ is hydrogen.

$R^5$ is Selected from One of the Following Groups (12a)-(12k):

(12a) $R^5$ is hydrogen, halogen, $C_{1-6}$alkyl, —$OR^{50}$, —$NR^{50}R^{50}$, —$N(R^{50})C(O)R^{50}$, or —$N(R^{50})S(O)_2R^{50}$, wherein each $R^{50}$ is independently hydrogen or $C_{1-6}$alkyl.

(12b) $R^5$ is hydrogen, halogen, $C_{1-4}$alkyl, —$OR^{50}$, —$NR^{50}R^{50}$, —$N(R^{50})C(R^{50})$, or —$N(R^{50})S(O)_2R^{50}$, wherein each $R^{50}$ is independently hydrogen or $C_{1-4}$alkyl.

(12c) $R^5$ is hydrogen, fluoro, chloro, methyl, methoxy, ethoxy, amino, acetylamino, or methylsulfonylamino (12d) $R^5$ is fluoro or chloro (12e) $R^5$ is fluoro (12f) $R^5$ is chloro (12g) $R^5$ is methyl (12h) $R^5$ is methoxy or ethoxy (12i) $R^5$ is amino, acetylamino, or methylsulfonylamino (12j) $R^5$ is hydrogen.

(12k) any one of (12a)-(12i), where $R^5$ is not hydrogen.

$R^6$ is Selected from One of the Following Groups (13a)-(13k):
- (13a) $R^6$ is hydrogen, halogen, $C_{1-6}$alkyl, —OR$^{60}$, —NR$^{60}$R$^{60}$, —N(R$^{60}$)C(O)R$^{60}$, or —N(R$^{60}$)S(O)$_2$R$^{60}$, wherein each R$^{60}$ is independently hydrogen or $C_{1-6}$alkyl.
- (13b) $R^6$ is hydrogen, halogen, $C_{1-4}$alkyl, —OR$^{60}$, —NR$^{60}$R$^{60}$, —N(R$^{60}$)C(O)R$^{60}$, or —N(R$^{60}$)S(O)$_2$R$^{60}$, wherein each R$^{60}$ is independently hydrogen or $C_{1-4}$alkyl.
- (13c) $R^6$ is hydrogen, fluoro, chloro, methyl, methoxy, ethoxy, amino, acetylamino, or methylsulfonylamino
- (13d) $R^6$ is fluoro or chloro
- (13e) $R^6$ is fluoro
- (13f) $R^6$ is chloro
- (13g) $R^6$ is methyl
- (13h) $R^6$ is methoxy or ethoxy
- (13i) $R^6$ is amino, acetylamino, or methylsulfonylamino
- (13j) $R^6$ is hydrogen.
- (13k) any one of (13a)-(13j), where $R^6$ is not hydrogen.

$R^5$ and $R^6$ are Selected from One of the Following Groups (14a)-(14o):
- (14a) $R^5$ and $R^6$ are each independently hydrogen, halogen, $C_{1-6}$alkyl, —OR$^7$, —NR$^7$R$^7$, —N(R$^7$)C(O)R$^7$, or —N(R$^7$)S(O)$_2$R$^7$, wherein each R$^7$ is independently hydrogen or $C_{1-6}$alkyl.
- (14b) one of $R^5$ and $R^6$ is hydrogen, and the other is halogen, $C_{1-6}$alkyl, —OR$^7$, —NR$^7$R$^7$, —N(R$^7$)C(O)R$^7$, or —N(R$^7$)S(O)$_2$R$^7$, wherein each R$^7$ is independently hydrogen or $C_{1-6}$alkyl.
- (14c) $R^5$ and $R^6$ are each independently hydrogen, halogen, $C_{1-4}$alkyl, —OR$^7$, —NR$^7$R$^7$, —N(R$^7$)C(O)R$^7$, or —N(R$^7$)S(O)$_2$R$^7$, wherein each R$^7$ is independently hydrogen or $C_{1-4}$alkyl.
- (14d) one of $R^5$ and $R^6$ is hydrogen, and the other is halogen, $C_{1-4}$alkyl, —OR$^7$, —NR$^7$R$^7$, —N(R$^7$)C(O)R$^7$, or —N(R$^7$)S(O)$_2$R$^7$, wherein each R$^7$ is independently hydrogen or $C_{1-4}$alkyl.
- (14e) $R^5$ and $R^6$ are each independently hydrogen, fluoro, chloro, methyl, methoxy, ethoxy, amino, acetylamino, or methylsulfonylamino
- (14f) one of $R^5$ and $R^6$ is hydrogen, and the other is fluoro, chloro, methyl, methoxy, ethoxy, amino, acetylamino, or methylsulfonylamino
- (14g) any one of (14a)-(14f), where one of $R^5$ and $R^6$ is not hydrogen.
- (14h) $R^5$ and $R^6$ are each hydrogen
- (14i) one of $R^5$ and $R^6$ is hydrogen, and the other is fluoro, or chloro
- (14j) one of $R^5$ and $R^6$ is hydrogen, and the other is methyl
- (14k) one of $R^5$ and $R^6$ is hydrogen, and the other is methoxy or ethoxy
- (14l) one of $R^5$ and $R^6$ is hydrogen, and the other is amino, acetylamino, or methylsulfonylamino
- (14m) one of $R^5$ and $R^6$ is hydrogen, and the other is amino
- (14n) one of $R^5$ and $R^6$ is hydrogen, and the other is acetylamino
- (14o) one of $R^5$ and $R^6$ is hydrogen, and the other is methylsulfonylamino $R^{Z1}$ is Selected from One of the Following Groups (15a)-(15j):
- (15a) $R^{Z1}$ is hydrogen, $C_{1-6}$alkyl, $C_{1-6}$haloalkyl, $C_{3-8}$cycloalkyl, heterocyclyl, aryl, heteroaryl, $C_{3-8}$ cycloalkyl($C_{1-6}$ alkyl), heterocyclyl($C_{1-6}$ alkyl), aryl($C_{1-6}$ alkyl), heteroaryl($C_{1-6}$ alkyl), —R$^{Z3}$, —$C_{1-6}$alkyl-R$^{Z3}$, or —$C_{1-6}$ alkyl-R$^{Z4}$, wherein R$^{Z3}$ is —C(O)R, —C(O)OR, —C(O)NR$_2$, or —S(O)$_2$NR$_2$; and R$^{Z4}$ is —OR, —SR, —NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, or —OP(O)(OR)$_2$.
- (15b) $R^{Z1}$ is hydrogen, $C_{1-6}$alkyl, $C_{1-6}$haloalkyl, $C_{3-8}$cycloalkyl, heterocyclyl, aryl, heteroaryl, $C_{3-8}$ cycloalkyl($C_{1-6}$ alkyl), heterocyclyl($C_{1-6}$ alkyl), aryl($C_{1-6}$ alkyl), heteroaryl($C_{1-6}$ alkyl), —R$^{Z3}$, —$C_{1-6}$alkyl-R$^{Z3}$, or —$C_{1-6}$ alkyl-R$^{Z4}$, wherein R$^{Z3}$ is —C(O)R$^{Z6}$, —C(O)OR$^{Z6}$, —C(O)NR$^{Z6}_2$, or —S(O)$_2$NR$^{Z5}_2$; and R$^{Z4}$ is —OR$^{Z5}$, —SR$^{Z5}$, —NR$^{Z5}_2$, —OC(O)R$^{Z5}$, —N(R$^{Z5}$)C(O)R$^{Z5}$, —OC(O)OR$^{Z5}$, —OC(O)NR$^{Z5}_2$, —N(R$^{Z5}$)C(O)OR$^{Z5}$, —N(R$^{Z5}$)C(O)NR$^{Z5}_2$, —N(R$^{Z5}$)S(O)$_2$R$^{Z5}$, or —OP(O)(OR$^{Z5}$)$_2$, and wherein each R$^{Z5}$ is independently hydrogen or $C_{1-6}$alkyl; and each R$^{Z6}$ is independently hydrogen or $C_{1-6}$alkyl, $C_{3-8}$cycloalkyl($C_{1-6}$alkyl), heterocyclyl($C_{1-6}$alkyl), aryl($C_{1-6}$alkyl), or heteroaryl($C_{1-6}$alkyl), each optionally substituted by one or two groups that are each independently —OR$^0$, —SR$^0$, —N(R$^0$)$_2$, —C(O)R$^0$, —C(O)OR$^0$, —C(O)N(R$^0$)$_2$, —S(O)$_2$N(R$^0$)$_2$, —OC(O)R$^0$, —N(R$^0$)C(O)R$^0$, —OC(O)OR$^0$, —OC(O)N(R$^0$)$_2$, —N(R$^0$)C(O)OR$^0$, —N(R$^0$)C(O)N(R$^0$)$_2$, or —N(R$^0$)S(O)$_2$R$^0$, wherein each R$^0$ is independently hydrogen or $C_{1-6}$alkyl.
- (15c) $R^{Z1}$ is hydrogen, $C_{1-6}$alkyl, heterocyclyl, heterocyclyl($C_{1-6}$alkyl), —$C_{1-6}$ alkyl-R$^{Z4}$, or —C(O)OR$^{Z6}$, wherein R$^{Z4}$ is —OR$^{Z5}$, —SR$^{Z5}$, —NR$^{Z5}_2$, —OC(O)R$^{Z5}$, —N(R$^{Z5}$)C(O)R$^{Z5}$, —OC(O)OR$^{Z5}$, —OC(O)NR$^{Z5}_2$, —N(R$^{Z5}$)C(O)OR$^{Z5}$, —N(R$^{Z5}$)C(O)NR$^{Z5}_2$, —N(R$^{Z5}$)S(O)$_2$R$^{Z5}$, or —OP(O)(OR$^{Z5}$)$_2$, wherein the heterocyclyl and heterocyclyl($C_{1-6}$alkyl) are each optionally substituted by one or two groups that are each independently halogen or $C_{1-6}$alkyl; and wherein each R$^{Z5}$ is independently hydrogen or $C_{1-6}$alkyl; and each R$^{Z6}$ is independently hydrogen or $C_{1-6}$alkyl, $C_{3-8}$cycloalkyl($C_{1-6}$alkyl), heterocyclyl($C_{1-6}$alkyl), aryl($C_{1-6}$alkyl), or heteroaryl($C_{1-6}$alkyl), each optionally substituted by —OR$^0$, —SR$^0$, —N(R$^0$)$_2$, —C(O)R$^0$, —C(O)OR$^0$, or —C(O)N(R$^0$)$_2$, wherein each R$^0$ is independently hydrogen or $C_{1-6}$alkyl.
- (15d) $R^{Z1}$ is hydrogen, $C_{1-6}$alkyl, heterocyclyl, heterocyclyl($C_{1-6}$ alkyl), —$C_{1-6}$ alkyl-OR$^{Z5}$, or —$C_{1-6}$alkyl-OP(O)(OR$^{Z5}$)$_2$, or —C(O)OR$^{Z6}$, wherein the heterocyclyl and heterocyclyl($C_{1-6}$alkyl) are each optionally substituted by one or two $C_{1-6}$alkyl groups; and wherein each R$^{Z5}$ is independently hydrogen or $C_{1-6}$alkyl; each R$^{Z6}$ is independently hydrogen or $C_{1-6}$alkyl or heteroaryl($C_{1-6}$ alkyl), each optionally substituted by —OR$^0$, or —N(R$^0$)$_2$, wherein each R$^0$ is independently hydrogen or $C_{1-6}$alkyl.
- (15e) $R^{Z1}$ is hydrogen, methyl, ethyl, isopropyl, 2-(morpholin-4-yl)ethyl, 2-(4-methylpiperazin-1-yl)ethyl, 3-hydroxypropyl, 3-ethoxypropyl, 4-tetrahydropyranyl, N-methylpiperidin-4-yl, —CH$_2$—OP(O)(OH)$_2$, or 3-(indol-3-yl)-2-aminopropyloxycarbonyl.
- (15f) $R^{Z1}$ is hydrogen, methyl, or 3-(indol-3-yl)-2-aminopropyloxycarbonyl.
- (15g) $R^{Z1}$ is hydrogen or methyl.
- (15h) $R^{Z1}$ is hydrogen.
- (15i) $R^{Z1}$ is methyl.
- (15j) $R^{Z1}$ is 3-(indol-3-yl)-2-aminopropyloxycarbonyl.

$R^{Z2}$ is Selected from One of the Following Groups (16a)-(16d):
- (16a) $R^{Z2}$ is hydrogen or halogen
- (16b) $R^{Z2}$ is hydrogen or $C_{1-6}$alkyl;
- (16c) $R^{Z2}$ is hydrogen or methyl;
- (16d) $R^{Z2}$ is hydrogen Particular embodiments of this aspect of the disclosure include compounds of any one of the Formula (II), each as defined in each of the following rows, wherein each entry is a group number as defined above, and a dash "—" indicates that the variable is as defined for formula (II) or defined according to any one of the applicable variable definitions (9a)-(16d) [e.g., when $R^{Z1}$ is a dash, it can be either as defined for Formula (II) or any one of definitions (15a)-(15j)]:

| $R^1$ & $R^2$ | $R^5$ & $R^6$ | $R^{Z1}$ | $R^{Z2}$ |
|---|---|---|---|
| (11d) | (14e) | (15e) | (16a) |
| (11d) | (14e) | (15e) | (16b) |
| (11d) | (14e) | (15g) | (16a) |
| (11d) | (14e) | (15g) | (16b) |
| (11d) | (14f) | (15e) | (16a) |
| (11d) | (14f) | (15e) | (16b) |
| (11d) | (14f) | (15g) | (16a) |
| (11d) | (14f) | (15g) | (16b) |
| (11d) | (14h) | (15e) | (16a) |
| (11d) | (14h) | (15e) | (16b) |
| (11d) | (14h) | (15g) | (16a) |
| (11d) | (14h) | (15g) | (16b) |
| (11d) | (14i) | (15e) | (16a) |
| (11d) | (14i) | (15e) | (16b) |
| (11d) | (14i) | (15g) | (16a) |
| (11d) | (14i) | (15g) | (16b) |
| (11e) | (14e) | (15e) | (16a) |
| (11e) | (14e) | (15e) | (16b) |
| (11e) | (14e) | (15g) | (16a) |
| (11e) | (14e) | (15g) | (16b) |
| (11e) | (14f) | (15e) | (16a) |
| (11e) | (14f) | (15e) | (16b) |
| (11e) | (14f) | (15g) | (16a) |
| (11e) | (14f) | (15g) | (16b) |
| (11e) | (14h) | (15e) | (16a) |
| (11e) | (14h) | (15e) | (16b) |
| (11e) | (14h) | (15g) | (16a) |
| (11e) | (14h) | (15g) | (16b) |
| (11e) | (14i) | (15e) | (16a) |
| (11e) | (14i) | (15e) | (16b) |
| (11e) | (14i) | (15g) | (16a) |
| (11e) | (14i) | (15g) | (16b) |
| (11f) | (14e) | (15e) | (16a) |
| (11f) | (14e) | (15e) | (16b) |
| (11f) | (14e) | (15g) | (16a) |
| (11f) | (14e) | (15g) | (16b) |
| (11f) | (14f) | (15e) | (16a) |
| (11f) | (14f) | (15e) | (16b) |
| (11f) | (14f) | (15g) | (16a) |
| (11f) | (14f) | (15g) | (16b) |
| (11f) | (14h) | (15e) | (16a) |
| (11f) | (14h) | (15e) | (16b) |
| (11f) | (14h) | (15g) | (16a) |
| (11f) | (14h) | (15g) | (16b) |
| (11f) | (14i) | (15e) | (16a) |
| (11f) | (14i) | (15e) | (16b) |
| (11f) | (14i) | (15g) | (16a) |
| (11f) | (14i) | (15g) | (16b) |

In certain embodiments of the compounds as described throughout this disclosure, Z is optionally substituted by one or two groups that are each independently halogen, $C_{1-6}$alkyl, $C_{1-6}$haloalkyl, —$R^Z$, or —$C_{1-6}$alkyl-$R^Z$, wherein each and $R^Z$ is cyano, —$CF_3$, —OR, —SR, —$NR^aR^a$, —C(O)R, —C(O)OR, —C(O)$NR^aR^a$, —S(O)$_2NR^aR^a$, —S(O)$_2R^O$, —OC(O)R, —N(R)C(O)R, —OC(O)OR, —OC(O)$NR^aR^a$, —N(R)C(O)OR, —N(R)C(O)$NR^aR^a$, —N(R)S(O)$_2$R, or —OP(O)(OR)$_2$. In certain such embodiments, each R is independently hydrogen, $C_{1-6}$alkyl, or $C_{1-6}$haloalkyl, each optionally substituted by 1-3 groups that are each independently $R^b$, —$OR^O$, —$SR^O$, —N($R^O$)$_2$, —C(O)$R^O$, —C(O)O$R^O$, —C(O)N($R^O$)$_2$, —S(O)$_2$N($R^O$)$_2$, —OC(O)$R^O$, —N($R^O$)C(O)$R^O$, —OC(O)$OR^O$, —O(CH$_2$)$_m$C(O)N($R^O$)$_2$, —N($R^O$)C(O)$OR^O$, —N($R^O$)C(O)N($R^O$)$_2$, or —N($R^O$)S(O)$_2R^O$, in which each $R^b$ is independently halogen, cyano, oxo, $C_{1-6}$alkyl, $C_{1-6}$haloalkyl or —$OR^{13}$, in which $R^{13}$ is hydrogen, $C_{1-6}$alkyl or $C_{1-6}$haloalkyl, each optionally substituted by 1-3 groups that are each independently halogen, cyano, oxo, $C_{1-6}$alkyl, $C_{1-6}$haloalkyl, —$OR^O$, —$SR^O$, —N($R^O$)$_2$, —C(O)$R^O$, —C(O)O$R^O$, —C(O)N($R^O$)$_2$, —S(O)$_2$N($R^O$)$_2$, —OC(O)$R^O$, —N($R^O$)C(O)$R^O$, —OC(O)$OR^O$, —O(CH$_2$)$_m$C(O)N($R^O$)$_2$, —N($R^O$)C(O)$OR^O$, —N($R^O$)C(O)N($R^O$)$_2$, or —N($R^O$)S(O)$_2R^O$, in which each $R^O$ is independently hydrogen, $C_{1-6}$haloalkyl or $C_{1-6}$alkyl optionally substituted with 1-3 $R^{b0}$, in which each $R^{b0}$ is independently halogen, cyano or oxo.

In certain embodiments of the compounds as described throughout this disclosure, each $R^a$ is independently hydrogen, $C_{1-6}$alkyl or $C_{1-6}$haloalkyl, each optionally substituted by 1-3 groups that are each independently $R^b$, —$OR^O$, —$SR^O$, —N($R^O$)$_2$, —C(O)$R^O$, —C(O)O$R^O$, —C(O)N($R^O$)$_2$, —S(O)$_2$N($R^O$)$_2$, —OC(O)$R^O$, —N($R^O$)C(O)$R^O$, —OC(O)$OR^O$, —O(CH$_2$)$_m$C(O)N($R^O$)$_2$, —N($R^O$)C(O)$OR^O$, —N($R^O$)C(O)N($R^O$)$_2$, or —N($R^O$)S(O)$_2R^O$, or two $R^a$ together with the nitrogen atom to which they are attached form a 3-8 membered heterocyclyl group, optionally including 1-4 additional heteroatoms selected from O, N and S and optionally substituted with 1-4 R groups.

In certain embodiments of the compounds as described throughout this disclosure, each $R^b$ is independently halogen, cyano, oxo, $C_{1-6}$alkyl, $C_{1-6}$haloalkyl or —$OR^{11}$, in which $R^{12}$ is hydrogen, $C_{1-6}$ alkyl, $C_{1-6}$haloalkyl, $C_{3-8}$cycloalkyl, heterocyclyl, aryl, heteroaryl, $C_{3-8}$ cycloalkyl($C_{1-6}$ alkyl), heterocyclyl($C_{1-6}$ alkyl), aryl($C_{1-6}$ alkyl), or heteroaryl($C_{1-6}$ alkyl), each optionally substituted by 1-3 groups that are each independently halogen, cyano, oxo, $C_{1-6}$alkyl, $C_{1-6}$haloalkyl, —$OR^O$, —$SR^O$, —N($R^O$)$_2$, —C(O)$R^O$, —C(O)O$R^O$, —C(O)N($R^O$)$_2$, —S(O)$_2$N($R^O$)$_2$, —OC(O)$R^O$, —N($R^O$)C(O)$R^O$, —OC(O)$OR^O$, —O(CH$_2$)$_m$C(O)N($R^O$)$_2$, —N($R^O$)C(O)$OR^O$, —N($R^O$)C(O)N($R^O$)$_2$, or —N($R^O$)S(O)$_2R^O$, in which each $R^O$ is independently hydrogen, $C_{1-6}$haloalkyl, $C_{1-6}$alkyl optionally substituted with 1-3 $R^{b0}$, $C_{3-8}$cycloalkyl optionally substituted with one or two $R^{b0}$ or, alternatively two $R^O$ together with a nitrogen atom to which they are bound (for example when R is —C(O)N($R^O$)$_2$) form a 3-8 membered heterocyclyl group, optionally including 1-4 additional heteroatoms selected from O, N and S and optionally substituted with 0-3 $R^{b0}$, in which each $R^{b0}$ is independently halogen, cyano or oxo.

In certain embodiments of the compounds as described throughout this disclosure, each $R^b$ is independently halogen, cyano, oxo, $C_{1-6}$alkyl, $C_{1-6}$haloalkyl or —$OR^{13}$, in which $R^{13}$ is hydrogen, $C_{1-6}$alkyl or $C_{1-6}$haloalkyl, each optionally substituted by 1-3 groups that are each independently halogen, cyano, oxo, $C_{1-6}$alkyl, $C_{1-6}$haloalkyl, —$OR^O$, —$SR^O$, —N($R^O$)$_2$, —C(O)$R^O$, —C(O)O$R^O$, —C(O)N($R^O$)$_2$, —S(O)$_2$N($R^O$)$_2$, —OC(O)$R^O$, —N($R^O$)C(O)$R^O$, —OC(O)$OR^O$, —O(CH$_2$)$_m$C(O)N($R^O$)$_2$, —N($R^O$)C(O)$OR^O$, —N($R^O$)C(O)N($R^O$)$_2$, or —N($R^O$)S(O)$_2R^O$, in which each $R^O$ is independently hydrogen, $C_{1-6}$haloalkyl or $C_{1-6}$alkyl optionally substituted with 1-3 $R^{b0}$, in which each $R^{b0}$ is independently halogen, cyano or oxo.

In certain embodiments of the compounds as described throughout this disclosure, each R is independently hydrogen, $C_{1-6}$alkyl, $C_{1-6}$haloalkyl, $C_{3-8}$cycloalkyl, heterocyclyl, aryl, heteroaryl, $C_{3-8}$ cycloalkyl($C_{1-6}$ alkyl), heterocyclyl ($C_{1-6}$ alkyl), aryl($C_{1-6}$ alkyl), or heteroaryl($C_{1-6}$ alkyl), each optionally substituted by 1-3 groups that are each independently $R^b$, —$OR^O$, —$SR^O$, —N($R^O$)$_2$, —C(O)$R^O$, —C(O)O$R^O$, —C(O)N($R^O$)$_2$, —S(O)$_2$N($R^O$)$_2$, —OC(O)$R^O$, —N($R^O$)C(O)$R^O$, —OC(O)$OR^O$, —O(CH$_2$)$_m$C(O)N($R^O$)$_2$, —N($R^O$)C (O)OR⁰, —N(R⁰)C(O)N(R⁰)₂, or —N(R⁰)S(O)₂R⁰. In certain such embodiments, each R⁰ is hydrogen, C₁₋₆haloalkyl or C₁₋₆alkyl.

In certain embodiments of the compounds as described throughout this disclosure, each R is independently hydrogen, C₁₋₆alkyl, or C₁₋₆haloalkyl, each optionally substituted by 1-3 groups that are each independently R^b, —OR⁰, —SR⁰, —N(R⁰)₂, —C(O)R⁰, —C(O)OR⁰, —C(O)N(R⁰)₂, —S(O)₂N(R⁰)₂, —OC(O)R⁰, —N(R⁰)C(O)R⁰, —OC(O)OR⁰, —O(CH₂)ₘC(O)N(R⁰)₂, —N(R⁰)C(O)OR⁰, —N(R⁰)C(O)N(R⁰)₂, or —N(R⁰)S(O)₂R⁰, in which each R^b is independently halogen, cyano, oxo, C₁₋₆alkyl, C₁₋₆haloalkyl or —OR¹³, in which R¹³ is hydrogen, C₁₋₆alkyl or C₁₋₆haloalkyl, each optionally substituted by 1-3 groups that are each independently halogen, cyano, oxo, C₁₋₆ alkyl, C₁₋₆haloalkyl, —OR⁰, —SR⁰, —N(R⁰)₂, —C(O)R⁰, —C(O)OR⁰, —C(O)N(R)₂, —S(O)₂N(R⁰)₂, —OC(O)R⁰, —N(R⁰)C(O)R⁰, —OC(O)OR⁰, —O(CH₂)ₘC(O)N(R⁰)₂, —N(R⁰)C(O)OR⁰, —N(R⁰)C(O)N(R⁰)₂, or —N(R⁰)S(O)₂R⁰, in which each R⁰ is independently hydrogen, C₁₋₆haloalkyl or C₁₋₆alkyl optionally substituted with 1-3 R^b⁰, in which each R^b⁰ is independently halogen, cyano or oxo.

In certain embodiments of the compounds as described throughout this disclosure, R⁰ is independently hydrogen, C₁₋₆haloalkyl, or C₁₋₆alkyl optionally substituted with 1-3 R^b⁰, in which each R^b⁰ is independently halogen, cyano or oxo.

In certain embodiments of the compounds as described throughout this disclosure, each C₁₋₆(halo)alkyl is a C₁₋₃(halo)alkyl. In other embodiments of the compounds as described throughout this disclosure, each C₁₋₆(halo)alkyl is a C₁₋₂(halo)alkyl.

In certain embodiments of the compounds as described throughout this disclosure, when R¹ and R² are attached to adjacent carbon atoms they are optionally taken together with the atoms to which they are attached to form a 5- or 6-membered ring optionally substituted with one or two groups that are each independently halogen, oxo, oxime, imino, C₁₋₆alkyl, C₁₋₆haloalkyl, or —R¹⁰. The ring can be for example, an aryl ring (e.g., a benzo) or a 5- or 6-membered heteroaryl ring (e.g. a pyrido or a thieno). When the ring is a heteroaryl ring, it can include 1 or 2 heteroatoms selected from N, O and S. In other embodiments, the ring is a cycloalkylene (e.g., 5 or 6 membered), or a heterocyclyl ring (e.g., 5 or 6 membered) including 1 or 2 heteroatoms selected from N, O and S.

In certain embodiments, the compound of formula (I) is one of the compounds of Table 1, optionally provided as a salt (e.g., the salt indicated in the Table):

| Cpd # | Structure | Salt |
|---|---|---|
| 1 | 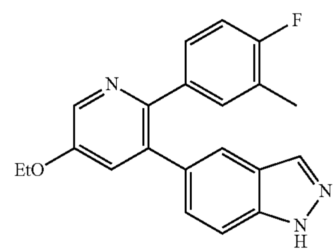 [SMILES: CCOc1cnc(-c2ccc(F)c(C)c2)c(-c2ccc3[nH]ncc3c2)c1] | TFA(2) |
| 2 | 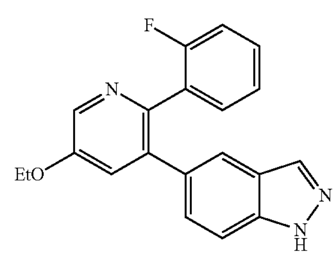 [SMILES: CCOc1cnc(-c2ccccc2F)c(-c2ccc3[nH]ncc3c2)c1] | TFA(2) |
| 3 | 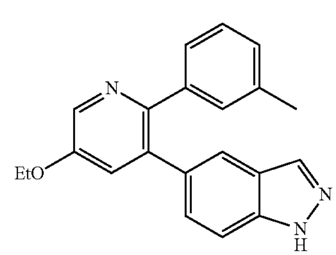 [SMILES: CCOc1cnc(-c2cccc(C)c2)c(-c2ccc3[nH]ncc3c2)c1] | Formic Acid(2) |

-continued

| Cpd # | Structure | Salt |
|---|---|---|
| 4 | 3-(5-ethoxy-2-(4-fluoro-2-isopropoxyphenyl)pyridin-3-yl)-1H-indazole | Formic Acid(2) |
| 5 | 3-(5-ethoxy-2-(3-fluorophenyl)pyridin-3-yl)-1H-indazole | Formic Acid(2) |
| 6 | 3-(5-ethoxy-2-(4-fluorophenyl)pyridin-3-yl)-1H-indazole | TFA(2) |
| 7 | 3-(5-ethoxy-2-(3,4-difluorophenyl)pyridin-3-yl)-1H-indazole | TFA(2) |
| 8 | 3-(2-(4-fluoro-3-methylphenyl)-5-methoxypyridin-3-yl)-1H-indazole | Formic Acid(2) |
| 9 | 3-(5-chloro-2-(4-fluoro-3-methylphenyl)pyridin-3-yl)-1H-indazole | TFA(2) |

-continued
| Cpd # | Structure | Salt |
|---|---|---|
| 10 | 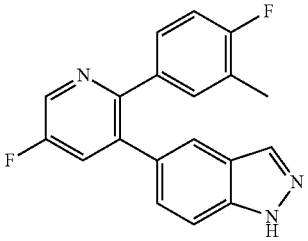 [SMILES: Cc1cc(-c2ncc(F)cc2-c2ccc3[nH]ncc3c2)ccc1F] | TFA(2) |
| 11 | 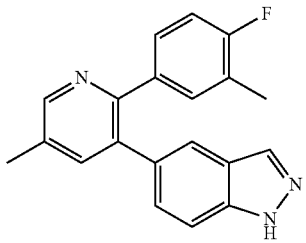 [SMILES: Cc1cnc(-c2ccc(F)c(C)c2)c(-c2ccc3[nH]ncc3c2)c1] | TFA(2) |
| 12 | 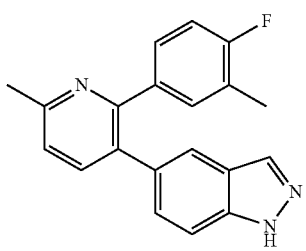 [SMILES: Cc1ccc(-c2ccc3[nH]ncc3c2)c(-c2ccc(F)c(C)c2)n1] | TFA(2) |
| 13 | 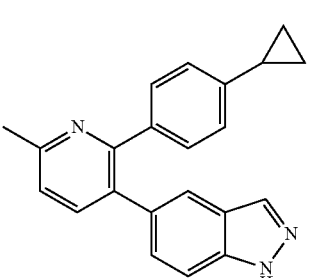 | TFA(2) |
| 14 | 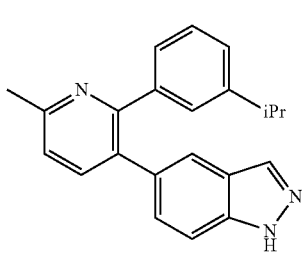 [SMILES: Cc1ccc(-c2ccc3[nH]ncc3c2)c(-c2cccc(C(C)C)c2)n1] | TFA(2) |
| 15 | 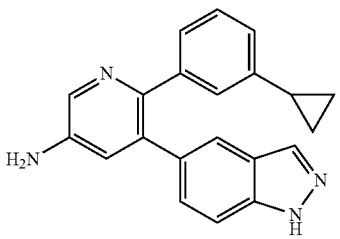 [SMILES: Nc1cnc(-c2cccc(C3CC3)c2)c(-c2ccc3[nH]ncc3c2)c1] | TFA(3) |

-continued
| Cpd # | Structure | Salt |
|---|---|---|
| 16 | 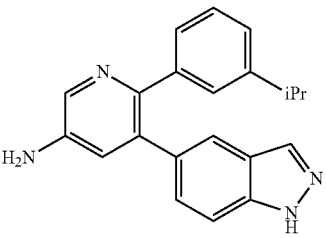 [SMILES: CC(C)c1cccc(-c2ncc(N)cc2-c2ccc3[nH]ncc3c2)c1] | TFA(3) |
| 17 | 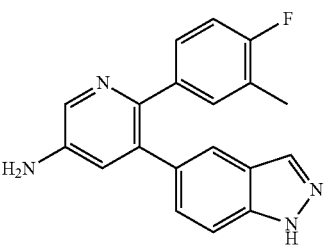 [SMILES: Cc1cc(-c2ncc(N)cc2-c2ccc3[nH]ncc3c2)ccc1F] | Formic Acid(3) |
| 18 | 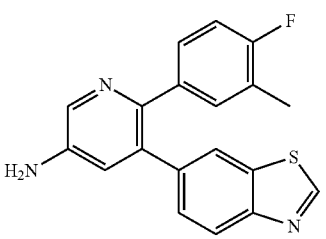 [SMILES: Cc1cc(-c2ncc(N)cc2-c2ccc3ncsc3c2)ccc1F] | TFA(3) |
| 19 | 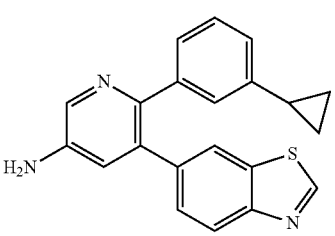 [SMILES: Nc1cnc(-c2cccc(C3CC3)c2)c(-c2ccc3ncsc3c2)c1] | TFA(3) |
| 20 | 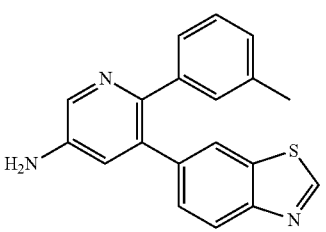 [SMILES: Cc1cccc(-c2ncc(N)cc2-c2ccc3ncsc3c2)c1] | TFA(3) |
| 21 | 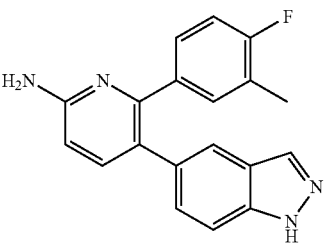 [SMILES: Cc1cc(-c2nc(N)ccc2-c2ccc3[nH]ncc3c2)ccc1F] | TFA(3) |

-continued

| Cpd # | Structure | Salt |
|---|---|---|
| 22 | 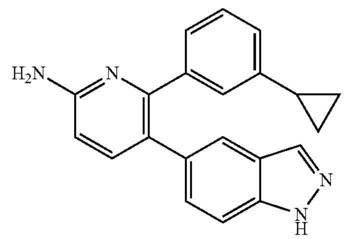 [SMILES: Nc1ccc(-c2ccc3[nH]ncc3c2)c(-c2cccc(C3CC3)c2)n1] | TFA(3) |
| 23 | 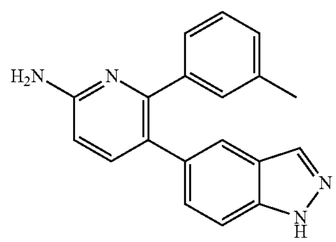 [SMILES: Cc1cccc(-c2nc(N)ccc2-c2ccc3[nH]ncc3c2)c1] | TFA(3) |
| 24 | 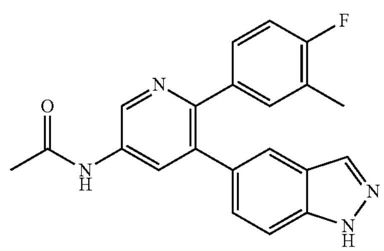 [SMILES: CC(=O)Nc1cnc(-c2ccc(F)c(C)c2)c(-c2ccc3[nH]ncc3c2)c1] | TFA(2) |
| 25 | 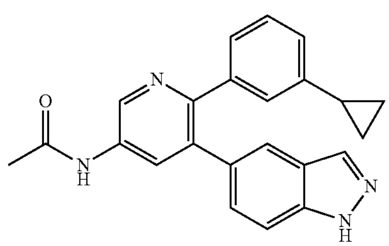 [SMILES: CC(=O)Nc1cnc(-c2cccc(C3CC3)c2)c(-c2ccc3[nH]ncc3c2)c1] | TFA(2) |
| 26 | 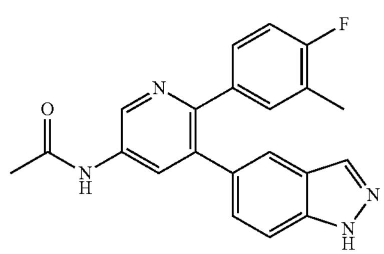 [SMILES: CC(=O)Nc1cnc(-c2ccc(F)c(C)c2)c(-c2ccc3[nH]ncc3c2)c1] | TFA(2) |
| 27 | 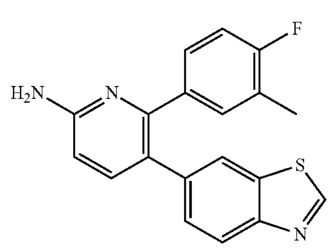 [SMILES: Cc1cc(-c2nc(N)ccc2-c2ccc3ncsc3c2)ccc1F] | TFA(3) |

-continued

| Cpd # | Structure | Salt |
|---|---|---|
| 28 | 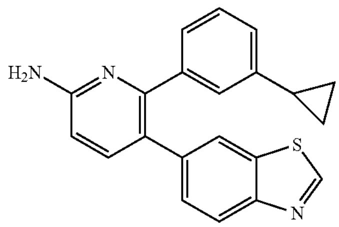 [SMILES: Nc1ccc(-c2ccc3ncsc3c2)c(-c2cccc(C3CC3)c2)n1] | TFA(3) |
| 29 | 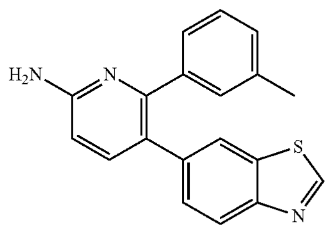 [SMILES: Cc1cccc(-c2nc(N)ccc2-c2ccc3ncsc3c2)c1] | TFA(3) |
| 30 | 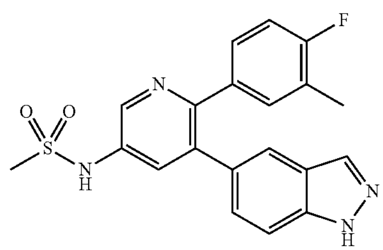 [SMILES: Cc1cc(-c2ncc(NS(C)(=O)=O)cc2-c2ccc3[nH]ncc3c2)ccc1F] | TFA(2) |
| 31 | 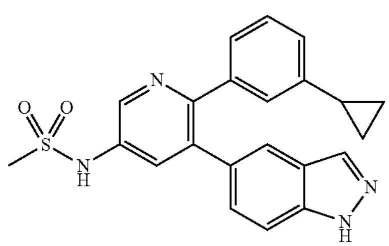 [SMILES: CS(=O)(=O)Nc1cnc(-c2cccc(C3CC3)c2)c(-c2ccc3[nH]ncc3c2)c1] | TFA(2) |
| 32 | 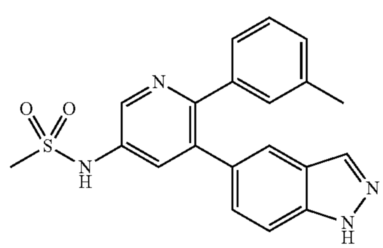 [SMILES: Cc1cccc(-c2ncc(NS(C)(=O)=O)cc2-c2ccc3[nH]ncc3c2)c1] | TFA(2) |
| 33 | 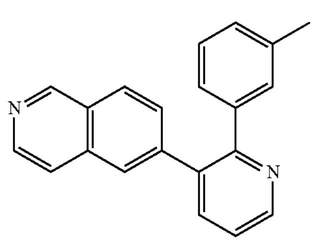 [SMILES: Cc1cccc(-c2ncccc2-c2ccc3cnccc3c2)c1] | Parent |

| Cpd # | Structure | Salt |
|---|---|---|
| 34 | 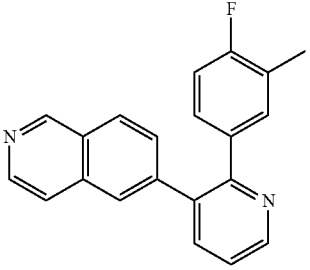 [SMILES: Cc1cc(-c2ncccc2-c2ccc3cnccc3c2)ccc1F] | Parent |
| 35 | 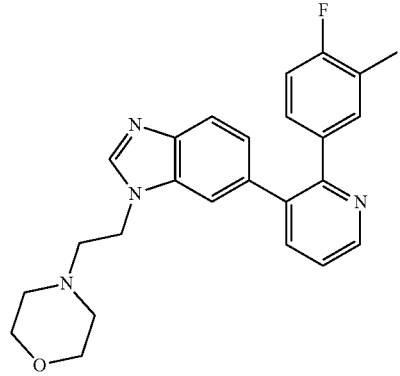 [SMILES: Cc1cc(-c2ncccc2-c2ccc3ncn(CCN4CCOCC4)c3c2)ccc1F] | Parent |
| 36 | 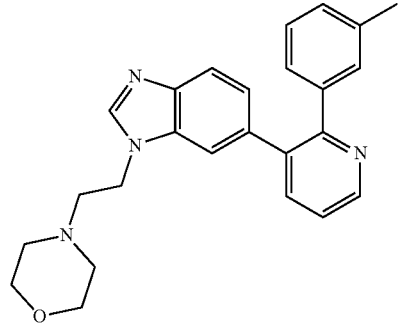 [SMILES: Cc1cccc(-c2ncccc2-c2ccc3ncn(CCN4CCOCC4)c3c2)c1] | Parent |
| 37 | 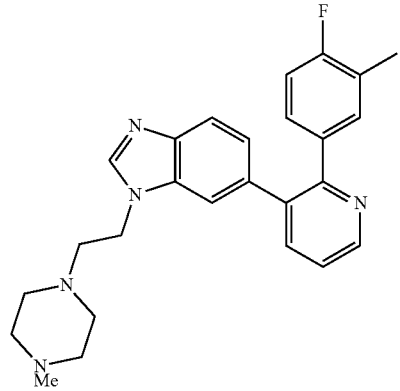 [SMILES: Cc1cc(-c2ncccc2-c2ccc3ncn(CCN4CCN(C)CC4)c3c2)ccc1F] | Parent |

-continued
| Cpd # | Structure | Salt |
|---|---|---|
| 38 | 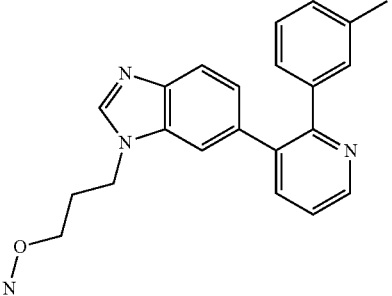 [SMILES: Cc1cccc(-c2ncccc2-c2ccc3ncn(CCCON)c3c2)c1] | Parent |
| 39 | 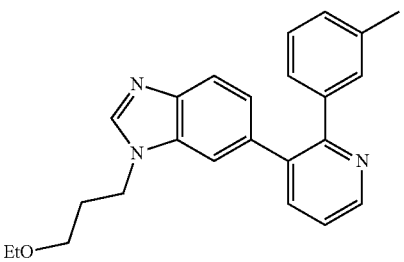 [SMILES: CCOCCCn1cnc2ccc(-c3cccnc3-c3cccc(C)c3)cc21] | Parent |
| 40 | 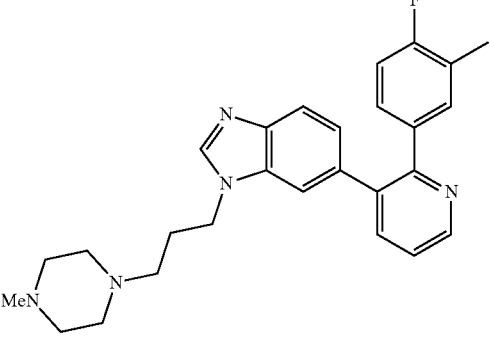 | Parent |
| 41 | 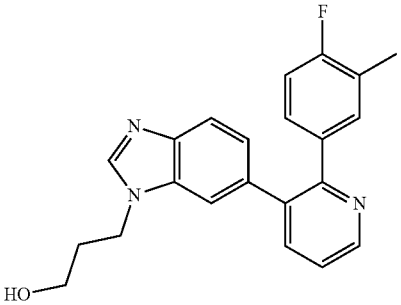 [SMILES: Cc1cc(-c2ncccc2-c2ccc3ncn(CCCO)c3c2)ccc1F] | Parent |
| 42 | 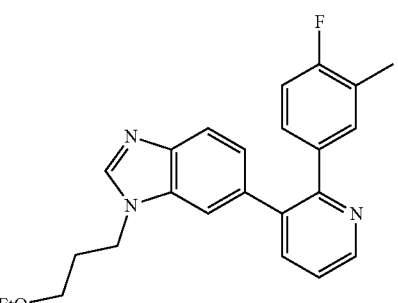 | Parent |

-continued
| Cpd # | Structure | Salt |
|---|---|---|
| 43 | 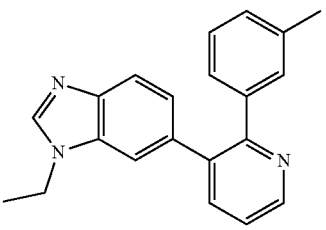 [SMILES: CCn1cnc2ccc(-c3cccnc3-c3cccc(C)c3)cc21] | Parent |
| 44 | 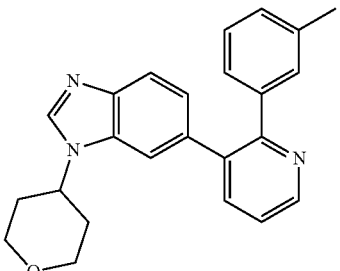 | Parent |
| 45 | 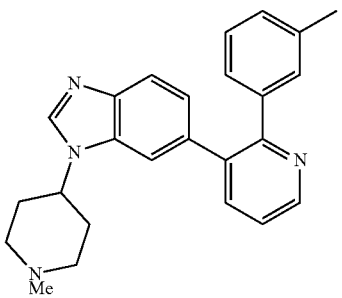 [SMILES: Cc1cccc(-c2ncccc2-c2ccc3ncn(C4CCN(C)CC4)c3c2)c1] | Parent |
| 46 | 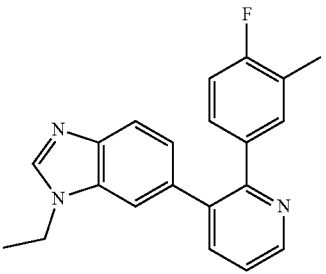 [SMILES: CCn1cnc2ccc(-c3cccnc3-c3ccc(F)c(C)c3)cc21] | Parent |
| 47 | 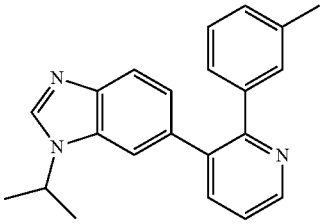 [SMILES: Cc1cccc(-c2ncccc2-c2ccc3ncn(C(C)C)c3c2)c1] | Parent |

-continued
| Cpd # | Structure | Salt |
|---|---|---|
| 48 | 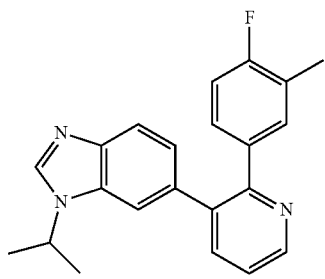 [SMILES: Cc1cc(-c2ncccc2-c2ccc3ncn(C(C)C)c3c2)ccc1F] | Parent |
| 49 | 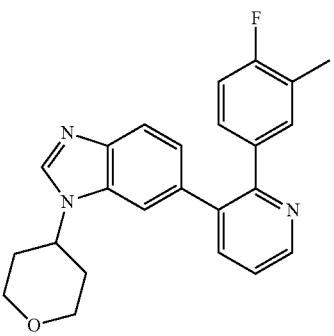 [SMILES: Cc1cc(-c2ncccc2-c2ccc3ncn(C4CCOCC4)c3c2)ccc1F] | Parent |
| 50 | 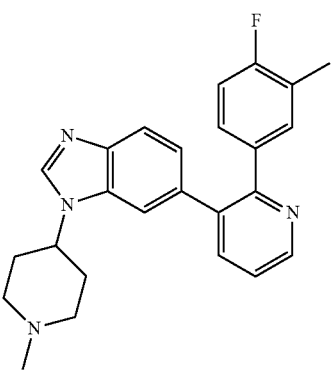 [SMILES: Cc1cc(-c2ncccc2-c2ccc3ncn(C4CCN(C)CC4)c3c2)ccc1F] | Parent |
| 51 | 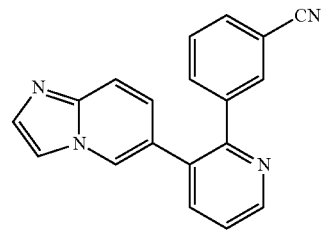 [SMILES: N#Cc1cccc(-c2ncccc2-c2ccc3nccn3c2)c1] | Parent |
| 52 | 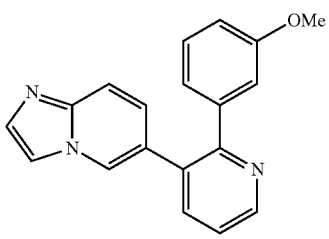 [SMILES: COc1cccc(-c2ncccc2-c2ccc3nccn3c2)c1] | Parent |

-continued
| Cpd # | Structure | Salt |
|---|---|---|
| 53 | 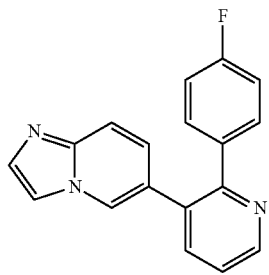 [SMILES: Fc1ccc(-c2ncccc2-c2ccc3nccn3c2)cc1] | Parent |
| 54 | 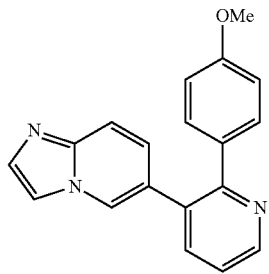 [SMILES: COc1ccc(-c2ncccc2-c2ccc3nccn3c2)cc1] | Parent |
| 55 | 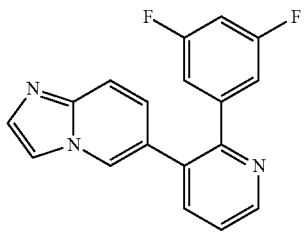 [SMILES: Fc1cc(F)cc(-c2ncccc2-c2ccc3nccn3c2)c1] | Parent |
| 56 | 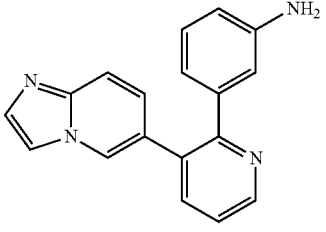 [SMILES: Nc1cccc(-c2ncccc2-c2ccc3nccn3c2)c1] | Parent |
| 57 | 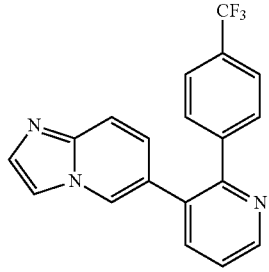 [SMILES: FC(F)(F)c1ccc(-c2ncccc2-c2ccc3nccn3c2)cc1] | Parent |

| Cpd # | Structure | Salt |
|---|---|---|
| 58 | 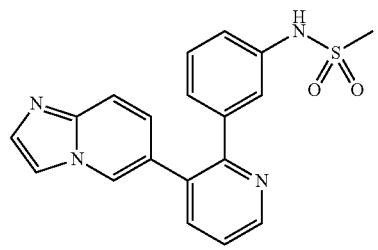 [SMILES: CS(=O)(=O)Nc1cccc(-c2ncccc2-c2ccc3nccn3c2)c1] | Parent |
| 59 | 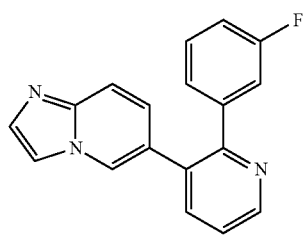 [SMILES: Fc1cccc(-c2ncccc2-c2ccc3nccn3c2)c1] | Parent |
| 60 | 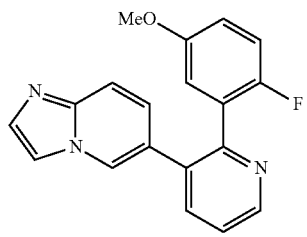 [SMILES: COc1ccc(F)c(-c2ncccc2-c2ccc3nccn3c2)c1] | Parent |
| 61 | 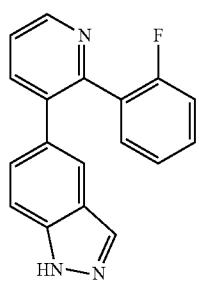 [SMILES: Fc1ccccc1-c1ncccc1-c1ccc2[nH]ncc2c1] | Parent |
| 62 | 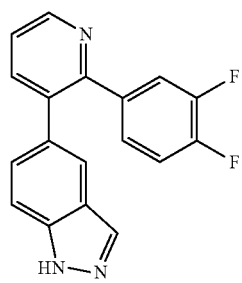 [SMILES: Fc1ccc(-c2ncccc2-c2ccc3[nH]ncc3c2)cc1F] | Parent |

| Cpd # | Structure | Salt |
|---|---|---|
| 63 | 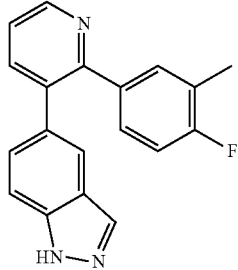 [SMILES: Cc1cc(-c2ncccc2-c2ccc3[nH]ncc3c2)ccc1F] | Parent |
| 64 | 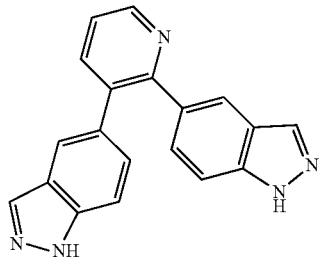 [SMILES: c1cnc(-c2ccc3[nH]ncc3c2)c(-c2ccc3[nH]ncc3c2)c1] | Parent |
| 65 | 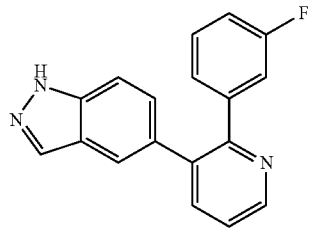 [SMILES: Fc1cccc(-c2ncccc2-c2ccc3[nH]ncc3c2)c1] | Parent |
| 66 | 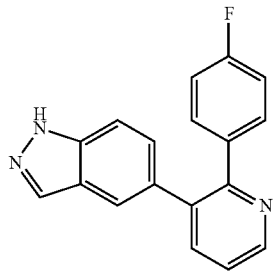 [SMILES: Fc1ccc(-c2ncccc2-c2ccc3[nH]ncc3c2)cc1] | Parent |
| 67 | 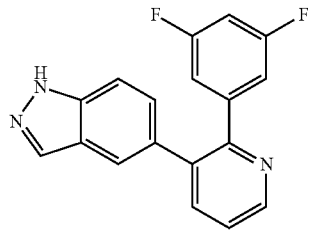 [SMILES: Fc1cc(F)cc(-c2ncccc2-c2ccc3[nH]ncc3c2)c1] | Parent |

-continued

| Cpd # | Structure | Salt |
|---|---|---|
| 68 | 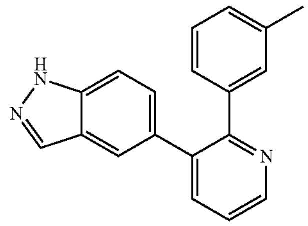 | Parent |
| 69 | 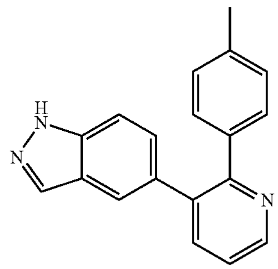 [SMILES: Cc1ccc(-c2ncccc2-c2ccc3[nH]ncc3c2)cc1] | Parent |
| 70 | 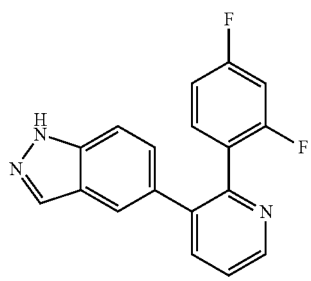 [SMILES: Fc1ccc(-c2ncccc2-c2ccc3[nH]ncc3c2)c(F)c1] | Parent |
| 71 | 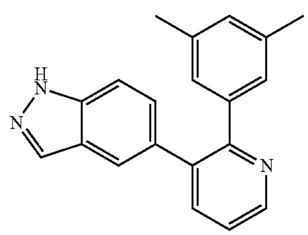 [SMILES: Cc1cc(C)cc(-c2ncccc2-c2ccc3[nH]ncc3c2)c1] | Parent |
| 72 | 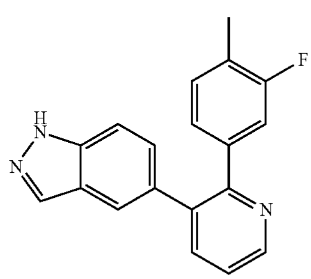 [SMILES: Cc1ccc(-c2ncccc2-c2ccc3[nH]ncc3c2)cc1F] | Parent |

-continued

| Cpd # | Structure | Salt |
|---|---|---|
| 73 | 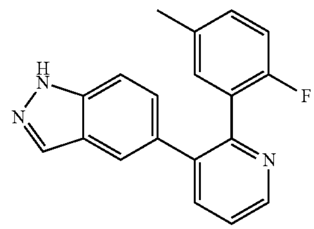 [SMILES: Cc1ccc(F)c(-c2ncccc2-c2ccc3[nH]ncc3c2)c1] | Parent |
| 74 | 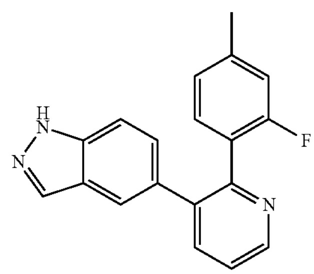 [SMILES: Cc1ccc(-c2ncccc2-c2ccc3[nH]ncc3c2)c(F)c1] | Parent |
| 75 | 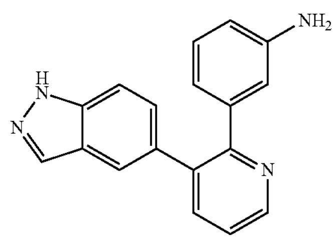 [SMILES: Nc1cccc(-c2ncccc2-c2ccc3[nH]ncc3c2)c1] | Parent |
| 76 | 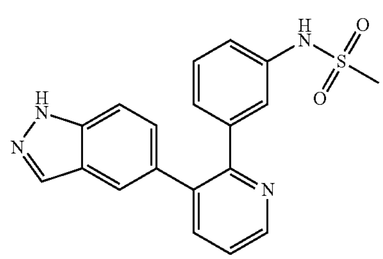 [SMILES: CS(=O)(=O)Nc1cccc(-c2ncccc2-c2ccc3[nH]ncc3c2)c1] | Parent |
| 77 | 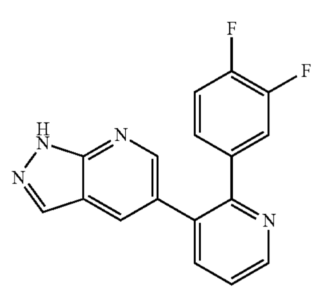 [SMILES: Fc1ccc(-c2ncccc2-c2cnc3[nH]ncc3c2)cc1F] | Parent |

-continued
| Cpd # | Structure | Salt |
|---|---|---|
| 78 | 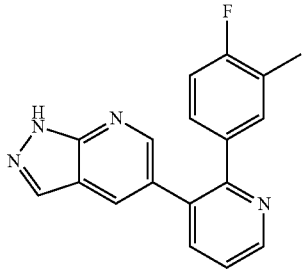 [SMILES: Cc1cc(-c2ncccc2-c2cnc3[nH]ncc3c2)ccc1F] | Parent |
| 79 | 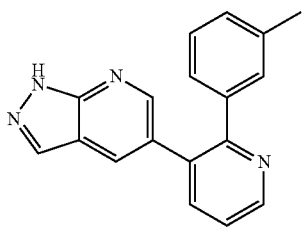 [SMILES: Cc1cccc(-c2ncccc2-c2cnc3[nH]ncc3c2)c1] | Parent |
| 80 | 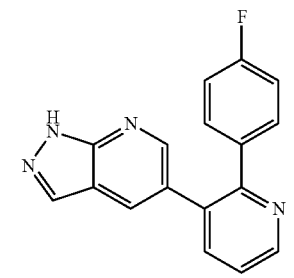 [SMILES: Fc1ccc(-c2ncccc2-c2cnc3[nH]ncc3c2)cc1] | Parent |
| 81 | 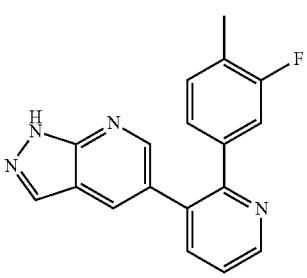 [SMILES: Cc1ccc(-c2ncccc2-c2cnc3[nH]ncc3c2)cc1F] | Parent |
| 82 | 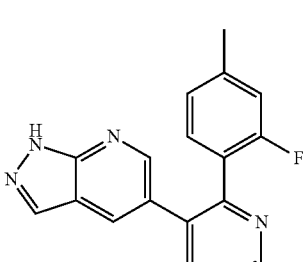 | Parent |

-continued
| Cpd # | Structure | Salt |
|---|---|---|
| 83 | 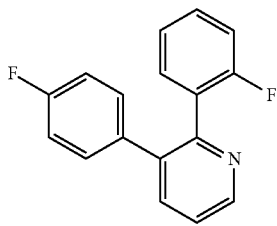 [SMILES: Fc1ccc(-c2cccnc2-c2ccccc2F)cc1] | Parent |
| 84 | 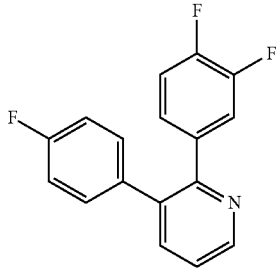 [SMILES: Fc1ccc(-c2cccnc2-c2ccc(F)c(F)c2)cc1] | Parent |
| 85 | 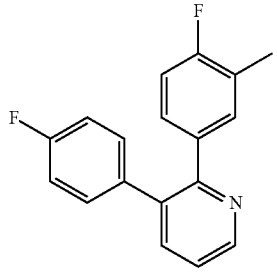 [SMILES: Cc1cc(-c2ncccc2-c2ccc(F)cc2)ccc1F] | Parent |
| 86 | 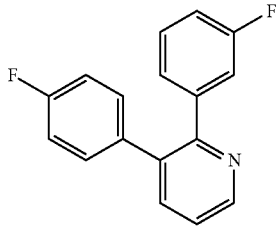 [SMILES: Fc1ccc(-c2cccnc2-c2cccc(F)c2)cc1] | Parent |
| 87 | 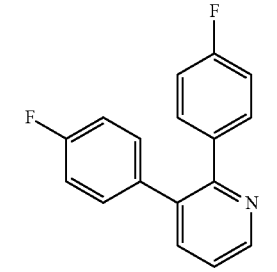 [SMILES: Fc1ccc(-c2cccnc2-c2ccc(F)cc2)cc1] | Parent |

| Cpd # | Structure | Salt |
|---|---|---|
| 88 | 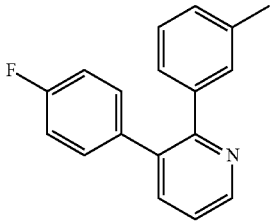 [SMILES: Cc1cccc(-c2ncccc2-c2ccc(F)cc2)c1] | Parent |
| 89 | 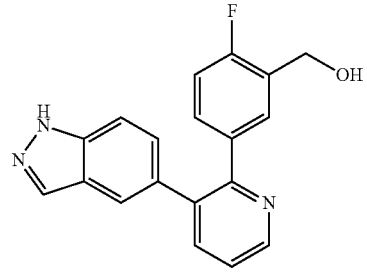 [SMILES: OCc1cc(-c2ncccc2-c2ccc3[nH]ncc3c2)ccc1F] | Parent |
| 90 | 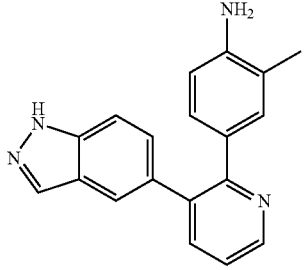 [SMILES: Cc1cc(-c2ncccc2-c2ccc3[nH]ncc3c2)ccc1N] | Parent |
| 91 | 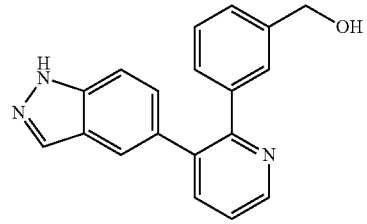 [SMILES: OCc1cccc(-c2ncccc2-c2ccc3[nH]ncc3c2)c1] | Parent |
| 92 | 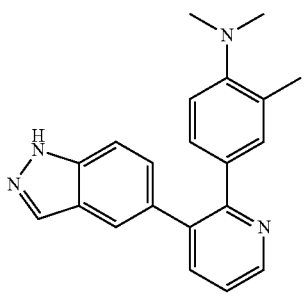 [SMILES: Cc1cc(-c2ncccc2-c2ccc3[nH]ncc3c2)ccc1N(C)C] | Parent |

| Cpd # | Structure | Salt |
|---|---|---|
| 93 | 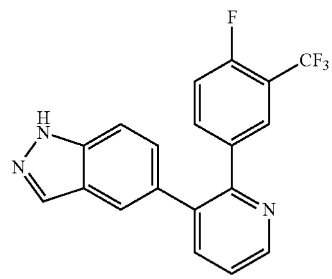 [SMILES: Fc1ccc(-c2ncccc2-c2ccc3[nH]ncc3c2)cc1C(F)(F)F] | Parent |
| 94 | 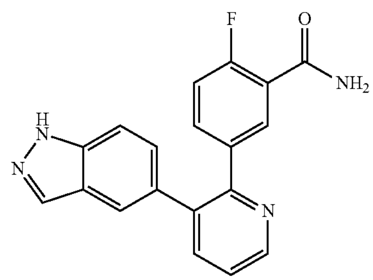 [SMILES: NC(=O)c1cc(-c2ncccc2-c2ccc3[nH]ncc3c2)ccc1F] | Parent |
| 95 | 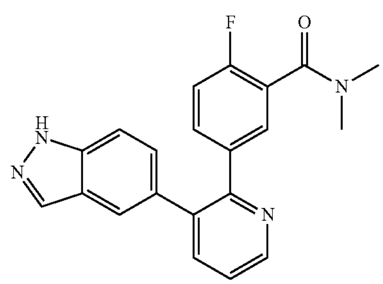 [SMILES: CN(C)C(=O)c1cc(-c2ncccc2-c2ccc3[nH]ncc3c2)ccc1F] | Parent |
| 96 | 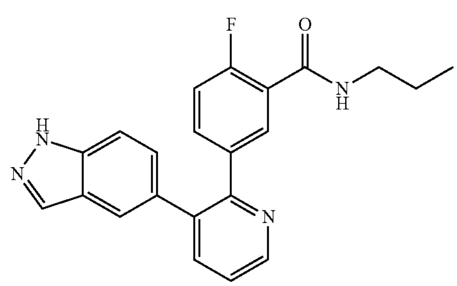 [SMILES: CCCNC(=O)c1cc(-c2ncccc2-c2ccc3[nH]ncc3c2)ccc1F] | Parent |
| 97 | 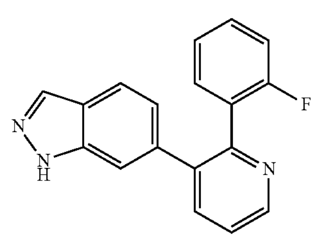 [SMILES: Fc1ccccc1-c1ncccc1-c1ccc2cn[nH]c2c1] | Parent |

-continued

| Cpd # | Structure | Salt |
|---|---|---|
| 98 | 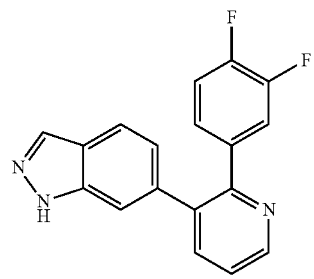 [SMILES: Fc1ccc(-c2ncccc2-c2ccc3cn[nH]c3c2)cc1F] | Parent |
| 99 | 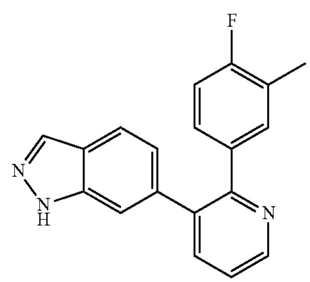 [SMILES: Cc1cc(-c2ncccc2-c2ccc3cn[nH]c3c2)ccc1F] | Parent |
| 100 | 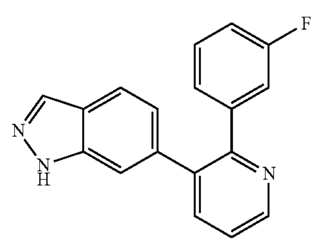 [SMILES: Fc1cccc(-c2ncccc2-c2ccc3cn[nH]c3c2)c1] | Parent |
| 101 | 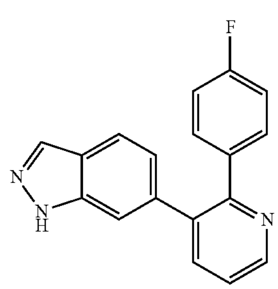 [SMILES: Fc1ccc(-c2ncccc2-c2ccc3cn[nH]c3c2)cc1] | Parent |
| 102 | 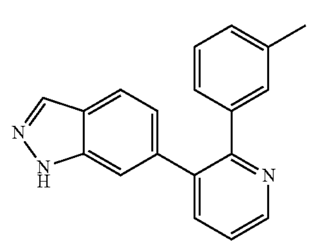 [SMILES: Cc1cccc(-c2ncccc2-c2ccc3cn[nH]c3c2)c1] | Parent |

-continued
| Cpd # | Structure | Salt |
|---|---|---|
| 103 | 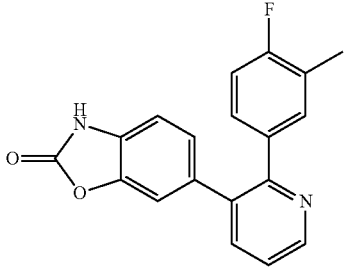 [SMILES: Cc1cc(-c2ncccc2-c2ccc3[nH]c(=O)oc3c2)ccc1F] | Parent |
| 104 | 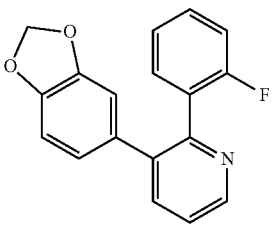 [SMILES: Fc1ccccc1-c1ncccc1-c1ccc2c(c1)OCO2] | Parent |
| 105 | 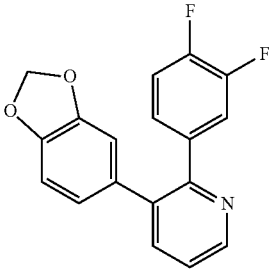 [SMILES: Fc1ccc(-c2ncccc2-c2ccc3c(c2)OCO3)cc1F] | Parent |
| 106 | 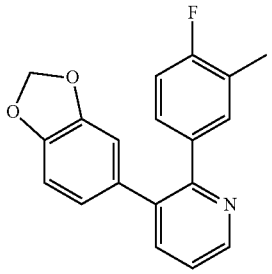 [SMILES: Cc1cc(-c2ncccc2-c2ccc3c(c2)OCO3)ccc1F] | Parent |
| 107 | 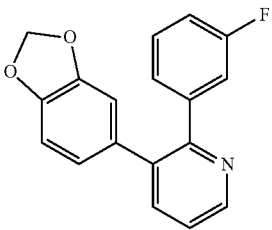 [SMILES: Fc1cccc(-c2ncccc2-c2ccc3c(c2)OCO3)c1] | Parent |

-continued

| Cpd # | Structure | Salt |
|---|---|---|
| 108 | 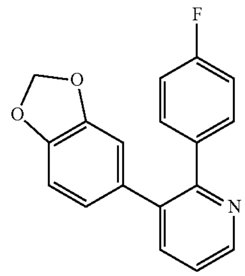 [SMILES: Fc1ccc(-c2ncccc2-c2ccc3c(c2)OCO3)cc1] | Parent |
| 109 | 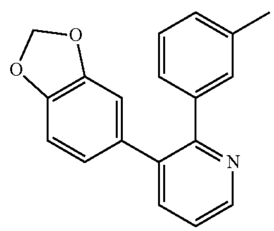 [SMILES: Cc1cccc(-c2ncccc2-c2ccc3c(c2)OCO3)c1] | Parent |
| 110 | 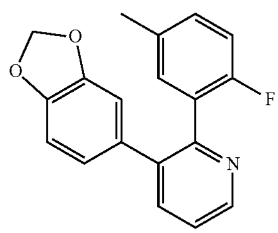 [SMILES: Cc1ccc(F)c(-c2ncccc2-c2ccc3c(c2)OCO3)c1] | Parent |
| 111 | 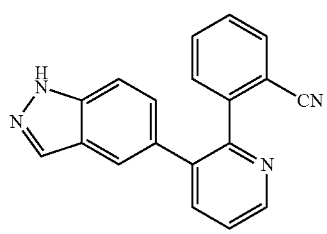 [SMILES: N#Cc1ccccc1-c1ncccc1-c1ccc2[nH]ncc2c1] | Parent |
| 112 | 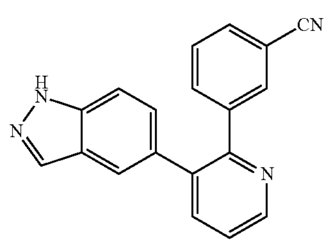 [SMILES: N#Cc1cccc(-c2ncccc2-c2ccc3[nH]ncc3c2)c1] | Parent |
| 113 | 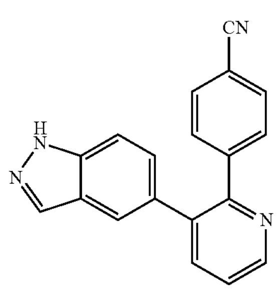 [SMILES: N#Cc1ccc(-c2ncccc2-c2ccc3[nH]ncc3c2)cc1] | Parent |

-continued
| Cpd # | Structure | Salt |
|---|---|---|
| 114 | 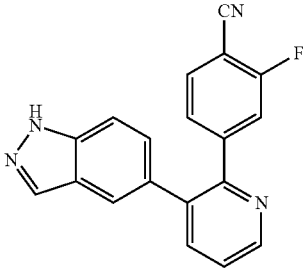 [SMILES: N#Cc1ccc(-c2ncccc2-c2ccc3[nH]ncc3c2)cc1F] | Parent |
| 115 | 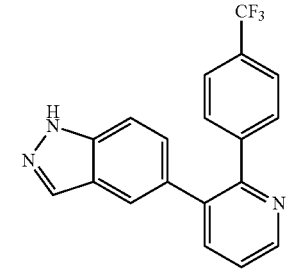 [SMILES: FC(F)(F)c1ccc(-c2ncccc2-c2ccc3[nH]ncc3c2)cc1] | Parent |
| 116 | 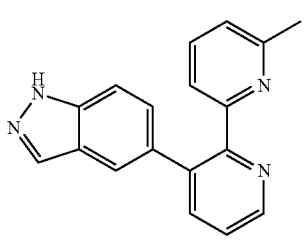 [SMILES: Cc1cccc(-c2ncccc2-c2ccc3[nH]ncc3c2)n1] | Parent |
| 117 | 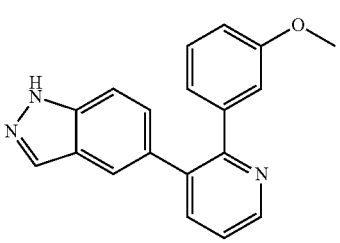 | Parent |
| 118 | 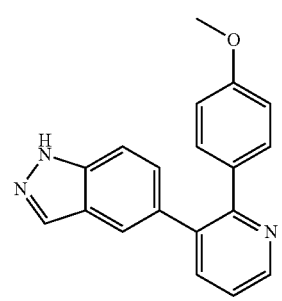 [SMILES: COc1ccc(-c2ncccc2-c2ccc3[nH]ncc3c2)cc1] | Parent |

-continued

| Cpd # | Structure | Salt |
|---|---|---|
| 119 | 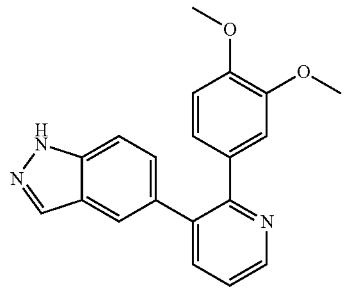 [SMILES: COc1ccc(-c2ncccc2-c2ccc3[nH]ncc3c2)cc1OC] | Parent |
| 120 | 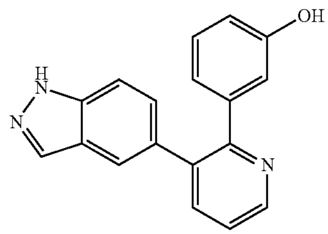 [SMILES: Oc1cccc(-c2ncccc2-c2ccc3[nH]ncc3c2)c1] | Parent |
| 121 | 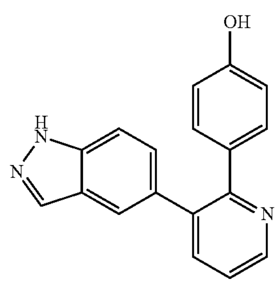 | Parent |
| 122 | 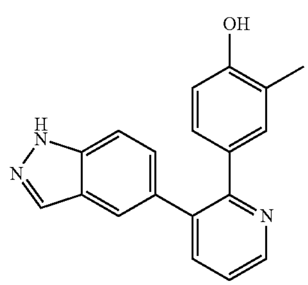 [SMILES: Cc1cc(-c2ncccc2-c2ccc3[nH]ncc3c2)ccc1O] | Parent |
| 123 | 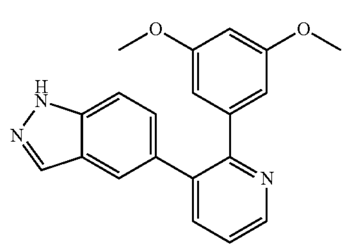 [SMILES: COc1cc(OC)cc(-c2ncccc2-c2ccc3[nH]ncc3c2)c1] | Parent |

-continued

| Cpd # | Structure | Salt |
|---|---|---|
| 124 | 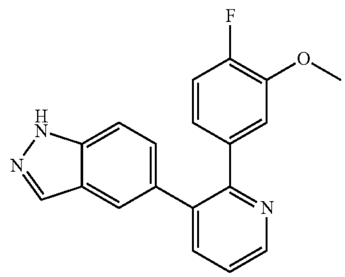 [SMILES: COc1cc(-c2ncccc2-c2ccc3[nH]ncc3c2)ccc1F] | Parent |
| 125 | 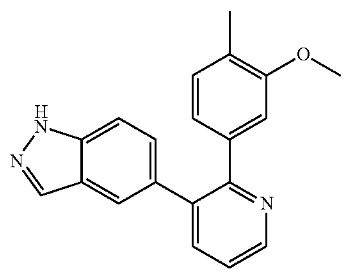 [SMILES: COc1cc(-c2ncccc2-c2ccc3[nH]ncc3c2)ccc1C] | Parent |
| 126 | 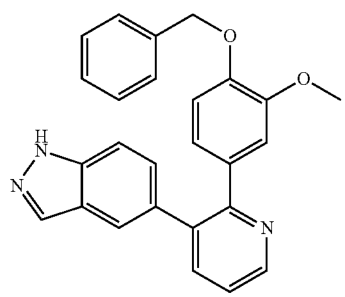 [SMILES: COc1cc(-c2ncccc2-c2ccc3[nH]ncc3c2)ccc1OCc1ccccc1] | Parent |
| 127 | 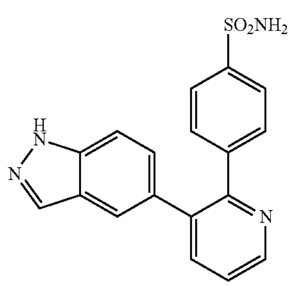 [SMILES: NS(=O)(=O)c1ccc(-c2ncccc2-c2ccc3[nH]ncc3c2)cc1] | Parent |
| 128 | 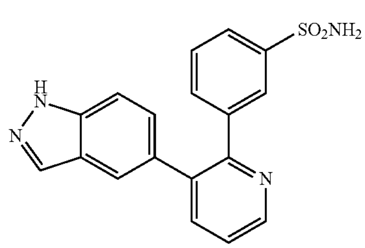 [SMILES: NS(=O)(=O)c1cccc(-c2ncccc2-c2ccc3[nH]ncc3c2)c1] | Parent |

-continued

| Cpd # | Structure | Salt |
|---|---|---|
| 129 | 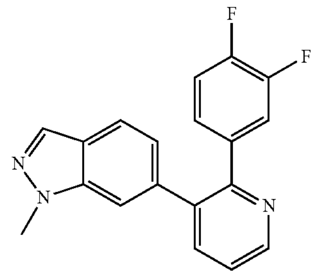 [SMILES: Cn1ncc2ccc(-c3cccnc3-c3ccc(F)c(F)c3)cc21] | Parent |
| 130 | 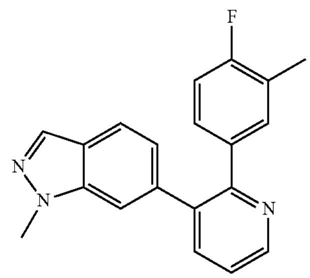 [SMILES: Cc1cc(-c2ncccc2-c2ccc3cnn(C)c3c2)ccc1F] | Parent |
| 131 | 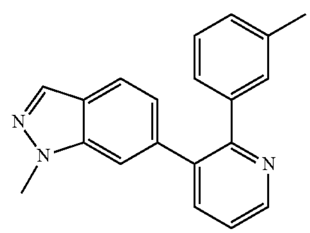 [SMILES: Cc1cccc(-c2ncccc2-c2ccc3cnn(C)c3c2)c1] | Parent |
| 132 | 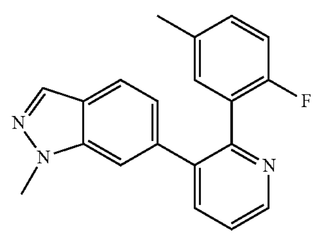 [SMILES: Cc1ccc(F)c(-c2ncccc2-c2ccc3cnn(C)c3c2)c1] | Parent |
| 133 | 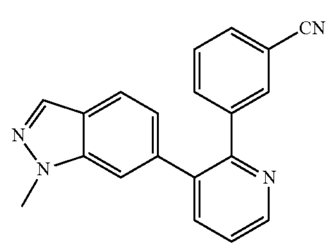 [SMILES: Cn1ncc2ccc(-c3cccnc3-c3cccc(C#N)c3)cc21] | Parent |
| 134 | 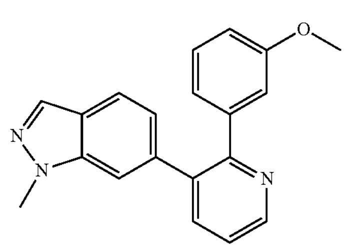 [SMILES: COc1cccc(-c2ncccc2-c2ccc3cnn(C)c3c2)c1] | Parent |

-continued
| Cpd # | Structure | Salt |
|---|---|---|
| 135 | 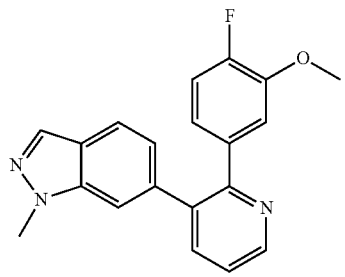 | Parent |
| 136 | 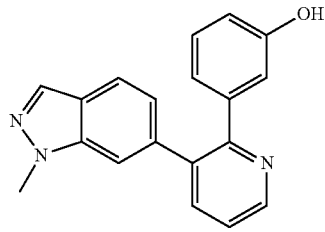 | Parent |
| 137 | 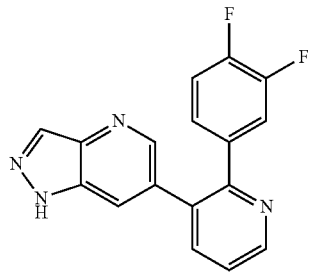 [SMILES: Fc1ccc(-c2ncccc2-c2cnc3cn[nH]c3c2)cc1F] | Parent |
| 138 | 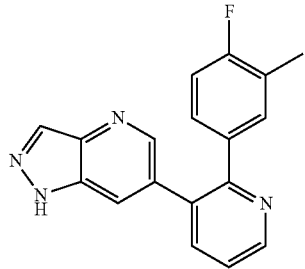 | Parent |
| 139 | 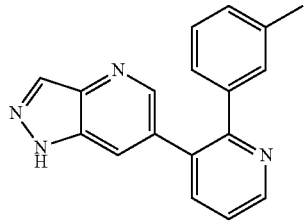 [SMILES: Cc1cccc(-c2ncccc2-c2cnc3cn[nH]c3c2)c1] | Parent |

-continued

| Cpd # | Structure | Salt |
|---|---|---|
| 140 | 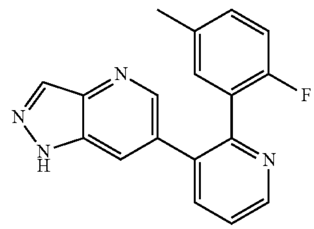 [SMILES: Cc1ccc(F)c(-c2ncccc2-c2cnc3cn[nH]c3c2)c1] | Parent |
| 141 | 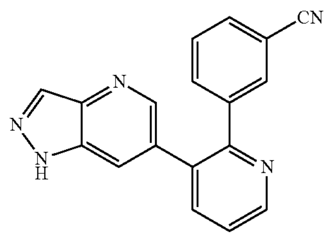 [SMILES: N#Cc1cccc(-c2ncccc2-c2cnc3cn[nH]c3c2)c1] | Parent |
| 142 | 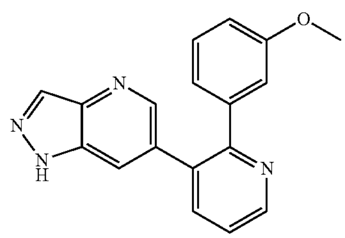 [SMILES: COc1cccc(-c2ncccc2-c2cnc3cn[nH]c3c2)c1] | Parent |
| 143 | 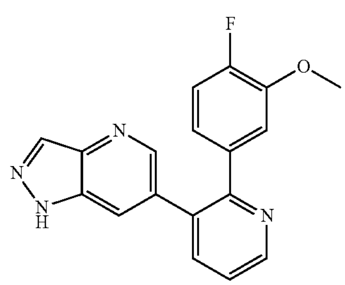 [SMILES: COc1cc(-c2ncccc2-c2cnc3cn[nH]c3c2)ccc1F] | Parent |
| 144 | 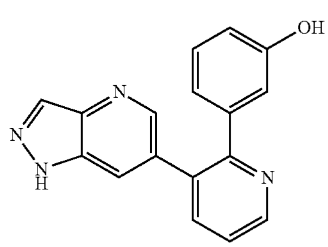 [SMILES: Oc1cccc(-c2ncccc2-c2cnc3cn[nH]c3c2)c1] | Parent |
| 145 | 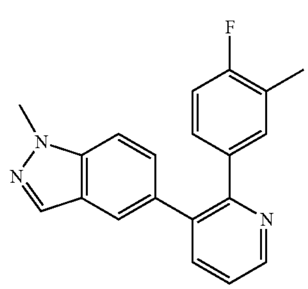 [SMILES: Cc1cc(-c2ncccc2-c2ccc3c(cnn3C)c2)ccc1F] | Parent |

-continued
| Cpd # | Structure | Salt |
|---|---|---|
| 146 | 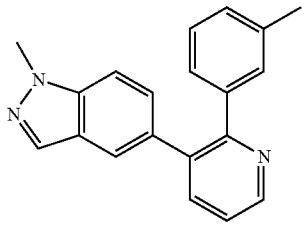 [SMILES: Cc1cccc(-c2ncccc2-c2ccc3c(cnn3C)c2)c1] | Parent |
| 147 | 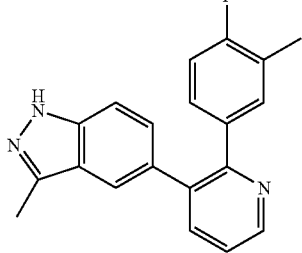 | Parent |
| 148 | 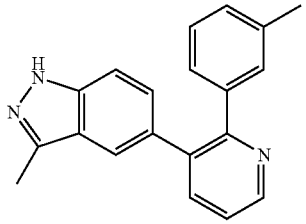 [SMILES: Cc1cccc(-c2ncccc2-c2ccc3[nH]nc(C)c3c2)c1] | Parent |
| 149 | 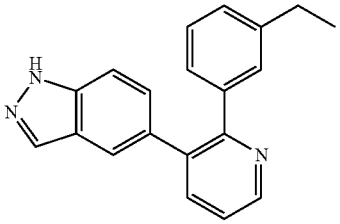 [SMILES: CCc1cccc(-c2ncccc2-c2ccc3[nH]ncc3c2)c1] | Parent |
| 150 | 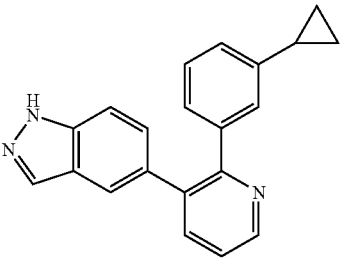 [SMILES: c1cc(-c2ncccc2-c2ccc3[nH]ncc3c2)cc(C2CC2)c1] | Parent |
| 151 | 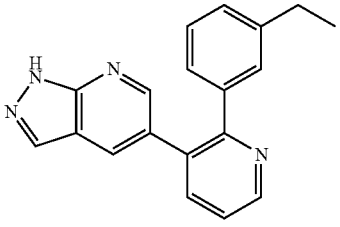 [SMILES: CCc1cccc(-c2ncccc2-c2cnc3[nH]ncc3c2)c1] | Parent |

-continued

| Cpd # | Structure | Salt |
|---|---|---|
| 152 | 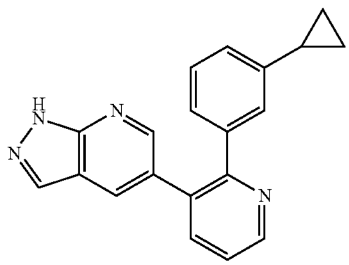 [SMILES: c1cc(-c2ncccc2-c2cnc3[nH]ncc3c2)cc(C2CC2)c1] | Parent |
| 153 | 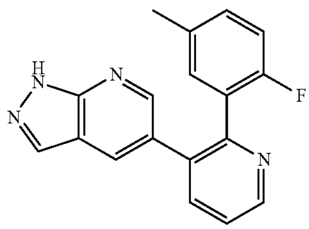 [SMILES: Cc1ccc(F)c(-c2ncccc2-c2cnc3[nH]ncc3c2)c1] | Parent |
| 154 | 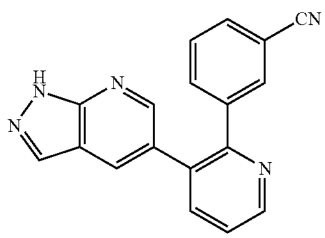 [SMILES: N#Cc1cccc(-c2ncccc2-c2cnc3[nH]ncc3c2)c1] | Parent |
| 155 | 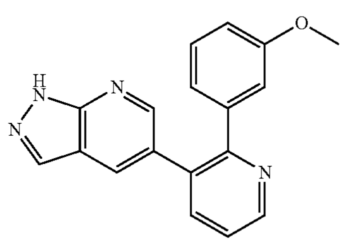 [SMILES: COc1cccc(-c2ncccc2-c2cnc3[nH]ncc3c2)c1] | Parent |
| 156 | 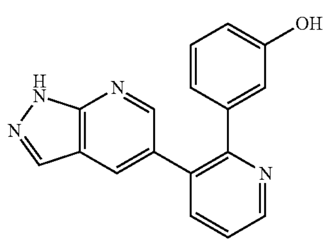 [SMILES: Oc1cccc(-c2ncccc2-c2cnc3[nH]ncc3c2)c1] | Parent |
| 157 | 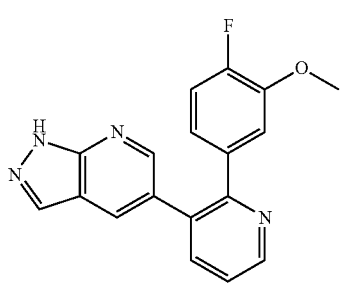 [SMILES: COc1cc(-c2ncccc2-c2cnc3[nH]ncc3c2)ccc1F] | Parent |

-continued
| Cpd # | Structure | Salt |
|---|---|---|
| 158 | 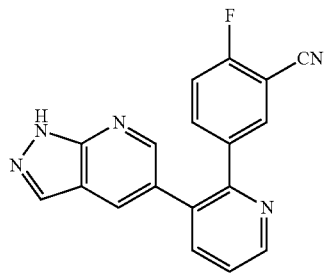 [SMILES: N#Cc1cc(-c2ncccc2-c2cnc3[nH]ncc3c2)ccc1F] | Parent |
| 159 | 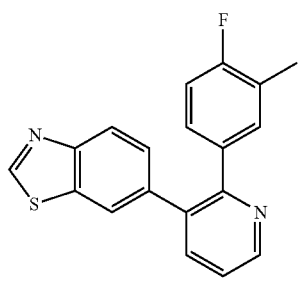 [SMILES: Cc1cc(-c2ncccc2-c2ccc3ncsc3c2)ccc1F] | Parent |
| 160 | 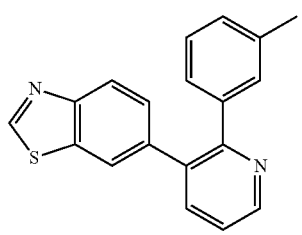 [SMILES: Cc1cccc(-c2ncccc2-c2ccc3ncsc3c2)c1] | Parent |
| 161 | 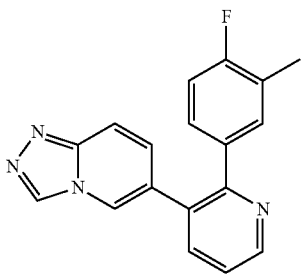 [SMILES: Cc1cc(-c2ncccc2-c2ccc3nncn3c2)ccc1F] | Parent |
| 162 | 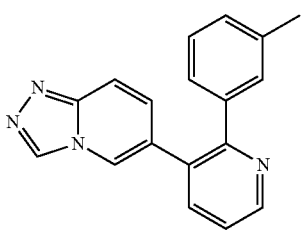 [SMILES: Cc1cccc(-c2ncccc2-c2ccc3nncn3c2)c1] | Parent |

| Cpd # | Structure | Salt |
|---|---|---|
| 163 | 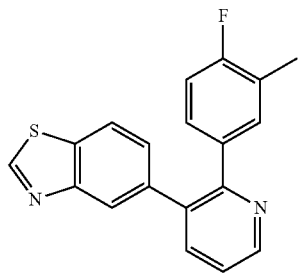 [SMILES: Cc1cc(-c2ncccc2-c2ccc3scnc3c2)ccc1F] | Parent |
| 164 | 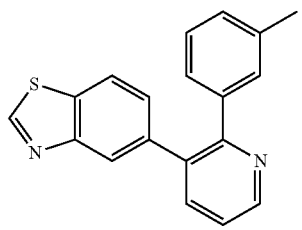 [SMILES: Cc1cccc(-c2ncccc2-c2ccc3scnc3c2)c1] | Parent |
| 165 | 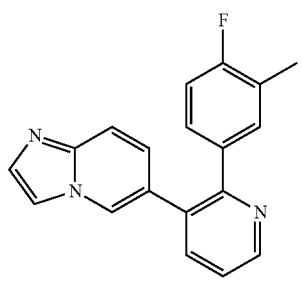 [SMILES: Cc1cc(-c2ncccc2-c2ccc3nccn3c2)ccc1F] | Parent |
| 166 | 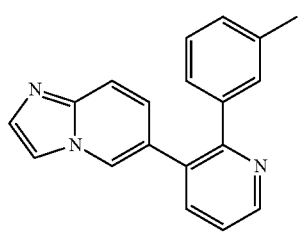 [SMILES: Cc1cccc(-c2ncccc2-c2ccc3nccn3c2)c1] | Parent |
| 167 | 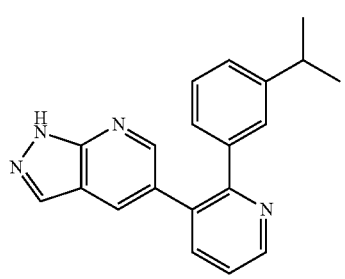 | Parent |

| Cpd # | Structure | Salt |
|---|---|---|
| 168 | 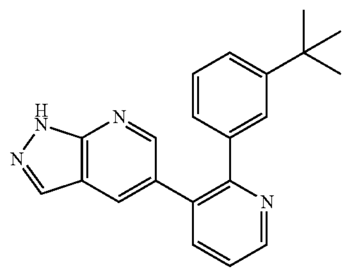 [SMILES: CC(C)(C)c1cccc(-c2ncccc2-c2cnc3[nH]ncc3c2)c1] | Parent |
| 169 | 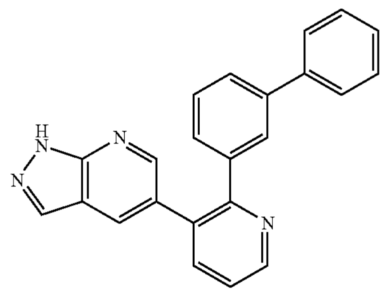 [SMILES: c1ccc(-c2cccc(-c3ncccc3-c3cnc4[nH]ncc4c3)c2)cc1] | Parent |
| 170 | 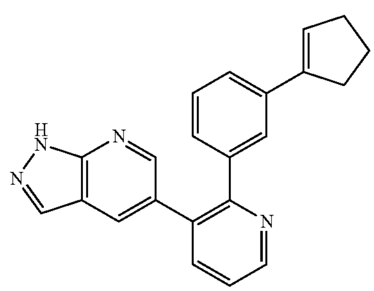 [SMILES: C1=C(c2cccc(-c3ncccc3-c3cnc4[nH]ncc4c3)c2)CCC1] | Parent |
| 171 | 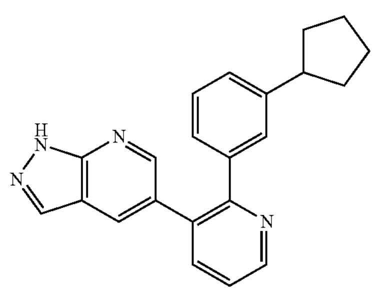 [SMILES: c1cc(-c2ncccc2-c2cnc3[nH]ncc3c2)cc(C2CCCC2)c1] | Parent |
| 172 | 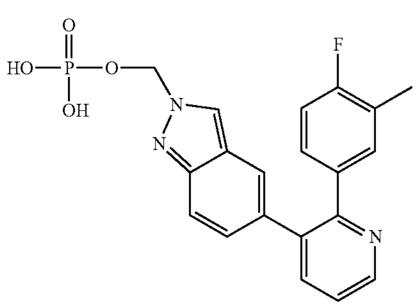 [SMILES: Cc1cc(-c2ncccc2-c2ccc3nn(COP(=O)(O)O)cc3c2)ccc1F] | Parent |

-continued
| Cpd # | Structure | Salt |
|---|---|---|
| 173 | 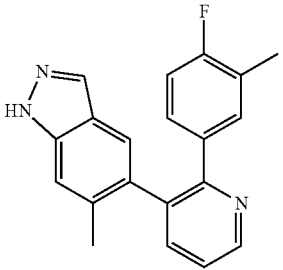 [SMILES: Cc1cc(-c2ncccc2-c2cc3cn[nH]c3cc2C)ccc1F] | Parent |
| 174 | 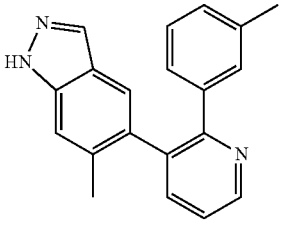 [SMILES: Cc1cccc(-c2ncccc2-c2cc3cn[nH]c3cc2C)c1] | Parent |
| 175 | 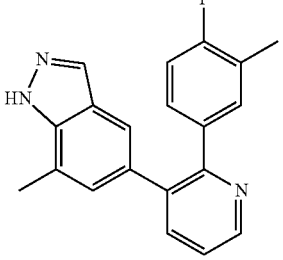 | Parent |
| 176 | 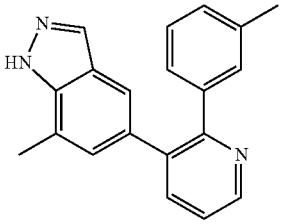 | Parent |
| 177 | 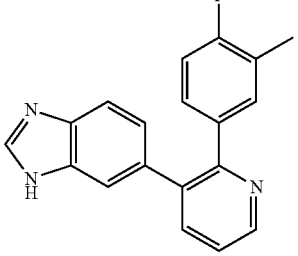 | Parent |

-continued
| Cpd # | Structure | Salt |
|---|---|---|
| 178 | 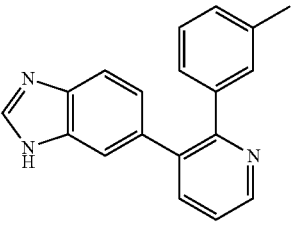 | Parent |
| 179 | 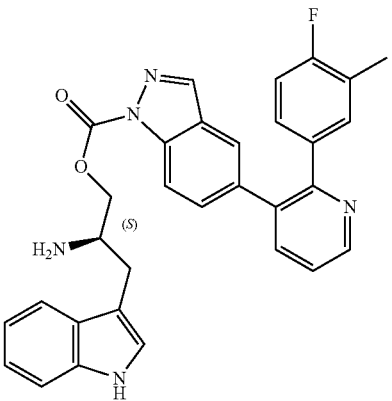 | TFA |
| 180 | 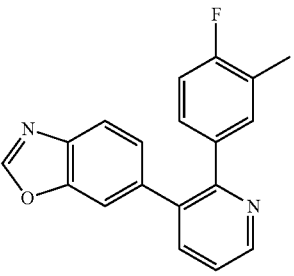 [SMILES: Cc1cc(-c2ncccc2-c2ccc3ncoc3c2)ccc1F] | Parent |
| 181 | 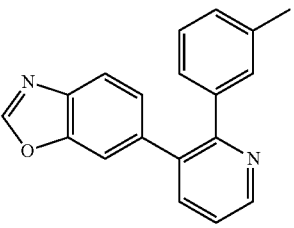 | Parent |
| 182 | 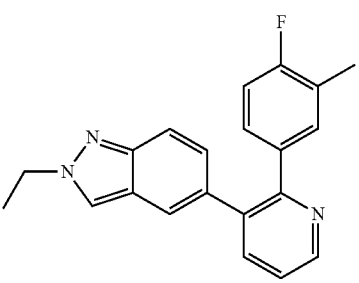 [SMILES: CCn1cc2cc(-c3cccnc3-c3ccc(F)c(C)c3)ccc2n1] | Parent |

-continued

| Cpd # | Structure | Salt |
|---|---|---|
| 183 | 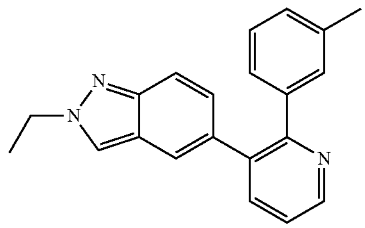 [SMILES: CCn1cc2cc(-c3cccnc3-c3cccc(C)c3)ccc2n1] | Parent |
| 184 | 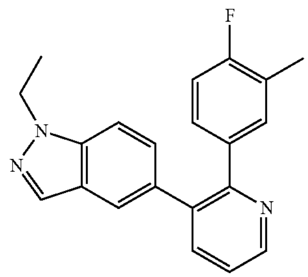 [SMILES: CCn1ncc2cc(-c3cccnc3-c3ccc(F)c(C)c3)ccc21] | Parent |
| 185 | 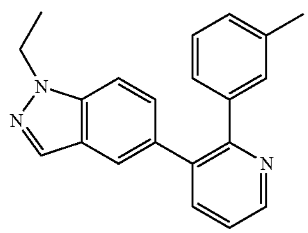 [SMILES: CCn1ncc2cc(-c3cccnc3-c3cccc(C)c3)ccc21] | Parent |
| 186 | 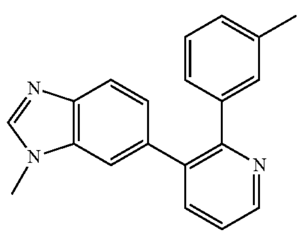 [SMILES: Cc1cccc(-c2ncccc2-c2ccc3ncn(C)c3c2)c1] | Parent |
| 187 | 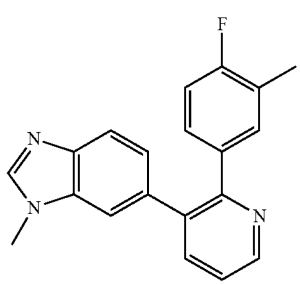 [SMILES: Cc1cc(-c2ncccc2-c2ccc3ncn(C)c3c2)ccc1F] | Parent |
| 188 | 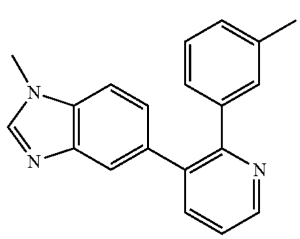 [SMILES: Cc1cccc(-c2ncccc2-c2ccc3c(c2)ncn3C)c1] | Parent |

-continued
| Cpd # | Structure | Salt |
|---|---|---|
| 189 | 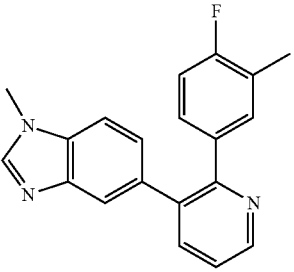 [SMILES: Cc1cc(-c2ncccc2-c2ccc3c(c2)ncn3C)ccc1F] | Parent |
| 190 | 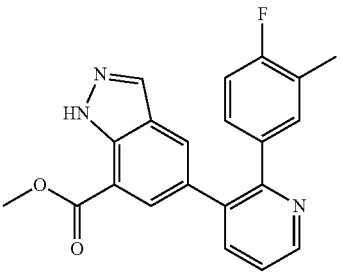 | Parent |
| 191 | 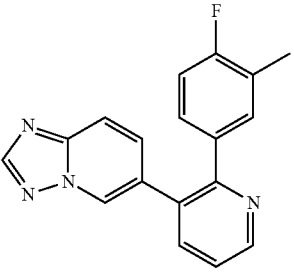 [SMILES: Cc1cc(-c2ncccc2-c2ccc3ncnn3c2)ccc1F] | Parent |
| 192 | 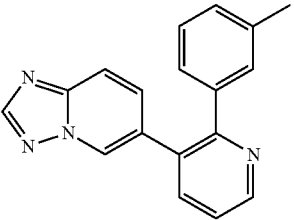 [SMILES: Cc1cccc(-c2ncccc2-c2ccc3ncnn3c2)c1] | Parent |
| 193 | 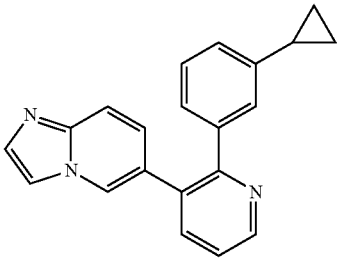 | Parent |

-continued

| Cpd # | Structure | Salt |
|---|---|---|
| 194 | 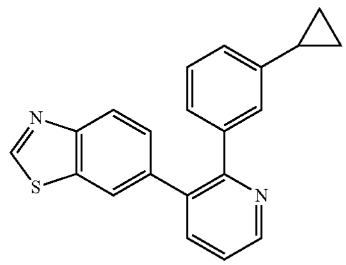 [SMILES: c1cc(-c2ncccc2-c2ccc3ncsc3c2)cc(C2CC2)c1] | Parent |
| 195 | 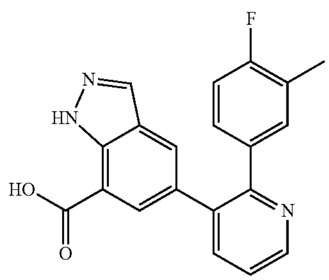 [SMILES: Cc1cc(-c2ncccc2-c2cc(C(=O)O)c3[nH]ncc3c2)ccc1F] | Parent |
| 196 | 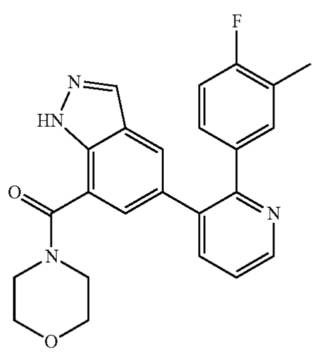 [SMILES: Cc1cc(-c2ncccc2-c2cc(C(=O)N3CCOCC3)c3[nH]ncc3c2)ccc1F] | Parent |
| 197 | 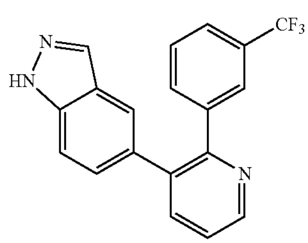 [SMILES: FC(F)(F)c1cccc(-c2ncccc2-c2ccc3[nH]ncc3c2)c1] | Parent |
| 198 | 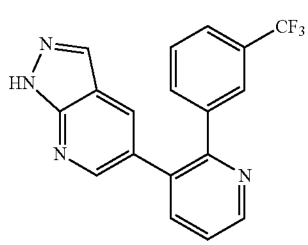 [SMILES: FC(F)(F)c1cccc(-c2ncccc2-c2cnc3[nH]ncc3c2)c1] | Parent |

| Cpd # | Structure | Salt |
|---|---|---|
| 199 | 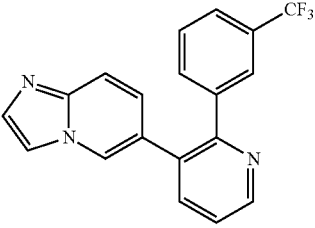 [SMILES: FC(F)(F)c1cccc(-c2ncccc2-c2ccc3nccn3c2)c1] | Parent |
| 200 | 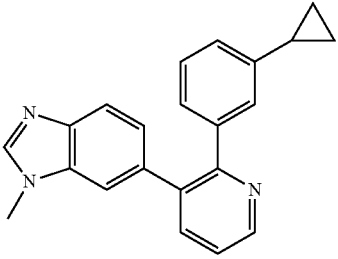 [SMILES: Cn1cnc2ccc(-c3cccnc3-c3cccc(C4CC4)c3)cc21] | Parent |
| 201 | 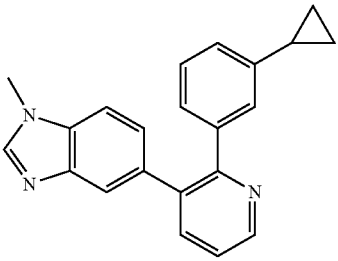 [SMILES: Cn1cnc2cc(-c3cccnc3-c3cccc(C4CC4)c3)ccc21] | Parent |
| 202 | 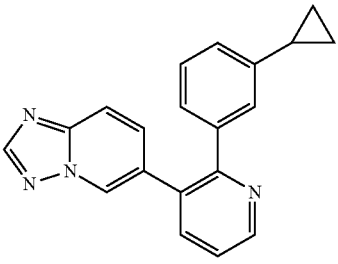 | Parent |
| 203 | 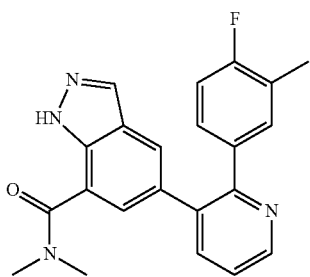 [SMILES: Cc1cc(-c2ncccc2-c2cc(C(=O)N(C)C)c3[nH]ncc3c2)ccc1F] | Parent |

-continued
| Cpd # | Structure | Salt |
|---|---|---|
| 204 | 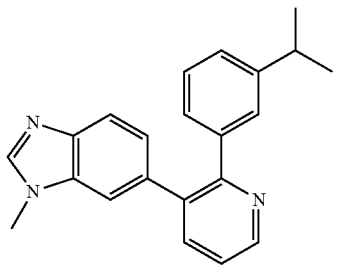 [SMILES: CC(C)c1cccc(-c2ncccc2-c2ccc3ncn(C)c3c2)c1] | Parent |
| 205 | 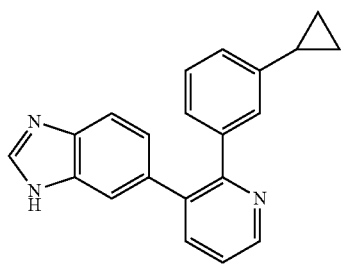 [SMILES: c1cc(-c2ncccc2-c2ccc3nc[nH]c3c2)cc(C2CC2)c1] | Parent |
| 206 | 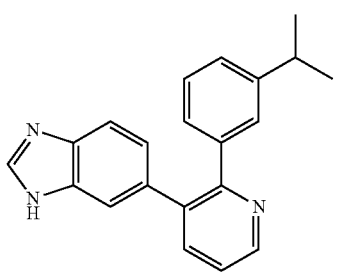 [SMILES: CC(C)c1cccc(-c2ncccc2-c2ccc3nc[nH]c3c2)c1] | Parent |
| 207 | 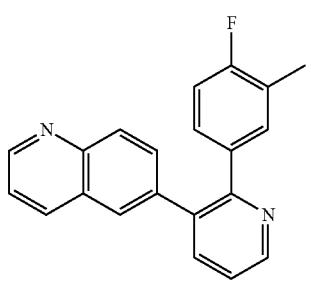 [SMILES: Cc1cc(-c2ncccc2-c2ccc3ncccc3c2)ccc1F] | Parent |
| 208 | 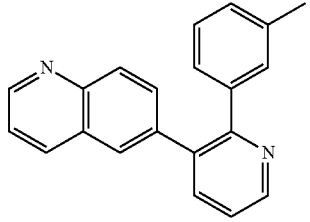 [SMILES: Cc1cccc(-c2ncccc2-c2ccc3ncccc3c2)c1] | Parent |

-continued

| Cpd # | Structure | Salt |
|---|---|---|
| 209 | 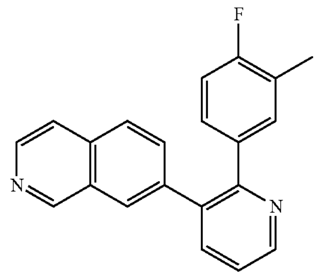 [SMILES: Cc1cc(-c2ncccc2-c2ccc3ccncc3c2)ccc1F] | Parent |
| 210 | 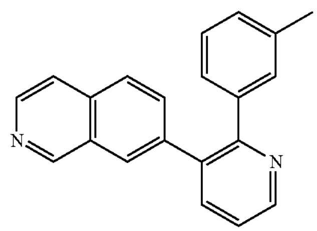 [SMILES: Cc1cccc(-c2ncccc2-c2ccc3ccncc3c2)c1] | Parent |
| 211 | 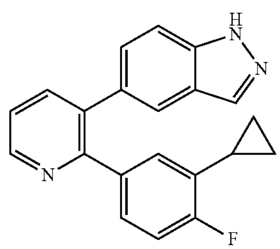 [SMILES: Fc1ccc(-c2ncccc2-c2ccc3[nH]ncc3c2)cc1C1CC1] | TFA(3) |
| 212 | 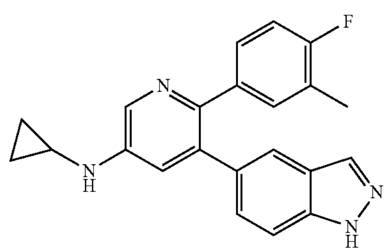 [SMILES: Cc1cc(-c2ncc(NC3CC3)cc2-c2ccc3[nH]ncc3c2)ccc1F] | TFA(3) |
| 213 | 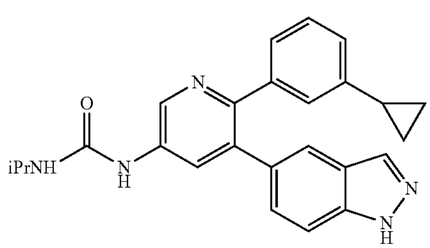 | TFA(2) |
| 214 | 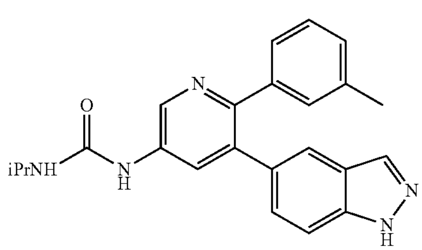 | TFA(2) |

-continued

| Cpd # | Structure | Salt |
|---|---|---|
| 215 | 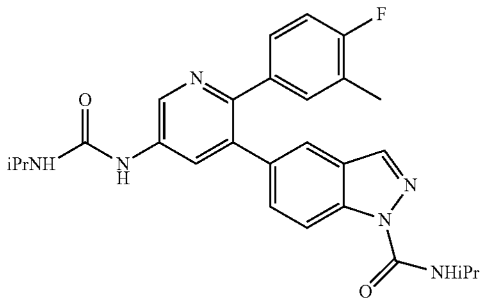 | TFA(2) |
| 216 | 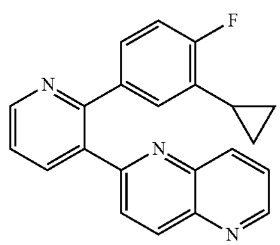 [SMILES: Fc1ccc(-c2ncccc2-c2ccc3ncccc3n2)cc1C1CC1] | TFA(2) |
| 217 | 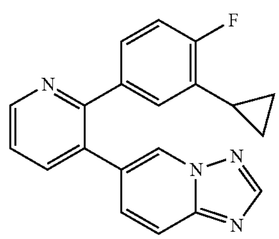 [SMILES: Fc1ccc(-c2ncccc2-c2ccc3ncnn3c2)cc1C1CC1] | TFA(2) |
| 218 | 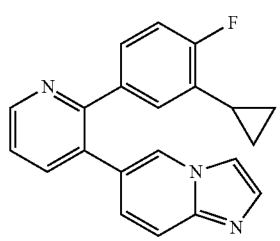 [SMILES: Fc1ccc(-c2ncccc2-c2ccc3nccn3c2)cc1C1CC1] | TFA(3) |
| 219 | 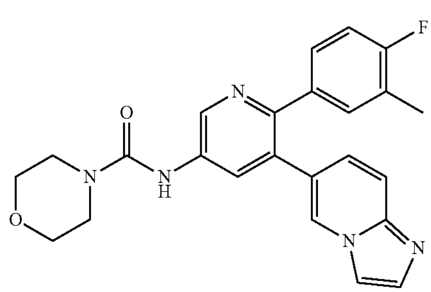 [SMILES: Cc1cc(-c2ncc(NC(=O)N3CCOCC3)cc2-c2ccc3nccn3c2)ccc1F] | TFA(3) |

-continued

| Cpd # | Structure | Salt |
|---|---|---|
| 220 | 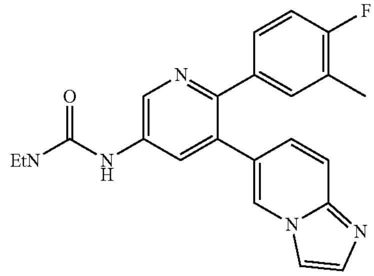 | TFA(3) |
| 221 | 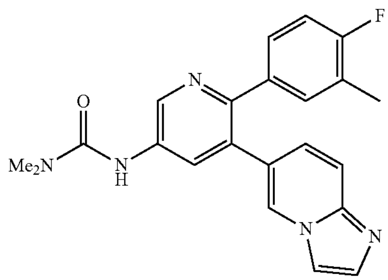 [SMILES: Cc1cc(-c2ncc(NC(=O)N(C)C)cc2-c2ccc3nccn3c2)ccc1F] | TFA(3) |
| 222 | 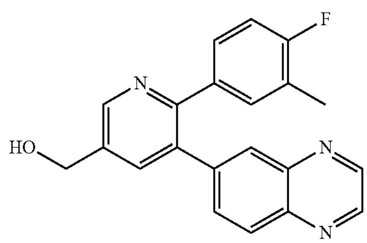 [SMILES: Cc1cc(-c2ncc(CO)cc2-c2ccc3nccnc3c2)ccc1F] | Parent |
| 223 | 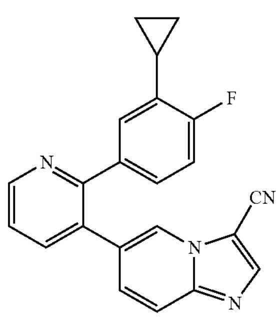 [SMILES: N#Cc1cnc2ccc(-c3cccnc3-c3ccc(F)c(C4CC4)c3)cn12] | TFA(3) |
| 224 | 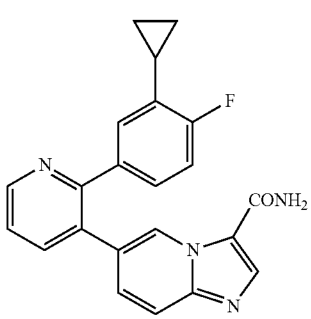 [SMILES: NC(=O)c1cnc2ccc(-c3cccnc3-c3ccc(F)c(C4CC4)c3)cn12] | TFA(3) |

-continued

| Cpd # | Structure | Salt |
|---|---|---|
| 225 | (morpholinomethyl-pyridine with 4-fluoro-3-methylphenyl and quinoxalinyl substituents) | TFA(2) |
| 226 | (dimethylaminomethyl-pyridine with 4-fluoro-3-methylphenyl and quinoxalinyl substituents) | TFA(3) |
| 227 | (HOOC-pyridine with 4-fluoro-3-methylphenyl and quinoxalinyl substituents) | Parent |
| 228 | (MeO-methyl-pyridine with 4-fluoro-3-methylphenyl and quinoxalinyl substituents) | TFA(3) |
| 229 | (EtO-methyl-pyridine with 4-fluoro-3-methylphenyl and quinoxalinyl substituents) | TFA |
| 230 | (4-methylpiperazinylmethyl-pyridine with 4-fluoro-3-methylphenyl and quinoxalinyl substituents) | TFA(3) |

| Cpd # | Structure | Salt |
|---|---|---|
| 231 | (structure) | TFA |
| 232 | (structure) | TFA(2) |
| 233 | (structure) | TFA(3) |
| 234 | (structure) | TFA |
| 235 | (structure) | TFA(2) |
| 236 | (structure) | TFA |

| Cpd # | Structure | Salt |
|---|---|---|
| 237 | 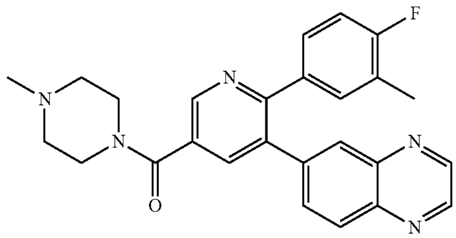 [SMILES: Cc1cc(-c2ncc(C(=O)N3CCN(C)CC3)cc2-c2ccc3nccnc3c2)ccc1F] | TFA(2) |
| 238 | 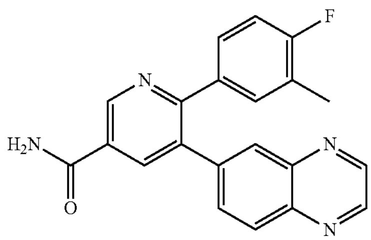 [SMILES: Cc1cc(-c2ncc(C(N)=O)cc2-c2ccc3nccnc3c2)ccc1F] | TFA(2) |
| 239 | 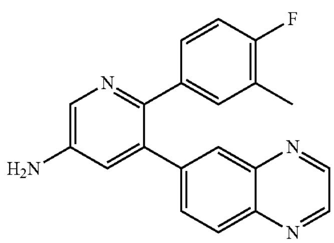 [SMILES: Cc1cc(-c2ncc(N)cc2-c2ccc3nccnc3c2)ccc1F] | TFA(2) |
| 240 | 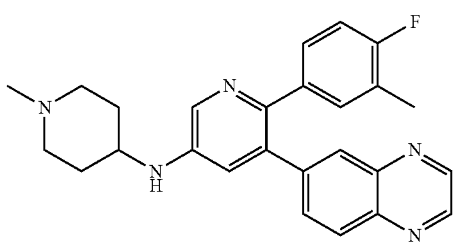 [SMILES: Cc1cc(-c2ncc(NC3CCN(C)CC3)cc2-c2ccc3nccnc3c2)ccc1F] | TFA(3) |
| 241 | 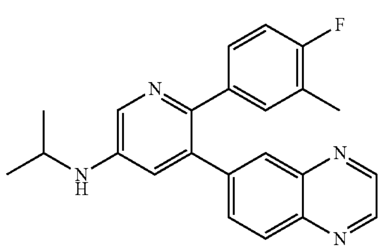 [SMILES: Cc1cc(-c2ncc(NC(C)C)cc2-c2ccc3nccnc3c2)ccc1F] | TFA(2) |
| 242 | 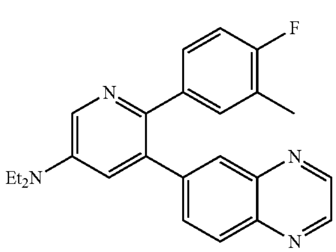 | TFA(2) |

-continued

| Cpd # | Structure | Salt |
|---|---|---|
| 243 | 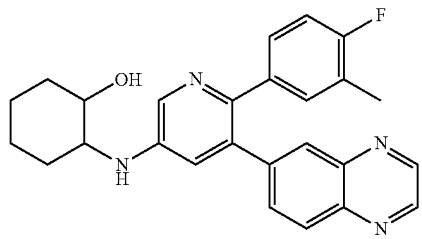 [SMILES: Cc1cc(-c2ncc(NC3CCCCC3O)cc2-c2ccc3nccnc3c2)ccc1F] | TFA(2) |
| 244 | 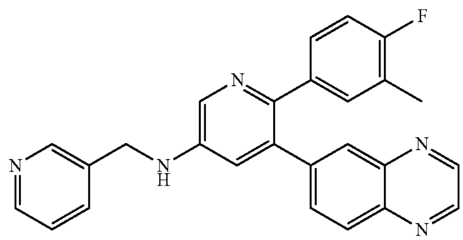 [SMILES: Cc1cc(-c2ncc(NCc3cccnc3)cc2-c2ccc3nccnc3c2)ccc1F] | TFA(3) |
| 245 | 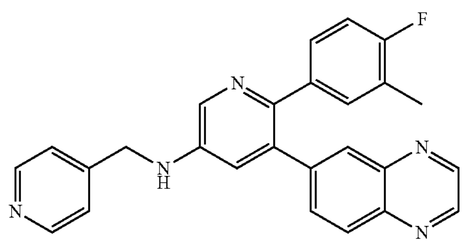 [SMILES: Cc1cc(-c2ncc(NCc3ccncc3)cc2-c2ccc3nccnc3c2)ccc1F] | TFA(3) |
| 246 | 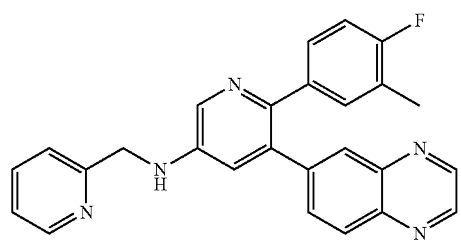 [SMILES: Cc1cc(-c2ncc(NCc3ccccn3)cc2-c2ccc3nccnc3c2)ccc1F] | TFA(3) |
| 247 | 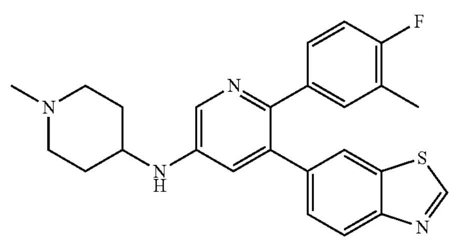 [SMILES: Cc1cc(-c2ncc(NC3CCN(C)CC3)cc2-c2ccc3ncsc3c2)ccc1F] | TFA(3) |
| 248 | 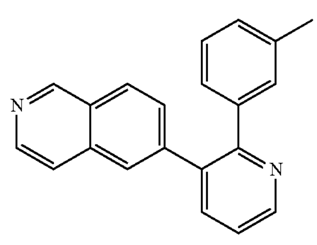 [SMILES: Cc1cccc(-c2ncccc2-c2ccc3cnccc3c2)c1] | Parent |

| Cpd # | Structure | Salt |
|---|---|---|
| 249 | 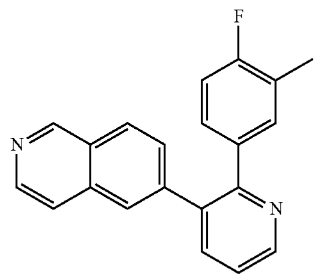 [SMILES: Cc1cc(-c2ncccc2-c2ccc3cnccc3c2)ccc1F] | Parent |
| 250 | 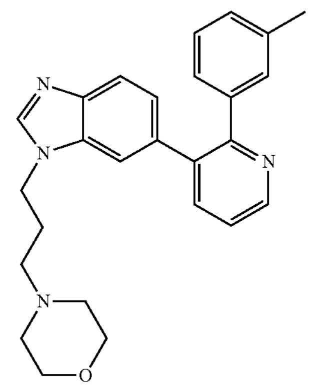 [SMILES: Cc1cccc(-c2ncccc2-c2ccc3ncn(CCCN4CCOCC4)c3c2)c1] | Parent |
| 251 | 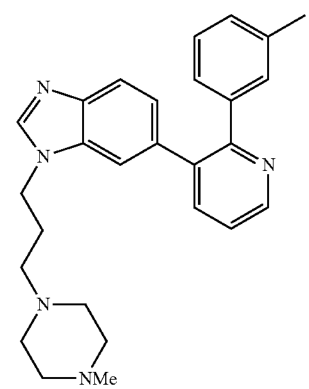 [SMILES: Cc1cccc(-c2ncccc2-c2ccc3ncn(CCCN4CCN(C)CC4)c3c2)c1] | Parent |
| 252 | 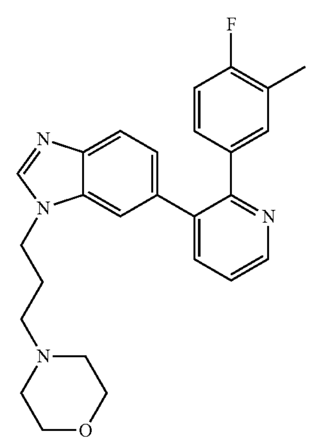 [SMILES: Cc1cc(-c2ncccc2-c2ccc3ncn(CCCN4CCOCC4)c3c2)ccc1F] | Parent |

-continued
| Cpd # | Structure | Salt |
|---|---|---|
| 253 | 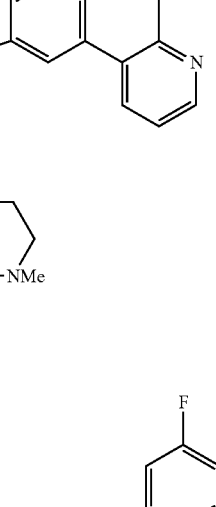 | Parent |
| 254 | 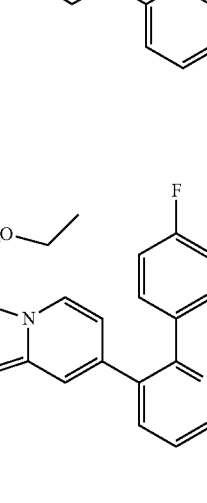 | Parent |
| 255 | 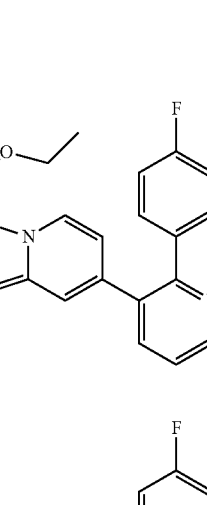 | Parent |
| 256 | 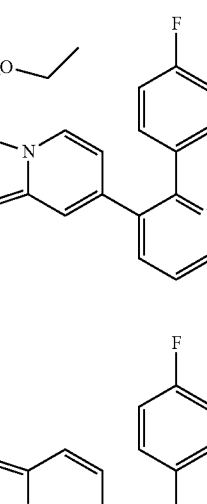 | Parent |

| Cpd # | Structure | Salt |
|---|---|---|
| 257 | 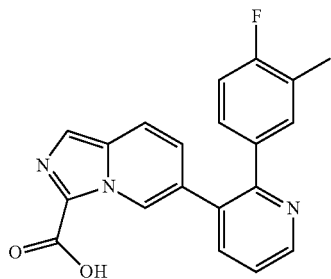 [SMILES: Cc1cc(-c2ncccc2-c2ccc3cnc(C(=O)O)n3c2)ccc1F] | Parent |
| 258 | 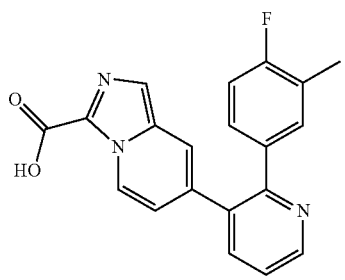 [SMILES: Cc1cc(-c2ncccc2-c2ccn3c(C(=O)O)ncc3c2)ccc1F] | Parent |
| 259 | 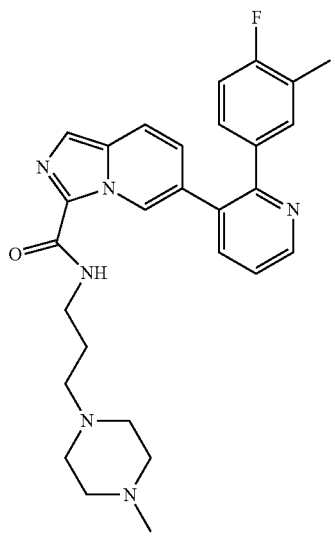 [SMILES: Cc1cc(-c2ncccc2-c2ccc3cnc(C(=O)NCCCN4CCN(C)CC4)n3c2)ccc1F] | Parent |

-continued

| Cpd # | Structure | Salt |
|---|---|---|
| 260 | 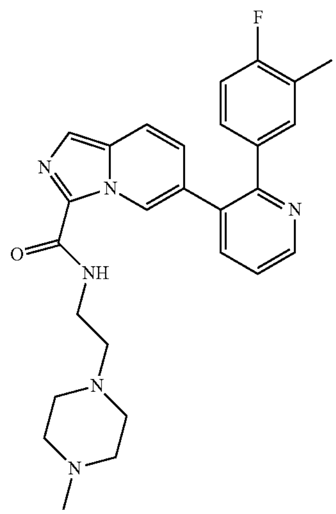 [SMILES: Cc1cc(-c2ncccc2-c2ccc3cnc(C(=O)NCCN4CCN(C)CC4)n3c2)ccc1F] | Parent |
| 261 | 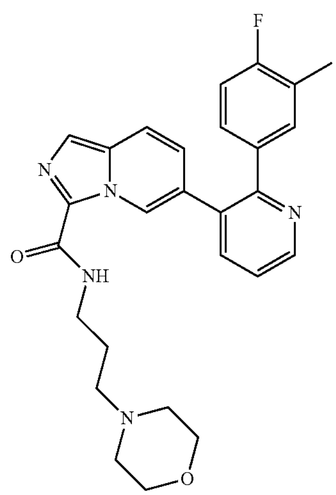 [SMILES: Cc1cc(-c2ncccc2-c2ccc3cnc(C(=O)NCCCN4CCOCC4)n3c2)ccc1F] | Parent |
| 262 | 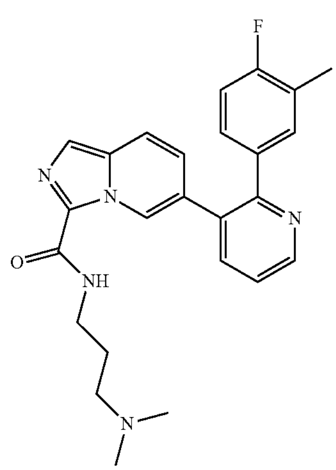 [SMILES: Cc1cc(-c2ncccc2-c2ccc3cnc(C(=O)NCCCN(C)C)n3c2)ccc1F] | Parent |

-continued
| Cpd # | Structure | Salt |
|---|---|---|
| 263 | 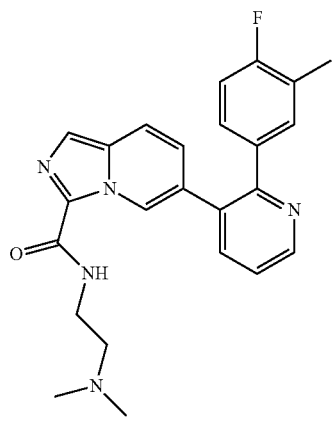 [SMILES: Cc1cc(-c2ncccc2-c2ccc3cnc(C(=O)NCCN(C)C)n3c2)ccc1F] | Parent |
| 264 | 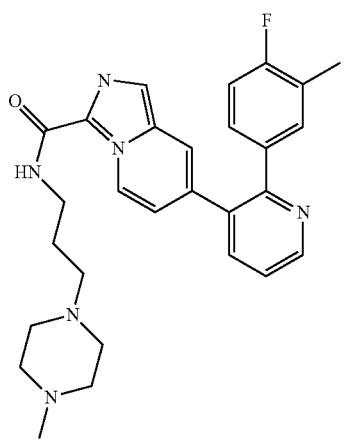 | Parent |
| 265 | 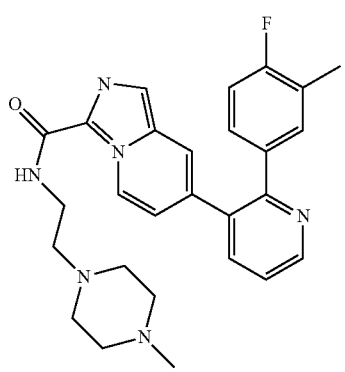 | Parent |

-continued

| Cpd # | Structure | Salt |
|---|---|---|
| 266 | 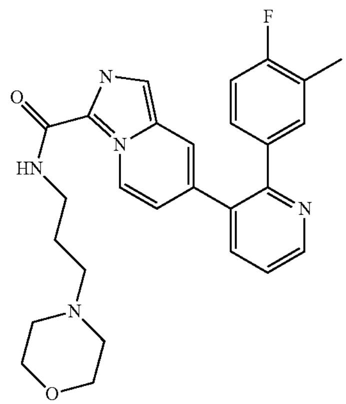 | Parent |
| 267 | 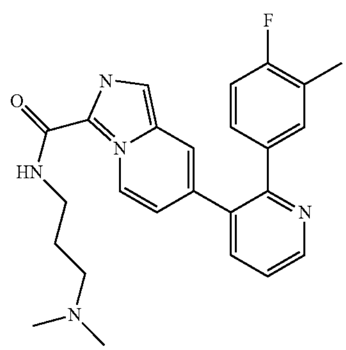 | Parent |
| 268 | 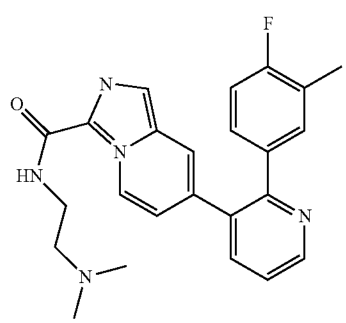 | Parent |
| 269 | 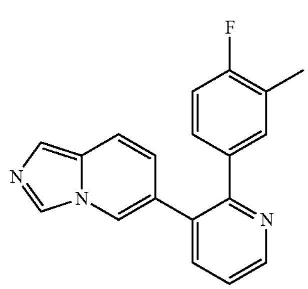 [SMILES: Cc1cc(-c2ncccc2-c2ccc3cncn3c2)ccc1F] | Parent |

| Cpd # | Structure | Salt |
|---|---|---|
| 270 | 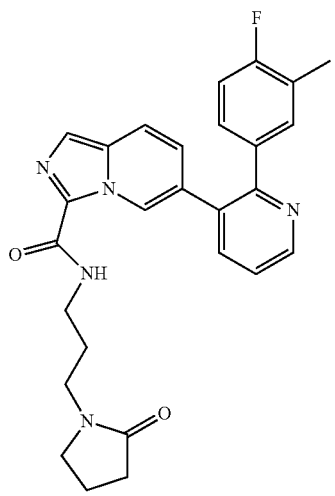 [SMILES: Cc1cc(-c2ncccc2-c2ccc3cnc(C(=O)NCCCN4CCCC4=O)n3c2)ccc1F] | Parent |
| 271 | 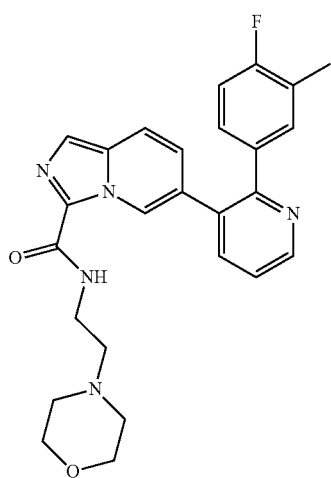 [SMILES: Cc1cc(-c2ncccc2-c2ccc3cnc(C(=O)NCCN4CCOCC4)n3c2)ccc1F] | Parent |
| 272 | 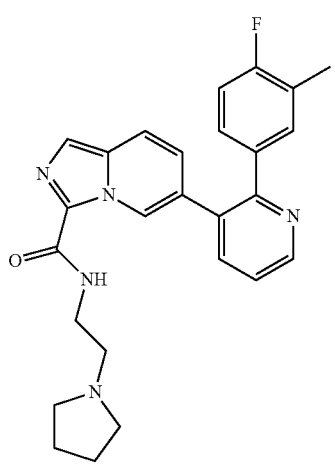 [SMILES: Cc1cc(-c2ncccc2-c2ccc3cnc(C(=O)NCCN4CCCC4)n3c2)ccc1F] | Parent |

-continued

| Cpd # | Structure | Salt |
|---|---|---|
| 273 | 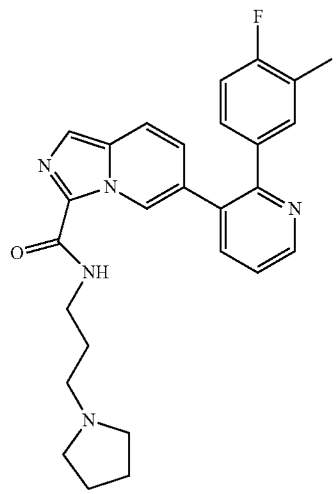 [SMILES: Cc1cc(-c2ncccc2-c2ccc3cnc(C(=O)NCCCN4CCCC4)n3c2)ccc1F] | Parent |
| 274 | 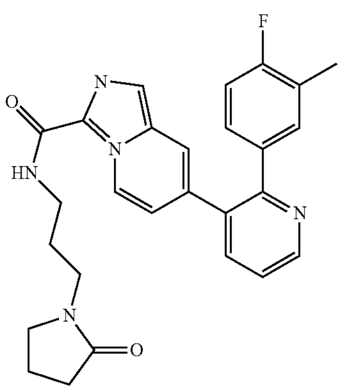 | Parent |
| 275 | 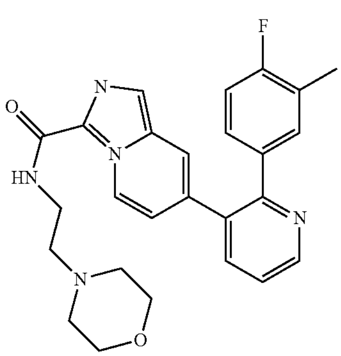 | Parent |

-continued

| Cpd # | Structure | Salt |
|---|---|---|
| 276 | 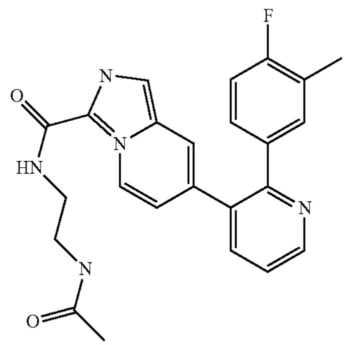 | Parent |
| 277 | 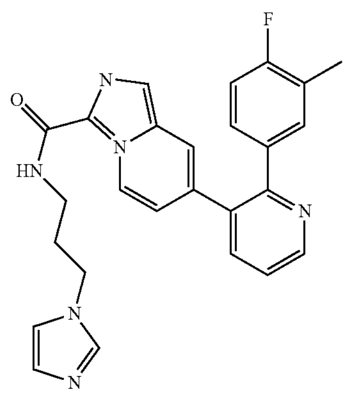 | Parent |
| 278 | 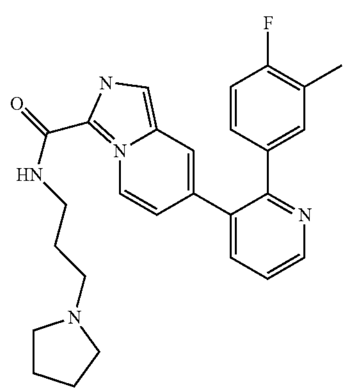 | Parent |
| 279 | 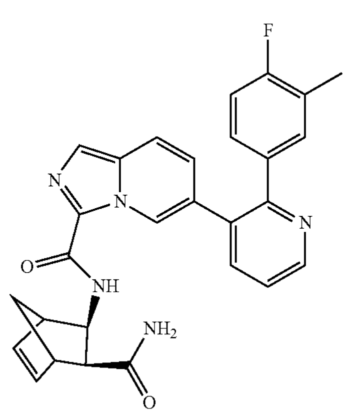 [SMILES: Cc1cc(-c2ncccc2-c2ccc3cnc(C(=O)N[C@@H]4C5C=CC(C5)[C@@H]4C(N)=O)n3c2)ccc1F] | Parent |

-continued
| Cpd # | Structure | Salt |
|---|---|---|
| 280 | 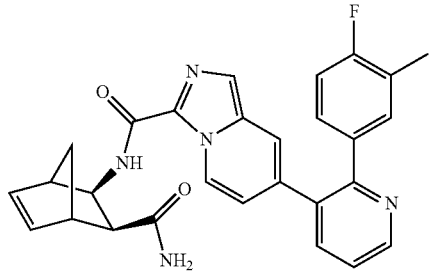 [SMILES: Cc1cc(-c2ncccc2-c2ccn3c(C(=O)N[C@@H]4C5C=CC(C5)[C@@H]4C(N)=O)ncc3c2)ccc1F] | Parent |
| 281 | 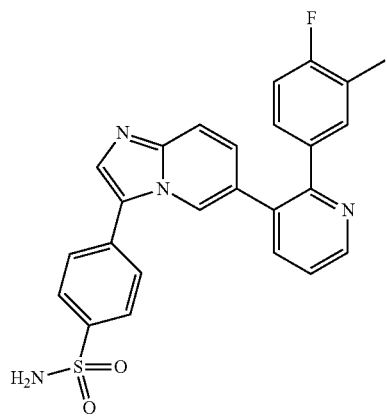 [SMILES: Cc1cc(-c2ncccc2-c2ccc3ncc(-c4ccc(S(N)(=O)=O)cc4)n3c2)ccc1F] | Parent |
| 282 | 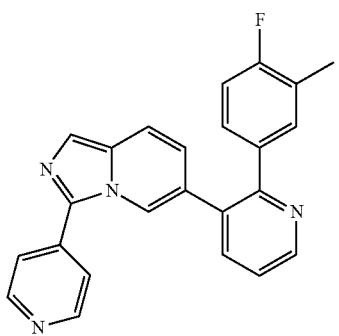 [SMILES: Cc1cc(-c2ncccc2-c2ccc3cnc(-c4ccncc4)n3c2)ccc1F] | Parent |
| 283 | 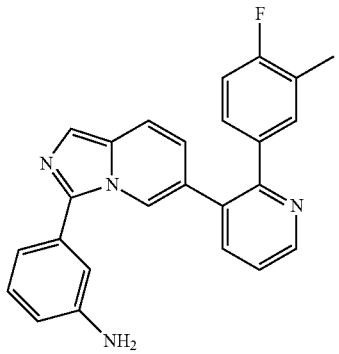 [SMILES: Cc1cc(-c2ncccc2-c2ccc3cnc(-c4cccc(N)c4)n3c2)ccc1F] | Parent |

-continued
| Cpd # | Structure | Salt |
|---|---|---|
| 284 | 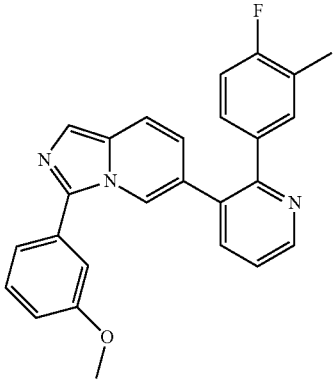 [SMILES: COc1cccc(-c2ncc3ccc(-c4cccnc4-c4ccc(F)c(C)c4)cn23)c1] | Parent |
| 285 | 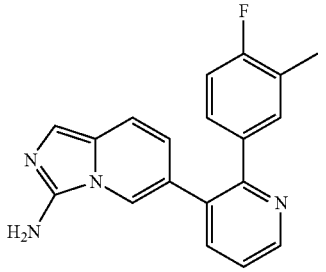 [SMILES: Cc1cc(-c2ncccc2-c2ccc3cnc(N)n3c2)ccc1F] | Parent |
| 286 | 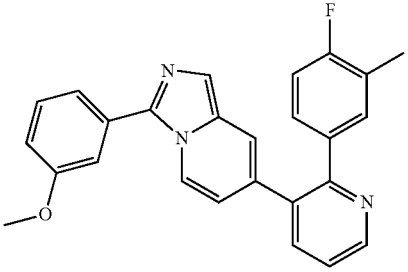 | Parent |
| 287 | 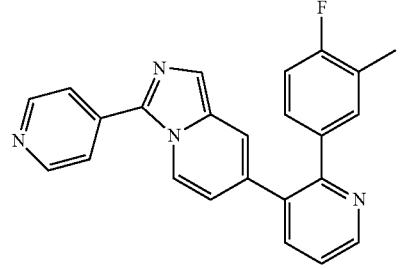 [SMILES: Cc1cc(-c2ncccc2-c2ccn3c(-c4ccncc4)ncc3c2)ccc1F] | Parent |
| 288 | 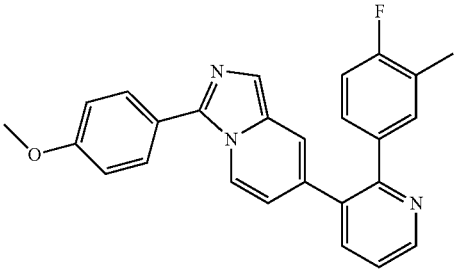 | Parent |

US 9,145,433 B2
147                                                                 148
-continued
| Cpd # | Structure | Salt |
|---|---|---|
| 289 | 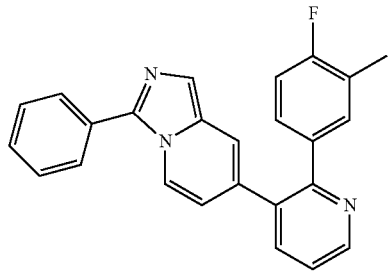 [SMILES: Cc1cc(-c2ncccc2-c2ccn3c(-c4ccccc4)ncc3c2)ccc1F] | Parent |
| 290 | 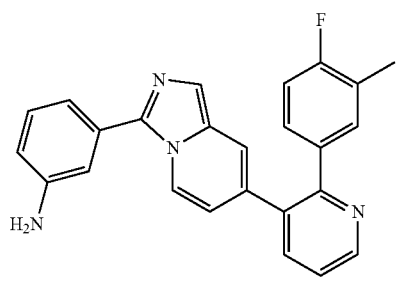 [SMILES: Cc1cc(-c2ncccc2-c2ccn3c(-c4cccc(N)c4)ncc3c2)ccc1F] | Parent |
| 291 | 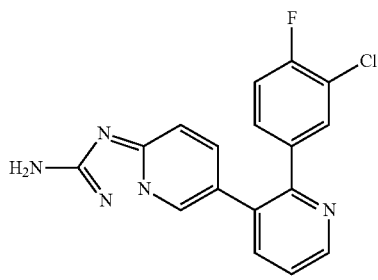 [SMILES: N=C(N)/N=c1/ccc(-c2cccnc2-c2ccc(F)c(Cl)c2)c[nH]1] | Parent |
| 292 | 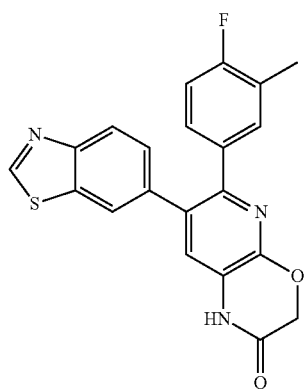 [SMILES: Cc1cc(-c2nc3c(cc2-c2ccc4ncsc4c2)NC(=O)CO3)ccc1F] | Parent |

| Cpd # | Structure | Salt |
|---|---|---|
| 296 | 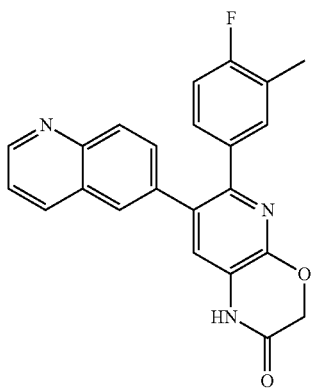 [SMILES: Cc1cc(-c2nc3c(cc2-c2ccc4ncccc4c2)NC(=O)CO3)ccc1F] | Parent |
| 294 | 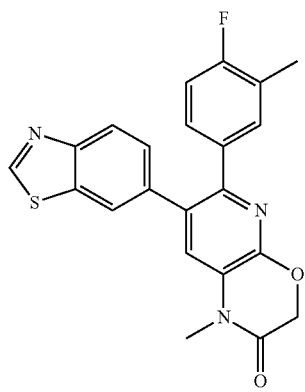 [SMILES: Cc1cc(-c2nc3c(cc2-c2ccc4ncsc4c2)N(C)C(=O)CO3)ccc1F] | Parent |
| 295 | 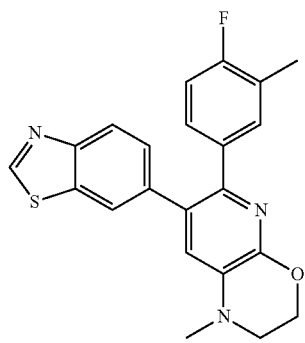 [SMILES: Cc1cc(-c2nc3c(cc2-c2ccc4ncsc4c2)N(C)CCO3)ccc1F] | Parent |
| 296 | 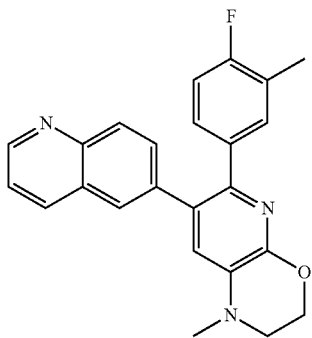 [SMILES: Cc1cc(-c2nc3c(cc2-c2ccc4ncccc4c2)N(C)CCO3)ccc1F] | Parent |

-continued
| Cpd # | Structure | Salt |
|---|---|---|
| 297 | 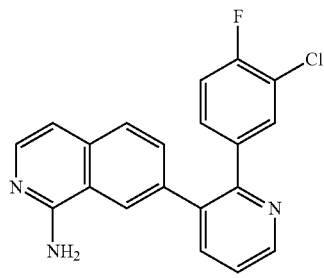 [SMILES: Nc1nccc2ccc(-c3cccnc3-c3ccc(F)c(Cl)c3)cc12] | Parent |
| 298 | 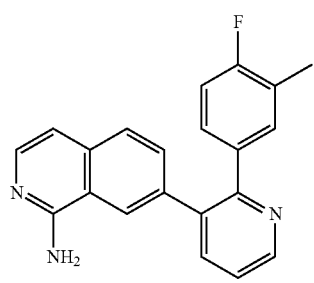 [SMILES: Cc1cc(-c2ncccc2-c2ccc3ccnc(N)c3c2)ccc1F] | Parent |
| 299 | 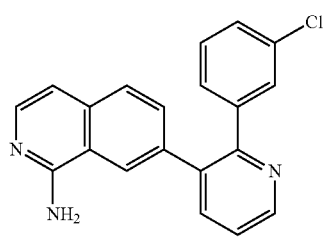 [SMILES: Nc1nccc2ccc(-c3cccnc3-c3cccc(Cl)c3)cc12] | Parent |
| 300 | 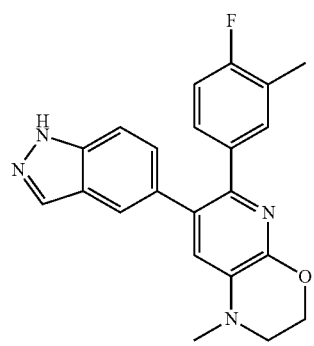 [SMILES: Cc1cc(-c2nc3c(cc2-c2ccc4[nH]ncc4c2)N(C)CCO3)ccc1F] | Parent |
| 301 | 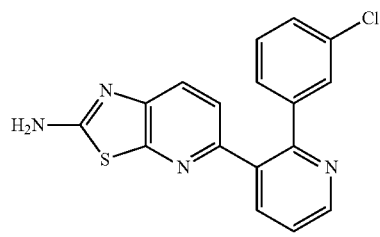 [SMILES: Nc1nc2ccc(-c3cccnc3-c3cccc(Cl)c3)nc2s1] | Parent |

-continued

| Cpd # | Structure | Salt |
|---|---|---|
| 302 | 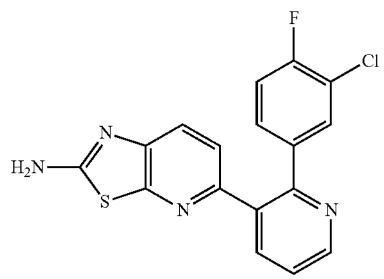 [SMILES: Nc1nc2ccc(-c3cccnc3-c3ccc(F)c(Cl)c3)nc2s1] | Parent |
| 303 | 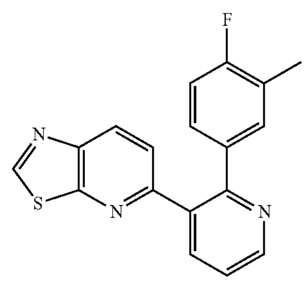 [SMILES: Cc1cc(-c2ncccc2-c2ccc3ncsc3n2)ccc1F] | Parent |
| 304 | 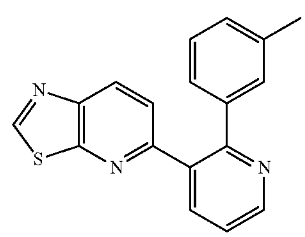 [SMILES: Cc1cccc(-c2ncccc2-c2ccc3ncsc3n2)c1] | Parent |
| 305 | 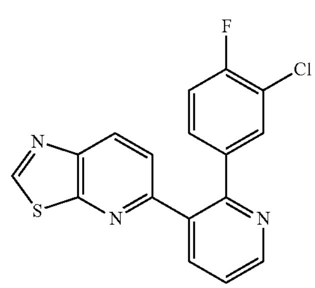 [SMILES: Fc1ccc(-c2ncccc2-c2ccc3ncsc3n2)cc1Cl] | Parent |
| 306 | 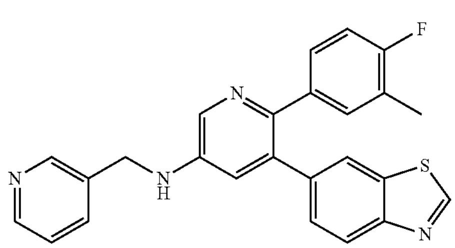 [SMILES: Cc1cc(-c2ncc(NCc3cccnc3)cc2-c2ccc3ncsc3c2)ccc1F] | TFA(3) |

155
-continued

| Cpd # | Structure | Salt |
|---|---|---|
| 307 | 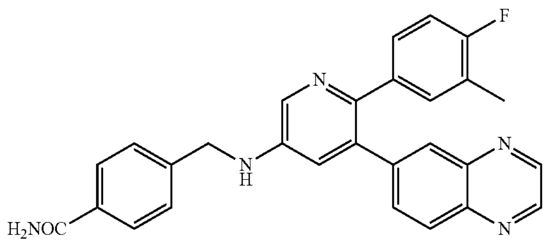 [SMILES: Cc1cc(-c2ncc(NCc3ccc(C(N)=O)cc3)cc2-c2ccc3nccnc3c2)ccc1F] | Parent |
| 308 | 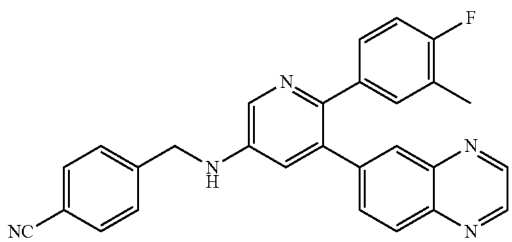 [SMILES: Cc1cc(-c2ncc(NCc3ccc(C#N)cc3)cc2-c2ccc3nccnc3c2)ccc1F] | Formic Acid(2) |
| 309 | 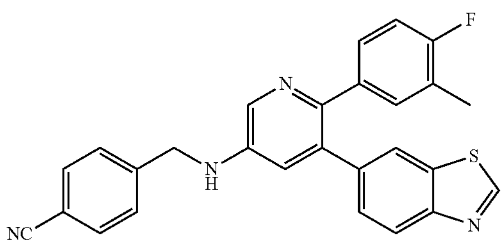 [SMILES: Cc1cc(-c2ncc(NCc3ccc(C#N)cc3)cc2-c2ccc3ncsc3c2)ccc1F] | Formic Acid(2) |
| 310 | 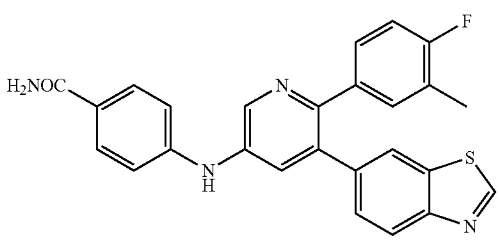 [SMILES: Cc1cc(-c2ncc(Nc3ccc(C(N)=O)cc3)cc2-c2ccc3ncsc3c2)ccc1F] | TFA(2) |
| 311 | 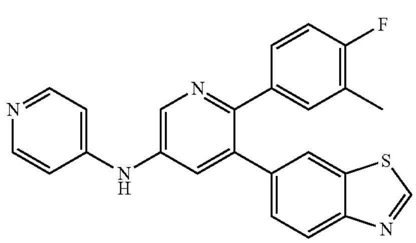 [SMILES: Cc1cc(-c2ncc(Nc3ccncc3)cc2-c2ccc3ncsc3c2)ccc1F] | Formic Acid(3) |
| 312 | 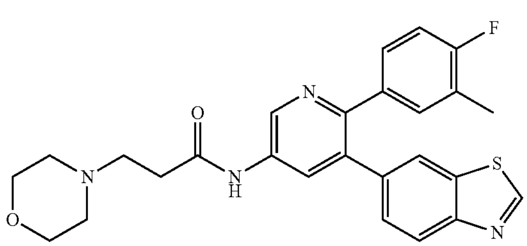 [SMILES: Cc1cc(-c2ncc(NC(=O)CCN3CCOCC3)cc2-c2ccc3ncsc3c2)ccc1F] | Formic Acid(2) |

156

| Cpd # | Structure | Salt |
|---|---|---|
| 313 | 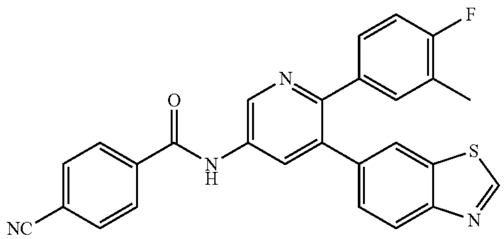 [SMILES: Cc1cc(-c2ncc(NC(=O)c3ccc(C#N)cc3)cc2-c2ccc3ncsc3c2)ccc1F] | Formic Acid(1) |
| 314 | 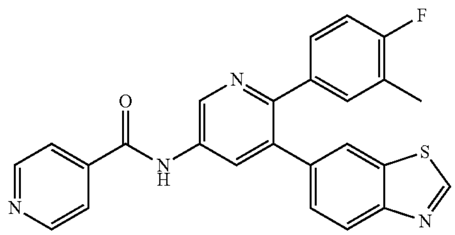 [SMILES: Cc1cc(-c2ncc(NC(=O)c3ccncc3)cc2-c2ccc3ncsc3c2)ccc1F] | Formic Acid(2) |
| 315 | 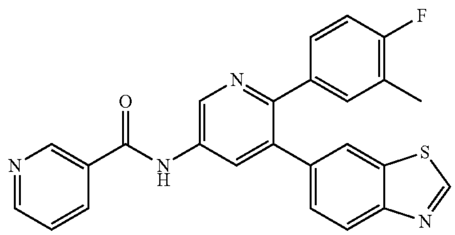 [SMILES: Cc1cc(-c2ncc(NC(=O)c3cccnc3)cc2-c2ccc3ncsc3c2)ccc1F] | Formic Acid(2) |
| 316 | 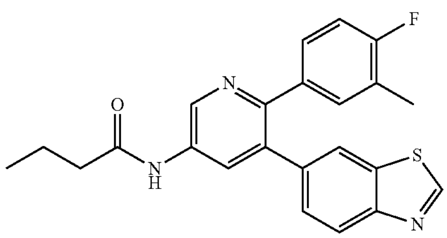 [SMILES: CCCC(=O)Nc1cnc(-c2ccc(F)c(C)c2)c(-c2ccc3ncsc3c2)c1] | Formic Acid(2) |
| 317 | 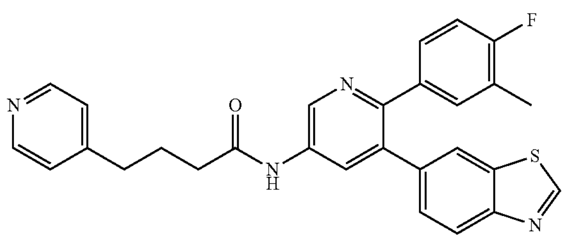 [SMILES: Cc1cc(-c2ncc(NC(=O)CCCc3ccncc3)cc2-c2ccc3ncsc3c2)ccc1F] | Formic Acid(2) |
| 318 | 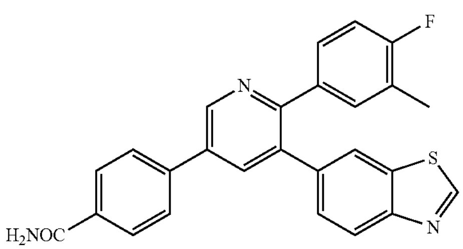 [SMILES: Cc1cc(-c2ncc(-c3ccc(C(N)=O)cc3)cc2-c2ccc3ncsc3c2)ccc1F] | Formic Acid(2) |

-continued

| Cpd # | Structure | Salt |
|---|---|---|
| 319 | 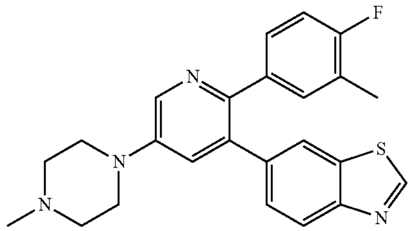 [SMILES: Cc1cc(-c2ncc(N3CCN(C)CC3)cc2-c2ccc3ncsc3c2)ccc1F] | Formic Acid(3) |
| 320 | 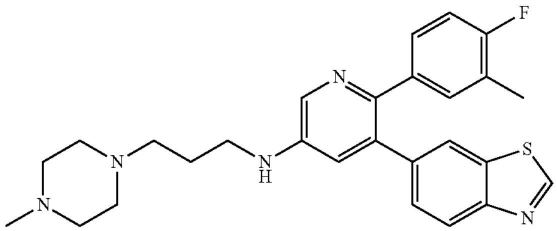 [SMILES: Cc1cc(-c2ncc(NCCCN3CCN(C)CC3)cc2-c2ccc3ncsc3c2)ccc1F] | Formic Acid(3) |
| 321 | 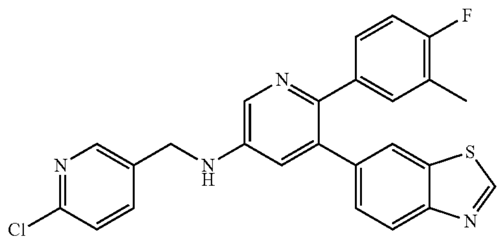 [SMILES: Cc1cc(-c2ncc(NCc3ccc(Cl)nc3)cc2-c2ccc3ncsc3c2)ccc1F] | TFA(3) |
| 322 | 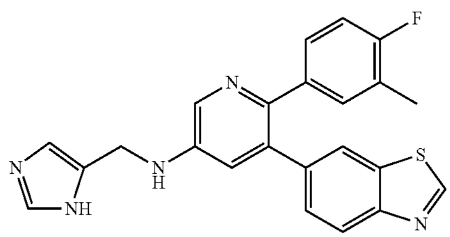 [SMILES: Cc1cc(-c2ncc(NCc3cnc[nH]3)cc2-c2ccc3ncsc3c2)ccc1F] | Formic Acid(3) |
| 323 | 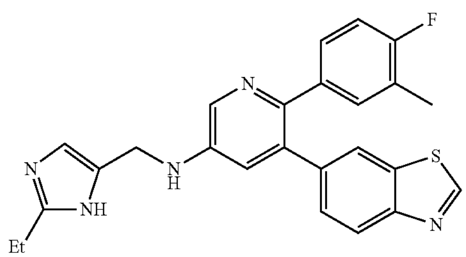 [SMILES: CCc1ncc(CNc2cnc(-c3ccc(F)c(C)c3)c(-c3ccc4ncsc4c3)c2)[nH]1] | Formic Acid(3) |
| 324 | 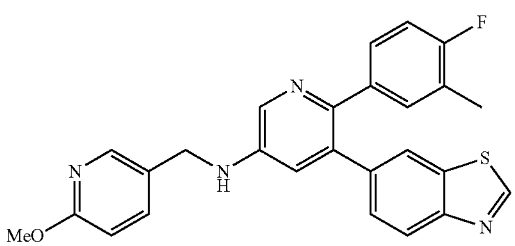 [SMILES: COc1ccc(CNc2cnc(-c3ccc(F)c(C)c3)c(-c3ccc4ncsc4c3)c2)cn1] | Formic Acid(3) |

| Cpd # | Structure | Salt |
|---|---|---|
| 325 | 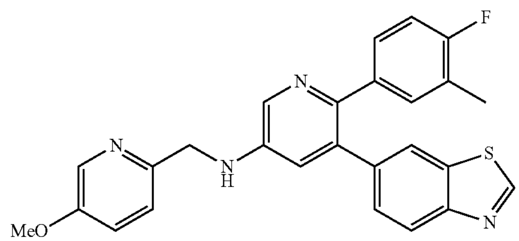 [SMILES: COc1ccc(CNc2cnc(-c3ccc(F)c(C)c3)c(-c3ccc4ncsc4c3)c2)nc1] | Formic Acid(3) |
| 326 | 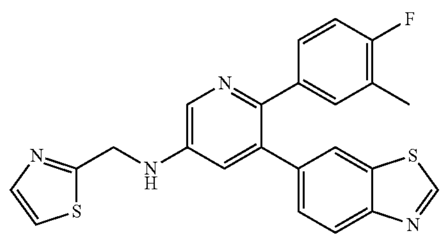 [SMILES: Cc1cc(-c2ncc(NCc3nccs3)cc2-c2ccc3ncsc3c2)ccc1F] | Formic Acid(3) |
| 327 | 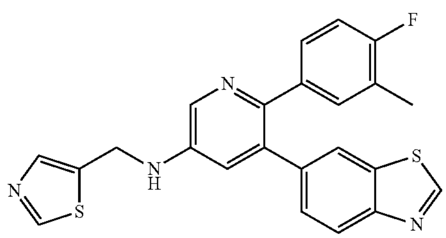 [SMILES: Cc1cc(-c2ncc(NCc3cncs3)cc2-c2ccc3ncsc3c2)ccc1F] | Formic Acid(3) |
| 328 | 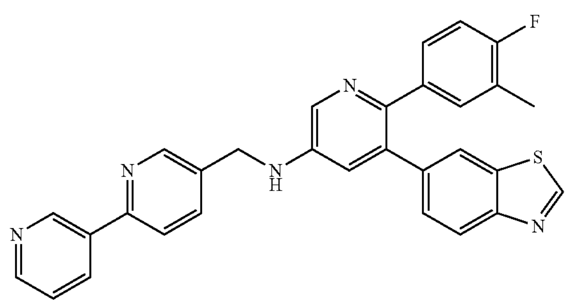 [SMILES: Cc1cc(-c2ncc(NCc3ccc(-c4cccnc4)nc3)cc2-c2ccc3ncsc3c2)ccc1F] | TFA(3) |
| 329 | 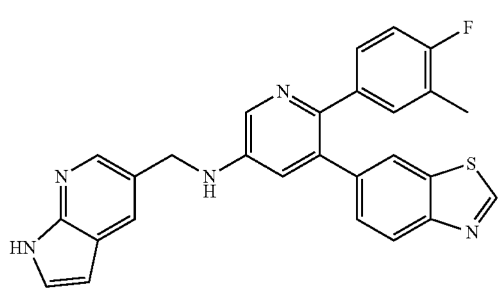 [SMILES: Cc1cc(-c2ncc(NCc3cnc4[nH]ccc4c3)cc2-c2ccc3ncsc3c2)ccc1F] | Formic Acid(3) |

-continued
| Cpd # | Structure | Salt |
|---|---|---|
| 330 | 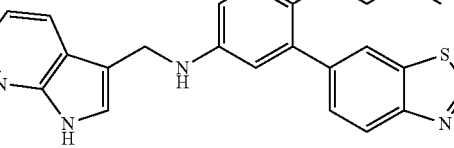 | Formic Acid(3) |
| 331 | 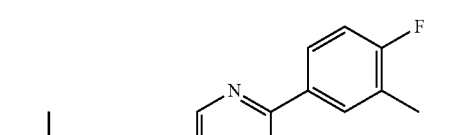 | Formic Acid(3) |
| 332 | 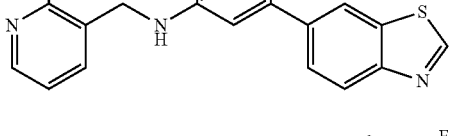 | Formic Acid(3) |
| 333 | 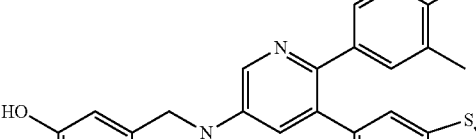 | Formic Acid(2) |
| 334 | 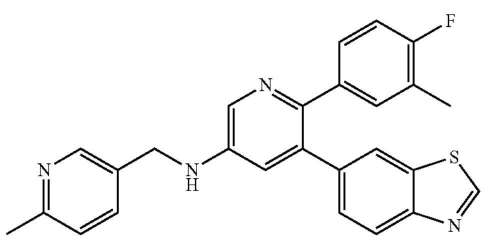 [SMILES: Cc1ccc(CNc2cnc(-c3ccc(F)c(C)c3)c(-c3ccc4ncsc4c3)c2)cn1] | Formic Acid(2) |
| 335 | 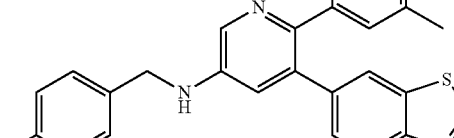 | Formic Acid(3) |

-continued

| Cpd # | Structure | Salt |
|---|---|---|
| 336 | 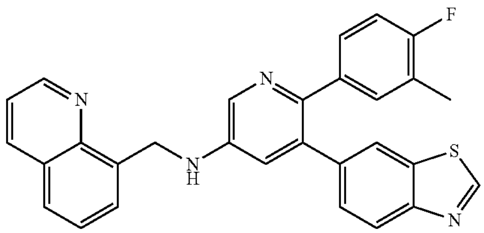 [SMILES: Cc1cc(-c2ncc(NCc3cccc4cccnc34)cc2-c2ccc3ncsc3c2)ccc1F] | Formic Acid(3) |
| 337 | 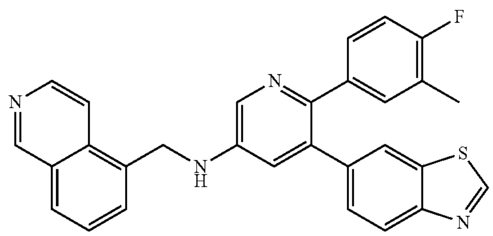 [SMILES: Cc1cc(-c2ncc(NCc3cccc4cnccc34)cc2-c2ccc3ncsc3c2)ccc1F] | Formic Acid(3) |
| 338 | 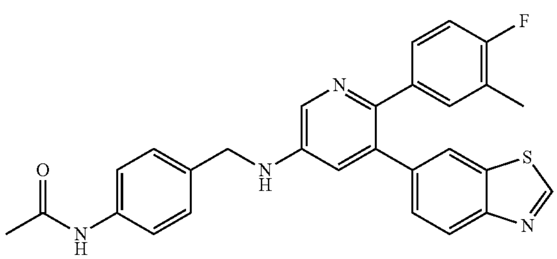 [SMILES: CC(=O)Nc1ccc(CNc2cnc(-c3ccc(F)c(C)c3)c(-c3ccc4ncsc4c3)c2)cc1] | Formic Acid(3) |
| 339 | 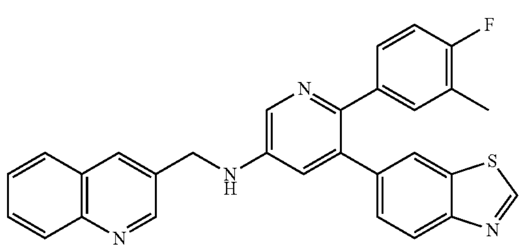 [SMILES: Cc1cc(-c2ncc(NCc3cnc4ccccc4c3)cc2-c2ccc3ncsc3c2)ccc1F] | Formic Acid(3) |
| 340 | 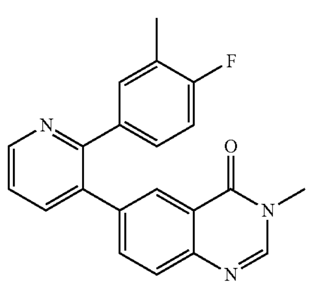 [SMILES: Cc1cc(-c2ncccc2-c2ccc3ncn(C)c(=O)c3c2)ccc1F] | Formic Acid(2) |

| Cpd # | Structure | Salt |
|---|---|---|
| 341 | 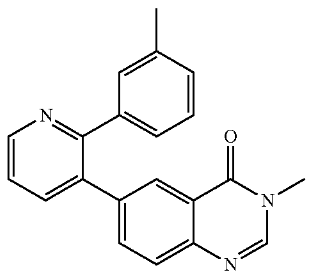 [SMILES: Cc1cccc(-c2ncccc2-c2ccc3ncn(C)c(=O)c3c2)c1] | Formic Acid(2) |
| 342 | 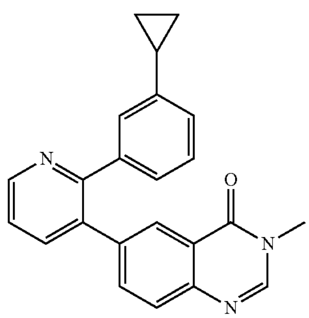 [SMILES: Cn1cnc2ccc(-c3cccnc3-c3cccc(C4CC4)c3)cc2c1=O] | Formic Acid(2) |
| 343 | 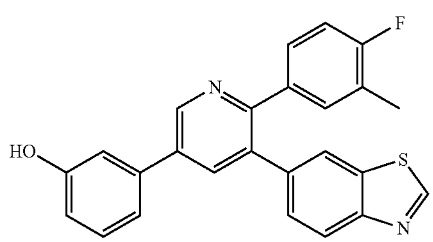 [SMILES: Cc1cc(-c2ncc(-c3cccc(O)c3)cc2-c2ccc3ncsc3c2)ccc1F] | TFA(2) |
| 344 | 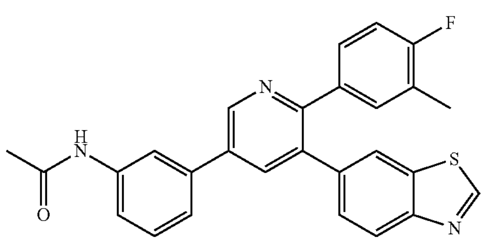 [SMILES: CC(=O)Nc1cccc(-c2cnc(-c3ccc(F)c(C)c3)c(-c3ccc4ncsc4c3)c2)c1] | TFA(2) |
| 345 | 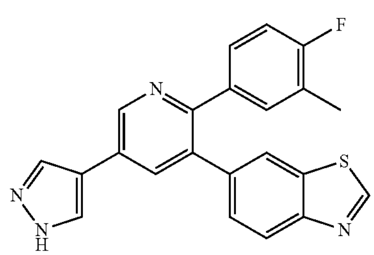 [SMILES: Cc1cc(-c2ncc(-c3cn[nH]c3)cc2-c2ccc3ncsc3c2)ccc1F] | TFA(3) |

-continued

| Cpd # | Structure | Salt |
|---|---|---|
| 346 | 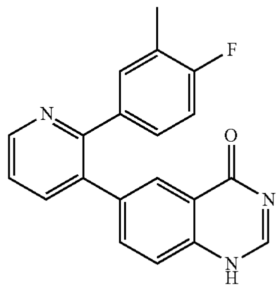 [SMILES: Cc1cc(-c2ncccc2-c2ccc3[nH]cnc(=O)c3c2)ccc1F] | Formic Acid(2) |
| 347 | 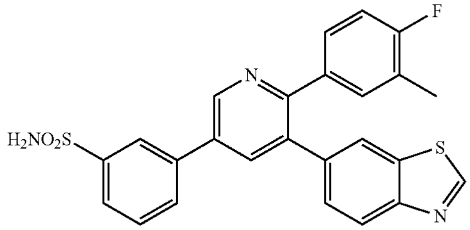 [SMILES: Cc1cc(-c2ncc(-c3cccc(S(N)(=O)=O)c3)cc2-c2ccc3ncsc3c2)ccc1F] | Formic Acid(3) |
| 348 | 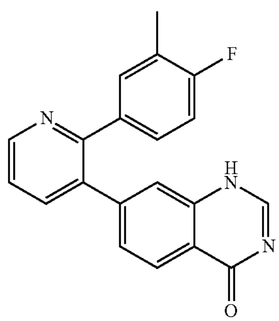 [SMILES: Cc1cc(-c2ncccc2-c2ccc3c(=O)nc[nH]c3c2)ccc1F] | TFA(2) |
| 349 | 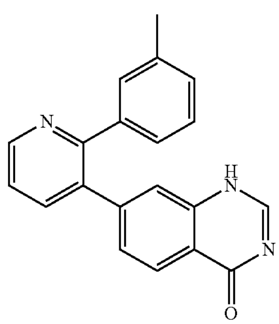 [SMILES: Cc1cccc(-c2ncccc2-c2ccc3c(=O)nc[nH]c3c2)c1] | TFA(2) |
| 350 | 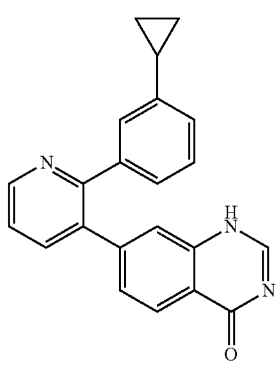 [SMILES: O=c1nc[nH]c2cc(-c3cccnc3-c3cccc(C4CC4)c3)ccc12] | TFA(2) |

-continued

| Cpd # | Structure | Salt |
|---|---|---|
| 351 | 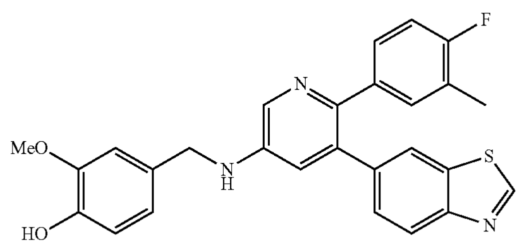 [SMILES: COc1cc(CNc2cnc(-c3ccc(F)c(C)c3)c(-c3ccc4ncsc4c3)c2)ccc1O] | Formic Acid(3) |
| 352 | 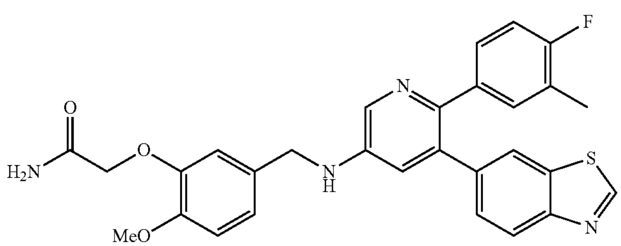 [SMILES: COc1ccc(CNc2cnc(-c3ccc(F)c(C)c3)c(-c3ccc4ncsc4c3)c2)cc1OCC(N)=O] | Formic Acid(3) |
| 353 | 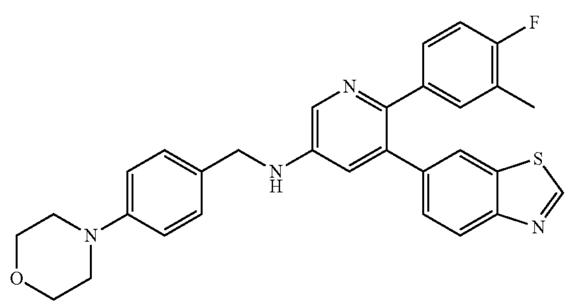 [SMILES: Cc1cc(-c2ncc(NCc3ccc(N4CCOCC4)cc3)cc2-c2ccc3ncsc3c2)ccc1F] | Formic Acid(3) |
| 354 | 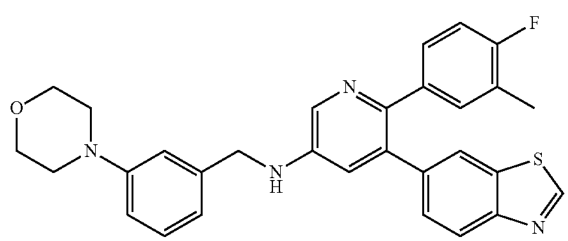 [SMILES: Cc1cc(-c2ncc(NCc3cccc(N4CCOCC4)c3)cc2-c2ccc3ncsc3c2)ccc1F] | Formic Acid(3) |
| 355 | 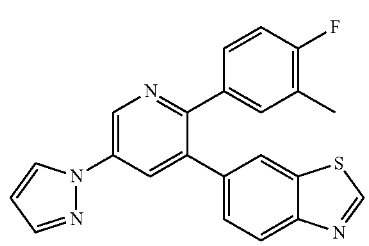 [SMILES: Cc1cc(-c2ncc(-n3cccn3)cc2-c2ccc3ncsc3c2)ccc1F] | Formic Acid(3) |
| 356 | 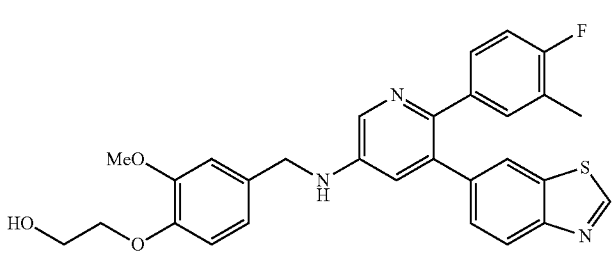 [SMILES: COc1cc(CNc2cnc(-c3ccc(F)c(C)c3)c(-c3ccc4ncsc4c3)c2)ccc1OCCO] | Formic Acid(3) |

-continued
| Cpd # | Structure | Salt |
|---|---|---|
| 357 | 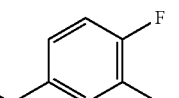 | Formic Acid(3) |
| 358 | 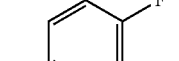 | Formic Acid(3) |
| 359 | 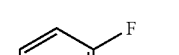 | Formic Acid(3) |
| 360 | 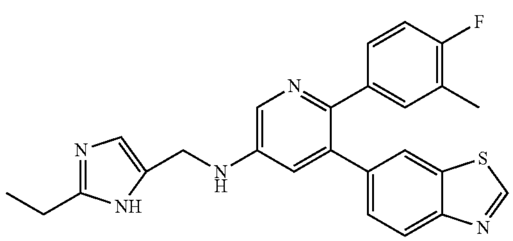 [SMILES: CCc1ncc(CNc2cnc(-c3ccc(F)c(C)c3)c(-c3ccc4ncsc4c3)c2)[nH]1] | TFA(3) |
| 361 | 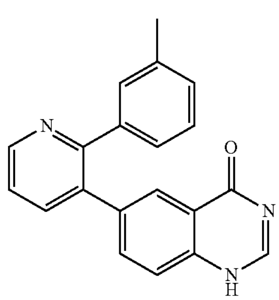 [SMILES: Cc1cccc(-c2ncccc2-c2ccc3[nH]cnc(=O)c3c2)c1] | Formic Acid(2) |

-continued
| Cpd # | Structure | Salt |
|---|---|---|
| 362 | 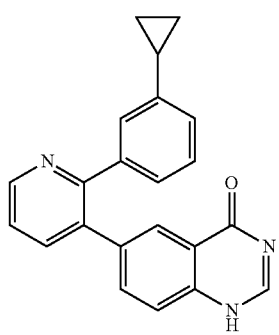 [SMILES: O=c1nc[nH]c2ccc(-c3cccnc3-c3cccc(C4CC4)c3)cc12] | Formic Acid(2) |
| 363 | 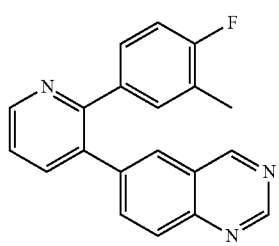 [SMILES: Cc1cc(-c2ncccc2-c2ccc3ncncc3c2)ccc1F] | TFA(3) |
| 364 | 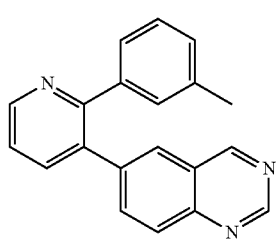 [SMILES: Cc1cccc(-c2ncccc2-c2ccc3ncncc3c2)c1] | TFA(3) |
| 365 | 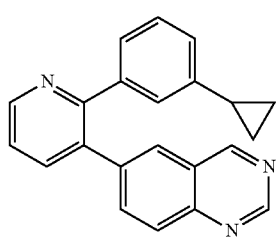 [SMILES: c1cc(-c2ncccc2-c2ccc3ncncc3c2)cc(C2CC2)c1] | TFA(3) |
| 366 | 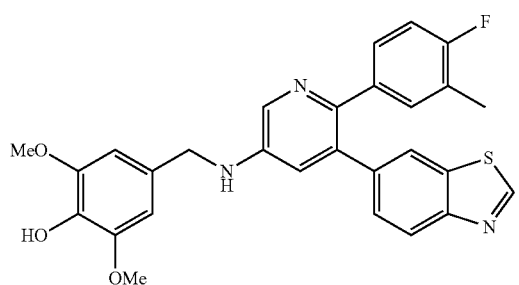 [SMILES: COc1cc(CNc2cnc(-c3ccc(F)c(C)c3)c(-c3ccc4ncsc4c3)c2)cc(OC)c1O] | Formic Acid(3) |

-continued

| Cpd # | Structure | Salt |
|---|---|---|
| 367 | 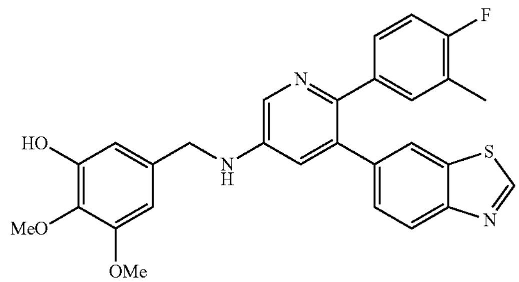 [SMILES: COc1cc(CNc2cnc(-c3ccc(F)c(C)c3)c(-c3ccc4ncsc4c3)c2)cc(O)c1OC] | Formic Acid(3) |
| 368 | 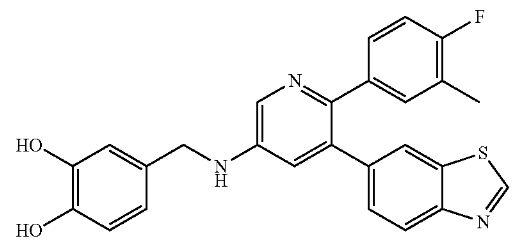 [SMILES: Cc1cc(-c2ncc(NCc3ccc(O)c(O)c3)cc2-c2ccc3ncsc3c2)ccc1F] | Formic Acid(3) |
| 369 | 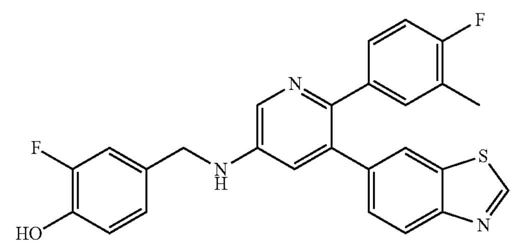 | Formic Acid(3) |
| 370 | 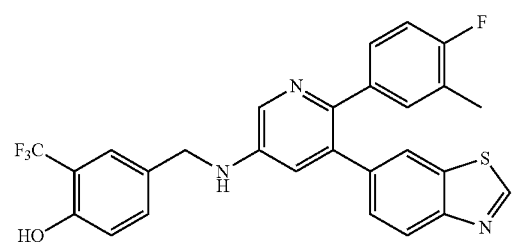 | Formic Acid(3) |
| 371 | 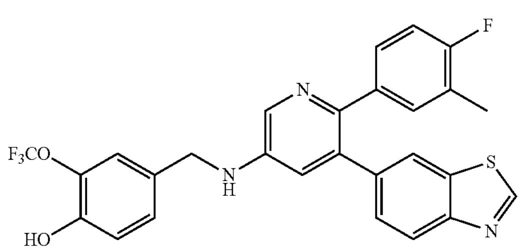 [SMILES: Cc1cc(-c2ncc(NCc3ccc(O)c(OC(F)(F)F)c3)cc2-c2ccc3ncsc3c2)ccc1F] | Formic Acid(3) |
| 372 | 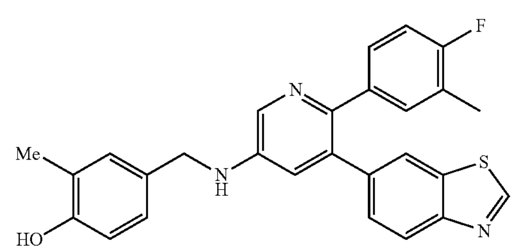 | Formic Acid(3) |

-continued

| Cpd # | Structure | Salt |
|---|---|---|
| 373 | 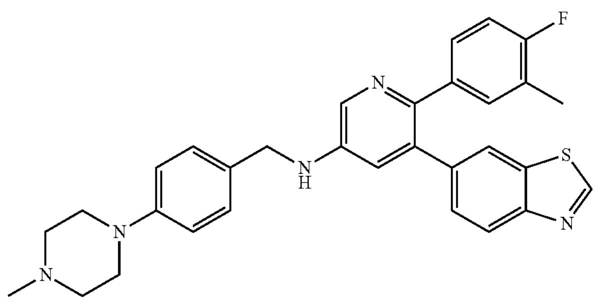 [SMILES: Cc1cc(-c2ncc(NCc3ccc(N4CCN(C)CC4)cc3)cc2-c2ccc3ncsc3c2)ccc1F] | Formic Acid(3) |
| 374 | 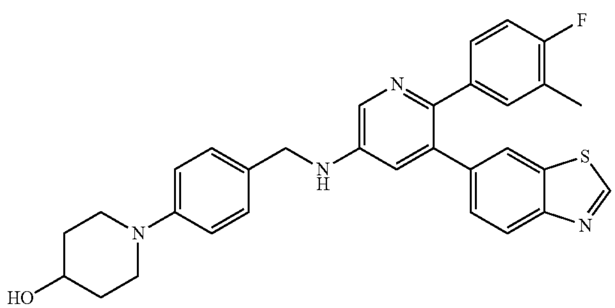 [SMILES: Cc1cc(-c2ncc(NCc3ccc(N4CCC(O)CC4)cc3)cc2-c2ccc3ncsc3c2)ccc1F] | Formic Acid(3) |
| 375 | 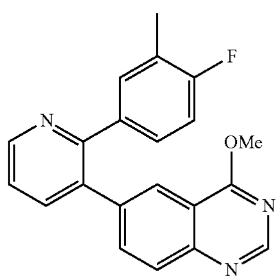 [SMILES: COc1ncnc2ccc(-c3cccnc3-c3ccc(F)c(C)c3)cc12] | Formic Acid(2) |
| 376 | 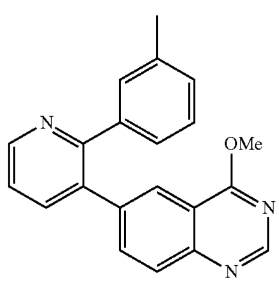 [SMILES: COc1ncnc2ccc(-c3cccnc3-c3cccc(C)c3)cc12] | Formic Acid(2) |
| 377 | 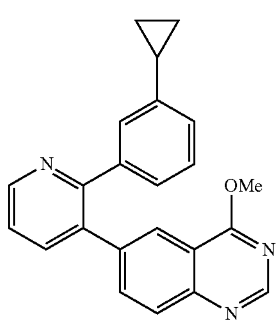 [SMILES: COc1ncnc2ccc(-c3cccnc3-c3cccc(C4CC4)c3)cc12] | Formic Acid(2) |

-continued

| Cpd # | Structure | Salt |
|---|---|---|
| 378 | 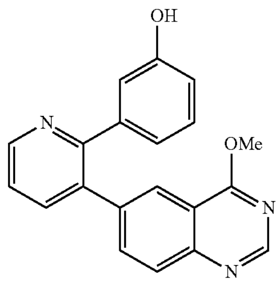 [SMILES: COc1ncnc2ccc(-c3cccnc3-c3cccc(O)c3)cc12] | Formic Acid(2) |
| 379 | 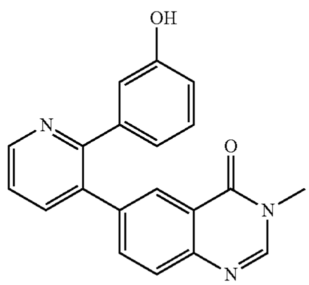 [SMILES: Cn1cnc2ccc(-c3cccnc3-c3cccc(O)c3)cc2c1=O] | Formic Acid(2) |
| 380 | 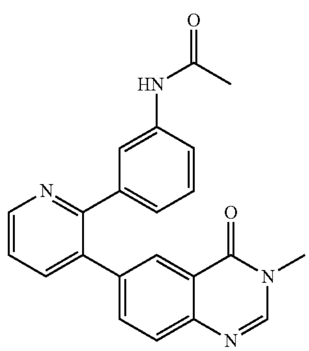 [SMILES: CC(=O)Nc1cccc(-c2ncccc2-c2ccc3ncn(C)c(=O)c3c2)c1] | Formic Acid(2) |
| 381 | 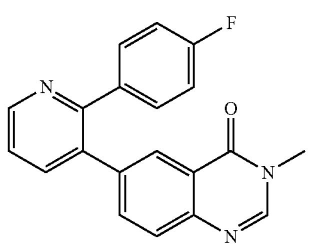 [SMILES: Cn1cnc2ccc(-c3cccnc3-c3ccc(F)cc3)cc2c1=O] | Formic Acid(2) |
| 382 | 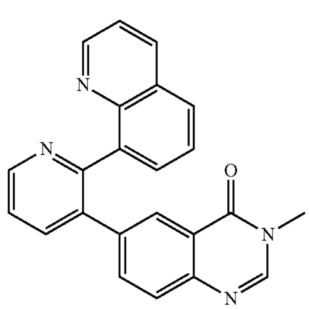 [SMILES: Cn1cnc2ccc(-c3cccnc3-c3cccc4cccnc34)cc2c1=O] | Formic Acid(2) |

-continued

| Cpd # | Structure | Salt |
|---|---|---|
| 383 | 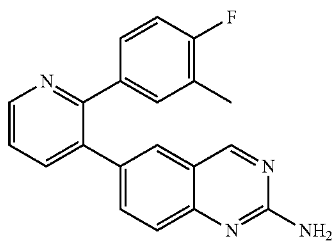 [SMILES: Cc1cc(-c2ncccc2-c2ccc3nc(N)ncc3c2)ccc1F] | Formic Acid(3) |
| 384 | 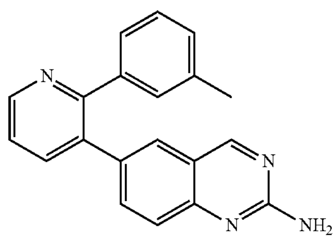 [SMILES: Cc1cccc(-c2ncccc2-c2ccc3nc(N)ncc3c2)c1] | Formic Acid(3) |
| 385 | 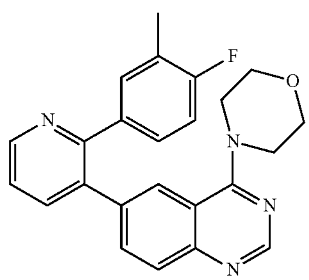 [SMILES: Cc1cc(-c2ncccc2-c2ccc3ncnc(N4CCOCC4)c3c2)ccc1F] | TFA(3) |
| 386 | 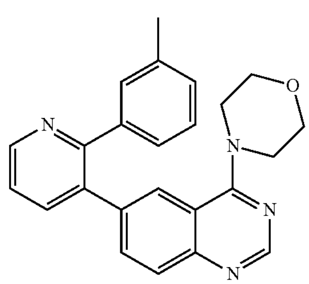 [SMILES: Cc1cccc(-c2ncccc2-c2ccc3ncnc(N4CCOCC4)c3c2)c1] | TFA(3) |
| 387 | 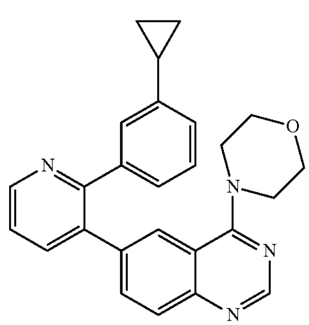 [SMILES: c1cc(-c2ncccc2-c2ccc3ncnc(N4CCOCC4)c3c2)cc(C2CC2)c1] | TFA(3) |

-continued

| Cpd # | Structure | Salt |
|---|---|---|
| 388 | 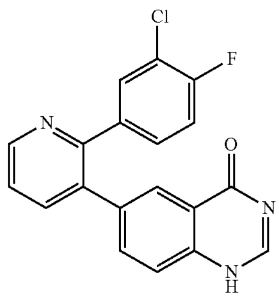 [SMILES: O=c1nc[nH]c2ccc(-c3cccnc3-c3ccc(F)c(Cl)c3)cc12] | Parent |
| 389 | 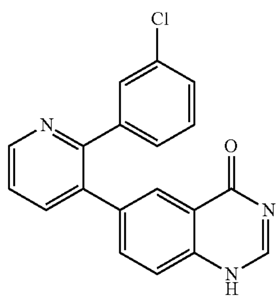 [SMILES: O=c1nc[nH]c2ccc(-c3cccnc3-c3cccc(Cl)c3)cc12] | Parent |
| 390 | 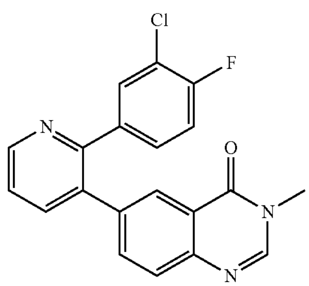 [SMILES: Cn1cnc2ccc(-c3cccnc3-c3ccc(F)c(Cl)c3)cc2c1=O] | TFA(2) |
| 391 | 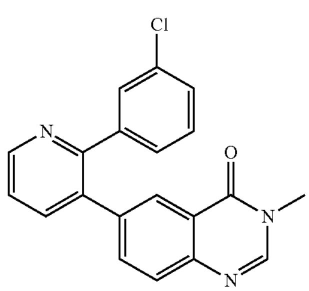 [SMILES: Cn1cnc2ccc(-c3cccnc3-c3cccc(Cl)c3)cc2c1=O] | TFA(2) |
| 392 | 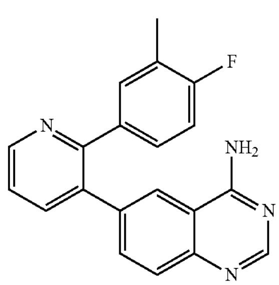 [SMILES: Cc1cc(-c2ncccc2-c2ccc3ncnc(N)c3c2)ccc1F] | Formic Acid(3) |

| Cpd # | Structure | Salt |
|---|---|---|
| 393 | 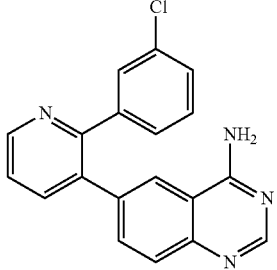 [SMILES: Nc1ncnc2ccc(-c3cccnc3-c3cccc(Cl)c3)cc12] | Formic Acid(3) |
| 394 | 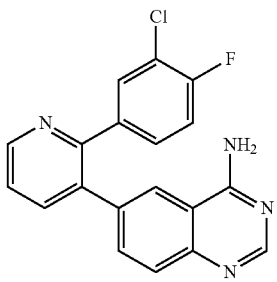 [SMILES: Nc1ncnc2ccc(-c3cccnc3-c3ccc(F)c(Cl)c3)cc12] | Formic Acid(3) |
| 395 | 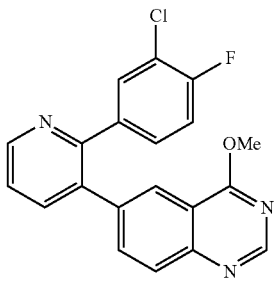 [SMILES: COc1ncnc2ccc(-c3cccnc3-c3ccc(F)c(Cl)c3)cc12] | Formic Acid(2) |
| 396 | 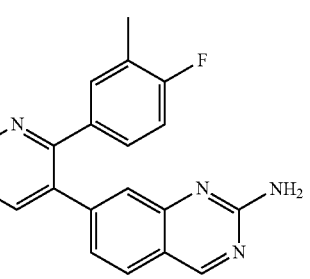 | Formic Acid(2) |
| 397 | 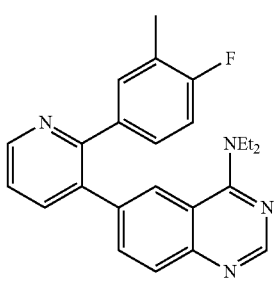 | Formic Acid(3) |

-continued

| Cpd # | Structure | Salt |
|---|---|---|
| 398 | 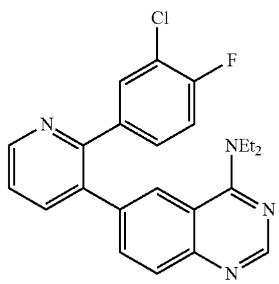 | Formic Acid(3) |
| 399 | 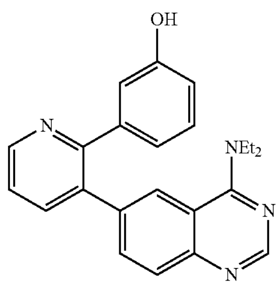 | Formic Acid(3) |
| 400 | 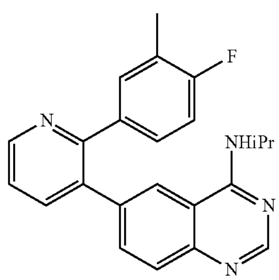 | Formic Acid(3) |
| 401 | 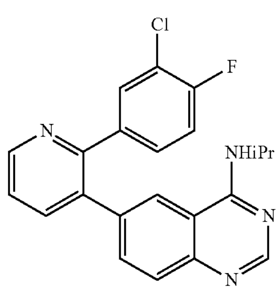 | Formic Acid(3) |
| 402 | 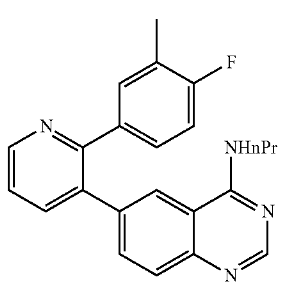 | Formic Acid(3) |

| Cpd # | Structure | Salt |
|---|---|---|
| 403 | 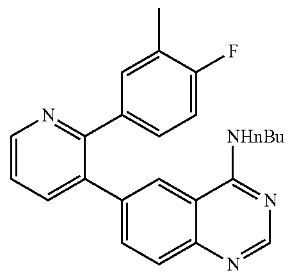 | Formic Acid(3) |
| 404 | 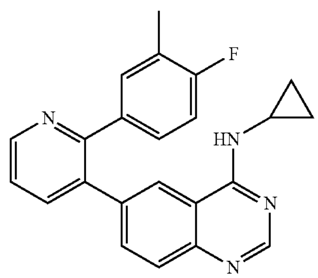 [SMILES: Cc1cc(-c2ncccc2-c2ccc3ncnc(NC4CC4)c3c2)ccc1F] | Formic Acid(3) |
| 405 | 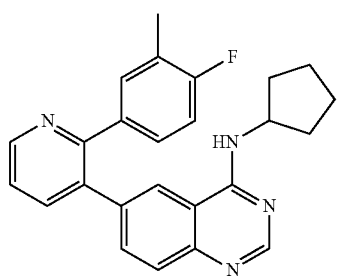 [SMILES: Cc1cc(-c2ncccc2-c2ccc3ncnc(NC4CCCC4)c3c2)ccc1F] | Formic Acid(3) |
| 406 | 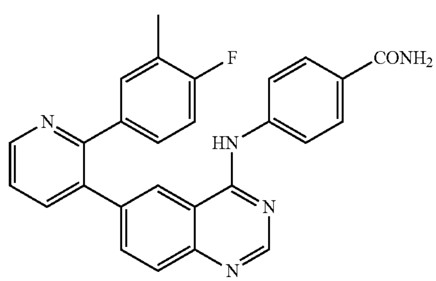 [SMILES: Cc1cc(-c2ncccc2-c2ccc3ncnc(Nc4ccc(C(N)=O)cc4)c3c2)ccc1F] | Formic Acid(3) |
| 407 | 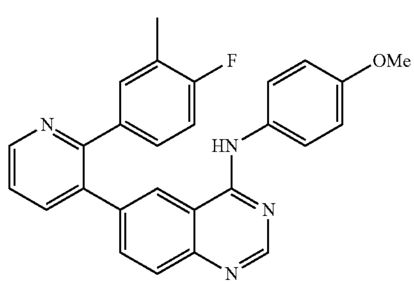 [SMILES: COc1ccc(Nc2ncnc3ccc(-c4cccnc4-c4ccc(F)c(C)c4)cc23)cc1] | Formic Acid(3) |

-continued

| Cpd # | Structure | Salt |
|---|---|---|
| 408 | 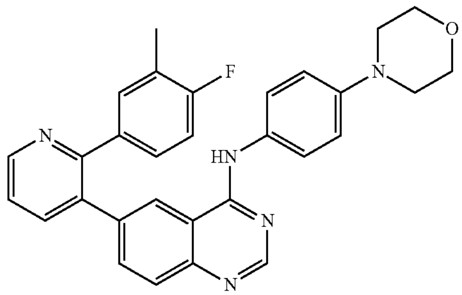 [SMILES: Cc1cc(-c2ncccc2-c2ccc3ncnc(Nc4ccc(N5CCOCC5)cc4)c3c2)ccc1F] | Formic Acid(3) |
| 409 | 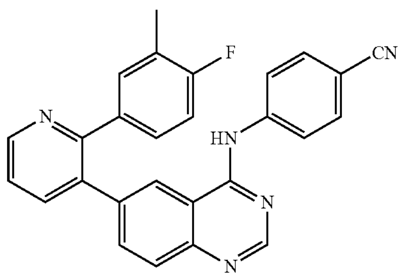 | Formic Acid(2) |
| 410 | 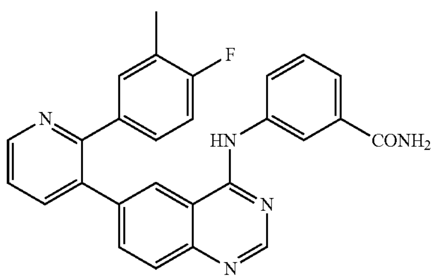 [SMILES: Cc1cc(-c2ncccc2-c2ccc3ncnc(Nc4cccc(C(N)=O)c4)c3c2)ccc1F] | Formic Acid(2) |
| 411 | 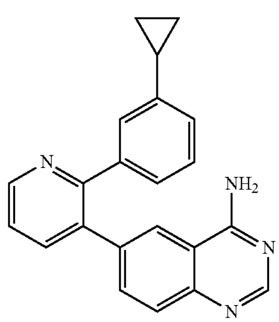 [SMILES: Nc1ncnc2ccc(-c3cccnc3-c3cccc(C4CC4)c3)cc12] | Formic Acid(3) |
| 412 | 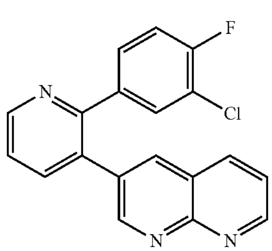 [SMILES: Fc1ccc(-c2ncccc2-c2cnc3ncccc3c2)cc1Cl] | Formic Acid(3) |

-continued

| Cpd # | Structure | Salt |
|---|---|---|
| 413 | 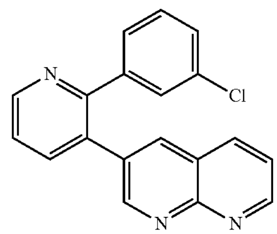 [SMILES: Clc1cccc(-c2ncccc2-c2cnc3ncccc3c2)c1] | Formic Acid(3) |
| 414 | 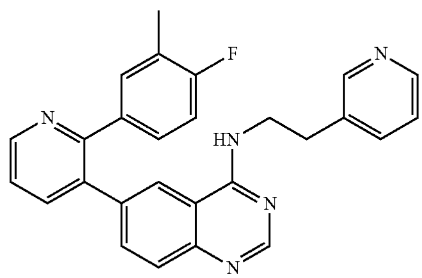 [SMILES: Cc1cc(-c2ncccc2-c2ccc3ncnc(NCCc4cccnc4)c3c2)ccc1F] | Formic Acid(3) |
| 415 | 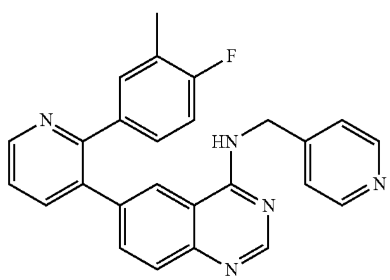 [SMILES: Cc1cc(-c2ncccc2-c2ccc3ncnc(NCc4ccncc4)c3c2)ccc1F] | Formic Acid(3) |
| 416 | 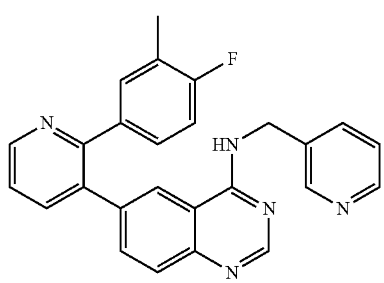 [SMILES: Cc1cc(-c2ncccc2-c2ccc3ncnc(NCc4cccnc4)c3c2)ccc1F] | Formic Acid(3) |
| 417 | 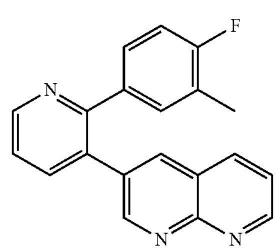 [SMILES: Cc1cc(-c2ncccc2-c2cnc3ncccc3c2)ccc1F] | Formic Acid(3) |

| Cpd # | Structure | Salt |
|---|---|---|
| 418 | 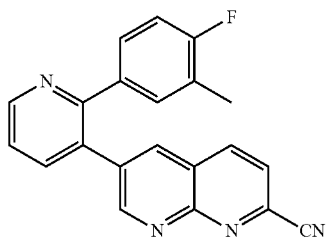 [SMILES: Cc1cc(-c2ncccc2-c2cnc3nc(C#N)ccc3c2)ccc1F] | Formic Acid(2) |
| 419 | 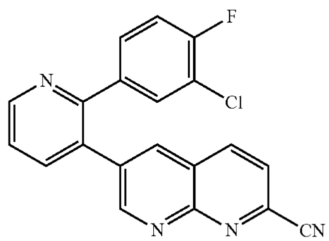 [SMILES: N#Cc1ccc2cc(-c3cccnc3-c3ccc(F)c(Cl)c3)cnc2n1] | Formic Acid(2) |
| 420 | 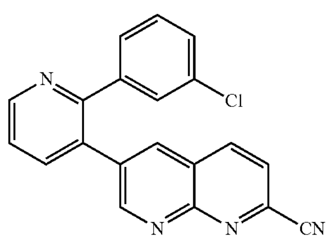 [SMILES: N#Cc1ccc2cc(-c3cccnc3-c3cccc(Cl)c3)cnc2n1] | Formic Acid(2) |
| 421 | 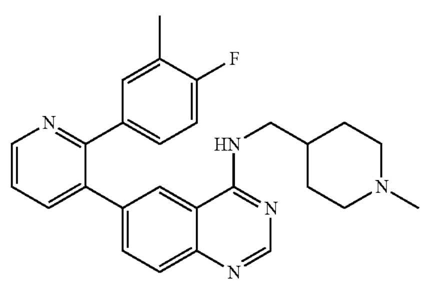 [SMILES: Cc1cc(-c2ncccc2-c2ccc3ncnc(NCC4CCN(C)CC4)c3c2)ccc1F] | Formic Acid(3) |
| 422 | 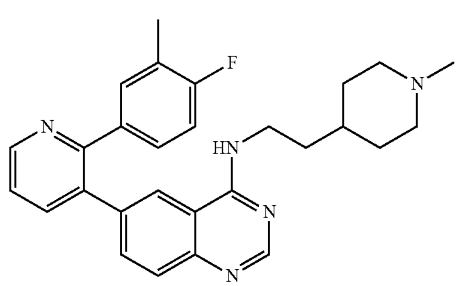 [SMILES: Cc1cc(-c2ncccc2-c2ccc3ncnc(NCCC4CCN(C)CC4)c3c2)ccc1F] | Formic Acid(3) |

| Cpd # | Structure | Salt |
|---|---|---|
| 423 | 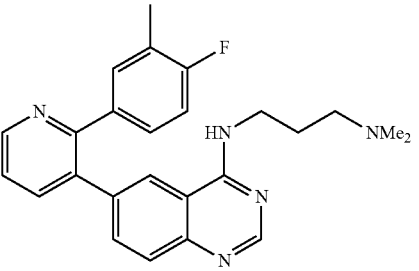 [SMILES: Cc1cc(-c2ncccc2-c2ccc3ncnc(NCCCN(C)C)c3c2)ccc1F] | TFA(3) |
| 424 | 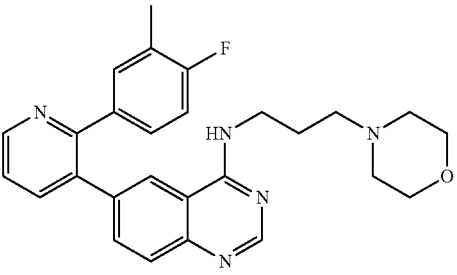 [SMILES: Cc1cc(-c2ncccc2-c2ccc3ncnc(NCCCN4CCOCC4)c3c2)ccc1F] | TFA(3) |
| 425 | 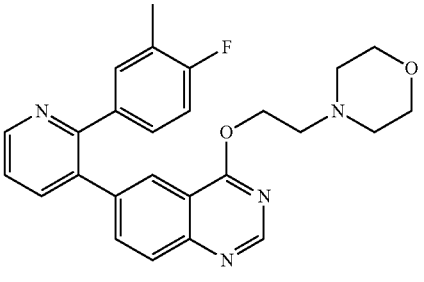 [SMILES: Cc1cc(-c2ncccc2-c2ccc3ncnc(OCCN4CCOCC4)c3c2)ccc1F] | Formic Acid(3) |
| 426 | 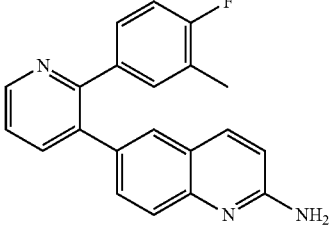 | Formic Acid(2) |
| 427 | 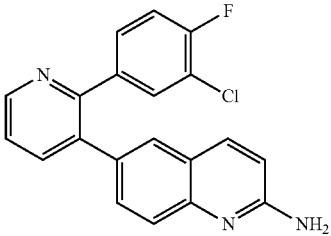 [SMILES: Nc1ccc2cc(-c3cccnc3-c3ccc(F)c(Cl)c3)ccc2n1] | Formic Acid(2) |

-continued
| Cpd # | Structure | Salt |
|---|---|---|
| 428 | 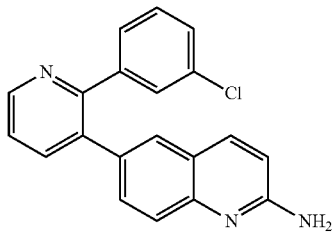 [SMILES: Nc1ccc2cc(-c3cccnc3-c3cccc(Cl)c3)ccc2n1] | Formic Acid(2) |
| 429 | 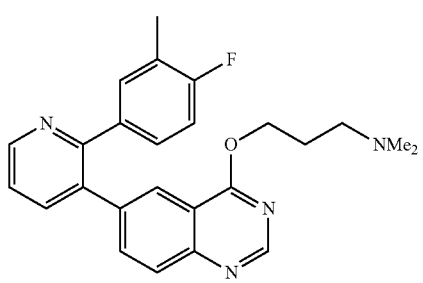 [SMILES: Cc1cc(-c2ncccc2-c2ccc3ncnc(OCCCN(C)C)c3c2)ccc1F] | Formic Acid(3) |
| 430 | 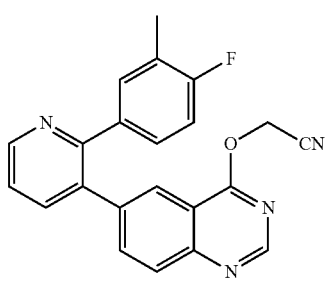 [SMILES: Cc1cc(-c2ncccc2-c2ccc3ncnc(OCC#N)c3c2)ccc1F] | Formic Acid(3) |
| 431 | 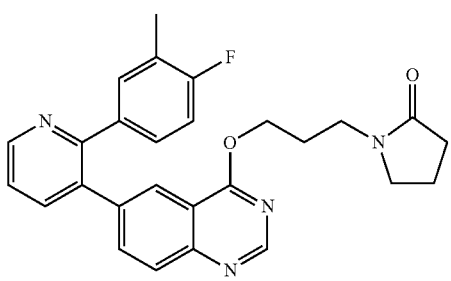 [SMILES: Cc1cc(-c2ncccc2-c2ccc3ncnc(OCCCN4CCCC4=O)c3c2)ccc1F] | Formic Acid(2) |
| 432 | 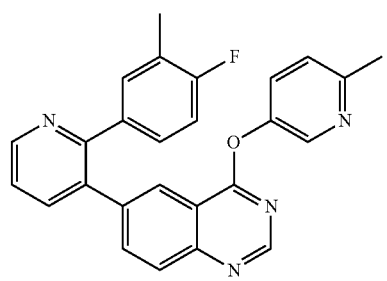 [SMILES: Cc1ccc(Oc2ncnc3ccc(-c4cccnc4-c4ccc(F)c(C)c4)cc23)cn1] | Formic Acid(3) |

| Cpd # | Structure | Salt |
|---|---|---|
| 433 | 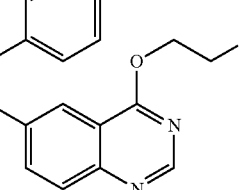 | Formic Acid(3) |
| 434 | 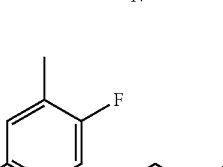 | Formic Acid(3) |
| 435 | 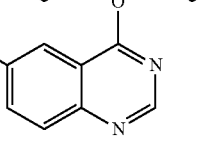 | Formic Acid(3) |
| 436 | 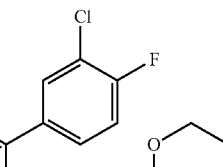 | Formic Acid(3) |
| 437 | 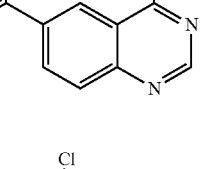 | Formic Acid(3) |

-continued

| Cpd # | Structure | Salt |
|---|---|---|
| 438 | 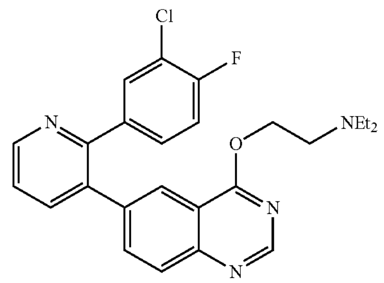 | Formic Acid(3) |
| 439 | 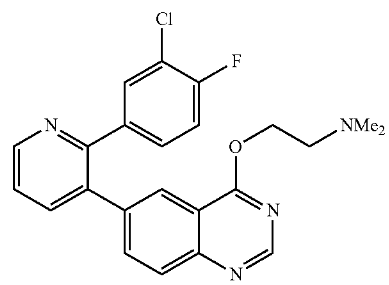 [SMILES: CN(C)CCOc1ncnc2ccc(-c3cccnc3-c3ccc(F)c(Cl)c3)cc12] | Formic Acid(3) |
| 440 | 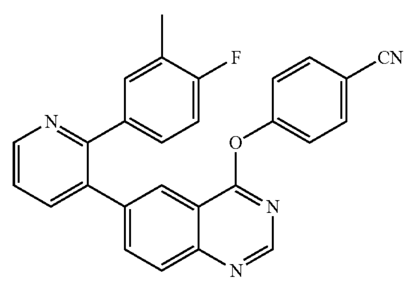 [SMILES: Cc1cc(-c2ncccc2-c2ccc3ncnc(Oc4ccc(C#N)cc4)c3c2)ccc1F] | Formic Acid(2) |
| 441 | 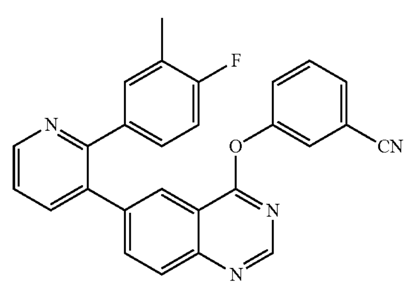 [SMILES: Cc1cc(-c2ncccc2-c2ccc3ncnc(Oc4cccc(C#N)c4)c3c2)ccc1F] | Formic Acid(2) |
| 442 | 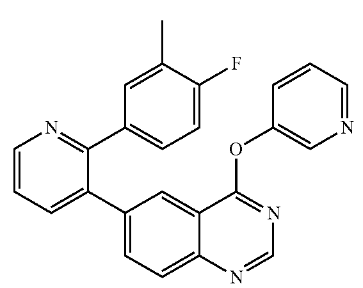 [SMILES: Cc1cc(-c2ncccc2-c2ccc3ncnc(Oc4cccnc4)c3c2)ccc1F] | Formic Acid(3) |

| Cpd # | Structure | Salt |
|---|---|---|
| 443 | 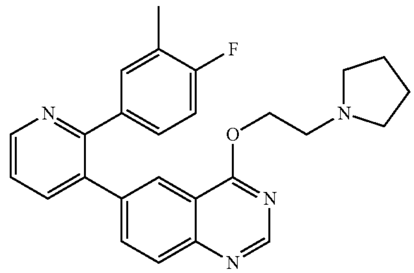 [SMILES: Cc1cc(-c2ncccc2-c2ccc3ncnc(OCCN4CCCC4)c3c2)ccc1F] | Formic Acid(3) |
| 444 | 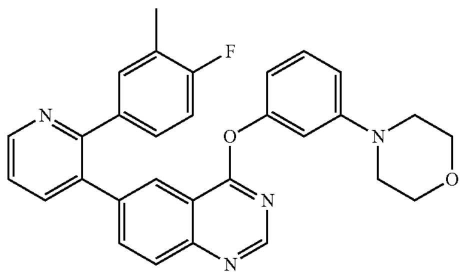 [SMILES: Cc1cc(-c2ncccc2-c2ccc3ncnc(Oc4cccc(N5CCOCC5)c4)c3c2)ccc1F] | Formic Acid(3) |
| 445 | 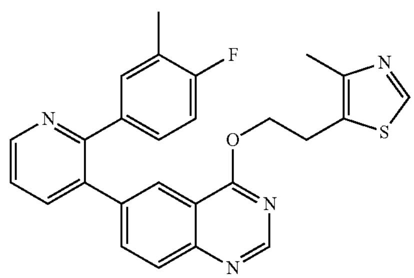 [SMILES: Cc1cc(-c2ncccc2-c2ccc3ncnc(OCCc4scnc4C)c3c2)ccc1F] | Formic Acid(3) |
| 446 | 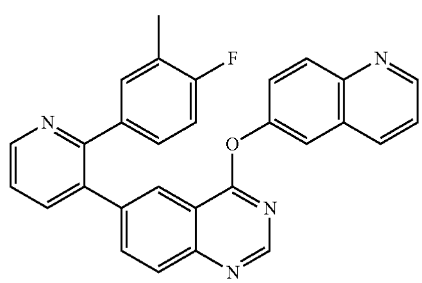 [SMILES: Cc1cc(-c2ncccc2-c2ccc3ncnc(Oc4ccc5ncccc5c4)c3c2)ccc1F] | Formic Acid(3) |
| 447 | 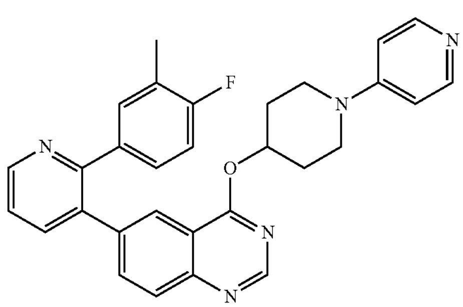 [SMILES: Cc1cc(-c2ncccc2-c2ccc3ncnc(OC4CCN(c5ccncc5)CC4)c3c2)ccc1F] | Formic Acid(3) |

-continued
| Cpd # | Structure | Salt |
|---|---|---|
| 448 | 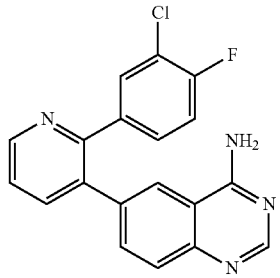 [SMILES: Nc1ncnc2ccc(-c3cccnc3-c3ccc(F)c(Cl)c3)cc12] | Parent |
| 449 | 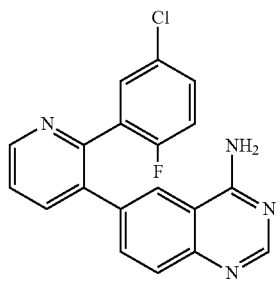 [SMILES: Nc1ncnc2ccc(-c3cccnc3-c3cc(Cl)ccc3F)cc12] | TFA(3) |
| 450 | 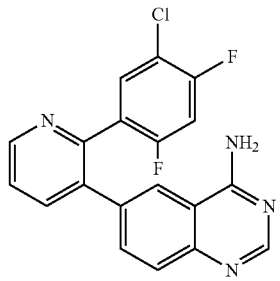 | TFA(3) |
| 451 | 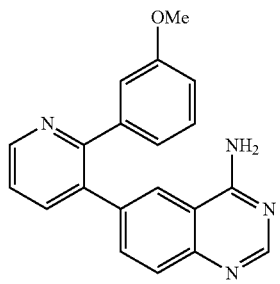 | TFA(3) |
| 452 | 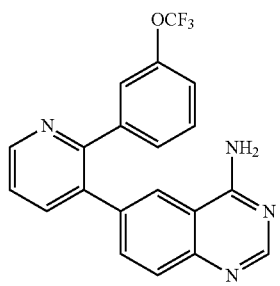 [SMILES: Nc1ncnc2ccc(-c3cccnc3-c3cccc(OC(F)(F)F)c3)cc12] | TFA(3) |

-continued

| Cpd # | Structure | Salt |
|---|---|---|
| 453 | 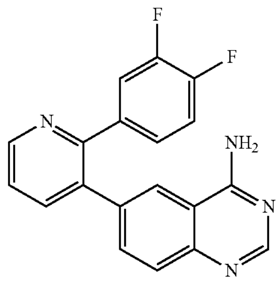 [SMILES: Nc1ncnc2ccc(-c3cccnc3-c3ccc(F)c(F)c3)cc12] | TFA(3) |
| 454 | 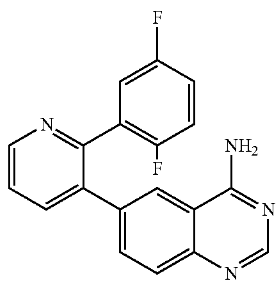 [SMILES: Nc1ncnc2ccc(-c3cccnc3-c3cc(F)ccc3F)cc12] | TFA(3) |
| 455 | 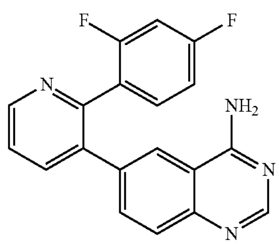 [SMILES: Nc1ncnc2ccc(-c3cccnc3-c3ccc(F)cc3F)cc12] | TFA(3) |
| 456 | 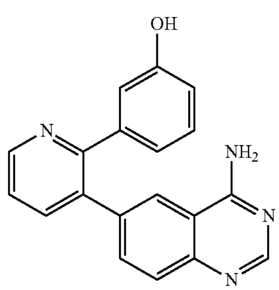 [SMILES: Nc1ncnc2ccc(-c3cccnc3-c3cccc(O)c3)cc12] | TFA(3) |
| 457 | 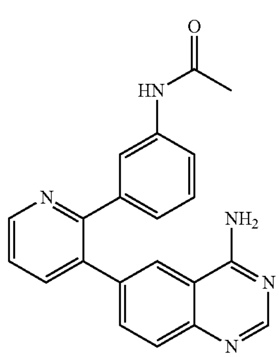 [SMILES: CC(=O)Nc1cccc(-c2ncccc2-c2ccc3ncnc(N)c3c2)c1] | TFA(3) |

| Cpd # | Structure | Salt |
|---|---|---|
| 458 | 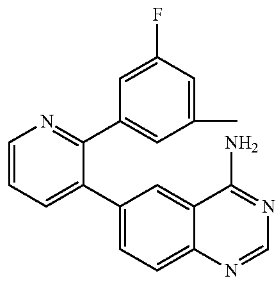 [SMILES: Cc1cc(F)cc(-c2ncccc2-c2ccc3ncnc(N)c3c2)c1] | Formic Acid(3) |
| 459 | 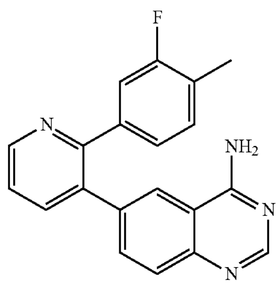 [SMILES: Cc1ccc(-c2ncccc2-c2ccc3ncnc(N)c3c2)cc1F] | Formic Acid(3) |
| 460 | 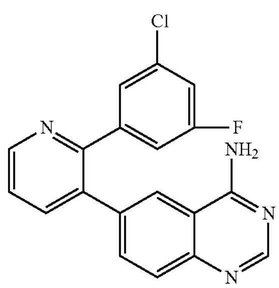 [SMILES: Nc1ncnc2ccc(-c3cccnc3-c3cc(F)cc(Cl)c3)cc12] | Formic Acid(3) |
| 461 | 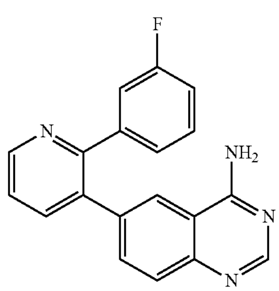 [SMILES: Nc1ncnc2ccc(-c3cccnc3-c3cccc(F)c3)cc12] | Formic Acid(3) |
| 462 | 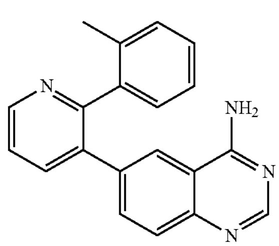 [SMILES: Cc1ccccc1-c1ncccc1-c1ccc2ncnc(N)c2c1] | Formic Acid(3) |

-continued

| Cpd # | Structure | Salt |
|---|---|---|
| 463 | 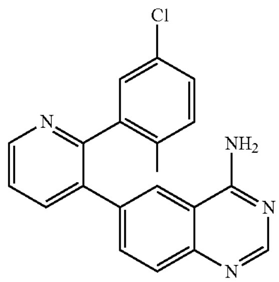 | Formic Acid(3) |
| 464 | 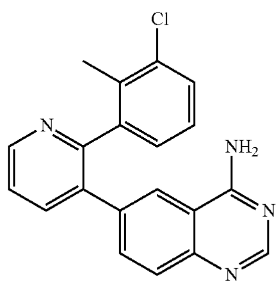 | Formic Acid(3) |
| 465 | 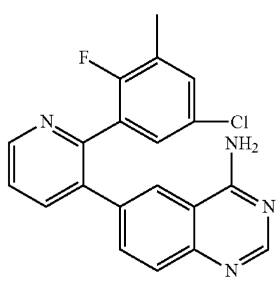 [SMILES: Cc1cc(Cl)cc(-c2ncccc2-c2ccc3ncnc(N)c3c2)c1F] | Formic Acid(3) |
| 466 | 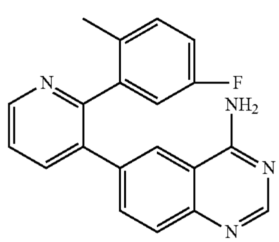 [SMILES: Cc1ccc(F)cc1-c1ncccc1-c1ccc2ncnc(N)c2c1] | Formic Acid(3) |
| 467 | 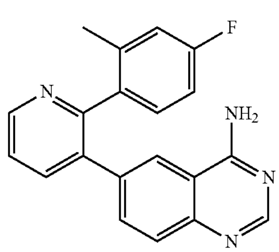 [SMILES: Cc1cc(F)ccc1-c1ncccc1-c1ccc2ncnc(N)c2c1] | Formic Acid(3) |

|Cpd #|Structure|Salt|
|---|---|---|
|468|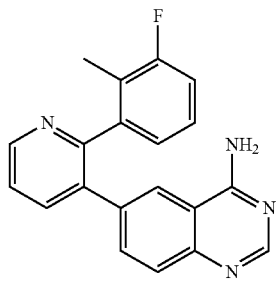 [SMILES: Cc1c(F)cccc1-c1ncccc1-c1ccc2ncnc(N)c2c1]|Formic Acid(3)|
|469|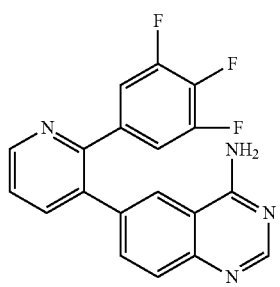 [SMILES: Nc1ncnc2ccc(-c3cccnc3-c3cc(F)c(F)c(F)c3)cc12]|Formic Acid(3)|
|470| 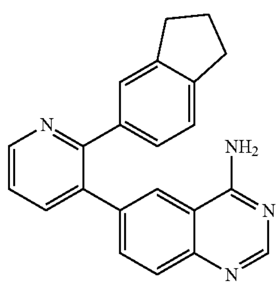 [SMILES: Nc1ncnc2ccc(-c3cccnc3-c3ccc4c(c3)CCC4)cc12] |Formic Acid(3)|
|471| 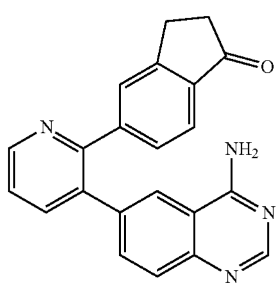 [SMILES: Nc1ncnc2ccc(-c3cccnc3-c3ccc4c(c3)CCC4=O)cc12] |Formic Acid(3)|
|472|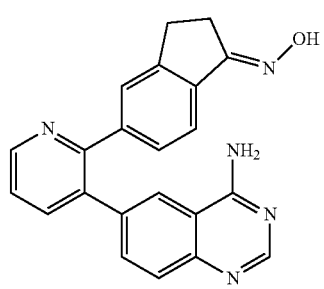 [SMILES: Nc1ncnc2ccc(-c3cccnc3-c3ccc4c(c3)CC/C4=N\O)cc12]|Formic Acid(3)|

-continued

| Cpd # | Structure | Salt |
|---|---|---|
| 473 | 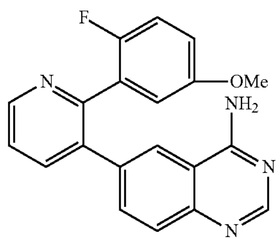 [SMILES: COc1ccc(F)c(-c2ncccc2-c2ccc3ncnc(N)c3c2)c1] | Formic Acid(3) |
| 474 | 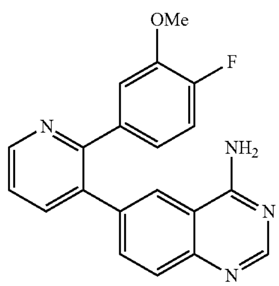 [SMILES: COc1cc(-c2ncccc2-c2ccc3ncnc(N)c3c2)ccc1F] | Formic Acid(3) |
| 475 | 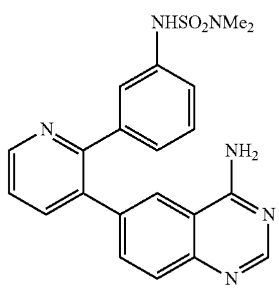 | Formic Acid(3) |
| 476 | 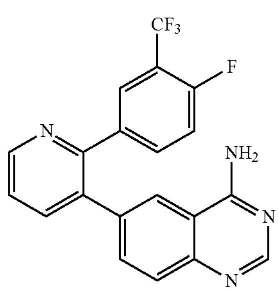 | Formic Acid(3) |
| 477 | 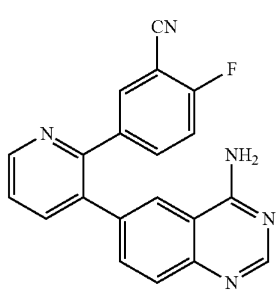 [SMILES: N#Cc1cc(-c2ncccc2-c2ccc3ncnc(N)c3c2)ccc1F] | Formic Acid(3) |

-continued

| Cpd # | Structure | Salt |
|---|---|---|
| 478 | 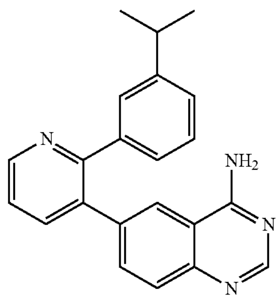 [SMILES: CC(C)c1cccc(-c2ncccc2-c2ccc3ncnc(N)c3c2)c1] | Formic Acid(3) |
| 479 | 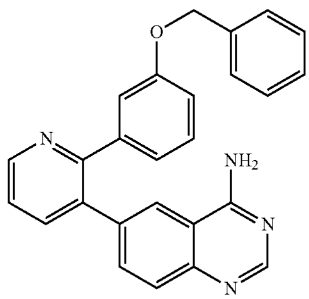 [SMILES: Nc1ncnc2ccc(-c3cccnc3-c3cccc(OCc4ccccc4)c3)cc12] | Formic Acid(3) |
| 480 | 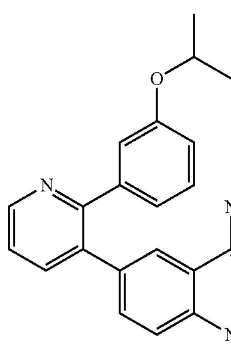 | Formic Acid(3) |
| 481 | 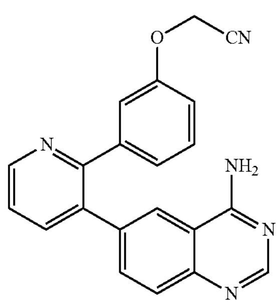 [SMILES: N#CCOc1cccc(-c2ncccc2-c2ccc3ncnc(N)c3c2)c1] | Formic Acid(3) |
| 482 | 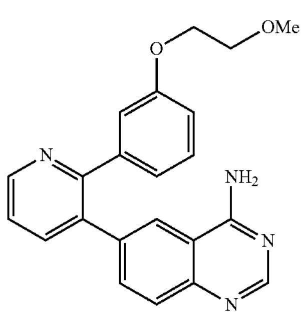 [SMILES: COCCOc1cccc(-c2ncccc2-c2ccc3ncnc(N)c3c2)c1] | Formic Acid(3) |

-continued

| Cpd # | Structure | Salt |
|---|---|---|
| 483 | 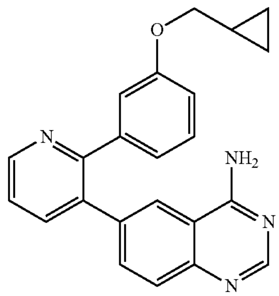 [SMILES: Nc1ncnc2ccc(-c3cccnc3-c3cccc(OCC4CC4)c3)cc12] | Formic Acid(3) |
| 484 | 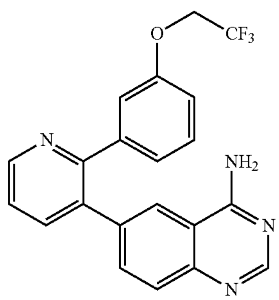 [SMILES: Nc1ncnc2ccc(-c3cccnc3-c3cccc(OCC(F)(F)F)c3)cc12] | Formic Acid(3) |
| 485 | 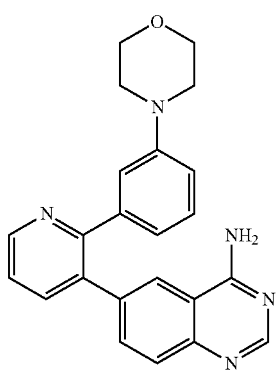 [SMILES: Nc1ncnc2ccc(-c3cccnc3-c3cccc(N4CCOCC4)c3)cc12] | Formic Acid(3) |
| 486 | 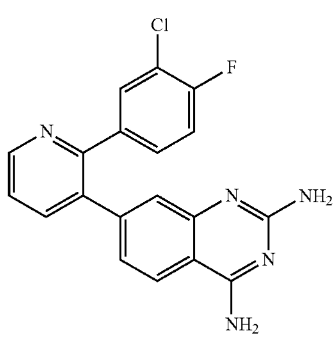 [SMILES: Nc1nc(N)c2ccc(-c3cccnc3-c3ccc(F)c(Cl)c3)cc2n1] | Formic Acid(3) |

| Cpd # | Structure | Salt |
|---|---|---|
| 487 | 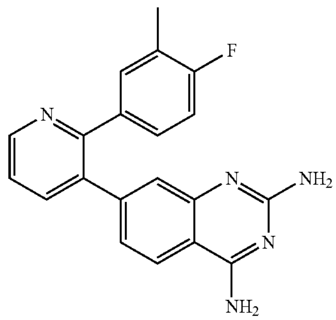 [SMILES: Cc1cc(-c2ncccc2-c2ccc3c(N)nc(N)nc3c2)ccc1F] | Formic Acid(3) |
| 488 | 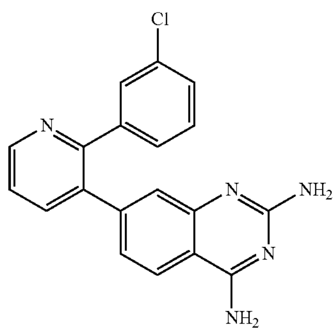 [SMILES: Nc1nc(N)c2ccc(-c3cccnc3-c3cccc(Cl)c3)cc2n1] | Formic Acid(3) |
| 489 | 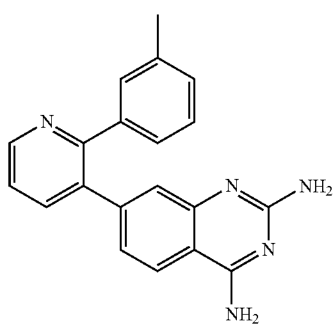 [SMILES: Cc1cccc(-c2ncccc2-c2ccc3c(N)nc(N)nc3c2)c1] | Formic Acid(3) |
| 490 | 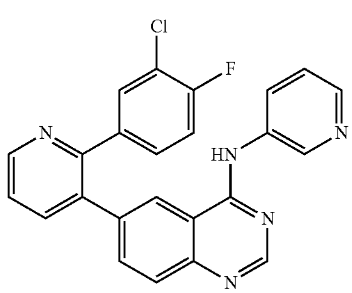 [SMILES: Fc1ccc(-c2ncccc2-c2ccc3ncnc(Nc4cccnc4)c3c2)cc1Cl] | Formic Acid(3) |

| Cpd # | Structure | Salt |
|---|---|---|
| 491 | 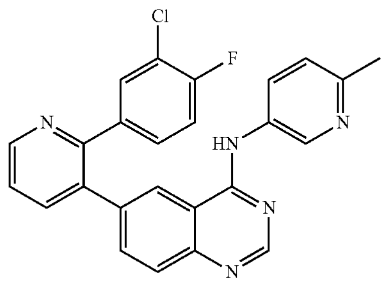 [SMILES: Cc1ccc(Nc2ncnc3ccc(-c4cccnc4-c4ccc(F)c(Cl)c4)cc23)cn1] | Parent |
| 492 | 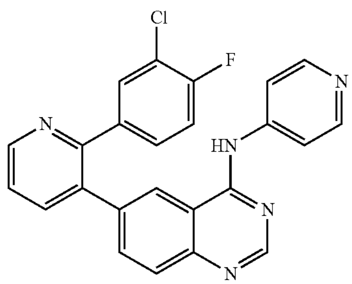 [SMILES: Fc1ccc(-c2ncccc2-c2ccc3ncnc(Nc4ccncc4)c3c2)cc1Cl] | Formic Acid(3) |
| 493 | 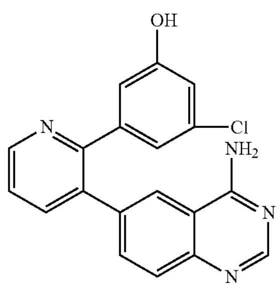 [SMILES: Nc1ncnc2ccc(-c3cccnc3-c3cc(O)cc(Cl)c3)cc12] | Formic Acid(3) |
| 494 | 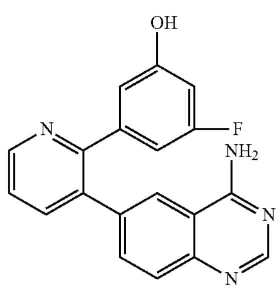 [SMILES: Nc1ncnc2ccc(-c3cccnc3-c3cc(O)cc(F)c3)cc12] | Formic Acid(3) |
| 495 | 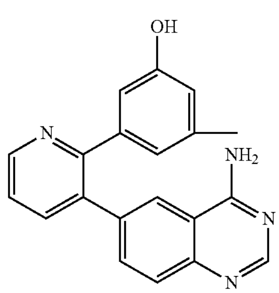 [SMILES: Cc1cc(O)cc(-c2ncccc2-c2ccc3ncnc(N)c3c2)c1] | Formic Acid(3) |

-continued

| Cpd # | Structure | Salt |
|---|---|---|
| 496 | 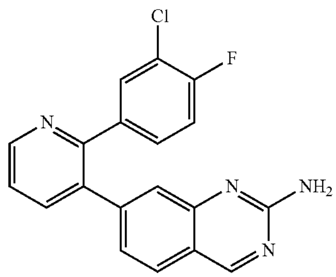 [SMILES: Nc1ncc2ccc(-c3cccnc3-c3ccc(F)c(Cl)c3)cc2n1] | Parent |
| 497 | 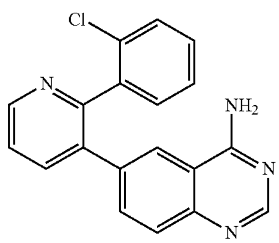 [SMILES: Nc1ncnc2ccc(-c3cccnc3-c3ccccc3Cl)cc12] | Formic Acid(3) |
| 498 | 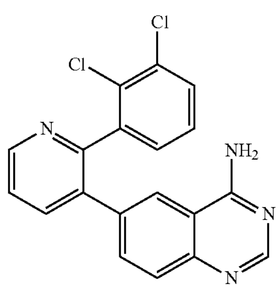 [SMILES: Nc1ncnc2ccc(-c3cccnc3-c3cccc(Cl)c3Cl)cc12] | Formic Acid(3) |
| 499 | 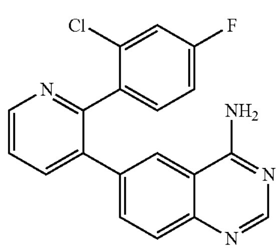 | Formic Acid(3) |
| 500 | 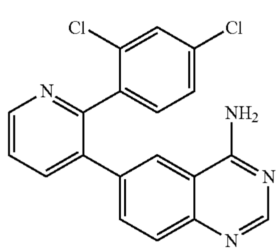 | Formic Acid(3) |

-continued

| Cpd # | Structure | Salt |
|---|---|---|
| 501 | 2,5-dichlorophenyl-pyridine linked to 4-aminoquinazoline | Formic Acid(3) |
| 502 | 2,4-difluoro-5-methoxyphenyl-pyridine linked to 4-aminoquinazoline | Formic Acid(3) |
| 503 | 2-chloro-3-fluorophenyl-pyridine linked to 4-aminoquinazoline | Formic Acid(3) |
| 504 | 2-chloro-5-fluorophenyl-pyridine linked to 4-aminoquinazoline | Formic Acid(3) |
| 505 | 2,4-dichloro-5-fluorophenyl-pyridine linked to 4-aminoquinazoline | Formic Acid(3) |

US 9,145,433 B2
233                                                                 234
-continued
| Cpd # | Structure | Salt |
|---|---|---|
| 506 | 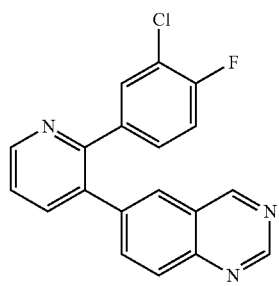 [SMILES: Fc1ccc(-c2ncccc2-c2ccc3ncncc3c2)cc1Cl] | Formic Acid(2) |
| 507 | 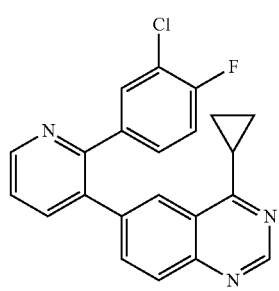 [SMILES: Fc1ccc(-c2ncccc2-c2ccc3ncnc(C4CC4)c3c2)cc1Cl] | TFA(2) |
| 508 | 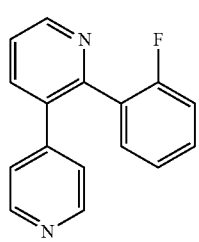 [SMILES: Fc1ccccc1-c1ncccc1-c1ccncc1] | Parent |
| 509 | 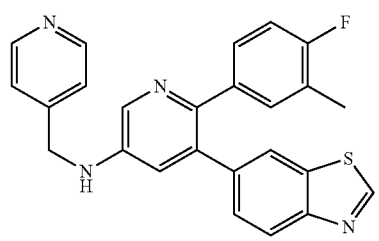 [SMILES: Cc1cc(-c2ncc(NCc3ccncc3)cc2-c2ccc3ncsc3c2)ccc1F] | TFA(3) |
| 510 | 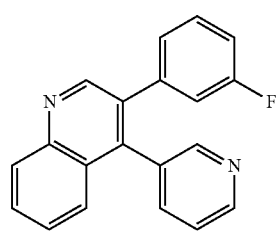 [SMILES: Fc1cccc(-c2cnc3ccccc3c2-c2cccnc2)c1] | Parent |

-continued
| Cpd # | Structure | Salt |
|---|---|---|
| 511 | 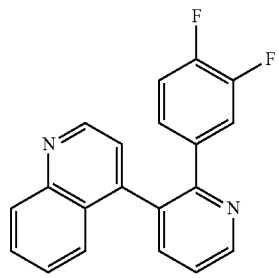 [SMILES: Fc1ccc(-c2ncccc2-c2ccnc3ccccc23)cc1F] | Parent |
| 512 | 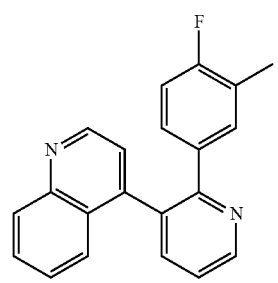 [SMILES: Cc1cc(-c2ncccc2-c2ccnc3ccccc23)ccc1F] | Parent |
| 513 | 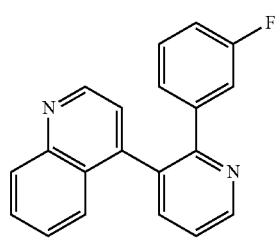 [SMILES: Fc1cccc(-c2ncccc2-c2ccnc3ccccc23)c1] | Parent |
| 514 | 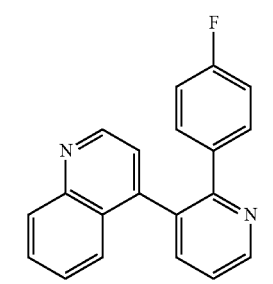 [SMILES: Fc1ccc(-c2ncccc2-c2ccnc3ccccc23)cc1] | Parent |
| 515 | 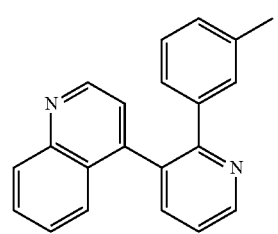 [SMILES: Cc1cccc(-c2ncccc2-c2ccnc3ccccc23)c1] | Parent |

-continued

| Cpd # | Structure | Salt |
|---|---|---|
| 516 | 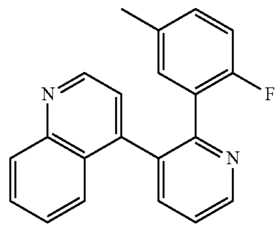 [SMILES: Cc1ccc(F)c(-c2ncccc2-c2ccnc3ccccc23)c1] | Parent |
| 517 | 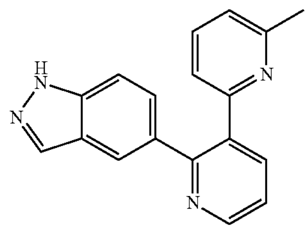 | Parent |
| 518 | 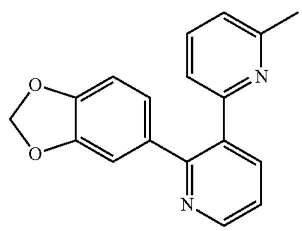 [SMILES: Cc1cccc(-c2cccnc2-c2ccc3c(c2)OCO3)n1] | Parent |
| 519 | 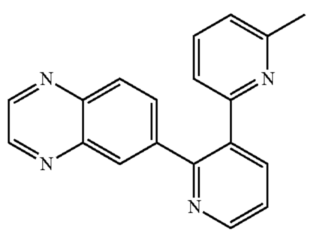 [SMILES: Cc1cccc(-c2cccnc2-c2ccc3nccnc3c2)n1] | Parent |
| 520 | 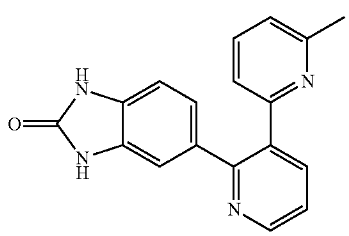 [SMILES: Cc1cccc(-c2cccnc2-c2ccc3[nH]c(=O)[nH]c3c2)n1] | Parent |
| 521 | 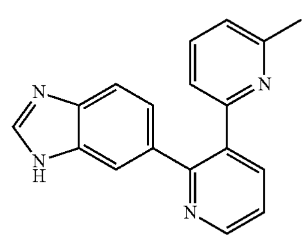 [SMILES: Cc1cccc(-c2cccnc2-c2ccc3nc[nH]c3c2)n1] | Parent |

-continued
| Cpd # | Structure | Salt |
|---|---|---|
| 522 | 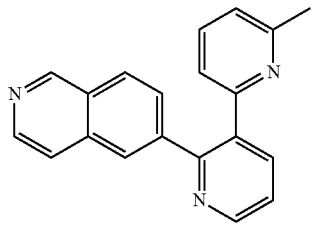 [SMILES: Cc1cccc(-c2cccnc2-c2ccc3cnccc3c2)n1] | Parent |
| 523 | 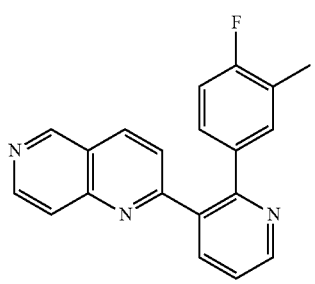 | Parent |
| 524 | 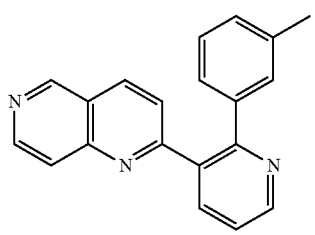 [SMILES: Cc1cccc(-c2ncccc2-c2ccc3cnccc3n2)c1] | Parent |
| 525 | 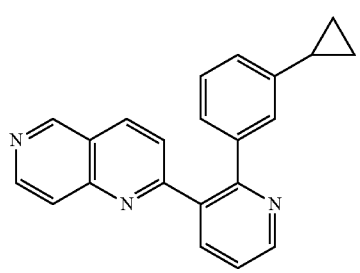 [SMILES: c1cc(-c2ncccc2-c2ccc3cnccc3n2)cc(C2CC2)c1] | Parent |
| 526 | 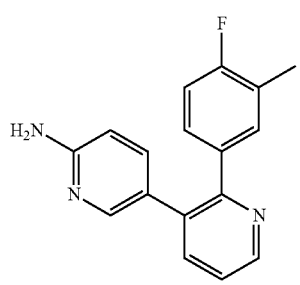 [SMILES: Cc1cc(-c2ncccc2-c2ccc(N)nc2)ccc1F] | Parent |

-continued
| Cpd # | Structure | Salt |
|---|---|---|
| 527 | 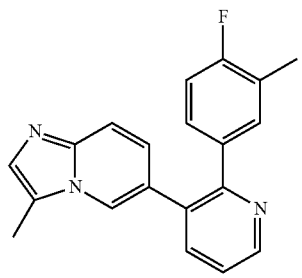 [SMILES: Cc1cc(-c2ncccc2-c2ccc3ncc(C)n3c2)ccc1F] | Parent |
| 528 | 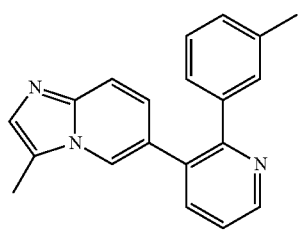 [SMILES: Cc1cccc(-c2ncccc2-c2ccc3ncc(C)n3c2)c1] | Parent |
| 529 | 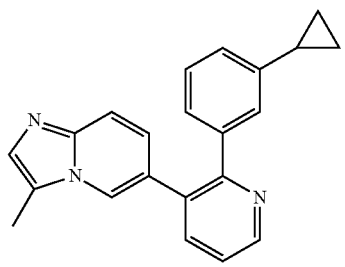 [SMILES: Cc1cnc2ccc(-c3cccnc3-c3cccc(C4CC4)c3)cn12] | Parent |
| 530 | 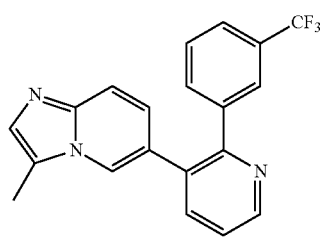 [SMILES: Cc1cnc2ccc(-c3cccnc3-c3cccc(C(F)(F)F)c3)cn12] | Parent |
| 531 | 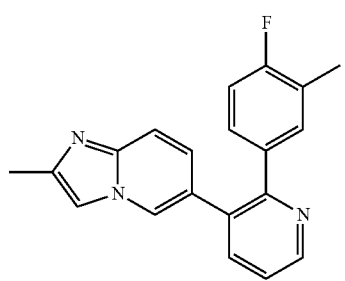 | Parent |

-continued
| Cpd # | Structure | Salt |
|---|---|---|
| 532 | 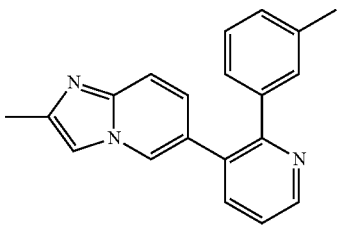 | Parent |
| 533 | 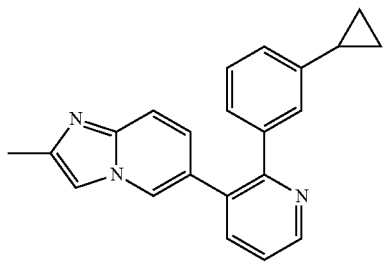 [SMILES: Cc1cn2cc(-c3cccnc3-c3cccc(C4CC4)c3)ccc2n1] | Parent |
| 534 | 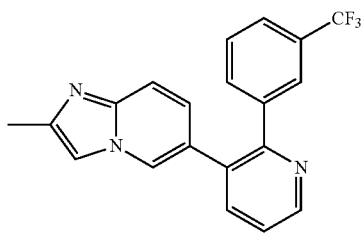 [SMILES: Cc1cn2cc(-c3cccnc3-c3cccc(C(F)(F)F)c3)ccc2n1] | Parent |
| 535 | 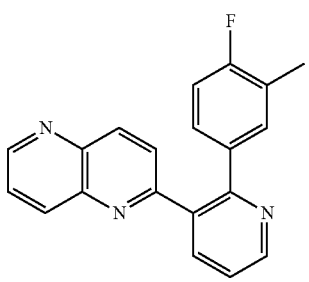 [SMILES: Cc1cc(-c2ncccc2-c2ccc3ncccc3n2)ccc1F] | Parent |
| 536 | 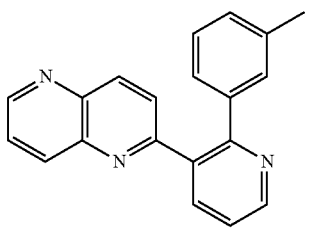 [SMILES: Cc1cccc(-c2ncccc2-c2ccc3ncccc3n2)c1] | Parent |

-continued
| Cpd # | Structure | Salt |
|---|---|---|
| 537 | 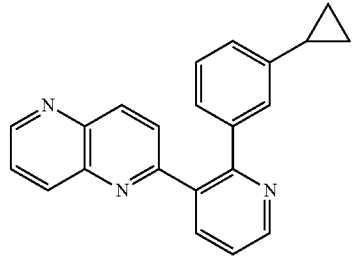 [SMILES: c1cc(-c2ncccc2-c2ccc3ncccc3n2)cc(C2CC2)c1] | Parent |
| 538 | 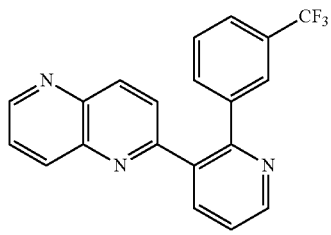 [SMILES: FC(F)(F)c1cccc(-c2ncccc2-c2ccc3ncccc3n2)c1] | Parent |
| 539 | 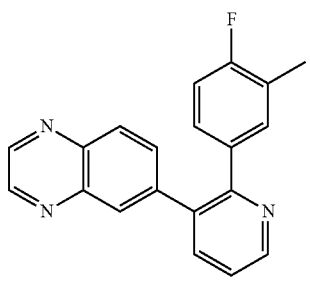 [SMILES: Cc1cc(-c2ncccc2-c2ccc3nccnc3c2)ccc1F] | Parent |
| 540 | 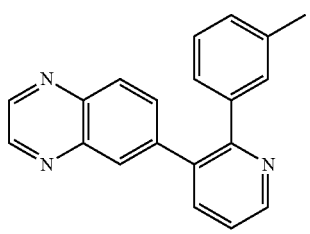 [SMILES: Cc1cccc(-c2ncccc2-c2ccc3nccnc3c2)c1] | Parent |
| 541 | 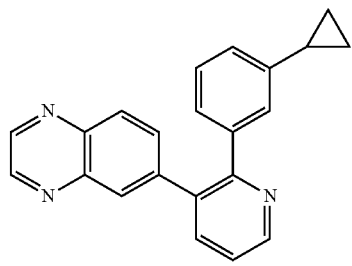 [SMILES: c1cc(-c2ncccc2-c2ccc3nccnc3c2)cc(C2CC2)c1] | Parent |

US 9,145,433 B2
247                                                                 248
-continued
| Cpd # | Structure | Salt |
|---|---|---|
| 542 | 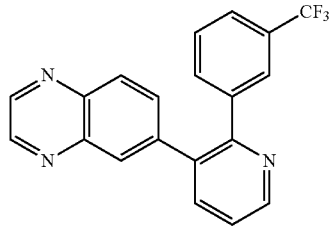 [SMILES: FC(F)(F)c1cccc(-c2ncccc2-c2ccc3nccnc3c2)c1] | Parent |
| 543 | 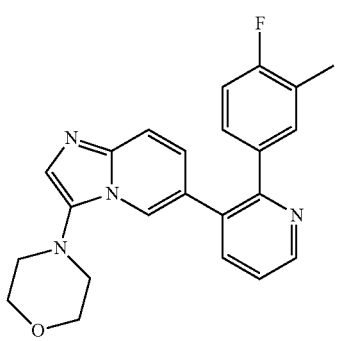 [SMILES: Cc1cc(-c2ncccc2-c2ccc3ncc(N4CCOCC4)n3c2)ccc1F] | Parent |
| 544 | 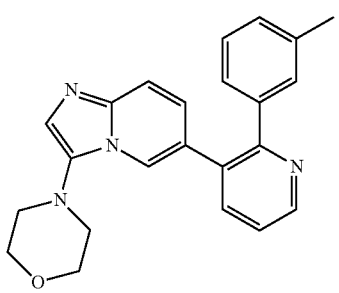 [SMILES: Cc1cccc(-c2ncccc2-c2ccc3ncc(N4CCOCC4)n3c2)c1] | Parent |
| 545 | 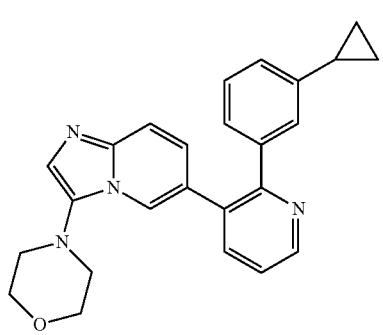 [SMILES: c1cc(-c2ncccc2-c2ccc3ncc(N4CCOCC4)n3c2)cc(C2CC2)c1] | Parent |
| 546 | 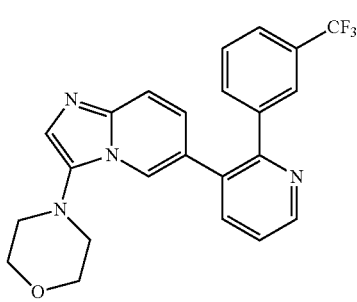 [SMILES: FC(F)(F)c1cccc(-c2ncccc2-c2ccc3ncc(N4CCOCC4)n3c2)c1] | Parent |

| Cpd # | Structure | Salt |
|---|---|---|
| 547 | 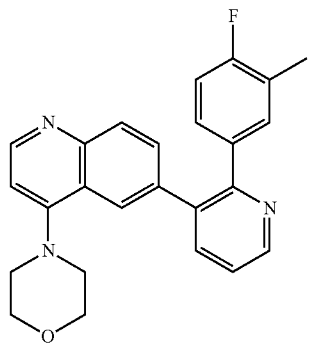 [SMILES: Cc1cc(-c2ncccc2-c2ccc3nccc(N4CCOCC4)c3c2)ccc1F] | Parent |
| 548 | 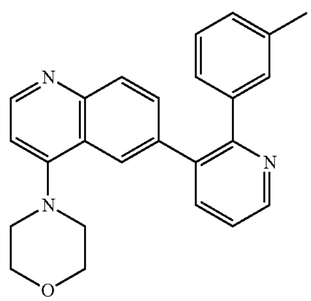 [SMILES: Cc1cccc(-c2ncccc2-c2ccc3nccc(N4CCOCC4)c3c2)c1] | Parent |
| 549 | 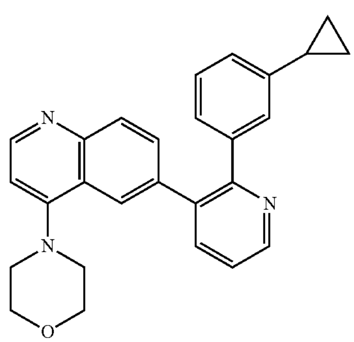 [SMILES: c1cc(-c2ncccc2-c2ccc3nccc(N4CCOCC4)c3c2)cc(C2CC2)c1] | Parent |
| 550 | 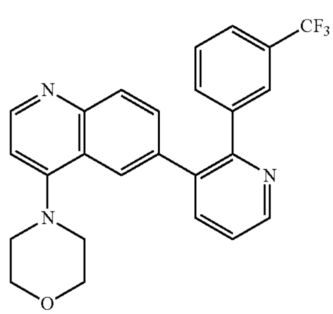 [SMILES: FC(F)(F)c1cccc(-c2ncccc2-c2ccc3nccc(N4CCOCC4)c3c2)c1] | Parent |

-continued
| Cpd # | Structure | Salt |
|---|---|---|
| 551 | 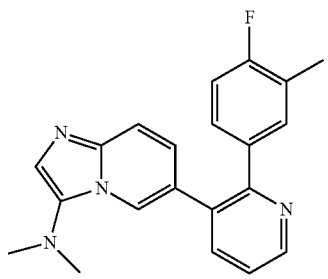 | Parent |
| 552 | 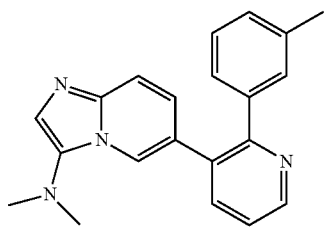 | Parent |
| 553 | 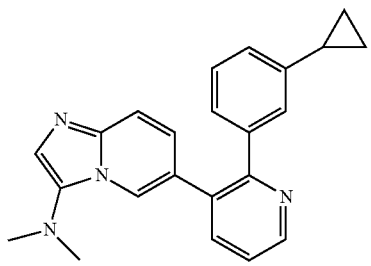 [SMILES: CN(C)c1cnc2ccc(-c3cccnc3-c3cccc(C4CC4)c3)cn12] | Parent |
| 554 | 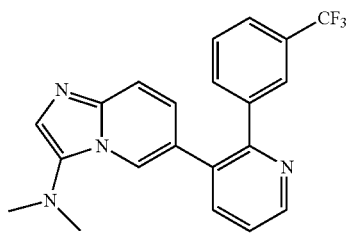 [SMILES: CN(C)c1cnc2ccc(-c3cccnc3-c3cccc(C(F)(F)F)c3)cn12] | Parent |
| 555 | 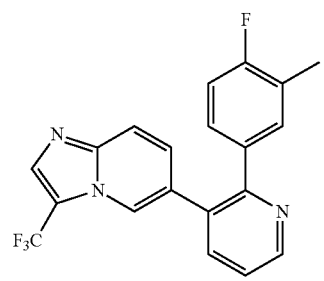 [SMILES: Cc1cc(-c2ncccc2-c2ccc3ncc(C(F)(F)F)n3c2)ccc1F] | Parent |

| Cpd # | Structure | Salt |
|---|---|---|
| 556 | 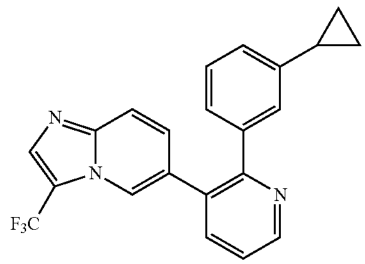 [SMILES: FC(F)(F)c1cnc2ccc(-c3cccnc3-c3cccc(C4CC4)c3)cn12] | Parent |
| 557 | 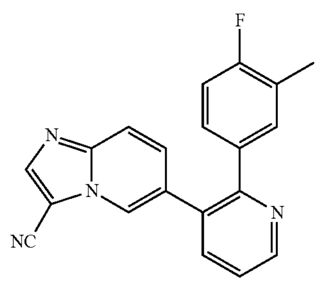 [SMILES: Cc1cc(-c2ncccc2-c2ccc3ncc(C#N)n3c2)ccc1F] | Parent |
| 558 | 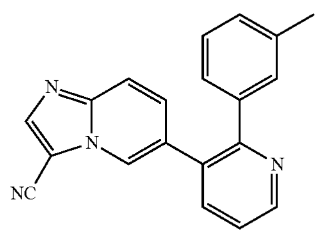 [SMILES: Cc1cccc(-c2ncccc2-c2ccc3ncc(C#N)n3c2)c1] | Parent |
| 559 | 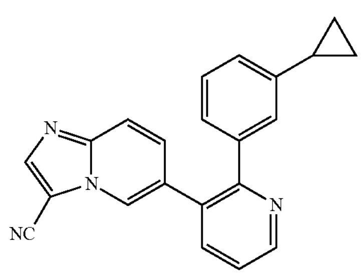 [SMILES: N#Cc1cnc2ccc(-c3cccnc3-c3cccc(C4CC4)c3)cn12] | Parent |
| 560 | 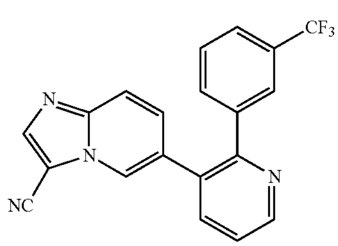 [SMILES: N#Cc1cnc2ccc(-c3cccnc3-c3cccc(C(F)(F)F)c3)cn12] | Parent |

-continued

| Cpd # | Structure | Salt |
|---|---|---|
| 561 | 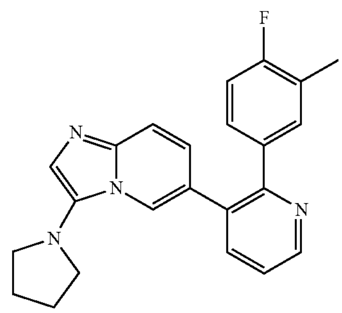 [SMILES: Cc1cc(-c2ncccc2-c2ccc3ncc(N4CCCC4)n3c2)ccc1F] | Parent |
| 562 | 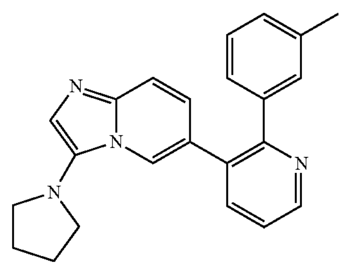 [SMILES: Cc1cccc(-c2ncccc2-c2ccc3ncc(N4CCCC4)n3c2)c1] | Parent |
| 563 | 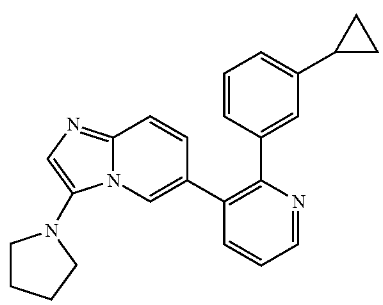 [SMILES: c1cc(-c2ncccc2-c2ccc3ncc(N4CCCC4)n3c2)cc(C2CC2)c1] | Parent |
| 564 | 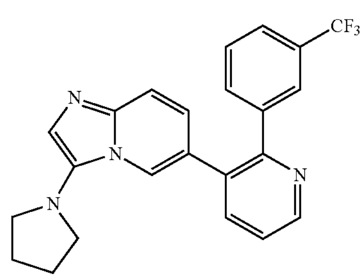 [SMILES: FC(F)(F)c1cccc(-c2ncccc2-c2ccc3ncc(N4CCCC4)n3c2)c1] | Parent |
| 565 | 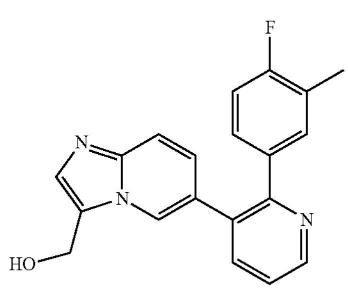 [SMILES: Cc1cc(-c2ncccc2-c2ccc3ncc(CO)n3c2)ccc1F] | Parent |

| Cpd # | Structure | Salt |
|---|---|---|
| 566 | 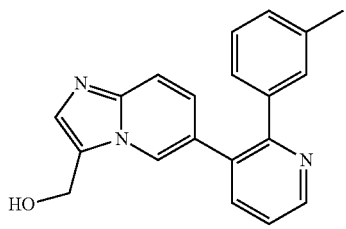 [SMILES: Cc1cccc(-c2ncccc2-c2ccc3ncc(CO)n3c2)c1] | Parent |
| 567 | 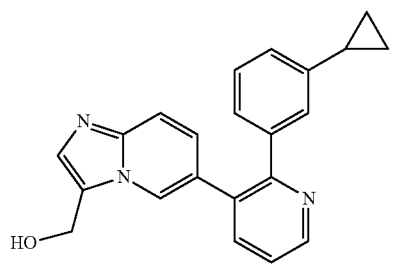 [SMILES: OCc1cnc2ccc(-c3cccnc3-c3cccc(C4CC4)c3)cn12] | Parent |
| 568 | 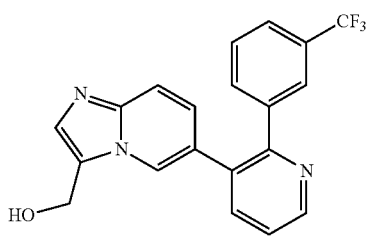 [SMILES: OCc1cnc2ccc(-c3cccnc3-c3cccc(C(F)(F)F)c3)cn12] | Parent |
| 569 | 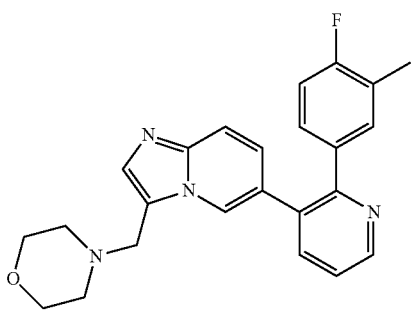 [SMILES: Cc1cc(-c2ncccc2-c2ccc3ncc(CN4CCOCC4)n3c2)ccc1F] | Parent |
| 570 | 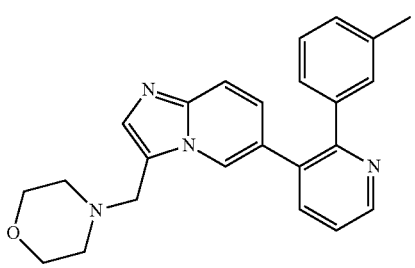 [SMILES: Cc1cccc(-c2ncccc2-c2ccc3ncc(CN4CCOCC4)n3c2)c1] | Parent |

-continued
| Cpd # | Structure | Salt |
|---|---|---|
| 571 | 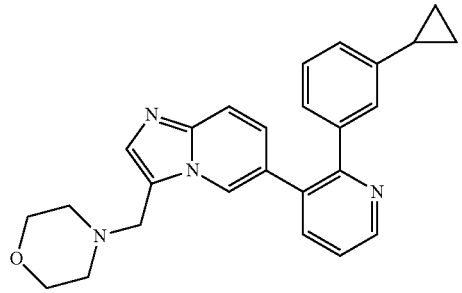 [SMILES: c1cc(-c2ncccc2-c2ccc3ncc(CN4CCOCC4)n3c2)cc(C2CC2)c1] | Parent |
| 572 | 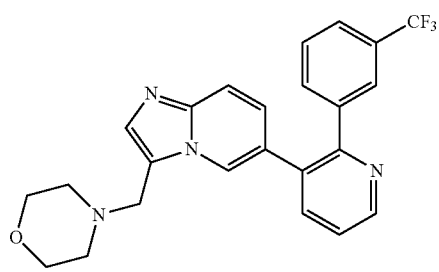 [SMILES: FC(F)(F)c1cccc(-c2ncccc2-c2ccc3ncc(CN4CCOCC4)n3c2)c1] | Parent |
| 573 | 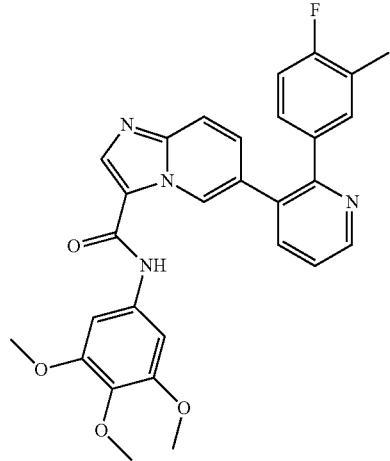 | Parent |
| 574 | 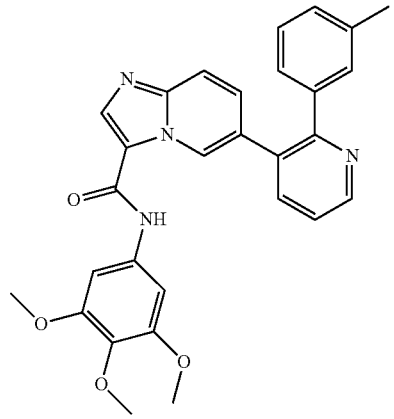 | Parent |

-continued
| Cpd # | Structure | Salt |
|---|---|---|
| 575 | 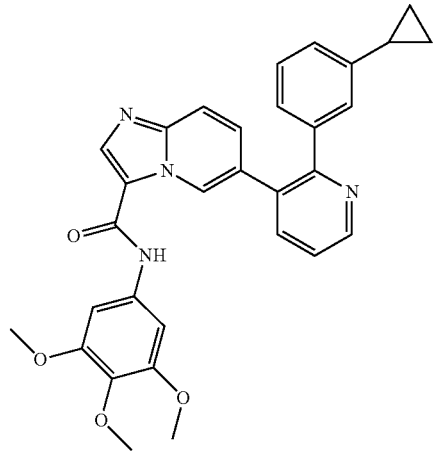 [SMILES: COc1cc(NC(=O)c2cnc3ccc(-c4cccnc4-c4cccc(C5CC5)c4)cn23)cc(OC)c1OC] | Parent |
| 576 | 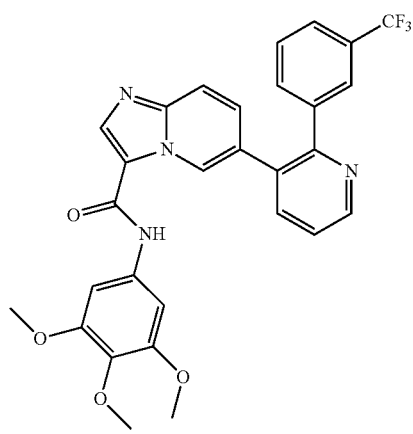 [SMILES: COc1cc(NC(=O)c2cnc3ccc(-c4cccnc4-c4cccc(C(F)(F)F)c4)cn23)cc(OC)c1OC] | Parent |
| 577 | 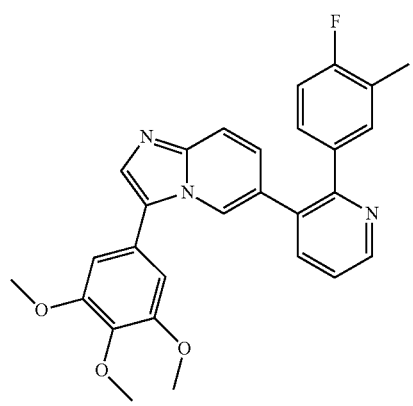 | Parent |

-continued
| Cpd # | Structure | Salt |
|---|---|---|
| 578 | 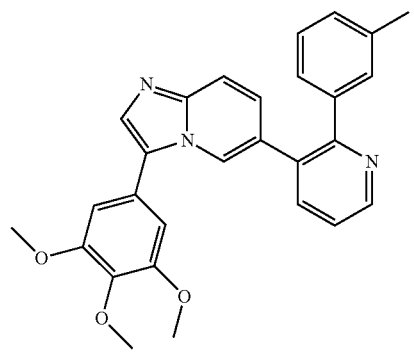 | Parent |
| 579 | 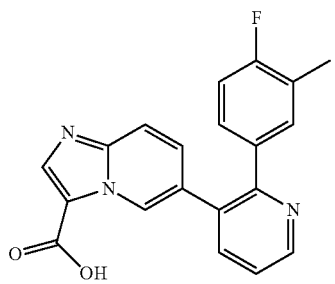 [SMILES: Cc1cc(-c2ncccc2-c2ccc3ncc(C(=O)O)n3c2)ccc1F] | Parent |
| 580 | 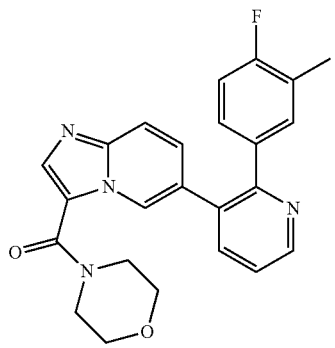 [SMILES: Cc1cc(-c2ncccc2-c2ccc3ncc(C(=O)N4CCOCC4)n3c2)ccc1F] | Parent |
| 581 | 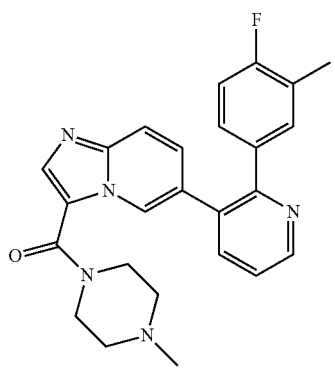 [SMILES: Cc1cc(-c2ncccc2-c2ccc3ncc(C(=O)N4CCN(C)CC4)n3c2)ccc1F] | Parent |

-continued

| Cpd # | Structure | Salt |
|---|---|---|
| 582 | 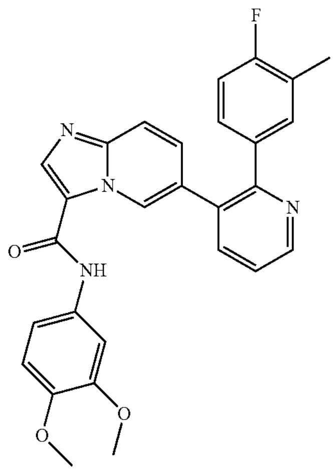 [SMILES: COc1ccc(NC(=O)c2cnc3ccc(-c4cccnc4-c4ccc(F)c(C)c4)cn23)cc1OC] | Parent |
| 583 | 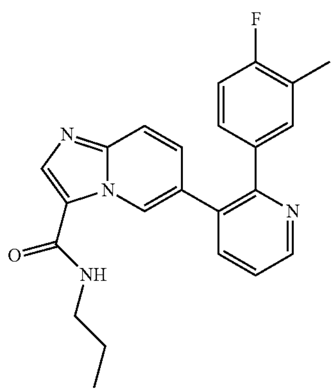 [SMILES: CCCNC(=O)c1cnc2ccc(-c3cccnc3-c3ccc(F)c(C)c3)cn12] | Parent |
| 584 | 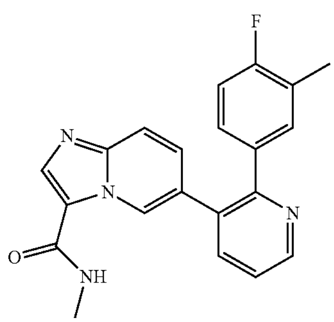 [SMILES: CNC(=O)c1cnc2ccc(-c3cccnc3-c3ccc(F)c(C)c3)cn12] | Parent |
| 585 | 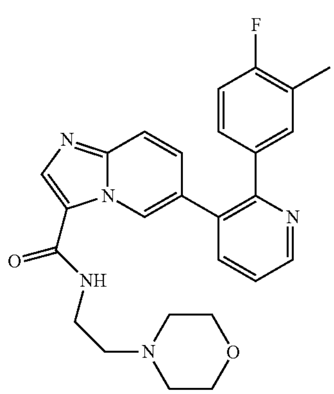 [SMILES: Cc1cc(-c2ncccc2-c2ccc3ncc(C(=O)NCCN4CCOCC4)n3c2)ccc1F] | Parent |

-continued
| Cpd # | Structure | Salt |
|---|---|---|
| 586 | 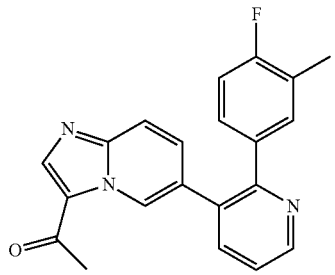 [SMILES: CC(=O)c1cnc2ccc(-c3cccnc3-c3ccc(F)c(C)c3)cn12] | Parent |
| 587 | 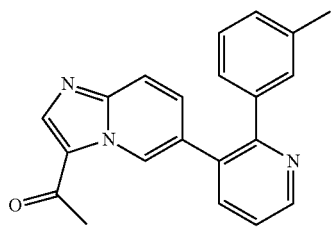 [SMILES: CC(=O)c1cnc2ccc(-c3cccnc3-c3cccc(C)c3)cn12] | Parent |
| 588 | 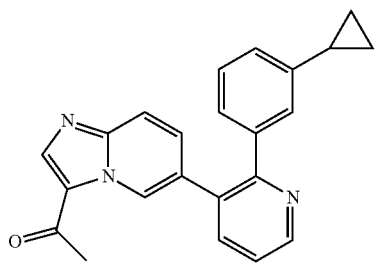 [SMILES: CC(=O)c1cnc2ccc(-c3cccnc3-c3cccc(C4CC4)c3)cn12] | Parent |
| 589 | 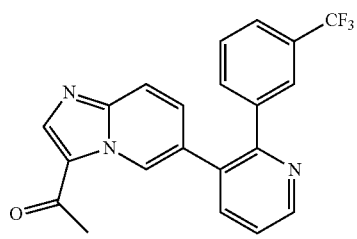 [SMILES: CC(=O)c1cnc2ccc(-c3cccnc3-c3cccc(C(F)(F)F)c3)cn12] | Parent |

-continued
| Cpd # | Structure | Salt |
|---|---|---|
| 590 | 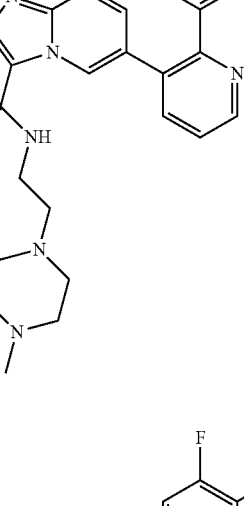 | Parent |
| 591 | 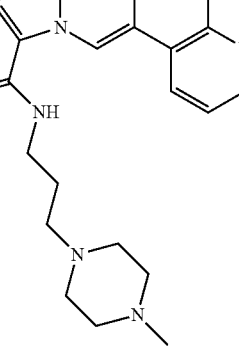 | Parent |
| 592 | 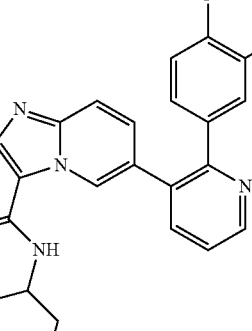 | Parent |

-continued

| Cpd # | Structure | Salt |
|---|---|---|
| 593 | 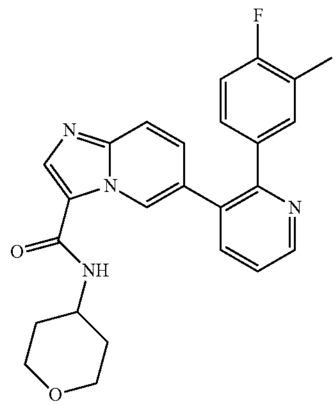 [SMILES: Cc1cc(-c2ncccc2-c2ccc3ncc(C(=O)NC4CCOCC4)n3c2)ccc1F] | Parent |
| 594 | 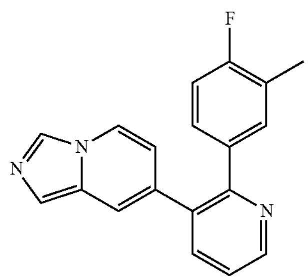 [SMILES: Cc1cc(-c2ncccc2-c2ccn3cncc3c2)ccc1F] | Parent |
| 595 | 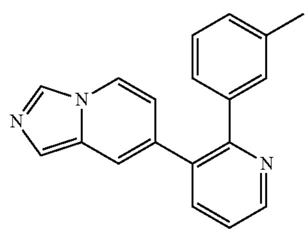 [SMILES: Cc1cccc(-c2ncccc2-c2ccn3cncc3c2)c1] | Parent |
| 596 | 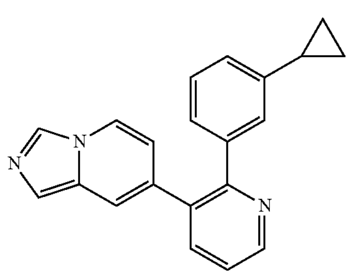 [SMILES: c1cc(-c2ncccc2-c2ccn3cncc3c2)cc(C2CC2)c1] | Parent |
| 597 | 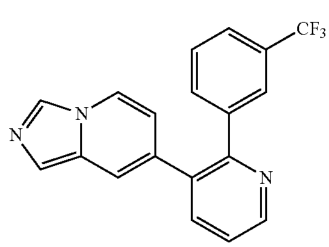 [SMILES: FC(F)(F)c1cccc(-c2ncccc2-c2ccn3cncc3c2)c1] | Parent |

| Cpd # | Structure | Salt |
|---|---|---|
| 598 | 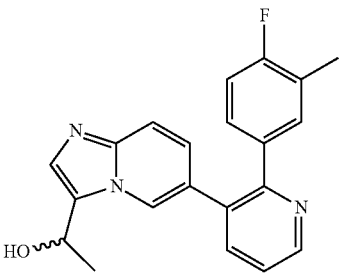 [SMILES: Cc1cc(-c2ncccc2-c2ccc3ncc(C(C)O)n3c2)ccc1F] | Parent |
| 599 | 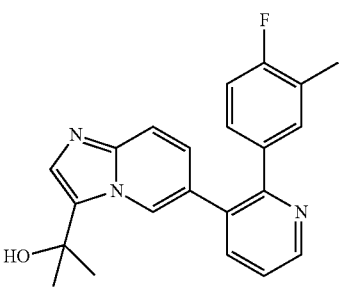 [SMILES: Cc1cc(-c2ncccc2-c2ccc3ncc(C(C)(C)O)n3c2)ccc1F] | Parent |
| 600 | 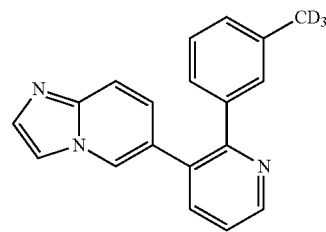 [SMILES: [2H]C([2H])([2H])c1cccc(-c2ncccc2-c2ccc3nccn3c2)c1] | Parent |
| 601 | 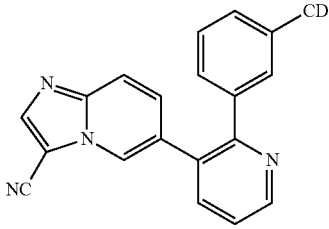 | Parent |
| 602 | 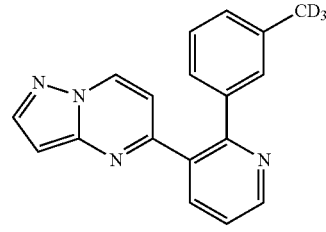 [SMILES: [2H]C([2H])([2H])c1cccc(-c2ncccc2-c2ccn3nccc3n2)c1] | Parent |
| 603 | 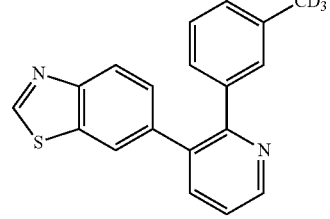 | Parent |

| Cpd # | Structure | Salt |
|---|---|---|
| 604 | 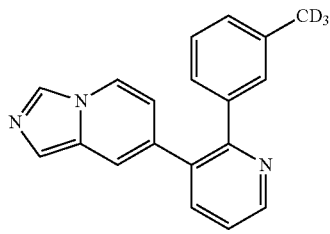 [SMILES: [2H]C([2H])([2H])c1cccc(-c2ncccc2-c2ccn3cncc3c2)c1] | Parent |
| 605 | 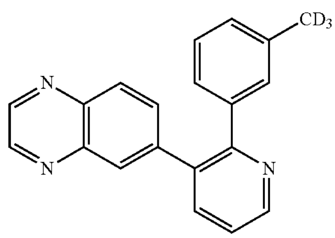 [SMILES: [2H]C([2H])([2H])c1cccc(-c2ncccc2-c2ccc3nccnc3c2)c1] | Parent |
| 606 | 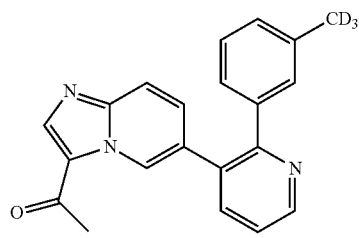 [SMILES: [2H]C([2H])([2H])c1cccc(-c2ncccc2-c2ccc3ncc(C(C)=O)n3c2)c1] | Parent |
| 607 | 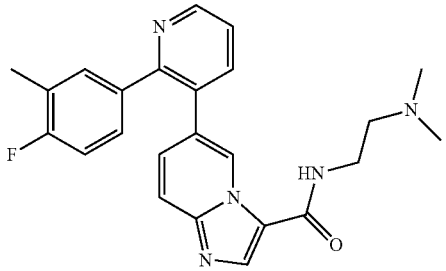 [SMILES: Cc1cc(-c2ncccc2-c2ccc3ncc(C(=O)NCCN(C)C)n3c2)ccc1F] | Parent |
| 608 | 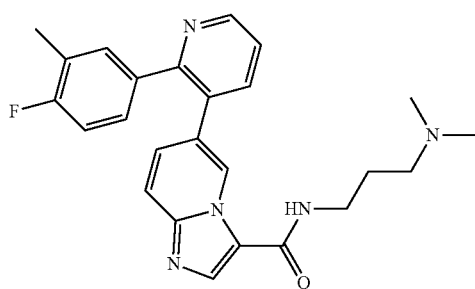 [SMILES: Cc1cc(-c2ncccc2-c2ccc3ncc(C(=O)NCCCN(C)C)n3c2)ccc1F] | Parent |

| Cpd # | Structure | Salt |
|---|---|---|
| 609 | 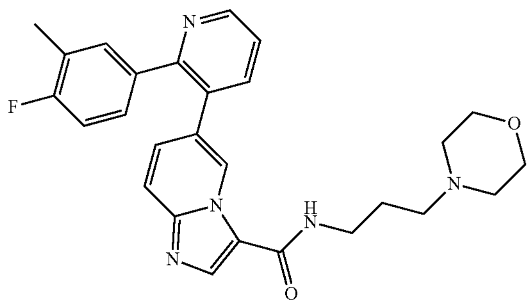 [SMILES: Cc1cc(-c2ncccc2-c2ccc3ncc(C(=O)NCCCN4CCOCC4)n3c2)ccc1F] | Parent |
| 610 | 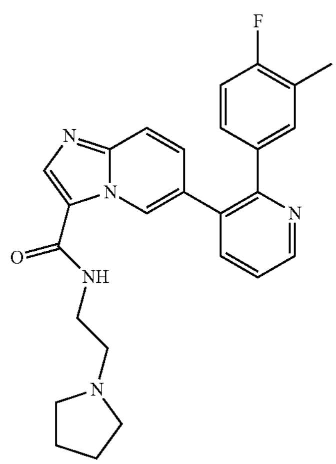 [SMILES: Cc1cc(-c2ncccc2-c2ccc3ncc(C(=O)NCCN4CCCC4)n3c2)ccc1F] | Parent |
| 611 | 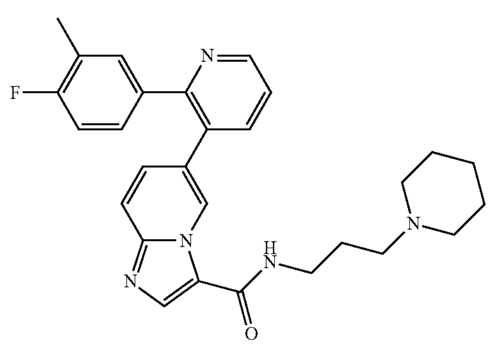 [SMILES: Cc1cc(-c2ncccc2-c2ccc3ncc(C(=O)NCCCN4CCCCC4)n3c2)ccc1F] | Parent |
| 612 | 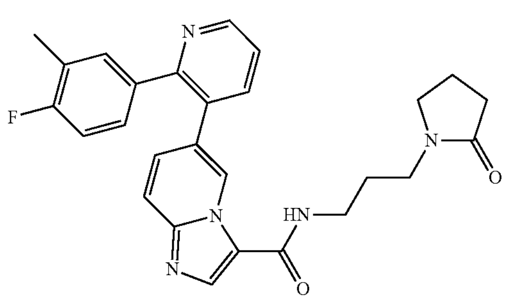 [SMILES: Cc1cc(-c2ncccc2-c2ccc3ncc(C(=O)NCCCN4CCCC4=O)n3c2)ccc1F] | Parent |

US 9,145,433 B2
279
-continued
280
| Cpd # | Structure | Salt |
|---|---|---|
| 613 | 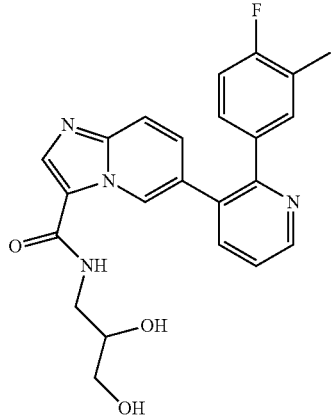 [SMILES: Cc1cc(-c2ncccc2-c2ccc3ncc(C(=O)NCC(O)CO)n3c2)ccc1F] | Parent |
| 614 | 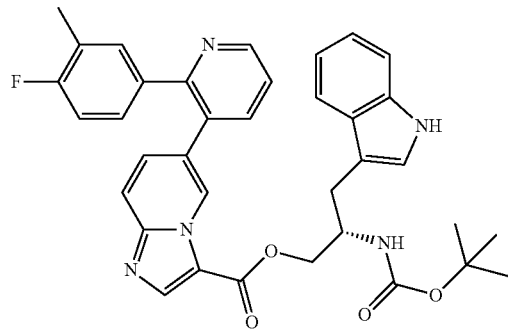 [SMILES: Cc1cc(-c2ncccc2-c2ccc3ncc(C(=O)OC[C@H](Cc4c[nH]c5ccccc45)NC(=O)OC(C)(C)C)n3c2)ccc1F] | Parent |
| 615 | 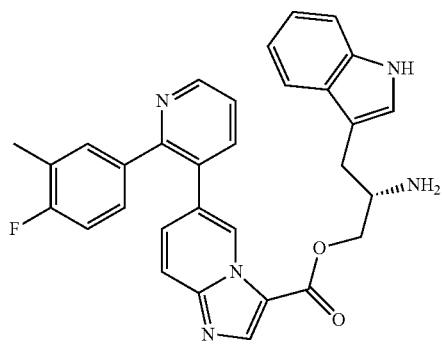 [SMILES: Cc1cc(-c2ncccc2-c2ccc3ncc(C(=O)OC[C@@H](N)Cc4c[nH]c5ccccc45)n3c2)ccc1F] | Formic Acid(1) |
| 616 | 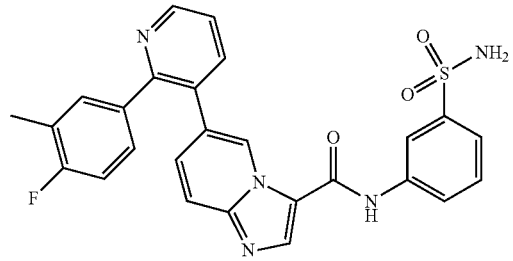 [SMILES: Cc1cc(-c2ncccc2-c2ccc3ncc(C(=O)Nc4cccc(S(N)(=O)=O)c4)n3c2)ccc1F] | Parent |

| Cpd # | Structure | Salt |
|---|---|---|
| 617 | 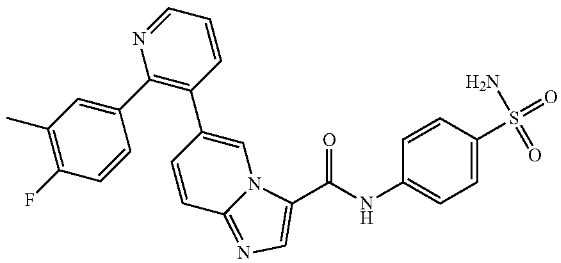 [SMILES: Cc1cc(-c2ncccc2-c2ccc3ncc(C(=O)Nc4ccc(S(N)(=O)=O)cc4)n3c2)ccc1F] | Parent |
| 618 | 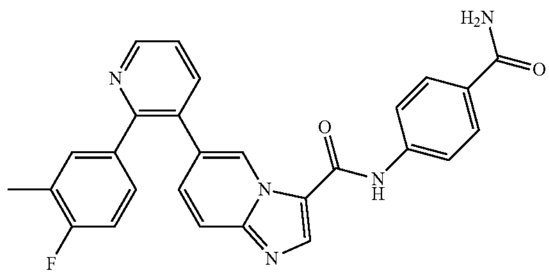 [SMILES: Cc1cc(-c2ncccc2-c2ccc3ncc(C(=O)Nc4ccc(C(N)=O)cc4)n3c2)ccc1F] | Parent |
| 619 | 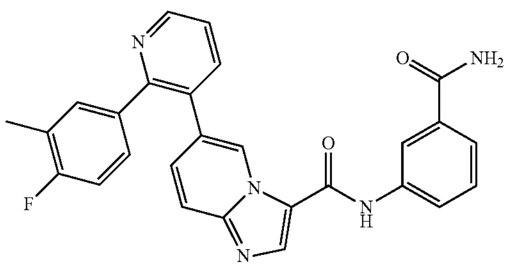 [SMILES: Cc1cc(-c2ncccc2-c2ccc3ncc(C(=O)Nc4cccc(C(N)=O)c4)n3c2)ccc1F] | Parent |
| 620 | 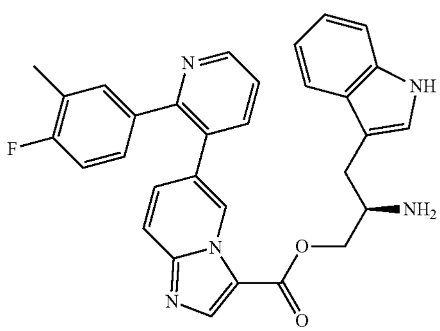 [SMILES: Cc1cc(-c2ncccc2-c2ccc3ncc(C(=O)OC[C@H](N)Cc4c[nH]c5ccccc45)n3c2)ccc1F] | Formic Acid(1) |
| 621 | 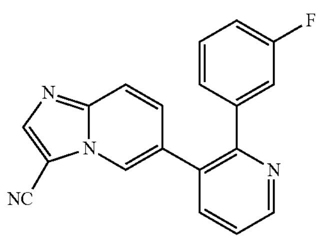 [SMILES: N#Cc1cnc2ccc(-c3cccnc3-c3cccc(F)c3)cn12] | Parent |

-continued

| Cpd # | Structure | Salt |
|---|---|---|
| 622 | 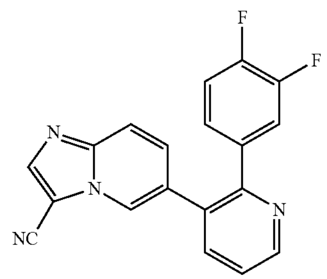 [SMILES: N#Cc1cnc2ccc(-c3cccnc3-c3ccc(F)c(F)c3)cn12] | Parent |
| 623 | 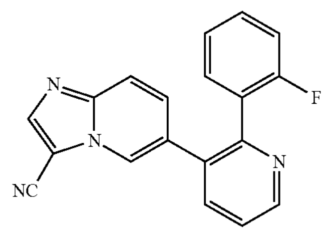 [SMILES: N#Cc1cnc2ccc(-c3cccnc3-c3ccccc3F)cn12] | Parent |
| 624 | 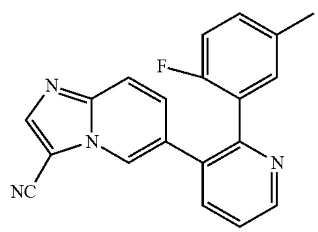 [SMILES: Cc1ccc(F)c(-c2ncccc2-c2ccc3ncc(C#N)n3c2)c1] | Parent |
| 625 | 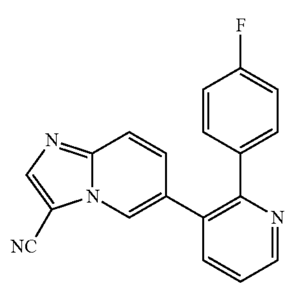 [SMILES: N#Cc1cnc2ccc(-c3cccnc3-c3ccc(F)cc3)cn12] | Parent |
| 626 | 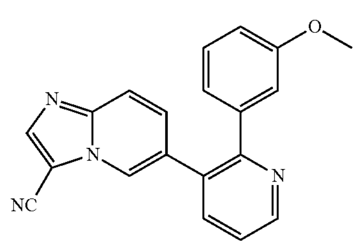 [SMILES: COc1cccc(-c2ncccc2-c2ccc3ncc(C#N)n3c2)c1] | Parent |
| 627 | 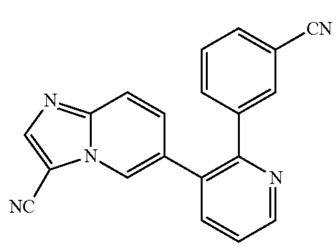 [SMILES: N#Cc1cccc(-c2ncccc2-c2ccc3ncc(C#N)n3c2)c1] | Parent |

-continued

| Cpd # | Structure | Salt |
|---|---|---|
| 628 | 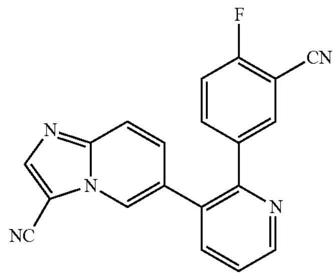 [SMILES: N#Cc1cc(-c2ncccc2-c2ccc3ncc(C#N)n3c2)ccc1F] | Parent |
| 629 | 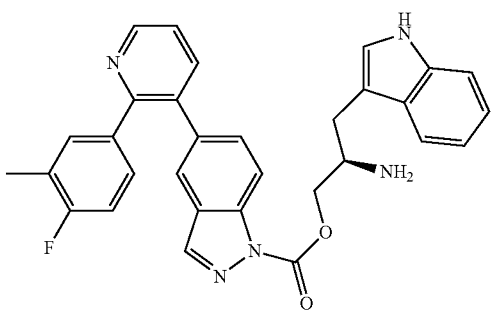 [SMILES: Cc1cc(-c2ncccc2-c2ccc3c(cnn3C(=O)OC[C@H](N)Cc3c[nH]c4ccccc34)c2)ccc1F] | TFA |
| 630 | 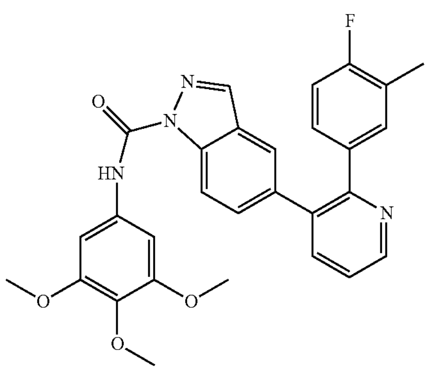 | Parent |
| 631 | 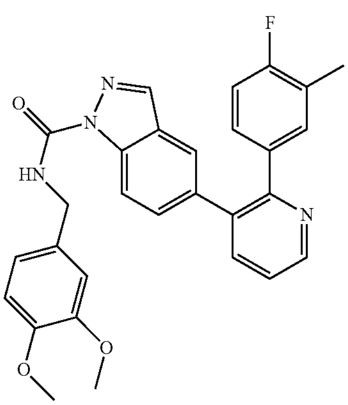 [SMILES: COc1ccc(CNC(=O)n2ncc3cc(-c4cccnc4-c4ccc(F)c(C)c4)ccc32)cc1OC] | Parent |

| Cpd # | Structure | Salt |
|---|---|---|
| 632 | 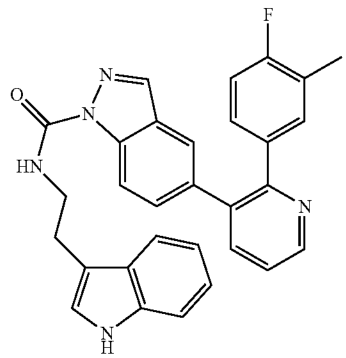 [SMILES: Cc1cc(-c2ncccc2-c2ccc3c(cnn3C(=O)NCCc3c[nH]c4ccccc34)c2)ccc1F] | Parent |
| 633 | 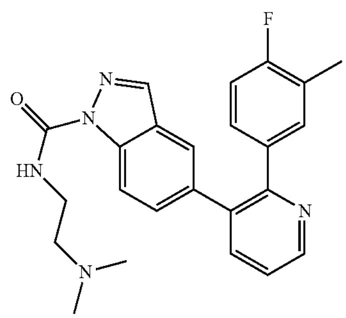 [SMILES: Cc1cc(-c2ncccc2-c2ccc3c(cnn3C(=O)NCCN(C)C)c2)ccc1F] | Parent |
| 634 | 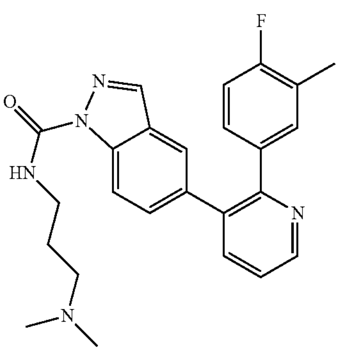 [SMILES: Cc1cc(-c2ncccc2-c2ccc3c(cnn3C(=O)NCCCN(C)C)c2)ccc1F] | Parent |
| 635 | 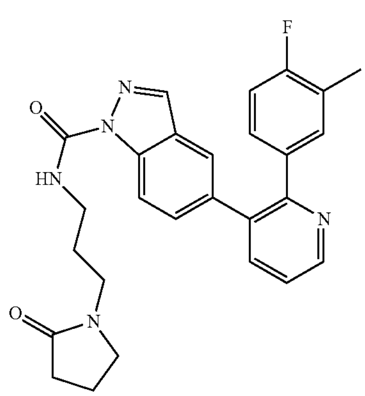 [SMILES: Cc1cc(-c2ncccc2-c2ccc3c(cnn3C(=O)NCCCN3CCCC3=O)c2)ccc1F] | Parent |

| Cpd # | Structure | Salt |
|---|---|---|
| 636 | 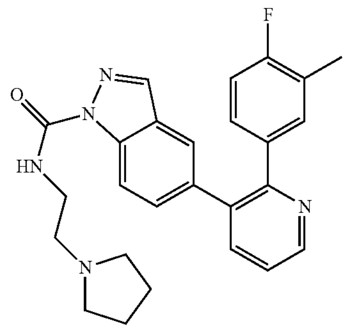 [SMILES: Cc1cc(-c2ncccc2-c2ccc3c(cnn3C(=O)NCCN3CCCC3)c2)ccc1F] | Parent |
| 637 | 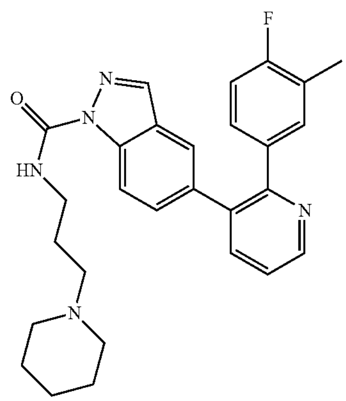 [SMILES: Cc1cc(-c2ncccc2-c2ccc3c(cnn3C(=O)NCCCN3CCCCC3)c2)ccc1F] | Parent |
| 638 | 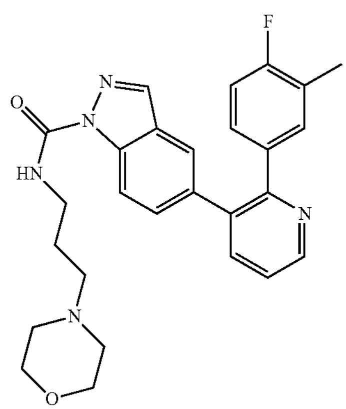 [SMILES: Cc1cc(-c2ncccc2-c2ccc3c(cnn3C(=O)NCCCN3CCOCC3)c2)ccc1F] | Parent |
| 639 | 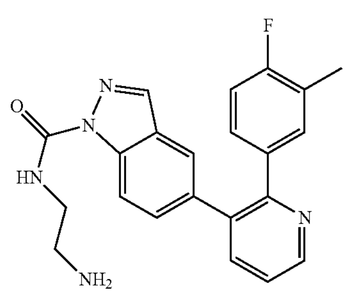 [SMILES: Cc1cc(-c2ncccc2-c2ccc3c(cnn3C(=O)NCCN)c2)ccc1F] | Parent |

291                                                             292
-continued

| Cpd # | Structure | Salt |
|---|---|---|
| 640 | 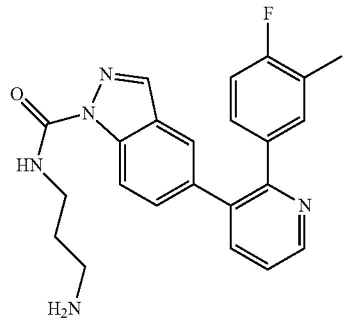 [SMILES: Cc1cc(-c2ncccc2-c2ccc3c(cnn3C(=O)NCCCN)c2)ccc1F] | Parent |
| 641 | 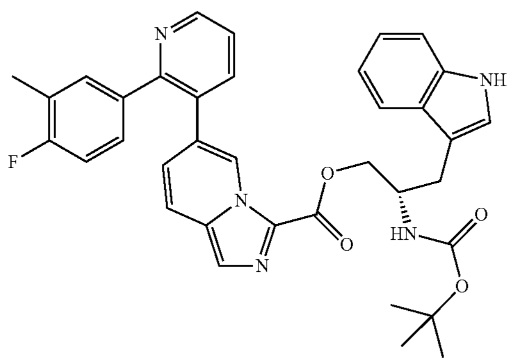 [SMILES: Cc1cc(-c2ncccc2-c2ccc3cnc(C(=O)OC[C@H](Cc4c[nH]c5ccccc45)NC(=O)OC(C)(C)C)n3c2)ccc1F] | Parent |
| 642 | 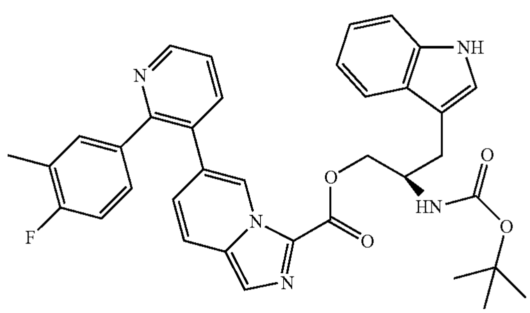 [SMILES: Cc1cc(-c2ncccc2-c2ccc3cnc(C(=O)OC[C@@H](Cc4c[nH]c5ccccc45)NC(=O)OC(C)(C)C)n3c2)ccc1F] | Parent |
| 643 | 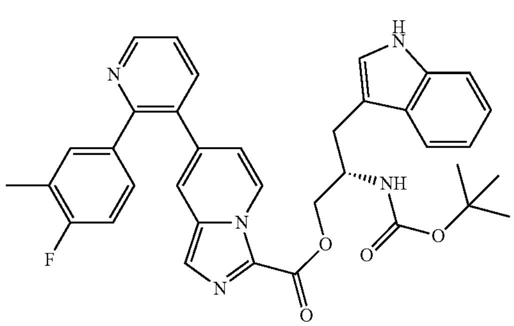 [SMILES: Cc1cc(-c2ncccc2-c2ccn3c(C(=O)OC[C@H](Cc4c[nH]c5ccccc45)NC(=O)OC(C)(C)C)ncc3c2)ccc1F] | Parent |

| Cpd # | Structure | Salt |
|---|---|---|
| 644 | 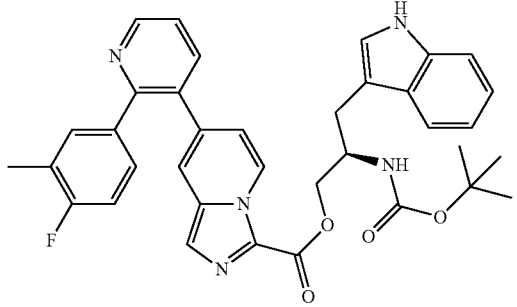 [SMILES: Cc1cc(-c2ncccc2-c2ccn3c(C(=O)OC[C@@H](Cc4c[nH]c5ccccc45)NC(=O)OC(C)(C)C)ncc3c2)ccc1F] | Parent |
| 645 | 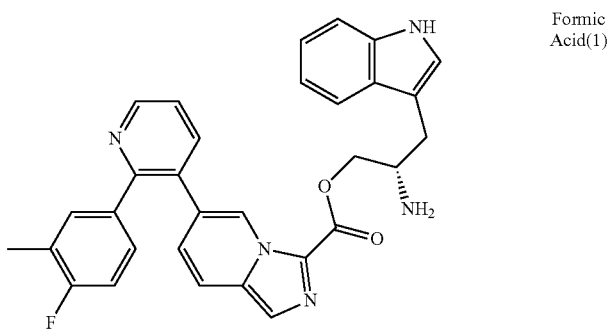 | Formic Acid(1) |
| 646 | 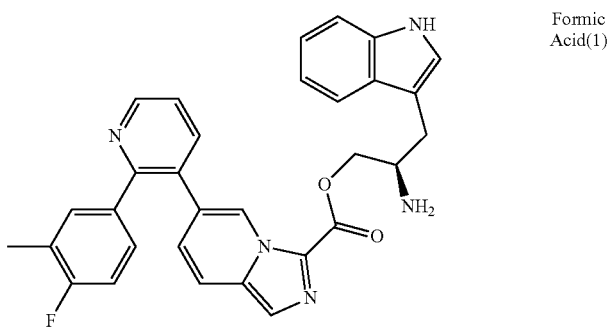 | Formic Acid(1) |
| 647 | 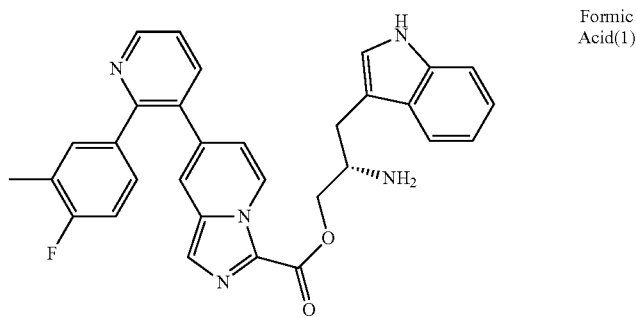 | Formic Acid(1) |

-continued

| Cpd # | Structure | Salt |
|---|---|---|
| 648 | 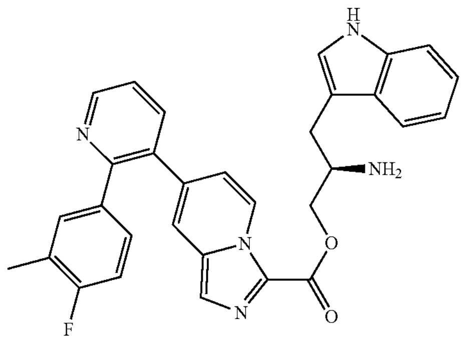 [SMILES: Cc1cc(-c2ncccc2-c2ccn3c(C(=O)OC[C@H](N)Cc4c[nH]c5ccccc45)ncc3c2)ccc1F] | Parent |
| 649 | 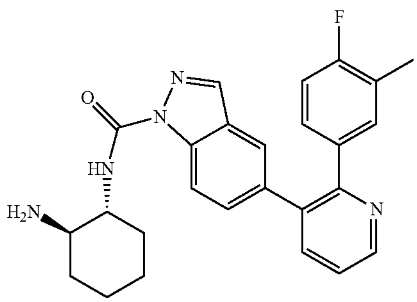 [SMILES: Cc1cc(-c2ncccc2-c2ccc3c(cnn3C(=O)N[C@@H]3CCCC[C@H]3N)c2)ccc1F] | HCl |
| 650 | 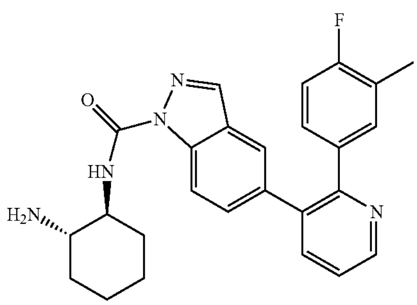 [SMILES: Cc1cc(-c2ncccc2-c2ccc3c(cnn3C(=O)N[C@H]3CCCC[C@@H]3N)c2)ccc1F] | HCl |
| 651 | 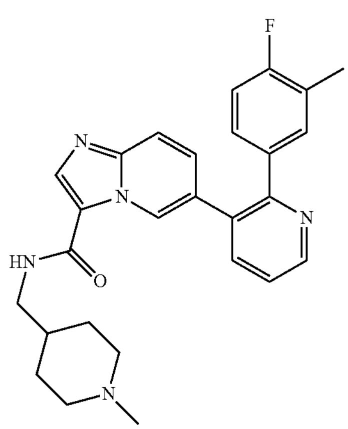 [SMILES: Cc1cc(-c2ncccc2-c2ccc3ncc(C(=O)NCC4CCN(C)CC4)n3c2)ccc1F] | Parent |

-continued
| Cpd # | Structure | Salt |
|---|---|---|
| 652 | 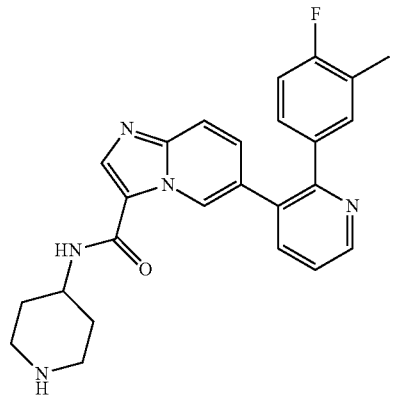 [SMILES: Cc1cc(-c2ncccc2-c2ccc3ncc(C(=O)NC4CCNCC4)n3c2)ccc1F] | Parent |
| 653 | 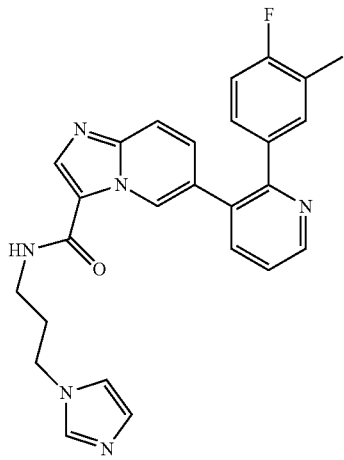 [SMILES: Cc1cc(-c2ncccc2-c2ccc3ncc(C(=O)NCCCn4ccnc4)n3c2)ccc1F] | Parent |
| 654 | 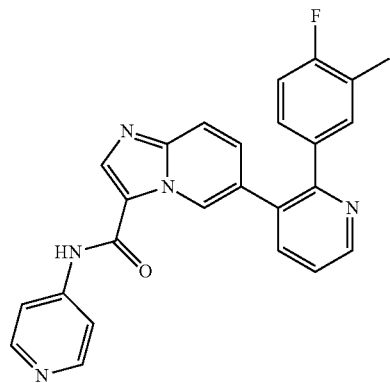 [SMILES: Cc1cc(-c2ncccc2-c2ccc3ncc(C(=O)Nc4ccncc4)n3c2)ccc1F] | Parent |

| Cpd # | Structure | Salt |
|---|---|---|
| 655 | 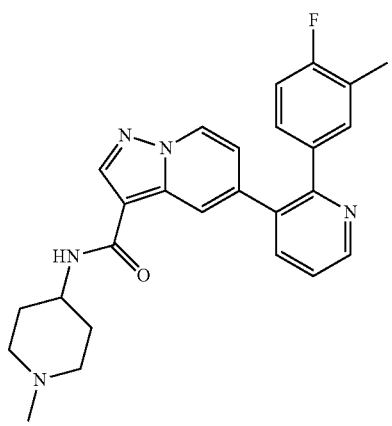 [SMILES: Cc1cc(-c2ncccc2-c2ccn3ncc(C(=O)NC4CCN(C)CC4)c3c2)ccc1F] | Parent |
| 656 | 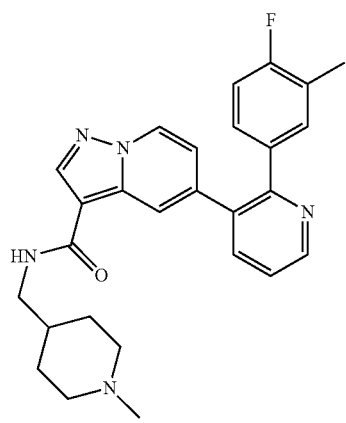 [SMILES: Cc1cc(-c2ncccc2-c2ccn3ncc(C(=O)NCC4CCN(C)CC4)c3c2)ccc1F] | Parent |
| 657 | 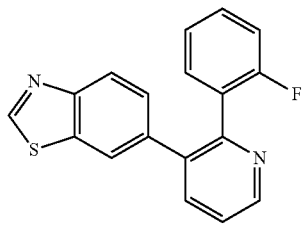 [SMILES: Fc1ccccc1-c1ncccc1-c1ccc2ncsc2c1] | Parent |
| 658 | 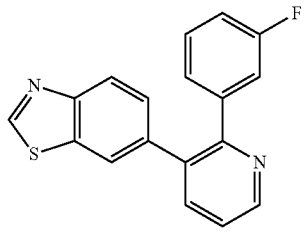 [SMILES: Fc1cccc(-c2ncccc2-c2ccc3ncsc3c2)c1] | Parent |

-continued

| Cpd # | Structure | Salt |
|---|---|---|
| 659 | 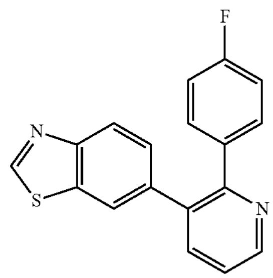 [SMILES: Fc1ccc(-c2ncccc2-c2ccc3ncsc3c2)cc1] | Parent |
| 660 | 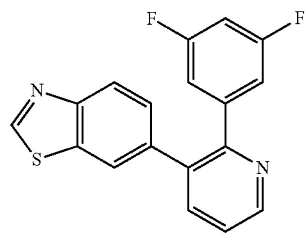 [SMILES: Fc1cc(F)cc(-c2ncccc2-c2ccc3ncsc3c2)c1] | Parent |
| 661 | 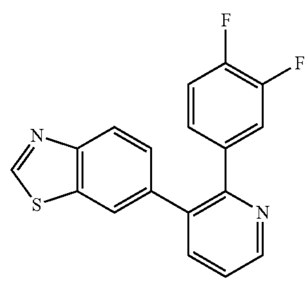 [SMILES: Fc1ccc(-c2ncccc2-c2ccc3ncsc3c2)cc1F] | Parent |
| 662 | 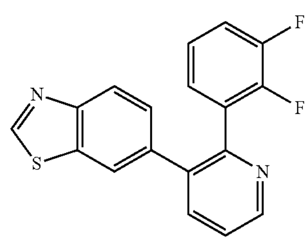 [SMILES: Fc1cccc(-c2ncccc2-c2ccc3ncsc3c2)c1F] | Parent |
| 663 | 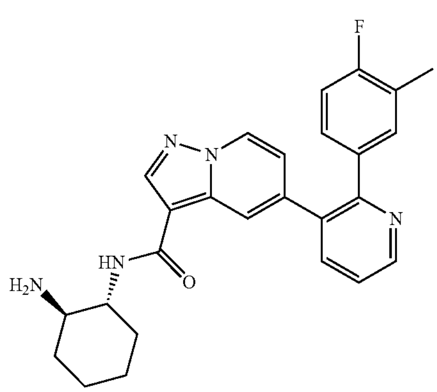 [SMILES: Cc1cc(-c2ncccc2-c2ccn3ncc(C(=O)N[C@@H]4CCCC[C@H]4N)c3c2)ccc1F] | Parent |

| Cpd # | Structure | Salt |
|---|---|---|
| 664 | 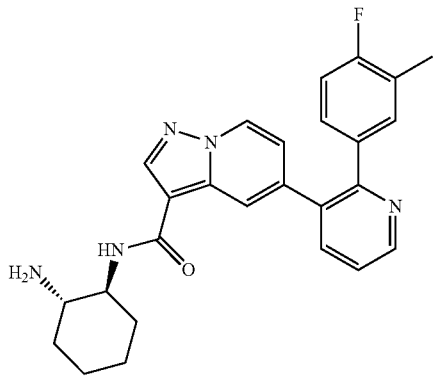 [SMILES: Cc1cc(-c2ncccc2-c2ccn3ncc(C(=O)N[C@H]4CCCC[C@@H]4N)c3c2)ccc1F] | Parent |
| 665 | 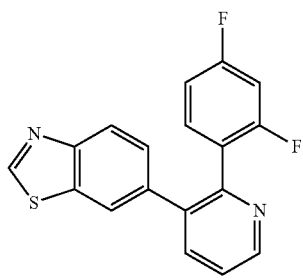 [SMILES: Fc1ccc(-c2ncccc2-c2ccc3ncsc3c2)c(F)c1] | Parent |
| 666 | 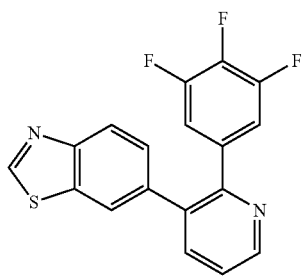 [SMILES: Fc1cc(-c2ncccc2-c2ccc3ncsc3c2)cc(F)c1F] | Parent |
| 667 | 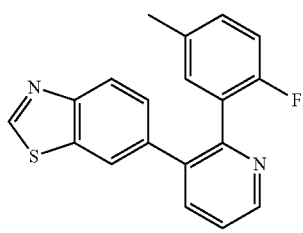 [SMILES: Cc1ccc(F)c(-c2ncccc2-c2ccc3ncsc3c2)c1] | Parent |
| 668 | 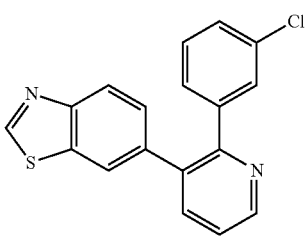 [SMILES: Clc1cccc(-c2ncccc2-c2ccc3ncsc3c2)c1] | Parent |

-continued

| Cpd # | Structure | Salt |
|---|---|---|
| 669 | 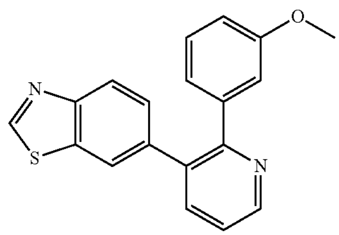 [SMILES: COc1cccc(-c2ncccc2-c2ccc3ncsc3c2)c1] | Parent |
| 670 | 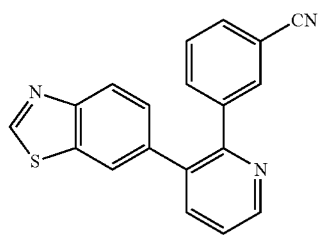 [SMILES: N#Cc1cccc(-c2ncccc2-c2ccc3ncsc3c2)c1] | Parent |
| 671 | 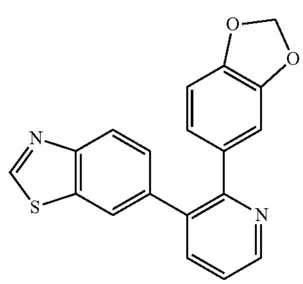 [SMILES: c1cnc(-c2ccc3c(c2)OCO3)c(-c2ccc3ncsc3c2)c1] | Parent |
| 672 | 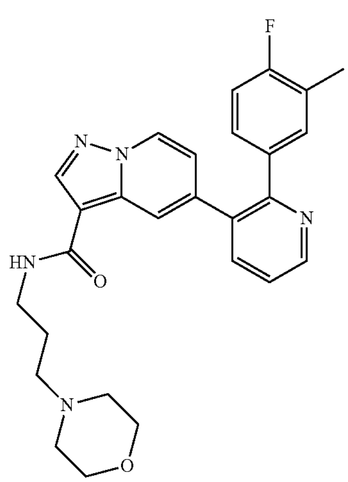 [SMILES: Cc1cc(-c2ncccc2-c2ccn3ncc(C(=O)NCCCN4CCOCC4)c3c2)ccc1F] | Parent |

| Cpd # | Structure | Salt |
|---|---|---|
| 673 | 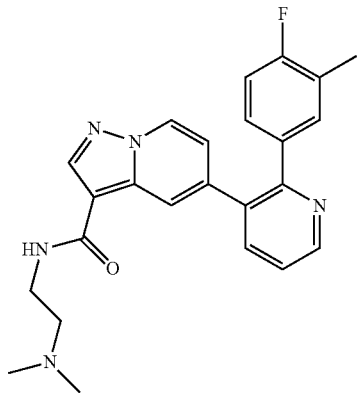 | Parent |
| 674 | 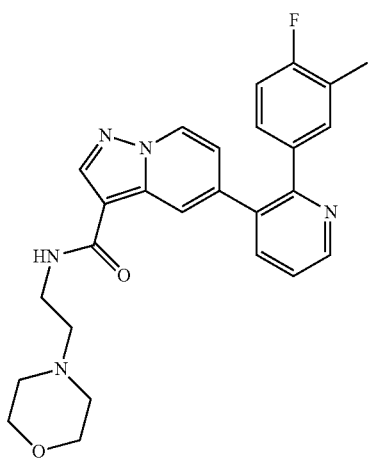 [SMILES: Cc1cc(-c2ncccc2-c2ccn3ncc(C(=O)NCCN4CCOCC4)c3c2)ccc1F] | Parent |
| 675 | 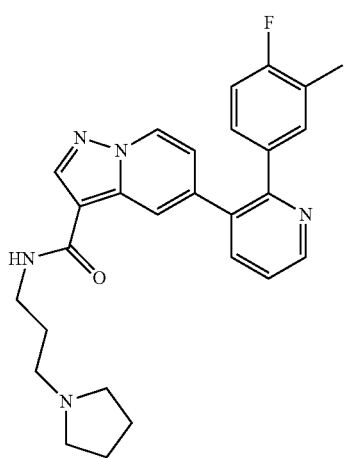 [SMILES: Cc1cc(-c2ncccc2-c2ccn3ncc(C(=O)NCCCN4CCCC4)c3c2)ccc1F] | Parent |

| Cpd # | Structure | Salt |
|---|---|---|
| 676 | 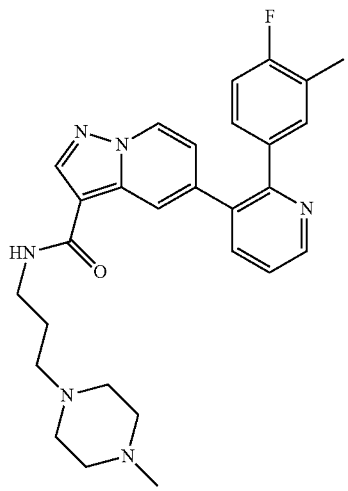 [SMILES: Cc1cc(-c2ncccc2-c2ccn3ncc(C(=O)NCCCN4CCN(C)CC4)c3c2)ccc1F] | Parent |
| 677 | 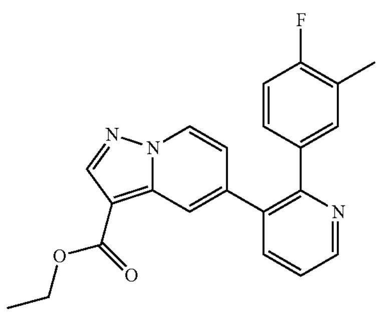 [SMILES: CCOC(=O)c1cnn2ccc(-c3cccnc3-c3ccc(F)c(C)c3)cc12] | Parent |
| 678 | 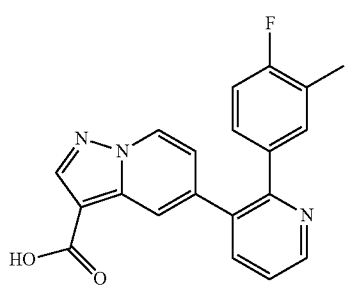 [SMILES: Cc1cc(-c2ncccc2-c2ccn3ncc(C(=O)O)c3c2)ccc1F] | Parent |
| 679 | 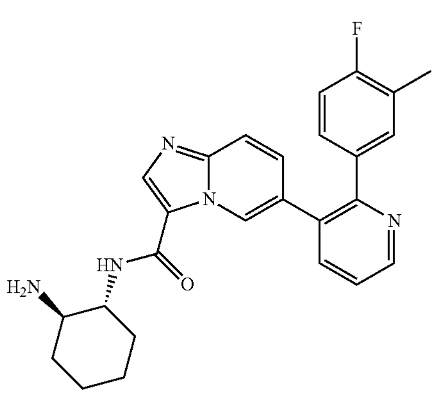 [SMILES: Cc1cc(-c2ncccc2-c2ccc3ncc(C(=O)N[C@@H]4CCCC[C@H]4N)n3c2)ccc1F] | Parent |

-continued

| Cpd # | Structure | Salt |
|---|---|---|
| 680 | 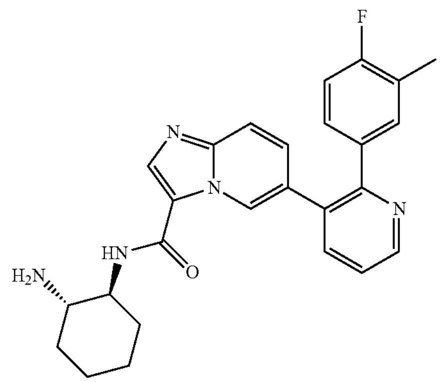 [SMILES: Cc1cc(-c2ncccc2-c2ccc3ncc(C(=O)N[C@H]4CCCC[C@@H]4N)n3c2)ccc1F] | Parent |
| 681 | 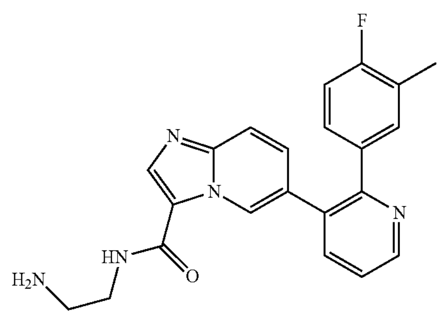 [SMILES: Cc1cc(-c2ncccc2-c2ccc3ncc(C(=O)NCCN)n3c2)ccc1F] | Parent |
| 682 | 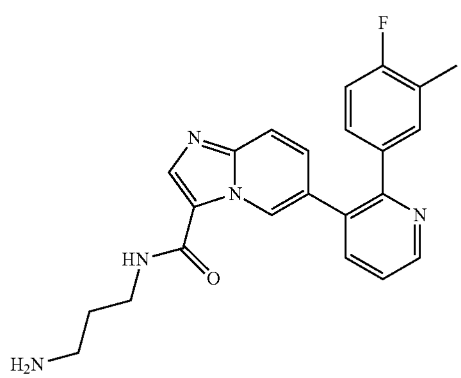 [SMILES: Cc1cc(-c2ncccc2-c2ccc3ncc(C(=O)NCCCN)n3c2)ccc1F] | Parent |
| 683 | 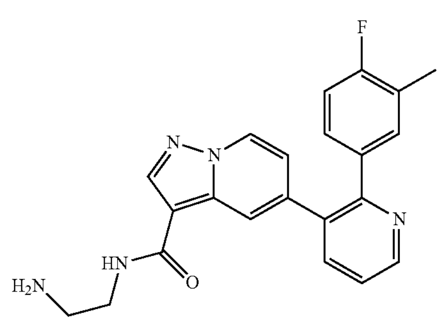 [SMILES: Cc1cc(-c2ncccc2-c2ccn3ncc(C(=O)NCCN)c3c2)ccc1F] | Parent |

| Cpd # | Structure | Salt |
|---|---|---|
| 684 | 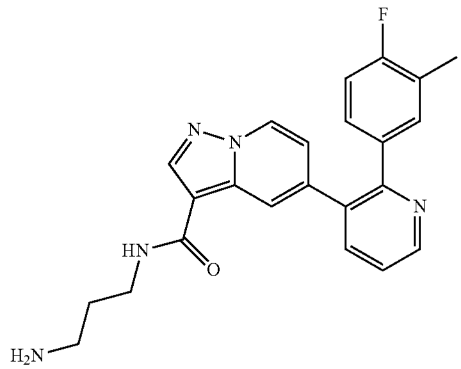 [SMILES: Cc1cc(-c2ncccc2-c2ccn3ncc(C(=O)NCCCN)c3c2)ccc1F] | Parent |
| 685 | 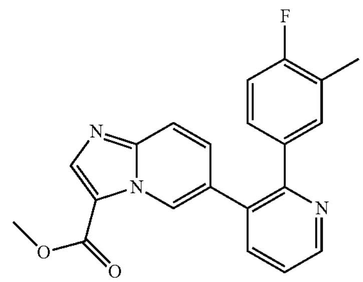 | Parent |
| 686 | 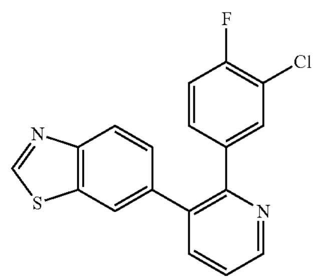 [SMILES: Fc1ccc(-c2ncccc2-c2ccc3ncsc3c2)cc1Cl] | Parent |
| 687 | 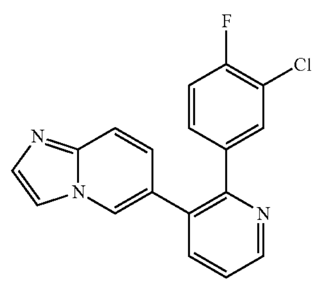 [SMILES: Fc1ccc(-c2ncccc2-c2ccc3nccn3c2)cc1Cl] | Parent |
| 688 | 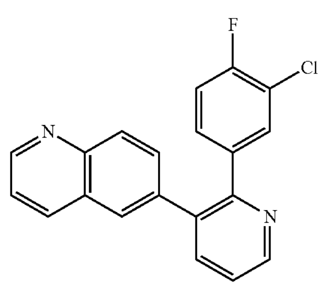 [SMILES: Fc1ccc(-c2ncccc2-c2ccc3ncccc3c2)cc1Cl] | Parent |

-continued
| Cpd # | Structure | Salt |
|---|---|---|
| 689 | 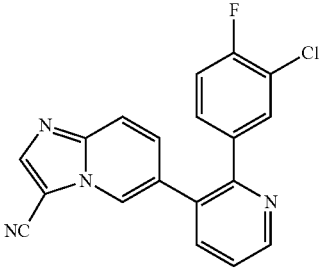 [SMILES: N#Cc1cnc2ccc(-c3cccnc3-c3ccc(F)c(Cl)c3)cn12] | Parent |
| 690 | 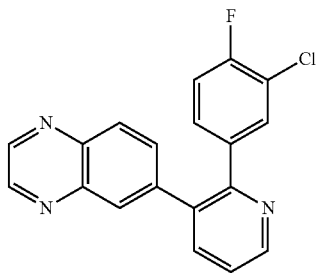 [SMILES: Fc1ccc(-c2ncccc2-c2ccc3nccnc3c2)cc1Cl] | Parent |
| 691 | 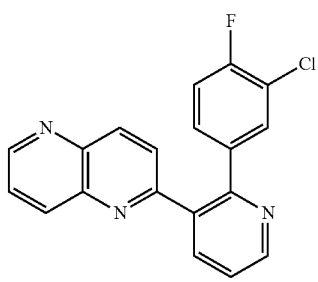 [SMILES: Fc1ccc(-c2ncccc2-c2ccc3ncccc3n2)cc1Cl] | Parent |
| 692 | 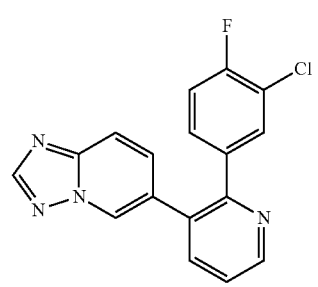 [SMILES: Fc1ccc(-c2ncccc2-c2ccc3ncnn3c2)cc1Cl] | Parent |
| 693 | 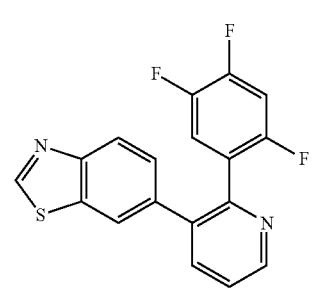 [SMILES: Fc1cc(F)c(-c2ncccc2-c2ccc3ncsc3c2)cc1F] | Parent |

-continued

| Cpd # | Structure | Salt |
|---|---|---|
| 694 | 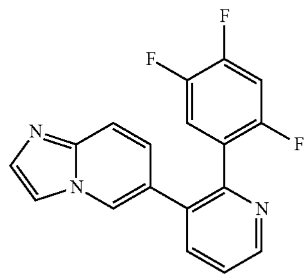 [SMILES: Fc1cc(F)c(-c2ncccc2-c2ccc3nccn3c2)cc1F] | Parent |
| 695 | 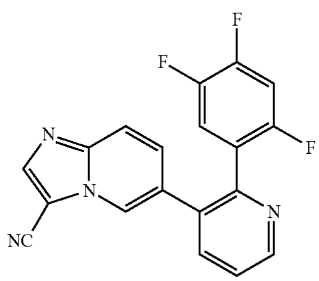 [SMILES: N#Cc1cnc2ccc(-c3cccnc3-c3cc(F)c(F)cc3F)cn12] | Parent |
| 696 | 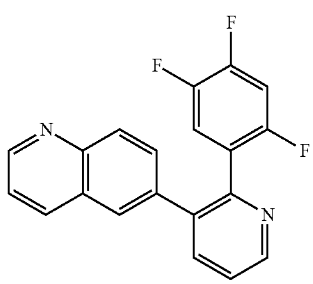 [SMILES: Fc1cc(F)c(-c2ncccc2-c2ccc3ncccc3c2)cc1F] | Parent |
| 697 | 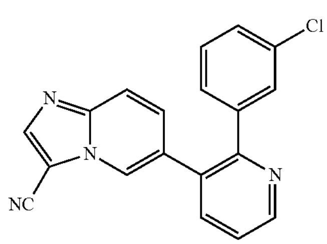 [SMILES: N#Cc1cnc2ccc(-c3cccnc3-c3cccc(Cl)c3)cn12] | Parent |
| 698 | 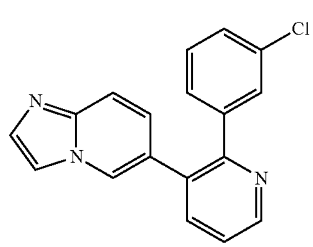 [SMILES: Clc1cccc(-c2ncccc2-c2ccc3nccn3c2)c1] | Parent |

| Cpd # | Structure | Salt |
|---|---|---|
| 699 | 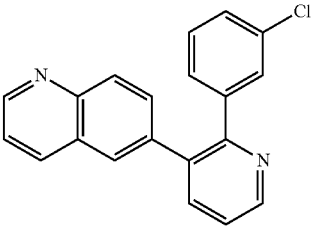 [SMILES: Clc1cccc(-c2ncccc2-c2ccc3ncccc3c2)c1] | Parent |
| 700 | 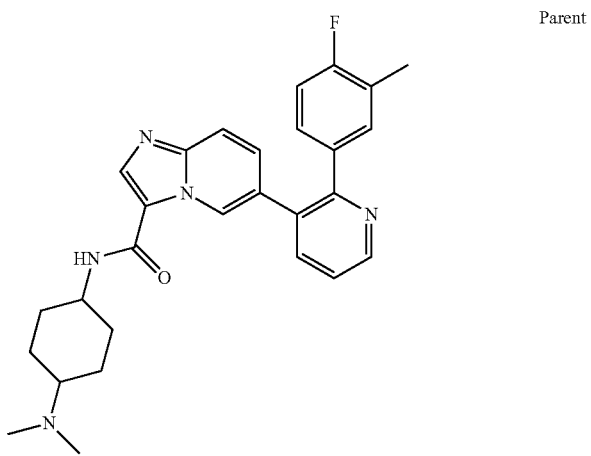 | Parent |
| 701 | 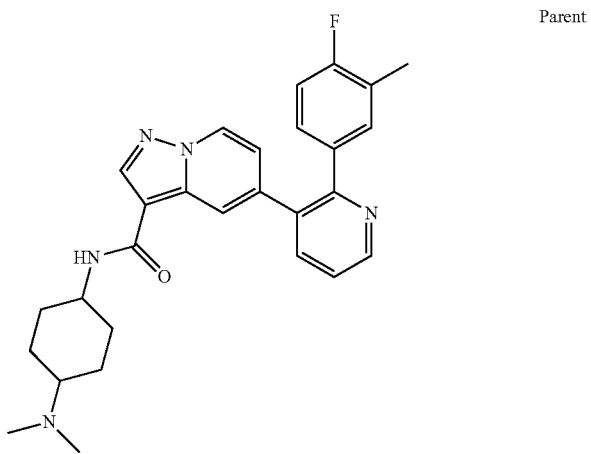 | Parent |

| Cpd # | Structure | Salt |
|---|---|---|
| 702 | 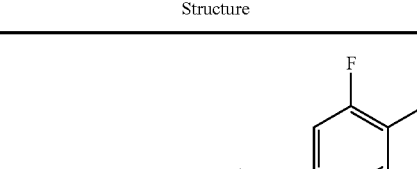 | Parent |
| 703 | 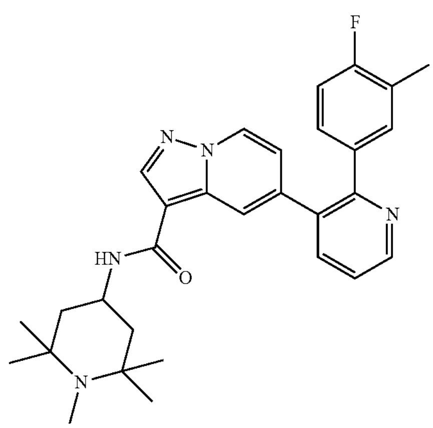 | Parent |
| 704 | 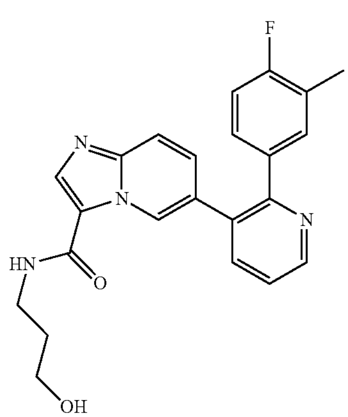 [SMILES: Cc1cc(-c2ncccc2-c2ccc3ncc(C(=O)NCCCO)n3c2)ccc1F] | Parent |

| Cpd # | Structure | Salt |
|---|---|---|
| 705 | 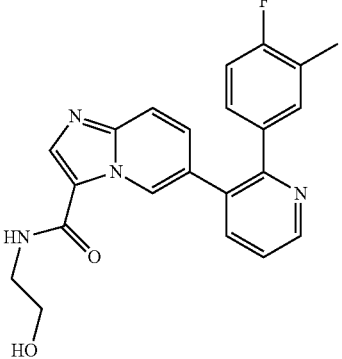 | Parent |
| 706 | 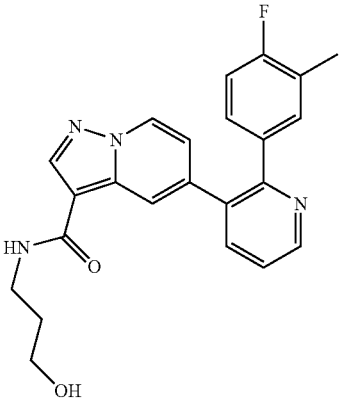 [SMILES: Cc1cc(-c2ncccc2-c2ccn3ncc(C(=O)NCCCO)c3c2)ccc1F] | Parent |
| 707 | 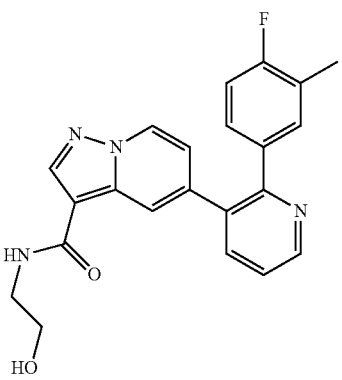 [SMILES: Cc1cc(-c2ncccc2-c2ccn3ncc(C(=O)NCCO)c3c2)ccc1F] | Parent |
| 708 | 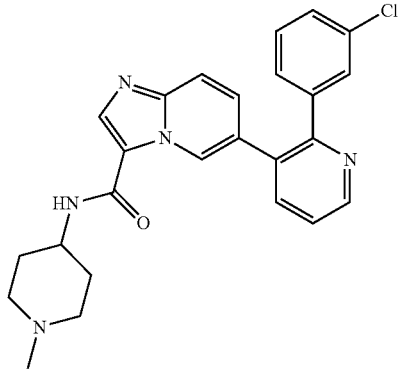 [SMILES: CN1CCC(NC(=O)c2cnc3ccc(-c4cccnc4-c4cccc(Cl)c4)cn23)CC1] | Parent |

-continued
| Cpd # | Structure | Salt |
|---|---|---|
| 709 | 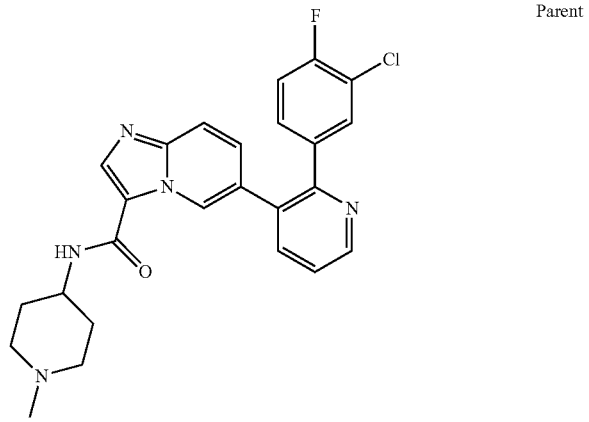 | Parent |
| 710 | 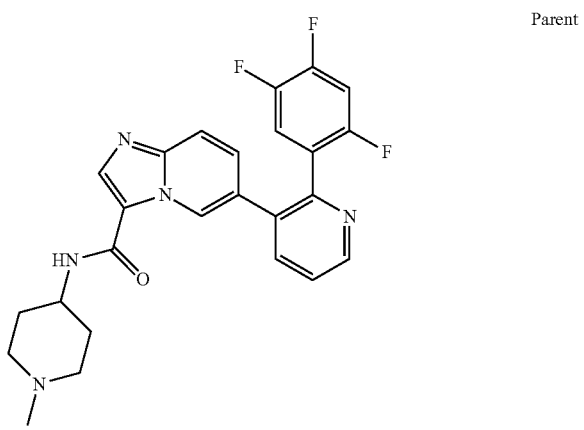 | Parent |
| 711 | 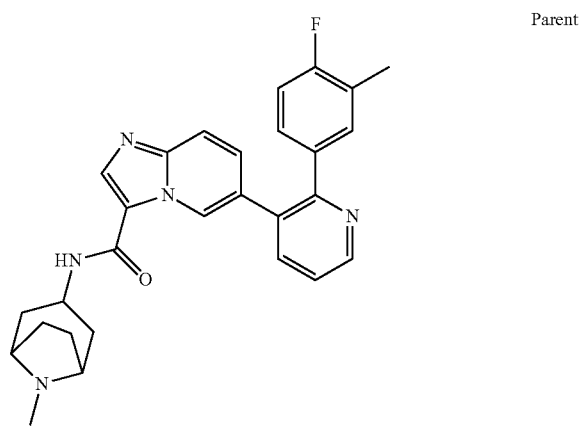 | Parent |

-continued
| Cpd # | Structure | Salt |
|---|---|---|
| 712 | 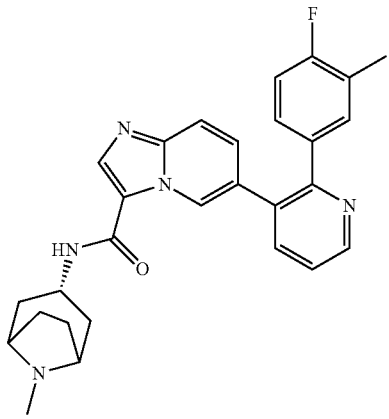 | Parent |
| 713 | 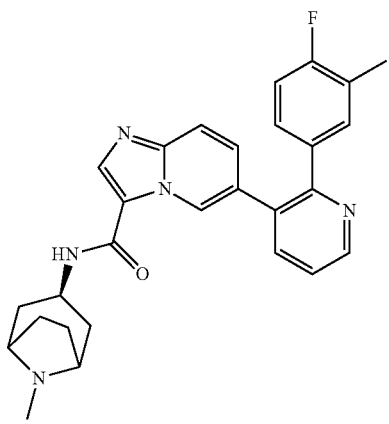 | Parent |
| 714 | 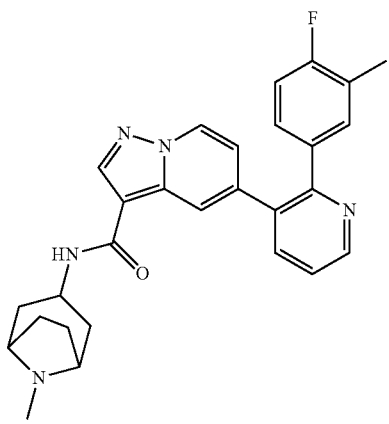 [SMILES: Cc1cc(-c2ncccc2-c2ccn3ncc(C(=O)NC4CC5CCC(C4)N5C)c3c2)ccc1F] | Parent |

US 9,145,433 B2
329                                                                 330
-continued
| Cpd # | Structure | Salt |
|---|---|---|
| 715 | 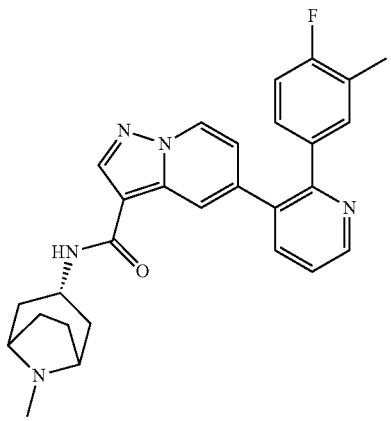 | Parent |
| 716 | 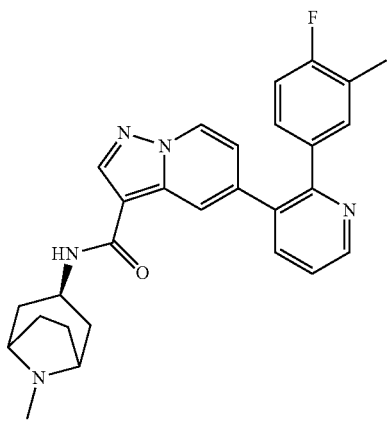 | Parent |
| 717 | 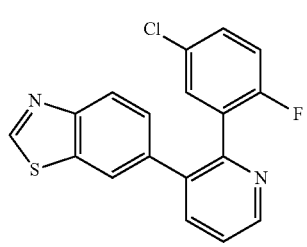 [SMILES: Fc1ccc(Cl)cc1-c1ncccc1-c1ccc2ncsc2c1] | Parent |
| 718 | 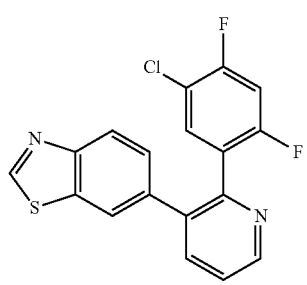 [SMILES: Fc1cc(F)c(-c2ncccc2-c2ccc3ncsc3c2)cc1Cl] | Parent |

| Cpd # | Structure | Salt |
|---|---|---|
| 719 | 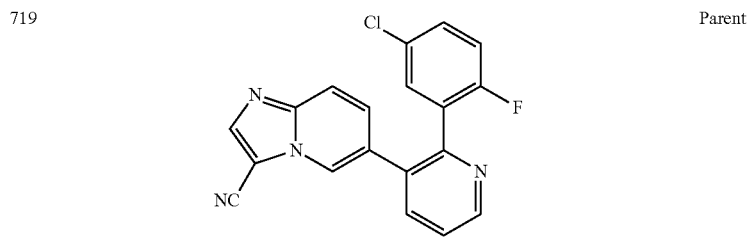 | Parent |
| 720 | 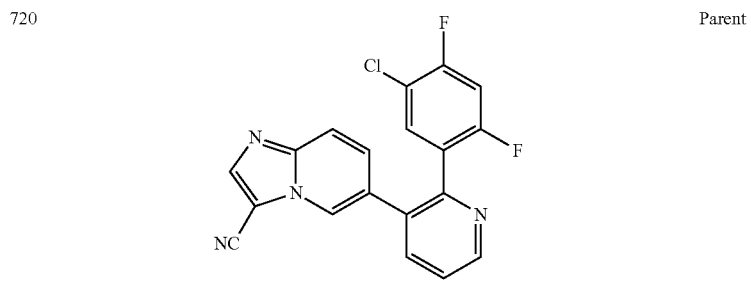 | Parent |
| 721 | 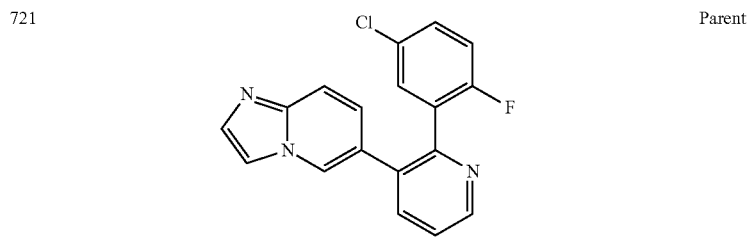 | Parent |
| 722 | 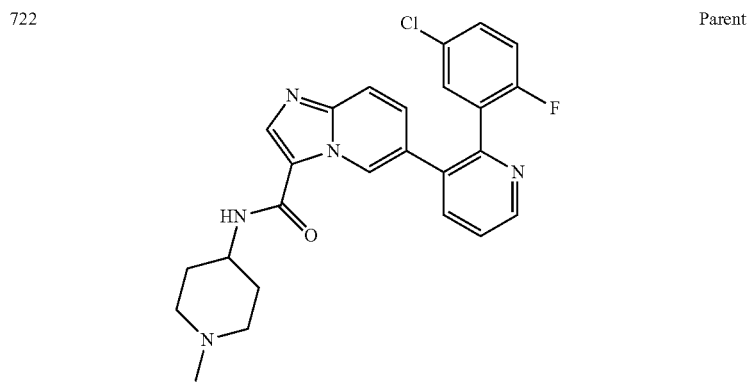 | Parent |

| Cpd # | Structure | Salt |
|---|---|---|
| 723 | 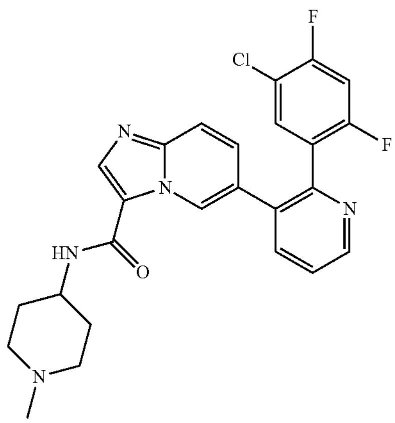 [SMILES: CN1CCC(NC(=O)c2cnc3ccc(-c4cccnc4-c4cc(Cl)c(F)cc4F)cn23)CC1] | Parent |
| 724 | 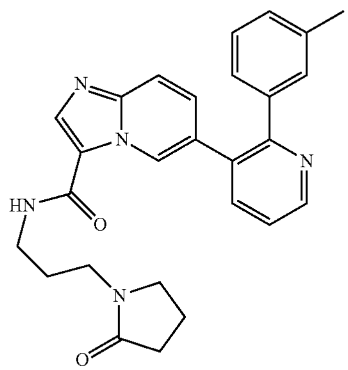 [SMILES: Cc1cccc(-c2ncccc2-c2ccc3ncc(C(=O)NCCCN4CCCC4=O)n3c2)c1] | Parent |
| 725 | 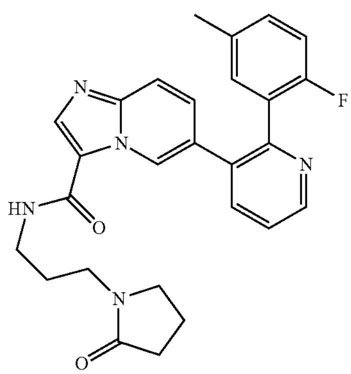 [SMILES: Cc1ccc(F)c(-c2ncccc2-c2ccc3ncc(C(=O)NCCCN4CCCC4=O)n3c2)c1] | Parent |
| 726 | 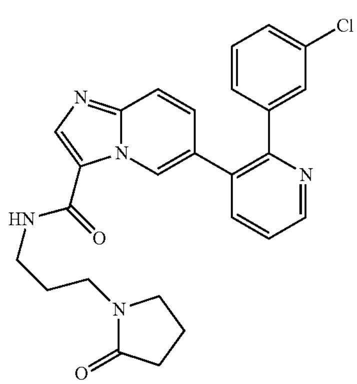 [SMILES: O=C(NCCCN1CCCC1=O)c1cnc2ccc(-c3cccnc3-c3cccc(Cl)c3)cn12] | Parent |

| Cpd # | Structure | Salt |
|---|---|---|
| 727 | 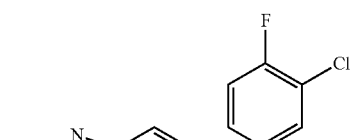 | Parent |
| 728 | 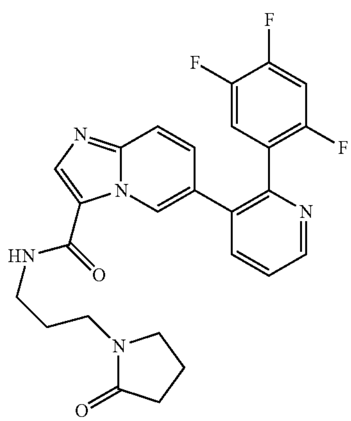 [SMILES: O=C(NCCCN1CCCC1=O)c1cnc2ccc(-c3cccnc3-c3cc(F)c(F)cc3F)cn12] | Parent |
| 729 | 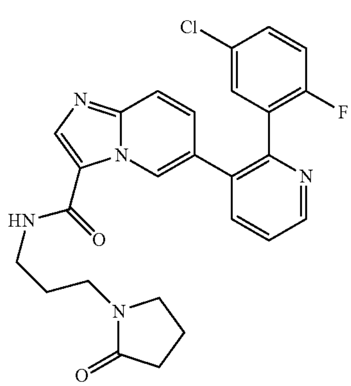 [SMILES: O=C(NCCCN1CCCC1=O)c1cnc2ccc(-c3cccnc3-c3cc(Cl)ccc3F)cn12] | Parent |

| Cpd # | Structure | Salt |
|---|---|---|
| 730 | 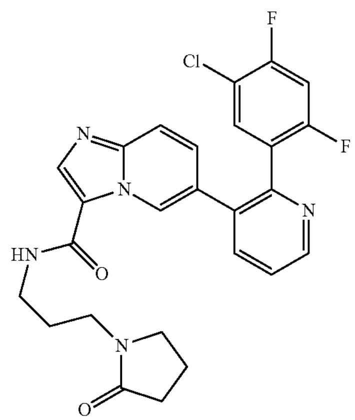 [SMILES: O=C(NCCCN1CCCC1=O)c1cnc2ccc(-c3cccnc3-c3cc(Cl)c(F)cc3F)cn12] | Parent |
| 731 | 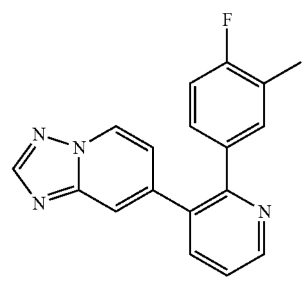 [SMILES: Cc1cc(-c2ncccc2-c2ccn3ncnc3c2)ccc1F] | Parent |
| 732 | 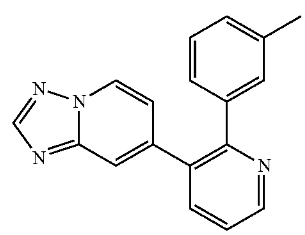 [SMILES: Cc1cccc(-c2ncccc2-c2ccn3ncnc3c2)c1] | Parent |
| 733 | 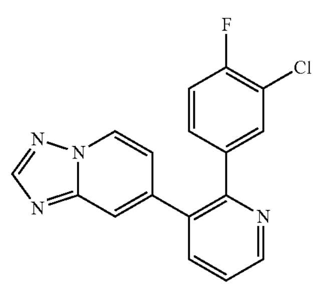 [SMILES: Fc1ccc(-c2ncccc2-c2ccn3ncnc3c2)cc1Cl] | Parent |
| 734 | 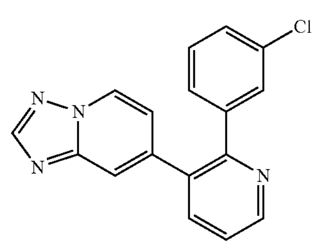 [SMILES: Clc1cccc(-c2ncccc2-c2ccn3ncnc3c2)c1] | Parent |

| Cpd # | Structure | Salt |
|---|---|---|
| 735 | 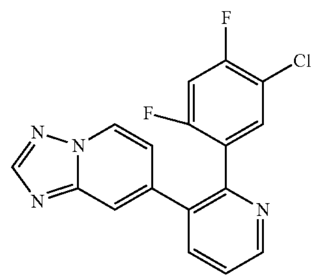 [SMILES: Fc1cc(F)c(-c2ncccc2-c2ccn3ncnc3c2)cc1Cl] | Parent |
| 736 | 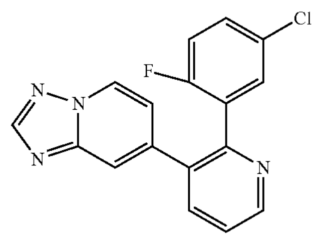 [SMILES: Fc1ccc(Cl)cc1-c1ncccc1-c1ccn2ncnc2c1] | Parent |
| 737 | 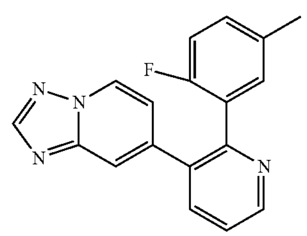 [SMILES: Cc1ccc(F)c(-c2ncccc2-c2ccn3ncnc3c2)c1] | Parent |
| 738 | 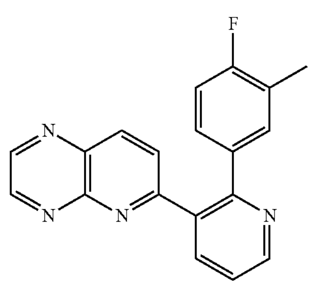 [SMILES: Cc1cc(-c2ncccc2-c2ccc3nccnc3n2)ccc1F] | Parent |
| 739 | 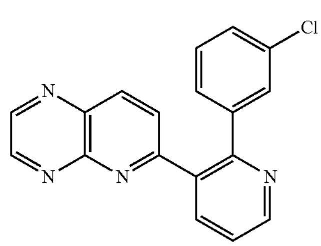 [SMILES: Clc1cccc(-c2ncccc2-c2ccc3nccnc3n2)c1] | Parent |

-continued

| Cpd # | Structure | Salt |
|---|---|---|
| 740 | 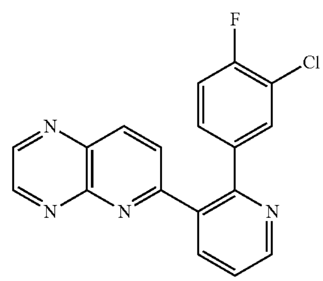 [SMILES: Fc1ccc(-c2ncccc2-c2ccc3nccnc3n2)cc1Cl] | Parent |
| 741 | 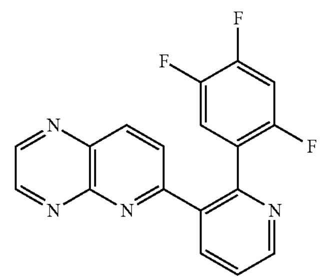 [SMILES: Fc1cc(F)c(-c2ncccc2-c2ccc3nccnc3n2)cc1F] | Parent |
| 742 | 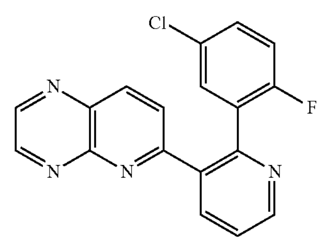 [SMILES: Fc1ccc(Cl)cc1-c1ncccc1-c1ccc2nccnc2n1] | Parent |
| 743 | 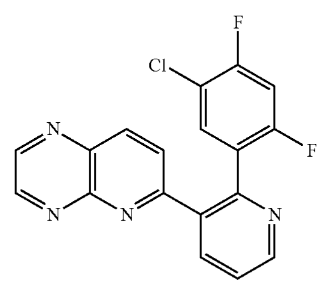 [SMILES: Fc1cc(F)c(-c2ncccc2-c2ccc3nccnc3n2)cc1Cl] | Parent |
| 744 | 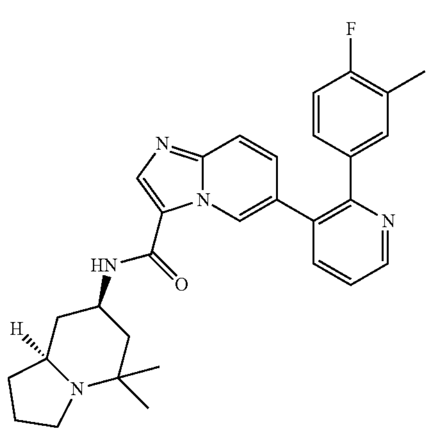 [SMILES: Cc1cc(-c2ncccc2-c2ccc3ncc(C(=O)N[C@@H]4C[C@@H]5CCCN5C(C)(C)C4)n3c2)ccc1F] | Parent |

-continued
| Cpd # | Structure | Salt |
|---|---|---|
| 745 | 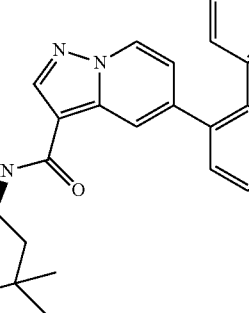 | Parent |
| 746 | 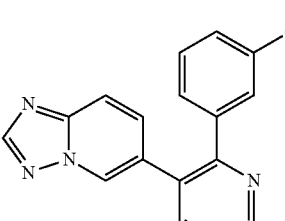 | Parent |
| 747 | 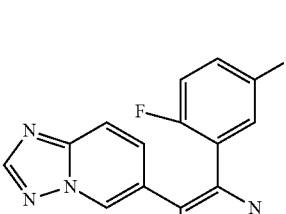 | Parent |
| 748 | 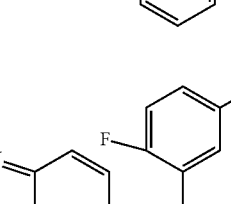 | Parent |
| 749 | 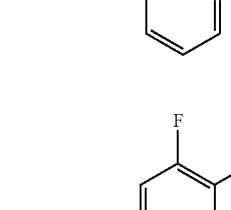 | Parent |

-continued

| Cpd # | Structure | Salt |
|---|---|---|
| 750 | 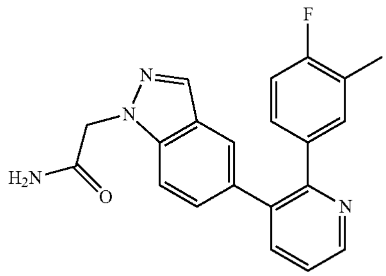 [SMILES: Cc1cc(-c2ncccc2-c2ccc3c(cnn3CC(N)=O)c2)ccc1F] | Parent |
| 751 | 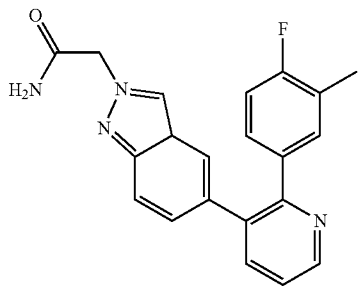 | Parent |
| 752 | 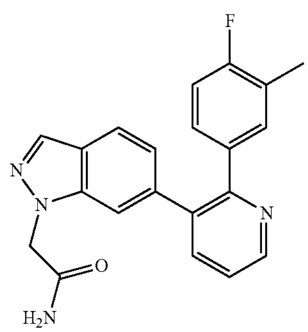 [SMILES: Cc1cc(-c2ncccc2-c2ccc3cnn(CC(N)=O)c3c2)ccc1F] | Parent |
| 753 | 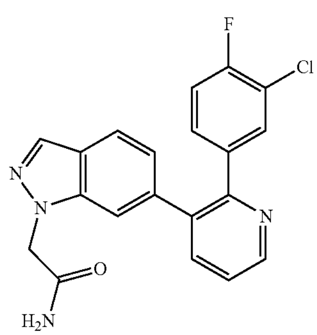 [SMILES: NC(=O)Cn1ncc2ccc(-c3cccnc3-c3ccc(F)c(Cl)c3)cc21] | Parent |
| 754 | 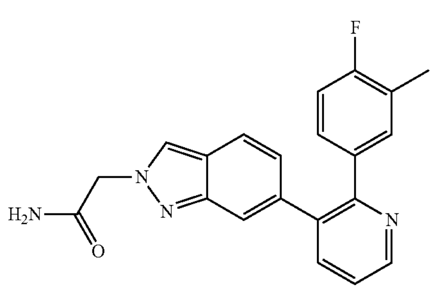 [SMILES: Cc1cc(-c2ncccc2-c2ccc3cn(CC(N)=O)nc3c2)ccc1F] | Parent |

| Cpd # | Structure | Salt |
|---|---|---|
| 755 | 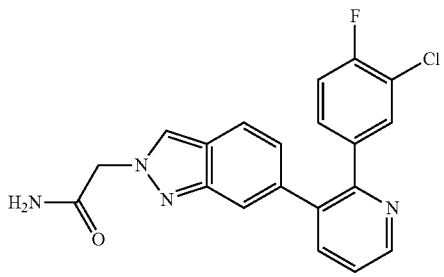 | Parent |
| 756 | 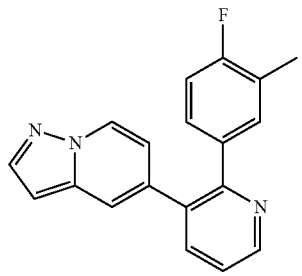 [SMILES: Cc1cc(-c2ncccc2-c2ccn3nccc3c2)ccc1F] | Parent |
| 757 | 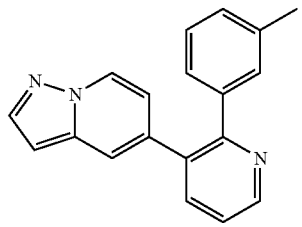 [SMILES: Cc1cccc(-c2ncccc2-c2ccn3nccc3c2)c1] | Parent |
| 758 | 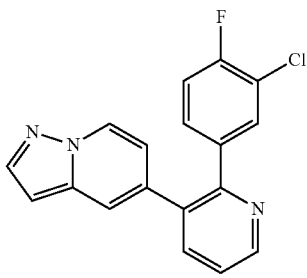 [SMILES: Fc1ccc(-c2ncccc2-c2ccn3nccc3c2)cc1Cl] | Parent |
| 759 | 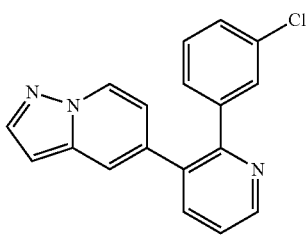 [SMILES: Clc1cccc(-c2ncccc2-c2ccn3nccc3c2)c1] | Parent |

| Cpd # | Structure | Salt |
|---|---|---|
| 760 | 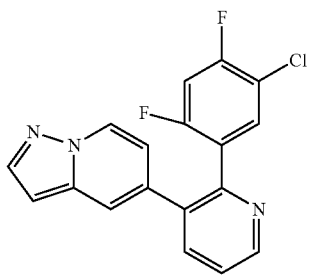 [SMILES: Fc1cc(F)c(-c2ncccc2-c2ccn3nccc3c2)cc1Cl] | Parent |
| 761 | 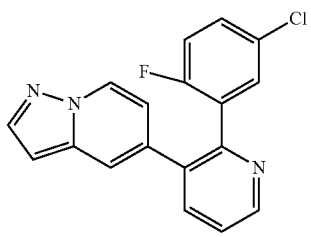 [SMILES: Fc1ccc(Cl)cc1-c1ncccc1-c1ccn2nccc2c1] | Parent |
| 762 | 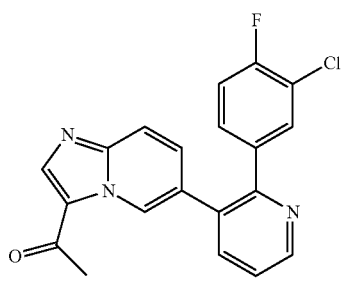 [SMILES: CC(=O)c1cnc2ccc(-c3cccnc3-c3ccc(F)c(Cl)c3)cn12] | Parent |
| 763 | 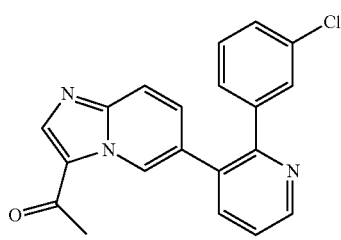 [SMILES: CC(=O)c1cnc2ccc(-c3cccnc3-c3cccc(Cl)c3)cn12] | Parent |
| 764 | 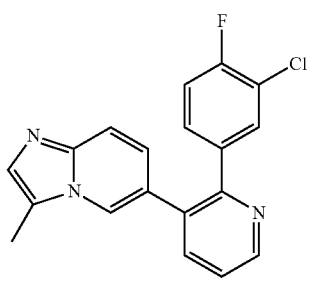 [SMILES: Cc1cnc2ccc(-c3cccnc3-c3ccc(F)c(Cl)c3)cn12] | Parent |

| Cpd # | Structure | Salt |
|---|---|---|
| 765 | 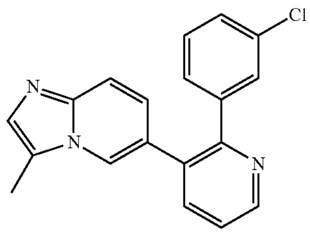 [SMILES: Cc1cnc2ccc(-c3cccnc3-c3cccc(Cl)c3)cn12] | Parent |
| 766 | 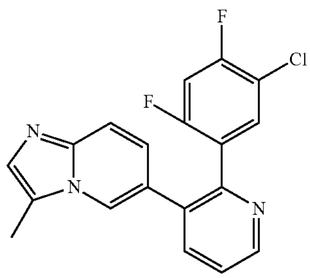 [SMILES: Cc1cnc2ccc(-c3cccnc3-c3cc(Cl)c(F)cc3F)cn12] | Parent |
| 767 | 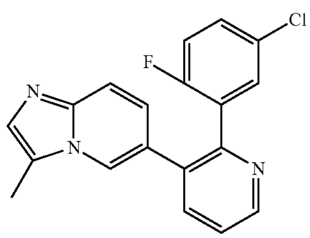 [SMILES: Cc1cnc2ccc(-c3cccnc3-c3cc(Cl)ccc3F)cn12] | Parent |
| 768 | 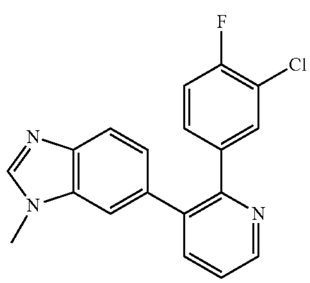 [SMILES: Cn1cnc2ccc(-c3cccnc3-c3ccc(F)c(Cl)c3)cc21] | Parent |
| 769 | 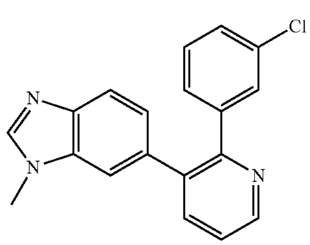 [SMILES: Cn1cnc2ccc(-c3cccnc3-c3cccc(Cl)c3)cc21] | Parent |
| 770 | 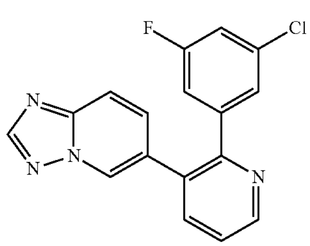 [SMILES: Fc1cc(Cl)cc(-c2ncccc2-c2ccc3ncnn3c2)c1] | Parent |

-continued
| Cpd # | Structure | Salt |
|---|---|---|
| 771 | 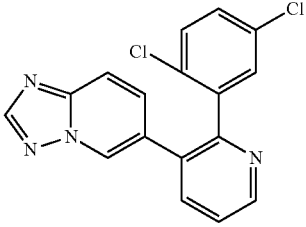 [SMILES: Clc1ccc(Cl)c(-c2ncccc2-c2ccc3ncnn3c2)c1] | Parent |
| 772 | 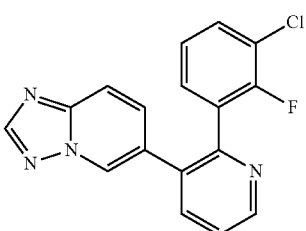 | Parent |
| 773 | 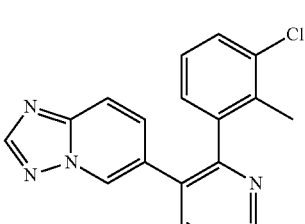 | Parent |
| 774 | 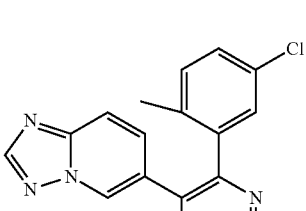 | Parent |
| 775 | 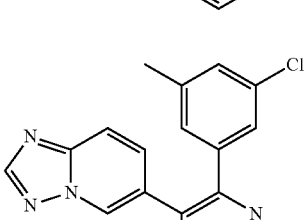 | Parent |
| 776 | 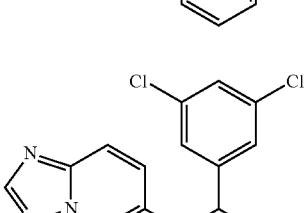 | Parent |

-continued
| Cpd # | Structure | Salt |
|---|---|---|
| 777 | 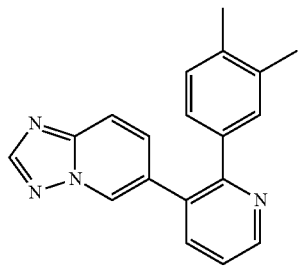 [SMILES: Cc1ccc(-c2ncccc2-c2ccc3ncnn3c2)cc1C] | Parent |
| 778 | 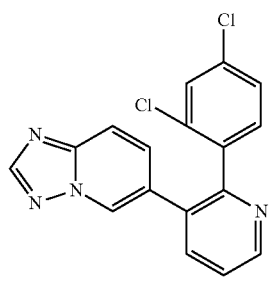 [SMILES: Clc1ccc(-c2ncccc2-c2ccc3ncnn3c2)c(Cl)c1] | Parent |
| 779 | 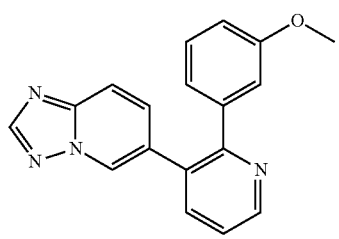 [SMILES: COc1cccc(-c2ncccc2-c2ccc3ncnn3c2)c1] | Parent |
| 780 | 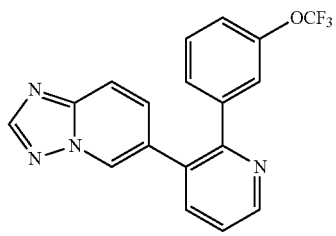 [SMILES: FC(F)(F)Oc1cccc(-c2ncccc2-c2ccc3ncnn3c2)c1] | Parent |
| 781 | 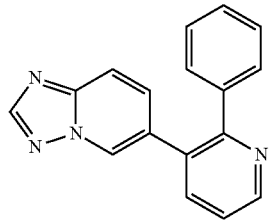 [SMILES: c1ccc(-c2ncccc2-c2ccc3ncnn3c2)cc1] | Parent |

| Cpd # | Structure | Salt |
|---|---|---|
| 782 | 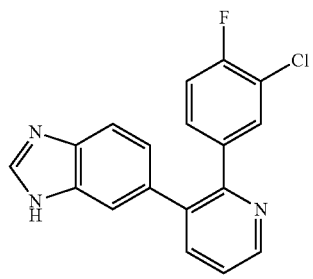 [SMILES: Fc1ccc(-c2ncccc2-c2ccc3nc[nH]c3c2)cc1Cl] | Parent |
| 783 | 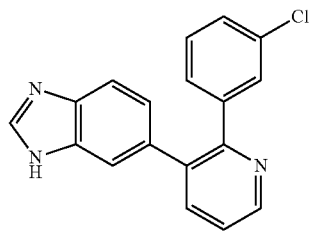 [SMILES: Clc1cccc(-c2ncccc2-c2ccc3nc[nH]c3c2)c1] | Parent |
| 784 | 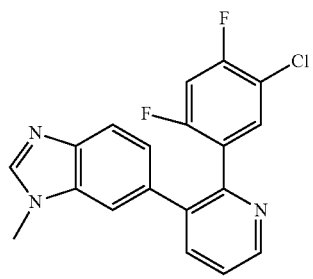 [SMILES: Cn1cnc2ccc(-c3cccnc3-c3cc(Cl)c(F)cc3F)cc21] | Parent |
| 785 | 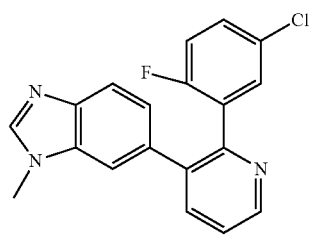 [SMILES: Cn1cnc2ccc(-c3cccnc3-c3cc(Cl)ccc3F)cc21] | Parent |
| 786 | 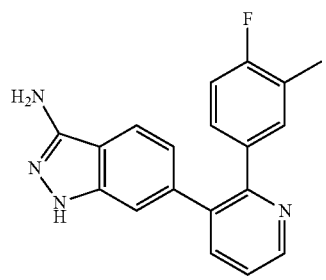 [SMILES: Cc1cc(-c2ncccc2-c2ccc3c(N)n[nH]c3c2)ccc1F] | Parent |

| Cpd # | Structure | Salt |
|---|---|---|
| 787 | 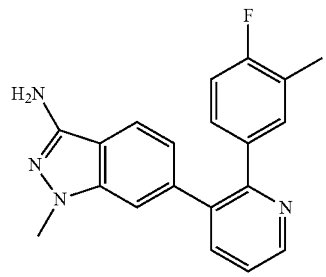 [SMILES: Cc1cc(-c2ncccc2-c2ccc3c(N)nn(C)c3c2)ccc1F] | Parent |
| 788 | 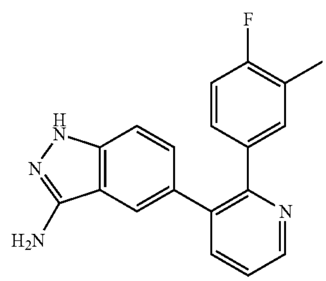 [SMILES: Cc1cc(-c2ncccc2-c2ccc3[nH]nc(N)c3c2)ccc1F] | Parent |
| 789 | 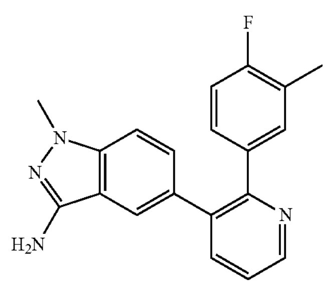 [SMILES: Cc1cc(-c2ncccc2-c2ccc3c(c2)c(N)nn3C)ccc1F] | Parent |
| 790 | 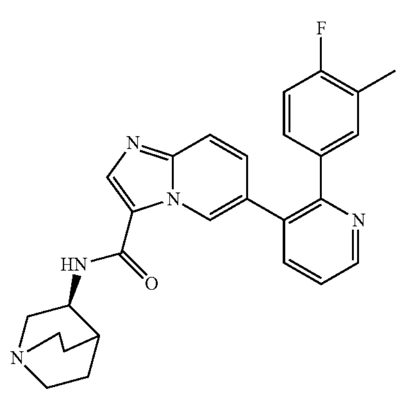 [SMILES: Cc1cc(-c2ncccc2-c2ccc3ncc(C(=O)N[C@@H]4CN5CCC4CC5)n3c2)ccc1F] | Parent |

| Cpd # | Structure | Salt |
|---|---|---|
| 791 | 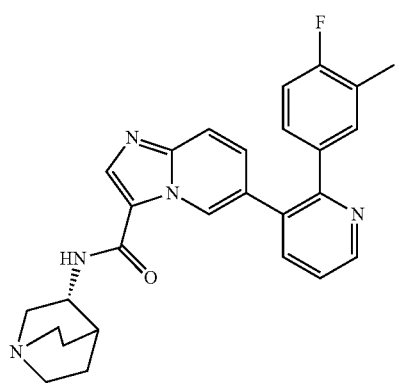 [SMILES: Cc1cc(-c2ncccc2-c2ccc3ncc(C(=O)N[C@H]4CN5CCC4CC5)n3c2)ccc1F] | Parent |
| 792 | 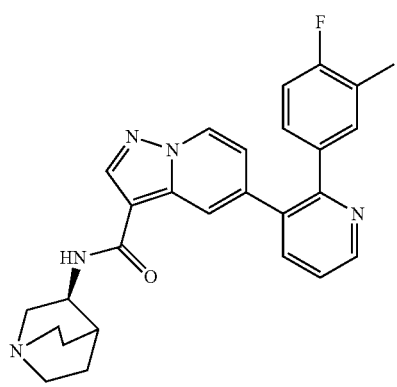 [SMILES: Cc1cc(-c2ncccc2-c2ccn3ncc(C(=O)N[C@@H]4CN5CCC4CC5)c3c2)ccc1F] | Parent |
| 793 | 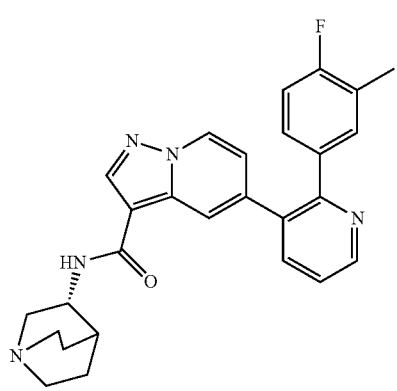 [SMILES: Cc1cc(-c2ncccc2-c2ccn3ncc(C(=O)N[C@H]4CN5CCC4CC5)c3c2)ccc1F] | Parent |
| 794 | 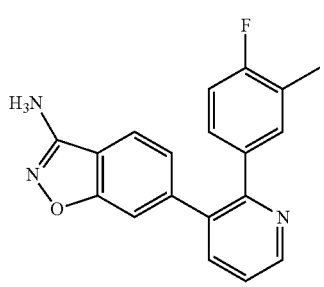 [SMILES: Cc1cc(-c2ncccc2-c2ccc3c(N)noc3c2)ccc1F] | Parent |

-continued

| Cpd # | Structure | Salt |
|---|---|---|
| 795 | 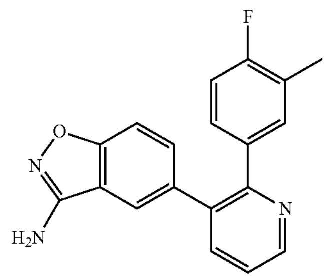 [SMILES: Cc1cc(-c2ncccc2-c2ccc3onc(N)c3c2)ccc1F] | Parent |
| 796 | 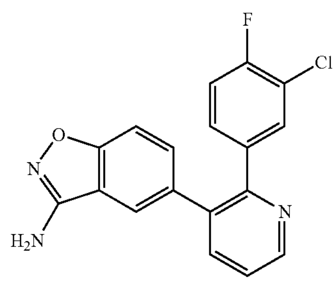 [SMILES: Nc1noc2ccc(-c3cccnc3-c3ccc(F)c(Cl)c3)cc12] | Parent |
| 797 | 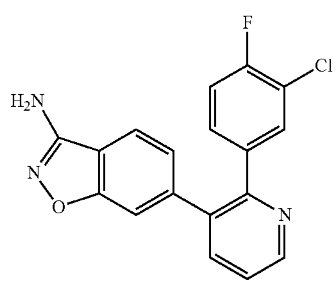 [SMILES: Nc1noc2cc(-c3cccnc3-c3ccc(F)c(Cl)c3)ccc12] | Parent |
| 798 | 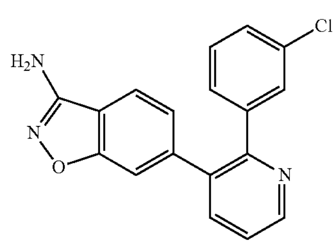 [SMILES: Nc1noc2cc(-c3cccnc3-c3cccc(Cl)c3)ccc12] | Parent |
| 799 | 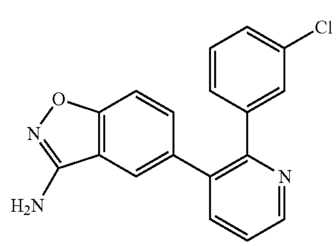 [SMILES: Nc1noc2ccc(-c3cccnc3-c3cccc(Cl)c3)cc12] | Parent |

| Cpd # | Structure | Salt |
|---|---|---|
| 800 | 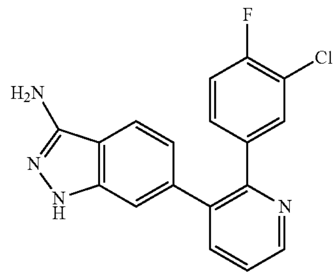 [SMILES: Nc1n[nH]c2cc(-c3cccnc3-c3ccc(F)c(Cl)c3)ccc12] | Parent |
| 801 | 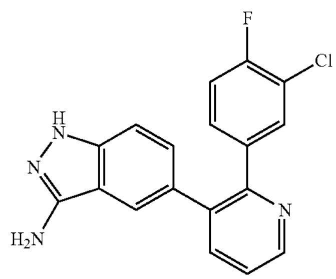 [SMILES: Nc1n[nH]c2ccc(-c3cccnc3-c3ccc(F)c(Cl)c3)cc12] | Parent |
| 802 | 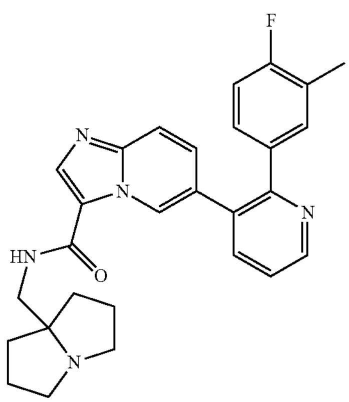 [SMILES: Cc1cc(-c2ncccc2-c2ccc3ncc(C(=O)NCC45CCCN4CCC5)n3c2)ccc1F] | Parent |
| 803 | 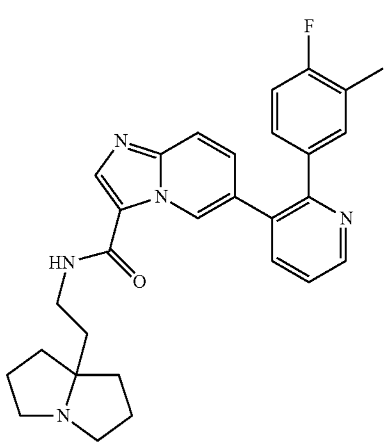 [SMILES: Cc1cc(-c2ncccc2-c2ccc3ncc(C(=O)NCCC45CCCN4CCC5)n3c2)ccc1F] | Parent |

| Cpd # | Structure | Salt |
|---|---|---|
| 804 | 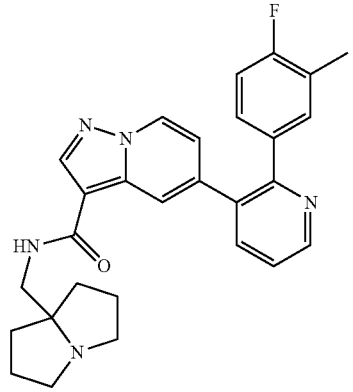 [SMILES: Cc1cc(-c2ncccc2-c2ccn3ncc(C(=O)NCC45CCCN4CCC5)c3c2)ccc1F] | Parent |
| 805 | 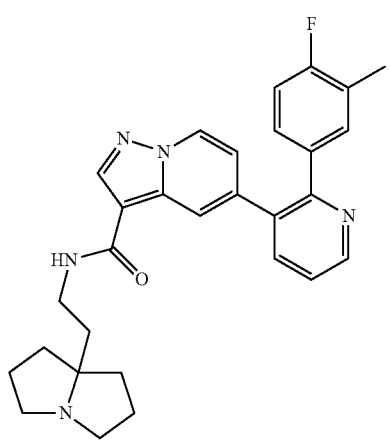 [SMILES: Cc1cc(-c2ncccc2-c2ccn3ncc(C(=O)NCCC45CCCN4CCC5)c3c2)ccc1F] | Parent |
| 806 | 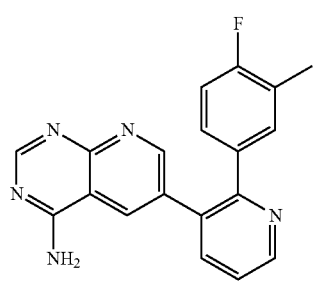 [SMILES: Cc1cc(-c2ncccc2-c2cnc3ncnc(N)c3c2)ccc1F] | Parent |
| 807 | 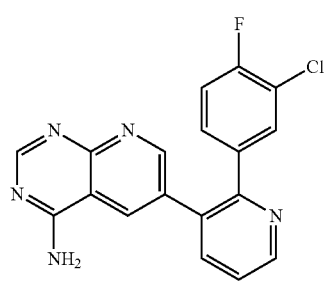 [SMILES: Nc1ncnc2ncc(-c3cccnc3-c3ccc(F)c(Cl)c3)cc12] | Parent |

-continued

| Cpd # | Structure | Salt |
|---|---|---|
| 808 | 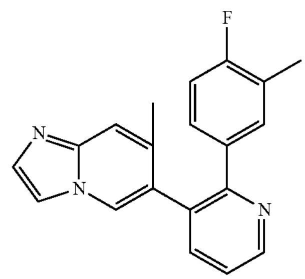 [SMILES: Cc1cc(-c2ncccc2-c2cn3ccnc3cc2C)ccc1F] | Parent |
| 809 | 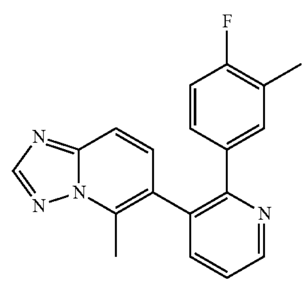 [SMILES: Cc1cc(-c2ncccc2-c2ccc3ncnn3c2C)ccc1F] | Parent |
| 810 | 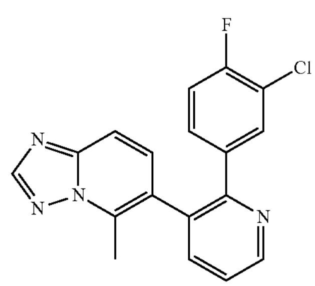 [SMILES: Cc1c(-c2cccnc2-c2ccc(F)c(Cl)c2)ccc2ncnn12] | Parent |
| 811 | 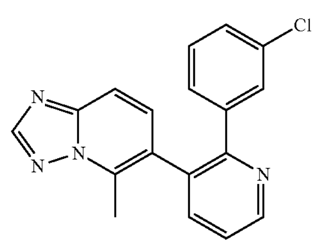 [SMILES: Cc1c(-c2cccnc2-c2cccc(Cl)c2)ccc2ncnn12] | Parent |
| 812 | 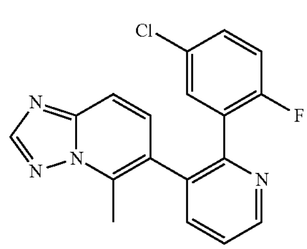 [SMILES: Cc1c(-c2cccnc2-c2cc(Cl)ccc2F)ccc2ncnn12] | Parent |

| Cpd # | Structure | Salt |
|---|---|---|
| 813 | 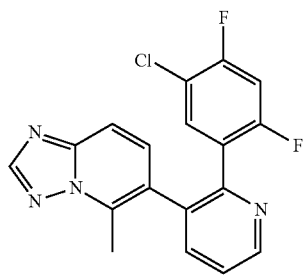 [SMILES: Cc1c(-c2cccnc2-c2cc(Cl)c(F)cc2F)ccc2ncnn12] | Parent |
| 814 | 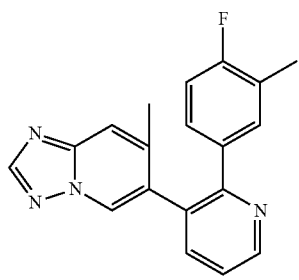 [SMILES: Cc1cc(-c2ncccc2-c2cn3ncnc3cc2C)ccc1F] | Parent |
| 815 | 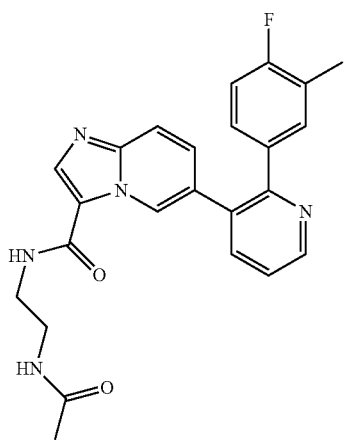 [SMILES: CC(=O)NCCNC(=O)c1cnc2ccc(-c3cccnc3-c3ccc(F)c(C)c3)cn12] | Parent |
| 816 | 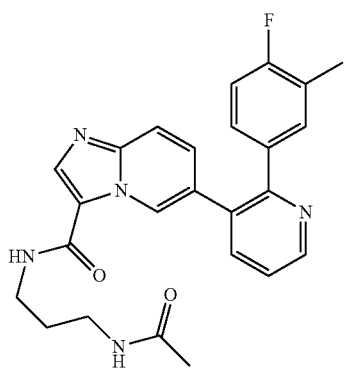 [SMILES: CC(=O)NCCCNC(=O)c1cnc2ccc(-c3cccnc3-c3ccc(F)c(C)c3)cn12] | Parent |

-continued

| Cpd # | Structure | Salt |
|---|---|---|
| 817 | 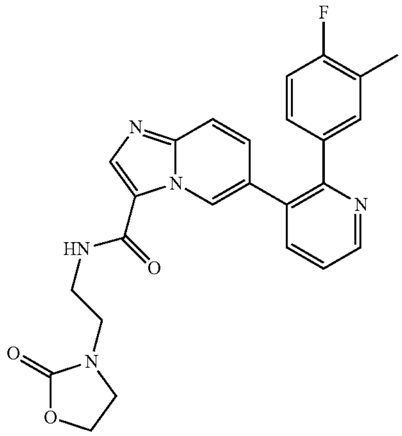 [SMILES: Cc1cc(-c2ncccc2-c2ccc3ncc(C(=O)NCCN4CCOC4=O)n3c2)ccc1F] | Parent |
| 818 | 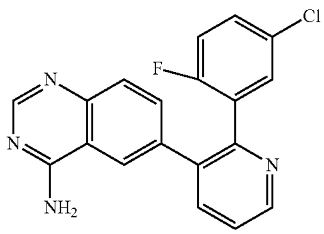 [SMILES: Nc1ncnc2ccc(-c3cccnc3-c3cc(Cl)ccc3F)cc12] | Parent |
| 819 | 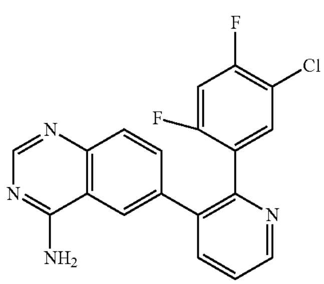 [SMILES: Nc1ncnc2ccc(-c3cccnc3-c3cc(Cl)c(F)cc3F)cc12] | Parent |
| 820 | 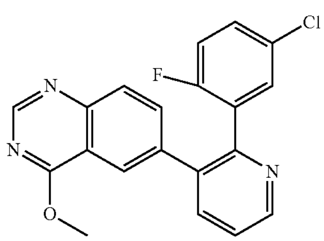 [SMILES: COc1ncnc2ccc(-c3cccnc3-c3cc(Cl)ccc3F)cc12] | Parent |
| 821 | 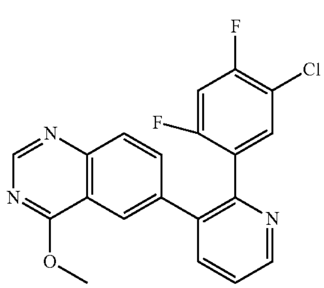 [SMILES: COc1ncnc2ccc(-c3cccnc3-c3cc(Cl)c(F)cc3F)cc12] | Parent |

| Cpd # | Structure | Salt |
|---|---|---|
| 822 | 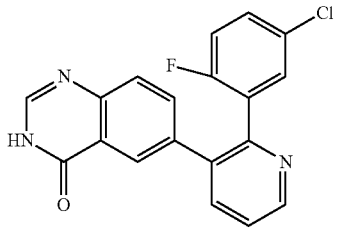 [SMILES: O=c1[nH]cnc2ccc(-c3cccnc3-c3cc(Cl)ccc3F)cc12] | Parent |
| 823 | 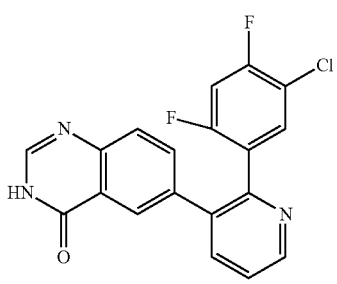 [SMILES: O=c1[nH]cnc2ccc(-c3cccnc3-c3cc(Cl)c(F)cc3F)cc12] | Parent |
| 824 | 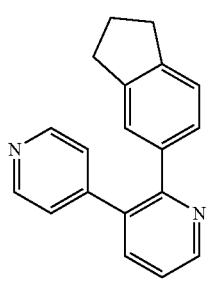 [SMILES: c1cnc(-c2ccc3c(c2)CCC3)c(-c2ccncc2)c1] | Parent |
| 825 | 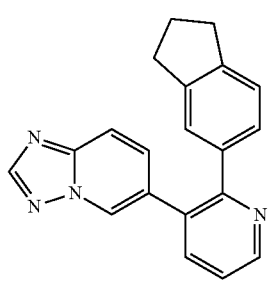 [SMILES: c1cnc(-c2ccc3c(c2)CCC3)c(-c2ccc3ncnn3c2)c1] | Parent |
| 826 | 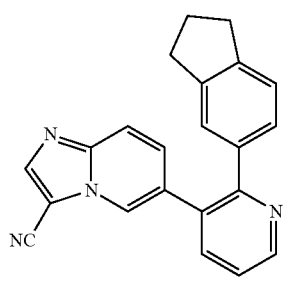 [SMILES: N#Cc1cnc2ccc(-c3cccnc3-c3ccc4c(c3)CCC4)cn12] | Parent |

US 9,145,433 B2
377
378
-continued
| Cpd # | Structure | Salt |
|---|---|---|
| 827 | 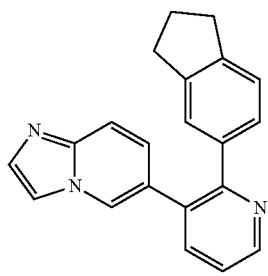 [SMILES: c1cnc(-c2ccc3c(c2)CCC3)c(-c2ccc3nccn3c2)c1] | Parent |
| 828 | 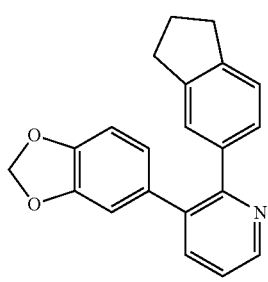 [SMILES: c1cnc(-c2ccc3c(c2)CCC3)c(-c2ccc3c(c2)OCO3)c1] | Parent |
| 829 | 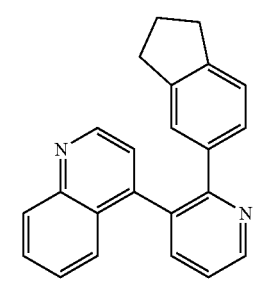 [SMILES: c1cnc(-c2ccc3c(c2)CCC3)c(-c2ccnc3ccccc23)c1] | Parent |
| 830 | 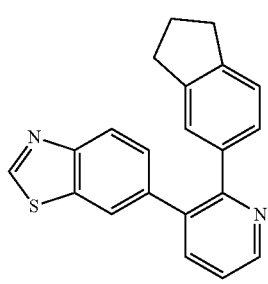 [SMILES: c1cnc(-c2ccc3c(c2)CCC3)c(-c2ccc3ncsc3c2)c1] | Parent |
| 831 | 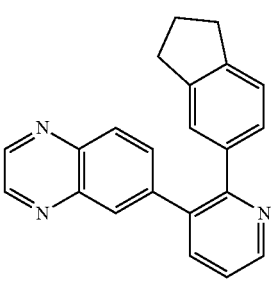 [SMILES: c1cnc(-c2ccc3c(c2)CCC3)c(-c2ccc3nccnc3c2)c1] | Parent |

-continued

| Cpd # | Structure | Salt |
|---|---|---|
| 832 | 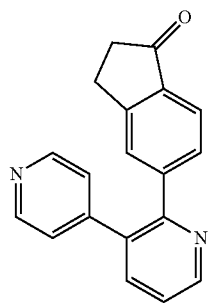 [SMILES: O=C1CCc2cc(-c3ncccc3-c3ccncc3)ccc21] | Parent |
| 833 | 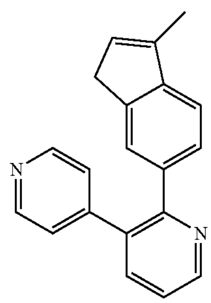 [SMILES: CC1=CCc2cc(-c3ncccc3-c3ccncc3)ccc21] | Parent |
| 834 | 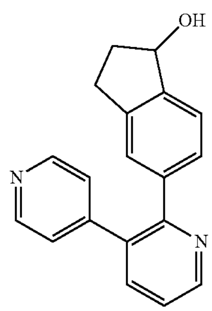 [SMILES: OC1CCc2cc(-c3ncccc3-c3ccncc3)ccc21] | Parent |
| 835 | 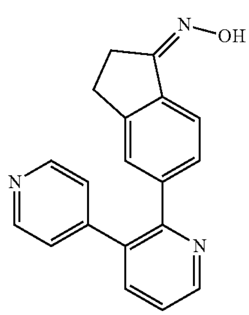 [SMILES: O/N=C1/CCc2cc(-c3ncccc3-c3ccncc3)ccc21] | Parent |
| 836 | 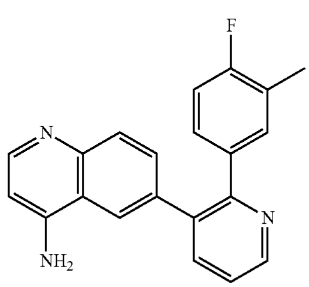 [SMILES: Cc1cc(-c2ncccc2-c2ccc3nccc(N)c3c2)ccc1F] | Parent |

US 9,145,433 B2
381                                                                 382
-continued
| Cpd # | Structure | Salt |
|---|---|---|
| 837 | 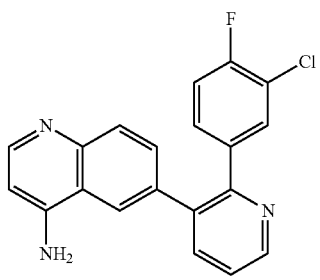 [SMILES: Nc1ccnc2ccc(-c3cccnc3-c3ccc(F)c(Cl)c3)cc12] | Parent |
| 838 | 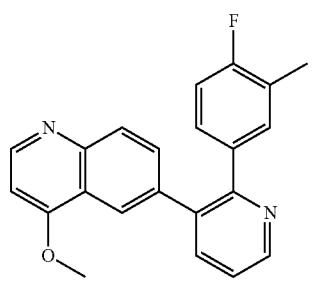 [SMILES: COc1ccnc2ccc(-c3cccnc3-c3ccc(F)c(C)c3)cc12] | Parent |
| 839 | 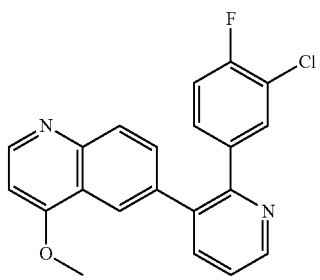 [SMILES: COc1ccnc2ccc(-c3cccnc3-c3ccc(F)c(Cl)c3)cc12] | Parent |
| 840 | 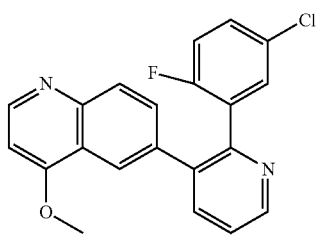 [SMILES: COc1ccnc2ccc(-c3cccnc3-c3cc(Cl)ccc3F)cc12] | Parent |
| 841 | 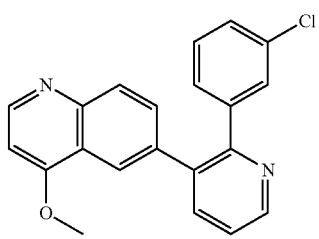 [SMILES: COc1ccnc2ccc(-c3cccnc3-c3cccc(Cl)c3)cc12] | Parent |

-continued
| Cpd # | Structure | Salt |
|---|---|---|
| 842 | 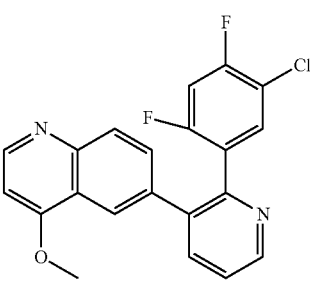 [SMILES: COc1ccnc2ccc(-c3cccnc3-c3cc(Cl)c(F)cc3F)cc12] | Parent |
| 843 | 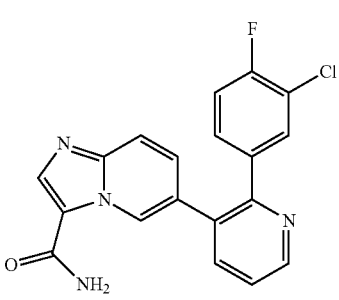 [SMILES: NC(=O)c1cnc2ccc(-c3cccnc3-c3ccc(F)c(Cl)c3)cn12] | Parent |
| 844 | 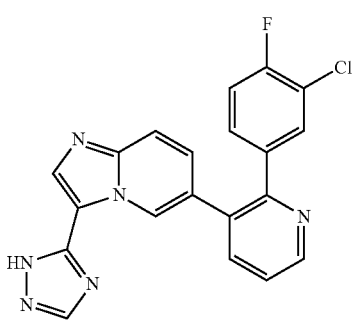 [SMILES: Fc1ccc(-c2ncccc2-c2ccc3ncc(-c4ncn[nH]4)n3c2)cc1Cl] | Parent |
| 845 | 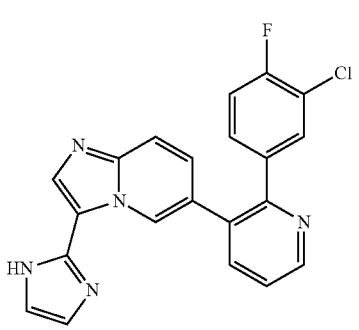 [SMILES: Fc1ccc(-c2ncccc2-c2ccc3ncc(-c4ncc[nH]4)n3c2)cc1Cl] | Parent |
| 846 | 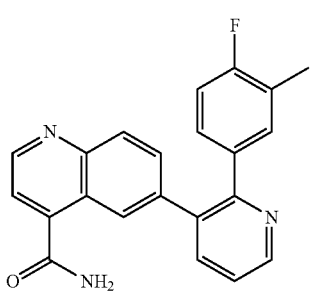 [SMILES: Cc1cc(-c2ncccc2-c2ccc3nccc(C(N)=O)c3c2)ccc1F] | Parent |

-continued

| Cpd # | Structure | Salt |
|---|---|---|
| 847 | 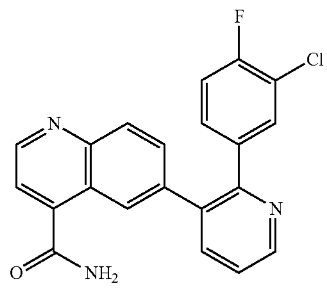 [SMILES: NC(=O)c1ccnc2ccc(-c3cccnc3-c3ccc(F)c(Cl)c3)cc12] | Parent |
| 848 | 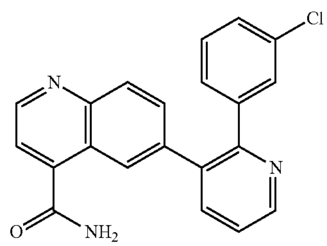 [SMILES: NC(=O)c1ccnc2ccc(-c3cccnc3-c3cccc(Cl)c3)cc12] | Parent |
| 849 | 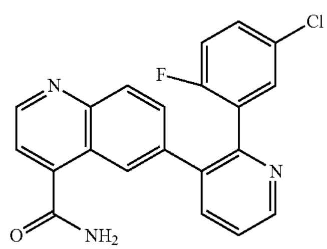 [SMILES: NC(=O)c1ccnc2ccc(-c3cccnc3-c3cc(Cl)ccc3F)cc12] | Parent |
| 850 | 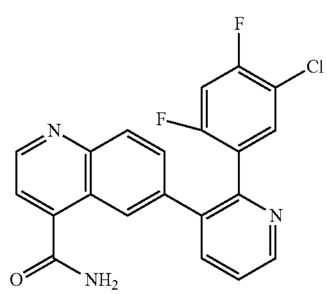 [SMILES: NC(=O)c1ccnc2ccc(-c3cccnc3-c3cc(Cl)c(F)cc3F)cc12] | Parent |
| 851 | 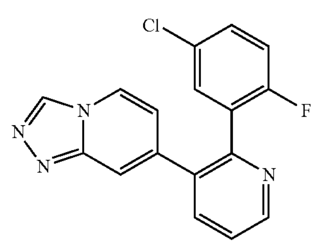 [SMILES: Fc1ccc(Cl)cc1-c1ncccc1-c1ccn2cnnc2c1] | Parent |

-continued
| Cpd # | Structure | Salt |
|---|---|---|
| 852 | 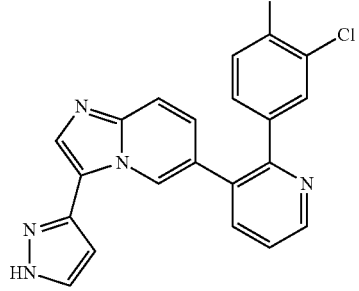 | Parent |
| 853 | 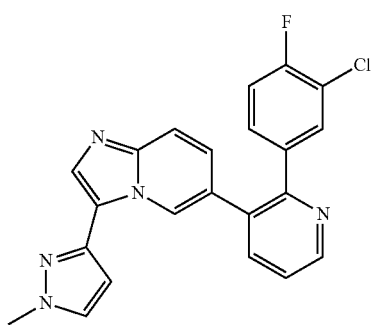 [SMILES: Cn1ccc(-c2cnc3ccc(-c4cccnc4-c4ccc(F)c(Cl)c4)cn23)n1] | Parent |
| 854 | 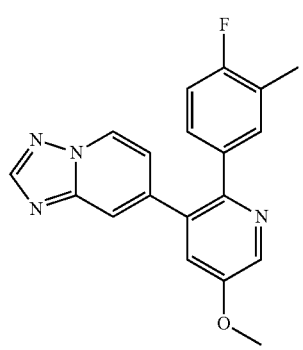 [SMILES: COc1cnc(-c2ccc(F)c(C)c2)c(-c2ccn3ncnc3c2)c1] | Parent |
| 855 | 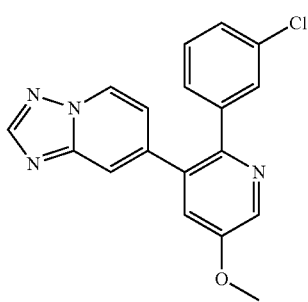 [SMILES: COc1cnc(-c2cccc(Cl)c2)c(-c2ccn3ncnc3c2)c1] | Parent |

| Cpd # | Structure | Salt |
|---|---|---|
| 856 | 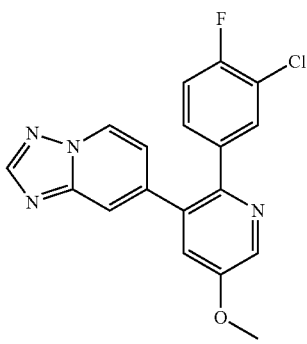 [SMILES: COc1cnc(-c2ccc(F)c(Cl)c2)c(-c2ccn3ncnc3c2)c1] | Parent |
| 857 | 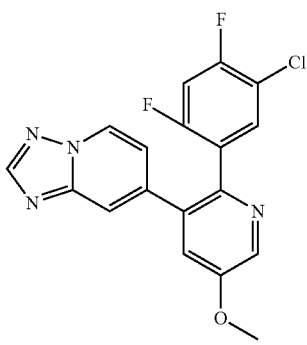 [SMILES: COc1cnc(-c2cc(Cl)c(F)cc2F)c(-c2ccn3ncnc3c2)c1] | Parent |
| 858 | 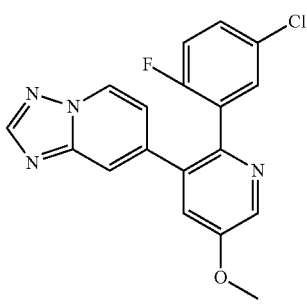 [SMILES: COc1cnc(-c2cc(Cl)ccc2F)c(-c2ccn3ncnc3c2)c1] | Parent |
| 859 | 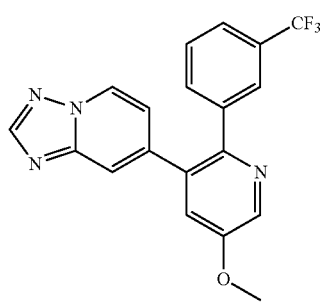 [SMILES: COc1cnc(-c2cccc(C(F)(F)F)c2)c(-c2ccn3ncnc3c2)c1] | Parent |

-continued

| Cpd # | Structure | Salt |
|---|---|---|
| 860 | 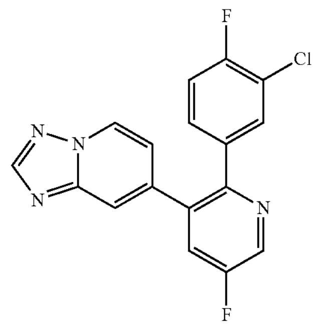 [SMILES: Fc1cnc(-c2ccc(F)c(Cl)c2)c(-c2ccn3ncnc3c2)c1] | Parent |
| 861 | 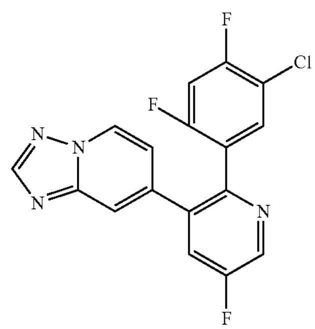 [SMILES: Fc1cnc(-c2cc(Cl)c(F)cc2F)c(-c2ccn3ncnc3c2)c1] | Parent |
| 862 | 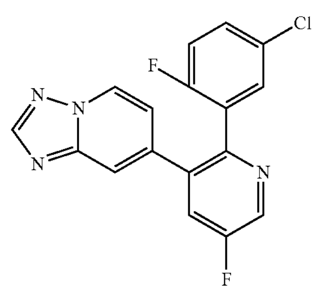 [SMILES: Fc1cnc(-c2cc(Cl)ccc2F)c(-c2ccn3ncnc3c2)c1] | Parent |
| 863 | 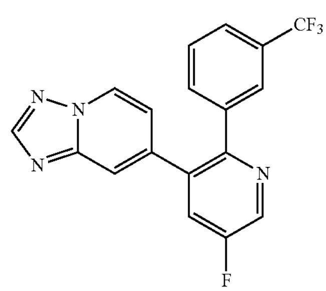 [SMILES: Fc1cnc(-c2cccc(C(F)(F)F)c2)c(-c2ccn3ncnc3c2)c1] | Parent |
| 864 | 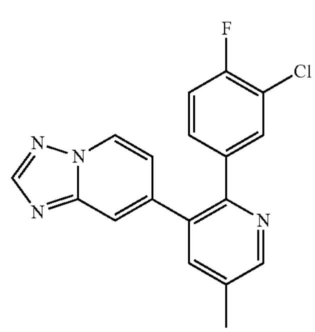 [SMILES: Cc1cnc(-c2ccc(F)c(Cl)c2)c(-c2ccn3ncnc3c2)c1] | Parent |

-continued
| Cpd # | Structure | Salt |
|---|---|---|
| 865 | 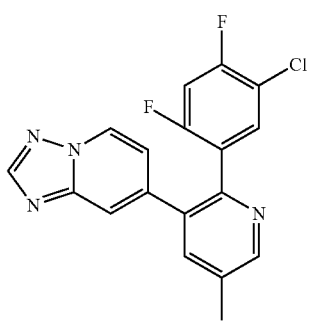 [SMILES: Cc1cnc(-c2cc(Cl)c(F)cc2F)c(-c2ccn3ncnc3c2)c1] | Parent |
| 866 | 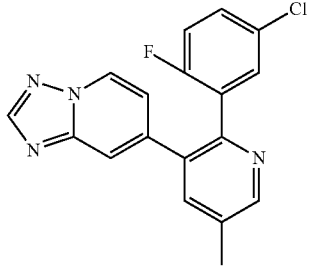 [SMILES: Cc1cnc(-c2cc(Cl)ccc2F)c(-c2ccn3ncnc3c2)c1] | Parent |
| 867 | 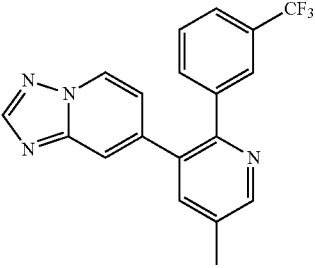 [SMILES: Cc1cnc(-c2cccc(C(F)(F)F)c2)c(-c2ccn3ncnc3c2)c1] | Parent |
| 868 | 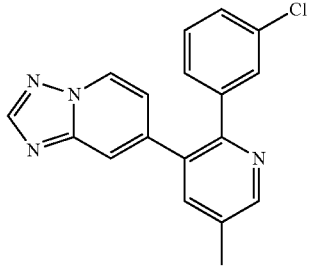 [SMILES: Cc1cnc(-c2cccc(Cl)c2)c(-c2ccn3ncnc3c2)c1] | Parent |
| 869 | 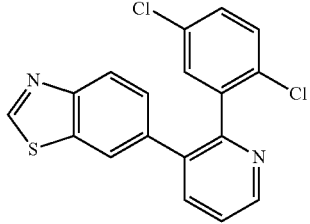 [SMILES: Clc1ccc(Cl)c(-c2ncccc2-c2ccc3ncsc3c2)c1] | Parent |

| Cpd # | Structure | Salt |
|---|---|---|
| 870 | 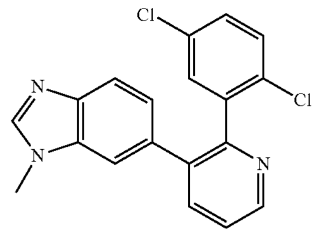 [SMILES: Cn1cnc2ccc(-c3cccnc3-c3cc(Cl)ccc3Cl)cc21] | Parent |
| 871 | 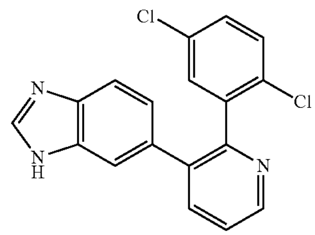 [SMILES: Clc1ccc(Cl)c(-c2ncccc2-c2ccc3nc[nH]c3c2)c1] | Parent |
| 872 | 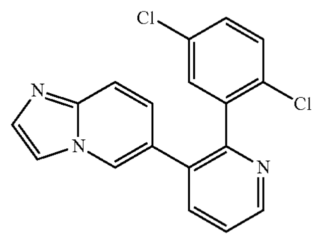 [SMILES: Clc1ccc(Cl)c(-c2ncccc2-c2ccc3nccn3c2)c1] | Parent |
| 873 | 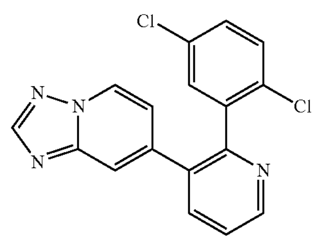 [SMILES: Clc1ccc(Cl)c(-c2ncccc2-c2ccn3ncnc3c2)c1] | Parent |
| 874 | 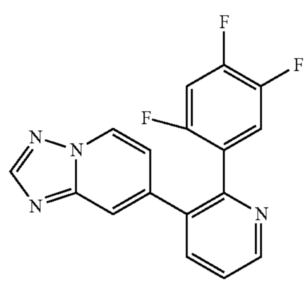 [SMILES: Fc1cc(F)c(-c2ncccc2-c2ccn3ncnc3c2)cc1F] | Parent |
| 875 | 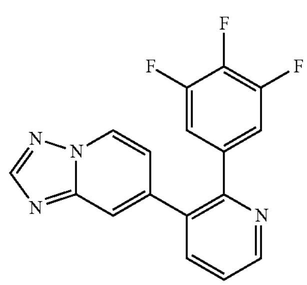 [SMILES: Fc1cc(-c2ncccc2-c2ccn3ncnc3c2)cc(F)c1F] | Parent |

| Cpd # | Structure | Salt |
|---|---|---|
| 876 | 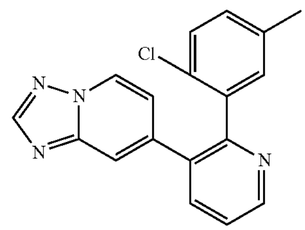 [SMILES: Cc1ccc(Cl)c(-c2ncccc2-c2ccn3ncnc3c2)c1] | Parent |
| 877 | 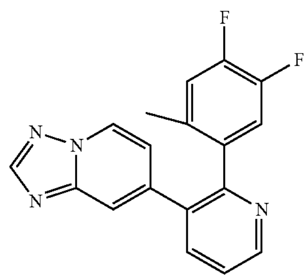 [SMILES: Cc1cc(F)c(F)cc1-c1ncccc1-c1ccn2ncnc2c1] | Parent |
| 878 | 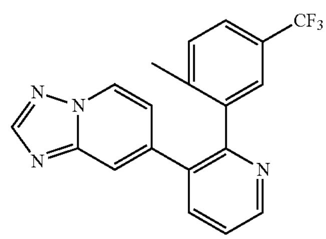 [SMILES: Cc1ccc(C(F)(F)F)cc1-c1ncccc1-c1ccn2ncnc2c1] | Parent |
| 879 | 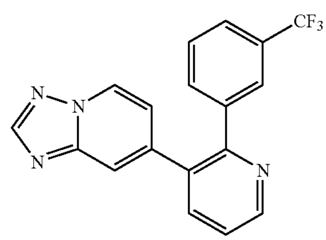 [SMILES: FC(F)(F)c1cccc(-c2ncccc2-c2ccn3ncnc3c2)c1] | Parent |
| 880 | 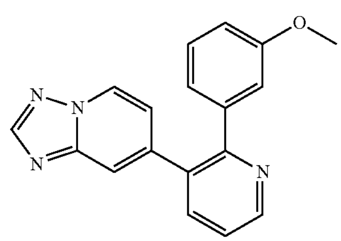 [SMILES: COc1cccc(-c2ncccc2-c2ccn3ncnc3c2)c1] | Parent |
| 881 | 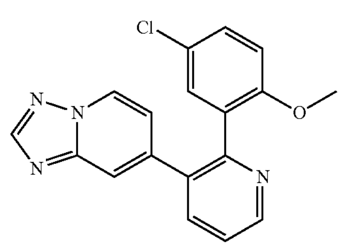 [SMILES: COc1ccc(Cl)cc1-c1ncccc1-c1ccn2ncnc2c1] | Parent |

| Cpd # | Structure | Salt |
|---|---|---|
| 882 | 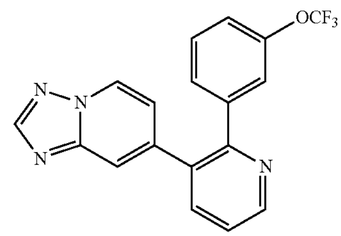 [SMILES: FC(F)(F)Oc1cccc(-c2ncccc2-c2ccn3ncnc3c2)c1] | Parent |
| 883 | 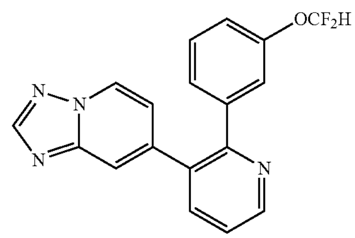 | Parent |
| 884 | 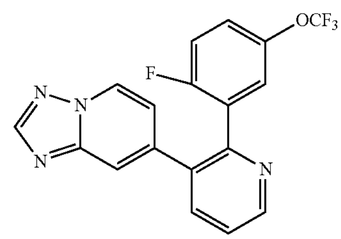 [SMILES: Fc1ccc(OC(F)(F)F)cc1-c1ncccc1-c1ccn2ncnc2c1] | Parent |
| 885 | 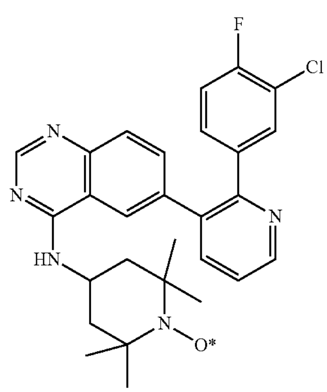 | Parent |
| 886 | 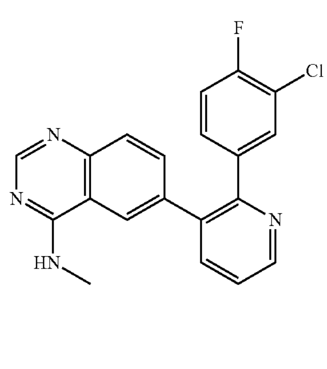 [SMILES: CNc1ncnc2ccc(-c3cccnc3-c3ccc(F)c(Cl)c3)cc12] | Parent |

-continued

| Cpd # | Structure | Salt |
|---|---|---|
| 887 | 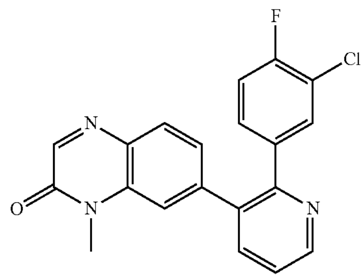 [SMILES: Cn1c(=O)cnc2ccc(-c3cccnc3-c3ccc(F)c(Cl)c3)cc21] | Parent |
| 888 | 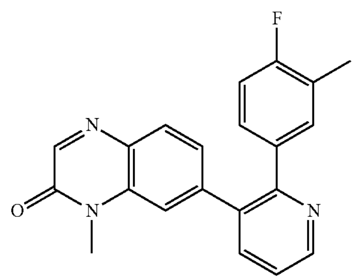 [SMILES: Cc1cc(-c2ncccc2-c2ccc3ncc(=O)n(C)c3c2)ccc1F] | Parent |
| 889 | 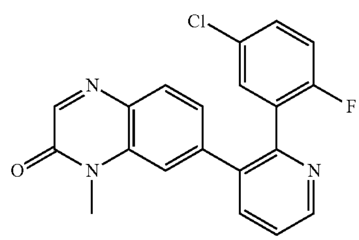 [SMILES: Cn1c(=O)cnc2ccc(-c3cccnc3-c3cc(Cl)ccc3F)cc21] | Parent |
| 890 | 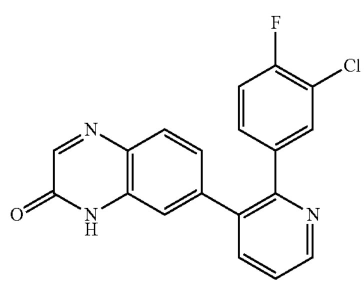 [SMILES: O=c1cnc2ccc(-c3cccnc3-c3ccc(F)c(Cl)c3)cc2[nH]1] | Parent |
| 891 | 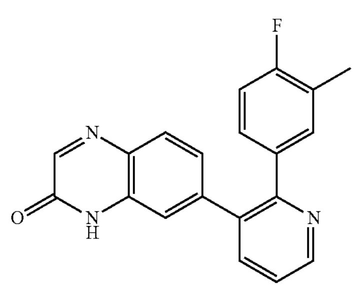 [SMILES: Cc1cc(-c2ncccc2-c2ccc3ncc(=O)[nH]c3c2)ccc1F] | Parent |

-continued

| Cpd # | Structure | Salt |
|---|---|---|
| 892 | 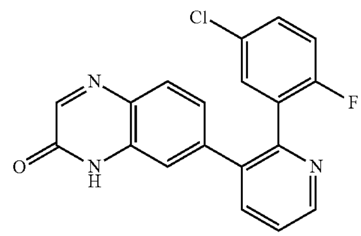 [SMILES: O=c1cnc2ccc(-c3cccnc3-c3cc(Cl)ccc3F)cc2[nH]1] | Parent |
| 893 | 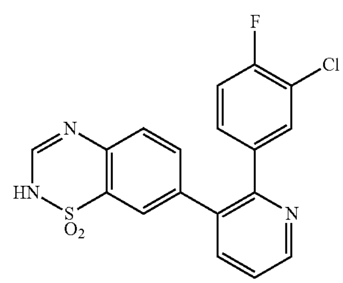 [SMILES: O=S1(=O)NC=Nc2ccc(-c3cccnc3-c3ccc(F)c(Cl)c3)cc21] | Parent |
| 894 | 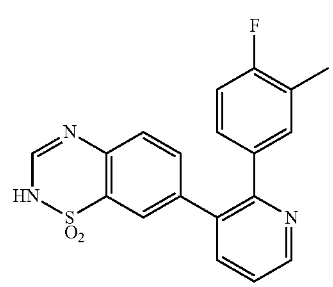 [SMILES: Cc1cc(-c2ncccc2-c2ccc3c(c2)S(=O)(=O)NC=N3)ccc1F] | Parent |
| 895 | 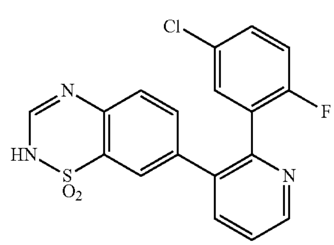 [SMILES: O=S1(=O)NC=Nc2ccc(-c3cccnc3-c3cc(Cl)ccc3F)cc21] | Parent |
| 896 | 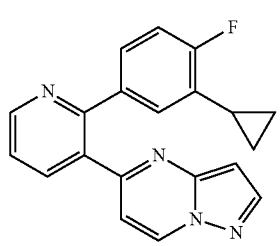 [SMILES: Fc1ccc(-c2ncccc2-c2ccn3nccc3n2)cc1C1CC1] | TFA(3) |

-continued
| Cpd # | Structure | Salt |
|---|---|---|
| 897 | 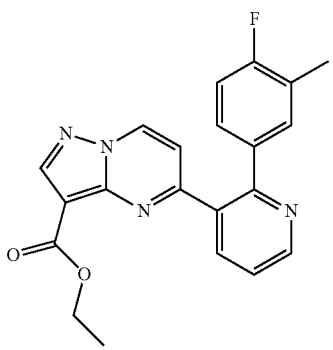 [SMILES: CCOC(=O)c1cnn2ccc(-c3cccnc3-c3ccc(F)c(C)c3)nc12] | Parent |
| 898 | 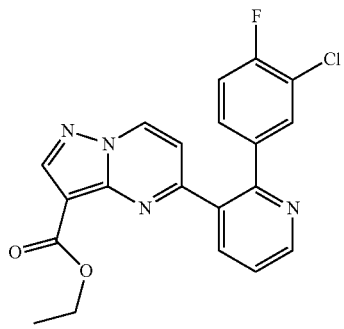 [SMILES: CCOC(=O)c1cnn2ccc(-c3cccnc3-c3ccc(F)c(Cl)c3)nc12] | Parent |
| 899 | 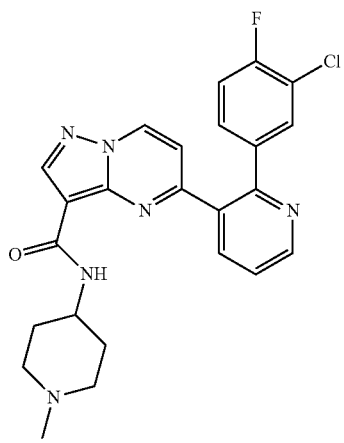 [SMILES: CN1CCC(NC(=O)c2cnn3ccc(-c4cccnc4-c4ccc(F)c(Cl)c4)nc23)CC1] | Parent |
| 900 | 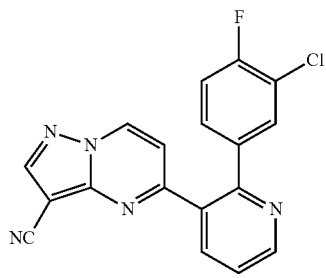 [SMILES: N#Cc1cnn2ccc(-c3cccnc3-c3ccc(F)c(Cl)c3)nc12] | Parent |

-continued

| Cpd # | Structure | Salt |
|---|---|---|
| 901 | 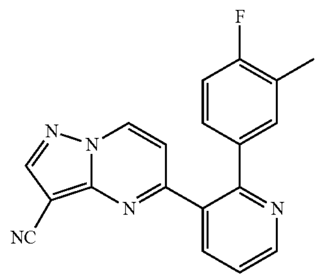 [SMILES: Cc1cc(-c2ncccc2-c2ccn3ncc(C#N)c3n2)ccc1F] | Parent |
| 902 | 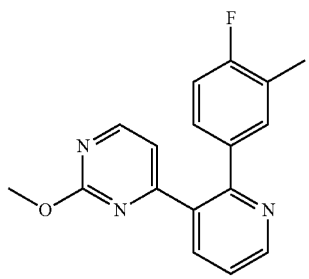 | Parent |
| 903 | 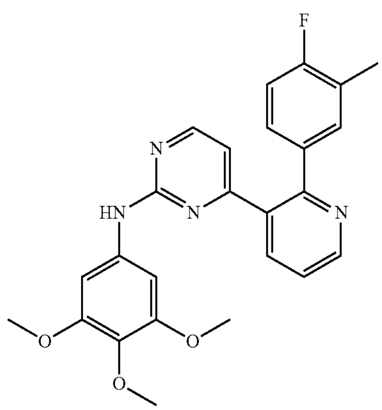 | Parent |
| 904 | 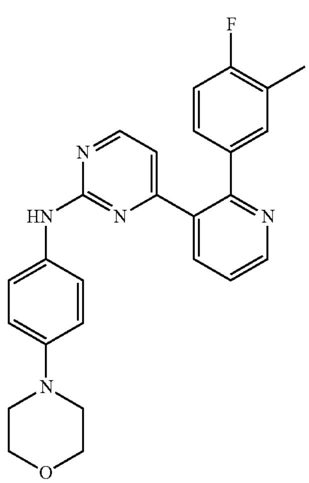 [SMILES: Cc1cc(-c2ncccc2-c2ccnc(Nc3ccc(N4CCOCC4)cc3)n2)ccc1F] | Parent |

| Cpd # | Structure | Salt |
|---|---|---|
| 905 | 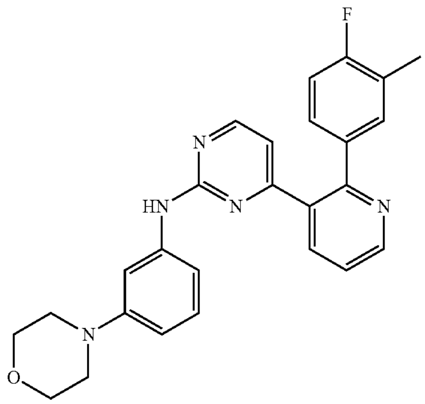 [SMILES: Cc1cc(-c2ncccc2-c2ccnc(Nc3cccc(N4CCOCC4)c3)n2)ccc1F] | Parent |
| 906 | 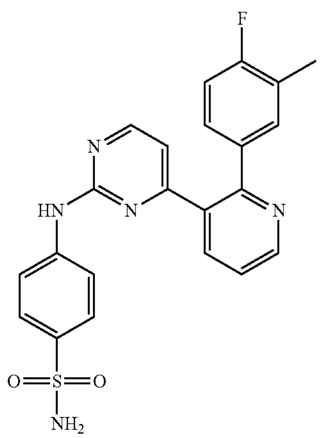 [SMILES: Cc1cc(-c2ncccc2-c2ccnc(Nc3ccc(S(N)(=O)=O)cc3)n2)ccc1F] | Parent |
| 907 | 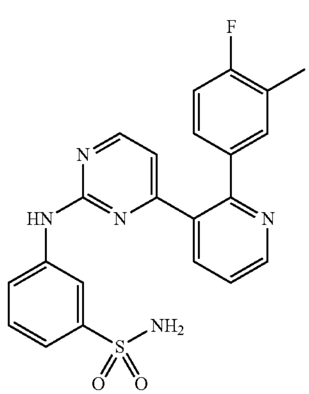 [SMILES: Cc1cc(-c2ncccc2-c2ccnc(Nc3cccc(S(N)(=O)=O)c3)n2)ccc1F] | Parent |

US 9,145,433 B2
411                                                                                     412
-continued
| Cpd # | Structure | Salt |
|---|---|---|
| 908 | 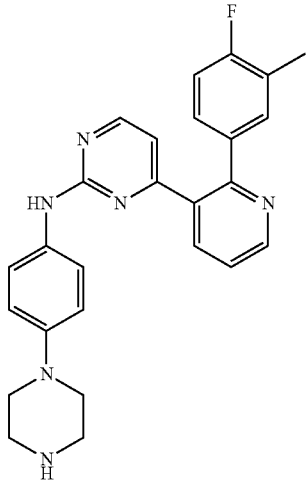 [SMILES: Cc1cc(-c2ncccc2-c2ccnc(Nc3ccc(N4CCNCC4)cc3)n2)ccc1F] | Parent |
| 909 | 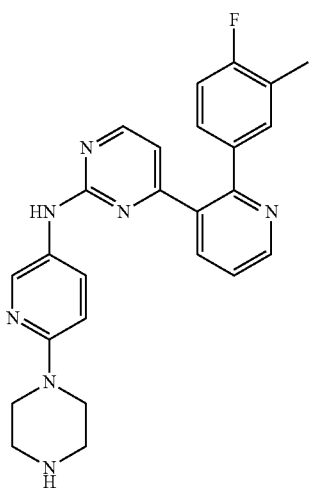 [SMILES: Cc1cc(-c2ncccc2-c2ccnc(Nc3ccc(N4CCNCC4)nc3)n2)ccc1F] | Parent |
| 910 | 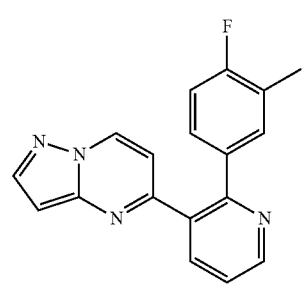 [SMILES: Cc1cc(-c2ncccc2-c2ccn3nccc3n2)ccc1F] | Parent |
| 911 | 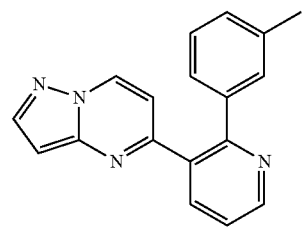 [SMILES: Cc1cccc(-c2ncccc2-c2ccn3nccc3n2)c1] | Parent |

-continued
| Cpd # | Structure | Salt |
|---|---|---|
| 912 | 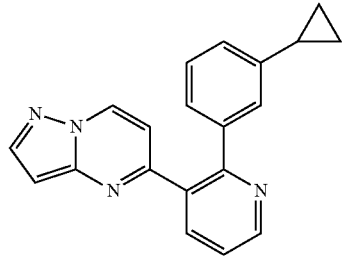 [SMILES: c1cc(-c2ncccc2-c2ccn3nccc3n2)cc(C2CC2)c1] | Parent |
| 913 | 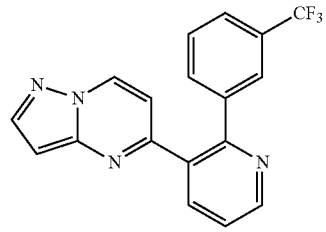 [SMILES: FC(F)(F)c1cccc(-c2ncccc2-c2ccn3nccc3n2)c1] | Parent |
| 914 | 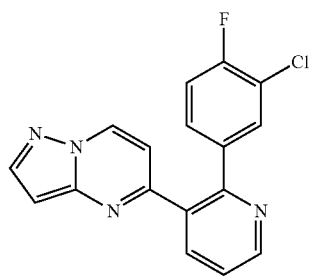 [SMILES: Fc1ccc(-c2ncccc2-c2ccn3nccc3n2)cc1Cl] | Parent |
| 915 | 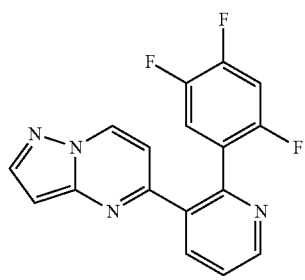 [SMILES: Fc1cc(F)c(-c2ncccc2-c2ccn3nccc3n2)cc1F] | Parent |
| 916 | 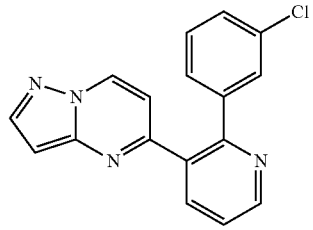 | Parent |

| Cpd # | Structure | Salt |
|---|---|---|
| 917 | 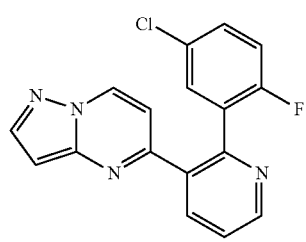 [SMILES: Fc1ccc(Cl)cc1-c1ncccc1-c1ccn2nccc2n1] | Parent |
| 918 | 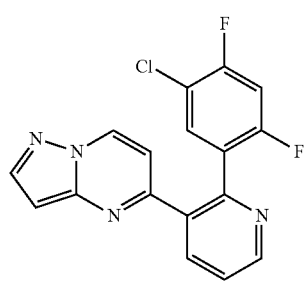 [SMILES: Fc1cc(F)c(-c2ncccc2-c2ccn3nccc3n2)cc1Cl] | Parent |
| 919 | 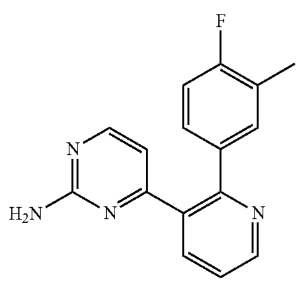 [SMILES: Cc1cc(-c2ncccc2-c2ccnc(N)n2)ccc1F] | Parent |
| 920 | 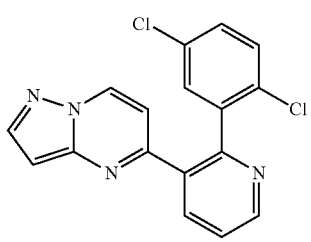 [SMILES: Clc1ccc(Cl)c(-c2ncccc2-c2ccn3nccc3n2)c1] | Parent |
| 921 | 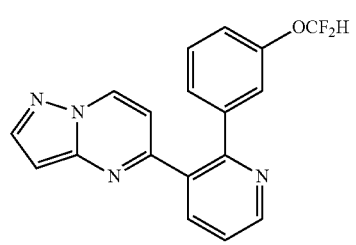 | Parent |

| Cpd # | Structure | Salt |
|---|---|---|
| 922 | 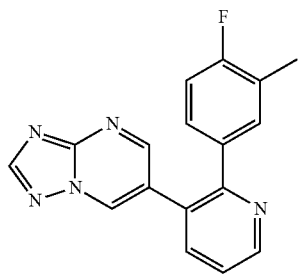 [SMILES: Cc1cc(-c2ncccc2-c2cnc3ncnn3c2)ccc1F] | Parent |
| 923 | 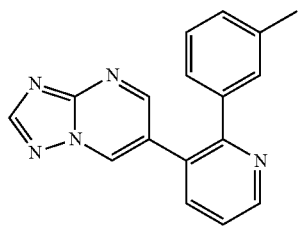 [SMILES: Cc1cccc(-c2ncccc2-c2cnc3ncnn3c2)c1] | Parent |
| 924 | 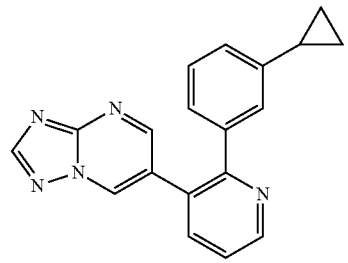 [SMILES: c1cc(-c2ncccc2-c2cnc3ncnn3c2)cc(C2CC2)c1] | Parent |
| 925 | 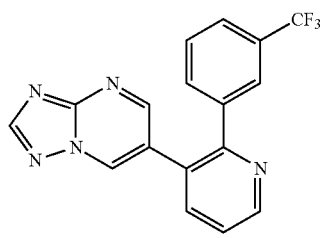 [SMILES: FC(F)(F)c1cccc(-c2ncccc2-c2cnc3ncnn3c2)c1] | Parent |
| 926 | 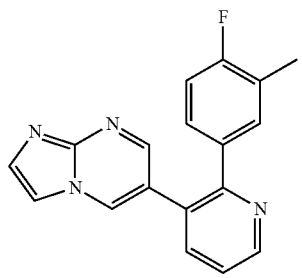 [SMILES: Cc1cc(-c2ncccc2-c2cnc3nccn3c2)ccc1F] | Parent |

-continued

| Cpd # | Structure | Salt |
|---|---|---|
| 927 | 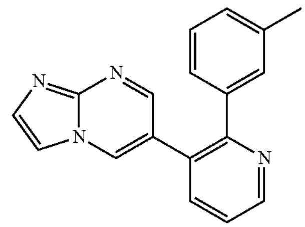 [SMILES: Cc1cccc(-c2ncccc2-c2cnc3nccn3c2)c1] | Parent |
| 928 | 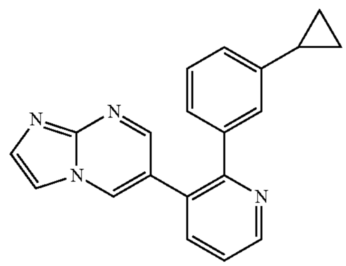 [SMILES: c1cc(-c2ncccc2-c2cnc3nccn3c2)cc(C2CC2)c1] | Parent |
| 929 | 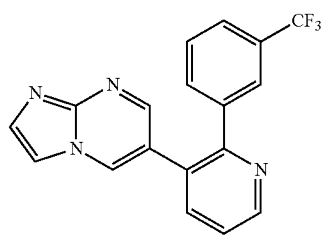 [SMILES: FC(F)(F)c1cccc(-c2ncccc2-c2cnc3nccn3c2)c1] | Parent |
| 930 | 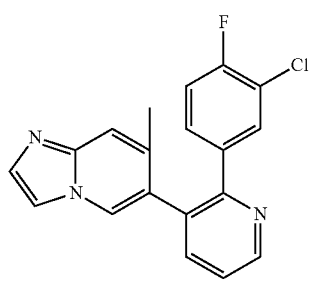 [SMILES: Cc1cc2nccn2cc1-c1cccnc1-c1ccc(F)c(Cl)c1] | Parent |
| 931 | 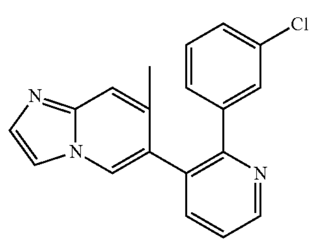 | Parent |
| 932 | 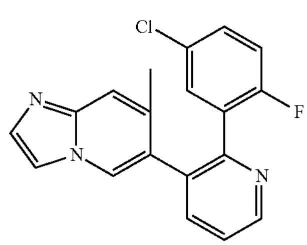 [SMILES: Cc1cc2nccn2cc1-c1cccnc1-c1cc(Cl)ccc1F] | Parent |

| Cpd # | Structure | Salt |
|---|---|---|
| 933 | 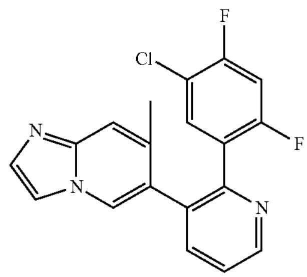 [SMILES: Cc1cc2nccn2cc1-c1cccnc1-c1cc(Cl)c(F)cc1F] | Parent |
| 934 | 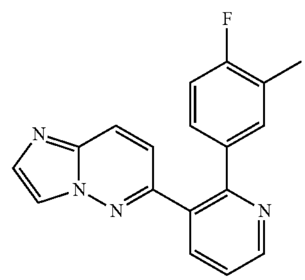 [SMILES: Cc1cc(-c2ncccc2-c2ccc3nccn3n2)ccc1F] | Parent |
| 935 | 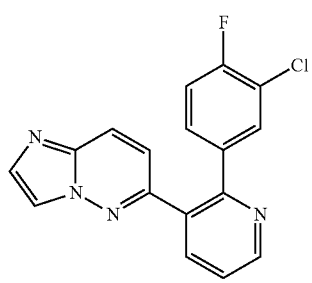 [SMILES: Fc1ccc(-c2ncccc2-c2ccc3nccn3n2)cc1Cl] | Parent |
| 936 | 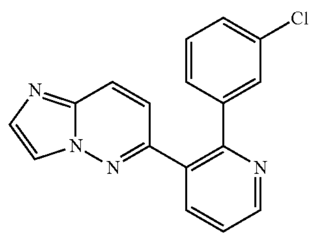 | Parent |
| 937 | 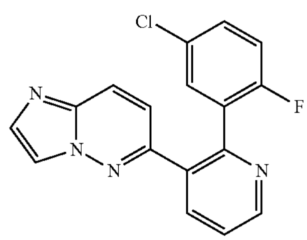 [SMILES: Fc1ccc(Cl)cc1-c1ncccc1-c1ccc2nccn2n1] | Parent |

-continued
| Cpd # | Structure | Salt |
|---|---|---|
| 938 | 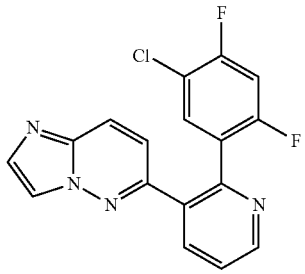 [SMILES: Fc1cc(F)c(-c2ncccc2-c2ccc3nccn3n2)cc1Cl] | Parent |
| 939 | 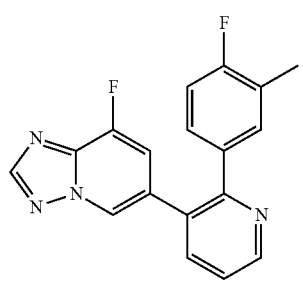 [SMILES: Cc1cc(-c2ncccc2-c2cc(F)c3ncnn3c2)ccc1F] | Parent |
| 940 | 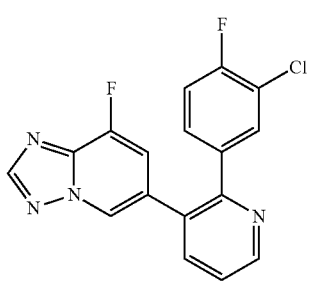 [SMILES: Fc1ccc(-c2ncccc2-c2cc(F)c3ncnn3c2)cc1Cl] | Parent |
| 941 | 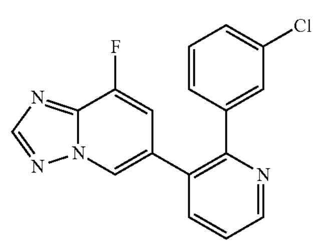 [SMILES: Fc1cc(-c2cccnc2-c2cccc(Cl)c2)cn2ncnc12] | Parent |
| 942 | 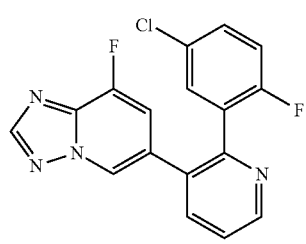 [SMILES: Fc1ccc(Cl)cc1-c1ncccc1-c1cc(F)c2ncnn2c1] | Parent |

-continued
| Cpd # | Structure | Salt |
|---|---|---|
| 943 | 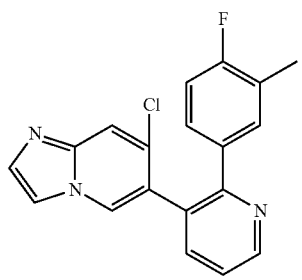 [SMILES: Cc1cc(-c2ncccc2-c2cn3ccnc3cc2Cl)ccc1F] | Parent |
| 944 | 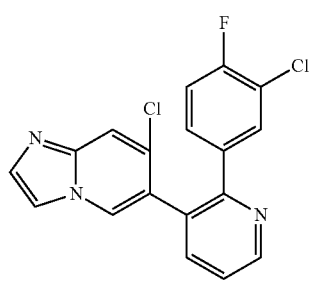 [SMILES: Fc1ccc(-c2ncccc2-c2cn3ccnc3cc2Cl)cc1Cl] | Parent |
| 945 | 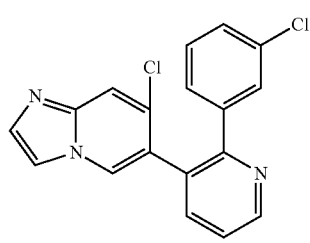 | Parent |
| 946 | 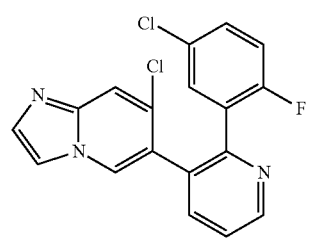 | Parent |
| 947 | 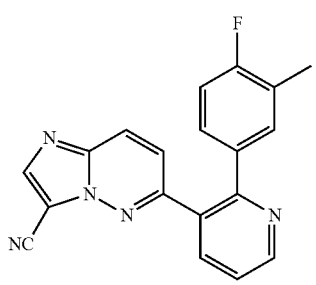 [SMILES: Cc1cc(-c2ncccc2-c2ccc3ncc(C#N)n3n2)ccc1F] | Parent |

-continued
| Cpd # | Structure | Salt |
|---|---|---|
| 948 | 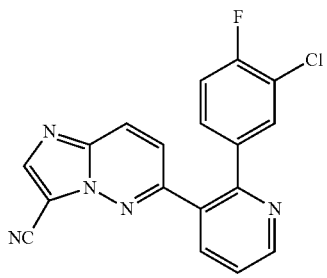 [SMILES: N#Cc1cnc2ccc(-c3cccnc3-c3ccc(F)c(Cl)c3)nn12] | Parent |
| 949 | 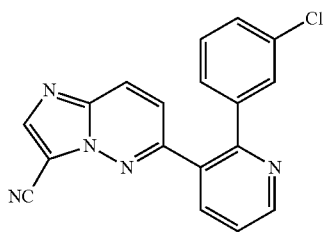 | Parent |
| 950 | 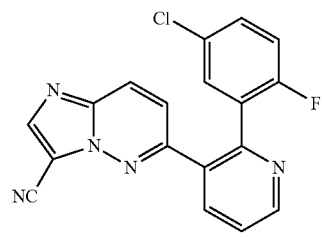 [SMILES: N#Cc1cnc2ccc(-c3cccnc3-c3cc(Cl)ccc3F)nn12] | Parent |
| 951 | 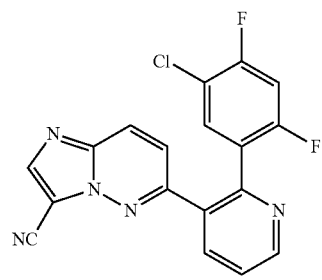 [SMILES: N#Cc1cnc2ccc(-c3cccnc3-c3cc(Cl)c(F)cc3F)nn12] | Parent |
| 952 | 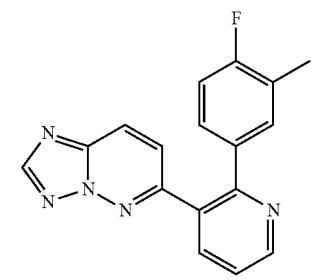 [SMILES: Cc1cc(-c2ncccc2-c2ccc3ncnn3n2)ccc1F] | Parent |

-continued
| Cpd # | Structure | Salt |
|---|---|---|
| 953 | 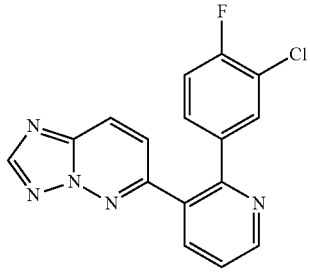 [SMILES: Fc1ccc(-c2ncccc2-c2ccc3ncnn3n2)cc1Cl] | Parent |
| 954 | 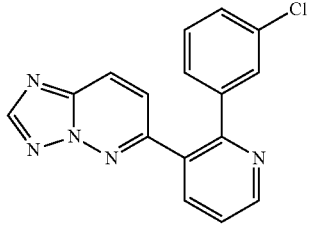 [SMILES: Clc1cccc(-c2ncccc2-c2ccc3ncnn3n2)c1] | Parent |
| 955 | 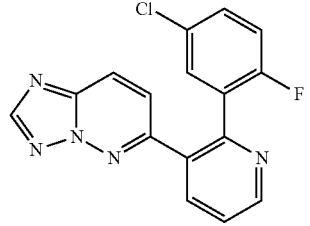 [SMILES: Fc1ccc(Cl)cc1-c1ncccc1-c1ccc2ncnn2n1] | Parent |
| 956 | 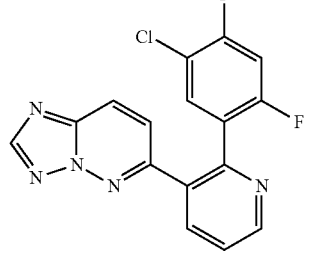 | Parent |
| 957 | 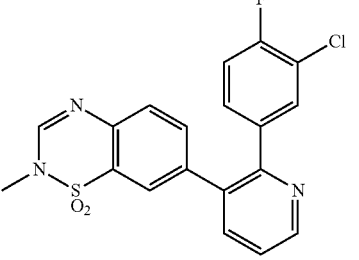 | Parent |

| Cpd # | Structure | Salt |
|---|---|---|
| 958 | 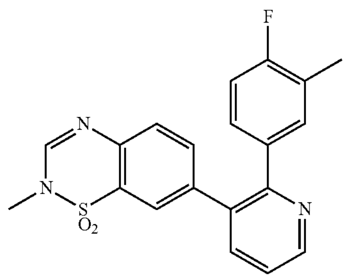 | Parent |
| 959 | 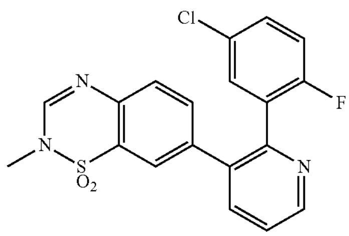 [SMILES: CN1C=Nc2ccc(-c3cccnc3-c3cc(Cl)ccc3F)cc2S1(=O)=O] | Parent |
| 960 | 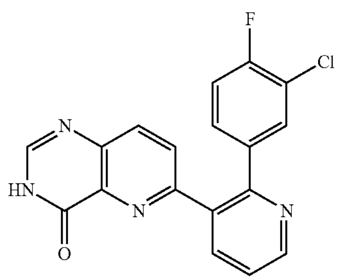 [SMILES: O=c1[nH]cnc2ccc(-c3cccnc3-c3ccc(F)c(Cl)c3)nc12] | Parent |
| 961 | 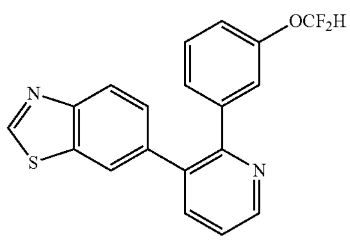 | Parent |
| 962 | 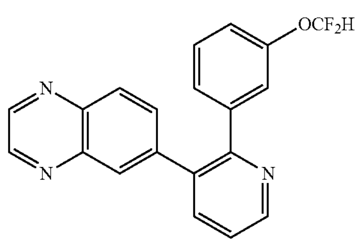 | Parent |
| 963 | 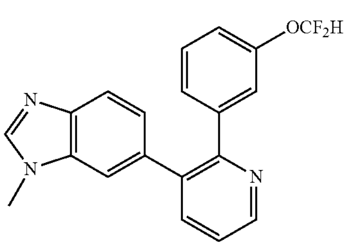 | Parent |

| Cpd # | Structure | Salt |
|---|---|---|
| 964 | 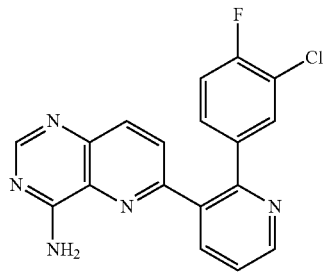 [SMILES: Nc1ncnc2ccc(-c3cccnc3-c3ccc(F)c(Cl)c3)nc12] | Parent |
| 965 | 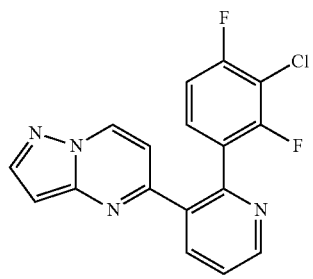 [SMILES: Fc1ccc(-c2ncccc2-c2ccn3nccc3n2)c(F)c1Cl] | Parent |
| 966 | 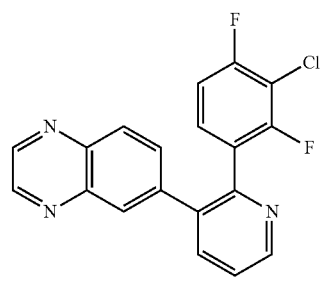 [SMILES: Fc1ccc(-c2ncccc2-c2ccc3nccnc3c2)c(F)c1Cl] | Parent |
| 967 | 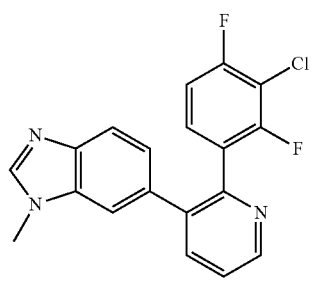 [SMILES: Cn1cnc2ccc(-c3cccnc3-c3ccc(F)c(Cl)c3F)cc21] | Parent |
| 968 | 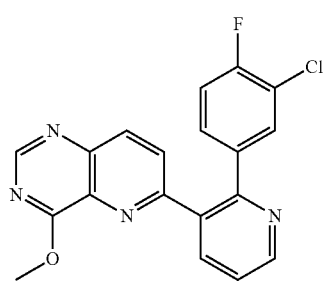 [SMILES: COc1ncnc2ccc(-c3cccnc3-c3ccc(F)c(Cl)c3)nc12] | Parent |

| Cpd # | Structure | Salt |
|---|---|---|
| 969 | 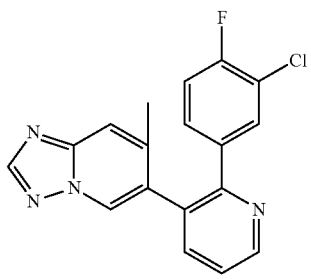 [SMILES: Cc1cc2ncnn2cc1-c1cccnc1-c1ccc(F)c(Cl)c1] | Parent |
| 970 | 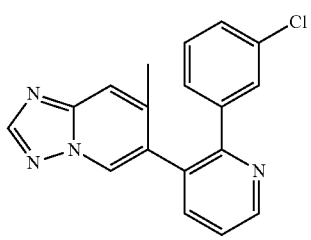 [SMILES: Cc1cc2ncnn2cc1-c1cccnc1-c1cccc(Cl)c1] | Parent |
| 971 | 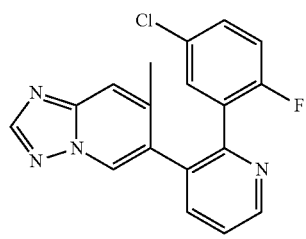 [SMILES: Cc1cc2ncnn2cc1-c1cccnc1-c1cc(Cl)ccc1F] | Parent |
| 972 | 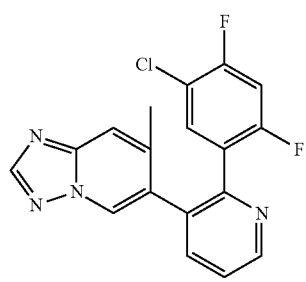 [SMILES: Cc1cc2ncnn2cc1-c1cccnc1-c1cc(Cl)c(F)cc1F] | Parent |
| 973 | 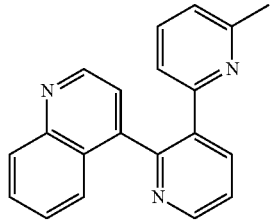 [SMILES: Cc1cccc(-c2cccnc2-c2ccnc3ccccc23)n1] | Parent |

| Cpd # | Structure | Salt |
|---|---|---|
| 974 | 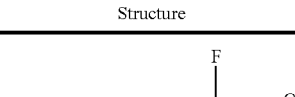 | Parent |

TFA = trifluoroacetate salt
(2) = bis(acid) salt
(3) = tris(acid) salt
Parent = free base compound General Synthetic Methodologies Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) can be prepared according to Schemes 1-49, or analogous synthetic schemes.

As is known to those of skill in the art of organic synthesis, esters and amides can be formed from the corresponding acids, alcohols and amines by conventional techniques. By way of example, organic acids can be converted to the corresponding acid chloride by reaction with oxalyl chloride. Acid chlorides can then be reacted with alcohols or amines to form the desired ester or amide, as shown in Schemes 1-4. Alternatively, activating reagents like HATU, TBTU or HBTU can be used in to condense an amine can be condensed with an organic acid to form the corresponding amide, as shown in Scheme 5.

Scheme 1

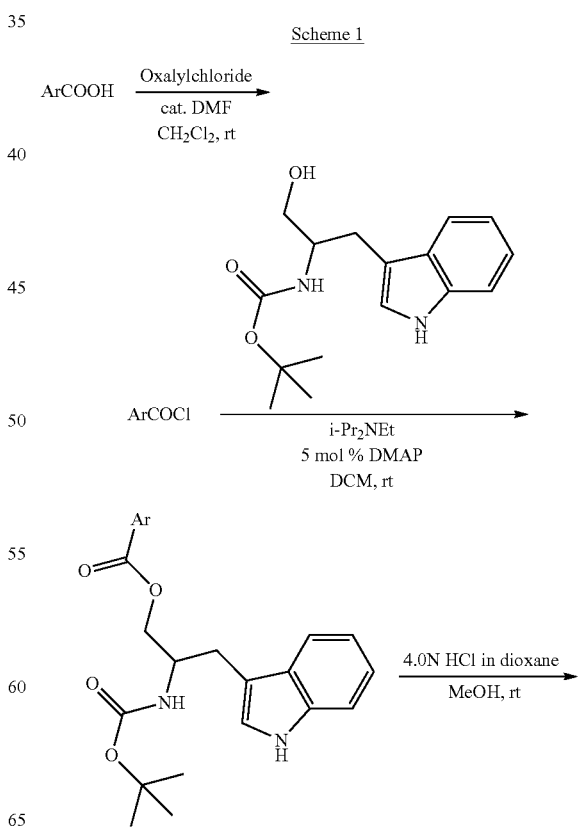

439
-continued
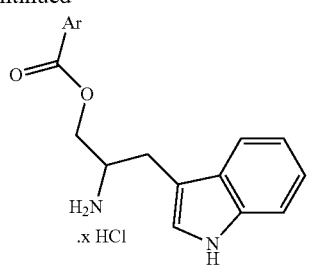
440
-continued
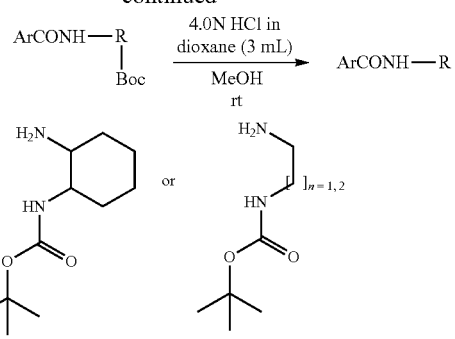
Scheme 2
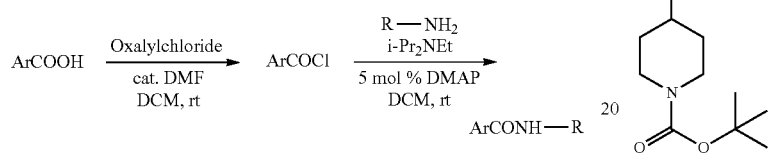
Scheme 4
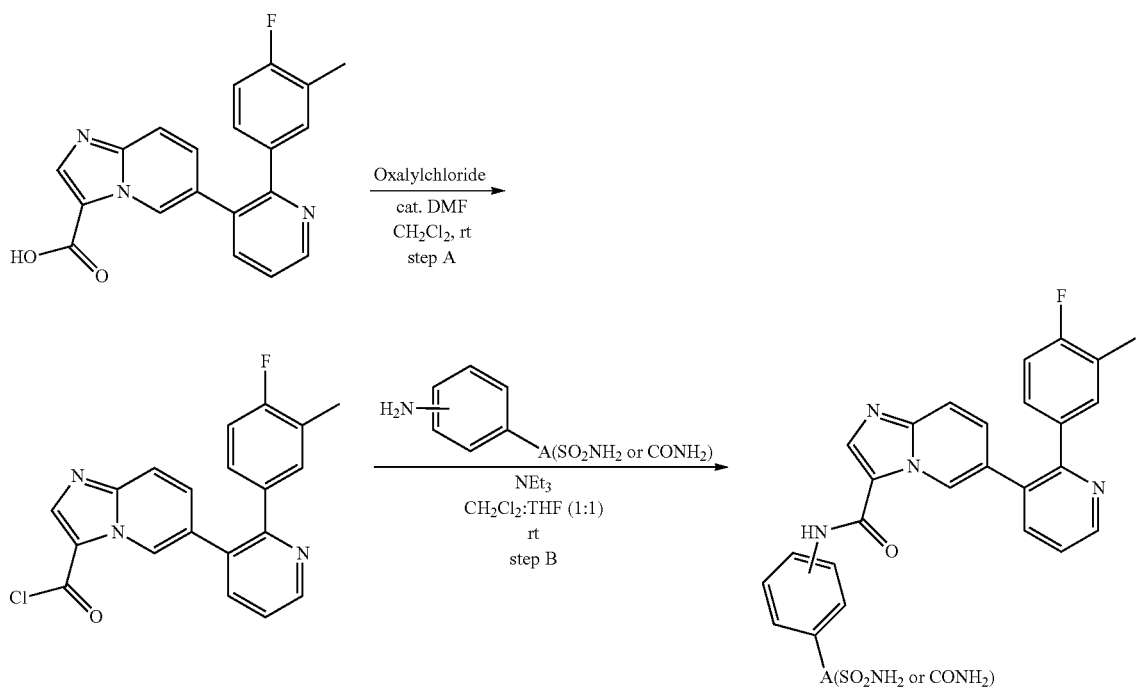
Scheme 3
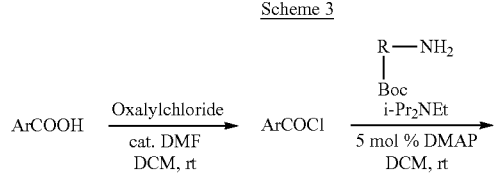
Scheme 5
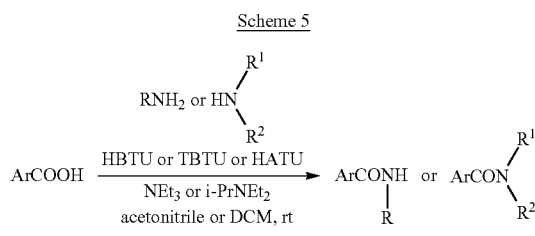

Boronate coupling reactions can be used to make certain compounds described herein, e.g., in the formation of (hetero)aryl-(hetero)aryl bonds. For example, compounds such as compounds 601-606 can be prepared as shown in Scheme 6.

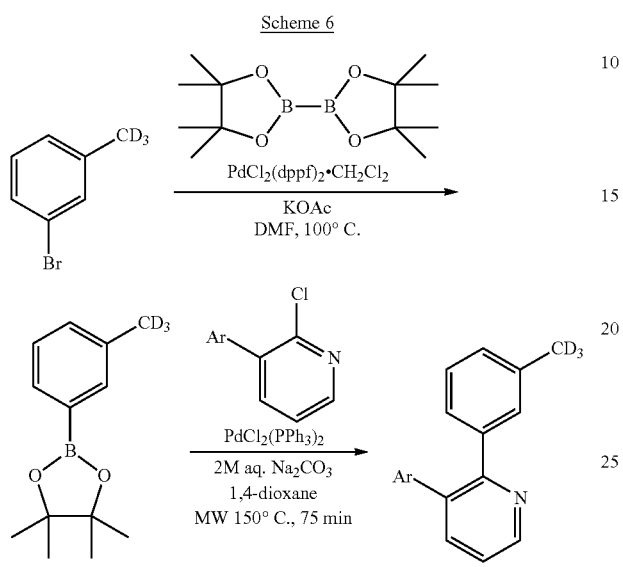

Compounds such as compounds 598 and 599 can be made using reduction and Grignard addition, respectively, as shown in Scheme 7.

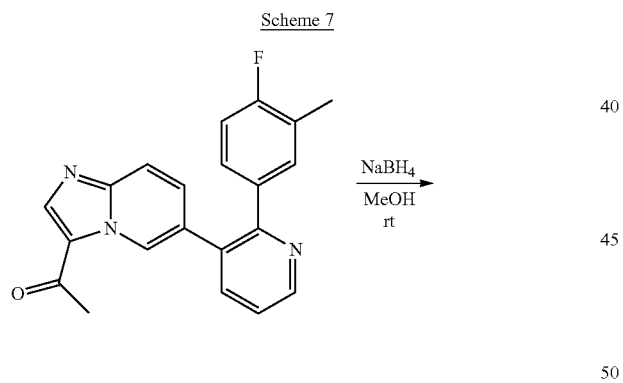

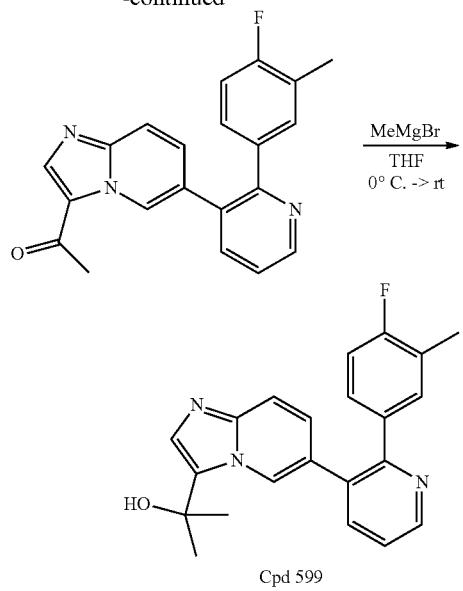

Carboxylic acids can be formed by hydrolysis of the corresponding nitrile, as shown for Compound 579 in Scheme 8. Carboxylic esters (e.g., compounds 677 and 685) can be prepared and hydrolyzed to the corresponding acid (e.g., compound 579) as shown in Schemes 9 and 10. The person of ordinary skill in the art will appreciate that a wide variety of other compounds described herein can be made using the general synthetic paths of Schemes 9 and 10, suitably adapted to provide the desired functional groups in the final molecule.

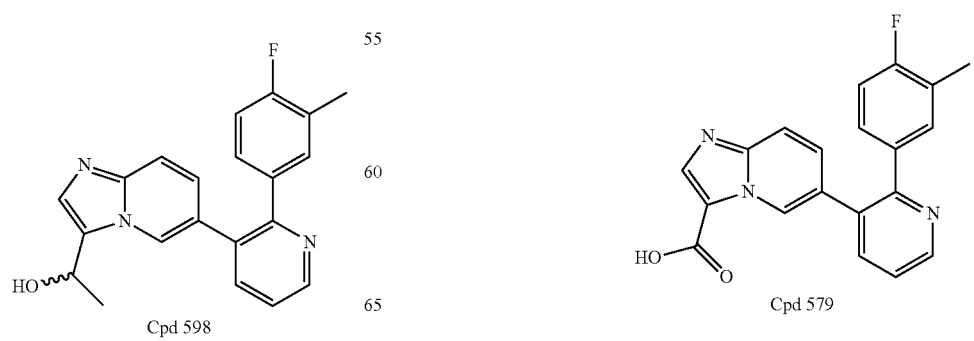

Scheme 9
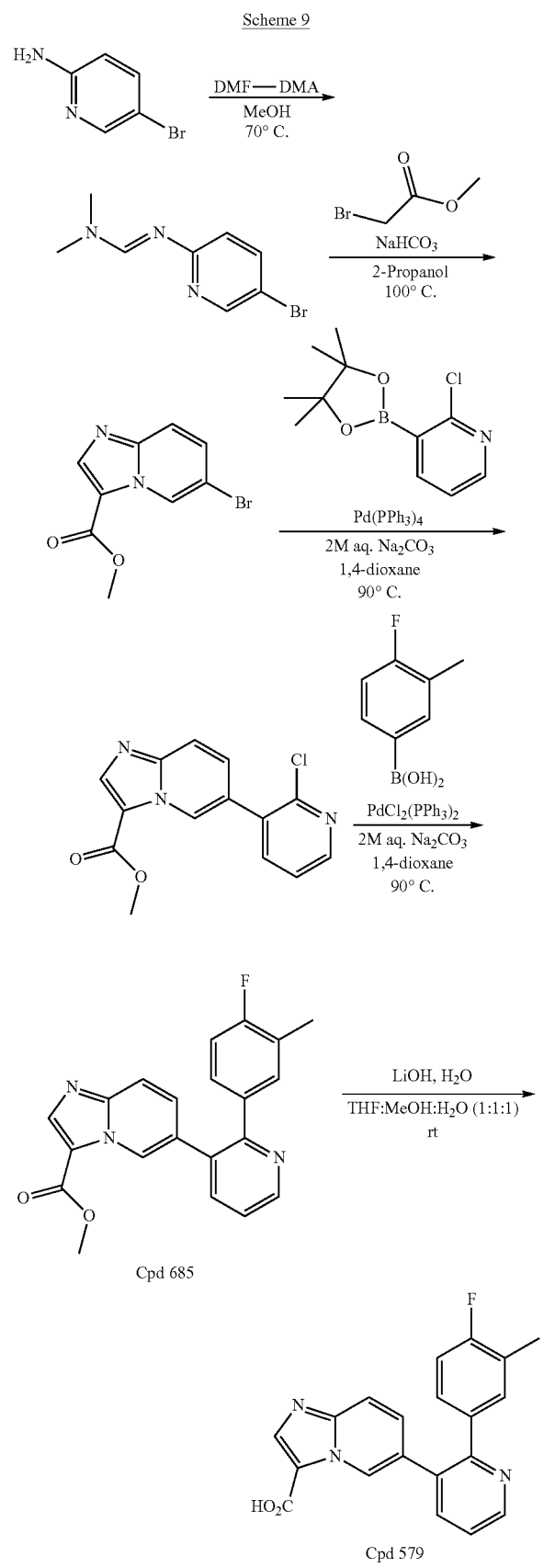
Scheme 10
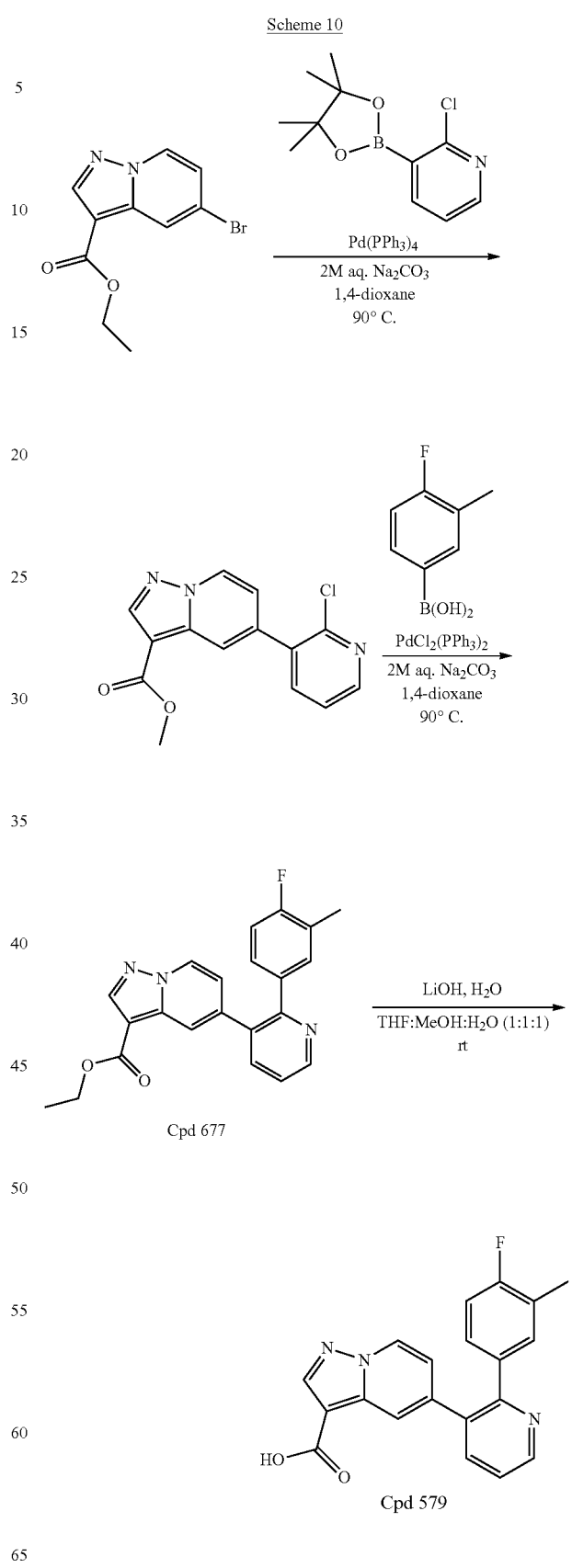
Pyrimidinyl compounds can be made via the reaction sequence shown in Scheme 11.

Scheme 11
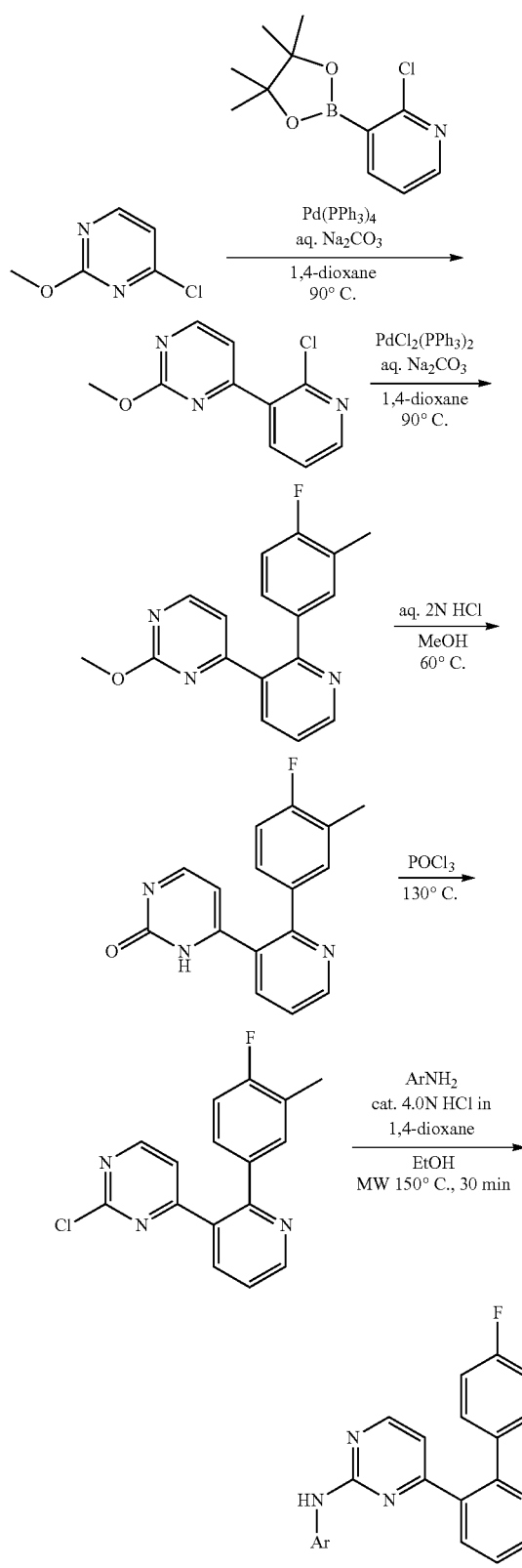
Scheme 12
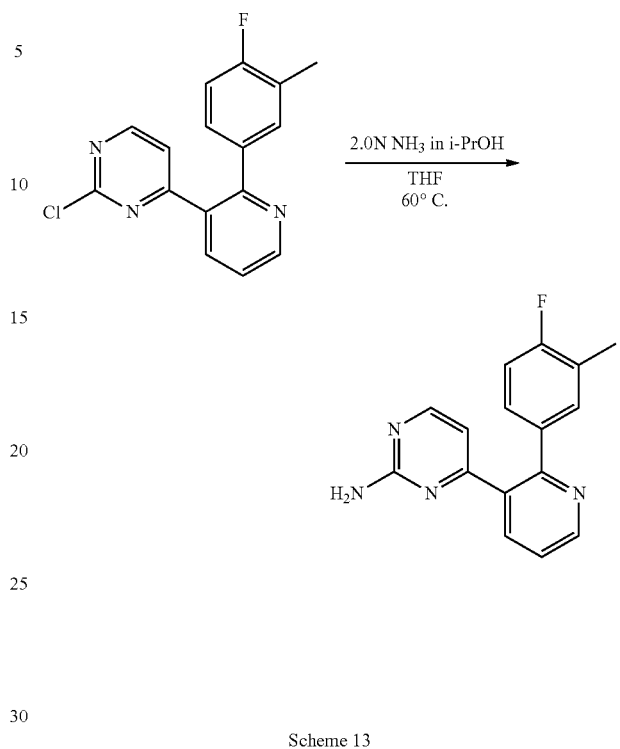
Scheme 13
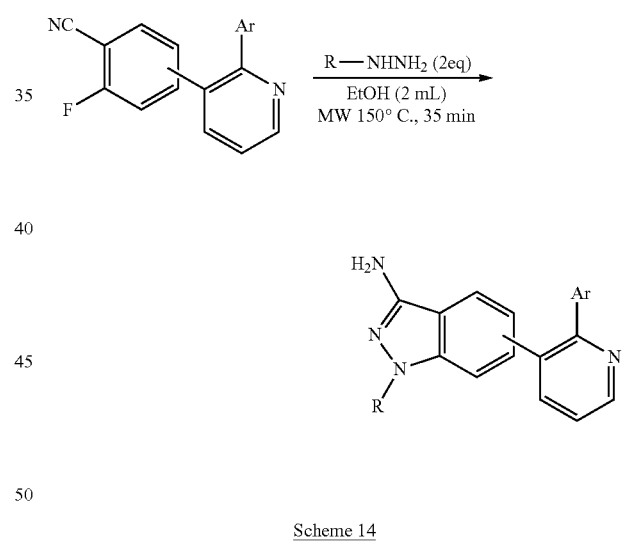
Scheme 14
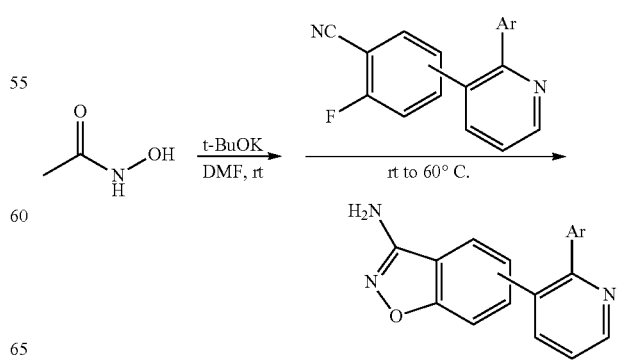
Various additional compounds of the disclosure can be made using the reactions shown in Schemes 12-27.

Scheme 15
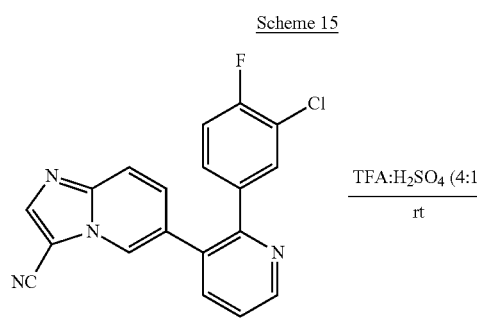
TFA:H₂SO₄ (4:1)
rt
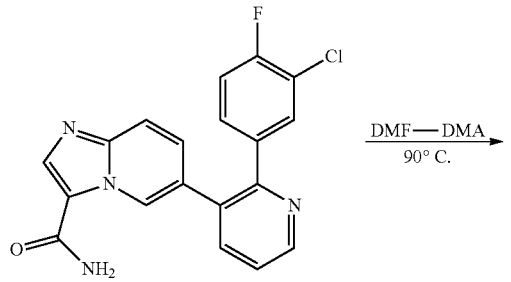
DMF—DMA
90° C.
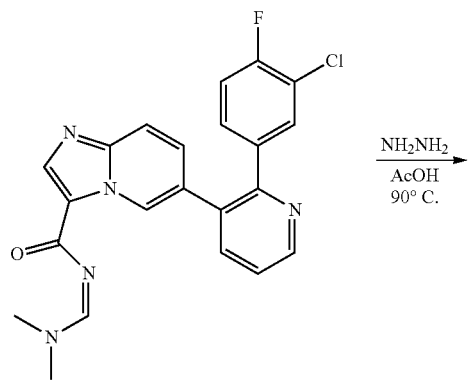
NH₂NH₂
AcOH
90° C.
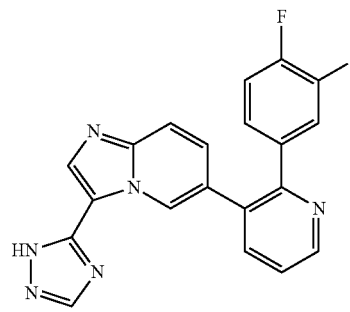
Cpd 844
Scheme 16
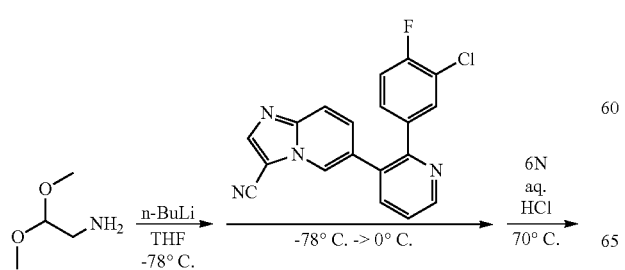
n-BuLi
THF
-78° C.
-78° C. → 0° C.
6N
aq.
HCl
70° C.
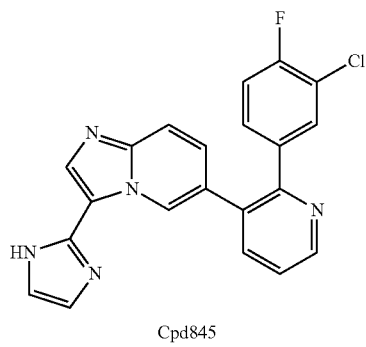
Cpd845
Scheme 17
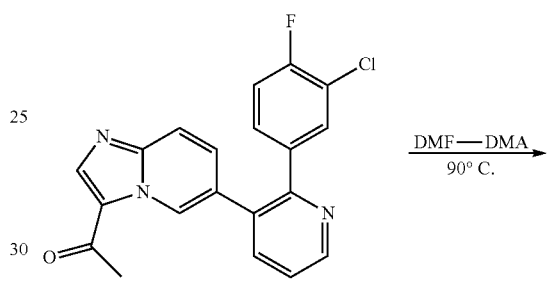
DMF—DMA
90° C.
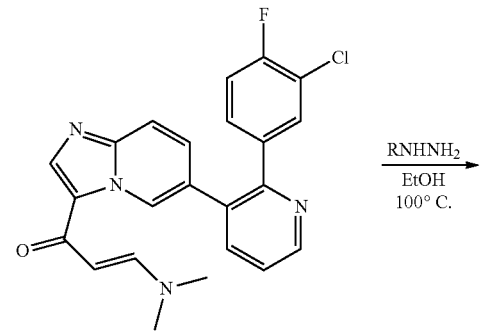
RNHNH₂
EtOH
100° C.
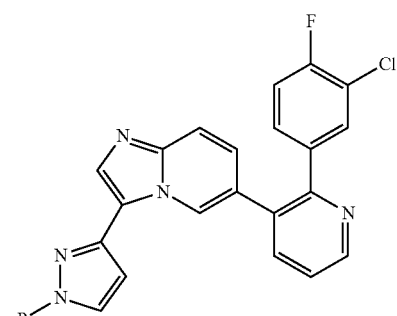
R = H, Cpd 852
R = Me, Cpd 853

Scheme 18
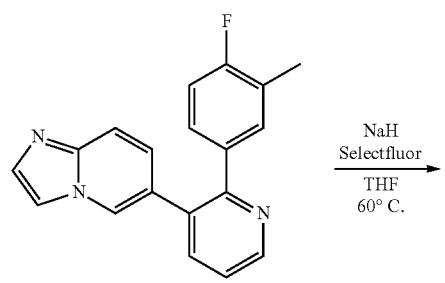
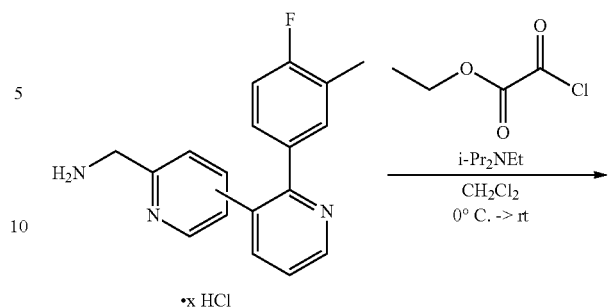
Scheme 19
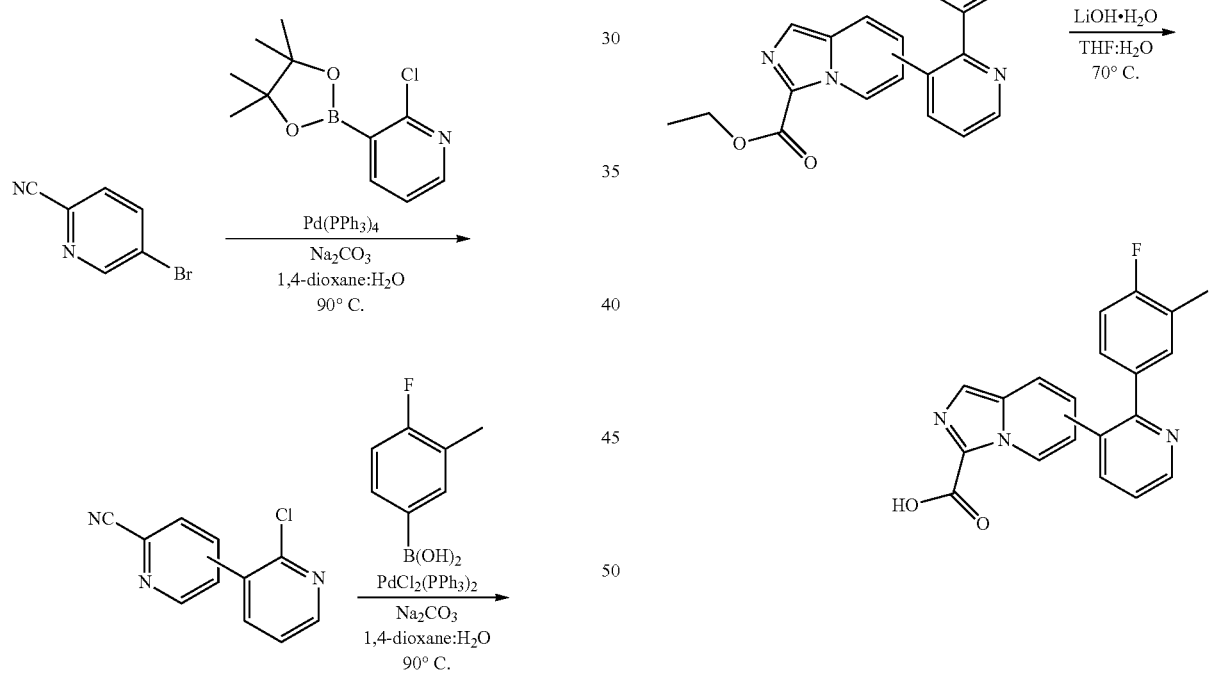
Scheme 20
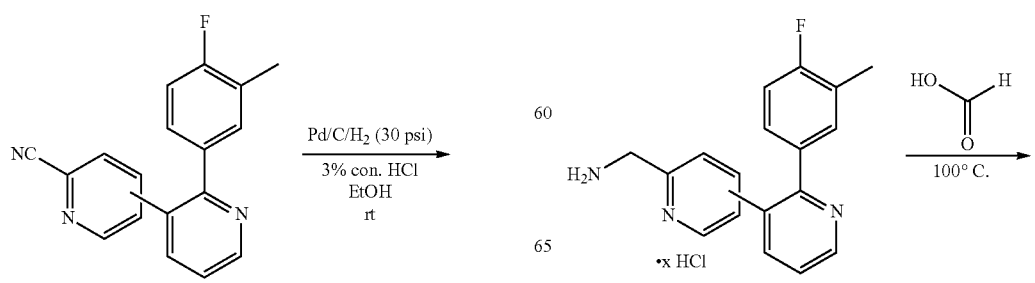

-continued
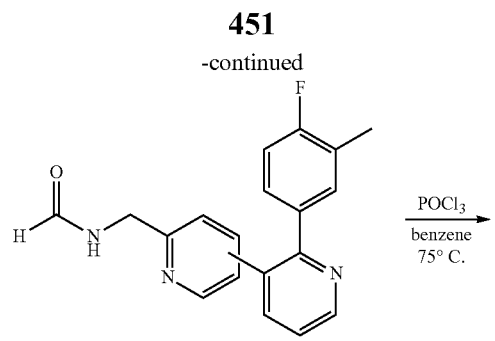
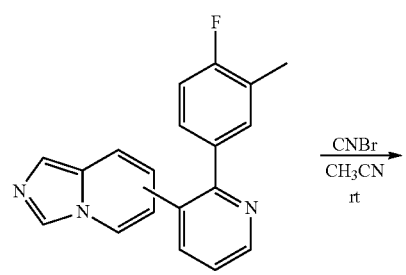
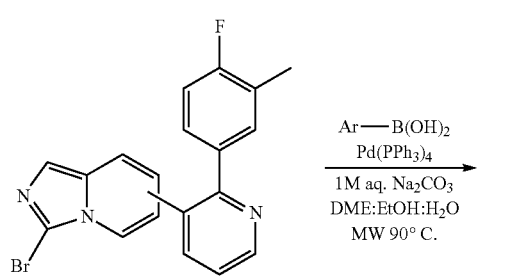
Scheme 21
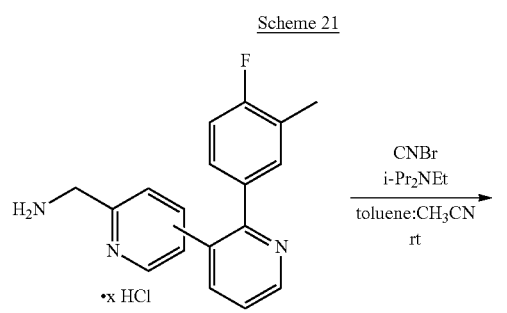
-continued
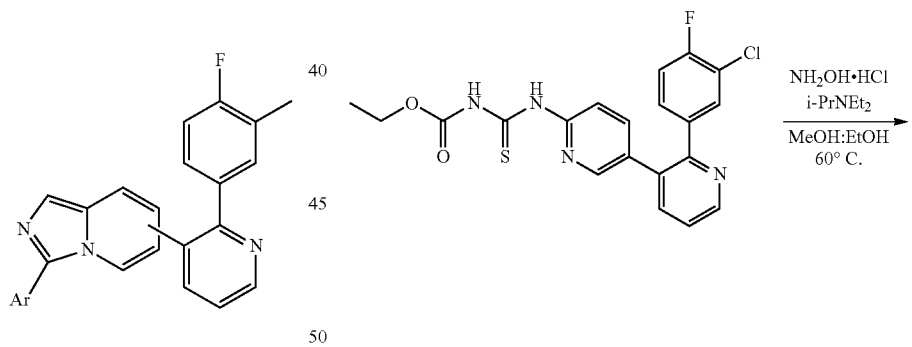
Scheme 22
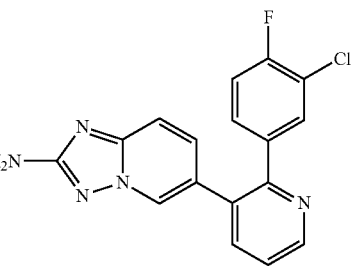
Cpd 291

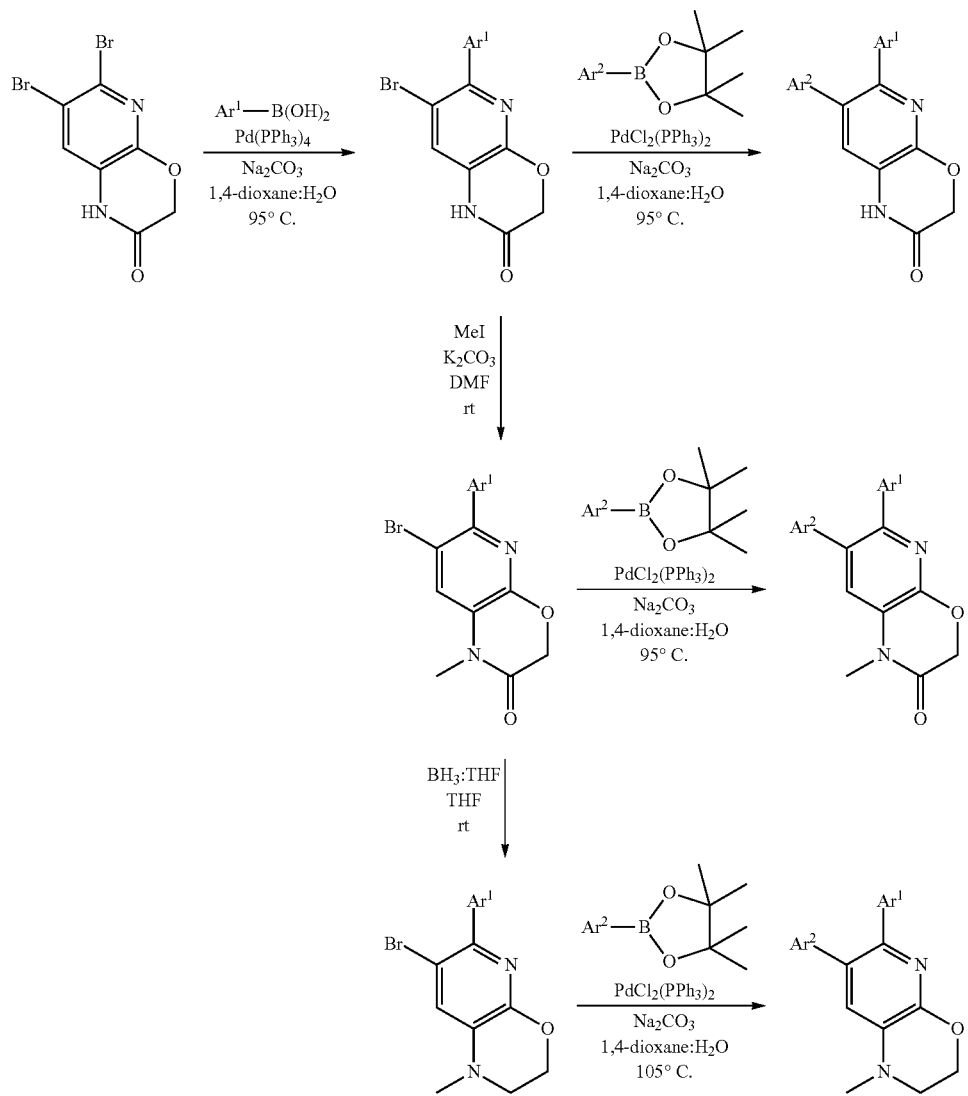
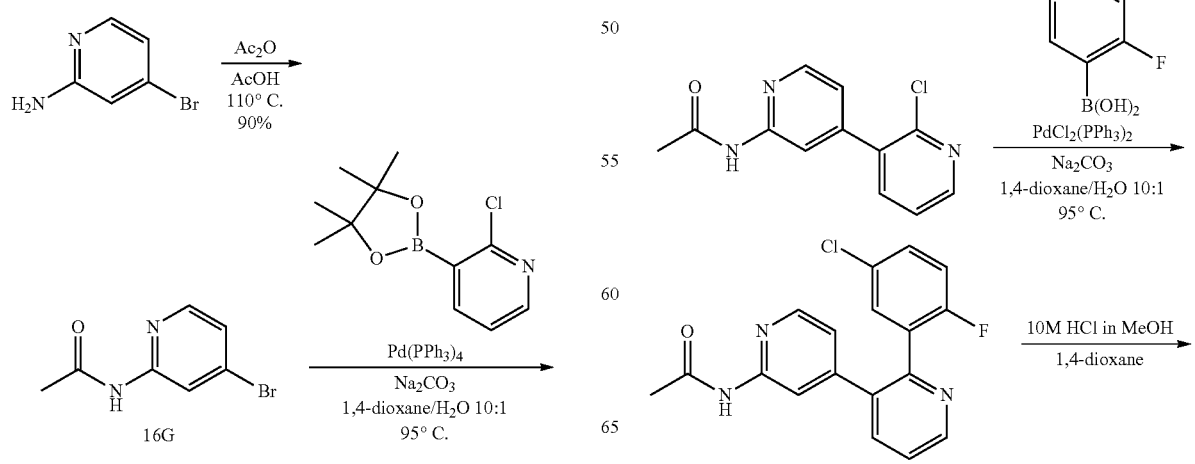

455
-continued
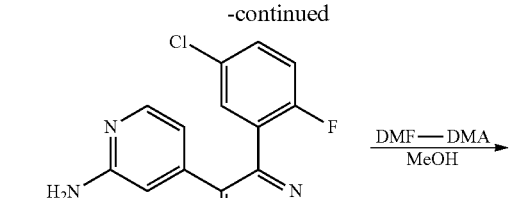
DMF—DMA / MeOH →
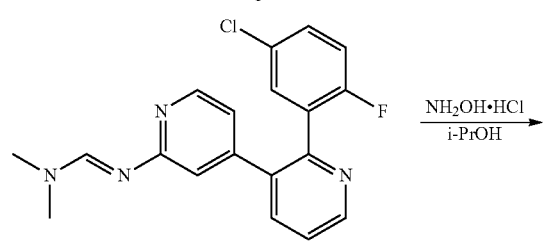
NH₂OH·HCl / i-PrOH →
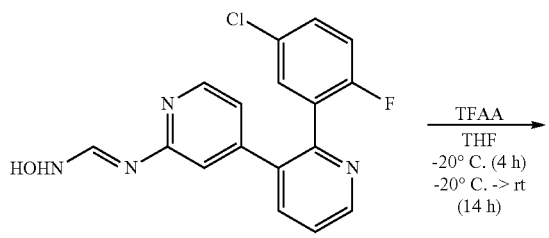
TFAA / THF
-20° C. (4 h)
-20° C. -> rt
(14 h)
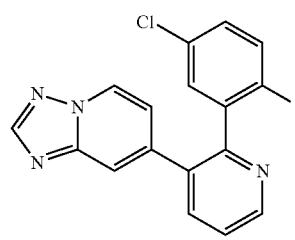
Cpd 736
Scheme 25
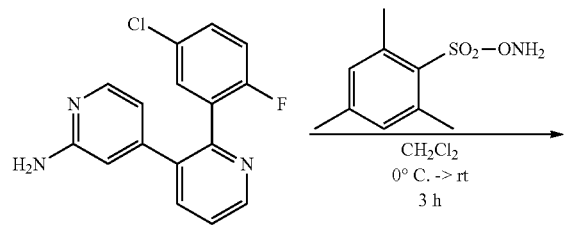
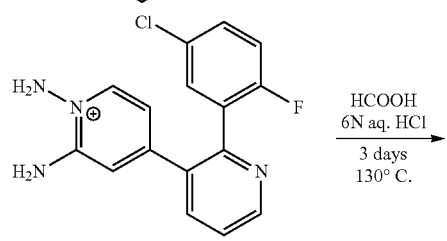
HCOOH
6N aq. HCl
3 days
130° C.
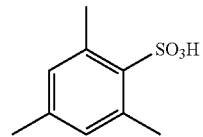
456
-continued
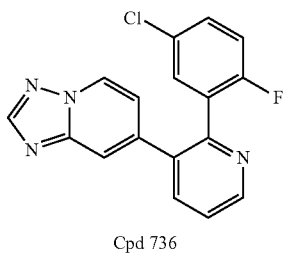 [SMILES: Fc1ccc(Cl)cc1-c1ncccc1-c1ccn2ncnc2c1]
Cpd 736
Scheme 26
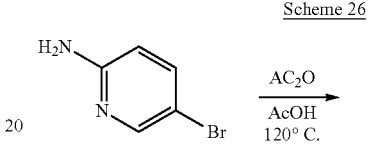
AC₂O / AcOH
120° C. →
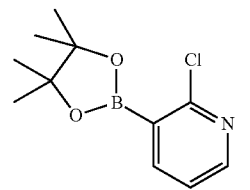
Pd(PPh₃)₄
2M aq. Na₂CO₃
1,4-dioxane
90° C. →
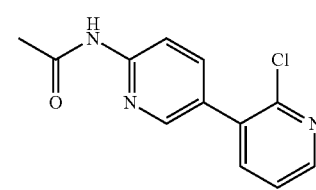
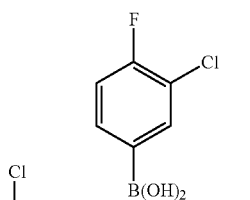
PdCl₂(PPh₃)₂
2M aq. Na₂CO₃
1,4-dioxane
90° C. →
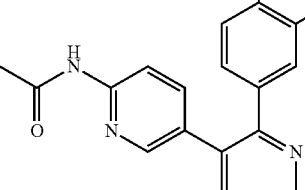
MeOH·HCl
Dioxane:MeOH
90° C. →
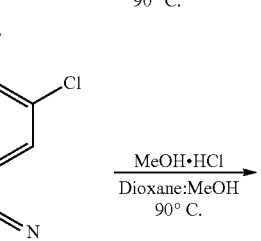
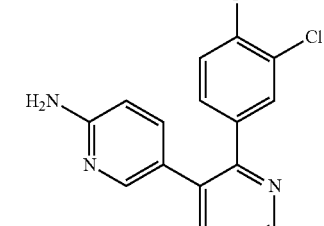
DMF—DMA →

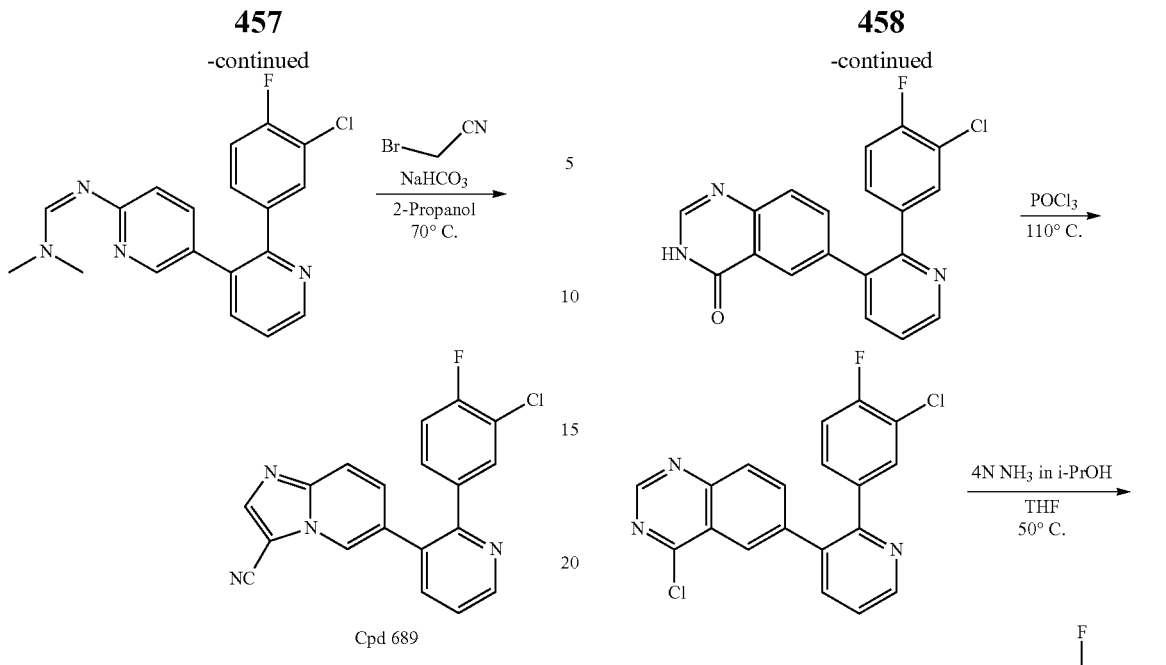
Cpd 689
Cpd 448
The conditions for boronate cross-coupling to form Compound 448 were ineffective when the corresponding bromopyrido[3,2-d]pyrimidine was used. Scheme 28 provides an alternative route to the pyrido[3,2-d]pyrimidine products.
Scheme 27
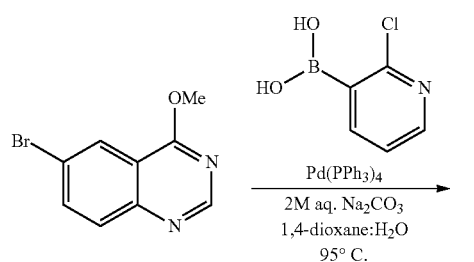
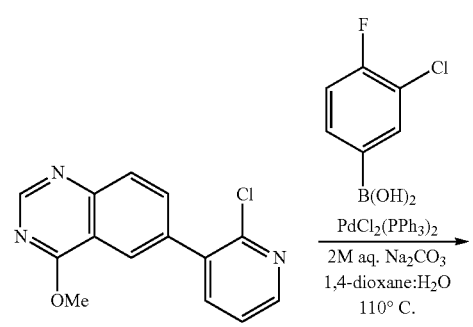
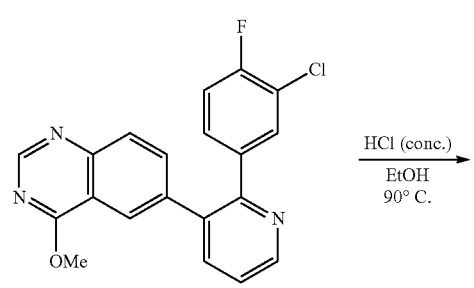
Scheme 28
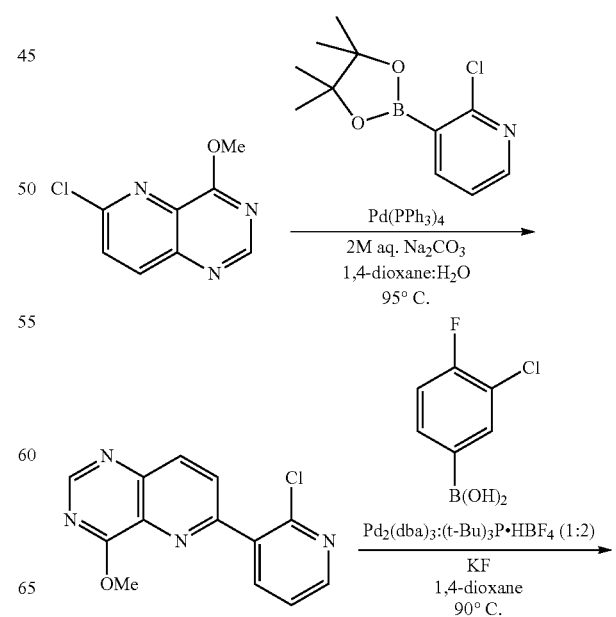

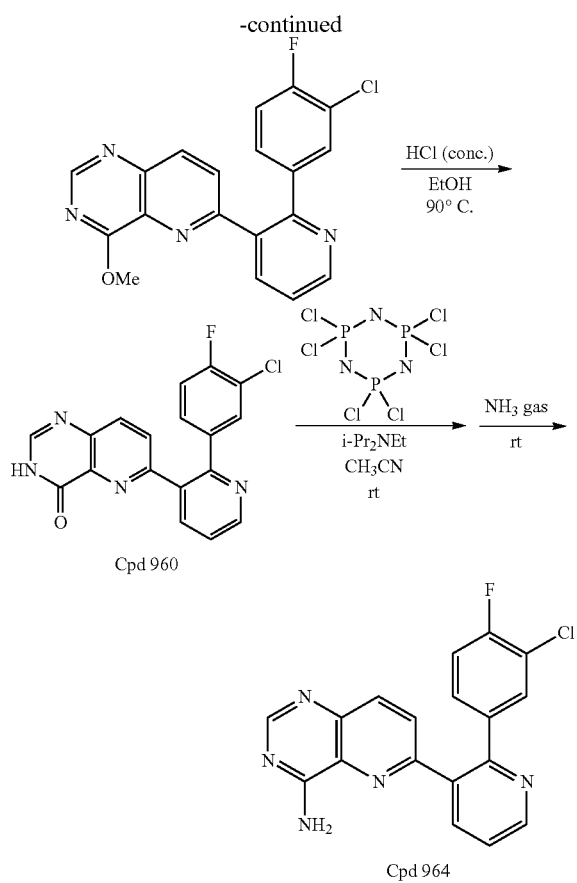

One of skill in the art can adapt the reaction sequences of Schemes 1-28 to fit the desired target molecule. Of course, in certain situations one of skill in the art will use different reagents to affect one or more of the individual steps or to use protected versions of certain of the substituents. Additionally, one skilled in the art would recognize that the compounds described herein can be synthesized using different routes altogether.

2-Chloro-3-(hetero)arylpyridine compounds

In another aspect, the present disclosure includes novel intermediates useful to prepare the present kinase inhibitors as well as other pharmaceutically effective compounds as is readily apparent to those of skill in the art of medicinal chemistry. For example, the 2-chloro-3-(hetero)arylpyridine compounds described herein are suitable for cross coupling, by for example, palladium mediated chemistry, such as a Suzuki reaction, to form the kinase inhibitors disclosed herein as well as other novel biologically active compounds. 2-Chloro-3-(hetero)arylpyridine compounds according to this aspect of the disclosure are described throughout the present specification.

Methods of Treating Disease

The compounds of the present disclosure are useful to prevent, diagnose, and treat various medical disorders in humans or animals. The compounds are used to inhibit or reduce one or more activities associated with the GDF protein, relative to a GDF protein not bound by the same compounds. Optionally, the compounds inhibit or reduce one or more of the activities of mature GDF-8 (regardless of whether in monomeric form, active dimeric form, or complexed in a GDF-8 latent complex) relative to a mature GDF-8 protein that is not bound by the same compounds. In an embodiment, the activity of the mature GDF-8 protein, when bound by one or more of the presently disclosed compounds, is inhibited at least 50%, optionally at least 60, 62, 64, 66, 68, 70, 72, 72, 76, 78, 80, 82, 84, 86, or 88%, optionally at least 90, 91, 92, 93, or 94%, and optionally at least 95% to 100% relative to a mature GDF-8 protein that is not bound by one or more of the presently disclosed compounds.

The medical disorder being diagnosed, treated, or prevented by the presently disclosed compounds is optionally a muscle and neuromuscular disorder; an adipose tissue disorder such as obesity; type 2 diabetes, impaired glucose tolerance, metabolic syndromes (e.g., syndrome X), insulin resistance induced by trauma such as burns; or bone degenerative disease such as osteoporosis. The medical condition is optionally a muscle or neuromuscular disorder, such as muscular dystrophy, muscle atrophy, congestive obstructive pulmonary disease, muscle wasting syndrome, sarcopenia, or cachexia and disorders associated with a loss of bone, which include osteoporosis, especially in the elderly and/or postmenopausal women, glucocorticoid-induced osteoporosis, osteopenia, and osteoporosis-related fractures. Other target metabolic bone diseases and disorders amendable to treatment with GDF-8 inhibitors of the disclosure include low bone mass due to chronic glucocorticoid therapy, premature gonadal failure, androgen suppression, vitamin D deficiency, secondary hyperparathyroidism, nutritional deficiencies, and anorexia nervosa. The antibodies are optionally used to prevent, diagnose, or treat such medical disorders in mammals, optionally in humans.

The compounds or compositions of the present disclosure are administered in therapeutically effective amounts. As used herein, an "effective amount" of the antibody is a dosage which is sufficient to reduce the activity of GDF proteins to achieve a desired biological outcome (e.g., increasing muscle mass or strength). Generally, a therapeutically effective amount may vary with the subject's age, condition, and sex, as well as the severity of the medical condition in the subject. The dosage may be determined by a physician and adjusted, as necessary, to suit observed effects of the treatment. Generally, the compositions are administered so that compounds are given at a dose between 1 µg/kg and 20 mg/kg. Optionally, the compounds are given as a bolus dose, to maximize the circulating levels of compounds for the greatest length of time after the dose. Continuous infusion may also be used after the bolus dose.

The methods of treating, diagnosing, or preventing the above medical conditions with the presently disclosed compounds can also be used on other proteins in the TGF-β superfamily. Many of these proteins, e.g., BMP-11, are related in structure to GDF-8. Accordingly, in another embodiment, the disclosure comprises methods of treating the aforementioned disorders by administering to a subject a compound capable of inhibiting BMP-11 or activin, either alone or in combination with other TGF-β inhibitors, such as a neutralizing antibody against GDF-8.

Accordingly, in one aspect, the disclosure. In provides methods for inhibiting GDF-8 in a cell comprising contacting the cell with an effective amount of a compound or pharmaceutically acceptable salt of formula (I) or (II) or any embodiment thereof, or a pharmaceutical composition comprising the same. In another aspect, the disclosure comprises methods for treating a patient suffering from a disease or disorder, wherein the patient would therapeutically benefit from an increase in mass or strength of muscle tissue, comprising administering to a patient a therapeutically effective amount of a compound or pharmaceutically acceptable salt of formula (I) or (II) or any embodiment thereof, or a pharmaceutical composition comprising the same. The disease or disorder can be a muscular disorder, adipose tissue disorder, neuromuscular disorders, metabolic disorder, diabetes, or bone degenerative disorder. In certain embodiments, the disease or disorder is a muscular disorder, such as, but not limited to, muscular dystrophy, muscle atrophy, congestive obstructive pulmonary disease, muscle wasting syndrome, sarcopenia, or cachexia. In certain other embodiments, the disease or disorder is muscular dystrophy. In other embodiments, the disease or disorder is obesity, type 2 diabetes, impaired glucose tolerance, syndrome X, insulin resistance induced by trauma, or osteoporosis. In particular embodiments, the disease or disorder is osteoporosis.

In yet other embodiments, the disease or disorder is low bone mass due to chronic glucocorticoid therapy, premature gonadal failure, androgen suppression, vitamin D deficiency, secondary hyperparathyroidism, nutritional deficiencies, and anorexia nervosa.

In another aspect, the disclosure comprises methods for increasing muscle mass in a mammal comprising administering a therapeutically effective amount of a compound or pharmaceutically acceptable salt of formula (I) or (II) or any embodiment thereof, or a pharmaceutical composition comprising the same. In another aspect, the disclosure comprises methods for increasing muscle strength in a mammal comprising administering a therapeutically effective amount of a compound or pharmaceutically acceptable salt of formula (I) or (II) or any embodiment thereof, or a pharmaceutical composition comprising the same. In another aspect, the disclosure comprises methods for increasing trabecular bone density in a patient in need thereof, comprising administering a therapeutically effective amount of a compound or pharmaceutically acceptable salt of formula (I) or (II) or any embodiment thereof, or a pharmaceutical composition comprising the same. In any of the preceding methods and embodiments, thereof, the subject can be a mammal. As used herein, the terms "individual" or "patient" or "subject" are used interchangeably, and refers to any animal, including mammals, preferably mice, rats, other odents, rabbits, dogs, cats, swine, cattle, sheep, horses, or primates, and most preferably humans.

Pharmaceutical Formulations and Dosage Forms

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as antiviral agents, vaccines, antibodies, immune enhancers, immune suppressants, anti-inflammatory agents and the like.

Definitions

As is understood by those of skill in the art, compounds of the formulae presented herein, such as but not limited to formula I above, may have asymmetric centers and accordingly include stereoisomeric forms (e.g., enantiomers, diastereomers, etc.) of compounds. And in addition compounds of the formulae presented herein encompass pharmaceutically acceptable salts, solvates, for example hydrates, and the like having such formulae. Likewise, the term "compound" as used herein is understood to include pharmaceutically acceptable salts, solvates, hydrates and the like of such compounds.

Terms used herein may be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl, arylalkyl-, and alkylaryl indicate the same functionality.

Further, certain terms herein may be used as both monovalent and divalent linking radicals as would be familiar to those skilled in the art, and by their presentation linking between two other moieties. For example, an alkyl group can be both a monovalent radical or divalent radical; in the latter case, it would be apparent to one skilled in the art that an additional hydrogen atom is removed from a monovalent alkyl radical to provide a suitable divalent moiety.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-dec enyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC (CH$_3$)—, —CH$_2$CH(CH$_2$CH$_3$)CH$_2$—.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzo furan-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3 (4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4 (3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl," "-alkylaryl," and "arylalkyl-" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo [3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. In certain examples, a haloalkyl can comprise one to five halogen atoms, or one to three halogen atoms. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring wherein the heteroatom(s) are selected from O, N, and S. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkylheteroaryl" as used herein, means a heteroaryl, as defined herein, appended to the parent molecular moiety through an alkyl group, as defined herein. Such groups are indicated herein subgenerically for example by "heteroaryl($C_{1-6}$alkyl) to indicate a heteroaryl moiety linked to the parent molecule through a $C_{1-6}$alkyl group, such as a methylene, ethylene, propylene moiety or the like. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "hydroxy" as used herein, means an —OH group.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a kinase with a compound includes the administration of a compound described herein to an individual or patient, such as a human, having the kinase (such as Alk4 or Alk5), as well as, for example, introducing a compound into a sample containing a cellular or purified preparation containing the kinase.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

As used herein, the phrase "pharmaceutically acceptable salt" refers to both pharmaceutically acceptable acid and base addition salts and solvates. Such pharmaceutically acceptable salts include salts of inorganic and organic acids. Examples of inorganic salts include, without limitation, those formed from hydrochloric, phosphoric, hydrobromic, sulfuric, sulfinic and hydroiodic acids. Examples of organic acids suitable for the formation of pharmaceutically acceptable salts of the presently disclosed compounds include acetic, formic, fumaric, glutaric, glycolic, trifluoroacetic, benzenesulfonic, ethanesulfonic, toluenesulfonic, methanesulfonic, nitric, benzoic, camphor sulfonic, citric, cinnamic, oxalic, tartaric, maleic, malonic, mandelic, pamoic, propionic, pyruvic and xinafoic acids, and the like. Non-toxic pharmaceutical base addition salts include salts formed from bases with inorganic and organic counterions. By way of example suitable inorganic counterions include sodium, potassium, calcium, ammonium, sulfate and the like. Pharmaceutically acceptable organic bases for the formation of base addition salts include, without limitation, arginine, choline, ethylenediamine, histidine, lysine, methylglucamine, piperazine, triethanolamine and tris(hydroxymethyl)aminomethane (tris). Those skilled in the art will recognize a wide variety of non-toxic pharmaceutically acceptable addition salts. For additional pharmaceutically acceptable salts, see, M. Berge, et al., "Pharmaceutical Salts," J. Pharm. Sci., 1977; 66: 1-19 which is incorporated herein by reference.

EXAMPLES

The following abbreviations and/or acronyms are used within the examples:

| Ph | Phenyl | DMF | N,N-dimethylformamide |
|---|---|---|---|
| aq. | Aqueous | dppf | 1,1'-Bis(diphenylphosphino)-ferrocene |
| MW | microwave | | |
| LC/MS or LCMS | Liquid chromatograph, mass spectrometry | HPLC | High-performance liquid chromatography |
| TFA | Trifluoroacetic acid | DMA | N,N-dimethylacetamide |
| EtOAc | Ethyl acetate | EtOH | Ethanol |
| MeOH | Methanol | dba | dibenzylideneacetone |
| DMSO | Dimethylsulfoxide | Me | Methyl |
| Et | Ethyl | Ac2O | Acetic anhydride |
| TLC | Thin layer chromatography | OAc | acetate |
| THF | Tetrahydrofuran | HBTU | O-Benzotriazole-N,N,N',N'-tetramethyl-uronium-hexafluoro-phosphate |
| rt | Room temperature | | |
| | | DMAP | 4-dimethylaminopyridine |
| t-BuOMe | Tert-butyl methyl ether | iPr2NEt | di(isopropyl)ethylamine |
| AcOH | Acetic acid | NBS | N-bromosuccinimide |

Example 1

General Synthetic Scheme A

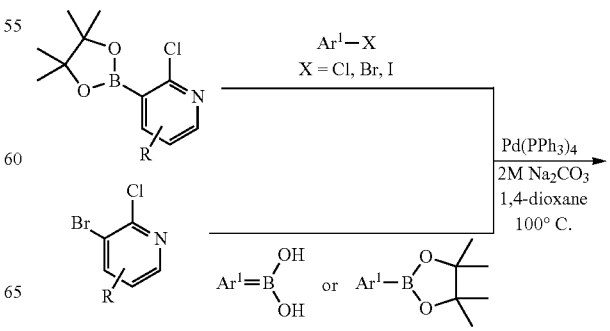

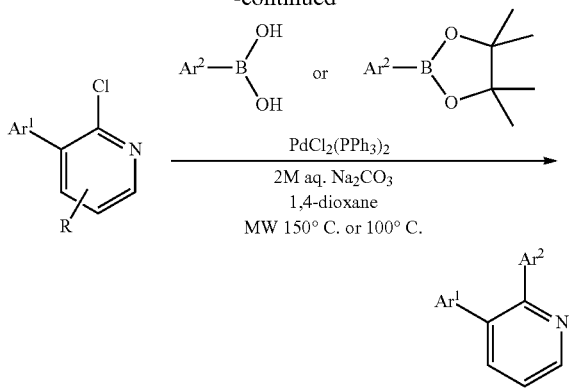

Example 2

General LC/MS Methods

LC/MS: room temperature (A or B)

Method A: Column: Luna 5μC8 (100×4.6 mm), Flow rate 1.0 ml/min, Mobile phase: A: $H_2O$ 0.05% TFA, B: $CH_3CN$ 0.05% TFA Method B: Column: Gemini 5μC18 (100×4.6 mm), Flow rate 1.5 ml/min, Mobile phase: A: $H_2O$ 0.05% HCOOH, B: $CH_3CN$ 0.05% HCOOH

Example 3

5-(2-Chloropyridin-3-yl)-1H-indazole

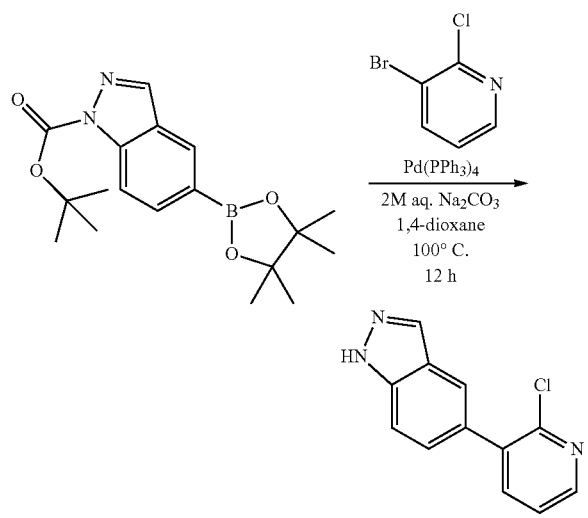

A single necked round bottom flask equipped with a magnetic stir bar was charged with 1-Boc-indazole-5-boronic acid pinacol ester (3.0 g, 8.7 mmol), 3-bromo-2-chloropyridine (2.0 g, 10.4 mmol), Pd(PPh$_3$)$_4$ (1 g, 0.86 mmol) and 2M aq. Na$_2$CO$_3$ (10 mL, 20 mmol) and 1,4-dioxane under nitrogen atmosphere. The reaction flask was fitted with a reflux condenser containing three-way stopcock equipped with argon filled balloon. The reaction contents were stirred and air was removed from the closed reaction system by vacuum and back filled with argon. Following three cycles of degassing, the reaction mixture was heated at 100° C. (oil-bath) under argon. Initial clear heterogeneous reaction mixture turned to clear biphasic off-yellow solution. After 12 h with no additional change in the proportion of the product, as analyzed by LC/MS, the reaction mixture was cooled to room temperature. Upon concentration of the reaction mixture, EtOAc/water (200 mL/100 mL) was transferred to the concentrate and stirred for 30 min. The organic layer was separated and the aqueous layer extracted with EtOAc (2×75 mL). MgSO$_4$ and Celite® were added to combined organic layers, stirred for 20 min and the contents suction filtered. The filter cake was washed with EtOAc (100 mL) and the combined filtrates concentrated by rotary evaporator under vacuum. The crude concentrate was dissolved in 1% MeOH/CH$_2$Cl$_2$ and absorbed on silica gel (20g) by evaporating the solvent followed by drying. Subsequent purification by flash silica gel column purification of the dry powder (Combiflash® companion System® with RediSep® silica gel column 120 g, 30-70% EtOAc/hexanes eluting solvent) provided 5-(2-chloropyridin-3-yl)-1H-indazole (1.0 g, 50%) as a white crystalline solid after concentration of the desired product fractions. $^1$H NMR (DMSO-d6): δ 13.2 (s, 1H), 8.41 (dd, 1H, J=1.8 and 4.7 Hz), 8.13 (s, 1H), 7.90 (dd, 1H, J=1.7 and 4.7 Hz), 7.84 (s, 1H), 7.62 (d, 1H, J=8.8 Hz), 7.51 (dd, 1H, J=4.7 and 7.3 Hz), 7.42 (dd, 1H, J=1.4 and 8.5 Hz). LCMS: 95%, MS (m/e) 230 (MH$^+$).

Example 4 tert-Butyl 5-bromo-1H-indazole-1-carboxylate

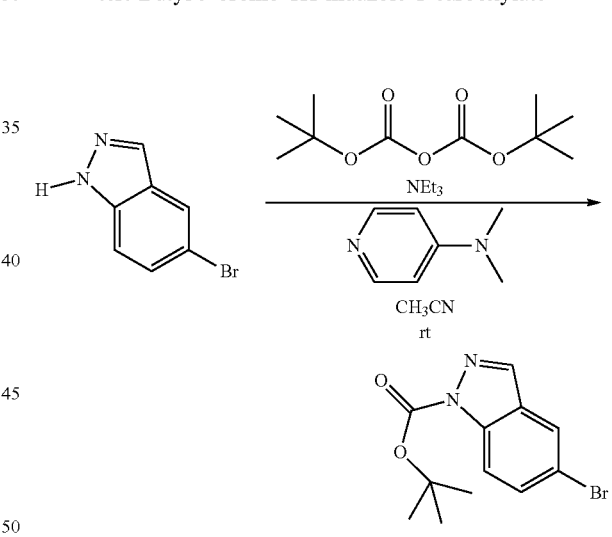

A single necked round bottom flask containing a with a magnetic stir bar was charged with 5-bromo-1H-indazole (3.0 g, 15.2 mmol), di-tert-butyl dicarbonate (4.2 g, 19.2 mmol) and acetonitrile (30 mL) under a mild stream of nitrogen at room temperature. Triethylamine (1.8 g, 2.5 mL, 17.7 mmol) was added in one portion to the above stirred homogeneous solution followed by portions-wise addition of 4-(dimethylamino)pyridine (2.2 g, 18 mmol) over a period of 15 min. The homogenous off-brown clear reaction mixture was stirred at room temperature under nitrogen and the progress of reaction monitored by TLC (50% EtOAc/hexanes). Stirring was discontinued after 3 h and the reaction mixture concentrated by rotary evaporator under vacuum. A clear viscous liquid was obtained and dissolved in EtOAc/hexanes (7:3, 200 mL), and diluted with water (75 mL). Organic layer was separated and the aqueous layer extracted with EtOAc/hexanes (1:1, 125 mL). The combined organic layers were washed with water (100 mL) followed by 1N aq. HCl (2×75 mL) to remove 4-(dimethylamino)pyridine. The combined organic layers were washed with water (2×75 mL), saturated aq. NaHCO$_3$ (2×75 mL) and saturated aqueous NaCl. Separated organic layers were dried over anhydrous MgSO$_4$, filtered, concentrated and dried under vacuum to provide tert-butyl 5-bromo-1H-indazole-carboxylate (4.5 g, purity 97%) as a pale yellow viscous liquid which was used without further purification. $^1$H NMR (DMSO-d6): δ 8.36 (d, 1H, J=0.8 Hz), 8.11 (app d, 1H, J=0.8 Hz), 8.00 (d, 1H, J=8.8 Hz), 7.71 (app dd, 1H, J=0.8 and 8.8 Hz), 1.62 (s, 9H). LCMS: 97%, MS (m/e) 241 (MH$^+$-t-Bu).

Example 5

5-(2-Chloropyridin-3-yl)-1H-indazole

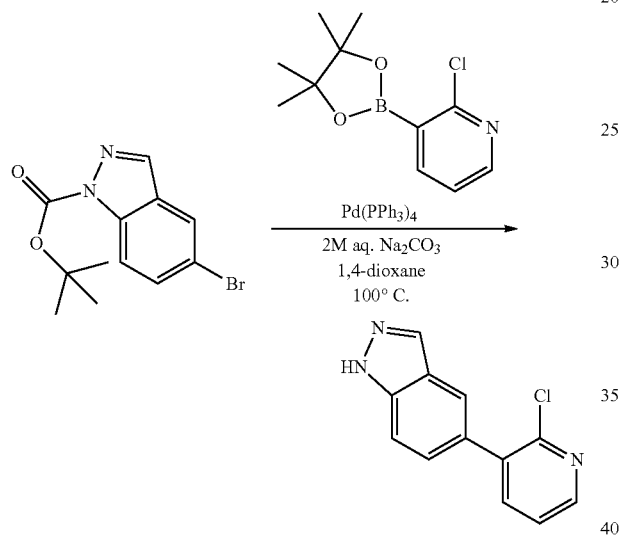

A single necked round bottom flask (250 mL) equipped with a magnetic stir bar was charged with tert-butyl 5-bromo-1H-indazole-carboxylate (4.0 g, 13.4 mmol) dissolved in 1,4-dioxane (130 mL), 2-chloro-3-pyridine boronic acid pinacol ester (4 g, 16.7 mmol), Pd(PPh$_3$)$_4$ (1.5 g, 1.3 mmol) and 2M aq.Na$_2$CO$_3$ (20 mL, 40 mmol) under nitrogen atmosphere. The rubber septum was replaced with reflux condenser containing three-way stopcock equipped with argon filled balloon. The reaction contents were stirred and air was removed from the closed reaction system by vacuum and back filled with argon. Following three cycles of degassing, the reaction mixture was heated at 100° C. (oil-bath) under argon. Inflated argon balloon was emptied, refilled with argon and remounted in the course of reaction. The initial pale yellow heterogeneous reaction mixture turned to clear biphasic off-brown solution. After 18 h with no additional change in the proportion of the product (62%) as analyzed by LC/MS, the reaction mixture was cooled to room temperature. Upon concentration of the reaction mixture, EtOAc/water (200 mL/75 mL) was transferred to the concentrate and stirred for 30 min. The organic layer was separated and the aqueous layer extracted with EtOAc (100 mL×2). MgSO$_4$ (20g) and Celite® (20g) were added to combined organic layers and the contents suction filtered after stirring for 1 h. The filter cake was washed with EtOAc (300 mL) and the combined filtrates concentrated by rotary evaporator under vacuum. The crude concentrate was dissolved in 1% MeOH/CH$_2$Cl$_2$ and absorbed on silica gel (20g) by evaporating the solvent followed by drying. Subsequent purification by flash silica gel column purification of the dry powder (Combiflash® companion System® with RediSep® silica gel column 120 g, 30-70% EtOAC/hexanes eluting solvent) provided 5-(2-chloropyridin-3-yl)-1H-indazole (1.5 g, 47%) as a white crystalline solid after concentration of the desired product fractions. $^1$H NMR (DMSO-d6): δ 13.2 (s, 1H), 8.41 (dd, 1H, J=1.8 and 4.7 Hz), 8.13 (s, 1H), 7.90 (dd, 1H, J=1.7 and 4.7 Hz), 7.84 (s, 1H), 7.62 (d, 1H, J=8.8 Hz), 7.51 (dd, 1H, J=4.7 and 7.3 Hz), 7.42 (dd, 1H, J=1.4 and 8.5 Hz). LCMS: 95%, MS (m/e) 230 (MH$^+$).

Example 6 tert-Butyl 5-bromo-1H-pyrazolo[3,4-b]pyridine-1-carboxylate

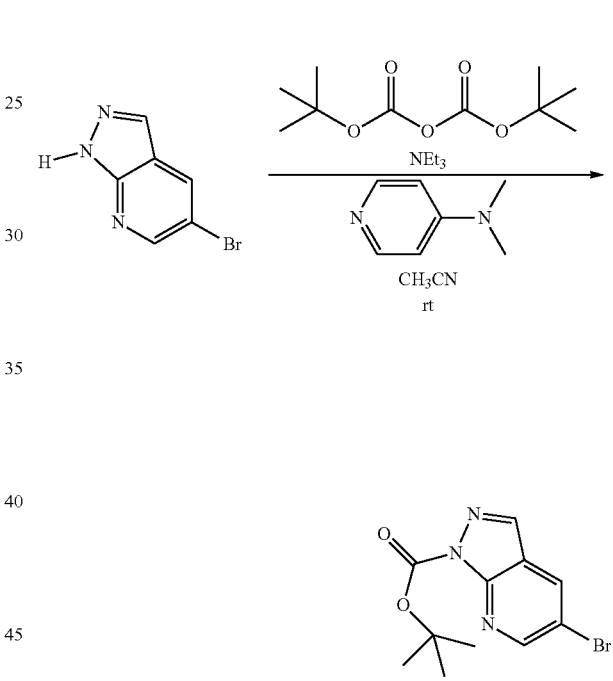

A single necked round bottom flask equipped with a magnetic stir bar was charged with 5-bromo-1H-pyrazolo[3,4-b]pyridine (1.0 g, 5 mmol), di-tert-butyl dicarbonate (1.4 g, 6.4 mmol) and acetonitrile (10 mL) under a mild stream of nitrogen at room temperature. Triethylamine (0.72 g, 1.0 mL, 7.1 mmol) was added in one portion to the above stirred homogeneous solution followed by portions-wise addition of 4-(dimethylamino)pyridine (0.74 g, 6.05 mmol) over a period of 15 min. The homogenous reaction mixture was stirred at room temperature and the progress of reaction was monitored by TLC (50% EtOAc/hexanes). Stirring was discontinued after 3 h, the reaction mixture concentrated and diluted with water (25 mL). The resultant off-brown solid was filtered and suction dried to provide the desired tert-butyl 5-bromo-1H-pyrazolo[3,4-b]pyridine-1-carboxylate (1.4 g, 93%). The material obtained was used in the next step without further purification. $^1$H NMR (DMSO-d6): δ 8.77 (d, 1H, J=2.0 Hz), 8.62 (d, 1H, J=2.0 Hz), 8.39 (s, 1H), 1.60 (s, 9H). (dd, 1H, J=1.8 and 4.7 Hz), 8.13 (s, 1H), 7.90 (dd, 1H, J=1.7 and 4.7

Hz), 7.84 (s, 1H), 7.62 (d, 1H, J=8.8 Hz), 7.51 (dd, 1H, J=4.7 and 7.3 Hz), 7.42 (dd, 1H, J=1.4 and 8.5 Hz). LCMS: 97%, MS (m/e) 226 (MH$^+$-t-Bu).

Example 7

5-(2-Chloropyridin-3-yl)-1H-pyrazolo[3,4-b]pyridine

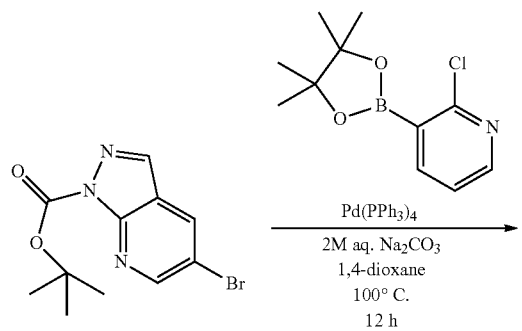

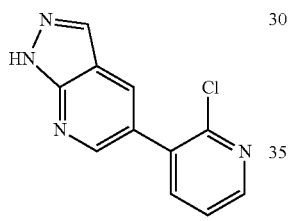

5-(2-chloropyridin-3-yl)-1H-pyrazolo[3,4-b]pyridine was prepared in the similar to the preparation of 5-(2-chloropyridin-3-yl)-1H-indazole by heating the mixture of tert-butyl 5-bromo-1H-pyrazolo[3,4-b]pyridine-1-carboxylate (2.0 g, 6.7 mmol), 2-chloro-3-pyridine boronic acid pinacol ester (1.9 g, 8.0 mmol), Pd(PPh$_3$)$_4$ (770 mg, 67 mmol), 1,4-dioxane (40 mL) and 2M aq.Na$_2$CO$_3$ (9 mL, 18 mmol) under argon atmosphere. After 12 h, the reaction mixture was cooled to room temperature and concentrated. The crude concentrate was diluted with EtOAc/water (200 mL/100 mL), allowed to stir for 30 min and the heterogeneous solution was filtered. The filter cake was washed with EtOAc (200 mL) and water (75 mL) successively. The filter cake thus obtained was analyzed as the desired product (0.55 g) and dissolved in a mixture of THF/MeOH (2:1, 50 mL). The homogeneous solution was passed through a pad of Celite® and the filtrate concentrated to provide desired product as a crystalline solid (0.45 g). Organic layer from combined filtrates was separated, stirred with MgSO$_4$/Celite® for 20 min and filtered. The filtrate was concentrated and subjected to flash silica gel column purification (Combiflash® companion System® with RediSep® silica gel column 12 g, 30-50-90EtOAC/hexanes eluting solvent gradient upon dry loading the sample by absorbing on silica gel) to obtain another 0.4 g of 5-(2-chloropyridin-3-yl)-1H-pyrazolo[3,4-b]pyridine. Total yield: 52%. $^1$H NMR (DMSO-d6): δ 13.83 (s, 1H), 8.59 (d, 1H, J=2.0 Hz), 8.45 (dd, 1H, J=1.7 and 4.7 Hz), 8.36 (d, 1H, J=2.0 Hz), 8.21 (s, 1H), 8.00 (dd, 1H, J=1.7 and 7.7 Hz), 7.59 (dd, 1H, J=4.7 and 7.7 Hz).LCMS: rt5.20 min (A), purity 94%, MS (m/e) 231 (MH$^+$).

Example 8

2-Chloro-3-(4-fluorophenyl)pyridine

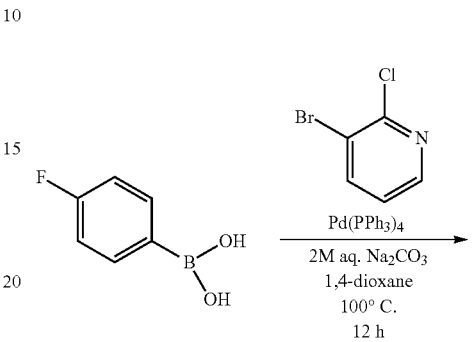

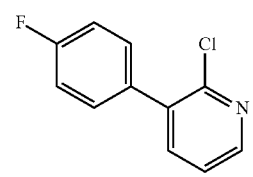

2-Chloro-3-(4-fluorophenyl)pyridine was synthesized analogous to the reaction conditions used in the preparation of 5-(2-chloropyridin-3-yl)-1H-indazole by heating the mixture of 4-fluorophenyl boronic acid (3.0 g, 21.4 mmol), 3-bromo-2-chloropyridine (4.9 g, 25.7 mmol), Pd(PPh$_3$)$_4$ (1.6 g, 1.3 mmol) and 2M aq. Na$_2$CO$_3$ (25 mL, 50 mmol) in 1,4-dioxane (125 mL) under argon atmosphere for 12 h. LC/MS indicated three products with MH$^+$ 208, 254 and 268. Upon work-up of the reaction mixture, as discussed in the preparation of 5-(2-chloropyridin-3-yl)-1H-indazole, the crude concentrated was purified by flash silica gel column chromatography [Combiflash® companion System® with RediSep® silica gel column 120 g, 10-50% EtOAC/hexanes eluting solvent gradient upon liquid loading on to column]. Two fractions containing the desired product were identified and concentrated. 2-Chloro-3-(4-fluorophenyl)pyridine was isolated as a crystalline solid (888 mg, 16%) from the fraction containing 2,3-bis(4-fluorophenyl)pyridine by suspending the semi solid fraction mixture in 10% EtOAc/hexanes and filtered. $^1$H NMR (DMSO-d6): δ 8.41 (dd, 1H, J=1.8 and 4.7 Hz), 7.86 (dd, 1H, J=2.0 and 7.6 Hz), 7.54-7.48 (m, 3H), 7.34-7.31 (m, 2H). ¹⁹F NMR (DMSO-d6): δ −114.06 (s). LCMS: rt 7.50 min (A), purity 99%, MS (m/e) 208 (MH⁺).

Example 9 tert-Butyl 6-bromo-1H-indazole-1-carboxylate

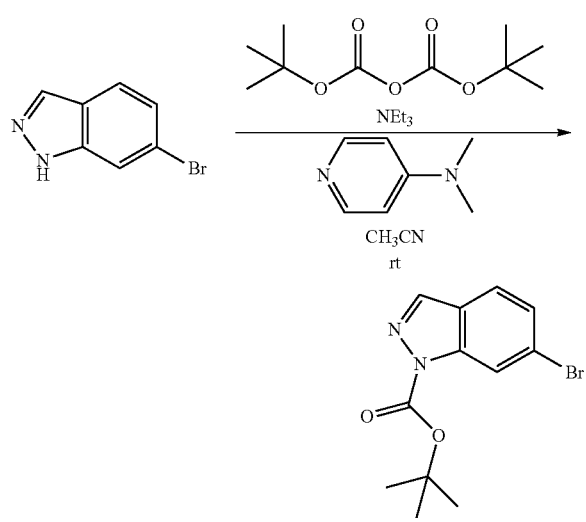

Analogous to the preparation and work-up procedure of tert-butyl 5-bromo-1H-indazole-carboxylate, tert-butyl 6-bromo-1H-indazole-carboxylate was obtained by the reaction of 6-bromo-1H-indazole (5.0 g, 25.4 mmol), di-tert-butyl dicarbonate (7.2 g, 32.9 mmol), triethylamine (3.6 g, 1.0 mL, 35.7 mmol) and 4-(dimethylamino)pyridine (3.1 g, 25 mmol) in acetonitrile (40 mL) under a mild stream of nitrogen at room temperature. tert-butyl 6-bromo-1H-indazole-carboxylate (7.5 g, 97%) as a pale yellow viscous liquid which was used without further purification. ¹H NMR (DMSO-d6): δ 8.36 (d, 1H, J=0.8 Hz), 8.11 (app d, 1H, J=0.8 Hz), 8.00 (d, 1H, J=8.8 Hz), 7.71 (app dd, 1H, J=0.8 and 8.8 Hz), 1.62 (s, 9H). LCMS: 97%, MS (m/e) 241 (MH⁺-t-Bu).

Example 10

6-(2-Chloropyridin-3-yl)-1H-indazole

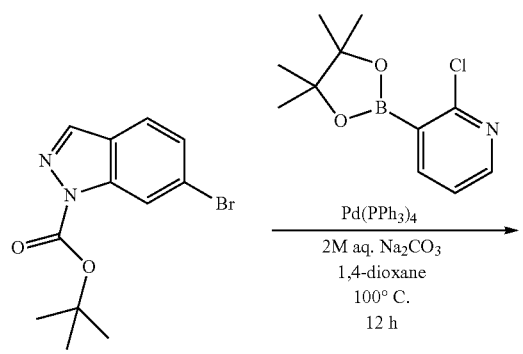

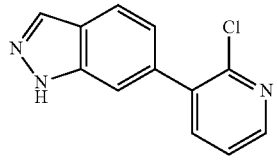

Analogous to the reaction conditions and work-up procedures used in the preparation of 5-(2-chloropyridin-3-yl)-1H-indazole, 5-(2-chloropyridin-3-yl)-1H-indazole was obtained by heating the mixture of tert-butyl 6-bromo-1H-indazole-carboxylate (7.3 g, 24.6 mmol), 2-chloro-3-pyridine boronic acid pinacol ester (7.0 g, 29.5 mmol), Pd(PPh₃)₄ (2 g, 1.7 mmol) and aq.Na₂CO₃ (44 mL, 88 mmol) in 1,4-dioxane (200 mL) under argon atmosphere. The crude concentrate that was obtained after the extractive work-up dissolved in CH₂Cl₂, adsorbed on to silica gel and dried. Subsequent purification by flash silica gel column chromatography (Combiflash® companion System® with RediSep® silica gel column 120 g, 30-70% EtOAC/hexanes eluting solvent gradient upon dry powder loading) provided 5-(2-chloropyridin-3-yl)-1H-indazole as a white solid (4.2 g, 74%). ¹H NMR (DMSO-d6): δ 13.21 (s, 1H), 8.43 (dd, 1H, J=1.7 and 4.7 Hz), 8.12 (s, 1H), 7.93 (dd, 1H, J=1.7 and 7.6 Hz), 7.84 (d, 1H, J=8.5 Hz), 7.59 (s, 1H), 7.52 (dd, 1H, J=4.7 and 7.6 Hz), 7.17 (d, 1H, J=8.5 Hz). LCMS: rt 6.17 min (A), purity 98%, MS (m/e) 230 (MH⁺).

Example 11

1-Trityl-6-bromo-2-benzoxazilinone

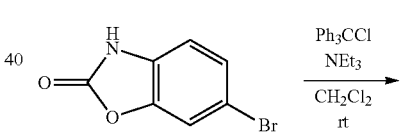

Triethylamine (0.72 g, 1.0 mL, 7.1 mmol) was added to a stirring a mixture of 6-bromo-2-benzoxazilinone (0.89 g, 4.2 mmol) and tritylchloride (1.21 g, 4.4 mmol) in CH₂Cl₂ (10 mL) for a period of 10 min. The reaction was monitored by TLC (silica gel) and concentrated after 1 h. The concentrate was diluted with water and sonicated to form a heterogeneous solution. The resulting off-white solid was suction filtered and dried to provide 1-trityl-6-bromo-2-benzoxazilinone (2.0 g). LCMS: rt 9.45 min (A), purity 96%, MS (m/e) 456 (MH+).

Example 12

6-(2-chloropyridin-3-yl)benzo[d]oxazol-2(3H)-one

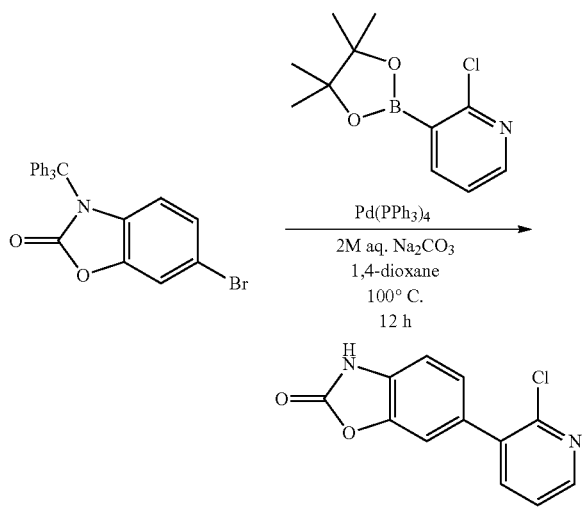

Analogous to the preparation of 5-(2-chloropyridin-3-yl)-1H-indazole,6-(2-chloropyridin-3-yl)benzo[d]oxazol-2(3H)-one was prepared by heating the mixture of 1-trityl-6-bromo-2-benzoxazilinone (2.0 g, 4.4 mmol), 2-chloro-3-pyridine boronic acid pinacol ester (1.3 g, 5.4 mmol), Pd(PPh3)4 (0.5 g, 0.43 mmol) and 2M aq. Na2CO3 (8 mL, 16 mmol) in 1,4-dioxane (75 mL) under argon atmosphere for 12 h. LC/MS indicated three products with MH+ 489, 245 and 566. Extractive work-up followed by flash silica gel column purification (Combiflash® companion System® with RediSep® silica gel column 40 g, 20-70% EtOAC/hexanes eluting solvent gradient upon dry loading the concentrate absorbed on silica gel) provided 6-(2-chloropyridin-3-yl)benzo[d]oxazol-2(3H)-one (0.44 g, 38%) as an off-white solid after concentration of the respective product fractions. LCMS: rt 5.85 min (A), purity 94%, MS (m/e) 247 (MH+).

Example 13

3-(Benzo[d][1,3]dioxol-6-yl)-2-chloropyridine

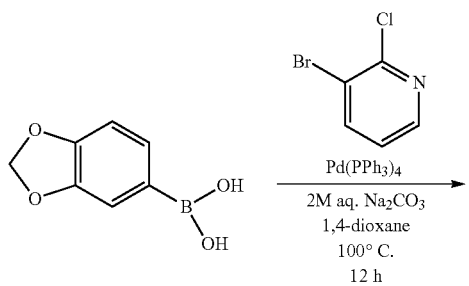

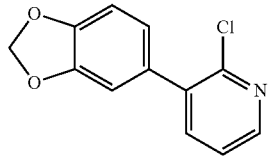

Analogous to the preparation of 5-(2-chloropyridin-3-yl)-1H-indazole,3-(benzo[d][1,3]dioxol-6-yl)-2-chloropyridine was prepared by heating the mixture of 3,4-(methylenedioxy)phenyl boronic acid (3.0 g, 18.1 mmol), 3-bromo-2-chloropyridine (4.2 g, 1.8 mmol), Pd(PPh3)4 (1.2 g, 1.0 mmol) and 2M aq. Na2CO3 (27 mL, 54 mmol) in 1,4-dioxane (125 mL) under argon atmosphere for 12 h. LC/MS indicated three products. The crude concentrate that was obtained after the extractive work-up dissolved in CH2Cl2, adsorbed on to silica gel and dried. Subsequent purification by flash silica gel column chromatography (Combiflash® companion System® with RediSep® silica gel column 120 g, 30-70% EtOAC/hexanes eluting solvent gradient upon dry powder loading) provided 3-(benzo[d][1,3]dioxol-6-yl)-2-chloropyridine as a white solid 2.3 g, (38%). $^1$H NMR (DMSO-d6): δ 8.38 (dd, 1H, J=1.7 and 4.7 Hz), 7.82 (dd, 1H, J=2.0 and 7.6 Hz), 7.47 (dd, 1H, J=4.7 and 7.6 Hz), 7.05 (d, 1H, J=1.7 Hz), 7.01 (d, 1H, J=7.9 Hz), 6.90 (dd, 1H, J=1.7 and 7.9 Hz), 6.07 (s, 2H LCMS: rt 7.27 min (A), purity 96%, MS (m/e) 234 (MH+).

Example 14

6-(2-Chloropyridin-3-yl)-1-methyl-1H-indazole

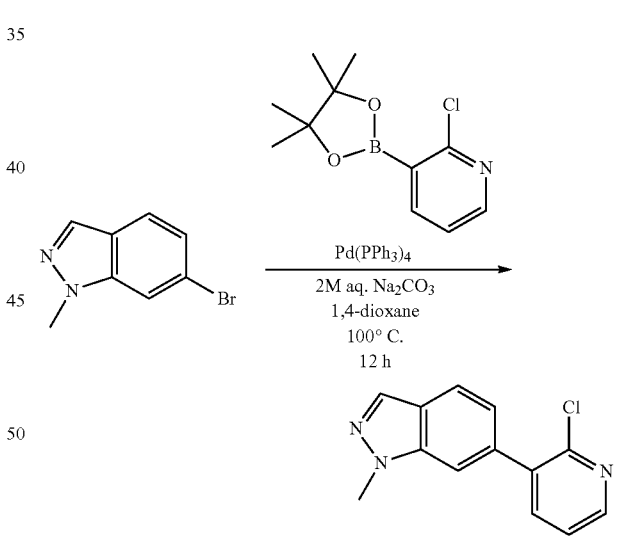

Analogous to the preparation of 5-(2-chloropyridin-3-yl)-1H-indazole,6-(-2-chloropyridin-3-yl)-1-methyl-1H-indazole was prepared by heating the mixture of 6-bromo-1-methyl-1H-indazole (2.0 g, 9.5 mmol), 2-chloro-3-pyridine boronic acid pinacol ester (2.2 g, 9.4 mmol), Pd(PPh3)4 (0.54 g, 0.46 mmol) and 2M aq. Na2CO3 (14 mL, 28 mmol) in 1,4-dioxane (75 mL) under argon atmosphere for 12 h. Upon extractive work-up as discussed in the preparation of 5-(2-chloropyridin-3-yl)-1H-indazole with CH2Cl2 and purification of the concentrate by flash silica gel column chromatography (Combiflash® companion System® with RediSep® silica gel column 40 g, 30-50% EtOAC/hexanes eluting solvent gradient upon dry loading the concentrate absorbed on silica gel) provided 6-(-2-chloropyridin-3-yl)-1-methyl-1H-indazole as a white solid (1.8 g, 77%). ¹H NMR (DMSO-d6): δ 8.45 (dd, 1H, J=1.7 and 4.7 Hz), 8.09 (s, 1H), 7.94 (dd, 1H, J=2.0 and 7.6 Hz), 7.82 (d, 1H, J=8.5 Hz), 7.74 (s, 1H), 7.54 (dd, 1H, J=4.7 and 7.6 Hz), 7.22 (d, 1H, J=8.5 Hz), 4.06 (s, 3H).LCMS: rt 6.80 min (A), purity 97%, MS (m/e) 244 (MH⁺)

Example 15 tert-Butyl 6-bromo-1H-pyrazolo[4,3-b]pyridine-1-carboxylate

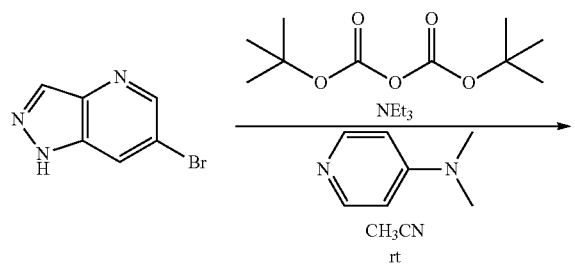

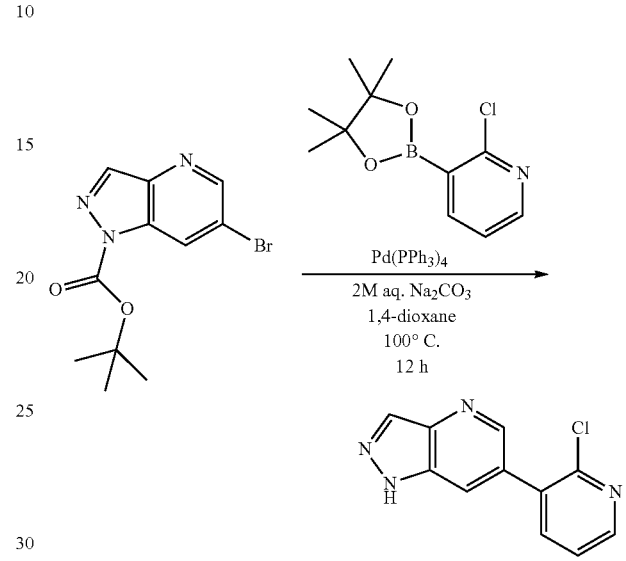

Analogous to the preparation of tert-butyl 5-bromo-1H-pyrazolo[3,4-b]pyridine-1-carboxylate, 6-bromo-1H-pyrazolo[4,3-b]pyridine (2.0 g, 10.10 mmol) was reacted with di-tert-butyl dicarbonate (2.8 g, 13.10 mmol), NEt₃ (1.44 g, 2.0 mL, 14 mmol) and 4-(dimethylamino)pyridine in acetonitrile (20 mL) for 3 h. Work-up as discussed previously in the preparation of tert-butyl 5-bromo-1H-pyrazolo[3,4-b]pyridine-1-carboxylate provided desired product of tert-butyl 6-bromo-1H-pyrazolo[4,3-b]pyridine-1-carboxylate as a brown solid (2.8 g, 93%).

Example 16

6-(2-Chloropyridin-3-yl)-1H-pyrazolo[4,3-b]pyridine 6-(2-Chloropyridin-3-yl)-1H-pyrazolo[4,3-b]pyridine was synthesized in the similar manner to the preparation of 5-(2-chloropyridin-3-yl)-1H-pyrazolo[3,4-b]pyridine by heating the mixture of tert-butyl 6-bromo-1H-pyrazolo[4,3-b]pyridine-1-carboxylate (2.5 g, 8.4 mmol), 2-chloro-3-pyridine boronic acid pinacol ester (2.2 g, 9.2 mmol), Pd(PPh₃)₄ (610 mg, 0.52 mmol) and 2M aq.Na₂CO₃ (12 mL, 24 mmol) in 1,4-dioxane (40 mL). Upon work-up of the reaction mixture similar to 5-(2-chloropyridin-3-yl)-1H-pyrazolo[3,4-b]pyridine provided 6-(2-chloropyridin-3-yl)-1H-pyrazolo[4,3-b]pyridine as an off-white crystalline solid. ¹H NMR (DMSO-d6): δ 13.50 (s, 1H), 8.57 (app s, 1H), 8.48 (dd, 1H, J=1.7 and 4.7 Hz), 8.35 (s, 1H), 8.12 (s, 1H), 8.02 (dd, 1H, J=1.7 and 7.6 Hz), 7.60 (dd, 1H, J=4.7 and 7.7 Hz).LCMS: rt 4.50 min (A), purity 94%, MS (m/e) 231 (MH⁺).

Example 17

6-(2-Chloropyridin-3-yl)-1-methyl-1H-indazole

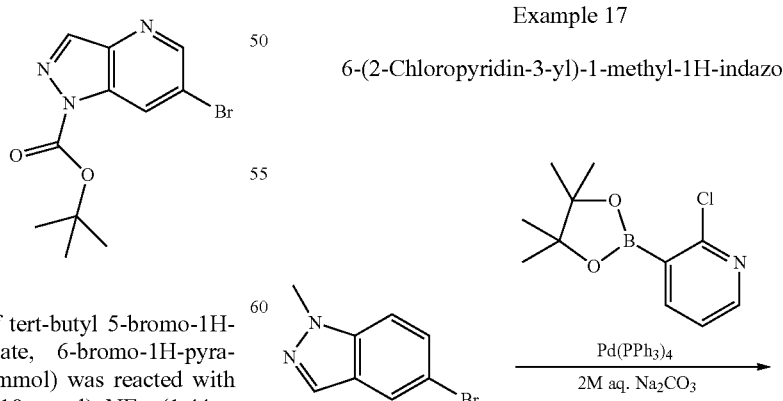

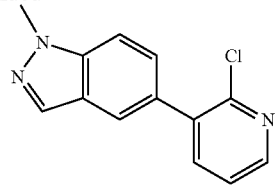

Analogous to the preparation of 5-(2-chloropyridin-3-yl)-1H-indazole,5-(2-chloropyridin-3-yl)-1-methyl-1H-indazole was prepared by heating the mixture of 5-bromo-1-methyl-1H-indazole (1.0 g, 4.7 mmol), 2-chloro-3-pyridine boronic acid pinacol ester (1.2 g, 5.2 mmol), Pd(PPh$_3$)$_4$ (270 mg, 0.23 mmol) and 2M aq. Na$_2$CO$_3$ (6 mL, 12 mmol) in 1,4-dioxane (75 mL) under argon atmosphere for 12 h. Upon work-up as discussed in the preparation of 5-(2-chloropyridin-3-yl)-1H-indazole and purification of the concentrate by flash silica gel column chromatography [Combiflash® companion System® with RediSep® silica gel column 40 g, 30-50% EtOAc/hexanes eluting solvent gradient upon dry loading the concentrate absorbed on silica gel] provided 5-(2-chloropyridin-3-yl)-1methyl-1H-indazole as white solid (0.84 g, 73%). $^1$H NMR (DMSO-d6): δ 8.41 (dd, 1H, J=1.7 and 4.7 Hz), 8.10 (s, 1H), 7.90 (dd, 1H, J=1.7 and 7.6 Hz), 7.83 (app t, 1H, J=0.6 Hz), 7.72 (dd, 1H, J=0.6 and 8.8 Hz), 7.51 (dd, 1H, J=4.7 and 7.6 Hz), 7.48 (dd, 1H, J=1.7 and 8.8 Hz), 4.07 (s, 3H).LCMS: rt 6.73 min (A), purity 99%, MS (m/e) 244 (MH$^+$).

Example 18 tert-Butyl 5-bromo-3-methyl-1H-indazole-1-carboxylate

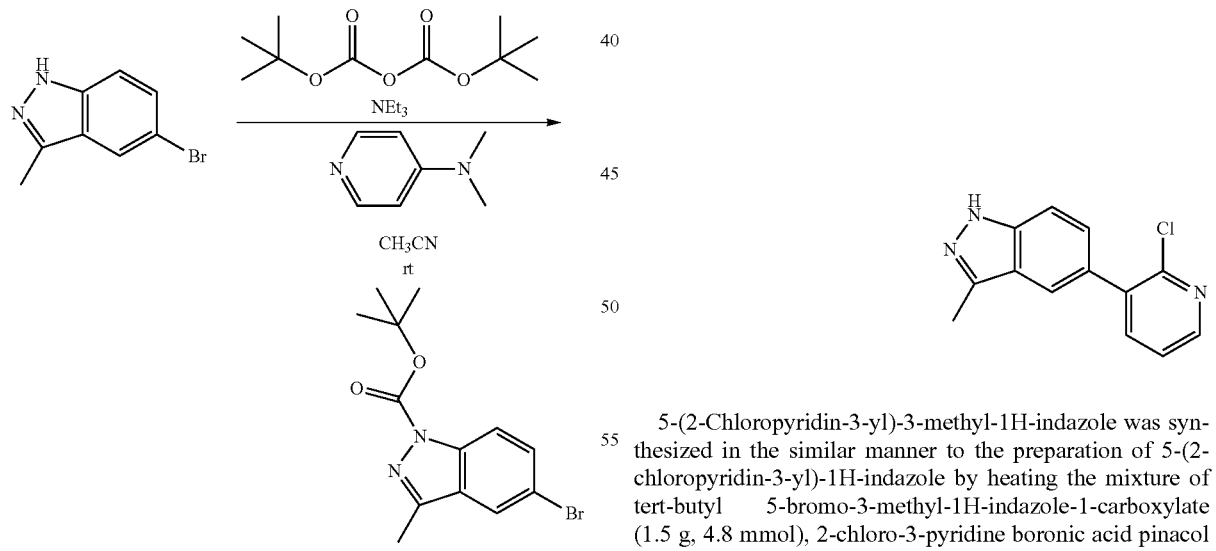

Analogous to the preparation tert-butyl 5-bromo-1H-pyrazolo[3,4-b]pyridine-1-carboxylate, tert-butyl 5-bromo-3-methyl-1H-indazole-1-carboxylate was prepared by reacting 5-bromo-3-methyl-1H-indazole (1.0 g, 4.7 mmol), di-tert-butyl dicarbonate (1.2 g, 6.4 mmol), NEt$_3$ (0.72 g, 1.0 mL, 7.1 mmol) and 4-(dimethylamino)pyridine (0.57 g, 4.7 mmol). The reaction mixture was concentrated and diluted with water. The resultant solid was collected by filtration and suction dried to provide tert-butyl 5-bromo-3-methyl-1H-indazole-1-carboxylate (1.5 g, 97%) as a white solid. $^1$H NMR (DMSO-d6): δ 8.10 (d, 1H, J=1.8 Hz), 7.96 (d, 1H, J=9.1 Hz), 7.71 (dd, 1H, J=1.8 and 9.1 Hz), 2.49 (s, 3H), 1.61 (s, 9H). LCMS: 97%, MS (m/e) 254 (MH$^+$-t-Bu).

Example 19

5-(2-Chloropyridin-3-yl)-3-methyl-1H-indazole

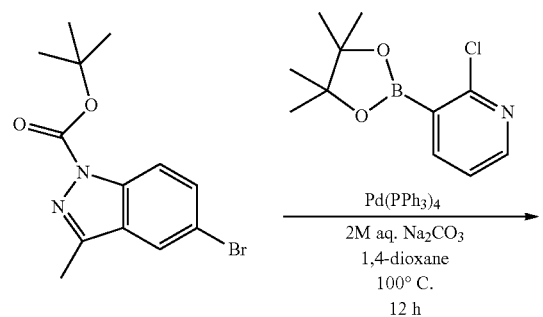

5-(2-Chloropyridin-3-yl)-3-methyl-1H-indazole was synthesized in the similar manner to the preparation of 5-(2-chloropyridin-3-yl)-1H-indazole by heating the mixture of tert-butyl 5-bromo-3-methyl-1H-indazole-1-carboxylate (1.5 g, 4.8 mmol), 2-chloro-3-pyridine boronic acid pinacol ester (1.3 g, 5.3 mmol), Pd(PPh$_3$)$_4$ (390 mg, 0.33 mmol) and 2M aq.Na$_2$CO$_3$ (7 mL, 14 mmol) in 1,4-dioxane (40 mL). Upon work-up and purification procedure used in the prepartion of 5-(2-chloropyridin-3-yl)-1H-indazole provided 5-(2-chloropyridin-3-yl)-3-methyl-1H-indazole (0.52, 43%) as a white crystalline solid. $^1$H NMR (DMSO-d6): δ 12.75 (s, 1H), 8.41 (dd, 1H, J=1.7 and 4.7 Hz), 7.91 (dd, 1H, J=1.7 and 7.6 Hz), 7.77 (s, 1H), 7.52 (d, 1H, J=8.5 Hz), 7.51 (dd, 1H, J=4.7 and 7.6 Hz), 7.41 (dd, 1H, J=1.4 and 8.5 Hz), 2.49 (s, 3H). LCMS: rt 6.28 min (A), purity 97%, MS (m/e) 244.

Example 20

6-(2-Chloropyridin-3-yl)benzo[d]thiazole

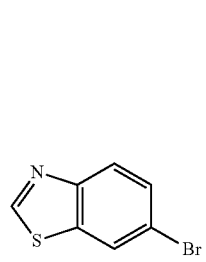
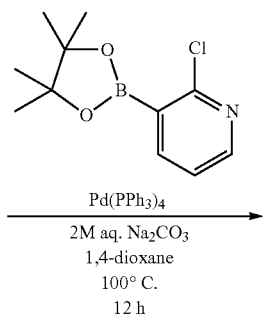

6-(2-Chloropyridin-3-yl)benzo[d]thiazole was prepared analogous to 5-(2-chloropyridin-3-yl)-1H-indazole by heating the mixture of 6-bromobenzo[d]thiazole (2.0 g, 9.3 mmol), 2-chloro-3-pyridine boronic acid pinacol ester (2.7 g, 11.2 mmol), Pd(PPh₃)₄ (500 mg, 0.43 mmol) and 2M aq.Na₂CO₃ (14 mL, 28 mmol) in 1,4-dioxane (100 mL). The reaction mixture was concentrated at the completion of the reaction (12 h) and diluted with CH₂Cl₂ (200 mL/100 mL). Mixed organic layers were stirred with MgSO₄ and Celite® for 30 min. The slurry was suction filtered and concentrated by rotary evaporator under vacuum. The crude concentrate was dissolved in CH₂Cl₂, adsorbed on silica gel and dried. The dry powder thus obtained was purified by silica gel flash column chromatography (Combiflash® companion System® with RediSep® silica gel column 40 g, 30-70% EtOAC/hexanes eluting solvent gradient). 6-(2-chloropyridin-3-yl)benzo[d]thiazole (1.9 g, 82%) was obtained as a white solid upon concentration of the product fractions. ¹H NMR (DMSO-d6): δ 9.46 (s, 1H), 8.46 (dd, 1H, J=1.7 and 4.7 Hz), 8.30 (d, 1H, J=1.4 Hz), 8.17 (d, 1H, J=8.2 Hz), 7.96 (dd, 1H, J=1.7 and 7.6 Hz), 7.63 (dd, 1H, J=1.4 and 8.5 Hz), 7.53 (dd, 1H, J=4.7 and 7.6 Hz). LCMS: rt 6.71 min (A), purity 99%, MS (m/e) 247.

Example 21

5-(2-Chloropyridin-3-yl)benzo[d]thiazole

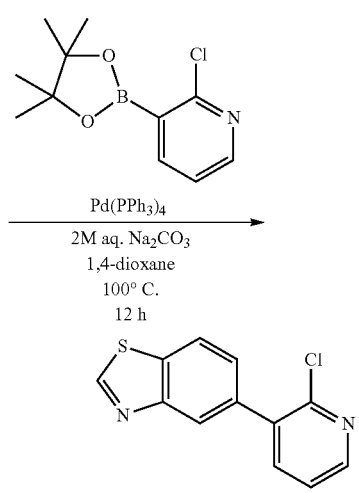

5-(2-chloropyridin-3-yl)benzo[d]thiazole was prepared in the similar manner of 6-(2-chloropyridin-3-yl)benzo[d]thiazole by heating the mixture of 5-bromobenzothiazole (1.0 g, 4.67 mmol), 2-chloro-3-pyridine boronic acid pinacol ester (1.34 g, 5.6 mmol), Pd(PPh₃)₄ (250 mg, 0.22 mmol) and 2M aq.Na₂CO₃ (7 mL, 14 mmol) in 1,4-dioxane (50 mL). Upon work-up and purification protocol used in the preparation of 6-(2-chloropyridin-3-yl)benzo[d]thiazole provided 5-(2-chloropyridin-3-yl)benzo[d]thiazole as a white solid (820 mg, 70%). ¹H NMR (DMSO-d6): δ 9.46 (s, 1H), 8.45 (dd, 1H, J=2.0 and 4.9 Hz), 8.27 (d, 1H, J=8.5 Hz), 8.17 (app s, 1H), 7.97 (dd, 1H, J=1.7 and 7.6 Hz), 7.58 (d, 1H, J=8.5 Hz), 7.53 (dd, 1H, J=4.7 and 7.6 Hz), LCMS: rt 6.73 min (A), purity 99%, MS (m/e) 247.

Example 22

6-(2-Chloropyridin-3-yl)-[1,2,4]triazolo[4,3-a]pyridine

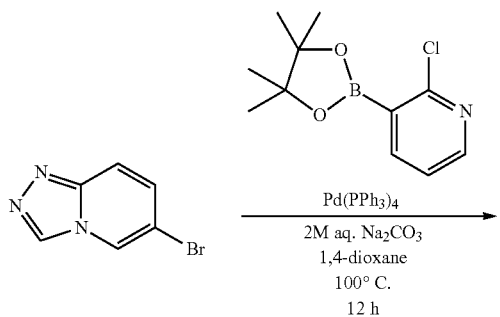

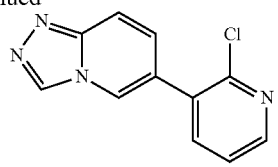

6-(2-chloropyridin-3-yl)-[1,2,4]triazolo[4,3-a]pyridine was synthesized in the similar to 6-(2-chloropyridin-3-yl)benzo[d]thiazole from 6-bromo[1,2,4]triazolo[4,3a]pyridine (1.0 g, 5.0 mmol), 2-chloro-3-pyridine boronic acid pinacol ester (1.45 g, 6.0 mmol), Pd(PPh$_3$)$_4$ (300 mg, 0.26 mmol) and 2M aq.Na$_2$CO$_3$ (8 mL, 16 mmol) in 1,4-dioxane (50 mL). Workup of the reaction mixture was carried out by sequential steps of concentrating the reaction mixture, extraction with CH$_2$Cl$_2$, drying over MgSO$_4$/Celite®, filtration and concentration. Thus obtained crude residue was dissolved in CH$_2$Cl$_2$ (10 mL) and the homogeneous solution stirred with 50% EtOAc/hexanes (40 mL). The resulting off-white precipitate was collected by filtration and dried to provide 6-(2-chloropyridin-3-yl)-[1,2,4]triazolo[4,3-a]pyridine (0.68 g, 58%). $^1$H NMR (DMSO-d6): δ 8.29 (s, 1H), 8.74 (s, 1H), 8.50 (dd, 1H, J=1.7 and 4.7 Hz), 8.01 (dd, 1H, J=1.7 and 7.6 Hz), 7.87 (d, 1H, J=9.7 Hz), 7.58 (dd, 1H, J=4.7 and 7.6 Hz), 7.51 (dd, 1H, J=1.4 and 9.7 Hz).LCMS: rt 3.90 min (A), purity 99%, MS (m/e) 231 (MH$^+$).

Example 23

6-(2-Chloropyridin-3-yl)imidazo[1,2-a]pyridine

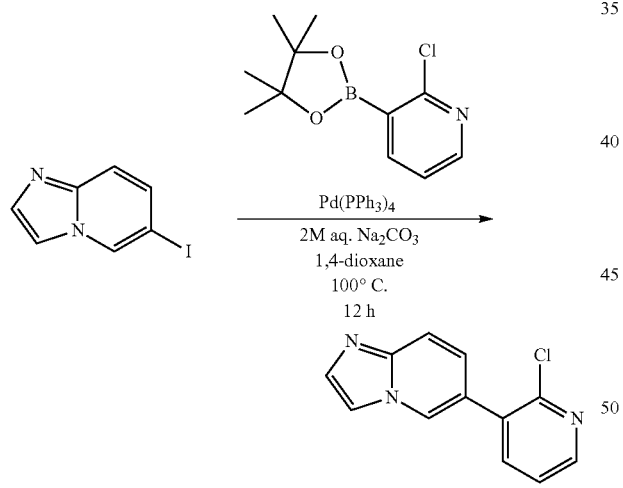

6-(2-Chloropyridin-3-yl)imidazo[1,2-a]pyridine was synthesized in the similar to 6-(2-chloropyridin-3-yl)benzo[d]thiazole from 6-iodo-imidazo[1,2-a]pyridine (1.0 g, 4.1 mmol), 2-chloro-3-pyridine boronic acid pinacol ester (1.2 g, 5.0 mmol), Pd(PPh$_3$)$_4$ (250 mg, 0.22 mmol) and 2M aq.Na$_2$CO$_3$ (7 mL, 12 mmol) in 1,4-dioxane (50 mL). Workup of the reaction mixture was carried out by sequential steps of concentrating the reaction mixture, extraction with CH$_2$Cl$_2$, drying over MgSO$_4$/Celite®, filtration and concentration. The crude residue was stirred in 50% EtOAc/hexanes (40 mL). The resulting white precipitate was filtered and dried to provide 6-(2-chloropyridin-3-yl)imidazo[1,2-a]pyridine (0.52 g, 55%). $^1$H NMR (DMSO-d6): δ 8.73 (dd, 1H, J=0.8 and 1.8 Hz), 8.47 (dd, 1H, J=2.0 and 4.7 Hz), 8.00 (dd, 1H, J=2.0 and 7.6 Hz), 7.98 (s, 1H), 7.64 (d, 1H, J=8.8 Hz), 7.63 (s, 1H), 7.56 (dd, 1H, J=4.7 and 7.6 Hz), 7.33 (dd, 1H, J=1.8 and 8.8 Hz), Hz).LCMS: rt 3.16 min (A), purity 99%, MS (m/e) 230 (MH$^+$).

Example 24 tert-Butyl 5-bromo-6-methyl-1H-indazole-1-carboxylate

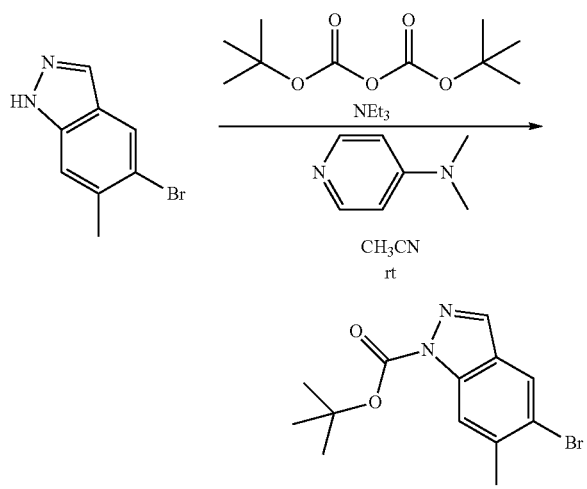

Analogous to the preparation tert-butyl 5-bromo-3-methyl-1H-indazole-1-carboxylate, tert-Butyl 5-bromo-6-methyl-1H-indazole-1-carboxylate was prepared by reacting 5-bromo-6-methyl-1H-indazole (1.0 g, 4.7 mmol), di-tert-butyl dicarbonate (1.2 g, 6.4 mmol), NEt$_3$ (0.72 g, 1.0 mL, 7.2 mmol) and 4-(dimethylamino)pyridine (0.57 g, 4.7 mmol). The reaction mixture was concentrated and diluted with water. The resultant precipitate was collected by filtration to obtain the desired product (1.4 g, 95%). $^1$H LCMS: 97%, MS (m/e) (MH$^+$-t-Bu).

Example 25

5-(2-Chloropyridin-3-yl)-6-methyl-1H-indazole

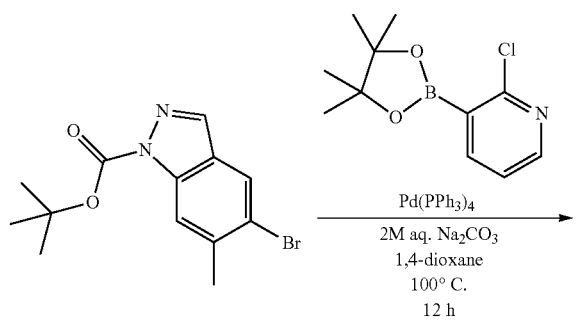

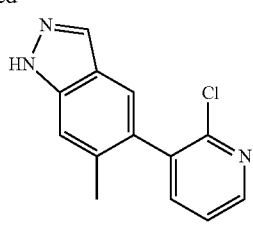

5-(2-Chloropyridin-3-yl)-6-methyl-1H-indazole was synthesized in the similar manner to the preparation of 5-(2-chloropyridin-3-yl)-1H-indazole by heating the mixture of tert-butyl 5-bromo-6-methyl-1H-indazole-1-carboxylate (1.4 g, 4.5 mmol), 2-chloro-3-pyridine boronic acid pinacol ester (1.4 g, 5.9 mmol), Pd(PPh$_3$)$_4$ (370 mg, 0.32 mmol) and 2M aq.Na$_2$CO$_3$ (7 mL, 14 mmol) in 1,4-dioxane (40 mL). Upon work-up and purification procedure used in the preparation of 5-(2-chloropyridin-3-yl)-1H-indazole provided 5-(2-chloropyridin-3-yl)-6-methyl-1H-indazole as a white solid (780 mg, 67%). $^1$H NMR (DMSO-d6): δ 13.02 (s, 1H), 8.44 (dt, 1H, J=1.7 and 4.7 Hz), 8.01 (s, 1H), 7.81 (dt, 1H, J=1.7 and 7.6 Hz), 7.53 (s, 1H), 7.51-7.48 (m, 1H), 7.45 (s, 1H), 2.12 (s, 3H).LCMS: rt 6.30 min (A), purity 98%, MS (m/e) 244.

Example 26 tert-Butyl 5-bromo-7-methyl-1H-indazole-1-carboxylate

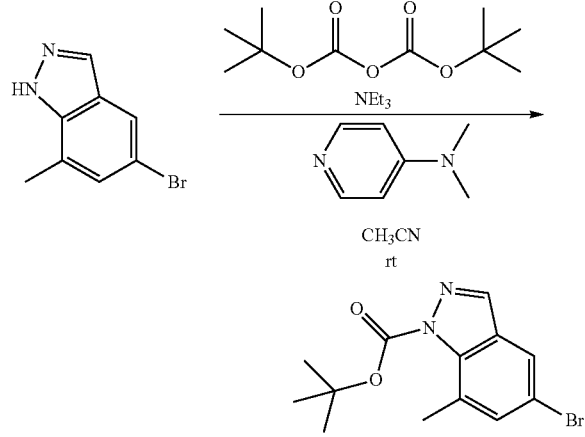

Analogous to the preparation tert-butyl 5-bromo-3-methyl-1H-indazole-1-carboxylate, tert-butyl 5-bromo-7-methyl-1H-indazole-1-carboxylate was prepared by reacting 5-bromo-7-methyl-1H-indazole (1.0 g, 4.7 mmol), di-tert-butyl dicarbonate (1.2 g, 6.4 mmol), NEt$_3$ (0.72 g, 1.0 mL, 7.2 mmol) and 4-(dimethylamino)pyridine (0.57 g, 4.7 mmol). The reaction mixture was concentrated, diluted with water (30 mL) and extracted with 50% EtOAc/hexanes (140 mL). Organic layer was washed with aq. 1N HCl, (15 mL), water (2×50 mL), aq. NaHCO$_3$ (2×30 mL) and saturated aq. NaCl (30 mL) successively, stirred with MgSO$_4$, filtered and concentrated to obtain tert-butyl 5-bromo-7-methyl-1H-indazole-1-carboxylate as a viscous liquid. The material thus obtained was used in the next step.

Example 27

5-(2-Chloropyridin-3-yl)-6-methyl-1H-indazole

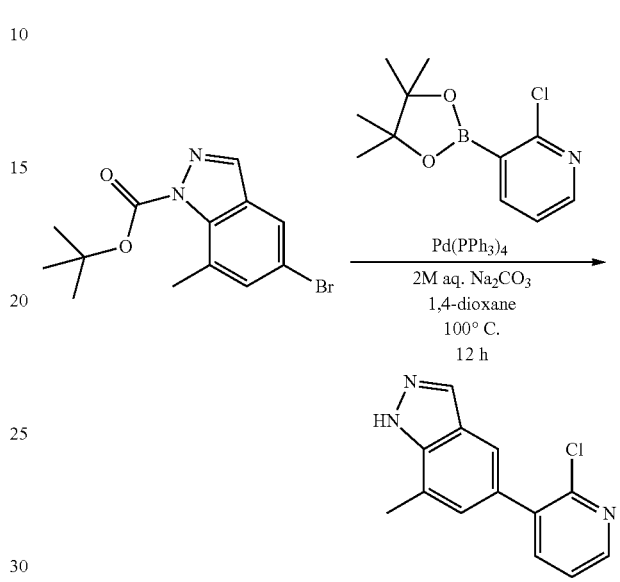

5-(2-Chloropyridin-3-yl)-7-methyl-1H-indazole was synthesized in the similar manner to the preparation of 5-(2-chloropyridin-3-yl)-1H-indazole by heating the mixture of tert-butyl 5-bromo-6-methyl-1H-indazole-1-carboxylate (1.4 g, 4.5 mmol), 2-chloro-3-pyridine boronic acid pinacol ester (1.4 g, 5.9 mmol), Pd(PPh$_3$)$_4$ (370 mg, 0.32 mmol) and 2M aq.Na$_2$CO$_3$ (7 mL, 14 mmol) in 1,4-dioxane (40 mL). Upon work-up and purification procedure used in the preparation of 5-(2-chloropyridin-3-yl)-1H-indazole provided white solid of 5-(2-chloropyridin-3-yl)-7-methyl-1H-indazole (840 mg, 73%). $^1$H NMR (DMSO-d6): δ 13.28 (s, 1H), 8.40 (dd, 1H, J=1.7 and 4.7 Hz), 8.11 (app d, 1H, J=1.2 Hz), 7.87 (dd, 1H, J=1.7 and 7.6 Hz), 7.64 (s, 1H), 7.49 (dd, 1H, J=4.7 and 7.6 Hz), 7.19 (s, 1H), 2.54 (s, 3H).LCMS: rt 6.41 min (A), purity 98%, MS (m/e) 244 (MH$^+$)

Example 28

6-(2-Chloropyridin-3-yl)-1H-benzimidazole

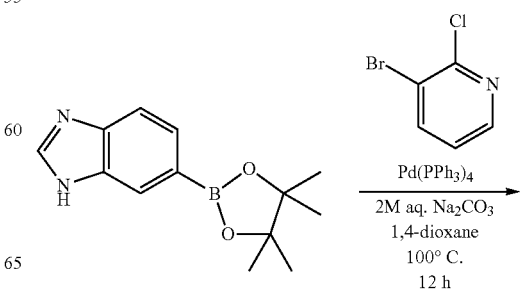

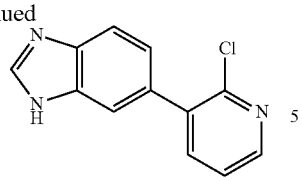

6-(2-Chloropyridin-3-yl)-1H-benzimidazole was synthesized in the similar manner to the preparation of 5-(2-chloropyridin-3-yl)-1H-indazole by heating the mixture of 3-bromo-2-chloropyridine (0.70 g, 3.63 mmol), 1H-benzimidazole-5-boronic acid pinacol ester (0.8 g, 3.27 mmole), Pd(PPh$_3$)$_4$ (330 mg, 0.28 mmol) and 2M aq.Na$_2$CO$_3$ (4 mL, 8 mmol) in 1,4-dioxane (30 mL). Upon extractive work-up with CH$_2$Cl$_2$ and purification of the concentrate by flash silica gel column chromatography (Combiflash® companion System® with RediSep® silica gel column 24 g, 3% MeOH/EtOAc as a eluting solvent upon dry loading the concentrate absorbed on silica gel) provided 6-(2-chloropyridin-3-yl)-1H-benzimidazole (200 mg, 26%). $^1$H NMR (DMSO-d6): δ 12.57 (s, 1H), 8.95 (dd, 1H, J=1.7 and 4.9 Hz), 8.28 (s, 1H), 7.90 (dd, 1H, J=1.7 and 7.6 Hz), 7.70-7.62 (m, 2H), 7.58 (dd, 1H, J=4.9 and 7.6 Hz), 7.29-7.27 (app s, 1H).LCMS: rt 3.71 min (A), purity 96%, MS (m/e) 230 (MH$^+$).

Example 29

6-(2-Chloropyridin-3-yl)-1H-benzimidazole

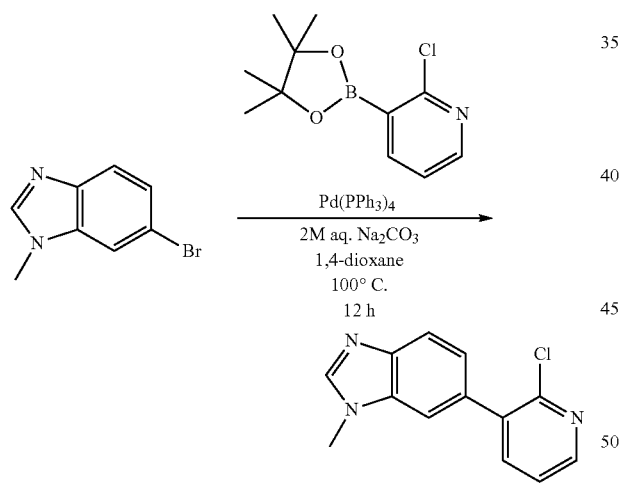

6-(2-Chloropyridin-3-yl)-1-methyl-1H-benzimidazole was synthesized in the similar manner to the preparation of 5-(2-chloropyridin-3-yl)-1H-indazole by heating the mixture of 6-bromo-1-methyl-1H-benzimidazole (1.0 g, 4.7 mmole), 2-chloro-3-pyridine boronic acid pinacol ester (1.4 g, 5.8 mmol), Pd(PPh$_3$)$_4$ (330 mg, 0.28 mmol) and 2M aq.Na$_2$CO$_3$ (7 mL, 14 mmol) in 1,4-dioxane (60 mL). Upon extractive work-up with CH$_2$Cl$_2$ and purification (Combiflash® companion System® with RediSep® silica gel column 24 g, 3% MeOH/EtOAc as a eluting solvent) provided off-white solid of 6-(2-chloropyridin-3-yl)-1H-benzimidazole (430 mg, 36%). $^1$H NMR (DMSO-d6): δ 8.42 (dd, 1H, J=1.7 and 4.7 Hz), 8.24 (s, 1H), 7.91 (dd, 1H, J=1.7 and 7.6 Hz), 7.60 (d, 1H, J=8.8 Hz), 7.67 (app d, 1H, J=0.7 Hz), 7.53 (dd, 1H, J=J=4.7 and 7.6 Hz), 7.29 (dd, 1H, J=1.7 and 8.8 Hz), 3.86 (s, 3H LCMS: rt 3.85 min (A), purity 94%, MS (m/e) 244 (MH$^+$)

Example 30

5-(2-Chloropyridin-3-yl)-1H-benzimidazole

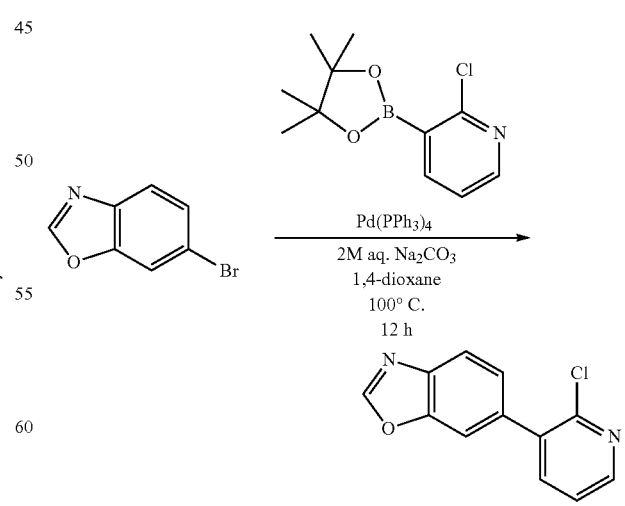

5-(2-Chloropyridin-3-yl)-1-methyl-1H-benzimidazole was synthesized in the similar manner to the preparation of 6-(2-Chloropyridin-3-yl)-1-methyl-1H-benzimidazole. $^1$H NMR (DMSO-d6): δ 8.41 (dd, 1H, J=1.7 and 4.7 Hz), 8.25 (s, 1H), 7.89 (dd, 1H, J=1.7 and 7.6 Hz), 7.71 (app d, 1H, J=0.7 Hz), 7.65 (d, 1H, J=8.5 Hz), 7.51 (dd, 1H, J=J=4.7 and 7.6 Hz), 7.35 (dd, 1H, J=1.4 and 8.5 Hz), 3.86 (s, 3H).LCMS: rt 3.86 min (A), purity 93%, MS (m/e) 244 (MH$^+$)

Example 31

6-(2-Chloropyridin-3-yl)benzoxazole

Analogous to the preparation of 5-(2-chloropyridin-3-yl)-1H-indazole, 6-(2-chloropyridin-3-yl)benzoxazole was prepared by heating the mixture of 6-bromo-benzoxazole (1.0 g, 5.1 mmol), 2-chloro-3-pyridine boronic acid pinacol ester (1.5 g, 6.6 mmol), Pd(PPh$_3$)$_4$ (400 mg, 0.34 mmol) and 2M aq.Na$_2$CO$_3$ (8 mL, 16 mmol) in 1,4-dioxane (40 mL). Upon extractive work-up with CH$_2$Cl$_2$ and purification (Combiflash® companion System® with RediSep® silica gel column 24 g, 30-50% EtOAc/hexanes as a eluting solvent) provided off-white solid f 6-(2-chloropyridin-3-yl)benzoxazole (440 mg, 37%). $^1$H NMR (DMSO-d6): δ 8.82 (s, 1H), 8.45 (dd, 1H, J=1.7 and 4.7 Hz), 7.95-7.92 (m, 2H), 7.89 (d, 1H, J=8.5 Hz), 7.55 (dd, 1H, J=4.7 and 7.6 Hz), 7.49 (d, 1H, J=8.5 Hz).LCMS: rt 5.93 min (B), purity 99%, MS (m/e) 231 (MH$^+$)

Example 32

5-(2-Chloropyridin-3-yl)benzoxazole

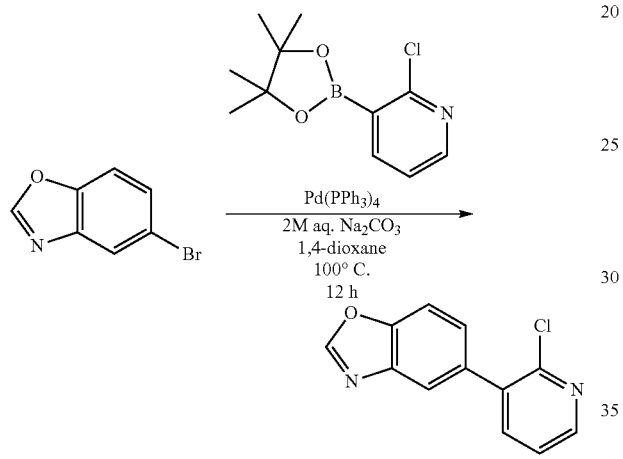

5-(2-Chloropyridin-3-yl)benzoxazole (310 mg, 25%) was prepared in the identical manner to the preparation of 6-(2-chloropyridin-3-yl)benzoxazole. $^1$H NMR (DMSO-d6): δ 8.82 (s, 1H), 8.44 (dd, 1H, J=1.7 and 4.7 Hz), 7.95-7.90 (m, 2H), 7.87 (d, 1H, J=8.5 Hz), 7.55-7.50 (m, 2H).LCMS: rt 5.96 min (A), purity 94%, MS (m/e) 231 (MH$^+$).

Example 33

Preparation of 5-bromo-1-ethyl-1H-indazole and 5-bromo-2-ethyl-2H-indazole

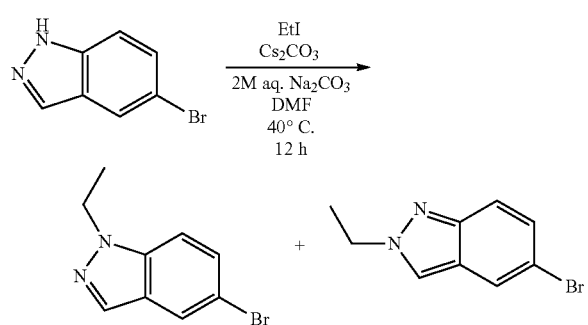

A stirred mixture of 5-bromo-1H-indazole (2.0 g, 10.1 mmol), iodoethane (2.0, 12.8 mmol), Cs$_2$CO$_3$ (4.0 g, 12.27 mmol) was heated in dry DMF at 40° C. for 12 h under argon. The reaction mixture was cooled, diluted with water and EtOAc. Aqueous layer was discarded and the organic layer was washed with water and aq. NaCl successively. Collected organic layer was stirred with MgSO$_4$ for 10 min, filtered and concentrated. The well separated (on TLC) regio-isomers were isolated by flash silica gel column chromatography (combiflash 0-30-50% EtOAc/hexanes, 80g). 5-Bromo-1-ethyl-1H-indazole (1.2 g, liquid, 52%). LCMS: rt 7.58 min (A), purity 99%, MS (m/e) 231 (MH$^+$). 5-bromo-2-ethyl-2H-indazole (900 mg, liquid, 39%). LCMS: rt 6.98 min (A), purity 97%, MS (m/e) 227 (MH$^+$).

Example 34

5-(2-Chloropyridin-3-yl)-2-ethyl-2H-indazole

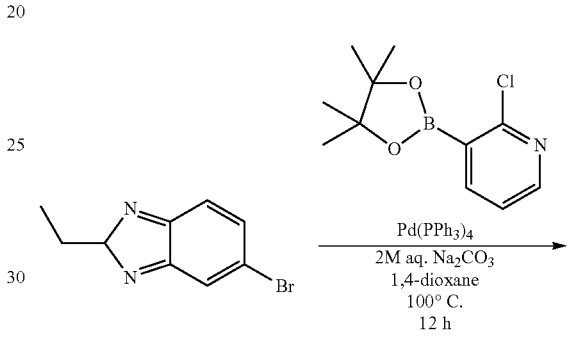

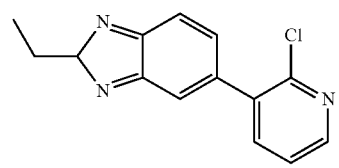

Analogous to the preparation of 5-(2-chloropyridin-3-yl)-1H-indazole, 5-(2-chloropyridin-3-yl)-2-ethyl-2H-indazole was prepared by the heating the mixture of 5-bromo-2-ethyl-2H-indazole (0.90 g, 3.98 mmol), 2-chloro-3-pyridine boronic acid pinacol ester (1.1 g, 4.60 mmol), Pd(PPh$_3$)$_4$ (300 mg, 0.34 mmol) and 2M aq.Na$_2$CO$_3$ (5 mL, 10 mmol) in 1,4-dioxane (40 mL). 5-(2-chloropyridin-3-yl)-2-ethyl-2H-indazole (732 mg, 70%) was isolated as an off-white solid after the workup and purificaiton by flash silica gel purification. $^1$H NMR (DMSO-d6): δ 8.45 (s, 1H), 8.40 (dd, 1H, J=1.7 and 4.7 Hz), 7.89 (dd, 1H, J=1.7 and 7.6 Hz), 7.76 (s, 1H), 7.67 (d, 1H, J=9.1 Hz), 7.49 (dd, 1H, J=4.9 and 7.5 Hz), 7.29 (d, 1H, J=9.1 Hz), 4.46 (qt, 2H, J=7.3 Hz), 1.40 (t, 3H, J=7.3 Hz).LCMS: rt 6.51 min (A), purity 98%, MS (m/e) 258 (MH⁺)

Example 35

5-(2-Chloropyridin-3-yl)-1-ethyl-2H-indazole

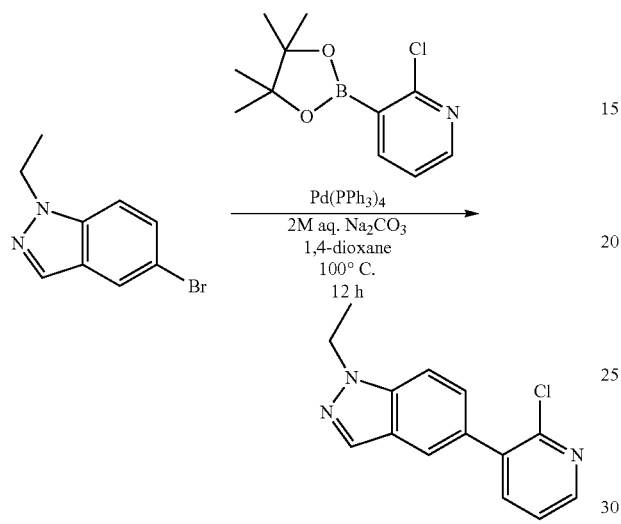

Analogous to the preparation of 5-(2-chloropyridin-3-yl)-1H-indazole, 5-(2-chloropyridin-3-yl)-1-ethyl-1H-indazole was prepared by heating the mixture of 5-bromo-1-ethyl-1H-indazole (0.90 g, 3.98 mmol), 2-chloro-3-pyridine boronic acid pinacol ester (1.1 g, 4.60 mmol), Pd(PPh₃)₄ (300 mg, 0.34 mmol) and 2M aq.Na₂CO₃ (5 mL, 10 mmol) in 1,4-dioxane (40 mL). 5-(2-chloropyridin-3-yl)-1-ethyl-1H-indazole (842 mg, 82%) was isolated as an off-white solid after the workup and flash silica gel purification. ¹H NMR (DMSO-d6): δ 8.41 (dd, 1H, J=1.7 and 4.7 Hz), 8.11 (s, 1H), 7.92 (dd, 1H, J=1.7 and 7.6 Hz), 7.83 (app t, 1H, J=0.6 Hz), 7.73 (dd, 1H, J=0.6 and 8.8 Hz), 7.51 (dd, 1H, J=4.7 and 7.6 Hz), 7.46 (dd, 1H, J=1.7 and 8.8 Hz), 4.46 (qt, 2H, J=7.3 Hz), 1.40 (t, 3H, J=7.3 Hz).LCMS: rt 5.46 min (B), purity 97%, MS (m/e) 258 (MH⁺).

Example 36

6-(2-Chloropyridin-3-yl)quinoline

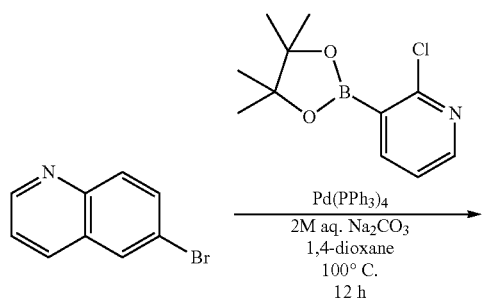

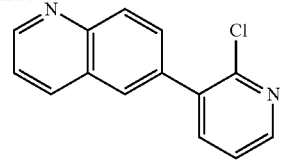

Analogous to the preparation of 5-(2-chloropyridin-3-yl)-1H-indazole, 6-(2-chloropyridin-3-yl)quinoline was prepared by heating the mixture of 6-bromoquinoline (1.0 g, 4.8 mmol), 2-chloro-3-pyridine boronic acid pinacol ester (1.5 g, 6.20 mmol), Pd(PPh3)4 (330 mg, 0.28 mmol) and 2M aq.Na₂CO₃ (7 mL, 14 mmol) in 1,4-dioxane (40 mL). 6-(2-Chloropyridin-3-yl)quinoline was isolated as a white solid (670 mg,) following the extractive work-up with CH₂Cl₂ and purification by flash silica gel purification. ¹H NMR (DMSO-d6): δ 8.95 (dd, 1H, J=1.2 and 4.4 Hz), 8.49 (dd, 1H, J=1.7 and 4.7 Hz), 8.43 (d, 1H, J=8.5 Hz), 8.11-8.09 (app m, 2H), 8.01 (dd, 1H, J=1.7 and 7.6 Hz), 7.86 (dd, 1H, J=1.4 and 8.8 Hz), 7.61-7.55 (m, 2H).LCMS: rt 4.13 min (A), purity 99%, MS (m/e) 241 (MH⁺).

Example 37

6-(2-Chloropyridin-3-yl)isoquinoline

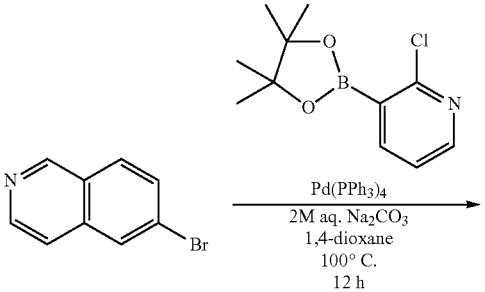

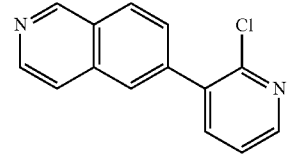

Analogous to the preparation of 5-(2-chloropyridin-3-yl)-1H-indazole, 6-(2-chloropyridin-3-yl)quinoline was prepared by heating the mixture of 6-bromoisoquinoline (1.0 g, 4.8 mmol), 2-chloro-3-pyridine boronic acid pinacol ester (1.5 g, 6.2 mmol), Pd(PPh₃)₄ (330 mg, 0.28 mmol) and 2M aq.Na₂CO₃ (7 mL, 14 mmol) in 1,4-dioxane (40 mL). 6-(2-Chloropyridin-3-yl)quinoline was isolated as a white solid (670 mg, 57%) upon work-up and purification by flash silica gel column purificaiton. ¹H NMR (DMSO-d6): δ 9.37 (s, 1H), 8.55 (dd, 1H, J=1.4 and 5.5 Hz), 8.50-8.48 (m, 1H), 8.22 (d, 1H, J=8.5 Hz), 8.07 (s, 1H), 8.01 (dt, 1H, J=1.2 and 7.6 Hz), 7.88 (d, 1H, J=5.8 Hz), 7.78 (dd, 1H, J=0.4 and 8.5 Hz), 7.58 (dd, 1H, J=4.7 and 7.3 Hz).LCMS: rt 4.01 min (A), purity 97%, MS (m/e) 241 (MH+).

Example 38

7-(2-Chloropyridin-3-yl)isoquinoline

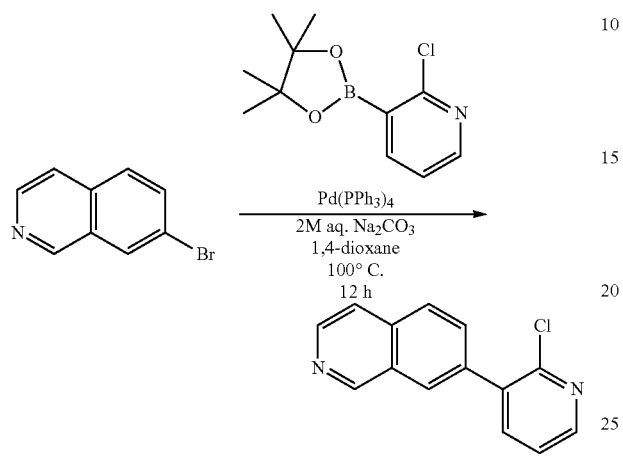

Analogous to the preparation of 5-(2-chloropyridin-3-yl)-1H-indazole, 7-(2-chloropyridin-3-yl)isoquinoline was prepared by heating the mixture of 7-bromoisoquinoline (1.0 g, 4.8 mmol), 2-chloro-3-pyridine boronic acid pinacol ester (1.5 g, 6.20 mmol), Pd(PPh$_3$)$_4$ (330 mg, 0.28 mmol) and 2M aq.Na$_2$CO$_3$ (7 mL, 14 mmol) in 1,4-dioxane (40 mL). 6-(2-Chloropyridin-3-yl)quinoline was isolated as a white solid (820 mg, 70%) after the CH$_2$Cl$_2$ work-up and silica gel flash column purification. $^1$H NMR (DMSO-d6): δ 9.37 (s, 1H), 8.55 (d, 1H, J=5.8 Hz), 8.49 (dd, 1H, J=1.7 and 4.7 Hz), 8.23 (s, 1H), 8.07 (d, 1H, J=7.5 Hz), 8.02 (dd, 1H, J=1.7 and 7.6 Hz), 7.91-7.88 (m, 2H), 7.58 (dd, 1H, J=4.7 and 7.6 Hz).LCMS: rt 3.96 min (A), purity 95%, MS (m/e) 241 (MH+).

Example 39

6-(2-Chloropyridin-3-yl)-[1,2,4]triazolo[1,5-a]pyridine

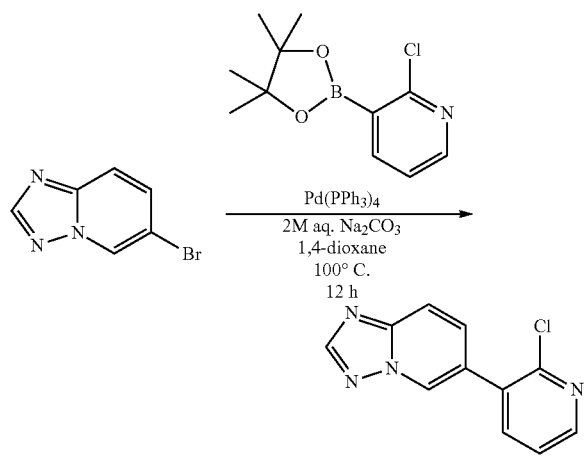

6-(2-Chloropyridin-3-yl)-[1,2,4]triazolo[1,5-a]pyridine was synthesized in the similar to 6-(2-chloropyridin-3-yl)benzo[d]thiazole from 6-bromo[1,2,4]triazolo[1,5-a]pyridine (1.0 g, 5.0 mmol), 2-chloro-3-pyridine boronic acid pinacol ester (1.45 g, 6.0 mmol), Pd(PPh$_3$)$_4$ (300 mg, 0.26 mmol) and 2M aq.Na$_2$CO$_3$ (8 mL, 16 mmol) in 1,4-dioxane (50 mL). Upon workup, the crude residue was dissolved in CH$_2$Cl$_2$ (10 mL) and stirred with 50% EtOAc/hexanes (40 mL). The resulting off-white precipitate was filtered and dried to provide 6-(2-chloropyridin-3-yl)-[1,2,4]triazolo[1,5-a]pyridine (0.68 g, 58%). $^1$H NMR (DMSO-d6): δ 9.18 (dd, 1H, J=0.86 and 1.7 Hz), 8.57 (s, 1H), 8.50 (dd, 1H, J=1.7 and 4.9 Hz), 8.05 (dd, 1H, J=2.0 and 7.8 Hz), 7.94 (dd, 1H, J=0.9 and 9.1 Hz), 7.80 (dd, 1H, J=1.7 and 9.1 Hz), 7.59 (dd, 1H, J=4.7 and 7.6 Hz).LCMS: rt 5.00 min (A), purity 97%, MS (m/e) 231.

Example 40

3-Chloro-2-(4-fluoro-3-methylphenyl)pyridine

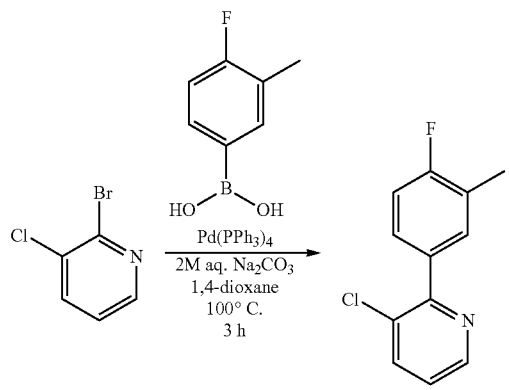

3-Chloro-2-(4-fluoro-3-methylphenyl)pyridine was synthesized analogous to the reaction conditions used in the preparation of 5-(2-chloropyridin-3-yl)-1H-indazole by heating the mixture of 4-fluoro-3-methylphenyl boronic acid (1.0 g, 6.5 mmol), 2-bromo-3-chloropyridine (1.4 g, 7.1 mmol), Pd(PPh$_3$)$_4$ (0.45 g, 0.38 mmol) and 2M aq. Na$_2$CO$_3$ (8 mL, 16 mmol) in 1,4-dioxane (125 mL) under argon atmosphere for 3 h. Upon work-up of the reaction mixture, as discussed in the preparation of 5-(2-chloropyridin-3-yl)-1H-indazole, the crude concentrate was purified by flash silica gel column chromatography [Combiflash® companion System® with RediSep® silica gel column 40 g, 10-30% EtOAC/hexanes eluting solvent gradient upon liquid loading on to column] to obtain 3-chloro-2-(4-fluoro-3-methylphenyl)pyridine as a white solid (790 mg, 54%). $^1$H NMR (DMSO-d6): δ 8.60 (dd, 1H, J=1.4 and 4.7 Hz), Hz), 8.02 (dd, 1H, J=1.4 and 8.2 Hz), 7.57 (app d, 1H, J=7.3 Hz), 7.54-7.49 (m, 1H), 7.42 (dd, 1H, J=4.7 and 8.2 Hz), 7.23 (t, 1H, J=8.8 Hz), 2.28 (s, 3H).LCMS: 97%, MS (m/e) 222.

Example 41

3-Chloro-2-(3-methylphenyl)pyridine

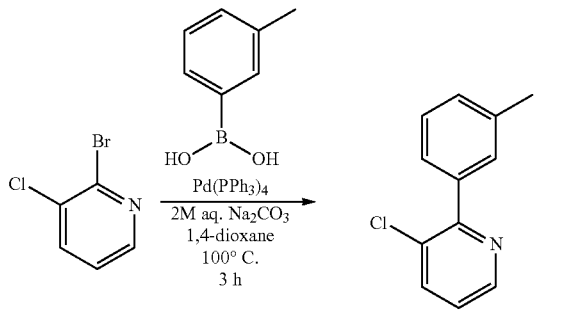

Chemical Formula: C₁₂H₁₀ClN
Molecular Weight: 203.67

3-Chloro-2-(3-methylphenyl)pyridine was synthesized analogous to the reaction conditions used in the preparation of 5-(2-chloropyridin-3-yl)-1H-indazole by heating the mixture of 3-methylphenyl boronic acid (1.76 g, 12.9 mmol), 2-bromo-3-chloropyridine (2.7 g, 14.2 mmol), Pd(PPh₃)₄ (0.9 g, 0.77 mmol) and 2M aq. Na₂CO₃ (16 mL, 32 mmol) in 1,4-dioxane (125 mL) under argon atmosphere for 3 h. Upon work-up of the reaction mixture, as discussed in the preparation of 5-(2-chloropyridin-3-yl)-1H-indazole, the crude concentrate was purified by flash silica gel column chromatography [Combiflash® companion System® with RediSep® silica gel column 40 g, 10-30% EtOAC/hexanes eluting solvent gradient upon liquid loading on to column] to obtain 3-chloro-2-(3-methylphenyl)pyridine (1.62 g, 61%) as a clear liquid. ¹H NMR (DMSO-d6): δ 8.60 (dd, 1H, J=1.4 and 4.7 Hz), 8.00 (dd, 1H, J=1.4 and 8.2 Hz), 7.44-7.37 (m, 3H), 7.25 (app d, 1H, J=8.2 Hz), 2.36 (s, 3H).LCMS: 97%, MS (m/e) 204.

Example 42

1-methyl-6-(2-m-tolylpyridin-3-yl)-1H-benzo[d]imidazole (Compound 186)

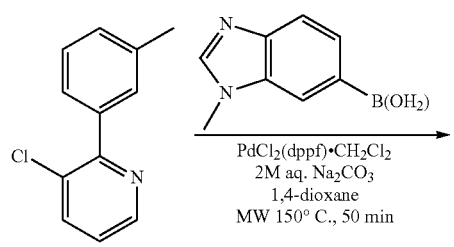

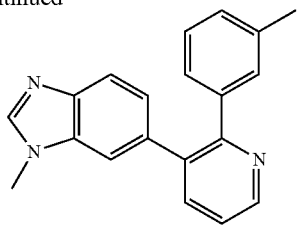

1,4-Dioxane (3 mL) was transferred to a microwave vial (Smith Creator®) containing 3-chloro-2-(3-methylphenyl)pyridine (100 mg, 0.49 mmol), 1-methyl-1H-benzimidazole boronic acid (95 mg, 0.54 mmol), PdCl₂(dppf)₂.CH₂Cl₂ (35 mg, 0.042 mmol) and 2M aq. Na₂CO₃ (0.6 mL, 1.2 mmol). Slow stream of argon was bubbled through the heterogeneous red solution while stirring the reaction mixture. The vial was capped and heated in a microwave at 150° C. for 50 min. Progress of the reaction was analyzed by LC/MS. The reaction mixture was passed through a pad of Celite® and washed the pad with EtOAc (10 mL). The filtrate was concentrated and purified by preparative HPLC. Subsequently, product fractions were concentrated, diluted with water, neutralized with aq. NaHCO₃ and extracted with EtOAc. Organic layer was dried over anhydrous Na₂SO₄, filtered and concentrated. The concentrate was dissolved in acetonitrile/water (1:1, 15 mL) and allowed to freeze by external cooling in dry ice/acetone. Lyophilization of the frozen residue resulted in an off-white solid of 1-methyl-6-(2-m-tolylpyridin-3-yl)-1H-benzo[d]imidazole. ¹H NMR (DMSO-d6): δ 8.64 (dd, 1H, J=1.7 and 4.7 Hz), 8.16 (s, 1H), 7.87 (dd, 1H, J=1.7 and 7.6 Hz), 7.51 (d, 1H, J=1.5 Hz), 7.47-7.43 (m, 2H), 7.27 (s, 1H), 7.03-6.97 (m, 2H), 6.90 (app d, 1H, J=6.7 Hz), 6.85 (dd, 1H, J=8.5 Hz), 3.76 (s, 3H), 2.19 (s, 3H). ¹⁹F NMR (DMSO-d6): δ −114.29 (s).LCMS: rt 3.16 min (A), purity 97%, MS (m/e) 300 (MH

Example 43

The following analogs are prepared by the reaction of respective 3-chloro-2-arylpyridine and benzimidazole boronic acids by identical reaction conditions and followed by compound purification procedure as discussed with the previous reaction.

6-(2-(4-Fluoro-3-methylphenyl)pyridin-3-yl)-1-methyl-1H-benzo[d]imidazole (Compound 187). ¹H NMR (DMSO-d6): δ 8.63 (dd, 1H, J=1.7 and 4.7 Hz), 8.17 (s, 1H), 7.86 (dd, 1H, J=1.7 and 7.6 Hz), 7.53 (s, 1H), 7.48 (d, 1H, J=8.2 Hz), 7.46 (dd, 1H, J=4.7 and 7.9 Hz), 7.38 (d, 1H, J=7.9 Hz), 6.92-6.83 (m, 3H), 3.77 (s, 3H), 2.12 (s, 3H). ¹⁹F NMR (DMSO-d6): δ −118.91 (s).LCMS: rt 3.51 min (A), purity 97%, MS (m/e) 318 (MH⁺).

1-Methyl-5-(2-m-tolylpyridin-3-yl)-1H-benzo[d]imidazole (Compound 188). ¹H NMR (DMSO-d6): δ 8.62 (dd, 1H, J=1.4 and 4.7 Hz), 8.15 (s, 1H), 7.82 (dd, 1H, J=1.4 and 7.6 Hz), 7.48-7.40 (m, 3H), 7.28 (s, 1H), 7.02-6.98 (m, 3H), 6.88 (d, 1H, J=7.2 Hz), 3.79 (s, 3H), 2.19 (s, 3H). ¹⁹F NMR (DMSO-d6): δ −118.91 (s).LCMS: rt 3.26 min (A), purity 97%, MS (m/e) 300 (MH⁺).

5-(2-(4-Fluoro-3-methylphenyl)pyridin-3-yl)-1-methyl-1H-benzo[d]imidazole (Compound 189). ¹H NMR (DMSO-d6): δ 8.62 (dd, 1H, J=1.7 and 4.7 Hz), 8.16 (s, 1H), 7.82 (dd, 1H, J=1.7 and 7.6 Hz), 7.49-7.37 (m, 4H), 7.00 (dd, 1H, J=1.4 and 8.5 Hz), 6.91-6.83 (m, 2H), 3.80 (s, 3H), 2.13 (s, 3H). $^{19}$F NMR (DMSO-d6): δ –119.03 (s).LCMS: rt 3.68 min (A), MS (m/e) 318 (MH$^+$).

Example 44

General Synthetic Method B

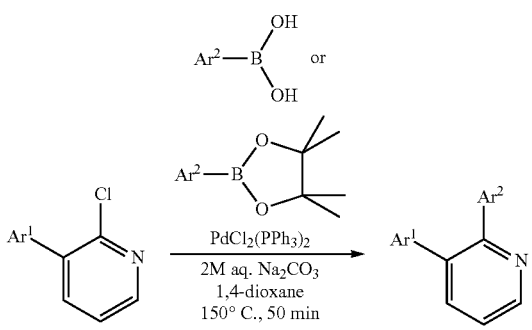

1,4-Dioxane (3 mL) was transferred to a microwave vial (Smith Creator®) containing 2-chloro-3-arylpyridine (1 eq), respective arylboronic acid/or pinacol ester (1.2-1.3 eq). PdCl$_2$(PPh$_3$)$_2$ (0.1 eq), and 2M aq. Na$_2$CO$_3$ (2.2 eq). Slow stream of argon was bubbled through the heterogeneous solution while stirring the reaction mixture. The vial was capped and heated in a microwave at 150° C. for 50 min. Progress of the reaction was analyzed by LC/MS. At the end of the microwave heating, the reaction mixture was passed through a pad of Celite® and washed the pad with EtOAc (10 mL). The filtrate was concentrated and purified by preparative HPLC. Subsequently, product fractions were concentrated, diluted with water, neutralized with aq. NaHCO$_3$ and extracted with EtOAc. Organic layer was dried over anhydrous Na$_2$SO$_4$, polish filtered and concentrated. The concentrate was dissolved in acetonitrile/water (1:1, 15 mL) and allowed to freeze by external cooling in dry ice/acetone. Lyophilization of the frozen residue provided respective analogs for further characterization.

The following compounds were prepared as described in Example 44 by use of the appropriate arylboronic acid/or pinacol ester:

5-(5-Ethoxy-2-(4-fluoro-3-methylphenyl)pyridin-3-yl)-1H-indazole (Compound 1). $^1$H NMR (CD$_3$OD, 300 MHz): 8.43 (s, 1H), 8.06 (s, 1H), 8.00 (m, 1H), 7.77 (bs, 1H), 7.47 (m, 1H), 7.35 (m, 1H), 7.15-7.05 (m, 2H), 6.99 (m, 1H), 4.34 (q, 2H), 2.17 (s, 3H), 1.51 (t, 3H); MS (ES) 348.32 (M+H);

5-(5-Ethoxy-2-(2-fluorophenyl)pyridin-3-yl)-1H-indazole (Compound 2). $^1$H NMR (CD$_3$OD, 300 MHz): 8.12 (s, 1H), 8.05 (bs, 1H), 7.87 (s, 1H), 7.67-7.44 (m, 7H), 6.99 (m, 1H), 4.17 (q, 2H), 1.43 (t, 3H); MS (ES) 334.32 (M+H);

5-(5-Ethoxy-2-m-tolylpyridin-3-yl)-1H-indazole (Compound 3). $^1$H NMR (CD$_3$OD, 300 MHz): 8.41 (s, 1H), 8.03 (s, 1H), 8.01 (m, 1H), 7.73 (s, 1H), 7.45 (m, 1H), 7.32-7.08 (m, 4H), 7.02 (m, 1H), 4.38 (q, 2H), 2.13 (s, 3H), 1.48 (t, 3H); MS (ES) 330.33 (M+H);

5-(5-Ethoxy-2-(4-fluoro-2-isopropoxyphenyl)pyridin-3-yl)-1H-indazole (Compound 4). $^1$H NMR (CD$_3$OD, 300 MHz): 8.13 (s, 1H), 8.08 (s, 1H), 8.01 (m, 1H), 7.77 (bs, 1H), 7.49 (m, 1H), 7.36 (m, 1H), 7.11-7.02 (m, 3H), 4.34 (q, 2H), 4.23 (t, 1H), 1.48 (t, 3H), 1.41 (d, 6H); MS (ES) 392.36 (M+H);

5-(5-Ethoxy-2-(3-fluorophenyl)pyridin-3-yl)-1H-indazole (Compound 5). $^1$H NMR (CD$_3$OD, 300 MHz): 8.29 (m, 1H), 8.01 (s, 1H), 7.68 (s, 1H), 7.46 (m, 2H), 7.17 (m, 2H), 6.99-6.94 (m, 3H), 4.22 (q, 2H), 1.46 (t, 3H); MS (ES) 334.34 (M+H);

5-(5-Ethoxy-2-(4-fluorophenyl)pyridin-3-yl)-1H-indazole (Compound 6). $^1$H NMR (CD$_3$OD, 300 MHz): 8.40 (m, 1H), 8.06 (s, 1H), 8.01 (m, 1H), 7.82 (bs, 1H), 7.44 (m, 1H), 7.26 (m, 2H), 7.12 (m, 2H), 7.03 (m, 1H), 4.34 (q, 2H), 1.51 (t, 3H); MS (ES) 334.33 (M+H);

5-(5-Ethoxy-2-(3,4-difluorophenyl)pyridin-3-yl)-1H-indazole (Compound 7). $^1$H NMR (CD$_3$OD, 300 MHz): 8.53 (s, 1H), 8.02 (s, 1H), 7.96 (m, 1H), 7.77 (bs, 1H), 7.43 (m, 1H), 7.38 (m, 1H), 7.12 (m, 2H), 7.02 (m, 1H), 4.36 (q, 2H), 1.49 (t, 3H); MS (ES) 352.31 (M+H);

5-(2-(4-Fluoro-3-methylphenyl)-5-methoxypyridin-3-yl)-1H-indazole (Compound 8). $^1$H NMR (CD$_3$OD, 300 MHz): 8.28 (bs, 1H), 8.02 (s, 1H), 7.64-7.39 (m, 3H), 7.18 (m, 1H), 7.09 (m, 1H), 6.96 (m, 1H), 6.80 (m, 1H), 3.95 (s, 3H), 2.11 (s, 3H); MS (ES) 334.46 (M+H);

5-(5-Chloro-2-(4-fluoro-3-methylphenyl)pyridin-3-yl)-1H-indazole (Compound 9). $^1$H NMR (CD$_3$OD, 300 MHz): 8.59 (bs, 1H), 8.02 (m, 1H), 7.94 (m, 1H), 7.70 (s, 1H), 7.59 (m, 1H), 7.25 (m, 1H), 7.12 (m, 1H), 7.02 (m, 1H), 6.84 (m, 1H), 2.12 (s, 3H); MS (ES) 338.29 (M+H);

5-(5-Fluoro-2-(4-fluoro-3-methylphenyl)pyridin-3-yl)-1H-indazole (Compound 10). $^1$H NMR (CD$_3$OD, 300 MHz): 8.50 (bs, 1H), 8.03 (s, 1H), 7.76 (m, 1H), 7.70 (m, 1H), 7.41 (m, 1H), 7.20 (m, 1H), 7.12 (m, 1H), 7.01 (m, 1H), 6.84 (m, 1H), 2.12 (s, 3H); MS (ES) 322.31 (M+H);

5-(2-(4-Fluoro-3-methylphenyl)-5-methylpyridin-3-yl)-1H-indazole (Compound 11). $^1$H NMR (CD$_3$OD, 300 MHz): 8.67 (bs, 1H), 8.53 (s, 1H), 8.07 (s, 1H), 7.79 (m, 1H), 7.51 (m, 1H), 7.36 (m, 1H), 7.17 (m, 2H), 7.02 (m, 1H), 2.65 (s, 3H), 2.20 (s, 3H); MS (ES) 318.36 (M+H);

5-(2-(4-Fluoro-3-methylphenyl)-6-methylpyridin-3-yl)-1H-indazole (Compound 12). $^1$H NMR (CD$_3$OD, 300 MHz): 8.53 (m, 1H), 8.06 (s, 1H), 7.90 (m, 1H), 7.75 (bs, 1H), 7.49 (m, 1H), 7.41 (m, 1H), 7.19-7.02 (m, 3H), 2.86 (s, 3H), 2.22 (s, 3H); MS (ES) 318.30 (M+H);

5-(2-(4-Cyclopropylphenyl)-6-methylpyridin-3-yl)-1H-indazole (Compound 13). $^1$H NMR (CD$_3$OD, 300 MHz): 8.49 (m, 1H), 8.04 (s, 1H), 7.89 (m, 1H), 7.74 (s, 1H), 7.47 (m, 1H), 7.28 (m, 2H), 7.10 (m, 3H), 2.86 (s, 3H), 1.92 (m, 1H), 1.03 (m, 2H), 0.69 (m, 2H); MS (ES) 326.28 (M+H);

5-(2-(3-Isopropylphenyl)-6-methylpyridin-3-yl)-1H-indazole (Compound 14). $^1$H NMR (CD$_3$OD, 300 MHz): 8.55 (m, 1H), 8.03 (s, 1H), 7.92 (m, 1H), 7.72 (s, 1H), 7.47-7.35 (m, 4H), 7.13 (m, 2H), 2.87 (s, 3H), 2.75 (t, 1H), 0.98 (3H), 0.96 (3H); MS (ES) 328.31 (M+H);

6-(3-Cyclopropylphenyl)-5-(1H-indazol-5-yl)pyridin-3-amine (Compound 15). $^1$H NMR (CD$_3$OD, 300 MHz): 8.01 (m, 2H), 7.60 (s, 1H), 7.36 (m, 1H), 7.25 (m, 1H), 7.06-6.93 (m, 4H), 6.76 (s, 1H), 1.69 (m, 1H), 0.73 (m, 2H), 0.27 (m, 2H); MS (ES) 327.27 (M+H);

5-(1H-Indazol-5-yl)-6-(3-isopropylphenyl)pyridin-3-amine (Compound 16). $^1$H NMR (CD$_3$OD, 300 MHz): 8.03 (m, 1H), 8.00 (s, 1H), 7.80 (m, 1H), 7.71 (m, 1H), 7.47 (m, 1H), 7.32-7.10 (m, 4H), 7.00 (s, 1H), 2.65 (t, 1H), 0.94 (d, 6H); MS (ES) 329.29 (M+H);

6-(4-Fluoro-3-methylphenyl)-5-(1H-indazol-5-yl)pyridin-3-amine (Compound 17). $^1$H NMR (CD$_3$OD, 300 MHz): 8.82 (m, 1H), 8.41 (s, 1H), 8.20 (m, 1H), 8.01 (m, 2H), 7.62 (m, 1H), 7.32 (m, 1H), 7.05-6.82 (m, 2H), 2.12 (s, 3H); MS (ES) 319.12 (M+H);

5-(Benzo[d]thiazol-6-yl)-6-(4-fluoro-3-methylphenyl)pyridin-3-amine (Compound 18). $^1$H NMR (CD$_3$OD, 300

MHz): 9.21 (s, 1H), 8.05 (s, 1H), 7.92 (m, 2H), 7.62 (m, 1H), 7.29 (m, 1H), 7.26-7.17 (m, 1H), 6.88 (m, 1H), 6.77 (m, 1H), 2.12 (s, 3H); MS (ES) 336.25 (M+H);

5-(Benzo[d]thiazol-6-yl)-6-(3-cyclopropylphenyl)pyridin-3-amine (Compound 19). $^1$H NMR (CD$_3$OD, 300 MHz): 9.21 (s, 1H), 8.05 (m, 1H), 7.91 (m, 1H), 7.84 (s, 1H), 7.29 (m, 1H), 7.25 (m, 1H), 7.08-6.93 (m, 3H), 6.75 (s, 1H), 1.70 (m, 1H), 0.73 (m, 2H), 0.27 (m, 2H); MS (ES) 344.28 (M+H);

5-(Benzo[d]thiazol-6-yl)-6-m-tolylpyridin-3-amine (Compound 20). $^1$H NMR (CD$_3$OD, 300 MHz): 9.21 (s, 1H), 8.06 (s, 1H), 7.91 (s, 1H), 8.84 (m, 1H), 7.29-7.01 (m, 5H), 6.90 (m, 1H), 2.19 (s, 3H); MS (ES) 318.28 (M+H);

6-(4-Fluoro-3-methylphenyl)-5-(1H-indazol-5-yl)pyridin-2-amine (Compound 21). $^1$H NMR (CD$_3$OD, 300 MHz): 8.10 (m, 1H), 8.01 (s, 1H), 7.66 (s, 1H), 7.42 (m, 1H), 7.31 (m, 1H), 7.13-7.00 (m, 3H), 6.96 (m, 1H), 2.19 (s, 3H); MS (ES) 319.25 (M+H);

6-(3-Cyclopropylphenyl)-5-(1H-indazol-5-yl)pyridin-2-amine (Compound 22). $^1$H NMR (CD$_3$OD, 300 MHz): 8.09 (m, 1H), 8.00 (s, 1H), 7.63 (s, 1H), 7.44 (m, 1H), 7.27-7.11 (m, 5H), 6.95 (s, 1H), 1.80 (m, 1H), 0.84 (m, 2H), 0.37 (m, 2H); MS (ES) 327.28 (M+H);

5-(1H-Indazol-5-yl)-6-m-tolylpyridin-2-amine (Compound 23). $^1$H NMR (CD$_3$OD, 300 MHz): 8.10 (m, 1H), 8.07 (s, 1H), 7.65 (s, 1H), 7.42 (m, 1H), 7.24 (m, 3H), 7.08 (m, 3H), 2.27 (s, 3H); MS (ES) 301.26 (M+H);

N-(6-(4-Fluoro-3-methylphenyl)-5-(1H-indazol-5-yl)pyridin-3-yl)acetamide (Compound 24). $^1$H NMR (CD$_3$OD, 300 MHz): 9.21 (s, 1H), 8.38 (m, 1H), 8.07 (s, 1H), 7.76 (s, 1H), 7.50 (m, 1H), 7.32 (m, 1H), 7.11 (m, 2H), 6.98 (m, 1H), 2.25 (s, 3H), 2.18 (s, 3H); MS (ES) 361.21 (M+H);

N-(6-(3-Cyclopropylphenyl)-5-(1H-indazol-5-yl)pyridin-3-yl)acetamide (Compound 25). $^1$H NMR (CD$_3$OD, 300 MHz): 9.24 (s, 1H), 8.38 (m, 1H), 8.06 (s, 1H), 7.74 (m, 1H), 7.49 (m, 1H), 7.26-7.11 (m, 3H), 6.95 (s, 1H), 2.25 (s, 3H), 1.82 (m, 1H), 0.85 (m, 2H), 0.37 (m, 2H); MS (ES) 369.27 (M+H);

N-(5-(1H-Indazol-5-yl)-6-m-tolylpyridin-3-yl)acetamide (Compound 26). $^1$H NMR (CD$_3$OD, 300 MHz): 9.25 (s, 1H), 8.40 (m, 1H), 8.05 (s, 1H), 7.74 (s, 1H), 7.48 (m, 1H), 7.24-7.06 (m, 4H), 2.26 (s, 3H), 2.25 (s, 3H); MS (ES) 343.27 (M+H);

5-(Benzo[d]thiazol-6-yl)-6-(4-fluoro-3-methylphenyl)pyridin-2-amine (Compound 27). $^1$H NMR (CD$_3$OD, 300 MHz): 9.26 (s, 1H), 8.11 (m, 1H), 8.08 (s, 1H), 7.95 (m, 1H), 7.35 (m, 2H), 7.11 (m, 2H), 7.01 (m, 1H), 2.20 (s, 3H); MS (ES) 336.26 (M+H);

5-(Benzo[d]thiazol-6-yl)-6-(3-cyclopropylphenyl)pyridin-2-amine (Compound 28). $^1$H NMR (CD$_3$OD, 300 MHz): 9.26 (s, 1H), 8.12 (m, 1H), 8.09 (m, 1H), 7.92 (s, 1H), 7.30-7.10 (m, 4H), 6.97 (s, 1H), 1.81 (m, 1H), 0.85 (m, 2H), 0.38 (m, 2H); MS (ES) 344.33 (M+H);

5-(Benzo[d]thiazol-6-yl)-6-m-tolylpyridin-2-amine (Compound 29). $^1$H NMR (CD$_3$OD, 300 MHz): 9.25 (s, 1H), 8.12 (m, 1H), 7.95 (m, 2H), 7.31-7.10 (m, 3H), 7.08 (m, 2H), 2.28 (s, 3H); MS (ES) 318.31 (M+H);

N-(6-(4-Fluoro-3-methylphenyl)-5-(1H-indazol-5-yl)pyridin-3-yl)methanesulfonamide (Compound 30). $^1$H NMR (CD$_3$OD, 300 MHz): 8.57 (s, 1H), 8.06 (s, 1H), 8.02 (m, 1H), 7.74 (m, 1H), 7.48 (m, 2H), 7.29 (m, 1H), 7.11 (m, 1H), 6.93 (m, 1H), 3.19 (s, 3H), 2.16 (s, 3H); MS (ES) 397.21 (M+H);

N-(6-(3-Cyclopropylphenyl)-5-(1H-indazol-5-yl)pyridin-3-yl)methanesulfonamide (Compound 31). $^1$H NMR (CD$_3$OD, 300 MHz): 8.58 (s, 1H), 8.08 (m, 2H), 7.72 (s, 1H), 7.47 (m, 1H), 7.21-7.10 (m, 4H), 6.92 (m, 1H), 3.20 (s, 3H), 1.77 (m, 1H), 0.81 (m, 2H), 0.34 (m, 2H); MS (ES) 405.26 (M+H);

N-(5-(1H-Indazol-5-yl)-6-m-tolylpyridin-3-yl)methanesulfonamide (Compound 32). $^1$H NMR (CD$_3$OD, 300 MHz): 8.61 (s, 1H), 8.15 (m, 1H), 8.05 (s, 1H), 7.74 (s, 1H), 7.48 (m, 1H), 7.44 (m, 1H), 7.23-7.05 (m, 4H), 3.23 (s, 3H), 2.26 (s, 3H); MS (ES) 379.25 (M+H).

6-(2-m-Tolylpyridin-3-yl)isoquinoline (Compound 33). $^1$H NMR (DMSO-d6): δ 9.77 (s, 1H), 9.03-8.73 (m, 1H), 8.65 (d, J=6.4 Hz, 1H), 8.34 (dd, J=18.1, 8.1 Hz, 3H), 8.22-8.03 (m, 1H), 7.67 (ddd, J=7.8, 5.0, 1.2 Hz, 1H), 7.58 (dd, J=8.6, 1.4 Hz, 1H), 7.27 (s, 1H), 7.07 (dt, J=15.0, 7.5 Hz, 2H), 6.95 (d, J=7.5 Hz, 1H), 2.17 (s, 3H).MS (m/e): 297 (MH$^+$).

6-(2-(4-Fluoro-3-methylphenyl)pyridin-3-yl)isoquinoline (Compound 34). $^1$H NMR (DMSO-d6): δ 9.79 (s, 1H), 8.83-8.72 (m, 1H), 8.66 (d, J=6.4 Hz, 1H), 8.45-8.22 (m, 3H), 8.09 (dd, J=7.8, 1.5 Hz, 1H), 7.71-7.51 (m, 2H), 7.38 (d, J=7.4 Hz, 1H), 6.97-6.88 (m, 2H), 2.09 (s, 3H). MS (m/e): 315 (MH$^+$).

6-(2-(3-Fluorophenyl)pyridin-3-yl)imidazo[1,2-a]pyridine (Compound 59). $^1$H NMR (DMSO-d6): δ 9.05-8.98 (m, 1H), 8.79 (dd, J=4.8, 1.6 Hz, 1H), 8.37-8.30 (m, 1H), 8.20 (d, J=2.1 Hz, 1H), 8.02 (dd, J=7.8, 1.7 Hz, 1H), 7.85 (d, J=9.3 Hz, 1H), 7.67-7.47 (m, 2H), 7.42-7.23 (m, 2H), 7.23-7.07 (m, 2H). MS (m/e): 290 (MH$^+$).

N-(3-(3-(Imidazo[1,2-a]pyridin-6-yl)pyridin-2-yl)phenyl)methylsulfonamide (Compound 58). $^1$H NMR (DMSO-d6): δ 9.63 (s, 1H), 9.02 (s, 1H), 8.79 (dd, J=4.8, 1.2 Hz, 1H), 8.33 (d, J=2.0 Hz, 1H), 8.19 (d, J=2.0 Hz, 1H), 8.01 (dd, J=7.8, 1.3 Hz, 1H), 7.85 (d, J=9.4 Hz, 1H), 7.60 (dd, J=7.8, 4.8 Hz, 1H), 7.46 (dd, J=9.3, 1.2 Hz, 1H), 7.33 (d, J=5.9 Hz, 2H), 7.12 (dd, J=10.0, 6.8 Hz, 2H), 2.71 (s, 3H).MS (m/e): 366 (MH$^+$).

3-(3-(Imidazo[1,2-a]pyridin-6-yl)pyridin-2-yl)benzenamine (Compound 56). $^1$H NMR (DMSO-d6): δ 9.04 (d, J=3.5 Hz, 1H), 8.80 (dd, J=4.8, 0.7 Hz, 1H), 8.34 (d, J=2.1 Hz, 1H), 8.24-8.16 (m, 1H), 8.03 (dd, J=7.8, 0.9 Hz, 1H), 7.85 (d, J=9.3 Hz, 1H), 7.62 (dd, J=7.5, 5.1 Hz, 1H), 7.47 (dd, J=9.3, 0.9 Hz, 1H), 7.39-7.09 (m, 4H). MS (m/e): 287 (MH$^+$).

6-(2-(3,5-Difluorophenyl)pyridin-3-yl)imidazo[1,2-a]pyridine (Compound 55). $^1$H NMR (DMSO-d6): δ 9.04-8.96 (m, 1H), 8.78 (dd, J=4.8, 1.6 Hz, 1H), 8.35 (d, J=2.0 Hz, 1H), 8.21 (d, J=2.1 Hz, 1H), 8.03 (dd, J=7.8, 1.6 Hz, 1H), 7.88 (d, J=9.3 Hz, 1H), 7.60 (dd, J=11.0, 8.6, 3.2 Hz, 2H), 7.27-6.96 (m, 3H). MS (m/e): 308 (MH$^+$).

6-(2-(4-Trifluoromethyl)phenyl)pyridin-3-yl)imidazo[1,2-a]pyridine (Compound 57). $^1$H NMR (DMSO-d6): δ 9.04 (s, 1H), 8.82 (dd, J=4.7, 1.1 Hz, 1H), 8.34 (s, 1H), 8.20 (d, J=2.0 Hz, 1H), 8.04 (dd, J=7.8, 1.1 Hz, 1H), 7.85 (d, J=9.3 Hz, 1H), 7.72-7.54 (m, 5H), 7.50 (d, J=9.3 Hz, 1H). MS (m/e): 340 (MH$^+$).

6-(2-(4-Methoxyphenyl)pyridin-3-yl)imidazo[1,2-a]pyridine (Compound 54). $^1$H NMR (DMSO-d6): δ 9.03 (s, 1H), 8.79 (dd, J=4.9, 1.5 Hz, 1H), 8.35 (d, J=1.5 Hz, 1H), 8.20 (d, J=2.0 Hz, 1H), 8.08 (dd, J=7.8, 1.5 Hz, 1H), 7.85 (d, J=9.3 Hz, 1H), 7.64 (dd, J=7.8, 5.0 Hz, 1H), 7.48 (dd, J=9.3, 1.5 Hz, 1H), 7.40-7.30 (m, 2H), 6.86 (d, J=8.8 Hz, 2H), 3.72 (s, 3H). MS (m/e): 302 (MH$^+$).

6-(2-(3-Methoxyphenyl)pyridin-3-yl)imidazo[1,2-a]pyridine (Compound 52). $^1$H NMR (DMSO-d6): δ 8.98 (s, 1H), 8.78 (d, J=4.8 Hz, 1H), 8.30 (s, 1H), 8.17 (d, J=1.0 Hz, 1H), 8.05 (d, J=7.2 Hz, 1H), 7.81 (d, J=9.3 Hz, 1H), 7.63 (dd, J=7.8, 4.9 Hz, 1H), 7.50 (d, J=9.4 Hz, 1H), 7.16 (t, J=7.9 Hz, 1H), 7.02 (s, 1H), 6.94-6.77 (m, 3H), 3.64 (s, 3H). MS (m/e): 302 (MH$^+$).

3-(3-(Imidazo[1,2-a]pyridin-6-yl)pyridin-2-yl)benzonitrile (Compound 51). $^1$H NMR (DMSO-d6): δ 9.01 (s, 1H), 8.81 (dd, J=4.8, 1.6 Hz, 1H), 8.33 (d, J=2.0 Hz, 1H), 8.20 (d, J=2.1 Hz, 1H), 8.03 (dd, J=7.8, 1.6 Hz, 1H), 7.91 (d, J=1.6 Hz, 1H), 7.88-7.74 (m, 2H), 7.66-7.60 (m, 2H), 7.56-7.37 (m, 2H). MS (m/e): 297

6-(2-(4-Fluorophenyl)pyridin-3-yl)imidazo[1,2-a]pyridine (Compound 53). $^1$H NMR (DMSO-d6): δ 9.01 (s, 1H), 8.78 (dd, J=4.8, 1.5 Hz, 1H), 8.37-8.30 (m, 1H), 8.20 (d, J=1.2 Hz, 1H), 8.02 (d, J=7.7 Hz, 1H), 7.84 (d, J=9.4 Hz, 1H), 7.60 (dd, J=7.8, 4.9 Hz, 1H), 7.54-7.38 (m, 3H), 7.11 (t, J=8.7 Hz, 2H). MS (m/e): 290 (MH$^+$).

5-(2-(2-Fluorophenyl)pyridin-3-yl)-1H-indazole (Compound 61). $^1$H NMR (DMSO-d6): δ 13.05 (s, 1H), 8.66 (dd, 1H, J=1.4 and 4.7 Hz), 7.98 (s, 1H), 7.90 (dd, 1H, J=1.4 and 7.6 Hz), 7.56 (app s, 1H), 7.51 (dd, 1H, J=4.7 and 7.9 Hz), 7.44-7.32 (m, 2H), 7.31-7.27 (m, 1H), 7.16 (dt, 1H, J=0.8 and 7.6 Hz), 7.01 (dd, 1H, J=1.4 and 8.5 Hz), 6.96 (app t, 1H, J=8.5 Hz). $^{19}$F NMR (DMSO-d6): δ −118.91. LCMS: rt 4.65 min (A), purity 97%, MS (m/e) 290 (MH$^+$).

5-(2-(3,4-Difluorophenyl)pyridin-3-yl)-1H-indazole (Compound 62). LCMS: rt 5.20 min (A), purity 98%, MS (m/e) 308 (MH$^+$).

5-(2-(4-Fluoro-3-methylphenyl)pyridin-3-yl)-1H-indazole (Compound 63). $^1$H NMR (DMSO-d6): δ 13.05 (s, 1H), 8.62 (dd, 1H, J=0.5 and 4.7 Hz), 8.04 (s, 1H), 7.83 (d, 1H, J=7.6 Hz), 7.66 (s, 1H), 7.45-7.34 (app m, 3H), 7.02 (d, 1H, J=8.5 Hz), 6.96-6.85 (m, 2H), 2.11 (s, 3H). $^{19}$F NMR (DMSO-d6): δ −118.91. LCMS: rt 4.87 min (A), purity 99% MS (m/e) 304 (MH$^+$).

5-(3-(1H-Indazol-5-yl)pyridin-2-yl)-1H-indazole (Compound 64). $^1$H NMR (DMSO-d6): δ 13.04 (s, 1H), 12.99 (s, 1H), 8.66 (dd, 1H, J=1.2 and 4.7 Hz), 8.01 (s, 1H), 7.95 (s, 1H), 7.85 (dd, 1H, J=1.2 and 7.9 Hz), 7.74 (s, 1H), 7.69 (s, 1H), 7.44 (dd, 1H, J=4.7 and 7.9 Hz), 7.34 (d, 1H, J=8.8 Hz), 7.30 (d, 1H, J=8.8 Hz), 7.22 (dd, 1H, J=1.4 and 8.8 Hz), 7.01 (d, 1H, J=8.8 Hz). LCMS: rt 3.87 min (A), purity 97%, MS (m/e) 312 (MH$^+$).

5-[2-(3-Fluorophenyl)pyridin-3-yl]-1H-indazole (Compound 65). $^1$H NMR (DMSO-d6): δ 13.10 (s, 1H), 8.68 (dd, 1H, J=1.4 and 4.4 Hz), 8.05 (s, 1H), 7.92 (dd, 1H, J=1.4 and 7.9 Hz), 7.67 (s, 1H), 7.53 (dd, 1H, J=4.9 and 7.6 Hz), 7.43 (d, 1H, J=8.5 Hz), 7.26-7.13 (m, 1H), 7.14-7.02 (m, 4H). $^{19}$F NMR (DMSO-d6): δ −113.58 (qt, J=8.6 Hz) (s). LCMS: rt 4.73 min (A), purity 99%, MS (m/e) 290 (MH$^+$).

5-[2-(4-Fluorophenyl)pyridin-3-yl]-1H-indazole (Compound 66). $^1$H NMR (DMSO-d6): δ 13.12 (s, 1H), 8.65 (dd, 1H, J=1.7 and 4.7 Hz), 8.04 (s, 1H), 7.89 (dd, 1H, J=1.7 and 7.9 Hz), 7.66 (s, 1H), 7.48 (dd, 1H, J=4.7 and 7.6 Hz), 7.41 (d, 1H, J=8.2 Hz), 7.34-7.29 (m, 2H), 7.07-6.99 (m, 3H). $^{19}$F NMR (DMSO-d6): δ −114.12 (qt, J=8.6 Hz) (s). LCMS: rt 4.53 min (A), purity 97%, MS (m/e) 290 (MH$^+$).

5-[2-(3,5-Difluorophenyl)pyridin-3-yl]-1H-indazole (Compound 67). $^1$H NMR (DMSO-d6): δ 13.12 (s, 1H), 8.65 (dd, 1H, J=1.7 and 4.7 Hz), 8.07 (s, 1H), 7.89 (dd, 1H, J=1.7 and 7.6 Hz), 7.68 (s, 1H), 7.54 (dd, 1H, J=4.7 and 7.6 Hz), 7.46 (d, 1H, J=8.2 Hz), 7.14-7.04 (m, 2H), 6.94-6.90 (m, 2H). $^{19}$F NMR (DMSO-d6): δ −110.30 (t, J=7.8 Hz)). LCMS: rt 5.62 min (A), purity 97%, MS (m/e) 308 (MH$^+$).

5-(2-m-Tolylpyridin-3-yl)-1H-indazole (Compound 68). $^1$H NMR (DMSO-d6): δ 13.12 (s, 1H), 8.70 (dd, 1H, J=1.7 and 4.7 Hz), 8.06-8.03 (m, 2H), 7.67 (s, 1H), 7.60 (dd, 1H, J=4.7 and 7.6 Hz), 7.42 (d, 1H, J=7.8 Hz), 7.28 (s, 1H), 7.08-6.94 (m, 4H), 2.19 (s, 3H).LCMS: rt 4.62 min (A), purity 97%, MS (m/e) 286 (MH$^+$).

5-(2-p-Tolylpyridin-3-yl)-1H-indazole (Compound 69). $^1$H NMR (DMSO-d6): δ 13.38 (s, 1H), 8.64 (dd, 1H, J=1.7 and 4.9 Hz), 8.03 (s, 1H), 7.86 (dd, 1H, J=1.4 and 7.6 Hz), 7.65 (s, 1H), 7.46 (dd, 1H, J=4.9 and 7.6 Hz), 7.39 (d, 1H, J=8.8 Hz), 7.18 (d, 2H, J=8.2 Hz), 7.03-6.99 (m, 3H), 2.21 (s, 3H).LCMS: rt 4.65 min (A), purity 97%, MS (m/e) 286 (MH$^+$).

5-[2-(2,4-Difluorophenyl)pyridin-3-yl]-1H-indazole (Compound 70). $^1$H NMR (DMSO-d6): δ 13.28 (s, 1H), 8.67 (dd, 1H, J=1.4 and 4.8 Hz), 8.01 (s, 1H), 7.94 (dd, 1H, J=1.4 and 7.9 Hz), 7.58-7.44 (m, 3H), 7.40 (d, 1H, J=8.5 Hz), 7.10-7.00 (app m, 3H). $^{19}$F NMR (DMSO-d6): δ −110.06 (q, J=8.6 Hz), −110.56 (qt, J=8.6 Hz) LCMS: rt 5.07 min (A), purity 97%, MS (m/e) 308 (MH$^+$).

5-[2-(3,5-Dimethylphenyl)pyridin-3-yl]-1H-indazole (Compound 71). $^1$H NMR (DMSO-d6): δ 13.38 (s, 1H), 8.73 (dd, 1H, J=1.4 and 4.9 Hz), 8.15 (dd, 1H, J=1.7 and 7.9 Hz), 8.06 (s, 1H), 7.69 (app t, 2H, J=6.7 Hz), 7.86 (dd, 1H, J=1.4 and 7.6 Hz), 7.43 (d, 1H, J=8.5 Hz), 7.03 (dd, 1H, J=1.7 and 8.8 Hz), 6.94 (s, 3H), 2.09 (s, 6H).LCMS: rt 4.93 min (A), purity 97%, MS (m/e) 300 (MH$^+$).

5-(2-(3-Fluoro-4-methylphenyl)pyridin-3-yl)-1H-indazole (Compound 72). $^1$H NMR (DMSO-d6): δ 8.72 (dd, 1H, J=1.4 and 4.9 Hz), 8.07 (d, 1H, J=0.8 Hz), 8.06 (dd, 1H, J=1.4 and 7.9 Hz), 7.69 (app d, 1H, J=0.8 Hz), 7.62 (dd, 1H, J=4.9 and 7.9 Hz), 7.44 (d, 1H, J=8.8 Hz), 7.15-7.09 (m, 2H), 7.04 (dd, 1H, J=1.7 and 8.5 Hz), 6.97 (dd, 1H, J=1.7 and 7.9 Hz), 2.19 (s, 3H).LCMS: rt 4.98 min (A), purity 97%, MS (m/e) 304 (MH$^+$).

5-(2-(2-Fluoro-5-methylphenyl)pyridin-3-yl)-1H-indazole (Compound 73). $^1$H NMR (DMSO-d6): δ 13.28 (s, 1H), 8.72 (dd, 1H, J=1.4 and 4.7 Hz), 8.05 (dd, 1H, J=1.4 and 7.9 Hz), 8.01 (s, 1H), 7.64 (dd, 1H, J=4.9 and 7.9 Hz), 7.60 (s, 1H), 7.39 (d, 1H, J=8.8 Hz), 7.32 (d, 1H, J=1.8 and 8.8 Hz), 7.17-7.14 (m, 1H), 7.07 (dd, 1H, J=1.7 and 8.5 Hz), 6.86 (app t, 1H, J=7.6 Hz), 2.25 (s, 3H). $^{19}$F NMR (DMSO-d6): δ −119.68.LCMS: rt 4.95 min (A), purity 97%, MS (m/e) 304 (MH$^+$).

5-(2-(2-Fluoro-4-methylphenyl)pyridin-3-yl)-1H-indazole (Compound 74). $^1$H NMR (DMSO-d6): δ 13.43 (s, 1H), 8.73 (dd, 1H, J=1.4 and 4.9 Hz), 8.11 (dd, 1H, J=1.4 and 7.9 Hz), 8.02 (s, 1H), 7.69 (dd, 1H, J=4.9 and 7.9 Hz), 7.61 (s, 1H), 7.40 (d, 1H, J=8.8 Hz), 7.33 (t, 1H, J=7.6 Hz), 7.06 (dd, 1H, J=1.4 and 8.5 Hz), 7.01 (d, 1H, J=7.6 Hz), 6.86 (d, 1H, J=11 Hz), 2.25 (s, 3H). $^{19}$F NMR (DMSO-d6): δ −115.46 (dd, J=7.6 and 11 Hz).LCMS: rt 4.88 min (A), purity 97%, MS (m/e) 304 (MH$^+$).

5-(2-(3-Aminophenyl)pyridin-3-yl)-1H-indazole (Compound 75).LCMS: rt 3.43 min (A), purity 97%, MS (m/e) 287 (MH$^+$).

5-(2-(3-Methylsulfphonylaminophenyl)pyridin-3-yl)-1H-indazole (Compound 76). $^1$H NMR (DMSO-d6): δ 9.67 (s, 1H), 8.72 (dd, 1H, J=1.4 and 4.9 Hz), 8.06 (d, 1H, J=7.9 Hz), 8.05 (s, 1H), 7.67 (s, 1H), 7.64 (dd, 1H, J=4.9 and 7.6 Hz), 7.42 (d, 1H, J=8.5 Hz), 7.21 (d, 1H, J=7.9 Hz), 7.18 (s, 1H), 7.10-7.02 (m, 3H), 2.56 (s, 3H).LCMS: rt 3.97 min (A), purity 97%, MS (m/e) 365 (MH$^+$).

5-(2-(3,4-Difluorophenyl)pyridin-3-yl)-1H-pyrazolo[3,4-b]pyridine (Compound 77). $^1$H NMR (DMSO-d6): δ 13.65 (s, 1H), 8.70 (d, 1H, J=4.7 Hz), 8.22 (s, 1H), 8.14 (s, 2H), 7.96 (d, 1H, J=7.6 Hz), 7.53 (dd, 1H, J=4.7 and 7.9 Hz), 7.39 (app t, 1H, J=9.7 Hz), 7.29 (qt, 1H, J=8.6 Hz), 7.03-6.98 (m, 1H). $^{19}$F NMR (DMSO-d6): δ −138.69-138.84 (app m), −139.47-139.55 (app m). LCMS: rt 4.26 min (B), purity 97%, MS (m/e) 309 (MH$^+$).

5-(2-(4-Fluoro-3-methylphenyl)pyridin-3-yl)-1H-pyrazolo[3,4-b]pyridine (Compound 78). $^1$H NMR (DMSO-d6): δ 13.65 (s, 1H), 8.67 (d, 1H, J=4.7 Hz), 8.18 (d, 1H, J=2.0 Hz), 8.12 (d, 2H, J=2.0 Hz), 7.92 (d, 1H, J=7.6 Hz), 7.49 (dd, 1H, J=4.7 and 7.6 Hz), 7.35 (d, 1H, J=7.6 Hz), 6.93 (d, 2H, J=7.9

Hz), 2.12 (s, 3H). $^{19}$F NMR (DMSO-d6): δ −118.53 (s).LCMS: rt 3.81 min (B), purity 97%, MS (m/e) 305 (MH$^+$).

5-(2-m-Tolylpyridin-3-yl)-1H-pyrazolo[3,4-b]pyridine (Compound 79). $^1$H NMR (DMSO-d6): δ 13.65 (s, 1H), 8.67 (d, 1H, J=4.7 Hz), 8.16 (s, 1H), 8.11 (s, 2H), 7.92 (d, 1H, J=6.7 Hz), 7.49 (dd, 1H, J=4.7 and 7.6 Hz), 7.23 (s, 1H), 7.05 (s, 1H), 7.04 (s, 1H), 6.91 (app d, 1H, J=6.7 Hz), 2.19 (s, 3H). $^{19}$F NMR (DMSO-d6): δ −118.91 (s).LCMS: rt 3.29 min (B), purity 97%, MS (m/e) 287 (MH$^+$).

5-(2-(4-Fluorophenyl)pyridin-3-yl)-1H-pyrazolo[3,4-b]pyridine (Compound 80). $^1$H NMR (DMSO-d6): δ 13.65 (s, 1H), 8.65 (dd, 1H, J=1.4 and 4.7 Hz), 8.17 (s, 1H), 8.12 (s, 2H), 7.93 (dd, 1H, J=1.4 and 7.6 Hz), 7.51 (dd, 1H, J=4.7 and 7.9 Hz), 7.30 (app d, 1H, J=4.7 and 8.8 Hz), 7.07 (app t, 2H, J=8.8 Hz). $^{19}$F NMR (DMSO-d6): δ −114.06 (s).LCMS: rt 3.42 min (B), purity 97%, MS (m/e) 291 (MH$^+$).

5-(2-(3-Fluoro-4-methylphenyl)pyridin-3-yl)-1H-pyrazolo[3,4-b]pyridine (Compound 81). LCMS: rt 4.17 min (B), purity 97%, MS (m/e) 305 (MH$^+$).

5-(2-(2-Fluoro-4-methylphenyl)pyridin-3-yl)-1H-pyrazolo[3,4-b]pyridine (Compound 82). LCMS: rt 4.07 min (B), purity 97%, MS (m/e) 305 (MH$^+$).

2-(2-Fluorophenyl)-3-(4-fluorophenyl)pyridine (Compound 83). LCMS: rt 5.89 min (B), purity 97%, MS (m/e) 268 (MH$^+$).

2-(3,4-Difluorophenyl)-3-(4-fluorophenyl)pyridine (Compound 84). LCMS: rt 6.52 min (B), purity 97%, MS (m/e) 286 (MH$^+$).

2-(4-Fluoro-3-methylphenyl)-3-(4-fluorophenyl)pyridine (Compound 85). $^1$H NMR (DMSO-d6): δ 8.77 (dd, 1H, J=1.4 and 5.3 Hz), 8.19 (d, 1H, J=7.6 Hz), 7.77 (dd, 1H, J=5.3 and 7.6 Hz), 7.36 (d, 1H, J=7.2 Hz), 7.26-7.15 (m, 4H), 7.08 (app d, 2H, J=8.5 Hz), 2.16 (s, 3H). $^{19}$F NMR (DMSO-d6): δ −113.94 (s), −116.31 (s). LCMS: 6.10 min (B), purity 97%, MS (m/e) 282 (MH$^+$).

2-(3-Fluorophenyl)-3-(4-fluorophenyl)pyridine (Compound 86). LCMS: rt 6.11 min (B), purity 97%, MS (m/e) 268 (MH$^+$).

2,3-Bis-(4-fluorophenyl)pyridine (Compound 87). LCMS: rt 5.70 min (B), purity 97%, MS (m/e) 268 (MH$^+$).

3-(4-Fluorophenyl)-2-m-tolylpyridine (Compound 88). LCMS: rt 5.70 min (B), purity 97%, MS (m/e) 264 (MH$^+$).

(5-(3-(1H-Indazol-5-yl)pyridin-2-yl)-2-fluorophenyl)methanol (Compound 89). $^1$H NMR (DMSO-d6): δ 8.64 (dd, 1H, J=1.4 and 4.7 Hz), 8.04 (s, 1H), 7.84 (dd, 1H, J=1.4 and 7.6 Hz), 7.67-7.64 (app m, 2H), 7.44 (d, 1H, J=4.7 and 7.6 Hz), 7.42 (d, 1H, J=8.8 Hz), 7.01 (dd, 1H, J=1.4 and 8.8 Hz), 6.98-6.93 (m, 1H), 6.87 (t, 1H, J=8.8 Hz), 5.20 (t, 1H, J=5.5 Hz), 4.45 (d, 2H, J=5.5 Hz). $^{19}$F NMR (DMSO-d6): δ −118.91 (s).LCMS: rt 2.87 min (B), purity 97%, MS (m/e) 320 (MH$^+$).

4-(3-(1H-Indazol-5-yl)pyridin-2-yl)-2-methylbenzenamine (Compound 90). LCMS: rt 2.22 min (B), purity 97%, MS (m/e) 301(MH$^+$).

[3-(3-(1H-Indazol-5-yl)pyridin-2-yl)phenyl]methanol (Compound 91). $^1$H NMR (DMSO-d6): δ 13.1 (s, 1H), 8.63 (dd, 1H, J=1.4 and 4.7 Hz), 8.02 (s, 1H), 7.83 (dd, 1H, J=1.7 and 7.9 Hz), 7.65 (s, 1H), 7.46-7.37 (m, 3H), 7.16 (d, 1H, J=7.6 Hz), 7.04 (d, 1H, J=7.9 Hz), 7.01 (dd, 1H, J=1.4 and 7.9 Hz), 6.95 (d, 1H, J=7.6 Hz), 5.13 (bs, 1H), 4.38 (s, 2H).LCMS: rt 2.54 min (B), purity 97%, MS (m/e) 302 (MH$^+$).

4-(3-(1H-Indazol-5-yl)pyridin-2-yl)-N,N,2-trimethylbenzenamine (Compound 92). $^1$H NMR (DMSO-d6): δ 13.01 (s, 1H), 8.58 (dd, 1H, J=0.4 and 4.4 Hz), 8.04 (s,1H), 7.77 (d, 1H, J=7.6 Hz), 7.67 (s, 1H), 7.41 (app d, 1H, J=7.6 Hz), 7.37 (dd, 1H, J=4.8 and 7.6 Hz), 7.25 (s, 1H). 7.03 (d, 1H, J=8.5 Hz), 6.90 (app d 1H, J=7.6 Hz), 6.72 (d, 1H, J=8.5 Hz), 2.55 (s, 6H), 2.11 (s, 3H). LCMS: rt 2.39 min (B), purity 97%, MS (m/e) 329 (MH$^+$).

5-(2-(4-Fluoro-3-(trifluoromethyl)phenyl)pyridin-3-yl)-1H-indazole (Compound 93). $^1$H NMR (DMSO-d6): δ 13.1 (s, 1H), 8.70 (dd, 1H, J=1.4 and 4.7 Hz), 8.06 (s, 1H), 7.94 (dd, 1H, J=1.7 and 7.9 Hz), 7.70 (app s, 2H), 7.56 (d, 1H, J=7.9 Hz), 7.54 (d, 1H, J=7.9 Hz), 7.45 (d, 1H, j=8.8 Hz), 7.33 (app t, 1H, J=8.8 Hz), 7.05 (dd, 1H, J 1.5 and 8.5 Hz). $^{19}$F NMR (DMSO-d6): δ −117.12 (app m), −60.34 (d, 1H, J=15 Hz).LCMS: rt 6.22 min (A), purity 97%, MS (m/e) 358 (MH$^+$).

2-Fluoro-5-(3-(1H-indazol-5-yl)pyridin-2-yl)benzamide (Compound 94). LCMS: rt 3.07 min (A), purity 97%, MS (m/e) 333 (MH$^+$).

2-Fluoro-5-(3-(1H-indazol-5-yl)pyridin-2-yl)-N,N-dimethylbenzamide (Compound 95). LCMS: rt 3.42 min (A), purity 97%, MS (m/e) 361 (MH$^+$).

5-(3-(1H-Indazol-5-yl)pyridin-2-yl)-2-fluoro-N-propylbenzamide (Compound 96). LCMS: rt 4.06 min (A), purity 97%, MS (m/e) 375 (MH$^+$).

6-(2-(2-Fluorophenyl)pyridin-3-yl)-1H-indazole (Compound 97). LCMS: rt 4.50 min (A), purity 97%, MS (m/e) 290 (MH$^+$).

6-(2-(3,4-Difluorophenyl)pyridin-3-yl)-1H-indazole (Compound 98). LCMS: rt 5.53 min (A), purity 97%, MS (m/e) 308 (MH$^+$).

6-(2-(4-Fluoro-3-methylphenyl)pyridin-3-yl)-1H-indazole (Compound 99). $^1$H NMR (DMSO-d6): δ 13.02 (s, 1H), 8.65 (d, 1H, J=4.7 Hz), 8.03 (d, 1H, J=0.5 Hz), 7.87 (d, 1H, J=7.6 Hz), 7.64 (d, 1H, J=8.2 Hz), 7.46 (dd, 1H, J=4.7 and 7.6 Hz), 7.38 (app s, 2H), 6.95-6.93 (m, 1H), 6.90 (d, 1H, J=8.2 Hz), 6.83 (d, 1H, J=8.5 Hz), 2.11 (s, 3H). $^{19}$F NMR (DMSO-d6): δ −118.78 (s).LCMS: rt 4.60 min (A), purity 97%, MS (m/e) 304 (MH$^+$).

6-(2-(3-Fluorophenyl)pyridin-3-yl)-1H-indazole (Compound 100). LCMS: rt 4.70 min (A), purity 97%, MS (m/e) 290 (MH$^+$).

6-(2-(4-Fluorophenyl)pyridin-3-yl)-1H-indazole (Compound 101). $^1$H NMR (DMSO-d6): δ 13.10 (s, 1H), 8.67 (dd, 1H, J=1.7 and 4.7 Hz), 8.03 (s, 1H), 7.88 (dd, 1H, J=1.4 and 7.6 Hz), 7.64 (d, 1H, J=7.2 Hz), 7.48 (dd, 1H, J=4.9 and 7.9 Hz), 7.38 (s, 1H), 7.34-7.30 (m, 2H), 7.04 (app t, 2H, J=8.8 Hz), 6.83 (d, 1H, J=8.5 Hz). $^{19}$F NMR (DMSO-d6): δ −114.29 (s).LCMS: rt 4.27 min, purity 97%, MS (m/e) 290 (MH$^+$).

6-(2-m-Tolylpyridin-3-yl)-1H-indazole (Compound 102). LCMS: rt 4.00 min (A), purity 97%, MS (m/e) 286 (MH$^+$).

6-(2-(4-Fluoro-3-methylphenyl)pyridin-3-yl)benzo[d]oxazol-2(3H)-one (Compound 103). LCMS: rt 4.68 min (A), purity 97%, MS (m/e) 321 (MH$^+$).

3-(Benzo[d][1,3]dioxol-6-yl)-2-(2-fluorophenyl)pyridine (Compound 104). LCMS: rt 5.39 min (B), purity 97%, MS (m/e) 294 (MH$^+$).

3-(Benzo[d][1,3]dioxol-6-yl)-2-(3,4-difluorophenyl)pyridine (Compound 105). LCMS: rt 6.10 min (B), purity 97%, MS (m/e) 312 (MH$^+$).

3-(Benzo[d][1,3]dioxol-6-yl)-2-(4-fluoro-3-methylphenyl)pyridine (Compound 106). $^1$H NMR (DMSO-d6): δ 8.71 (dd, 1H, J=1.4 and 4.9 Hz), 8.05 (d, 1H, J=7.6 Hz), 7.65 (dd, 1H, J=4.9 and 7.9 Hz), 7.39 (d, 1H, J=7.6 Hz), 7.07 (d, 2H, J=7.6 Hz), 6.87 (d, 1H, J=8.2 Hz), 6.76 (d, 1H, J=1.4 Hz), 6.63 (dd, 1H, J=1.4 and 8.2 Hz), 6.01 (s, 2H), 2.19 (s, 3H). $^{19}$F NMR (DMSO-d6): δ −114.29 (s).LCMS: rt 5.43 min (B), purity 97%, MS (m/e) 308 (MH$^+$).

3-(Benzo[d][1,3]dioxol-6-yl)-2-(3-fluorophenyl)pyridine (Compound 107). LCMS: rt 5.61 min (B), purity 97%, MS (m/e) 294 (MH+).

3-(Benzo[d][1,3]dioxol-6-yl)-2-(4-fluorophenyl)pyridine (Compound 108). LCMS: rt 5.10 min (B), purity 97%, MS (m/e) 294 (MH+).

3-(Benzo[d][1,3]dioxol-6-yl)-2-m-tolylpyridine (Compound 109). LCMS: rt 4.78 min (B), purity 97%, MS (m/e) 290 (MH+).

3-(Benzo[d][1,3]dioxol-6-yl)-2-(2-fluoro-5-methylphenyl)pyridine (Compound 110). LCMS: rt 5.79 min (B), purity 97%, MS (m/e) 308 (MH+).

2-(3-(1H-Indazol-5-yl)pyridin-2-yl)benzonitrile (Compound 111). LCMS: rt 4.28 min (B), purity 97%, MS (m/e) 297 (MH+).

3-(3-(1H-Indazol-5-yl)pyridin-2-yl)benzonitrile (Compound 112). LCMS: rt 4.42 min (B), purity 97%, MS (m/e) 297 (MH+).

4-(3-(1H-Indazol-5-yl)pyridin-2-yl)benzonitrile (Compound 113). LCMS: rt 4.50 min (B), purity 97%, MS (m/e) 297 (MH+).

4-(3-(1H-Indazol-5-yl)pyridin-2-yl)-2-fluorobenzonitrile (Compound 114). LCMS: rt 5.11 min (B), purity 97%, MS (m/e) 315 (MH+).

5-(2-(4-(Trifluoromethyl)phenyl)pyridin-3-yl)-1H-indazole (Compound 115). $^1$H NMR (DMSO-d6): δ 133.18 (s, 1H), 8.69 (dd, 1H, J=1.4 and 4.7 Hz), 8.04 (s, 1H), 7.90 (dd, 1H, J=1.4 and 7.9 Hz), 7.68 (s, 1H), 7.59-7.47 (m, 5H), 7.42 (d, 1H, J=8.8 Hz), 7.02 (dd, 1H, J=1.4 and 8.8 Hz).LCMS: rt 5.47 min (B), purity 97%, MS (m/e) 340 (MH+).

5-(2-(3-Methoxyphenyl)pyridin-3-yl)-1H-indazole (Compound 117). $^1$H NMR (DMSO-d6): δ 13.02 (s, 1H), 8.64 (dd, 1H, J=1.4 and 4.8 Hz), 8.03 (s, 1H), 7.84 (d, 1H, J=7.9 Hz), 7.65 (s, 1H), 7.45 (dd, 1H, J=4.7 and 7.6 Hz), 7.40 (d, 1H, J=8.5 Hz)7.08 (t, 1H, J=7.9 Hz), 7.03 (d, 1H, J=8.5 Hz), 6.86 (m, 3H), 3.68 (s, 3H).LCMS: rt 3.49 min (B), purity 97%, MS (m/e) 302 (MH+).

5-(2-(4-Methoxyphenyl)pyridin-3-yl)-1H-indazole (Compound 118). LCMS: rt 2.99 min (B), purity 97%, MS (m/e) 302 (MH+).

5-(2-(3,4-Dimethoxyphenyl)pyridin-3-yl)-1H-indazole (Compound 119). LCMS: rt 2.85 min (B), purity 97%, MS (m/e) 332 (MH+).

3-(3-(1H-Indazol-5-yl)pyridin-2-yl)phenol (Compound 120). $^1$H NMR (DMSO-d6): δ 13.10 (s, 1H), 8.61 (dd, 1H, J=1.7 and 4.7 Hz), 8.03 (s, 1H), 7.82 (dd, 1H, J=1.7 and 7.6 Hz), 7.65 (s, 1H), 7.43 (dd, 1H, J=4.7 and 7.6 Hz), 7.39 (d, 1H, J=8.2 Hz), 7.02 (dd, 1H, J=1.4 and 8.5 Hz), 6.94 (t, 1H, J=7.6 Hz), 6.77 (s, 1H), 6.59 (dd, 2H, J=2.0 and 7.6 Hz).LCMS: rt 2.63 min (B), purity 97%, MS (m/e) 288 (MH+).

4-(3-(1H-Indazol-5-yl)pyridin-2-yl)phenol (Compound 121). LCMS: rt 2.27 min (B), purity 97%, MS (m/e) 288 (MH+).

4-(3-(1H-Indazol-5-yl)pyridin-2-yl)-2-methylphenol (Compound 122). LCMS: rt 2.42 min (B), purity 97%, MS (m/e) 302 (MH+).

5-(2-(3,5-dimethoxyphenyl)pyridin-3-yl)-1H-indazole (Compound 123). LCMS: rt 3.79 min (B), purity 97%, MS (m/e) 332 (MH+).

5-(2-(4-Fluoro-3-methoxyphenyl)pyridin-3-yl)-1H-indazole (Compound 124). $^1$H NMR (DMSO-d6): δ 13.01 (s, 1H), 8.65 (dd, 1H, J=4.4 Hz), 8.04 (s, 1H), 7.85 (dd, 1H, J=1.7 and 7.9 Hz), 7.67 (s, 1H), 7.45 (dd, 1H, J=4.7 and 7.9 Hz), 7.44 (d, 1H, J=8.2 Hz), 7.07-6.97 (m, 3H), 6.82-6.77 (m, 1H), 3.49 (d, 3H). $^{19}$F NMR (DMSO-d6): δ –117.70 (q, H=4.2 Hz).LCMS: rt 3.95 min (B), purity 97%, MS (m/e) 320 (MH+).

5-(2-(3-Methoxy-4-methylphenyl)pyridin-3-yl)-1H-indazole (Compound 125). LCMS: rt 4.86 min (B), purity 97%, MS (m/e) 316 (MH+).

5-(2-(4-(Benzyloxy)-3-methoxyphenyl)pyridin-3-yl)-1H-indazole (Compound 126). $^1$H NMR (DMSO-d6): δ 13.01 (s, 1H), 8.61 (d, 1H, J=4.7 Hz), 8.05 (s, 1H), 7.79 (d, 1H, J=7.9 Hz), 7.67 (s, 1H), 7.43-7.29 (m, 7H), 7.04 (d, 1H, J=9.1 Hz), 6.91 (s, 1H), 6.87 (d, 1H, J=7.9 Hz), 6.78 (d, 1H, J=9.1 Hz), 4.98 (s, 2H), 3.49 (s, 3H).LCMS: rt 4.51 min (B), purity 97%, MS (m/e) 408 (MH+).

5-(2-(4-Aminosulfonylphenyl)pyridin-3-yl)-1H-indazole (Compound 127). LCMS: rt 3.40 min (B), purity 97%, MS (m/e) 351 (MH+).

5-(2-(3-Amino sulfonylphenyl)pyridin-3-yl)-1H-indazole (Compound 128). LCMS: rt 3.36 min (B), purity 97%, MS (m/e) 351 (MH+).

6-(2-(3,4-Difluorophenyl)pyridin-3-yl)-1-methyl-1H-indazole (Compound 129). LCMS: rt 6.10 min (A), purity 97%, MS (m/e) 322 (MH+).

6-(2-(4-Fluoro-3-methylphenyl)pyridin-3-yl)-1-methyl-1H-indazole (Compound 130). $^1$H NMR (DMSO-d6): δ 8.72 (dd, 1H, J=1.4 and 4.9 Hz), 8.04 (dd, 1H, J=1.4 and 7.9 Hz), 8.01 (s, 1H), 7.67 (s, 1H), 7.60 (dd, 2H, J=4.8 and 7.9 Hz), 7.41 (d, 1H, J=7.6 Hz), 7.01-6.99 (m, 2H), 6.74 (d, 1H, J=8.2 Hz), 4.00 (s, 3H), 2.13 (s, 3H). $^{19}$F NMR (DMSO-d6): δ –117.88 (s).LCMS: rt 5.55 min (A), purity 97%, MS (m/e) 318 (MH+).

1-Methyl-6-(2-m-tolylpyridin-3-yl)-1H-indazole (Compound 131). LCMS: rt 5.25 min (A), purity 97%, MS (m/e) 300 (MH+).

6-(2-(2-Fluoro-5-methylphenyl)pyridin-3-yl)-1-methyl-1H-indazole (Compound 132). LCMS: rt 5.78 min (A), purity 97%, MS (m/e) 318 (MH+).

3-(3-(1-Methyl-1H-indazol-6-yl)pyridin-2-yl)benzonitrile (Compound 133). LCMS: rt 5.86 min (A), purity 97%, MS (m/e) 311 (MH+).

6-(2-(3-methoxyphenyl)pyridin-3-yl)-1-methyl-1H-indazole (Compound 134). LCMS: rt 5.10 min (A), purity 97%, MS (m/e) 316 (MH+).

6-(2-(4-Fluoro-3-methoxyphenyl)pyridin-3-yl)-1-methyl-1H-indazole (Compound 135). LCMS: rt 5.41 min (A), purity 97%, MS (m/e) 334 (MH+).

3-(3-(1-Methyl-1H-indazol-6-yl)pyridin-2-yl)phenol (Compound 136). LCMS: rt 4.41 min (A), purity 97%, MS (m/e) 302 (MH+).

6-(2-(3,4-Difluorophenyl)pyridin-3-yl)-1H-pyrazolo[4,3-b]pyridine (Compound 137). LCMS: rt 4.83 min (A), purity 97%, MS (m/e) 309 (MH+).

6-(2-(4-Fluoro-3-methylphenyl)pyridin-3-yl)-1H-pyrazolo[4,3-b]pyridine (Compound 138). $^1$H NMR (DMSO-d6): δ 8.75 (dd, 1H, J=1.5 and 5.1 Hz), 8.27 (app s 1H), 8.19 (d, 1H, J=4.8 Hz), 8.09 (dd, 1H, J=1.5 and 4.8 Hz), 7.93 (t, 1H, J=0.79 Hz), 7.62 (dd, 1H, J=4.8 and 8.1 Hz), 7.39 (d, 1H, J=0.79 Hz), 7.62 (dd, 1H, J=4.8 and 8.1 Hz), 6.98-6.92 (m, 2H), 2.13 (s, 3H).LCMS: rt 4.35 min (A), purity 97%, MS (m/e) 305 (MH+).

6-(2-m-Tolylpyridin-3-yl)-1H-pyrazolo[4,3-b]pyridine (Compound 139). LCMS: rt 4.00 min (A), purity 97%, MS (m/e) 287 (MH+).

6-(2-(2-Fluoro-5-methylphenyl)pyridin-3-yl)-1H-pyrazolo[4,3-b]pyridine (Compound 140). LCMS: rt 4.60 min (A), purity 97%, MS (m/e) 305 (MH+).

3-(3-(1H-Pyrazolo[4,3-b]pyridin-6-yl)pyridin-2-yl)benzonitrile (Compound 141). LCMS: rt 4.48 min, purity 97%, MS (m/e) 298 (MH+).

6-(2-(3-Methoxyphenyl)pyridin-3-yl)-1H-pyrazolo[4,3-b]pyridine (Compound 142). LCMS: rt 3.90 min (A), purity 97%, MS (m/e) 303 (MH$^+$).

6-(2-(4-Fluoro-3-methoxyphenyl)pyridin-3-yl)-1H-pyrazolo[4,3-b]pyridine (Compound 143). LCMS: rt 4.21 min (A), purity 97%, MS (m/e) 321 (MH$^+$).

3-(3-(1H-Pyrazolo[4,3-b]pyridin-6-yl)pyridin-2-yl)phenol (Compound 144). LCMS: rt 3.11 min (A), purity 97%, MS (m/e) 289 (MH$^+$).

5-(2-(4-Fluoro-3-methylphenyl)pyridin-3-yl)-1-methyl-1H-indazole (Compound 145). $^1$H NMR (DMSO-d6): δ 8.71 (dd, 1H, J=0.4 and 4.9 Hz), 8.06 (dd, 1H, J=1.4 and 7.9 Hz), 8.03 (s, 1H), 7.68 (s, 1H), 7.63 (dd, 1H, J=4.9 and 7.9 Hz), 7.53 (d, 1H, J=8.8 Hz), 7.41 (d, 1H, J=7.9 Hz), 7.07 (dd, 1H, J=1.4 and 8.8 Hz), 6.97-6.95 (m, 2H), 4.01 (s, 3H), 2.14 (s, 3H). $^{19}$F NMR (DMSO-d6): δ –118.70 (s).LCMS: rt 5.36 min (A), purity 97%, MS (m/e) 318 (MH$^+$).

1-Methyl-5-(2-m-tolylpyridin-3-yl)-1H-indazole (Compound 146). LCMS: rt 5.11 min (A), purity 97%, MS (m/e) 300 (MH$^+$).

5-(2-(4-Fluoro-3-methylphenyl)pyridin-3-yl)-3-methyl-1H-indazole (Compound 147). $^1$H NMR (DMSO-d6): δ 8.69 (dd, 1H, J=1.4 and 4.7 Hz), 8.07 (dd, 1H, J=1.7 and 7.9 Hz), 7.68 (s, 1H), 7.63-7.58 (m, 1H), 7.38 (d, 1H, J=7.3 Hz), 7.30 (d, 1H, J=8.8 Hz), 6.99-6.91 (m, 3H), 2.44 (s, 3H), 2.13 (s, 3H). $^{19}$F NMR (DMSO-d6): δ –117.70 (s).LCMS: rt 5.01 min (A), purity 97%, MS (m/e) 318 (MH$^+$).

3-Methyl-5-(2-m-tolylpyridin-3-yl)-1H-indazole (Compound 148). LCMS: rt 4.78 min (A), purity 97%, MS (m/e) 300 (MH$^+$).

5-(2-(3-Ethylphenyl)pyridin-3-yl)-1H-indazole (Compound 149). $^1$H NMR (DMSO-d6): δ 8.64 (dd, 1H, J=1.4 and 4.7 Hz), 8.02 (s, 1H), 7.84 (dd, 1H, J=1.4 and 7.6 Hz), 7.63 (s, 1H), 7.44 (dd, 1H, J=4.9 and 8.7 Hz), 7.39 (d, 1H, J=8.8 Hz), 7.10 (s, 1H), 7.09 (s, 1H), 7.06-7.04 (m, 1H), 7.01 (dd, 1H, J=1.4 and 8.7 Hz), 2.42 (qt, 2H, J=7.6 Hz), 0.86 (t, 3H, J=7.6 Hz).LCMS: rt 4.93 min (A), purity 97%, MS (m/e) 300 (MH$^+$).

5-(2-(3-Cyclopropylphenyl)pyridin-3-yl)-1H-indazole (Compound 150). $^1$H NMR (DMSO-d6): δ 13.02 (s, 1H), 8.63 (dd, 1H, J=1.4 and 4.8 Hz), 8.03 (s, 1H), 7.82 (dd, 1H, J=7.6 Hz), 7.62 (s, 1H), 7.43 (dd, 1H, J=4.8 and 7.6 Hz), 7.40 (d, 1H, J=7.9 Hz), 7.07 (s, 1H), 7.05 (s, 1H), 7.02-6.94 (m, 2H), 6.86 (s, 1H), 1.76-1.67 (m, 1H), 0.76-0.68 (m, 2H), 0.24-0.19 (m, 2H).LCMS: rt 4.96 min (A), purity 97%, MS (m/e) 312 (MH$^+$).

5-(2-(3-Ethylphenyl)pyridin-3-yl)-1H-pyrazolo[3,4-b]pyridine (Compound 151). $^1$H NMR (DMSO-d6): δ 13.58 (s, 1H), 8.69 (dd, 1H, J=1.4 and 4.7 Hz), 8.15 (dd, 1H, J=0.5 and 2.0 Hz), 7.93 (dd, 1H, J=1.4 and 7.9 Hz), 7.50 (d, 1H, J=4.8 and 7.9 Hz), 7.16-7.05 (m, 4H), 2.41 (qt, 2H, J=7.3 Hz), 0.86 (t, 3H, J=7.3 Hz).LCMS: rt 4.48 min (A), purity 97%, MS (m/e) 301 (MH$^+$).

5-(2-(3-Cyclopropylphenyl)pyridin-3-yl)-1H-pyrazolo[3,4-b]pyridine (Compound 152). $^1$H NMR (DMSO-d6): δ 13.6 (s, 1H), 8.75 (dd, 1H, J=1.4 and 4.7 Hz), 8.19 (d, 1H, J=7.9 Hz), 8.17 (d, 1H, J=5.3 Hz), 7.98 (d, 1H, J=7.6 Hz), 7.56 (dd, 1H, J==4.8 and 7.9 Hz), 7.18-7.04 (m, 3H), 6.92 (s, 1H), 1.85-1.78 (m, 2H), 0.84-0.78 (m, 2H), 0.33-0.12 (m, 2H).LCMS: rt 4.56 min, purity 97%, MS (m/e) 313 (MH$^+$).

5-(2-(2-Fluoro-5-methylphenyl)pyridin-3-yl)-1H-pyrazolo[3,4-b]pyridine (Compound 153). $^1$H NMR (DMSO-d6): δ 13.6 (s, 1H), 8.70 (dd, 1H, J=1.4 and 4.7 Hz), 8.22 (d, 1H, J=1.7 Hz), 8.08 (d, 1H, J=1.2 Hz), 8.03 (d, 1H, J=1.4 Hz), 7.96 (dd, 1H, J=1.4 and 7.9 Hz), 7.56 (dd, 1H, J=4.9 and 7.9 Hz), 7.35 (dd, 1H, 1.4 and 4.7 Hz), 7.15-7.11 (m, 1H), 6.81 (t, 1H, J=8.8 Hz), 2.27 (s, 3H). $^{19}$F NMR (DMSO-d6): δ –120.40 (s).LCMS: rt 4.71 min (A), purity 97%, MS (m/e) 305 (MH$^+$).

3-(3-(1H-Pyrazolo[3,4-b]pyridin-5-yl)pyridin-2-yl)benzonitrile (Compound 154). LCMS: rt 4.61 min (A), purity 97%, MS (m/e) 298 (MH$^+$).

5-(2-(3-Methoxyphenyl)pyridin-3-yl)-1H-pyrazolo[3,4-b]pyridine (Compound 155). $^1$H NMR (DMSO-d6): δ 13.58 (s, 1H), 8.71 (dd, 1H, J=1.7 and 4.7 Hz), 8.18 (d, 1H, J=2.0 Hz), 8.13 (d, 1H, J=2.0 Hz), 8.12 (s, 1H), 7.97 (dd, 1H, J=1.7 and 7.6 Hz), 7.54 (dd, 1H, J=4.6 and 7.6 Hz), 7.12 (t, 1H, J=7.9 Hz), 6.89-6.88 (app m, 1H), 6.82 (dd, 1H, J=2.3 and 8.5 Hz), 6.78 (d, 1H, J=8.5 Hz), 3.56 (s, 3H).LCMS: rt 3.96 min (A), purity 97%, MS (m/e) 303 (MH$^+$).

3-(3-(1H-Pyrazolo[3,4-b]pyridin-5-yl)pyridin-2-yl)phenol (Compound 156). LCMS: rt 3.30 min, purity 97%, MS (m/e) 289 (MH$^+$).

5-(2-(4-Fluoro-3-methoxyphenyl)pyridin-3-yl)-1H-pyrazolo[3,4-b]pyridine (Compound 157). LCMS: rt 4.26 min (A), purity 97%, MS (m/e) 321 (MH$^+$).

5-(3-(1H-Pyrazolo[3,4-b]pyridin-5-yl)pyridin-2-yl)-2-fluorobenzonitrile (Compound 158). LCMS: rt 5.18 min (A), purity 97%, MS (m/e) 316 (MH$^+$).

6-(2-(4-Fluoro-3-methylphenyl)pyridin-3-yl)benzo[d]thiazole (Compound 159). $^1$H NMR (DMSO-d6): δ 9.37 (d, 1H, J=2.1 Hz), 8.66 (app d, 1H, J=4.7 Hz), 8.08 (s, 1H), 7.96 (d, 1H, J=8.5 Hz), 7.88 (d, 1H, J=7.6 Hz), 7.48 (dd, 1H, J=4.7 and 7.6 Hz), 7.36 (d, 1H, J=7.9 Hz), 7.22 (dd, 1H, J=0.88 and 8.5 Hz), 6.93-6.87 (m, 2H), 2.11 (s, 3H). $^{19}$F NMR (DMSO-d6): δ –118.59 (s).LCMS: rt 5.51 min (A), purity 97%, MS (m/e) 321 (MH$^+$).

6-(2-m-Tolylpyridin-3-yl)benzo[d]thiazole (Compound 160). $^1$H NMR (DMSO-d6): δ 9.36 (d, 1H, J=2.1 Hz), 8.67 (app d, 1H, J=4.7 Hz), 8.07 (s, 1H), 7.93 (d, 1H, J=8.2 Hz), 7.88 (d, 1H, J=8.2 Hz), 7.47 (dd, 1H, J=4.9 and 7.9 Hz), 7.25-7.20 (m, 2H), 7.03-6.99 (m, 2H), 6.91 (d, 1H, J=4.9 Hz), 2.18 (s, 3H).LCMS: rt 5.15 min (A), purity 97%, MS (m/e) 303 (MH$^+$).

6-(2-(4-Fluoro-3-methylphenyl)pyridin-3-yl)-[1,2,4]triazolo[4,3-a]pyridine (Compound 161). $^1$H NMR (DMSO-d6): δ 9.24 (s, 1H), 8.71 (dd, 1H, J=1.4 and 4.7 Hz), 8.63 (s, 1H), 7.93 (d, 1H, J=7.6 Hz), 7.61 (d, 1H, J=9.4 Hz), 7.52 (dd, 1H, J=4.7 and 7.7 Hz), 7.43 (d, 1H, J=7.6 Hz), 7.12-7.08 (m, 1H), 6.99 (app t, 1H, J=9.3 Hz), 6.90 (d, 1H, J=9.7 Hz), 2.16 (s, 3H). $^{19}$F NMR (DMSO-d6): δ –117.98 (s). LCMS: rt 4.20 min (A), purity 97%, MS (m/e) 305 (MH$^+$).

6-(2-m-Tolylpyridin-3-yl)-[1,2,4]triazolo[4,3-a]pyridine (Compound 162). $^1$H NMR (DMSO-d6): δ 9.23 (s, 1H), 8.72 (dd, 1H, J=1.4 and 7.9 Hz), 8.62 (s, 1H), 7.93 (dd, 1H, J=1.4 and 7.9 Hz), 7.58 (d, 1H, J=9.4 Hz), 7.51 (dd, 1H, J=4.9 and 7.9 Hz), 7.32 (s, 1H), 7.12 (app d, 1H, J=4.9 Hz), 7.11 (s, 1H), 7.07-7.05 (app m, 1H), 6.89 (dd, 1H, J=1.4 and 8.7 Hz), 2.23 (s, 3H).LCMS: rt 3.76 min (A), purity 97%, MS (m/e) 287 (MH$^+$).

5-(2-(4-Fluoro-3-methylphenyl)pyridin-3-yl)benzo[d]thiazole (Compound 163). $^1$H NMR (DMSO-d6): δ 9.38 (d, 1H, J=1.7 Hz), 8.66 (dd, 1H, J=1.4 and 4.7 Hz), 8.06 (d, 1H, J=8.5 Hz), 7.95 (s, 1H), 7.90 (dd, 1H, J=1.4 and 7.9 Hz), 7.49 (dd, 1H, J=4.7 and 7.9 Hz), 7.37 (d, 1H, J=7.6 Hz), 7.20 (d, 1H, J=8.2 Hz), 6.97-6.87 (m, 2H), 2.12 (s, 3H). $^{19}$F NMR (DMSO-d6): δ –118.65 (s).LCMS: rt 5.56 min (A), purity 97%, MS (m/e) 321 (MH$^+$).

5-(2-m-Tolylpyridin-3-yl)benzo[d]thiazole (Compound 164). LCMS: rt 5.23 min (A), purity 97%, MS (m/e) 303 (MH$^+$).

6-(2-(4-Fluoro-3-methylphenyl)pyridin-3-yl)imidazo[1,2-a]pyridine (Compound 165). $^1$H NMR (DMSO-d6): δ 8.69

(s, 2H), 8.02 (s, 1H), 7.92 (d, 1H, J=1.5 and 7.6 Hz), 7.72 (s, 1H), 7.52-7.49 (m, 2H), 7.44 (d, 1H, J=7.2 Hz), 7.09-7.04 (m, 1H), 7.00-6.94 (m, 2H), 2.16 (s, 3H).$^{19}$F NMR (DMSO-d6): δ −118.16 (s).LCMS: rt 3.56 min (A), purity 97%, MS (m/e) 304 (MH$^+$).

6-(2-m-Tolylpyridin-3-yl)imidazo[1,2-a]pyridine (Compound 166). $^1$H NMR (DMSO-d6): δ 8.68 (d, 1H, J=5.7 Hz), 8.57 (s, 1H), 7.92-7.89 (m, 2H), 7.55 (s, 1H), 7.48 (dd, 1H, J=4.9 and 8.1 Hz), 7.38 (d, 1H, J=8.3 Hz), 7.31 (s, 1H), 7.10-7.04 (app m, 2H), 7.04-7.02 (app m, 1H), 6.79 (d, 1H, J=8.4 Hz), 2.22 (s, 3H).LCMS: rt 3.05 min (A), purity 97%, MS (m/e) 286 (MH$^+$).

5-(2-(3-Isopropylphenyl)pyridin-3-yl)-1H-pyrazolo[3,4-b]pyridine (Compound 167). LCMS: rt 4.81 min (A), purity 97%, MS (m/e) 315 (MH$^+$).

5-(2-(3-tert-Butylphenyl)pyridin-3-yl)-1H-pyrazolo[3,4-b]pyridine (Compound 168). LCMS: rt 5.08 min (A), purity 97%, MS (m/e) 329 (MH$^+$).

5-(2-(3-Biphenyl)pyridin-3-yl)-1H-pyrazolo[3,4-b]pyridine (Compound 169). LCMS: rt 5.30 min (A), purity 97%, MS (m/e) 349 (MH$^+$).

5-(2-(3-Cyclopentenylphenyl)pyridin-3-yl)-1H-pyrazolo[3,4-b]pyridine (Compound 170). LCMS: rt 5.33 min (A), purity 97%, MS (m/e) 339 (MH$^+$).

5-(2-(4-Fluoro-3-methylphenyl)pyridin-3-yl)-6-methyl-1H-indazole (Compound 173). $^1$H NMR (DMSO-d6): δ 8.75 (dd, 1H, J=1.4 and 4.9 Hz), 7.98 (s, 1H), 7.93 (dd, 1H, J=1.4 and 7.6 Hz), 7.61 (dd, 1H, J=4.9 and 7.6 Hz), 7.53 (s, 1H), 7.37 (d, 1H, J=7.6 Hz), 7.33 (s, 1H), 7.02-6.97 (m, 1H), 6.98 (t, 1H, J=8.8 Hz), 2.07 (s, 3H), 1.93 (s, 3H). $^{19}$F NMR (DMSO-d6): δ −117.35 (s).LCMS: rt 5.01 min(A), purity 97%, MS (m/e) 318 (MH$^+$).

6-Methyl-5-(2-m-tolylpyridin-3-yl)-1H-indazole (Compound 174). LCMS: rt 4.73 min (A), purity 97%, MS (m/e) 300 (MH$^+$).

5-(2-(4-Fluoro-3-methylphenyl)pyridin-3-yl)-7-methyl-1H-indazole (Compound 175). $^1$H NMR (DMSO-d6): δ 8.69 (d, 1H, J=1.7 and 4.9 Hz), 8.08 (d, 1H, J=7.6 Hz), 8.02 (s, 1H), 7.64 (app t, 1H, J=7.6 Hz), 7.43-7.41 (app m, 2H), 7.01-6.91 (m, 3H), 2.40 (s, 3H), 2.13 (s, 3H). $^{19}$F NMR (DMSO-d6): δ −117.30 (s).LCMS: rt 4.80 min, purity 97%, MS (m/e) 318 (MH$^+$).

7-Methyl-5-(2-m-tolylpyridin-3-yl)-1H-indazole (Compound 176). $^1$H NMR (DMSO-d6): δ 13.04 (s, 1H), 8.73 (d, 1H, J=2.8 Hz), 8.14 (d, 1H, J=7.9 Hz), 8.00 (s, 1H), 7.69 (dd, 1H, J=4.9 and 7.9 Hz), 7.41 (s, 1H), 7.31 (s, 1H), 7.14-7.06 (m, 2H), 6.97 (d, 1H, J=7.2 Hz), 6.90 (s, 1H), 2.38 (s, 3H), 2.21 (s, 3H).LCMS: rt 5.03 min (A), purity 97%, MS (m/e) 300 (MH$^+$).

6-(2-(4-Fluoro-3-methylphenyl)pyridin-3-yl)-1H-benzo[d]imidazole (Compound 177). $^1$H NMR (DMSO-d6): δ 8.62 (d, 1H, J=0.2 and 3.7 Hz), 8.24 (s, 1H), 7.83 (dd, 1H, J=1.5 and 7.6 Hz), 7.49 (d, 1H, =8.1 Hz), 7.45 (d, 1H, J=4.7 Hz), 7.43-7.42 (m, 1H), 7.36 (d, 1H, J=7.3 Hz), 6.96-6.84 (m, 3H), 2.11 (s, 3H).).$^{19}$F NMR (DMSO-d6): δ −118.99 (s).LCMS: rt 3.41 min, purity 97%, MS (m/e) 304 (MH$^+$).

6-(2-m-Tolylpyridin-3-yl)-1H-benzo[d]imidazole (Compound 178). $^1$H NMR (DMSO-d6): δ 8.64 (d, 1H, J=5.1 Hz), 8.42 (s, 1H), 7.84 (d, 1H, J=7.3 Hz), 7.51 (d, 1H, J=8.5 Hz), 7.44 (dd, 1H, J=4.5 and 7.5 Hz), 7.26 (s, 1H), 7.02 (s, 2H), 6.98 (d, 1H, J=7.6 Hz), 6.90 (d, 1H, J=7.3 Hz), 2.18 (s, 3H).LCMS: rt 1.75 min (A), purity 97%, MS (m/e) 286 (MH$^+$).

6-(2-(4-Fluoro-3-methylphenyl)pyridin-3-yl)benzo[d]oxazole (Compound 180). $^1$H NMR (DMSO-d6): δ 8.71 (d, 1H, J=2.0 Hz), 8.66 (app d, 1H, J=2.8 Hz), 7.87 (d, 1H, J=7.3 Hz), 7.69 (d, 1H, J=8.8 Hz), 7.68 (app s, 1H), 7.47 (dd, 1H, J=4.8 and 7.9 Hz), 7.33 (d, 1H, J=7.0 Hz), 7.12 (dd, 1H, J=1.7 and 8.4 Hz), 6.93-6.87 (m, 2H), 2.12 (s, 3H). $^{19}$F NMR (DMSO-d6): δ −118.61 (s).LCMS: rt 5.33 min (A), purity 97%, MS (m/e) 305 (MH$^+$).

6-(2-m-Tolylpyridin-3-yl)benzo[d]oxazole (Compound 181). LCMS: rt 4.90 min (A), purity 92%, MS (m/e) 287 (MH$^+$).

2-Ethyl-5-(2-(4-fluoro-3-methylphenyl)pyridin-3-yl)-2H-indazole (Compound 182). $^1$H NMR (DMSO-d6): δ 8.69 (d, 1H, J=4.9 Hz), 8.37 (s, 1H), 8.02 (d, 1H, J=7.9 Hz), 7.63 (s, 1H), 7.60 (dd, 1H, J=5.2 and 7.6 Hz), 7.45 (app t 2H, J=9.1 Hz), 7.02-6.92 (app m, 2H), 6.88 (d, 1H, J=8.1 Hz), 4.35 (qt, 2H, J=7.0 Hz), 2.14 (s, 3H), 1.48 (t, 3H, J=7.0 Hz). $^{19}$F NMR (DMSO-d6): δ −117.62 (s).LCMS: rt 5.30 min (A), purity 97%, MS (m/e) 332 (MH$^+$).

2-Ethyl-5-(2-m-tolylpyridin-3-yl)-2H-indazole (Compound 183). LCMS: rt 5.06 min (A), purity 97%, MS (m/e) 314 (MH$^+$).

1-Ethyl-5-(2-(4-fluoro-3-methylphenyl)pyridin-3-yl)-1H-indazole (Compound 184). $^1$H NMR (DMSO-d6): δ 8.70 (dd, 1H, J=1.7 and 4.9 Hz), 8.08-8.04 (m, 2H), 7.68 (d, 1H, J=0.9 Hz), 7.66-7.55 (m, 1H), 7.57 (d, 1H, J=8.8 Hz), 7.40 (d, 1H, J=7.9 Hz), 7.05 (dd, 1H, J=1.8 and 8.8 Hz), 7.03-6.92 (m, 2H), 4.39 (qt, 2H, J−7.0 Hz), 2.13 (s, 3H), 1.35 (t, 3H, J=7.3 Hz).$^{19}$F NMR (DMSO-d6): δ −117.42 (s).LCMS: rt 5.71 min(A), purity 97%, MS (m/e) 332 (MH$^+$).

1-Ethyl-5-(2-m-tolylpyridin-3-yl)-1H-indazole (Compound 185). LCMS: rt 5.43 min (A), purity 97%, MS (m/e) 314 (MH$^+$).

6-(2-(4-Fluoro-3-methylphenyl)pyridin-3-yl)-[1,2,4]triazolo[1,5-a]pyridine (Compound 191). $^1$H NMR (DMSO-d6): δ 9.01 (t, 1H, J=0.77 Hz), 8.71 (dd, 1H, J=1.7 and 4.7 Hz), 8.50 (s, 1H), 8.00 (dd, 1H, J=1.7 and 7.9 Hz), 7.70 (dd, 1H, J=1.7 and 9.1 Hz), 7.51 (dd, 1H, J=4.6 and 7.6 Hz), 7.43 (dd, 1H, J=1.7 and 7.9 Hz), 7.23 (dd, 1H, J=1.7 and 9.3 Hz), 7.08-7.04 (m, 1H), 6.97 (app t, 1H, J=9.3 Hz), 2.16 (s, 3H).$^{19}$F NMR (DMSO-d6): δ −118.12 (s).LCMS: 4.76 min (A), purity 97%, MS (m/e) 305 (MH$^+$).

6-(2-m-Tolylpyridin-3-yl)-[1,2,4]triazolo[1,5-a]pyridine (Compound 192). $^1$H NMR (DMSO-d6): δ 8.98 (s, 1H), 8.72 (dd, 1H, J=1.7 and 4.7 Hz), 8.49 (s, 1H), 8.01 (d, 1H, J=1.7 and 7.9 Hz), 7.68 (d, 1H, J=9.2 Hz), 7.54-7.49 (m, 1H), 7.30 (s, 1H), 7.23 (dd, 1H, J=1.4 and 7.6 Hz), 7.10-7.09 (app m, 2H), 7.03-7.02 (m, 1H), 2.22 (s, 3H).$^{19}$F NMR (DMSO-d6): δ −118.31 (s).LCMS: rt 4.31 min (A), purity 95%, MS (m/e) 287 (MH$^+$).

6-(2-(3-Cyclopropylphenyl)pyridin-3-yl)H-imidazo[1,2-a]pyridine (Compound 193). $^1$H NMR (DMSO-d6): δ 8.68 (dd, 1H, J=1.7 and 4.7 Hz), 8.53 (app s, 1H), 7.91 (dd, 1H, J=1.6 and 9.3 Hz), 7.90 (s, 1H), 7.53 (d, 1H, J=1.2 Hz), 7.46 (dd, 1H, J=4.6 and 7.6 Hz), 7.38 (dd, 1H, J=9.3 Hz), 7.12-7.04 (m, 2H), 7.02-6.99 (m, 2H), 6.78 (dd, 1H, J=1.7 and 9.3 Hz), 1.81-1.76 (m, 1H), 0.79-0.75 (m, 2H), 0.36-0.32 (m, 2H).LCMS: rt 4.73 min (A), purity 97%, MS (m/e) 312 (MH$^+$).

6-(2-(3-Cyclopropylphenyl)pyridin-3-yl)benzo[d]thiazole (Compound 194). $^1$H NMR (DMSO-d6): δ 9.19 (s, 1H), 8.68 (dd, 1H, J=1.4 and 4.7 Hz), 8.05 (d, 1H, J=1.2 Hz), 7.96 (d, 1H, J=8.5 Hz), 7.86 (app dd, 1H, J=1.4 and 7.6 Hz), 7.47 (dd, 1H, J=4.7 and 7.6 Hz), 7.21 (dd, 1H, J=1.7 and 7.6 Hz), 7.09-7.07 (m, 2H), 6.99-6.97 (m, 1H), 6.84 (s, 1H), 1.76-1.71 (m, 1H), 0.75-0.69 (m, 2H), 0.24-0.19 (m, 2H).LCMS: rt 5.53 min (A), purity 97%, MS (m/e) 329 (MH$^+$).

5-(2-(3-(Trifluoromethyl)phenyl)pyridin-3-yl)-1H-indazole (Compound 197). $^1$H NMR (DMSO-d6): δ 13.02 (s, 1H), 8.70 (dd, 1H, J=1.4 and 4.7 Hz), 8.04 (s, 1H), 7.91 (dd, 1H, J=0.7 and 7.6 Hz), 7.68 (s, 1H), 7.63 (s, 1H), 7.58 (d, 1H, J=8.2 Hz), 7.54-7.50 (m, 2H), 7.50-7.41 (m, 2H), 7.03 (d, 1H, J=8.5 Hz).$^{19}$F NMR (DMSO-d6): δ −61.47.LCMS: rt 5.78 min (A), purity 97%, MS (m/e) 340 (MH$^+$).

5-(2-(3-(Trifluoromethyl)phenyl)pyridin-3-yl)-1H-pyrazolo[3,4-b]pyridine (Compound 198). $^1$H NMR (DMSO-d6): δ 13.65 (s, 1H), 8.75 (dd, 1H, J=1.7 and 4.7 Hz), 8.20 (d, 1H, J=2.0 Hz), 8.15 (d, 1H, J=1.4 Hz), 8.12 (s, 1H), 7.99 (d, 1H, J=1.4 and 7.9 Hz), 7.64-7.44 (m, 5H).$^{19}$F NMR (DMSO-d6): δ −61.40.LCMS: rt 5.55 min (A), purity 97%, MS (m/e) 341 (MH$^+$).

6-(2-(3-(Trifluoromethyl)phenyl)pyridin-3-yl)H-imidazo[1,2-a]pyridine (Compound 199). $^1$H NMR (DMSO-d6): δ 8.62 (dd, 1H, J=1.4 and 4.7 Hz), 8.06 (s, 1H), 7.65 (dd, 1H, J=1.7 and 8.2 Hz), 7.46-7.42 (m, 3H), 7.05-7.04 (m, 2H), 6.97-6.95 (m, 1H), 6.90 (s, 1H), 6.85 (dd, 1H, J=1.4 and 8.2 Hz), 3.86 (s, 3H), 1.76-1.69 (m, 1H), 0.84-0.70 (m, 2H), 0.28-0.23 (m, 2H).LCMS: rt 4.68 min (A), purity 97%, MS (m/e) 340 (MH$^+$).

6-(2-(3-Cyclopropylphenyl)pyridin-3-yl)-1-methyl-1H-benzo[d]imidazole (Compound 200). $^1$H NMR (DMSO-d6): δ 8.63 (dd, 1H, J=1.4 and 4.7 Hz), 8.12 (s, 1H), 7.85 (dd, 1H, J=1.7 and 8.2 Hz), 7.48-7.42 (m, 3H), 7.05-7.04 (app m, 2H), 6.97-6.95 (m, 1H), 6.90 (s, 1H), 6.85 (dd, 1H, J=1.4 and 8.2 Hz), 3.73 (s, 3H), 1.78-1.69 (m, 1H), 0.76-0.70 (m, 2H), 0.28-0.23 (m, 2H).LCMS: rt 3.68 min (A), purity 97%, MS (m/e) 326 (MH$^+$).

5-(2-(3-Cyclopropylphenyl)pyridin-3-yl)-1-methyl-1H-benzo[d]imidazole (Compound 201). $^1$H NMR (DMSO-d6): δ 8.63 (dd, 1H, J=1.4 and 4.7 Hz), 8.16 (s, 1H), 7.82 (dd, 1H, J=1.4 and 7.6 Hz), 7.82 (dd, 1H, J=1.4 and 7.6 Hz), 7.47-7.41 (m, 3H), 7.05-6.67 (m, 5H), 3.81 (s, 3H), 1.78-1.71 (m, 1H), 0.78-0.72 (m, 2H), 0.31-0.26 (m, 3H).LCMS: rt 3.76 min (A), purity 97%, MS (m/e) 326 (MH$^+$).

6-(2-(3-Cyclopropylphenyl)pyridin-3-yl)-[1,2,4]triazolo[1,5-a]pyridine (Compound 202). $^1$H NMR (DMSO-d6): δ 8.96 (s, 3H), 8.72 (dd, 1H, J=1.7 and 4.9 Hz), 8.50 (s, 1H), 7.99 (dd, 1H, J=1.4 and 7.6 Hz), 7.69 (dd, 1H, J=0.9 and 9.1 Hz), 7.52 (dd, 1H, J=4.7 and 7.7 Hz), 7.24 (dd, 1H, J=0.8 and 9.1 Hz), 7.14 (m, 2H), 7.03 (s, 1H), 6.98 (m, 1H), 1.78-1.71 (m, 1H), 0.82-0.72 (m, 2H), 0.31-0.30 (m, 2H).LCMS: rt 4.93 min (A), purity 97%, MS (m/e) 313 (MH$^+$).

6-(2-(3-Isopropylphenyl)pyridin-3-yl)-1-methyl-1H-benzo[d]imidazole (Compound 204). LCMS: rt 4.16 min (A), purity 97%, MS (m/e) 328 (MH$^+$).

6-(2-(3-Cyclopropylphenyl)pyridin-3-yl)-1H-benzo[d]imidazole (Compound 205). LCMS: rt 3.80 min (A), purity 97%, MS (m/e) 312 (MH$^+$).

6-(2-(3-Isopropylphenyl)pyridin-3-yl)-1H-benzo[d]imidazole (Compound 206). LCMS: rt 4.06 min (A), purity 97%, MS (m/e) 314 (MH$^+$).

6-(2-(4-Fluoro-3-methylphenyl)pyridin-3-yl)quinoline (Compound 207). $^1$H NMR (DMSO-d6): δ 9.11 (dd, 1H, J=1.4 and 4.7 Hz), 8.77 (dd, 2H, J=1.4 and 4.9 Hz), 8.20 (d, 1H, 1.4 Hz), 8.13-8.08 (m, 2H), 7.84 (dd, 1H, J=4.8 and 8.2 Hz), 7.66-7.59 (m, 2H), 7.40 (d, 1H, J=7.6 Hz), 6.99-6.90 (m, 2H), 2.12 (s, 3H).$^{19}$F NMR (DMSO-d6): δ −117.48 (s).LCMS: rt 4.23 min (A), purity 97%, MS (m/e) 315 (MH$^+$).

6-(2-m-Tolylpyridin-3-yl)quinoline (Compound 208). $^1$H NMR (300 MHz, DMSO-d$_6$): δ 9.02 (dd, J=4.6, 1.6 Hz, 1H), 8.75 (dd, J=4.9, 1.7 Hz, 1H), 8.59 (d, J=7.7 Hz, 1H), 8.09 (d, J=1.9 Hz, 1H), 8.06 (dd, J=7.8, 1.7 Hz, 1H), 8.01 (d, J=8.8 Hz, 1H), 7.72 (dd, J=8.3, 4.6 Hz, 1H), 7.61 (dd, J=7.8, 4.9 Hz, 1H), 7.53 (dd, J=8.8, 2.0 Hz, 1H), 7.28 (dd, J=1.5, 0.9 Hz, 1H), 7.14-7.01 (m, 2H), 6.96 (ddd, J=6.4, 2.5, 1.4 Hz, 1H), 2.18 (s, 3H). LCMS: rt 3.88 min (A), purity 99%, MS (m/e) 297 (MH$^+$).

7-(2-(4-Fluoro-3-methylphenyl)pyridin-3-yl)isoquinoline (Compound 209). LCMS: rt 4.12 min (A), purity 97%, MS (m/e) 315 (MH$^+$).

7-(2-m-Tolylpyridin-3-yl)isoquinoline (Compound 210). $^1$H NMR (300 MHz, DMSO-d6): δ 9.69 (s, 1H), 8.79 (dd, J=4.9, 1.6 Hz, 1H), 8.64 (d, J=6.3 Hz, 1H), 8.45 (s, 1H), 8.30 (s, 1H), 8.08 (s, 2H), 7.84-7.50 (m, 2H), 7.28 (s, 1H), 7.07 (dt, J=14.8, 7.5 Hz, 2H), 6.96 (d, J=7.2 Hz, 1H), 2.19 (s, 3H). LCMS: rt 3.75 min (A), purity 99%, MS (m/e) 296 (MH$^+$).

Example 45

Synthetic scheme towards the preparation of 6-(2-(4-fluoro-3-methylphenyl)pyridin-3-yl)-1-(subtituted)-1H-benzo[d]imidazole

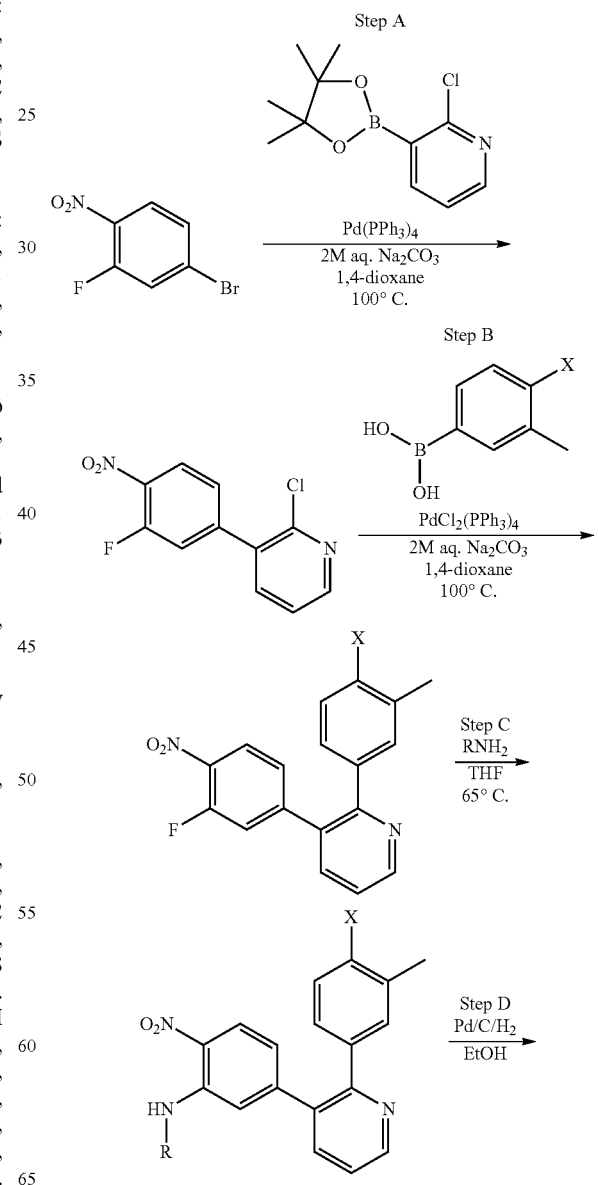

-continued

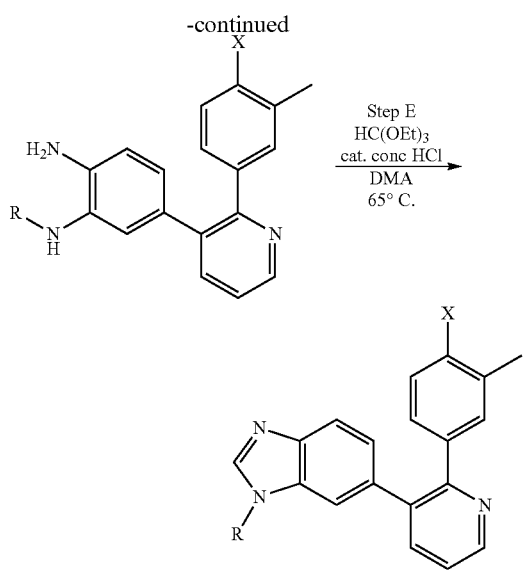

X = F, H

Example 46

6-(2-(4-Fluoro-3-methylphenyl)pyridin-3-yl)-1-(2-morpholinoethyl)-1H-benzo[d]imidazole (Compound 35)

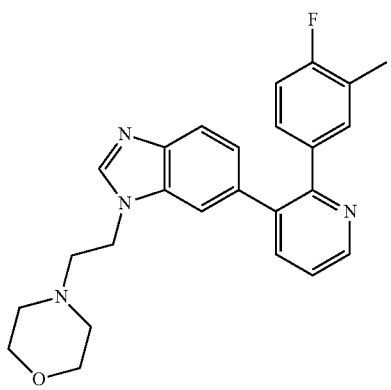 [SMILES: Cc1cc(-c2ncccc2-c2ccc3ncn(CCN4CCOCC4)c3c2)ccc1F]

Step C: 5-(2-(4-Fluoro-3-methylphenyl)pyridin-3-yl)-N-(2-morpholinoethyl)-2-nitrobenzenamine To solution of 2-(4-fluoro-3-methylphenyl)-3-(3-fluoro-4-nitrophenyl)pyridine (100 mg) in 2 ml, THF was added 2-morpholinoethanamine (64 uL) and K$_2$CO$_3$ (76 mg). The reaction was heated at 60° C. for 15 hours in a sealed vial. The reaction mixture was cooled to room temperature, concentrated by rotary evaporation under vacuum and partitioned the concentrate between CH$_2$Cl$_2$/water. The organic layer was separated, dried with anhydrous Na$_2$SO$_4$, filtered and evaporated. The crude residue of 5-(2-(4-fluoro-3-methylphenyl)pyridin-3-yl)-N-(2-morpholinoethyl)-2-nitrobenzenamine was used in the next step with no further purification.

Step D: 5-(2-(4-Fluoro-3-methylphenyl)pyridin-3-yl)-N-(2-morpholino ethyl)-2-nitrobenzenamine The above residue of 5-(2-(4-fluoro-3-methylphenyl)pyridin-3-yl)-N-(2-morpholinoethyl)-2-nitrobenzenamine was dissolved in 2 mL EtOH and charged with Pd/C (25 mg) and the reaction was hydrogenated overnight under a hydrogen balloon atmosphere. The reaction was filtered through a bed of celite and evaporated. Subsequently the crude containing 5-(2-(4-fluoro-3-methylphenyl)pyridin-3-yl)-N-(2-morpholinoethyl)-2-nitrobenzenamine was used in the next with no further purification.

Step E: 6-(2-(4-Fluoro-3-methylphenyl)pyridin-3-yl)-1-(2-morpholino ethyl)-1H-benzo[d]imidazole The above residue containing 5-(2-(4-fluoro-3-methylphenyl)pyridin-3-yl)-N-(2-morpholinoethyl)-2-nitrobenzenamine was added DMA (1 mL), triethyl orthoformate (250 uL) and treated with one drop of concentrated HCl. The homogeneous solution was heated at 65° C. for 15 hours in a sealed vial. The reaction was cooled and the volatiles were removed with a stream of nitrogen gas. The residue was triturated with aq. NaHCO$_3$, resulting solid collected by filtration and purified by HPLC to yield 25 mg of the desired product 6-(2-(4-fluoro-3-methylphenyl)pyridin-3-yl)-1-(2-morpholino ethyl)-1H-benzo[d]imidazole. $^1$H NMR (DMSO-d6): δ 8.58 (dd, J=4.7, 1.6 Hz, 1H), 8.15 (s, 1H), 7.84 (dd, J=7.8, 1.6 Hz, 1H), 7.56 (d, J=8.3 Hz, 1H), 7.43 (dd, J=7.8, 4.7 Hz, 1H), 7.28 (d, J=4.8 Hz, 2H), 7.05 (dd, J=8.3, 1.5 Hz, 1H), 7.03-6.75 (m, 2H), 4.19 (t, J=6.4 Hz, 2H), 3.55-3.36 (m, 4H), 2.44-2.15 (m, 6H), 2.06 (s, 3H). MS (m/e): 417 (MH$^+$).

Example 47

6-(2-(4-Fluoro-3-methylphenyl)pyridin-3-yl)-1-isopropyl-1H-benzo[d]imidazole (Compound 48)

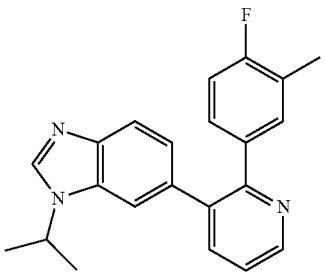 [SMILES: Cc1cc(-c2ncccc2-c2ccc3ncn(C(C)C)c3c2)ccc1F]

In like manner to the preparation of 6-(2-(4-Fluoro-3-methylphenyl)pyridin-3-yl)-1-(2-morpholinoethyl)-1H-benzo[d]imidazole, the reaction of 2-(4-fluoro-3-methylphenyl)-3-(3-fluoro-4-nitrophenyl)pyridine and propan-2-amine yielded 6-(2-(4-Fluoro-3-methylphenyl)pyridin-3-yl)-1-isopropyl-1H-benzo[d]imidazole. $^1$H NMR (DMSO-d6): δ 9.58 (s, 1H), 8.75 (d, J=4.9 Hz, 1H), 8.11 (d, J=7.8 Hz, 1H), 7.89 (s, 1H), 7.79 (d, J=8.5 Hz, 1H), 7.65 (dd, J=7.8, 5.0 Hz, 1H), 7.43-7.29 (m, 2H), 7.15-6.87 (m, 2H), 4.98-4.79 (m, 1H), 2.11 (s, 3H), 1.48 (d, J=6.6 Hz, 6H). MS (m/e): 346 (MH$^+$).

Example 48

1-(2-Morpholinoethyl)-6-(2-m-tolylpyridin-3-yl)-1H-benzo[d]imidazole (Compound 36)

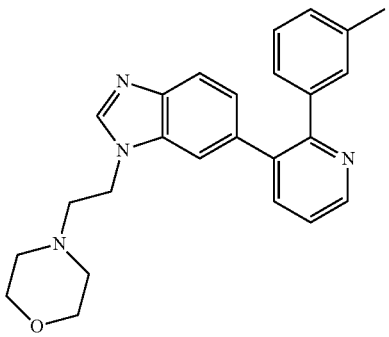 [SMILES: Cc1cccc(-c2ncccc2-c2ccc3ncn(CCN4CCOCC4)c3c2)c1]

In like manner to the preparation of 6-(2-(4-Fluoro-3-methylphenyl)pyridin-3-yl)-1-(2-morpholino ethyl)-1H-benzo[d]imidazole, the reaction of 2-(3-methylphenyl)-3-(3-fluoro-4-nitrophenyl)pyridine and 2-morpholinoethanamine yielded 1-(2-Morpholinoethyl)-6-(2-m-tolylpyridin-3-yl)-1H-benzo[d]imidazole. $^1$H NMR (DMSO-d6): δ 9.46 (s, 1H), 8.81 (dd, J=5.0, 1.3 Hz, 1H), 8.23 (dd, J=7.8, 1.3 Hz, 1H), 8.05 (s, 1H), 7.89-7.62 (m, 2H), 7.33 (s, 1H), 7.18-7.07 (m, 3H), 6.96 (d, J=7.3 Hz, 1H), 4.88 (m, 2H), 3.84 (s, 4H), 3.62 (m, 2H), 3.34 (s, 4H) 2.22 (s, 3H). MS (m/e): 399 (MH$^+$).

Example 49

6-(2-(4-Fluoro-3-methylphenyl)pyridin-3-yl)-1-(2-(4-methylpiperazin-1-yl)ethyl)-1H-benzo[d]imidazole (Compound 37)

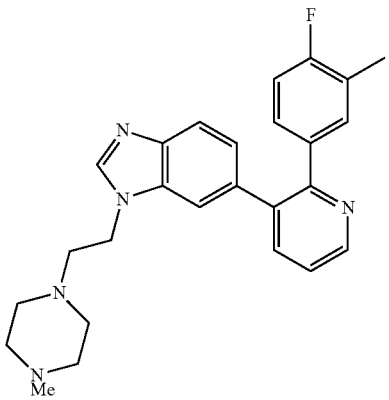 [SMILES: Cc1cc(-c2ncccc2-c2ccc3ncn(CCN4CCN(C)CC4)c3c2)ccc1F]

In like manner to the preparation of 6-(2-(4-Fluoro-3-methylphenyl)pyridin-3-yl)-1-(2-morpholinoethyl)-1H-benzo[d]imidazole, the reaction of 2-(4-fluoro-3-methylphenyl)-3-(3-fluoro-4-nitrophenyl)pyridine and 2-(4-methylpiperazin-1-yl)ethanamine yielded 6-(2-(4-Fluoro-3-methylphenyl)pyridin-3-yl)-1-(2-(4-methylpiperazin-1-yl)ethyl)-1H-benzo[d]imidazole. $^1$H NMR (DMSO-d6): δ 9.52 (d, J=1.3 Hz, 1H), 8.89-8.65 (m, 1H), 8.19 (dd, J=7.8, 1.6 Hz, 1H), 7.95 (s, 1H), 7.89-7.65 (m, 2H), 7.46-7.20 (m, 2H), 7.11 (t, J=7.7 Hz, 1H), 6.95 (d, J=5.7 Hz, 1H), 4.55 (s, 2H), 2.82-2.75 (m, 10H), 2.52 (s, 3H), 2.20 (s, 3H). MS (m/e): 430 (MH$^+$).

Example 50

1-(3-Ethoxypropyl)-6-(2-m-tolylpyridin-3-yl)-1H-benzo[d]imidazole (Compound 39)

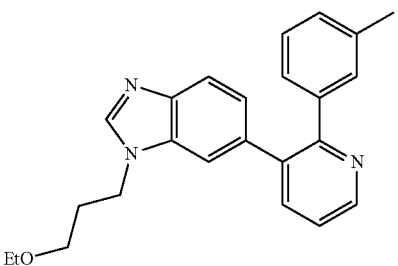 [SMILES: CCOCCCn1cnc2ccc(-c3cccnc3-c3cccc(C)c3)cc21]

In like manner to the preparation of 6-(2-(4-Fluoro-3-methylphenyl)pyridin-3-yl)-1-(2-morpholino ethyl)-1H-benzo[d]imidazole, the reaction of 2-(3-methylphenyl)-3-(3-fluoro-4-nitrophenyl)pyridine and 3-ethoxypropan-1-amine yielded 1-(3-Ethoxypropyl)-6-(2-m-tolylpyridin-3-yl)-1H-benzo[d]imidazole. $^1$H NMR (DMSO-d6): δ 9.55 (d, J=1.2 Hz, 1H), 8.97-8.67 (m, 1H), 8.32-8.13 (m, 1H), 7.86 (s, 1H), 7.82-7.66 (m, 2H), 7.36 (d, J=8.6 Hz, 1H), 7.25 (s, 1H), 7.21-7.01 (m, 2H), 6.96 (d, J=6.4 Hz, 1H), 4.45 (t, J=6.7 Hz, 2H), 3.43-3.10 (m, 4H), 2.19 (s, 3H), 2.00-1.78 (m, 2H), 0.95 (td, J=7.0, 1.1 Hz, 3H). MS (m/e): 372 (MH$^+$).

Example 51

6-(2-(4-Fluoro-3-methylphenyl)pyridin-3-yl)-1-(3-(4-methylpiperazin-1-yl)propyl)-1H-benzo[d]imidazole (Compound 40)

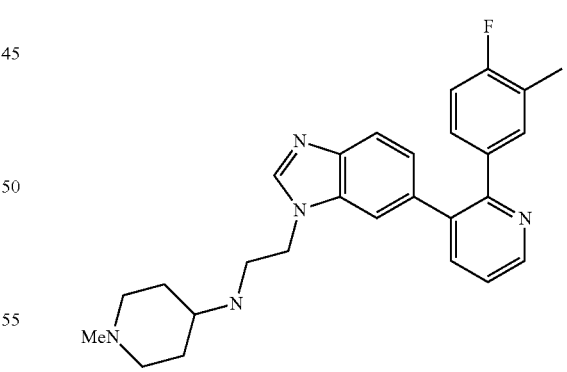

In like manner to the preparation of 6-(2-(4-Fluoro-3-methylphenyl)pyridin-3-yl)-1-(2-morpholinoethyl)-1H-benzo[d]imidazole, the reaction of 2-(4-fluoro-3-methylphenyl)-3-(3-fluoro-4-nitrophenyl)pyridine and 2-(4-methylpiperazin-1-yl)ethanamine yielded 6-(2-(4-Fluoro-3-methylphenyl)pyridin-3-yl)-1-(2-(4-methylpiperazin-1-yl)ethyl)-1H-benzo[d]imidazole. $^1$H NMR (DMSO-d6): δ 9.42 (s, 1H), 8.79 (d, J=5.4 Hz, 1H), 8.74-7.84 (m, 1H), 7.75 (d, J=8.6 Hz, 2H), 7.35 (d, J=8.5 Hz, 1H), 7.07-6.63 (m, 2H), 4.55 (s, 2H), 3.15 (s, 2H), 2.93-2.86 (m, 8H), 2.78 (s, 2H), 2.52 (s, 3H), 2.09 (s, 3H). MS (m/e): 444 (MH⁺).

Example 52

3-(6-(2-(4-Fluoro-3-methylphenyl)pyridin-3-yl)-1H-benzo[d]imidazol-1-yl)propan-1-ol (Compound 41)

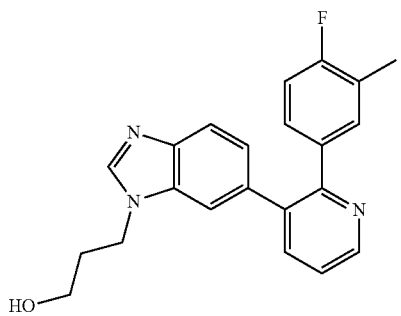 [SMILES: Cc1cc(-c2ncccc2-c2ccc3ncn(CCCO)c3c2)ccc1F]

In like manner to the preparation of 6-(2-(4-fluoro-3-methylphenyl)pyridin-3-yl)-1-(2-morpholinoethyl)-1H-benzo[d]imidazole, the reaction of 2-(4-fluoro-3-methylphenyl)-3-(3-fluoro-4-nitrophenyl)pyridine and 3-aminopropan-1-ol yielded 3-(6-(2-(4-Fluoro-3-methylphenyl)pyridin-3-yl)-1H-benzo[d]imidazol-1-yl)propan-1-ol. ¹H NMR (DMSO-d6): δ 9.51 (s, 1H), 8.78 (dd, J=5.1, 1.5 Hz, 1H), 8.37-8.13 (m, 1H), 7.87 (s, 1H), 7.82-7.69 (m, 2H), 7.35 (dd, J=8.5, 1.4 Hz, 2H), 6.98 (dd, J=9.5, 5.7 Hz, 2H), 3.35 (t, J=5.7 Hz, 2H), 2.52 (s, 2H), 2.10 (s, 3H), 1.95-1.62 (m, 2H). MS (m/e): 362 (MH⁺).

Example 53

1-(3-Ethoxypropyl)-6-(2-(4-fluoro-3-methylphenyl)pyridin-3-yl)-1H-benzo[d]imidazole (Compound 42)

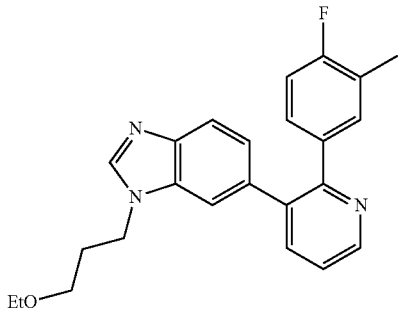

In like manner to the preparation of 6-(2-(4-Fluoro-3-methylphenyl)pyridin-3-yl)-1-(2-morpholinoethyl)-1H-benzo[d]imidazole, the reaction of 2-(4-fluoro-3-methylphenyl)-3-(3-fluoro-4-nitrophenyl)pyridine and 3-ethoxypropan-1-amine yielded 1-(3-ethoxypropyl)-6-(2-(4-Fluoro-3-methylphenyl)pyridin-3-yl)-1H-benzo[d]imidazole. ¹H NMR (DMSO-d6): δ 9.55 (d, J=1.3 Hz, 1H), 8.83-8.65 (m, 1H), 8.10 (dd, J=7.8, 1.6 Hz, 1H), 7.87 (s, 1H), 7.80 (d, J=8.5 Hz, 1H), 7.72-7.58 (m, 1H), 7.46-7.26 (m, 2H), 6.96 (t, J=7.2 Hz, 2H), 4.46 (t, J=6.5 Hz, 2H), 3.32-3.25 (m, 4H), 2.11 (s, 3H), 2.02-1.74 (m, 2H), 0.96 (t, J=7.0, 3H). MS (m/e): 390 (MH⁺).

Example 54

1-Ethyl-6-(2-m-tolylpyridin-3-yl)-1H-benzo[d]imidazole (Compound 43)

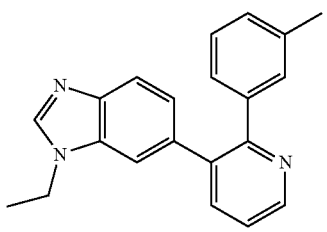 [SMILES: CCn1cnc2ccc(-c3cccnc3-c3cccc(C)c3)cc21]

In like manner to the preparation of 6-(2-(4-Fluoro-3-methylphenyl)pyridin-3-yl)-1-(2-morpholino ethyl)-1H-benzo[d]imidazole, the reaction of 2-(3-methylphenyl)-3-(3-fluoro-4-nitrophenyl)pyridine and ethanamine yielded 1-Ethyl-6-(2-m-tolylpyridin-3-yl)-1H-benzo[d]imidazole ¹H NMR (DMSO-d6): δ 9.53 (s, 1H), 8.77 (dd, J=5.0, 1.5 Hz, 1H), 8.13 (dd, J=7.8, 1.5 Hz, 1H), 7.92 (s, 1H), 7.76 (d, J=8.6 Hz, 1H), 7.67 (dd, J=7.8, 5.0 Hz, 1H), 7.43-7.19 (m, 2H), 7.16-6.97 (m, 2H), 6.93 (d, J=6.6 Hz, 1H), 4.42 (q, J=7.2 Hz, 2H), 2.20 (s, 3H), 1.35 (t, J=7.2 Hz, 3H). MS (m/e): 314 (MH⁺).

Example 55

1-(Tetrahydro-2H-pyran-4-yl)-6-(2-m-tolylpyridin-3-yl)-1H-benzo[d]imidazole (Compound 44)

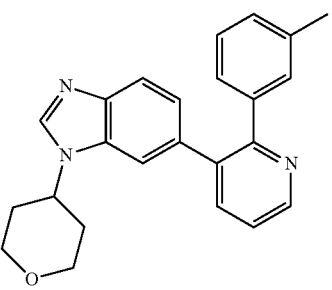 [SMILES: Cc1cccc(-c2ncccc2-c2ccc3ncn(C4CCOCC4)c3c2)c1]

In like manner to the preparation of 6-(2-(4-Fluoro-3-methylphenyl)pyridin-3-yl)-1-(2-morpholino ethyl)-1H-benzo[d]imidazole, the reaction of 2-(3-methylphenyl)-3-(3-fluoro-4-nitrophenyl)pyridine and tetrahydro-2H-pyran-4-amine yielded 1-(tetrahydro-2H-pyran-4-yl)-6-(2-m-tolylpyridin-3-yl)-1H-benzo[d]imidazole ¹H NMR (DMSO-d6): δ 9.59 (d, J=1.3 Hz, 1H), 8.90-8.68 (m, 1H), 8.27-8.11 (m, 1H), 7.96 (s, 1H), 7.89-7.63 (m, 2H), 7.75-7.61 (m, 1H), 7.38 (d, J=8.6 Hz, 1H), 7.30 (s, 1H), 7.19-6.98 (m, 2H), 6.92

(d, J=7.1 Hz, 1H), 4.82 (s, 1H), 3.98 (m, 2H), 3.47 (m, 2H), 2.21 (s, 3H), 1.96 (bs, 4H). MS (m/e): 370 (MH⁺).

Example 56

1-(1-Methylpiperidin-4-yl)-6-(2-m-tolylpyridin-3-yl)-1H-benzo[d]imidazole (Compound 45)

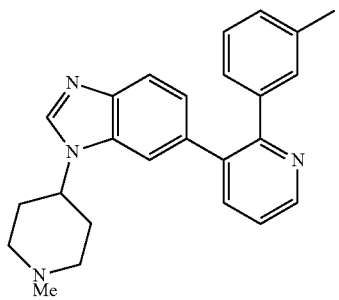 [SMILES: Cc1cccc(-c2ncccc2-c2ccc3ncn(C4CCN(C)CC4)c3c2)c1]

In like manner to the preparation of 6-(2-(4-Fluoro-3-methylphenyl)pyridin-3-yl)-1-(2-morpholino ethyl)-1H-benzo[d]imidazole, the reaction of 2-(3-methylphenyl)-3-(3-fluoro-4-nitrophenyl)pyridine and 1-methylpiperidin-4-amine yielded 1-(1-Methylpiperidin-4-yl)-6-(2-m-tolylpyridin-3-yl)-1H-benzo[d]imidazole. ¹H NMR (DMSO-d6): δ 9.43 (s, 1H), 8.78 (d, J=3.9 Hz, 1H), 8.15 (d, J=7.2 Hz, 1H), 7.94 (s, 1H), 7.76 (d, J=8.5 Hz, 1H), 7.68 (dd, J=7.7, 5.0 Hz, 1H), 7.43-7.19 (m, 2H), 7.08 (d, J=7.2 Hz, 2H), 6.93 (d, J=6.9 Hz, 1H), 4.87 (s, 1H), 3.62 (m, 2H), 3.17 (m, 2H), 2.85 (s, 3H), 2.26 (s, 4H), 2.20 (s, 3H). MS (m/e): 383 (MH⁺).

Example 57

1-Ethyl-6-(2-(4-fluoro-3-methylphenyl)pyridin-3-yl)-1H-benzo[d]imidazole (Compound 46)

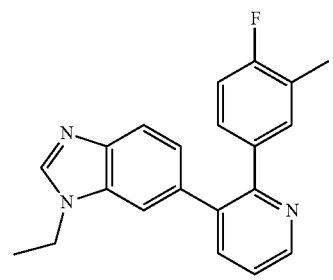 [SMILES: CCn1cnc2ccc(-c3cccnc3-c3ccc(F)c(C)c3)cc21]

In like manner to the preparation of 6-(2-(4-Fluoro-3-methylphenyl)pyridin-3-yl)-1-(2-morpholinoethyl)-1H-benzo[d]imidazole, the reaction of 2-(4-fluoro-3-methylphenyl)-3-(3-fluoro-4-nitrophenyl)pyridine and ethanamine yielded 1-Ethyl-6-(2-(4-fluoro-3-methylphenyl)pyridin-3-yl)-1H-benzo[d]imidazole. ¹H NMR (DMSO-d6): δ 9.38 (s, 1H), 8.76 (d, J=5.4 Hz, 1H), 8.38 (d, J=7.8 Hz, 1H), 7.99-7.67 (m, 2H), 7.74 (d, J=8.6 Hz, 1H), 7.34 (t, J=6.1 Hz, 2H), 7.16-6.87 (m, 2H), 4.49-4.29 (m, 2H), 2.08 (s, 3H), 1.32 (t, J=7.2 Hz, 3H). MS (m/e): 332 (MH⁺).

Example 58

5-(2-(3-Cyclopentylphenyl)pyridin-3-yl)-1H-pyrazolo[3,4-b]pyridine (Compound 171)

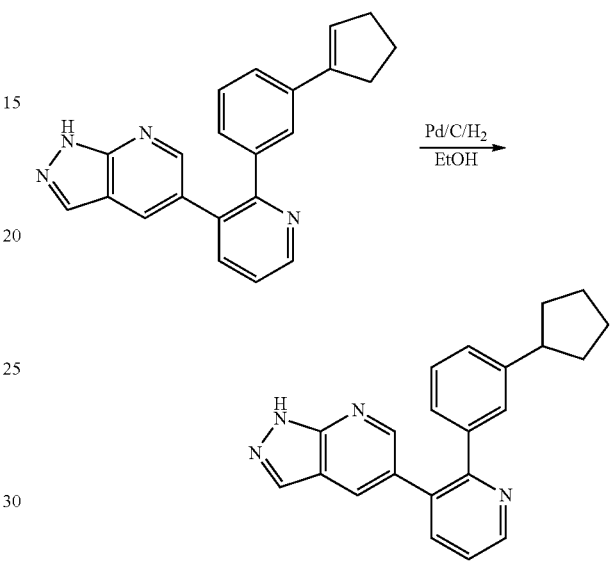

5-(2-(3-cyclopentenylphenyl)pyridin-3-yl)-1H-pyrazolo[3,4-b]pyridine (130 mg) was hydrogenated with Pd/C (15 mg) in EtOH (15 mL) over a period of 10 h under balloon H₂ after degassing and back filling the flask with the hydrogen. The reaction mixture was filtered through celite and purified by preparative HPLC to provide 5-(2-(3-cyclopentylphenyl)pyridin-3-yl)-1H-pyrazolo[3,4-b]pyridine as a white solid. ¹H NMR (DMSO-d6): δ 8.84 (d, 1H, J=4.7 Hz), 8.41 (d, 1H, J=7.9 Hz), 8.16 (app s, 2H), 8.14 (app s, 1H), 7.89 (app t, 1H, J=7.5 Hz), 7.23 (app s, 2H), 7.22-7.20 (m, 1H), 7.08 (s, 1H), 2.80 (q, 1H, J=8.2 Hz), 1.75-1.68 (m, 2H), 1.48-1.39 (m, 4H), 1.17-1.07 (m, 2H).LCMS: rt 5.13 min (A), purity 97%, MS (m/e) 341 (MH⁺).

Example 59

5-(2-(6-Methylpyridin-2-yl)pyridin-3-yl)-1H-indazole (Compound 116)

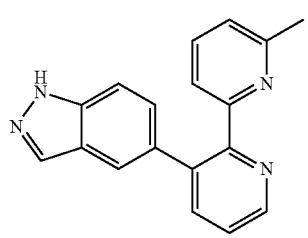 [SMILES: Cc1cccc(-c2ncccc2-c2ccc3[nH]ncc3c2)n1]

A vial with a piercable teflon cap containing a magetic stir was charged with 5-[2-(4-fluoro-3-methylphenyl)pyridin-3-yl]-1H-indazole (0.2 g, 0.87 mmol), Pd₂(dba)₃(30 mg, 0.03 mmol) and 2-dicyclohexylphosphino-2',4',6'-triisopropylbiphenyl (XPHOS, 60 mg, 0.13 mmol) under argon atmosphere. 6-Methyl-2-pyridylzinc bromide (0.5 M in THF, 4.0 mL, 2 mmol) was added to above reactants and degassed under vacuum. After three degas cycles, the reaction mixture was heated at 65° C. under argon. After 6 h, the reaction mixture was cooled to the room temperature and diluted with Rochelle salt (5 mL) and concentrated to remove the volatiles. The concentrated aqueous solution was diluted with EtOAc (30 mL) and separated the organic layer. Aqueous solution was further extracted with EtOAc (30 mL). Combined organic layers washed with aq. NaCl (10 mL), stirred over MgSO$_4$, and filtered through a pad of Florosil/celite. The filtrate was concentrated and purified by preparative HPLC. The collected fractions were concentrated, diluted with water and neutralized with aq. NaHCO$_3$. The resultant solid formed was collected by filtration and dried to provide 5-(2-(6-Methylpyridin-2-yl)pyridin-3-yl)-1H-indazole (118 mg, 47%) as a white solid. $^1$H NMR (DMSO-d6): δ 13.01 (s, 1H), 8.63 (dd, 1H, J=0.8 and 4.7 Hz), 7.99 (s, 1H), 7.89 (d, 1H, J=7.9 Hz), 7.57 (app d, 2H, J=8.5 Hz), 7.51 (dd, 1H, J=4.9 and 7.6 Hz), 7.34 (d, 1H, J=8.8 Hz), 7.26 (d, 1H, J=7.6 Hz), 7.07 (d, 1H, J=7.6 Hz), 6.97 (d, 1H, J=8.8 Hz), 2.15 (s, 3H).LCMS: rt 2.13 min (B), purity 97%, MS (m/e) 287 (MH$^+$).

Example 60

Methyl 2-Amino-5-bromo-3-methylbenzoate

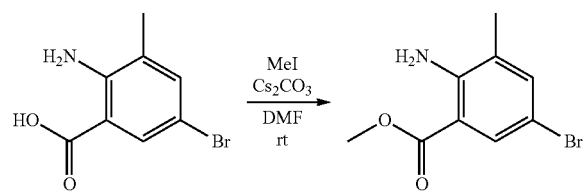

2-Amino-5-bromo-3-methylbenzoic acid (5.0 g, 21.7 mmol) in dry DMF (35 mL) was stirred with Cs$_2$CO$_3$ (10.62 g, 32.6 mmol) at room temperature for 1 h under nitrogen. Iodomethane (3.4 g, 1.5 mL, 23.95 mmol) in dry DMF (7 ml) was added dropwise to the above stirring reaction mixture over a period of 30 min and continued the reaction for 24 h. Reaction mixture was diluted with water (200 mL) and stirred to observe hetergeneous suspension. The purple solid was collected by filtration and dried to obtain methyl 2-amino-5-bromo-3-methylbenzoate (4.72 g, 89%). $^1$H NMR (DMSO-d6): δ 7.67 (app d, 1H, J=2.1 Hz), 7.34 (s, 1H), 6.60 (s, 2H), 3.78 (s, 3H), 2.09 (s, 3H).LCMS: rt 7.98 min (A), purity 99%, MS (m/e) 245 (MH$^+$).

Example 61

Methyl 5-bromo-1H-indazole-7-carboxylate

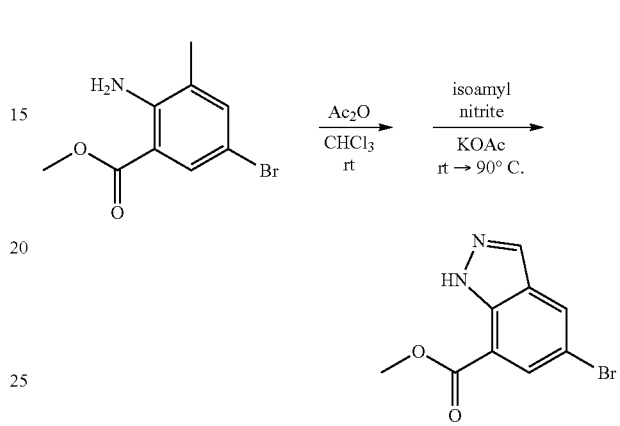

Acetic anhydride (4.5 g, 4.1 mL, 44 mmol) was added dropwise to the homogenous solution of methyl 2-amino-5-bromo-3-methylbenzoate (4.72 g, 19 mmol) in chloroform (55 mL) over a period of 20 min at room temperature and allowed to stir for 1 h. Potassium acetate (5.7 g, 58 mmol) and isoamyl nitrate (6.6 g, 7.6 mL, 57 mmol) were added at once to the reaction mixture under nitrogen. The clear reaction mixture turned to dark upon heating at 90° C. The reaction mixture was cooled to room temperature after overnight reflux, concentrated, diluted with water and stirred. The beige solid formed was collected by filtration and dried to obtain methyl 5-bromo-1H-indazole-7-carboxylate (2.1 g, 42%). $^1$H NMR (DMSO-d6): δ 13.44 (s, 1H), 8.33 (s, 1H), 8.21 (s, 1H), 7.99 (s, 1H), 3.95 (s, 3H).LCMS: rt 6.86 min (A), purity 99%, MS (m/e) 255 (MH$^+$).

Example 62

Methyl 5-(2-chloropyridin-3-yl)-1H-indazole-7-carboxylate

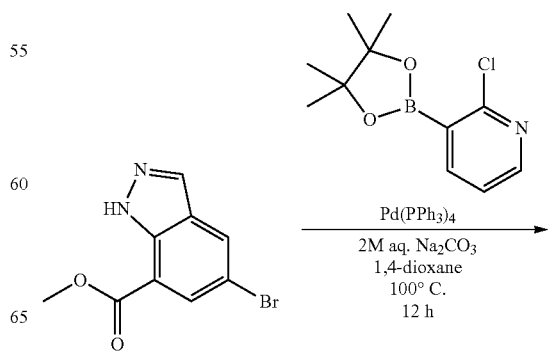

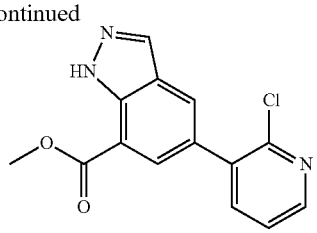

Analogous to the preparation of 5-(2-chloropyridin-3-yl)-1H-indazole, methyl 5-(2-chloropyridin-3-yl)-1H-indazole-7-carboxylate was prepared by heating the mixture of methyl 5-bromo-1H-indazole-7-carboxylate (2.0 g, 7.8 mmol), 2-chloro-3-pyridine boronic acid pinacol ester (1.9 g, 7.9 mmol), Pd(PPh$_3$)$_4$ (540 mg, 0.46 mmol) and 2M aq. Na$_2$CO$_3$ (8 mL, 16 mmol) in 1,4-dioxane (70 mL). Methyl 5-(2-chloropyridin-3-yl)-1H-indazole-7-carboxylate was isolated as a white solid (920 mg, 41%) upon work-up and purification genaralized in the preparation of 5-(2-chloropyridin-3-yl)-1H-indazole. $^1$H NMR (DMSO-d6): δ 13.41 (s, 1H), 8.45 (d, 1H, J=4.7 Hz), 8.31 (s, 1H), 8.21 (s, 1H), 7.97 (d, 1H, J=7.3 Hz), 7.54 (dd, 1H, J=4.7 and 7.3 Hz), 3.99 (s, 3H).LCMS: rt 6.41 min (A), purity 95%, MS (m/e) 288 (MH$^+$)

Example 63

Methyl 5-(2-(4-fluoro-3-methylphenyl)pyridin-3-yl)-1H-indazole-7-carboxylate (Compound 190)

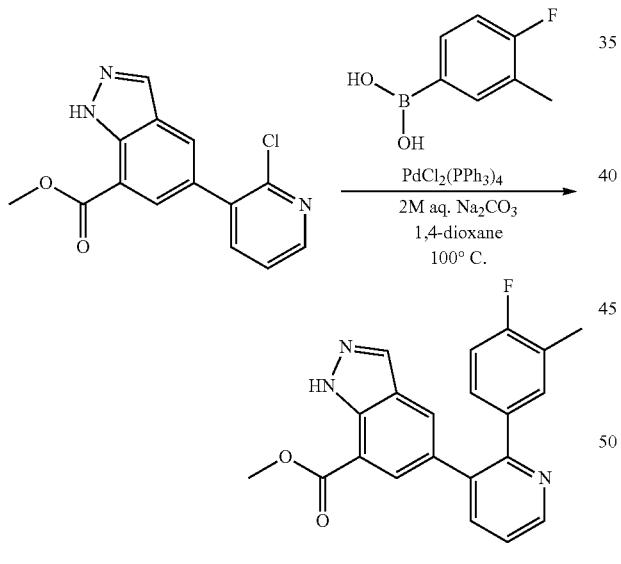

A single necked round bottom flask (100 mL) equipped with a magnetic stirring bar was charged with methyl 5-(2-chloropyridin-3-yl)-1H-indazole-7-carboxylate (0.88 g, 3.0 mmol), 4-fluoro-3-methylphenyl boronic acid (0.56 g, 3.63 mmol), PdCl$_2$(PPh$_3$)$_4$ (214 mg g, 1.0 mmol), 1,4-dioxane (75 mL) and 2M aq. Na$_2$CO$_3$ (4.2 mL, 8.4 mmol mL) under argon atmosphere. The rubber septum was replaced with reflux condenser containing three-way stopcock. The system was then evacuated three times and back filled with argon and externally heated at 100° C. (oil bath) for 48 h. The heterogeneous reaction mixture was allowed to cool to room temperature and concentrated under vacuum to remove the volatiles by rotary evaporator. The crude concentrate flask was charged with chloroform (100 mL)/water (30 mL) and stirred. Organic layer was separated and the aqueous layer further extracted with chloroform (75 mL). Combined organic layers were stirred over MgSO$_4$/Celite® for 20 min, suction filtered and filter cake washed with chloroform (30 mL). The filtrate collected was concentrated and purified by silica gel flash chromatography [Combiflash® companion System® with RediSep® silica gel column (24g), solvent eluent gradient 30-50% EtOAc/hexanes] to obtain methyl 5-(2-(4-fluoro-3-methylphenyl)pyridin-3-yl)-1H-indazole-7-carboxylate (420 mg, 39%) as a white solid. $^1$H NMR (DMSO-d6): δ 13.1 (s, 1H), 8.62 (dd, 1H, J=0.5 and 4.7 Hz), 8.04 (s, 1H), 7.83 (d, 1H, J=7.6 Hz), 7.66 (s, 1H), 7.45-7.34 (app m, 3H), 7.02 (d, 1H, J=8.5 Hz), 6.96-6.85 (m, 2H), 2.11 (s, 3H). $^{19}$F NMR (DMSO-d6): δ −118.91. LCMS: rt 5.23 min (A), purity 93%, MS (m/e) 362 (MH$^+$).

Example 64

5-(2-(4-Fluoro-3-methylphenyl)pyridin-3-yl)-1H-indazole-7-carboxylic acid (Compound 195)

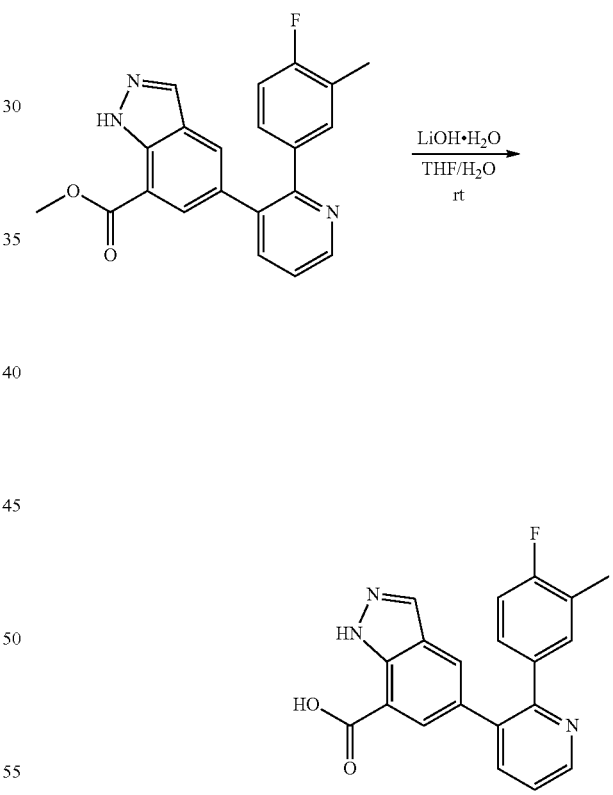

Methyl 5-(2-(4-fluoro-3-methylphenyl)pyridin-3-yl)-1H-indazole-7-carboxylate (300 mg, 0.55 mmol) was saponified by LiOH (0.12 g,) in THF/H$_2$O (1:1, 8 mL) for 2 days. The reaction mixture was concentrated to dryness, diluted with water (4 mL) and neutralized by the addition of aq. 2N HCl. The solid formed after the neutralization was filtered and suction dried to obtain the title compound as a white solid (220 mg). $^1$H NMR (DMSO-d6): δ 13.15 (s, 1H),8.67 (app dd, 1H, J=1.4 and 4.7 Hz), 8.17 (s, 1H), 7.97-7.92 (m, 2H), 7.68 (d, 1H, J=1.7 Hz), 7.51 (dd, 1H, J=4.7 and 7.6 Hz), 7.38

(d, 1H, 7.6 Hz), 6.93-6.90 (m, 2H), 2.12 (s, 3H). $^{19}$F NMR (DMSO-d6): δ −118.43 (s). LCMS: 97%, MS (m/e) 348 (MH$^+$).

Example 65

(5-(2-(4-fluoro-3-methylphenyl)pyridin-3-yl)-1H-indazol-7-yl)(morpholino)methanone (Compound 196)

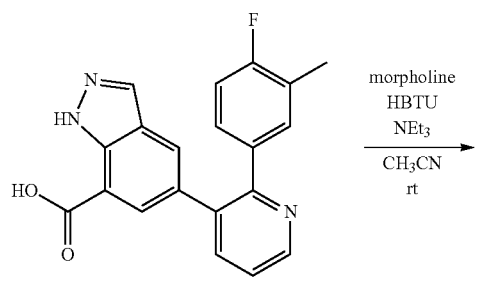

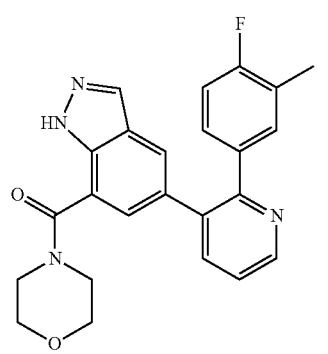

A capped vial containing a stir-bar, was charged with 5-(2-(4-fluoro-3-methylphenyl)pyridin-3-yl)-1H-indazole-7-carboxylic acid (100 mg, 0.28 mmol), HBTU (140 mg, 0.36 mmol), morpholine (29 mg, 0.03 mL, 0.34 mmol), NEt$_3$ (57 mg, 0.08 mL, 0.57 mmol) and acetonitrile (3 ml) successively and stirred the contents at room temperature. After 12 h, the reaction mixture was concentrated and diluted with EtOAc (15 mL)/H$_2$O (5 mL). Organic layer was separated, washed with brine, dried over anhydrous Na$_2$SO$_4$, concentrated and purified by preparative HPLC. Product fractions were concentrated, diluted with water and neutralized with aq. Na$_2$CO$_3$ solution. The resulting white precipitate was filtered and dried to obtain (5-(2-(4-fluoro-3-methylphenyl)pyridin-3-yl)-1H-indazol-7-yl)(morpholino)methanone. $^1$H NMR (DMSO-d6): δ 13.27 (s, 1H), 8.66 (d, 1H, J=4.7 Hz), 8.17 (s, 1H), 7.97-7.92 (m, 2H), 7.48 (dd, 1H, J=4.9 and 7.6 Hz), 7.33 (d, 1H, J=7.8 Hz), 6.97-6.88 (m, 3H), 3.62-3.42 (m, 8H), 2.10 (s, 3H). $^{19}$F NMR (DMSO-d6): δ −118.69 (s). LCMS: rt 4.45 min (A), purity 97%, MS (m/e) 417 (MH$^+$)

Example 66

5-(2-(4-fluoro-3-methylphenyl)pyridin-3-yl)-N,N-dimethyl-1H-indazole-7-carboxamide (Compound 203)

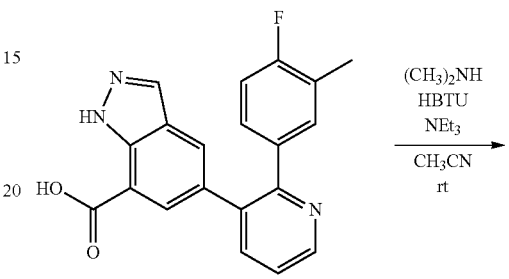

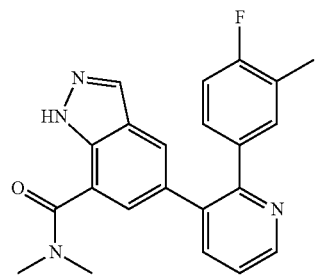

5-(2-(4-fluoro-3-methylphenyl)pyridin-3-yl)-N,N-dimethyl-1H-indazole-7-carboxamide was prepared analogous to the preparation of 5-(2-(4-fluoro-3-methylphenyl)pyridin-3-yl)-1H-indazol-7-yl)(morpholino)methanone by the reaction of dimethyl amine (0.55 mL, 1.1 mmol, 2M in THF) with 5-(2-(4-fluoro-3-methylphenyl)pyridin-3-yl)-1H-indazole-7-carboxylic acid (100 mg, 0.28 mmol), HBTU (140 mg, 0.36 mmol), NEt$_3$ (57 mg, 0.08 mL, 0.57 mmol) in acetonitrile (4 mL). Extractive work-up followed by preparative HPLC purification and neutralization procedure as discussed previously provided desired 5-(2-(4-fluoro-3-methylphenyl)pyridin-3-yl)-N,N-dimethyl-1H-indazole-7-carboxamide as a white solid. $^1$H NMR (DMSO-d6): δ 13.05 (s, 1H), 8.63 (dd, 1H, J=1.7 and 4.7 Hz), 8.13 (s, 1H), 7.87 (dd, 1H, J=1.4 and 7.6 Hz), 7.81 (s, 1H), 7.46 (dd, 1H, J=4.7 and 7.6 Hz), 7.32 (d, 1H, J=7.3 Hz), 7.02-6.98 (m, 1H), 6.95-6.89 (app m. 2H), 2.93 (br s, 3H), 2.57 (br s, 3H), 2.09 (s, 3H). $^{19}$F NMR (DMSO-d6): δ −118.91. LCMS: rt 4.63 min (A), purity 97%, MS (m/e) 375 (MH$^+$).

Example 67

[5-(2-(4-Fluoro-3-methylphenyl)pyridin-3-yl)-2H-indazol-2-yl]methyl dihydrogen phosphate (Compound 172)

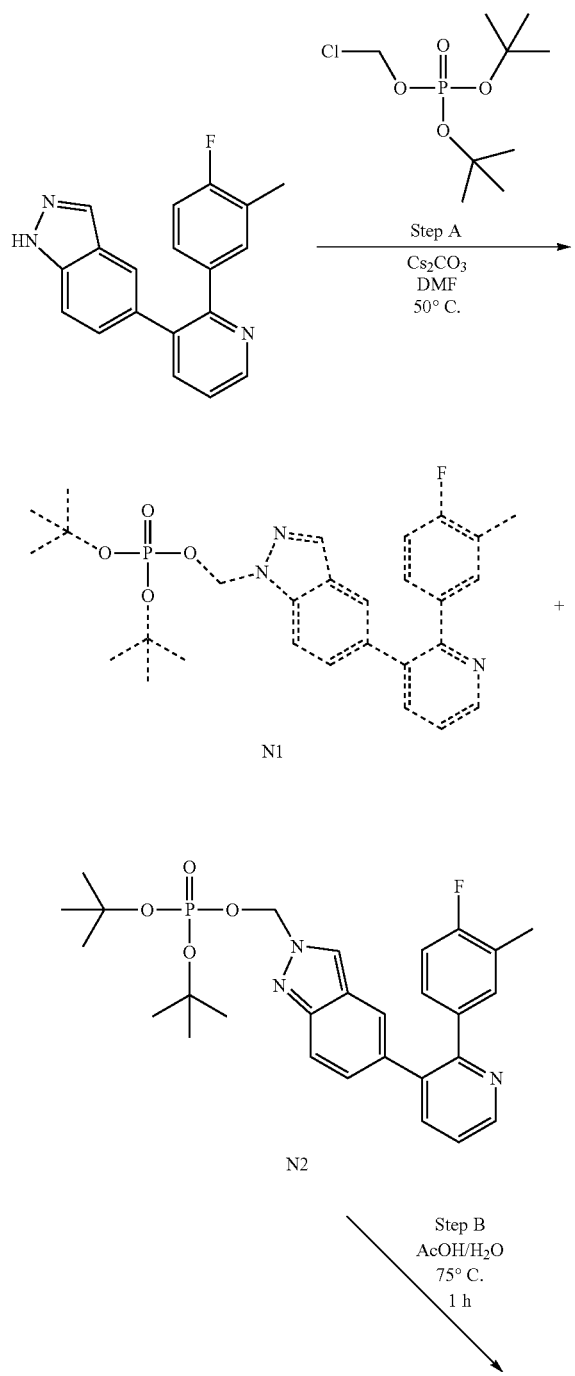

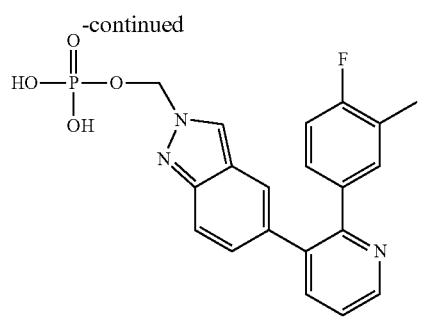

Step A: Di-tert-butyl[5-(2-(4-fluoro-3-methylphenyl)pyridin-3-yl)-2H-indazol-2-yl]methyl phosphate Freshly prepared chloromethyl di-tert-butylphosphate (93% pure, 0.5 g, 1.93 mmol) dissolved in anhydrous DMF (1 mL) was added in one portion to a heterogeneous stirring mixture of 5-[2-(4-fluoro-3-methylphenyl)pyridin-3-yl]-1H-indazole (0.5 g, 1.65 mmol), cesium carbonate (0.64 g, 1.96 mmol) and DMF (3 mL) at room temperature under argon. The contents were heated at 50° C. and the progress of the reaction monitored by LC/MS. After 24 h, anlysis of the reaction indicated the consumption of 5-[2-(4-fluoro-3-methylphenyl)pyridin-3-yl]-1H-indazole (3%) with the generation of alkylated regio-isomeric product mixture of di-tert-butyl[5-(2-(4-fluoro-3-methylphenyl)pyridin-3-yl)-2H-indazol-2-yl]methyl phosphate (N2, 28%) and di-tert-butyl [5-(2-(4-fluoro-3-methylphenyl)pyridin-3-yl)-1H-indazol-1-yl]methyl phosphate (N1, 60%). The reaction mixture was diluted with EtOAc (15 mL), upon cooling to room temperature, stirred for 10 min and suction filtered. The filter cake was washed with EtOAc (15 mL) and discarded. Upon dilution of the filtrate with H$_2$O (20 mL)/t-BuOMe (30 mL), the aqueous layer was separated and the organic layer was washed with water (20 mL). The combined aqueous layers were re-extracted with a mixture of t-BuOMe/EtOAc (1/1, 30 mL). The combined organic layers were washed with saturated aq. NaCl (30 mL), stirred over MgSO$_4$, filtered and resulting filtrate evaporated under vacuum by rotary evaporator (water bath temperature 26-28° C.). The crude (1.2 g) product was subjected to purification by flash chromatography [Combiflash® companion System® with RediSep® silica gel column 40 g (pretreated with 5% NEt$_3$ in 30% EtOAc/hexanes followed by wash with 30% EtOAc/hexanes), 30/50/60/90% EtOAC/hexanes eluting solvent gradient upon liquid loading on to column]. Concentration of the fractions by rotary evaporator under vacuum provided the desired minor N2-regio-isomer, di-tert-butyl[5-(2-(4-fluoro-3-methylphenyl)pyridin-3-yl)-2H-indazol-2-yl]methyl phosphate, as a viscous material (110 mg, 12%). $^1$H NMR (DMSO-d6): δ 8.63 (dd, 1H, J=1.7 and 4.7 Hz), 8.51 (d, 1H, J=0.9 Hz), 7.84 (dd, 1H, J=1.8 and 8.0 Hz), 7.66 (d, 1H, J=0.9 Hz), 7.52 (d, 1H, J=8.8 Hz), 7.43 (dd, 1H, J=4.5 and 7.6 Hz), 7.37 (d, 1H, J=2.0 and 7.6 Hz), 7.01-6.85 (m, 3H), 6.10 (d, 2H, $^3J_{PH}$=11 Hz), 2.11 (s, 3H), 1.34 (s, 18 Hz). $^{31}$P NMR (DMSO-d6): δ −11.9. LCMS: 94%, MS (m/e) 526 (MH$^+$).

Step B: [5-(2-(4-fluoro-3-methylphenyl)pyridin-3-yl)-2H-indazol-2-yl]methyl dihydrogen phosphate Di-tert-butyl[5-(2-(4-fluoro-3-methylphenyl)pyridin-3-yl)-2H-indazol-2-yl]methyl phosphate (N2, 100 mg, 0.21 mmol) was dissolved in AcOH:H$_2$O (0.5 mL, 4:1) and the clear homogenous solution heated at 60° C. After 1 h, analysis of the reaction mixture LC/MS indicated the 97% consumption of di-tert-butyl[5-(2-(4-fluoro-3-methylphenyl)pyridin-3-yl)-2H-indazol-2-yl]methyl phosphate leading to the desired product of [5-(2-(4-fluoro-3-methylphenyl)pyridin-3-yl)-2H-indazol-2-yl]methyl dihydrogen phosphate (AUC 85%). At this stage heating was discontinued and the reaction mixture was polish filtered by suction. Concentration of the filtrate by rotary evaporator under vacuum (water bath temp 26-28° C.) resulted in a thick viscous liquid which was diluted with acetone (7 mL). The white heterogenous suspension was stirred for 30 min and filtered. The filter cake was washed with acetone (25 mL) and suction dried for a period of 1 h. The collected filter cake was further processed by drying under high vacuum over $P_2O_5$ for 24 h to provide [5-(2-(4-fluoro-3-methylphenyl)pyridin-3-yl)-2H-indazol-2-yl]methyl dihydrogen phosphate (63 mg, 71%). $^1$H NMR (DMSO-d6): δ 8.64 (dd, 1H, J=0.5 and 4.7 Hz), 8.51 (s, 1H), 7.86 (d, 1H, J=7.6 Hz), 7.70 (s, 1H), 7.50-7.41 (app m, 3H), 7.00-6.88 (m, 3H), 6.05 (d, 2H, $^3J_{PH}$=10 Hz), 2.13 (s, 3H). $^{19}$F NMR (DMSO-d6): δ −118.60. $^{31}$P NMR (DMSO-d6): δ −2.63. LCMS: 97%, MS (m/e) 414 (MH$^+$).

Example 68

(S)-2-Amino-3-(1H-indol-3-yl)propyl 5-(2-(4-fluoro-3-methylphenyl)pyridin-3-yl)-1H-indazole-1-carboxylate trifluoroacetic acid salt (Compound 179)

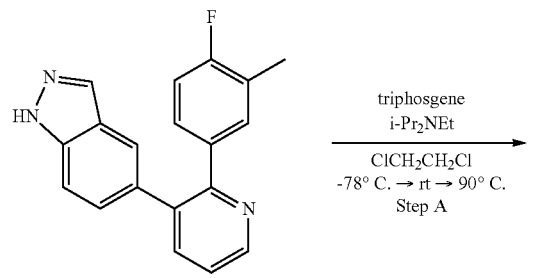

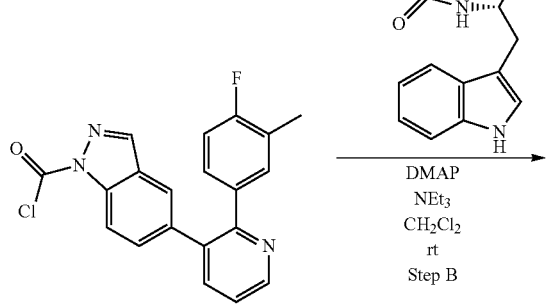

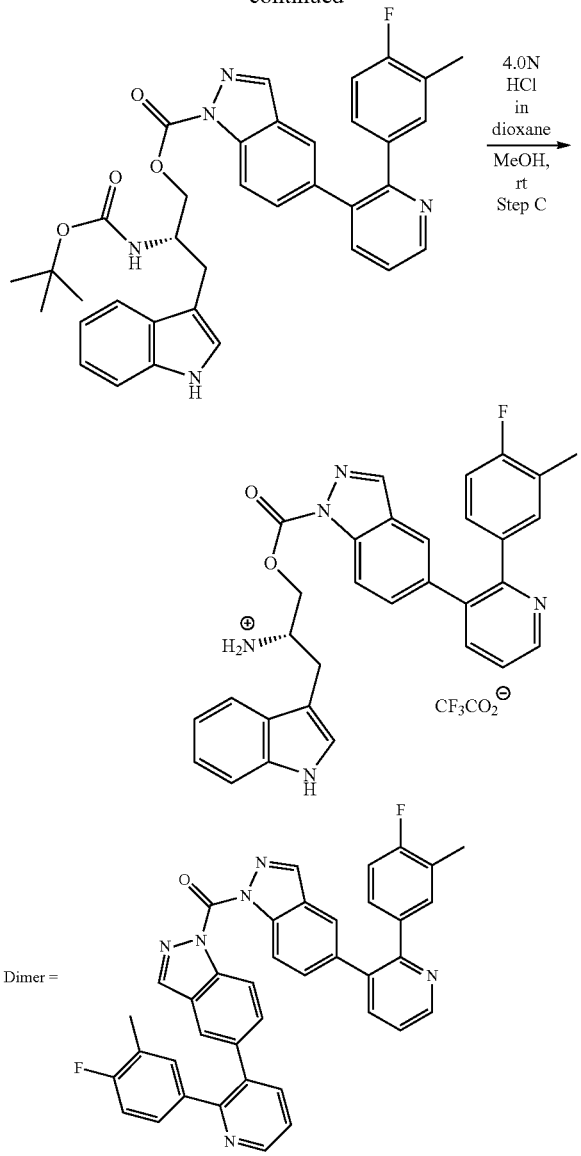

Step A: 5-(2-(4-Fluoro-3-methylphenyl)pyridin-3-yl)-1H-indazole-1-carbonyl chloride A single neck round bottom flask with a stir bar was charged with 5-[2-(4-fluoro-3-methylphenyl)pyridin-3-yl]-1H-indazole (100 mg, 0.33 mmol) and triphosgene (120 mg, 0.40 mmol). The reaction flask was capped with a septum with a nitrogen inlet subsequently. Dichloroethane (3 mL) was transferred and cooled the reaction flask to −70° C. i-Pr$_2$NEt (80 mg, 0.11 mL, 0.60 mmol) was added dropwise to the above stirring reaction mixture over a period 5 min and allowed to stir for 15 min after the competion of addition. The heterogenous suspension was allowed to warm to room temperature and heated at 90° C. Analysis of the reaction by LC/MS after 18 h of heating indicated the formation of 5-(2-(4-fluoro-3-methylphenyl)pyridin-3-yl)-1H-indazole-1-carbonyl chloride [rt 6.55 min (A), AUC 59%] and bis(5-(2-(4-fluoro-3-methylphenyl)pyridin-3-yl)-1H-indazol-1-yl) methanone [dimer, rt 6.16 min (A), 27%, MH+ 634]. The reaction mixture was cooled to room temperature and concentrated to dryness under vacuum by rotary evaporation.

Step B: (S)-tert-Butyl-1-(5-(2-(4-fluoro-3-methylphenyl)pyridin-3-yl)-1H-indazole-1-carboxyloyloxy)-3-(1H-indol-3-yl)propan-2-ylcarbamate N-(tert-Butoxycarbonyl)-L-tryptophanol (100 mg, 33 mmol), DMAP (40 mg, 0.33 mmol) and $CH_2Cl_2$ (3 mL) were added sequentially to the above concentrate containing 5-(2-(4-fluoro-3-methylphenyl)pyridin-3-yl)-1H-indazole-1-carbonyl chloride under nitrogen atmosphere at room temperature. The resulting pale yellow heterogenous stirring solution was treated with $NEt_3$ (0.5 mL) over a period of 5 min. The resulting clear dark reaction mixture was stirred for 30 min at room temperature. Analysis of the reaction mixture indicated the formation of desired product (S)-tert-butyl-1-(5-(2-(4-fluoro-3-methylphenyl)pyridin-3-yl)-1H-indazole-1-carboxyloyloxy)-3-(1H-indol-3-yl)propan-2-ylcarbamate [rt 7.10 min (A) AUC 56%] and dimer [rt 6.16 min (A), 20%, MH+634] with complete consumption of starting material. The reaction mixture was concentrated, diluted with EtOAc/$H_2O$ (30 mL/10 mL) and separated the organic layer. Aqueous layer was re-extracted with EtOAc (15 mL), stirred the combined organic layers over $MgSO_4$ and filtered. Filtrate was concentrated and used in the next step with no further purification.

Step C: (S)-2-Amino-3-(1H-indol-3-yl)propyl 5-(2-(4-fluoro-3-methylphenyl)pyridin-3-yl)-1H-indazole-1-carboxylate trifluoroacetic acid salt The above concentrate (220 mg) containing (S)-tert-butyl-1-(5-(2-(4-fluoro-3-methylphenyl)pyridin-3-yl)-1H-indazole-1-carboxyloyloxy)-3-(1H-indol-3-yl)propan-2-ylcarbamate dissolved in MeOH (2 mL) was treated with 4.0 N HCl (3 mL) at room temperature and stirred the resulting homogenous solution. After 1 h, the reaction mixture was concentrated and purified by reverse phase preparative HPLC containing TFA as a modifier in the mobile phase of acetonitrile/water. The collected product fractions were allowed to freeze by external cooling in dry ice/acetone. The frozen residue was lyophilized to provide (S)-2-amino-3-(1H-indol-3-yl)propyl 5-(2-(4-fluoro-3-methylphenyl)pyridin-3-yl)-1H-indazole-1-carboxylate as an off-white solid (67 mg, 0.33%) as a TFA salt. $^1$H NMR (DMSO-d6): δ 11.04 (s, 1H), 8.68 (d, 1H, J=4.5 Hz), 8.49 (s, 1H), 8.17 (br s, 3H), 7.99 (d, 1H, J=8.5 Hz), 7.90 (d, 1H, J=7.9 Hz),7.80 (s, 1H), 7.60 (d, 1H, J=7.9 Hz), 7.50 (dd, 1H, J=4.5 and 7.9 Hz), 7.36-7.31 (app m, 4H), 7.09 (t, 1H, J=7.9 Hz), 6.98 (t, 1H, J=7.9 Hz), 6.92-6.86 (m, 3H), 4.62 (app d, 1H, J=9.2 Hz), 4.52 (dd, 1H, J=J=7.0 and 9.4 Hz), 3.92-3.87 (br s, 1H), 3.12 (d, 2H, J=7.0 Hz), 2.13 (s, 3H). $^{19}$F NMR (DMSO-d6): δ –118.91 (s) and –74.47 (s).LCMS: rt 5.15 min (A), purity 94%, MS (m/e) 520 (MH$^+$)-TFA.

Example 69

Certain starting materials suitable for use in making the compounds described herein can be synthesized using the following reference syntheses.

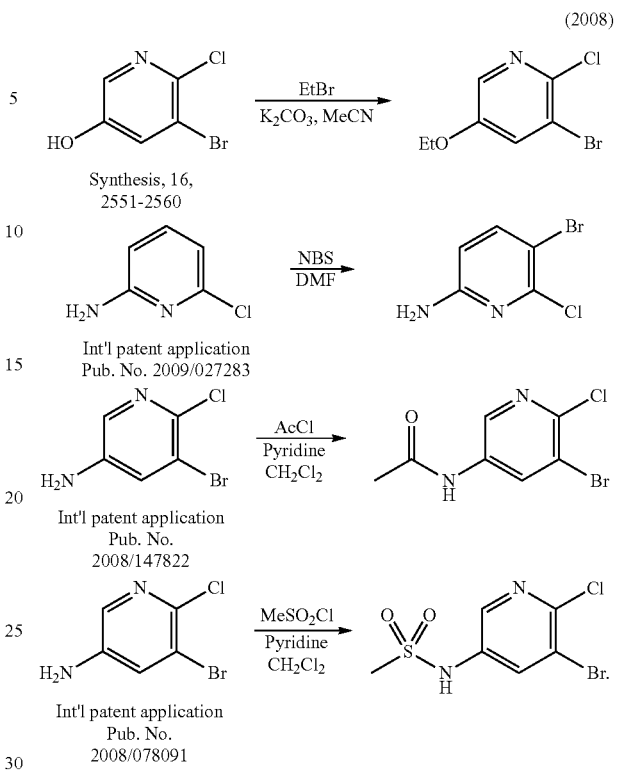

Example 70

Certain intermediates useful in making compounds of the disclosure (e.g., compounds 786-89, 795, 796 and 798-801) according to Schemes 12 and 13 were prepared. General procedures are first provided. Particular structures, compound names and synthetic data are provided thereafter.

General procedure for the preparation of 5- or 6-(2-(aryl)pyridin-3-yl)-1H-indazol-3-amine: 2-Fluoro-4- or -5-(2-aryl)pyridin-3-yl)benzonitrile (75 mg) and EtOH (3 mL) were transferred to a microwave tube containing a stir bar. Corresponding hydrazine was added to the stirring solution, sealed the tube with the cap and heated at 150° C. in the microwave for 35 min. The homogeneous solution was concentrated and diluted with water. The resultant solid was collected by filtration and suction dried overnight. Samples that were not solids were purified by preparative HPLC and lyophilized the purified samples after the processing the samples to neutralization.

General procedure for 5 or 6-(2-(phenyl)pyridin-3-yl)benzo[d]isoxazol-3-amine: t-BuOK (0.077 g, 0.69 mmol) was added to a stirring solution of N-acetyl hydroxylamine (0.051 g, 0.69 mmol) in DMF (3 mL) at room temperature under argon in a screw capped vial (20 mL). After 20 min, corresponding 2-fluoro-4 or 5-(2-aryl)pyridin-3-yl)benzonitrile (1 eq) was added all at once to the heterogeneous suspension stirred for 30 min at rt. The pale yellow heterogeneous reaction mixture was stirred eventually at 60° C. After 8 h, the reaction mixture was diluted with water and solid formed was collected by filtration. Thus collected solid was purified by either crystallization in EtOAc or preparative HPLC. Preparative HPLC purified product samples were neutralized with aq. NaHCO₃, subsequently filtered the heterogeneous suspension and dried the collected solids.

2-Fluoro-4-(2-(4-fluoro-3-methylphenyl)pyridin-3-yl)benzonitrile (intermediate for compounds 786, 787)

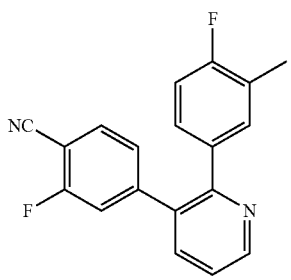 [SMILES: Cc1cc(-c2ncccc2-c2ccc(C#N)c(F)c2)ccc1F]

$^1$H NMR (300 MHz, DMSO-d$_6$) δ 8.70 (dd, J=4.7, 1.7 Hz, 1H), 7.89 (dd, J=7.8, 1.7 Hz, 1H), 7.84 (dd, J=8.1, 7.0 Hz, 1H), 7.51 (dd, J=7.8, 4.8 Hz, 1H), 7.46 (dd, J=10.5, 1.5 Hz, 1H), 7.33 (dd, J=7.4, 1.7 Hz, 2H), 7.14 (dd, J=8.1, 1.6 Hz, 1H), 7.06-6.91 (m, 2H), 2.17 (d, J=1.7 Hz, 5H). $^{19}$F NMR (282 MHz, DMSO-d$_6$) δ −108.32 (dd, J=10.5, 7.0 Hz), −118.03 (q, J=7.8 Hz).

4-(2-(3-Chlorophenyl)pyridin-3-yl)-2-fluorobenzonitrile (intermediate for compounds 798)

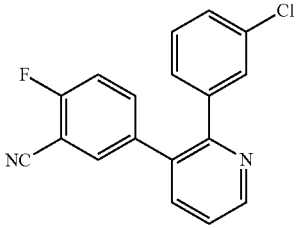

$^1$H NMR (300 MHz, DMSO-d$_6$): δ 8.74 (dd, J=4.8, 1.7 Hz, 1H), 7.94 (dd, J=7.8, 1.7 Hz, 1H), 7.87 (t, J=7.5 Hz, 1H), 7.56 (dd, J=7.8, 4.8 Hz, 1H), 7.49 (d, J=10.6 Hz, 1H), 7.47-7.41 (m, 1H), 7.41-7.34 (m, 1H), 7.28 (t, J=7.8 Hz, 1H), 7.18 (d, J=8.1 Hz, 1H), 7.10 (d, J=8.8 Hz, 1H). $^{19}$F NMR (282 MHz, DMSO-d$_6$) δ −108.32 (dd, J=10.5, 7.1 Hz).

2-Fluoro-5-(2-(4-fluoro-3-methylphenyl)pyridin-3-yl)benzonitrile (intermediate for compounds 795, 788, 789)

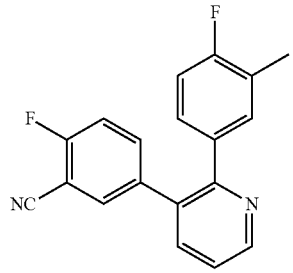 [SMILES: Cc1cc(-c2ncccc2-c2ccc(F)c(C#N)c2)ccc1F]

$^1$H NMR (300 MHz, DMSO-d$_6$): δ 8.68 (dd, J=4.7, 1.7 Hz, 1H), 7.98 (s, 1H), 7.94-7.82 (m, 2H), 7.53-7.38 (m, 3H), 7.32 (d, J=7.5 Hz, 1H), 7.00 (dd, J=8.9, 3.1 Hz, 1H), 2.17 (d, J=1.5 Hz, 3H). $^{19}$F NMR (282 MHz, DMSO-d$_6$): δ −110.59 (q, J=6.9 Hz), −118.29.

5-(2-(3-Chlorophenyl)pyridin-3-yl)-2-fluorobenzonitrile (intermediate for compound 799)

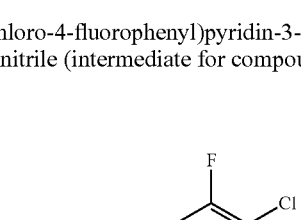

$^1$H NMR (300 MHz, DMSO-d$_6$): δ 8.71 (dd, J=4.8, 1.6 Hz, 1H), 7.92 (dd, J=7.8, 1.7 Hz, 1H), 7.90-7.86 (m, 1H), 7.58-7.44 (m, 3H), 7.44-7.33 (m, 2H), 7.27 (t, J=7.8 Hz, 1H), 7.16-7.04 (m, 1H). $^{19}$F NMR (282 MHz, DMSO-d$_6$) δ −110.39 (dt, J=9.1, 5.9 Hz).

4-(2-(3-Chloro-4-fluorophenyl)pyridin-3-yl)-2-fluorobenzonitrile (intermediate for compound 800)

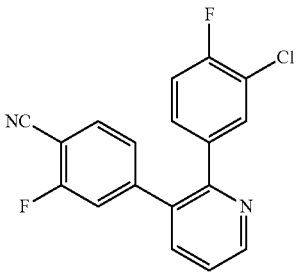 [SMILES: N#Cc1ccc(-c2cccnc2-c2ccc(F)c(Cl)c2)cc1F]

$^1$H NMR (300 MHz, DMSO-d$_6$) δ 8.73 (dd, J=4.7, 1.6 Hz, 1H), 7.92 (dd, J=7.8, 1.7 Hz, 1H), 7.87 (dd, J=8.0, 7.0 Hz, 1H), 7.63-7.47 (m, 3H), 7.27 (t, J=7.8 Hz, 1H), 7.18 (dd,

J=8.0, 1.5 Hz, 1H), 7.16-7.09 (m, 1H). $^{19}$F NMR (282 MHz, DMSO-d$_6$) δ −108.18 (dd, J=10.5, 7.0 Hz), −116.79 (td, J=8.6, 4.9 Hz).

5-(2-(3-Chloro-4-fluorophenyl)pyridin-3-yl)-2-fluorobenzonitrile (intermediate for compound 796, 801)

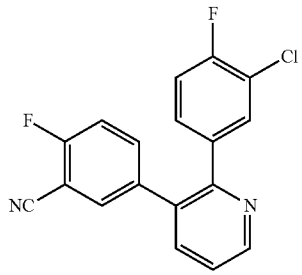 [SMILES: N#Cc1cc(-c2cccnc2-c2ccc(F)c(Cl)c2)ccc1F]

$^1$H NMR (300 MHz, DMSO-d$_6$): δ 8.71 (d, J=1.6 Hz, 1H), 7.92 (t, J=1.7 Hz, 1H), 7.90 (d, J=1.7 Hz, 1H), 7.62-7.41 (m, 4H), 7.37-7.24 (m, 1H), 7.14 (ddd, J=8.6, 4.8, 2.2 Hz, 1H). $^{19}$F NMR (282 MHz, DMSO-d$_6$): δ −110.28 (dt, J=8.9, 5.9 Hz), −117.04 (ddd, J=9.3, 7.3, 4.7 Hz).

Example 73

Compound 291 was prepared according to the reaction sequence shown in Scheme 22. The starting amine, 2'-(3-chloro-4-fluorophenyl)-[3,3'-bipyridin]-6-amine, was prepared from N-(2'-(3-chloro-4-fluorophenyl)-[3,3'-bipyridin]-6-yl)acetamide ($^1$H NMR (300 MHz, DMSO-d$_6$) δ 10.51 (s, 1H), 8.67 (dd, J=4.7, 1.7 Hz, 1H), 8.08 (dd, J=2.5, 0.8 Hz, 1H), 8.02 (d, J=8.6 Hz, 1H), 7.90 (dd, J=7.8, 1.7 Hz, 1H), 7.60 (dd, J=8.6, 2.5 Hz, 1H), 7.55 (dd, J=7.4, 4.4 Hz, 1H), 7.51 (dd, J=7.4, 4.4 Hz, 1H), 7.31 (t, J=8.6 Hz, 1H), 7.18 (ddd, J=8.6, 4.8, 2.2 Hz, 1H), 2.07 (s, 3H); $^{19}$F NMR (282 MHz, DMSO-d$_6$) δ −117.24 (td, J=8.3, 4.8 Hz)) via the following procedure: N-(2'-chloro-[3,3'-bipyridin]-6-yl)acetamide (2.5 g) and freshly prepared MeOH.HCl (10 mL) in 1,4-dioxane (35 mL) were heated to stir at 90° C. for 4 h. The reaction mixture was concentrated and the crude residue was diluted with water (25 mL). The clear solution was neutralized with aq. NaHCO$_3$ and extracted into CH$_2$Cl$_2$ (2×125 mL). Work-up and drying of the pale yellow residue under high vacuum for 2 days provided 2'-(3-chloro-4-fluorophenyl)-[3,3'-bipyridin]-6-amine as a pale yellow solid. (1.9 g, purity: 96%). $^1$H NMR (300 MHz, DMSO-d$_6$) δ 8.59 (dd, J=4.8, 1.7 Hz, 1H), 7.79 (dd, J=7.8, 1.7 Hz, 1H), 7.73 (d, J=2.5 Hz, 1H), 7.53 (dd, J=7.3, 2.1 Hz, 1H), 7.44 (dd, J=7.8, 4.7 Hz, 1H), 7.33 (t, J=8.6 Hz, 1H), 7.24 (ddd, J=8.6, 4.9, 2.1 Hz, 1H), 7.12 (dd, J=8.5, 2.5 Hz, 1H), 6.35 (dd, J=8.6, 0.8 Hz, 1H), 6.04 (s, 2H).

Example 74

Compounds in which the Z group is an amine-substituted pyrimidine (e.g., Compounds 903-909 and 919) can be prepared via the reactions outlined in Scheme 29, described in more detail below:

Scheme 29

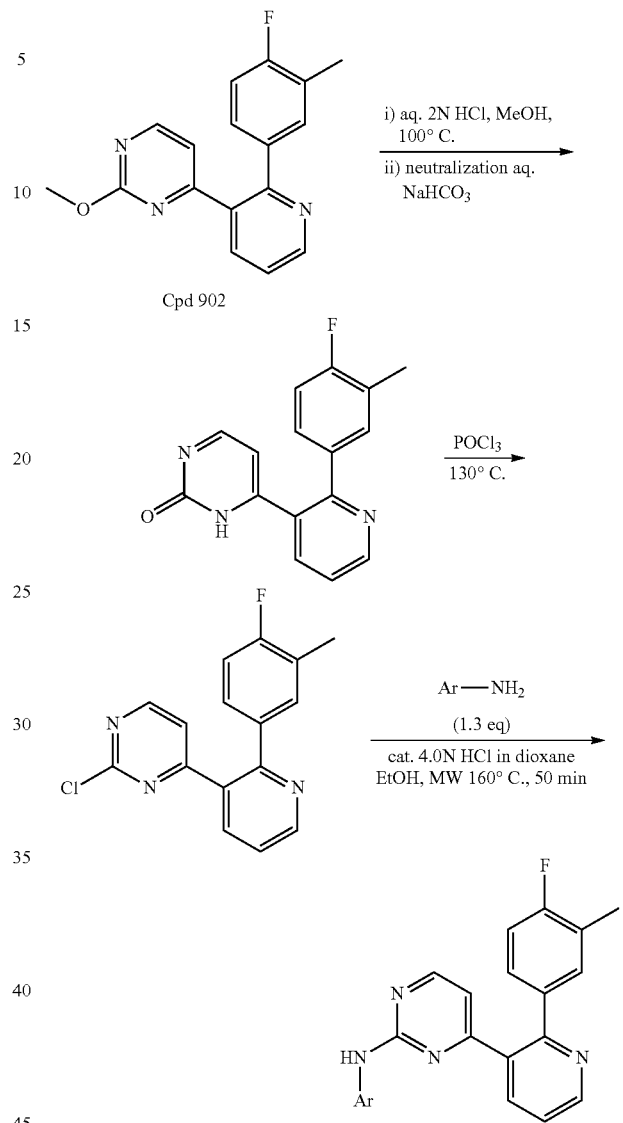

4-(2-(4-Fluoro-3-methylphenyl)pyridin-3-yl)-2-methoxypyrimidine (Compound 207)

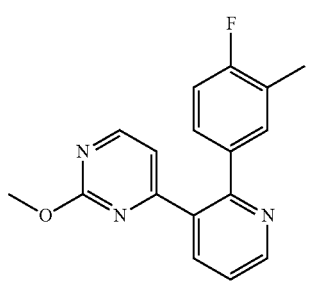

$^1$H NMR (300 MHz, DMSO-d$_6$): δ 8.74 (dd, J=4.8, 1.7 Hz, 1H), 8.48 (d, J=5.1 Hz, 1H), 8.08 (dd, J=7.8, 1.7 Hz, 1H), 7.54 (dd, J=7.8, 4.8 Hz, 1H), 7.34 (dd, J=7.6, 2.1 Hz, 0H), 7.11-

6.98 (m, 2H), 6.90 (d, J=5.1 Hz, 1H), 3.77 (s, 3H), 2.18 (app d, J=2.1 Hz, 2H). $^{19}$F NMR (282 MHz, DMSO-d$_6$): δ −118.09 (q, J=8.0, 7.5 Hz). LCMS: rt 5.04 min (B), purity 99%, MS (m/e) 296 (MH$^+$).

6-(2-(4-Fluoro-3-methylphenyl)pyridin-3-yl)pyrimidin-2(1H)-one

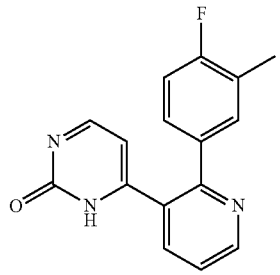 [SMILES: Cc1cc(-c2ncccc2-c2ccnc(=O)[nH]2)ccc1F]

Aqueous HCl (2N, 20 mL) was added to the stirring solution of 4-(2-(4-fluoro-3-methylphenyl)pyridin-3-yl)-2-methoxypyrimidine (1.3 g) in MeOH (10 mL) and heated at 90° C. for 12 h. The reaction mixture was concentrated by rotary evaporator under reduced pressure and neutralized the resultant pale yellow viscous material with aq. NaHCO$_3$ solution. The slurry thus formed upon neutralization was stirred at room temperature for 20 min. The solid was collected by filtration, washed with water, suction dried. After 6 h, the solid was further dried over P$_2$O$_5$ under high vacuum to provide 6-(2-(4-fluoro-3-methylphenyl)pyridin-3-yl)pyrimidin-2(1H)-one as a white solid (0.87 g). $^1$H NMR (300 MHz, DMSO-d$_6$): δ 11.92 (s, 1H), 8.74 (dd, J=4.8, 1.7 Hz, 1H), 7.98 (dd, J=7.8, 1.7 Hz, 1H), 7.80 (app d, J=6.0 Hz, 1H), 7.51 (dd, J=7.8, 4.8 Hz, 1H), 7.43 (dd, J=7.7, 2.1 Hz, 1H), 7.24-7.02 (m, 2H), 5.96 (d, J=6.0 Hz, 1H), 2.22 (app s, 3H). $^{19}$F NMR (282 MHz, DMSO-d$_6$) δ −117.63.

2-Chloro-4-(2-(4-fluoro-3-methylphenyl)pyridin-3-yl)pyrimidine

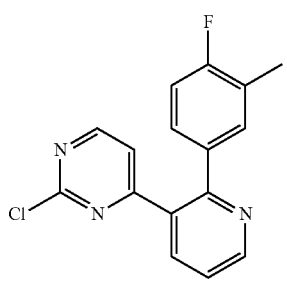 [SMILES: Cc1cc(-c2ncccc2-c2ccnc(Cl)n2)ccc1F]

6-(2-(4-Fluoro-3-methylphenyl)pyridin-3-yl)pyrimidin-2(1H)-one (0.83 g) and POCl$_3$ (3 mL) were heated at 130° C. under nitrogen. The reaction mixture was cooled to room temperature upon completion of the reaction (2 h). The volatiles were removed and quenched the concentrate with ice. The semi-heterogeneous slurry was neutralized with aq. NaHCO$_3$ solution while stirring, warmed to room temperature and diluted with EtOAc (200 mL). The organic layer was separated, stirred over MgSO$_4$, filtered, concentrated and purified by flash chromatography (Combiflash® companion System® with RediSep® silica gel column 12 g and 10-50% EtOAc/Hexanes as eluting solvent) to obtain 2-chloro-4-(2-(4-fluoro-3-methylphenyl)pyridin-3-yl)pyrimidine as a clear viscous liquid.

General procedure for 4-(2-(4-Fluoro-3-methylphenyl)pyridin-3-yl)-N-arylpyrimidin-2-amine: 2-chloro-4-(2-(4-fluoro-3-methylphenyl)pyridin-3-yl)pyrimidine (1 eq), Ar—NH$_2$ (1.3 eq), EtOH (3 mL) and catalytic amount of 4.0 M HCl (0.02 mL) were added successively to a microwave tube containing a stir bar. The contents were stirred for 2 min and heated in the microwave at 160° C. for 50 min. The reaction mixture was concentrated and purified by preparative HPLC. The concentrated product fractions thus obtained as salts were neutralized with aq. NaHCO$_3$ solution and extracted into EtOAc. Organic layer was dried over anhydrous Na$_2$SO$_4$, filtered and concentrated. The concentrate was dissolved in acetonitrile/water (1:1) and lyophilized upon freezing the samples to obtain the desired compounds as solids.

4-(2-(4-Fluoro-3-methylphenyl)pyridin-3-yl)pyrimidin-2-amine (Compound 919) was prepared as follows: A screw capped vial was charged with 2-chloro-4-(2-(4-fluoro-3-methylphenyl)pyridin-3-yl)pyrimidine (125 mg), 28% aq. Ammonia (3 mL), 1,4-dioxane (3 mL) and a stir bar. The vial was capped tightly, heated and stirred at 60° C. for 12 h. The heterogeneous solution was cooled to room temperature, diluted with water, filtered. The solid (90 mg) was suspended in 50% EtOAc/hexanes, stirred and heated at 80° C. for 30 min. Upon cooling to room temperature, the suspension was filtered and the solid was suction dried to provide 4-(2-(4-fluoro-3-methylphenyl)pyridin-3-yl)pyrimidin-2-amine as a white solid (73 mg). $^1$H NMR (300 MHz, DMSO-d$_6$): δ 8.69 (dd, J=4.7, 1.7 Hz, 1H), 8.07 (d, J=5.0 Hz, 1H), 7.93 (dd, J=7.8, 1.7 Hz, 1H), 7.47 (dd, J=7.8, 4.8 Hz, 1H), 7.38 (dd, J=7.4, 1.6 Hz, 1H), 7.18-6.95 (m, 2H), 6.70 (s, 2H), 6.20 (d, J=5.0 Hz, 1H), 2.19 (s, 3H). $^{19}$F NMR (282 MHz, DMSO-d$_6$): δ −118.16 (q, J=7.7 Hz).LCMS: rt 4.40 min (A), purity 99%, MS (m/e) 281 MH$^+$.

Example 75

N-alkyl indazole compounds (e.g., Compounds 750 and 751) can be prepared from the corresponding indazoles via the reaction outlined in Scheme 29, described in more detail below:

Scheme 29

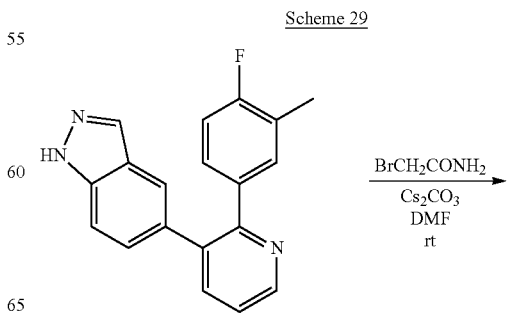

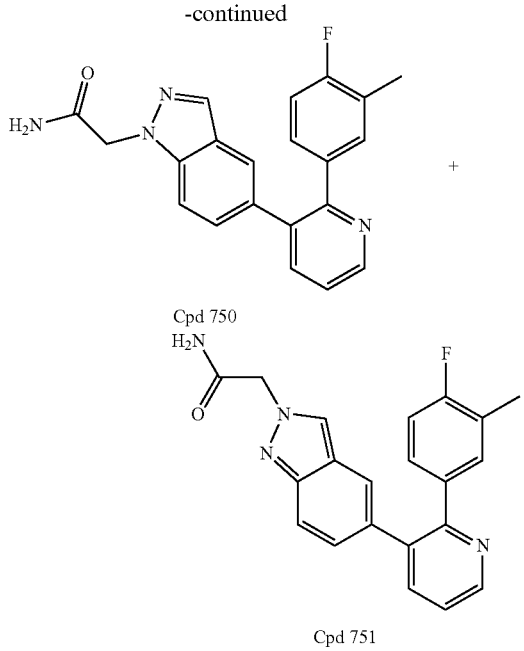

Cpd 750

Cpd 751

2-(5-(2-(4-Fluoro-3-methylphenyl)pyridin-3-yl)-1H-indazol-1-yl)acetamide (Compound 750) and 2-(5-(2-(4-fluoro-3-methylphenyl)pyridin-3-yl)-2H-indazol-2-yl)acetamide (Compound 751). 5-(2-(4-Fluoro-3-methylphenyl)pyridin-3-yl)-1H-indazole (0.2 g, 0.66 mmol), 2-bromoacetamide (0.1 g, 0.72 mmol) and Cs$_2$CO$_3$ (0.25 g, 0.79 mmol) in dry DMF (2.5 mL) was stirred under argon in a screw capped vial at room temperature. The reaction mixture was diluted with water after 2 days and the resultant solid was collected by filtration. Individual alkylated indazole regio-isomers (2:1 ratio Cpd 750:751) were isolated from the crude solid by flash column chromatographic purification (Combiflash® companion System® with RediSep® silica gel column 12 g and 0-1.5% MeOH/EtOAc as an eluting solvent).

Example 76

6- or 7-(2-(Aryl)pyridin-3-yl)imidazo[1,5-a]pyridine-3-carboxylic acids or esters via the reaction outlined in Scheme 19.

For example, ethyl 6-(2-(4-fluoro-3-methylphenyl)pyridin-3-yl)imidazo[1,5-a]pyridine-3-carboxylate (Compound 256) and 6-(2-(4-fluoro-3-methylphenyl)pyridin-3-yl)imidazo[1,5-a]pyridine-3-carboxylic acid (Compound 257) can be prepared using the intermediates and preparations described below:

2'-(4-Fluoro-3-methylphenyl)-[3,3'-bipyridine]-6-carbonitrile. $^1$H NMR (300 MHz, DMSO-d$_6$): δ 8.73 (dd, J=4.7, 1.3 Hz, 1H), 8.52 (d, J=1.9 Hz, 1H), 8.01 (d, J=8.0 Hz, 1H), 7.96 (dd, J=7.8, 1.3 Hz, 1H), 7.87 (dd, J=8.0, 2.1 Hz, 1H), 7.54 (dd, J=7.8, 4.8 Hz, 1H), 7.31 (d, J=7.7 Hz, 1H), 7.06-6.93 (m, 2H), 2.16 (s, 3H). $^{19}$F NMR (282 MHz, DMSO-d$_6$) δ −117.91 (q, J=7.6, 6.9 Hz).

(2'-(4-Fluoro-3-methylphenyl)-[3,3'-bipyridin]-6-yl)methanamine. 2'-(4-Fluoro-3-methylphenyl)-[3,3'-bipyridine]-6-carbonitrile (2.2 g), Pd/C (0.4 g) and conc. HCl (3 mL) in EtOH (100 mL) was hydrogenated in a par shaker at 40 psi overnight. The reaction mixture was filtered through Celite® and concentrated. The concentrate was treated with CH$_2$Cl$_2$ (120 mL) and sat. aq. NaHCO$_3$ (25 mL). Organic layer was separated and the aqueous layer was re-extracted with CH$_2$Cl$_2$ (2×50 ml). Combined organic layers were stirred over anhydrous Na$_2$SO$_4$ for 30 min, filtered, concentrated and dried under high vacuum to obtain thick viscous liquid of (2'-(4-Fluoro-3-methylphenyl)-[3,3'-bipyridin]-6-yl)methanamine (2.1 g, purity 97%). $^1$H NMR (300 MHz, DMSO-d$_6$): δ 8.66 (dd, J=4.7, 1.6 Hz, 1H), 8.26 (s, 1H), 7.86 (d, J=1.6 Hz, 1H), 7.54 (dd, J=8.0, 2.2 Hz, 1H), 7.48 (dd, J=7.7, 4.8 Hz, 1H), 7.37 (d, J=8.1 Hz, 1H), 7.32 (d, J=8.0 Hz, 1H), 6.97 (dd, J=6.9, 1.5 Hz, 2H), 3.78 (s, 2H), 2.58 (br s, 2H), 2.16 (s, 3H).

Ethyl 2-(((2'-(4-fluoro-3-methylphenyl)-[3,3'-bipyridin]-6-yl)methyl)amino)-2-oxoacetate. To a stirring solution of (2'-(4-fluoro-3-methylphenyl)-[3,3'-bipyridin]-6-yl)methanamine (2.0 g) in CH$_2$Cl$_2$ (30 mL) under nitrogen atmosphere, i-Pr$_2$NEt (2.6 mL) was added and stirred for 10 min at room temperature. Ethyl 2-chloro-2-oxoacetate (1.1 mL) as neat was added dropwise for 10 min. After 1 h, the reaction mixture was concentrated, partitioned between CH$_2$Cl$_2$ (75 mL)/aq. NaCl (20 mL) and the organic layer was separated. Usual workup and purification by chromatography (Combiflash® companion System® with RediSep® silica gel column 40 g and 50-100% EtOAc/hexanes as an elutant) provided 1.4 g of ethyl 2-(((2'-(4-fluoro-3-methylphenyl)-[3,3'-bipyridin]-6-yl)methyl)amino)-2-oxoacetate as an off-white solid. $^1$H NMR (300 MHz, DMSO-d$_6$): δ 9.41 (t, J=6.2 Hz, 1H), 8.67 (dd, J=4.7, 1.7 Hz, 1H), 8.30 (dd, J=2.4, 0.9 Hz, 1H), 7.87 (dd, J=7.8, 1.7 Hz, 1H), 7.56 (dd, J=8.1, 2.3 Hz, 1H), 7.49 (dd, J=7.8, 4.8 Hz, 1H), 7.29-7.22 (m, 2H), 6.98 (dd, J=7.7, 1.1 Hz, 2H), 4.42 (d, J=6.1 Hz, 2H), 4.23 (q, J=7.1 Hz, 2H), 2.21-2.09 (m, 3H), 1.26 (t, J=7.1 Hz, 3H).

Ethyl 6-(2-(4-fluoro-3-methylphenyl)pyridin-3-yl)imidazo[1,5-a]pyridine-3-carboxylate (Compound 256). Ethyl 2-((2'-(4-fluoro-3-methylphenyl)-[3,3'-bipyridin]-6-yl)methyl)amino)-2-oxoacetate (1.4 g) and POCl$_3$ (15 mL) were stirred and heated at 105° C. under argon balloon. The reaction mixture was cooled to room temperature, added an additional amount of POCl$_3$ (10 mL) was added to the reaction mixture and heated at 90° C. for 2 days. The reaction mixture was cooled to room temperature and concentrated. Subsequently, ice/water solution was added to the crude residue followed by CH$_2$Cl$_2$ and aq. NaHCO$_3$. Upon allowing the contents warm to room temperature, organic layer was separated, stirred over Na$_2$SO$_4$, filtered and concentrated. Purification of the crude residue by flash column chromatography (Combiflash® companion System® with RediSep® silica gel column 40 g and 0-50-75% EtOAC/hexanes as an eluting solvent) provided 315 mg of Ethyl 6-(2-(4-fluoro-3-methylphenyl)pyridin-3-yl)imidazo[1,5-a]pyridine-3-carboxylate as a white pale yellow solid.

6-(2-(4-Fluoro-3-methylphenyl)pyridin-3-yl)imidazo[1,5-a]pyridine-3-carboxylic acid (Compound 257). Ethyl 6-(2-(4-fluoro-3-methylphenyl)pyridin-3-yl)imidazo[1,5-a]pyridine-3-carboxylate (2.1 g) and LiOH.H$_2$O (400 mg) were stirred in THF/H$_2$O (1:1, 60 mL) at 70° C. for 2 h. The reaction mixture was concentrated to dryness and diluted the pale yellow solid with water. The resulting semi-heterogeneous suspension was cooled in ice-bath, stirred and neutralized with aq. 3N HCl to pH 6. The solid aggregate was collected by filtration on Buchner funnel, washed with water and suction dried. Further processing the sample by drying over P$_2$O$_5$ in a vacuum desiccator provided the desired 6-(2-(4-Fluoro-3-methylphenyl)pyridin-3-yl)imidazo[1,5-a]pyridine-3-carboxylic acid (1.5 g, purity: 97%) as a pale yellow solid.

Similarly, ethyl 7-(2-(4-fluoro-3-methylphenyl)pyridin-3-yl)imidazo[1,5-a]pyridine-3-carboxylate (Compound 255) and 7-(2-(4-fluoro-3-methylphenyl)pyridin-3-yl)imidazo[1,5-a]pyridine-3-carboxylic acid (Compound 258) can be prepared using the intermediates described below:

2-(4-Fluoro-3-methylphenyl)-[3,4'-bipyridine]-2'-carbonitrile. $^1$H NMR (300 MHz, DMSO-d$_6$): δ 8.74 (dd, J=4.8, 1.6 Hz, 1H), 8.63 (dd, J=5.1, 0.7 Hz, 1H), 8.02-7.90 (m, 2H), 7.54 (dd, J=7.8, 4.8 Hz, 1H), 7.45 (dd, J=5.1, 1.7 Hz, 1H), 7.33 (d, J=6.4 Hz, 1H), 7.09-6.94 (m, 2H), 2.17 (s, 3H). $^{19}$F NMR (282 MHz, DMSO-d$_6$): δ –117.73 (q, J=7.7, 7.2 Hz).

(2-(4-Fluoro-3-methylphenyl)-[3,4'-bipyridin]-2'-yl)methanamine. $^1$H NMR (300 MHz, DMSO-d$_6$): δ 8.69 (dd, J=4.7, 1.6 Hz, 1H), 8.34 (d, J=3.8 Hz, 1H), 7.87 (d, J=1.6 Hz, 1H), 7.50 (dd, J=7.8, 4.7 Hz, 1H), 7.42-7.22 (m, 2H), 6.99-6.90 (m, 3H)), 3.76 (s, 2H), 3.28 (br s, 2H), 2.16 (s, 3H). $^{19}$F NMR (282 MHz, DMSO-d$_6$): δ –118.23 (d, J=7.8 Hz). 3HCL: $^{19}$F NMR (282 MHz, DMSO-d$_6$): δ 11.13 (s, 2H), 8.87 (d, J=4.9 Hz, 3H), 8.54 (d, J=5.3 Hz, 1H), 8.30 (d, J=7.6 Hz, 1H), 8.06-7.80 (m, 2H), 7.43 (d, J=6.9 Hz, 1H), 7.31-6.88 (m, 3H), 4.23 (d, J=5.2 Hz, 3H), 2.18 (s, 3H).

Ethyl 2-(((2-(4-fluoro-3-methylphenyl)-[3,4'-bipyridin]-2'-yl)methyl)amino)-2-oxoacetate. $^1$H NMR (300 MHz, DMSO-d$_6$): δ 9.29 (t, J=6.0 Hz, 1H), 8.69 (d, J=4.7 Hz, 1H), 8.42 (d, J=5.0 Hz, 1H), 7.83 (d, J=7.8 Hz, 1H), 7.50 (dd, J=8.0, 4.5 Hz, 1H), 7.25 (d, J=7.5 Hz, 1H), 7.14 (s, 1H), 7.07 (d, J=5.0 Hz, 1H), 7.01-6.88 (m, 2H), 4.37 (d, J=6.1 Hz, 2H), 4.23 (q, J=6.9 Hz, 2H), 2.13 (s, 3H), 1.27 (t, J=6.9 Hz, 3H).

Example 75

6-(2-(4-Fluoro-3-methylphenyl)pyridin-3-yl)imidazo[1,5-a]pyridine (Compound 269) can be prepared via the reactions shown in the first two steps of Scheme 20: (2'-(4-Fluoro-3-methylphenyl)-[3,3'-bipyridin]-6-yl)methanamine (2.18 g) and formic acid (15 mL) were stirred and heated under nitrogen atmosphere at 100° C. After 72 h, the reaction mixture was concentrated and partitioned between CH$_2$Cl$_2$/aq. NaHCO$_3$. Usual work-up and purification by flash column chromatography (Combiflash® companion System® with RediSep® silica gel column 40 g and 50-100% EtOAC/hexanes as elutant) provided 630 mg of N-((2'-(4-fluoro-3-methylphenyl)-[3,3'-bipyridin]-6-yl)methyl)formamide as an off white solid. N-((2'-(4-fluoro-3-methylphenyl)-[3,3'-bipyridin]-6-yl)methyl)formamide (630 mg) and POCl$_3$ (3 mL) were stirred and heated in benzene (20 mL) overnight at 75° C. The reaction mixture was cooled to room temperature and concentrated. Subsequently, ice/water solution was added to the crude residue followed by CH$_2$Cl$_2$ and aq. NaHCO$_3$. Upon allowing the solution warm to room temperature, organic layer was separated, stirred over Na$_2$SO$_4$, filtered and concentrated. Purification of the crude residue by flash column chromatography (Combiflash® companion System® with RediSep® silica gel column 40 g and 2-8% MeOH/CH$_2$Cl$_2$ as an eluting solvent) provided 320 mg of 6-(2-(4-fluoro-3-methylphenyl)pyridin-3-yl)imidazo[1,5-a]pyridine as an off-white solid.

Example 76

6-(2-(4-Fluoro-3-methylphenyl)pyridin-3-yl)imidazo[1,5-a]pyridin-3-amine (Compound 285) can be prepared via the reactions shown in Scheme 30, below:

Scheme 30

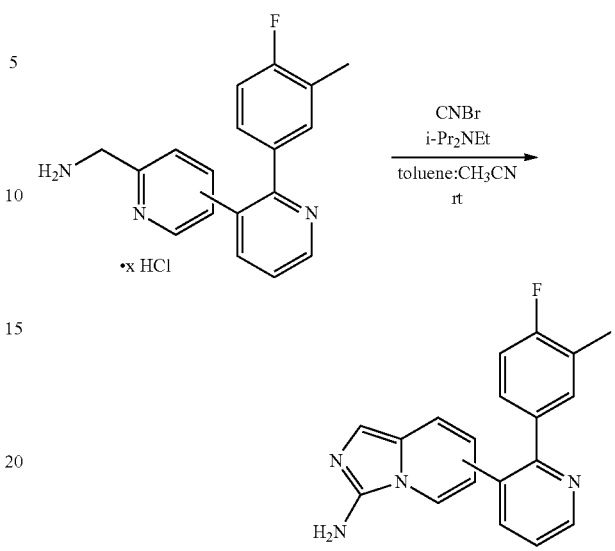

Cyanogen bromide (62 mg) in dry acetonitrile (1 mL) was added to a screw capped vial containing a stirring solution of (2'-(4-fluoro-3-methylphenyl)-[3,3'-bipyridin]-6-yl)methanamine.xHCl (120 mg), i-Pr$_2$NEt (0.2 mL) and anhydrous toluene. After 4 h, the reaction mixture was concentrated and purified by reverse phase preparative HPLC conditions provided 6-(2-(4-fluoro-3-methylphenyl)pyridin-3-yl)imidazo[1,5-a]pyridin-3-amine (28 mg).

Example 77

6-(2-(3-Chloro-4-fluorophenyl)pyridin-3-yl)-[1,2,4]triazolo[1,5-a]pyridin-2-amine (Compound 291) can be prepared via the reactions shown in Scheme 22: Ethoxycarbonyl isothiocyanate (66 mg) added to a screw capped vial containing 2'-(3-Chloro-4-fluorophenyl)-[3,3'-bipyridin]-6-amine (150 mg) and 1,4-dioxane (1.5 mL). After 6 h, the reaction mixture was concentrated in the same vial to dryness and the residue was transferred to a microwave vial by dissolving in MeOH (1 mL) and EtOH (1 mL). Subsequently, hydroxylamine hydrochloride (35 mg) was added, capped the vial, introduced i-Pr$_2$NEt (87 µL) and heated at 150° C. Reaction mixture was concentrated after overnight and diluted with water. The solid was collected by filtration and purified by reverse phase preparative HPLC conditions.

Example 78

Pyrido[3,2-d]pyrimidine compounds can be prepared via the reactions shown in Scheme 31, below:

Scheme 31

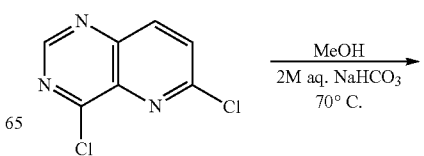

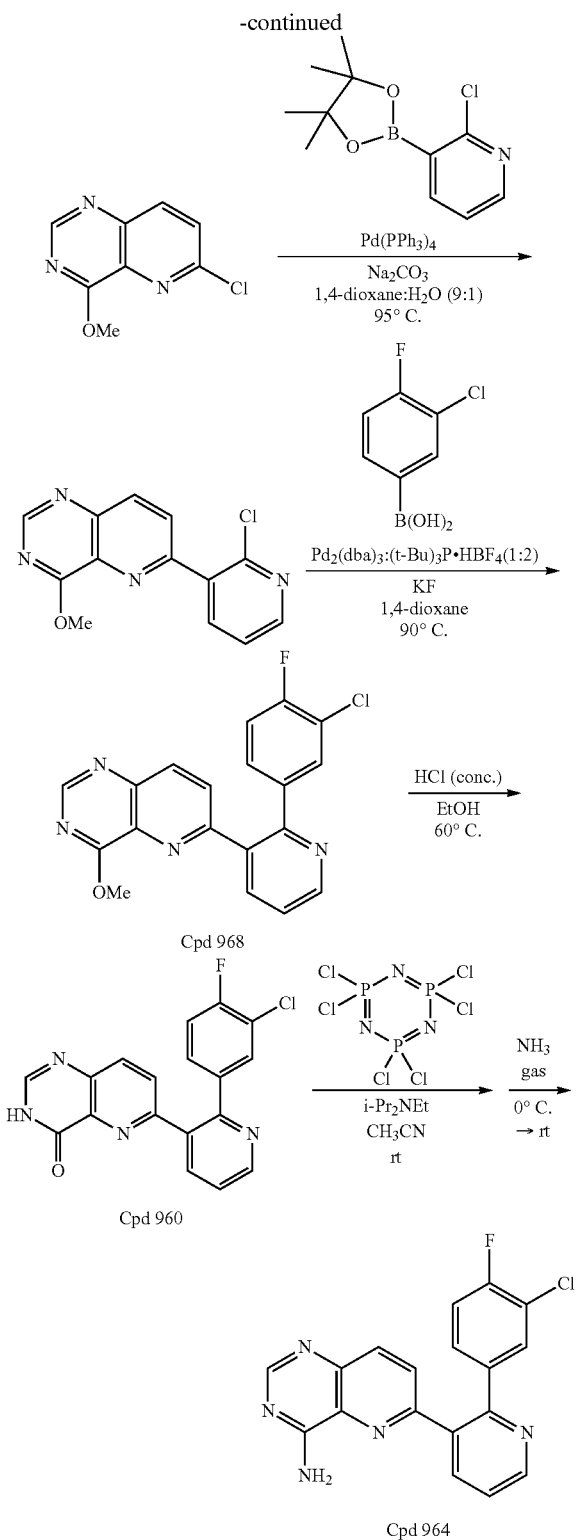

6-Chloro-4-methoxypyrido[3,2-d]pyrimidine 4,6-Dichloropyrido[3,2-d]pyrimidine (prepared from Int'l Pat. App. Pubs. nos. 2005058913, 2011131741 and 201009469) (2.5 g, 12.4 mmol) and NaHCO$_3$ (3.1 g, 31 mmol) in MeOH (20 mL) were heated at 70° C. for 12 h under nitrogen atmosphere. The reaction mixture was filtered and concentrated the filtrate. The crude concentrate was diluted with water and filtered.

The suction dried solid was stirred in EtOAc (20 mL) and filtered to obtain 6-chloro-4-methoxypyrido[3,2-d]pyrimidine (1.8 g) as an off-white solid. $^1$H NMR (300 MHz, DMSO-d$_6$): δ 8.88 (s, 1H), 8.37 (d, J=8.8 Hz, 1H), 8.00 (d, J=8.8 Hz, 1H), 4.14 (s, 3H).

6-(2-Chloropyridin-3-yl)-4-methoxypyrido[3,2-d]pyrimidine. A reaction flask was charged 6-chloro-4-methoxypyrido[3,2-d]pyrimidine (3.5 g, 17.8 mmol), 2-chloro-3-pyridineboronic acid pinacol ester (4.35 g, 18.2 mmol), Na$_2$CO$_3$ (4.0 g, 38.2 mmol) and 1,4-dioxane (100 mL) and a stir bar. The contents were degassed by vacuum and back filled with argon three times while stirring. Subsequently, Pd(PPh$_3$)$_3$ (0.87 g, 0.75 mmol) was added to the reaction contents, repeated degassing cycles and heated under argon at 98° C. The heating was stopped after overnight, the yellow hot heterogeneous reaction mixture was suction filtered on a Buchner funnel and washed the cake with additional amount of dioxane (30 mL). The pale yellow clear filtrate solution was passed through a pad of Celite® and concentrated the filtrate. The crude pale yellow solid residue was partitioned between CH$_2$Cl$_2$ (150 mL)/water (50 mL). The organic layer was separated, dried over MgSO$_4$, filtered and concentrated. The crude concentrate was stirred in EtOAc (30 mL) and suction filtered. The filter cake was washed further with EtOAc (10 mL) and dried to obtain 1.6 g of 6-(2-chloropyridin-3-yl)-4-methoxypyrido[3,2-d]pyrimidine (purity: 95%) as a white solid. The filtrate was concentrated and purified the concentrate by flash column chromatography (Combiflash® companion System® with RediSep® silica gel column 40 g, 0-30-60% EtOAC/hexanes eluting solvent gradient) to obtain additional 0.65 g of titled compound. $^1$H NMR (300 MHz, DMSO-d$_6$): δ 8.92 (s, 1H), 8.57 (dd, J=4.8, 2.0 Hz, 1H), 8.45 (d, J=8.7 Hz, 1H), 8.28 (d, J=8.7 Hz, 1H), 8.13 (dd, J=7.6, 2.0 Hz, 1H), 7.63 (dd, J=7.6, 4.8 Hz, 1H), 4.16 (s, 3H).

6-(2-(3-chloro-4-fluorophenyl)pyridin-3-yl)-4-methoxypyrido[3,2-d]pyrimidine (Compound 968). 6-(2-chloropyridin-3-yl)-4-methoxypyrido[3,2-d]pyrimidine (2.0 g, 7.3 mmol), 3-chloro-4-fluoro-phenylboronic acid (2.5 g, 14.3 mmol), KF (2.5 g, 43.0 mmol) and 1,4-dioxane (75 mL) and stir bar were added to a reaction flask. The contents were degassed by vacuum and back filled with argon three times while stirring. Subsequently, commercially available catalyst Pd$_2$(dba)$_3$.t-Bu$_3$P.HBF$_4$ (1:2) (1 g, 0.67 mmol) was added to the reaction contents, repeated degassing cycles and heated at 90° C. under argon. Colorimetric changes were observed after the introduction of catalyst and as the reaction progressed from pale pink to yellow to off-green slurries. After 6 h, the reaction stirring was stopped, filtered the hot slurry and washed the cake with additional amount of dioxane (30 mL). The pale yellow clear filtrate solution was passed through a pad of Celite® and concentrated the filtrate. The crude solid residue was partitioned between CH$_2$Cl$_2$ (150 mL)/water (50 mL). The organic layer was separated, dried over MgSO$_4$, filtered and concentrated. The crude concentrate was stirred in 60% EtOAc/hexanes (30 mL), suction filtered and dried the solid to obtain 1.6 g of (purity: 95%) 6-(2-(3-chloro-4-fluorophenyl)pyridin-3-yl)-4-methoxypyrido[3,2-d]pyrimidine as an off-white solid. The filtrate was concentrated and purified the concentrate by flash column chromatography (Combiflash® companion System® with RediSep® silica gel column 40 g, 0-30-60% EtOAC/hexanes eluting solvent gradient) to obtain additional 0.65 of titled compound.

6-(2-(3-Chloro-4-fluorophenyl)pyridin-3-yl)pyrido[3,2-d]pyrimidin-4 (3H)-one (Compound 960). Conc. HCl (0.2 ml) was added to a stirring heterogeneous slurry of 6-(2-(3-chloro-4-fluorophenyl)pyridin-3-yl)-4-methoxypyrido[3,2-d]pyrimidine (2.2 g) in EtOH (25 mL) at room temperature and heated the slurry gradually to 60° C. The pale yellow heterogeneous slurry transformed to homogeneous solution in 15 min and turned to heterogeneous slurry back again after 2 h of heating. Heating and stirring was continued for 4 h and cooled the reaction mixture to room temperature. The solid was collected by filtration and concentrated the filtrate. The solid was neutralized with aq.NaHCO$_3$, filtered and dried to obtain title compound as a white solid (1.3 g).

6-(2-(3-Chloro-4-fluorophenyl)pyridin-3-yl)pyrido[3,2-d]pyrimidin-4-amine (Compound 964). 6-(2-(3-Chloro-4-fluorophenyl)pyridin-3-yl)pyrido[3,2-d]pyrimidin-4 (3H)-one (100 mg, 0.28 mmol), phosphonitrilic chloride (100 mg, 0.28 mmol) and as stir bar were transferred to a vial, capped and placed under nitrogen atmosphere. Dry acetonitrile (3 mL) was transferred and allowed the contents to stir at room temperature. i-Pr$_2$NEt was added for 2 min to the heterogeneous slurry. Upon stirring the red homogeneous slurry for 2 h, nitrogen balloon was replaced with NH$_3$ balloon and stirred. After stirring the contents for 6 h, the reaction mixture was concentrated and the crude residue was partitioned between chloroform/water. Organic layer was removed and re-extracted the aqueous layer with chloroform. Usual workup and purification by preparative HPLC provided 6-(2-(3-Chloro-4-fluorophenyl)pyridin-3-yl)pyrido[3,2-d]pyrimidin-4-amine (16 mg) as a white solid.

Example 79

6,7-Diaryl-1H-pyrido[2,3-b][1,4]oxazin-2(3H)-ones (e.g., Compounds 292, 293, 294) and 6,7-diaryl-1-methyl-2,3-dihydro-1H-pyrido[2,3-b][1,4]oxazines (e.g., Compounds 295, 296, 300) can be prepared from 6,7-dibromo-2H-pyrido[3,2-b][1,4]oxazin-3(4H)-one (Int'l Pat. App. Publication no. 2011/077098) by adopting analogous Suzuki-Miyaura reaction conditions from previous examples, as shown in Scheme 23. Particular intermediates and reactions are described below.

7-Bromo-6-(4-fluoro-3-methylphenyl)-2H-pyrido[3,2-b][1,4]oxazin-3(4H)-one. $^1$H NMR (300 MHz, DMSO-d$_6$) δ 10.97 (s, 1H), 7.56-7.26 (m, 3H), 7.19 (dd, J=9.8, 8.4 Hz, 1H), 4.83 (s, 2H), 2.26 (d, J=2.0 Hz, 3H). $^{19}$F NMR (282 MHz, DMSO-d$_6$) δ −117.58 (ddt, J=8.5, 6.0, 3.0 Hz).

7-Bromo-6-(4-fluoro-3-methylphenyl)-1-methyl-1H-pyrido[2,3-b][1,4]oxazin-2(3H)-one. $^1$H NMR (300 MHz, DMSO-d$_6$): δ 7.84 (s, 1H), 7.59-7.34 (m, 2H), 7.20 (dd, J=9.8, 8.5 Hz, 1H), 4.90 (s, 2H), 3.27 (s, 3H), 2.27 (d, J=1.8 Hz, 3H). $^{19}$F NMR (282 MHz, DMSO-d$_6$) δ −117.43 (m).

7-Bromo-6-(4-fluoro-3-methylphenyl)-1-methyl-2,3-dihydro-1H-pyrido[2,3-b][1,4]oxazine. To the stirring solution of 7-bromo-6-(4-fluoro-3-methylphenyl)-1-methyl-1H-pyrido[2,3-b][1,4]oxazin-2(3H)-one (595 mg) and THF (15 mL) under argon was added BH$_3$.THF (5.1 mL, 1N solution in THF) dropwise for 20 min. After 12 h, the reaction mixture was cooled in ice-bath and transferred 1N aq. HCl (16 mL). Subsequently, cooling bath was removed and heated at 80° C. for 1 h. The reaction mixture was concentrated, basified with aq. NaHCO$_3$ solution and extracted with EtOAc (2×125 mL). Workup of the combined organic layers followed by flash column chromatographic purification (Combiflash® companion System® with RediSep® silica gel column 24 g and 30-50% EtOAc/hexanes eluting solvent) provided 450 mg of 7-bromo-6-(4-fluoro-3-methylphenyl)-1-methyl-2,3-dihydro-1H-pyrido[2,3-b][1,4]oxazine as an off-white solid. $^1$H NMR (300 MHz, DMSO-d$_6$): δ 7.45-7.32 (m, 2H), 7.21 (s, 1H), 7.13 (dd, J=9.8, 8.5 Hz, 1H), 4.59-4.21 (m, 2H), 3.47-3.25 (m, 2H), 2.88 (s, 3H), 2.25 (d, J=1.9 Hz, 3H). $^{19}$F NMR (282 MHz, DMSO-d$_6$) δ −118.92 (m).

Example 80

Free amino-substituted amide compounds (e.g., Compounds 514, 663, 679) can be prepared according to Scheme 32, below. General synthetic procedures are also provided.

Scheme 32

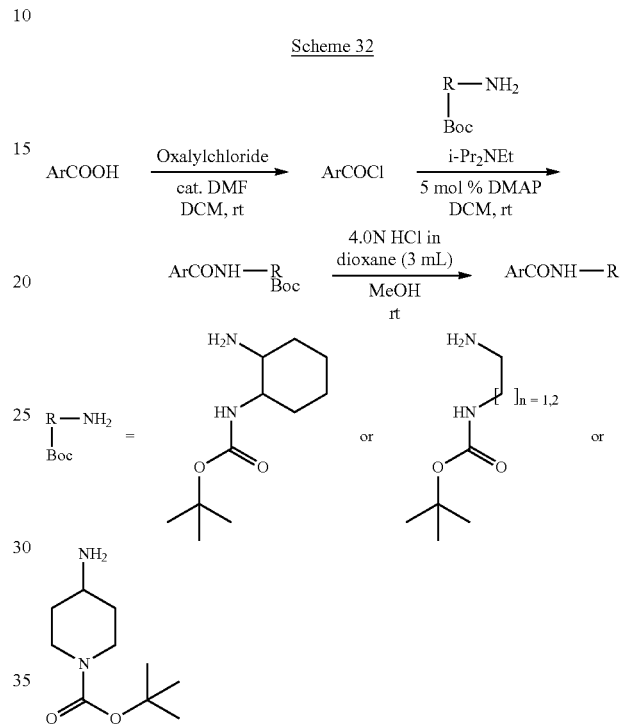

Step A: A single necked pear shaped round bottom flask containing a stir bar and acid ArCOOH (100 mg, 1 eq) is stoppered with a rubber septum and nitrogen is introduced. Methylene chloride (4 mL) is added and stirred for 5 min. Oxalyl chloride is added all at once followed by catalytic DMF (0.05 mL from stock solution of 0.05 mL of dry DMF dissolved in 4 mL of dry DMF) at room temp. The heterogeneous reaction solution turns to clear solution upon addition of DMF which eventually progresses to a heterogeneous slurry. After 3 h, reaction mixture is concentrated by rotary evaporator under nitrogen atmosphere to dryness to form acid chloride ArCOCl.

Step B: DMAP (5 mol %) and the desired N-Boc-diamine (Boc-R—NH$_2$) (1.2 eq) are weighed into the flask containing the acid chloride (as a semi-solid) with the stir bar. The flask is stoppered with a rubber septum and nitrogen is introduced. Methylene chloride (7 mL) is transferred and allowed to stir with the reaction contents. After stirring the contents for 10 min, i-Pr$_2$NEt is added drop-wise over a period of 5 min. The pale yellow homogeneous reaction mixture is concentrated after 1 h to yield crude amide ArCONHR-Boc.

Step C: The crude residue from step B is stirred with 4.0 N HCl in dioxane (3 mL) and MeOH (3 mL) at room temperature for 1 h. At the end of the reaction, the reaction mixture is concentrated and purified by preparative reverse HPLC. The purified concentrate (obtained as either TFA salt or formic acid salt/solvate) is neutralized with aq. NaHCO$_3$ solution and extracted with EtOAc. The organic layer is stirred with Na₂SO₄, polish filtered and concentrated. The concentrate is dissolved in acetonitrile/water and lyophilized to obtain the desired product ArCONHR.

Example 81

The following additional compounds were prepared substantially as described herein. In certain cases, synthetic preparations are provided below.

5-(2-(3-Cyclopropyl-4-fluorophenyl)pyridin-3-yl)-1H-indazole (Compound 211). LCMS: rt 5.21 min (A), MS (m/e) 330 MH⁺. ¹H NMR (CD₃OD, 300 MHz): 8.78 (dd, J=5.4, 1.5 Hz, 1H),): 8.55 (dd, J=7.8, 1.5 Hz, 1H), 8.08 (m, 1H), 7.98 (dd, J=7.8, 5.4 Hz, 1H), 7.75 (m, 1H), 7.50 (m, 1H), 7.28 (m, 1H), 7.14-7.05 (m, 2H), 6.88 (dd, J=6.9, 2.1 Hz, 1H), 1.96 (m, 1H), 0.82 (m, 2H), 0.24 (m, 2H);

N-Cyclopropyl-6-(4-fluoro-3-methylphenyl)-5-(1H-indazol-5-yl)pyridin-3-amine (Compound 212). LCMS: rt 5.65 min (A), MS (m/e) 359 MH⁺.

1-(6-(3-Cyclopropylphenyl)-5-(1H-indazol-5-yl)pyridin-3-yl)-3-isopropylurea (Compound 213). LCMS: rt 5.48 min (A), MS (m/e) 412 MH⁺.

1-(5-(1H-Indazol-5-yl)-6-(m-tolyl)pyridin-3-yl)-3-isopropylurea (Compound 214). LCMS: rt 5.15 min (A), MS (m/e) 386 MH⁺.

5-(2-(4-Fluoro-3-methylphenyl)-5-(3-isopropylureido)pyridin-3-yl)-N-isopropyl-1H-indazole-1-carboxamide (Compound 215). LCMS: rt 6.56 min (A), MS (m/e) 489 MH⁺.

2-(2-(3-cyclopropyl-4-fluorophenyl)pyridin-3-yl)-1,5-naphthyridine (Compound 216). LCMS: rt 5.81 min (A), MS (m/e) 342 MH⁺. ¹H NMR (CD₃OD, 300 MHz): 9.03 (dd, J=4.5, 1.8 Hz, 1H), 8.85 (dd, J=5.4, 1.8 Hz, 1H), 8.57-8.50 (m, 2H), 8.28 (dd, J=8.7, 0.9 Hz, 1H), 7.87 (m, 2H), 7.46 (d, J=8.7 Hz, 1H), 7.22 (m, 1H), 7.04 (dd, J=10.2, 8.7 Hz, 1H), 6.88 (dd, J=7.2, 2.4 Hz, 1H), 1.98 (m, 1H), 0.82 (m, 2H), 0.26 (m, 2H).

6-(2-(3-Cyclopropyl-4-fluorophenyl)pyridin-3-yl)-[1,2,4]triazolo[1,5-a]pyridine (Compound 217). LCMS: rt 5.35 min (A), MS (m/e) 331 MH⁺. ¹H NMR (CD₃OD, 300 MHz): 8.81 (dd, J=1.8, 0.9 Hz, 1H), 8.45 (s, 1H), 8.18 (dd, J=7.8, 1.8 Hz, 1H), 7.69-7.64 (m, 2H), 7.38 (dd, J=9.3, 1.8 Hz, 1H), 7.21 (m, 1H), 7.01 (dd, J=9.9, 8.4 Hz, 1H), 6.92 (dd, J=7.2, 2.4 Hz, 1H), 2.03 (m, 1H), 0.85 (m, 2H), 0.36 (m, 2H).

6-(2-(3-Cyclopropyl-4-fluorophenyl)pyridin-3-yl)imidazo[1,2-a]pyridine (Compound 218). LCMS: rt 4.23 min (A), MS (m/e) 330 MH⁺. ¹H NMR (CD₃OD, 300 MHz): 8.85 (m, 1H), 8.85 (dd, J=4.8, 1.5 Hz, 1H), 8.22 (dd, J=2.1, 0.9 Hz, 1H), 8.07 (d, J=2.1 Hz, 1H), 8.04 (dd, J=7.8, 1.5 Hz, 1H), 7.80 (m, 1H), 7.62-7.55 (m, 2H), 7.13 (m, 1H), 7.04 (dd, J=7.5, 2.4 Hz, 1H), 6.95 (d, J=1.5 Hz, 1H), 2.03 (m, 1H), 0.92 (m, 2H), 0.48 (m, 2H).

N-(6-(4-Fluoro-3-methylphenyl)-5-(imidazo[1,2-a]pyridin-6-yl)pyridin-3-yl)morpholine-4-carboxamide (Compound 219). LCMS: rt 4.00 min (A), MS (m/e) 432 MH⁺.

1-Ethyl-3-(6-(4-fluoro-3-methylphenyl)-5-(imidazo[1,2-a]pyridin-6-yl)pyridin-3-yl)urea (Compound 220). LCMS: rt 4.01 min (A), MS (m/e) 390 MH⁺.

3-(6-(4-Fluoro-3-methylphenyl)-5-(imidazo[1,2-a]pyridin-6-yl)pyridin-3-yl)-1,1-dimethylurea (Compound 221). LCMS: rt 3.91 min (A), MS (m/e) 390 MH⁺.

(6-(4-Fluoro-3-methylphenyl)-5-(quinoxalin-6-yl)pyridin-3-yl)methanol (Compound 222). LCMS: rt 5.16 min (b), MS (m/e) 346 MH⁺.

6-(2-(3-Cyclopropyl-4-fluorophenyl)pyridin-3-yl)imidazo[1,2-a]pyridine-3-carbonitrile (Compound 223). LCMS: rt 5.90 min (A), MS (m/e) 355 MH⁺.

6-(2-(3-Cyclopropyl-4-fluorophenyl)pyridin-3-yl)imidazo[1,2-a]pyridine-3-carboxamide (Compound 224). LCMS: rt 4.28 min (A), MS (m/e) 373 MH⁺. ¹H NMR (CD₃OD, 300 MHz): 9.69 (dd, J=1.8, 0.9 Hz, 1H), 8.79 (dd, J=5.1, 1.5 Hz, 1H), 8.52 (s, 1H), 8.27 (dd, J=7.8, 1.8 Hz, 1H), 7.78 (m, 2H), 7.54 (dd, J=9.3, 1.5 Hz, 1H), 7.16 (m, 1H), 7.03 (dd, J=7.2, 2.1 Hz, 1H), 6.99 (dd, J=10.2, 8.7 Hz, 1H), 2.03 (m, 1H), 0.92 (m, 2H), 0.51 (m, 2H).

4-((6-(4-Fluoro-3-methylphenyl)-5-(quinoxalin-6-yl)pyridin-3-yl)methyl)morpholine (Compound 225). LCMS: rt 5.06 min (A), MS (m/e) 415 MH⁺.

1-(6-(4-Fluoro-3-methylphenyl)-5-(quinoxalin-6-yl)pyridin-3-yl)-N,N-dimethylmethanamine (Compound 226). LCMS: rt 4.98 min (A), MS (m/e) 373 MH⁺.

6-(4-Fluoro-3-methylphenyl)-5-(quinoxalin-6-yl)nicotinic acid (Compound 227). LCMS: rt 6.33 min (A), MS (m/e) 360 MH⁺.

6-(2-(4-Fluoro-3-methylphenyl)-5-(methoxymethyl)pyridin-3-yl)quinoxaline (Compound 228). LCMS: rt 5.81 min (A), MS (m/e) 360 MH⁺.

6-(5-(Ethoxymethyl)-2-(4-fluoro-3-methylphenyl)pyridin-3-yl)quinoxaline (Compound 229). LCMS: rt 6.18 min (A), MS (m/e) 374 MH⁺.

6-(2-(4-Fluoro-3-methylphenyl)-5-((4-methylpiperazin-1-yl)methyl)pyridin-3-yl)quinoxaline (Compound 230). LCMS: rt 4.60 min (A), MS (m/e) 428 MH⁺.

2-((6-(4-Fluoro-3-methylphenyl)-5-(quinoxalin-6-yl)pyridin-3-yl)methoxy)-N,N-dimethylacetamide (Compound 231). LCMS: rt 5.41 min (A), MS (m/e) 431 MH⁺.

2-((6-(4-Fluoro-3-methylphenyl)-5-(quinoxalin-6-yl)pyridin-3-yl)methoxy)-N-methylacetamide (Compound 232). LCMS: rt 5.36 min (A), MS (m/e) 417 MH⁺.

2-((6-(4-Fluoro-3-methylphenyl)-5-(quinoxalin-6-yl)pyridin-3-yl)methoxy)acetamide (Compound 233). LCMS: rt 5.11 min (A), MS (m/e) 403 MH⁺.

6-(4-Fluoro-3-methylphenyl)-N,N-dimethyl-5-(quinoxalin-6-yl)nicotinamide (Compound 234). LCMS: rt 6.38 min (A), MS (m/e) 387 MH⁺.

6-(4-Fluoro-3-methylphenyl)-N-methyl-5-(quinoxalin-6-yl)nicotinamide (Compound 235). LCMS: rt 6.28 min (A), MS (m/e) 373 MH⁺.

6-(4-Fluoro-3-methylphenyl)-5-(quinoxalin-6-yl)pyridin-3-yl)(morpholino)methanone (Compound 236). LCMS: rt 6.41 min (A), MS (m/e) 429 MH⁺.

(6-(4-Fluoro-3-methylphenyl)-5-(quinoxalin-6-yl)pyridin-3-yl)(4-methylpiperazin-1-yl)methanone (Compound 237). LCMS: rt 4.98 min (A), MS (m/e) 442 MH⁺.

6-(4-Fluoro-3-methylphenyl)-5-(quinoxalin-6-yl)nicotinamide (Compound 238). LCMS: rt 5.98 min (A), MS (m/e) 359 MH⁺.

6-(4-Fluoro-3-methylphenyl)-5-(quinoxalin-6-yl)pyridin-3-amine (Compound 239). LCMS: rt 4.81 min (A), MS (m/e) 331 MH⁺. ¹H NMR (CD₃OD, 300 MHz): 8.93 (m, 2H), 8.09 (d, J=2.7 Hz, 1H), 8.05 (d, J=1.8 Hz, 1H), 8.04 (d, J=9.0 Hz, 1H), 7.83 (d, J=2.4 Hz, 1H), 7.62 (dd, J=8.7, 1.8 Hz, 1H), 7.32 (dd, J=7.2, 2.1 Hz, 1H), 7.07 (m, 1H), 6.96 (m, 1H), 2.18 (s, 3H).

6-(4-Fluoro-3-methylphenyl)-N-(1-methylpiperidin-4-yl)-5-(quinoxalin-6-yl)pyridin-3-amine (Compound 240). LCMS: rt 4.26 min (A), MS (m/e) 428 MH⁺.

6-(4-Fluoro-3-methylphenyl)-N-isopropyl-5-(quinoxalin-6-yl)pyridin-3-amine (Compound 241). LCMS: rt 5.56 min (A), MS (m/e) 373 MH⁺.

N,N-Diethyl-6-(4-fluoro-3-methylphenyl)-5-(quinoxalin-6-yl)pyridin-3-amine (Compound 242). LCMS: rt 5.75 min (A), MS (m/e) 387 MH⁺.

2-((6-(4-Fluoro-3-methylphenyl)-5-(quinoxalin-6-yl)pyridin-3-yl)amino)cyclohexan-1-ol (Compound 243). LCMS: rt 5.41 min (A), MS (m/e) 429 MH⁺.

6-(4-Fluoro-3-methylphenyl)-N-(pyridin-3-ylmethyl)-5-(quinoxalin-6-yl)pyridin-3-amine (Compound 244). LCMS: rt 4.28 min (A), MS (m/e) 422 MH⁺. $^1$H NMR (CD$_3$OD, 300 MHz): 8.91 (m, 3H), 8.75 (d, J=4.5 Hz, 1H), 8.53 (dd, J=8.4, 1.5 Hz, 1H), 8.17 (d, J=2.7 Hz, 1H), 8.01 (m, 2H), 7.95 (dd, J=7.8, 5.7 Hz, 1H), 7.84 (d, J=8.7 Hz, 1H), 7.58 (dd, J=8.4, 1.8 Hz, 1H), 7.31 (dd, J=7.8, 1.8 Hz, 1H), 7.05 (m, 1H), 6.96 (m, 1H), 4.81 (s, 2H), 2.17 (s, 3H).

6-(4-Fluoro-3-methylphenyl)-N-(pyridin-4-ylmethyl)-5-(quinoxalin-6-yl)pyridin-3-amine (Compound 245). LCMS: rt 4.26 min (A), MS (m/e) 422 MH⁺.

6-(4-Fluoro-3-methylphenyl)-N-(pyridin-2-ylmethyl)-5-(quinoxalin-6-yl)pyridin-3-amine (Compound 246). LCMS: rt 4.43 min (A), MS (m/e) 422 MH⁺.

5-(Benzo[d]thiazol-6-yl)-6-(4-fluoro-3-methylphenyl)-N-(1-methylpiperidin-4-yl)pyridin-3-amine (Compound 247). LCMS: rt 4.56 min (A), MS (m/e) 433 MH⁺.

6-(2-m-Tolylpyridin-3-yl)isoquinoline (Compound 248).

6-(2-(4-Fluoro-3-methylphenyl)pyridin-3-yl)isoquinoline (Compound 249)

4-(3-(6-(2-m-Tolylpyridin-3-yl)-1H-benzo[d]imidazol-1-yl)propyl)morpholine (Compound 250).

1-(3-(4-Methylpiperazin-1-yl)propyl)-6-(2-m-tolylpyridin-3-yl)-1H-benzo[d]imidazole (Compound 251).

4-(3-(6-(2-(4-fluoro-3-methylphenyl)pyridin-3-yl)-1H-benzo[d]imidazol-1-yl)propyl)morpholine (Compound 252).

1-(3-(4-Methylpiperazin-1-yl)propyl)-6-(2-(4-fluoro-3-methylphenyl)pyridin-3-yl)-1H-benzo[d]imidazole (Compound 253).

2-Fluoro-6-(2-(4-fluoro-3-methylphenyl)pyridin-3-yl)imidazo[1,2-a]pyridine (Compound 254). Anhydrous THF (25 mL) was introduced to a mixture of 6-(2-(4-fluoro-3-methylphenyl)pyridin-3-yl)imidazo[1,2-a]pyridine (0.42 g) and NaH (165 mg, 60% in mineral oil) under argon. The reaction mixture was stirred for 10 min and Selectofluor™ (750 mg) as solid was added in portions for 10 min. After complete addition of Selectofluor™, the reaction mixture was heated at 60° C. After 8 h, the reaction mixture was cooled to room temperature and additional amount of NaH (165 mg) and Selectofluor™ were added to the brown reaction mixture and continued to heat at 60° C. overnight. The reaction mixture was cooled with ice-bath, quenched with water slowly and concentrated. Usual work-up and purification by reverse phase preparative HPLC provided 2-fluoro-6-(2-(4-fluoro-3-methylphenyl)pyridin-3-yl)imidazo[1,2-a]pyridine as a pale yellow solid (23 mg). $^1$H NMR (300 MHz, DMSO-d$_6$) δ 8.74-8.56 (m, 1H), 8.31 (dd, J=1.9, 1.0 Hz, 1H), 7.92 (dt, J=7.7, 1.3 Hz, 1H), 7.56-7.35 (m, 3H), 7.35-7.21 (m, 2H), 7.06 (ddd, J=8.1, 5.2, 2.3 Hz, 1H), 6.94 (dd, J=9.8, 8.4 Hz, 1H), 6.68 (dt, J=9.5, 1.3 Hz, 1H), 2.12 (s, 3H). $^{19}$F NMR (282 MHz, DMSO-d$_6$) δ −118.22, −157.61 (d, J=7.1 Hz). LCMS: purity 99%, MS (m/e) 322 MH⁺.

Ethyl 7-(2-(4-fluoro-3-methylphenyl)pyridin-3-yl)imidazo[1,5-a]pyridine-3-carboxylate (Compound 255). $^1$H NMR (300 MHz, DMSO-d6) δ 9.03 (d, J=7.4 Hz, 1H), 8.70 (dd, J=4.7, 1.7 Hz, 1H), 7.95 (dd, J=7.8, 1.7 Hz, 1H), 7.86 (d, J=1.7 Hz, 1H), 7.69 (s, 1H), 7.56-7.41 (m, 2H), 7.13-6.93 (m, 2H), 6.71 (dd, J=7.5, 1.8 Hz, 1H), 4.36 (q, J=7.1 Hz, 2H), 2.17 (s, 3H), 1.33 (t, J=7.1 Hz, 3H). LCMS: rt 5.83 min (B), purity 96%, MS (m/e) 376 MH⁺.

Ethyl 6-(2-(4-fluoro-3-methylphenyl)pyridin-3-yl)imidazo[1,5-a]pyridine-3-carboxylate (Compound 256). LCMS: rt 5.81 min (B), purity 98%, MS (m/e) 376 MH⁺.

6-(2-(4-Fluoro-3-methylphenyl)pyridin-3-yl)imidazo[1,5-a]pyridine-3-carboxylic acid (Compound 257). $^1$H NMR (300 MHz, DMSO-d$_6$) δ 9.23 (q, J=1.2 Hz, 1H), 8.71 (dd, J=4.8, 1.7 Hz, 1H), 7.97 (dd, J=7.8, 1.7 Hz, 1H), 7.77-7.57 (m, 2H), 7.52 (dd, J=7.8, 4.8 Hz, 1H), 7.48-7.38 (m, 1H), 7.10 (ddd, J=8.0, 5.1, 2.3 Hz, 1H), 6.97 (dd, J=9.7, 8.5 Hz, 1H), 6.75 (dd, J=9.2, 1.5 Hz, 1H), 2.16 (s, 3H).LCMS: rt4.11 min (A), purity 96%, MS (m/e) 348 MH⁺.

7-(2-(4-Fluoro-3-methylphenyl)pyridin-3-yl)imidazo[1,5-a]pyridine-3-carboxylic acid (Compound 258). $^1$H NMR (300 MHz, DMSO-d$_6$) δ 9.19-8.96 (m, 1H), 8.68 (dd, J=4.8, 1.6 Hz, 1H), 7.94 (dd, J=7.8, 1.7 Hz, 1H), 7.80 (d, J=1.9 Hz, 1H), 7.63 (d, J=1.6 Hz, 1H), 7.56-7.37 (m, 2H), 7.16-6.88 (m, 2H), 6.63 (dt, J=7.5, 1.7 Hz, 1H), 2.17 (s, 3H).LCMS: rt3.93 min (A), purity 95%, MS (m/e) 348 MH⁺.

6-(2-(4-Fluoro-3-methylphenyl)pyridin-3-yl)-N-(3-(4-methylpiperazin-1-yl)propyl)imidazo[1,5-a]pyridine-3-carboxamide (Compound 259). $^1$H NMR (300 MHz, DMSO-d$_6$) δ 9.42 (t, J=1.3 Hz, 1H), 8.88-8.54 (m, 2H), 8.24 (d, J=1.1 Hz, 0H), 7.93 (dt, J=7.8, 1.4 Hz, 1H), 7.59 (dd, J=9.3, 1.2 Hz, 1H), 7.55-7.35 (m, 3H), 7.11 (td, J=6.3, 4.9, 3.0 Hz, 1H), 6.97 (t, J=9.1 Hz, 1H), 6.60 (dt, J=9.4, 1.3 Hz, 1H), 3.31 (q, J=6.5 Hz, 2H), 2.33 (t, J=6.7 Hz, 2H), 2.16 (s, 3H), 2.14 (s, 3H), 1.67 (p, J=6.8 Hz, 2H).LCMS: rt3.35 min (B), purity 99%, MS (m/e) 487 MH⁺.

6-(2-(4-Fluoro-3-methylphenyl)pyridin-3-yl)-N-(2-(4-methylpiperazin-1-yl)ethyl)imidazo[1,5-a]pyridine-3-carboxamide (Compound 260). LCMS: rt3.54 min (B), purity 99%, MS (m/e) 473 MH⁺.

(6-(2-(4-Fluoro-3-methylphenyl)pyridin-3-yl)imidazo[1,5-a]pyridin-3-yl)((3-morpholinopropyl)-12-azanyl)methanone (Compound 261). LCMS: rt3.72 min (B), purity 99%, MS (m/e) 474 MH⁺.

N-(3-(Dimethylamino)propyl)-6-(2-(4-fluoro-3-methylphenyl)pyridin-3-yl)imidazo[1,5-a]pyridine-3-carboxamide (Compound 262). LCMS: rt3.64 min (B), purity 99%, MS (m/e) 432 MH⁺.

N-(2-(Dimethylamino)ethyl)-6-(2-(4-fluoro-3-methylphenyl)pyridin-3-yl)imidazo[1,5-a]pyridine-3-carboxamide (Compound 263). LCMS: rt3.57 min (B), purity 99%, MS (m/e) 418 MH⁺.

7-(2-(4-Fluoro-3-methylphenyl)pyridin-3-yl)-N-(3-(4-methylpiperazin-1-yl)propyl)imidazo[1,5-a]pyridine-3-carboxamide (Compound 264). $^1$H NMR (300 MHz, DMSO-d$_6$) δ 9.18 (dt, J=7.5, 1.0 Hz, 1H), 8.74 (t, J=5.8 Hz, 1H), 8.68 (dd, J=4.7, 1.7 Hz, 1H), 7.93 (dd, J=7.8, 1.7 Hz, 1H), 7.74 (dd, J=1.8, 1.1 Hz, 1H), 7.56 (d, J=0.8 Hz, 1H), 7.52-7.39 (m, 2H), 7.21-6.90 (m, 2H), 6.55 (dd, J=7.5, 1.9 Hz, 1H), 3.30 (q, J=6.5 Hz, 2H), 2.43-2.22 (m, 2H), 2.18 (s, 3H), 2.14 (s, 3H), 1.66 (p, J=6.8 Hz, 2H).LCMS: rt3.25 min (B), purity 99%, MS (m/e) 487 MH⁺.

7-(2-(4-Fluoro-3-methylphenyl)pyridin-3-yl)-N-(2-(4-methylpiperazin-1-yl)ethyl)imidazo[1,5-a]pyridine-3-carboxamide (Compound 265). LCMS: rt3.43 min (B), purity 99%, MS (m/e) 473 MH⁺.

7-(2-(4-Fluoro-3-methylphenyl)pyridin-3-yl)-N-(3-morpholinopropyl)imidazo[1,5-a]pyridine-3-carboxamide (Compound 266). LCMS: rt3.62 min (B), purity 99%, MS (m/e) 474 MH⁺.

N-(3-(Dimethylamino)propyl)-7-(2-(4-fluoro-3-methylphenyl)pyridin-3-yl)imidazo[1,5-a]pyridine-3-carboxamide (Compound 267). LCMS: rt3.53 min (B), purity 99%, MS (m/e) 432 MH⁺.

N-(2-(Dimethylamino)ethyl)-7-(2-(4-fluoro-3-methylphenyl)pyridin-3-yl)imidazo[1,5-a]pyridine-3-carboxamide (Compound 268). LCMS: rt3.47 min (B), purity 99%, MS (m/e) 418 MH⁺.

6-(2-(4-Fluoro-3-methylphenyl)pyridin-3-yl)imidazo[1,5-a]pyridine (Compound 269). $^1$H NMR (300 MHz, DMSO-d$_6$) δ 8.68 (dd, J=4.8, 1.5 Hz, 1H), 8.38 (d, J=14.4 Hz, 2H), 7.91 (dd, J=7.8, 1.6 Hz, 1H), 7.55-7.42 (m, 2H), 7.38 (d, J=9.5 Hz, 1H), 7.31 (s, 1H), 7.14 (ddd, J=7.8, 5.0, 2.2 Hz, 1H), 7.00 (t, J=9.1 Hz, 1H), 6.31 (dd, J=9.4, 1.4 Hz, 1H), 2.17 (s, 3H).LCMS: rt2.70 min (B), purity 99%, MS (m/e) 304 MH$^+$.

6-(2-(4-Fluoro-3-methylphenyl)pyridin-3-yl)-N-(3-(2-oxopyrrolidin-1-yl)propyl)imidazo[1,5-a]pyridine-3-carboxamide (Compound 270). LCMS: rt5.94 min (B), purity 99%, MS (m/e) 472 MH$^+$.

6-(2-(4-Fluoro-3-methylphenyl)pyridin-3-yl)-N-(2-morpholino ethyl)imidazo[1,5-a]pyridine-3-carboxamide (Compound 271). LCMS: rt3.66 min (B), purity 99%, MS (m/e) 460 MH$^+$.

6-(2-(4-Fluoro-3-methylphenyl)pyridin-3-yl)-N-(2-(pyrrolidin-1-yl)ethyl)imidazo[1,5-a]pyridine-3-carboxamide (Compound 272). LCMS: rt3.74 min (B), purity 99%, MS (m/e) 445 MH$^+$.

6-(2-(4-Fluoro-3-methylphenyl)pyridin-3-yl)-N-(3-(pyrrolidin-1-yl)propyl)imidazo[1,5-a]pyridine-3-carboxamide (Compound 273). LCMS: rt3.81 min (B), purity 99%, MS (m/e) 458 MH$^+$.

7-(2-(4-Fluoro-3-methylphenyl)pyridin-3-yl)-N-(3-(2-oxopyrrolidin-1-yl)propyl)imidazo[1,5-a]pyridine-3-carboxamide (Compound 274). LCMS: rt5.88 min (B), purity 99%, MS (m/e) 472 MH$^+$.

7-(2-(4-Fluoro-3-methylphenyl)pyridin-3-yl)-N-(2-morpholino ethyl)imidazo[1,5-a]pyridine-3-carboxamide (Compound 275). LCMS: rt3.58 min (B), purity 99%, MS (m/e) 460 MH$^+$.

N-(2-Acetamidoethyl)-7-(2-(4-fluoro-3-methylphenyl)pyridin-3-yl)imidazo[1,5-a]pyridine-3-carboxamide (Compound 276). LCMS: rt5.21 min (B), purity 99%, MS (m/e) 432 MH$^+$.

N-(3-(1H-Imidazol-1-yl)propyl)-7-(2-(4-fluoro-3-methylphenyl)pyridin-3-yl)imidazo[1,5-a]pyridine-3-carboxamide (Compound 277). LCMS: rt3.70 min (B), purity 99%, MS (m/e) 455 MH$^+$.

7-(2-(4-Fluoro-3-methylphenyl)pyridin-3-yl)-N-(3-(pyrrolidin-1-yl)propyl)imidazo[1,5-a]pyridine-3-carboxamide (Compound 278). LCMS: rt3.71 min (B), purity 99%, MS (m/e) 457 MH$^+$.

N-((1R,2R,3S,4S)-3-Carbamoylbicyclo[2.2.1]hept-5-en-2-yl)-6-(2-(4-fluoro-3-methylphenyl)pyridin-3-yl)imidazo[1,5-a]pyridine-3-carboxamide (Compound 279). LCMS: rt6.67 min (B), purity 99%, MS (m/e) 482 MH$^+$.

N-((1R,2R,3S,4S)-3-Carbamoylbicyclo[2.2.1]hept-5-en-2-yl)-7-(2-(4-fluoro-3-methylphenyl)pyridin-3-yl)imidazo[1,5-a]pyridine-3-carboxamide (Compound 280). LCMS: rt6.65 min (B), purity 99%, MS (m/e) 482 MH$^+$.

4-(6-(2-(4-Fluoro-3-methylphenyl)pyridin-3-yl)imidazo[1,2-a]pyridin-3-yl)benzenesulfonamide (Compound 281). $^1$H NMR (300 MHz, DMSO-d$_6$) δ 8.67 (d, J=4.7 Hz, 1H), 8.46 (s, 1H), 8.02 (d, J=7.8 Hz, 1H), 7.88 (d, J=7.7 Hz, 3H), 7.69 (d, J=7.0 Hz, 2H), 7.58 (d, J=9.3 Hz, 1H), 7.54-7.39 (m, 4H), 7.03 (dt, J=9.2, 4.6 Hz, 2H), 2.21 (s, 3H). LCMS: rt 3.16 min (B), purity 99%, MS (m/e) 459 MH$^+$.

6-(2-(4-Fluoro-3-methylphenyl)pyridin-3-yl)-3-(pyridin-4-yl)imidazo[1,5-a]pyridine (Compound 282). LCMS: rt3.73 min (B), purity 99%, MS (m/e) 381 MH$^+$.

3-(6-(2-(4-Fluoro-3-methylphenyl)pyridin-3-yl)imidazo[1,5-a]pyridin-3-yl)aniline (Compound 283). LCMS: rt3.95 min (B), purity 99%, MS (m/e) 395 MH$^+$.

6-(2-(4-Fluoro-3-methylphenyl)pyridin-3-yl)-3-(3-methoxyphenyl)imidazo[1,5-a]pyridine (Compound 284). LCMS: rt5.35 min (B), purity 99%, MS (m/e) 410 MH$^+$.

6-(2-(4-Fluoro-3-methylphenyl)pyridin-3-yl)imidazo[1,5-a]pyridin-3-amine (Compound 285). $^1$H NMR (300 MHz, DMSO-d$_6$) δ 8.74-8.57 (m, 1H), 8.22 (d, J=2.1 Hz, 1H), 7.93-7.78 (m, 2H), 7.47 (qd, J=5.3, 4.7, 2.9 Hz, 2H), 7.19 (dd, J=5.5, 2.8 Hz, 1H), 7.03 (ddd, J=10.3, 8.5, 1.7 Hz, 2H), 6.82 (s, 1H), 5.98-5.79 (m, 2H), 2.20 (s, 3H).LCMS: rt2.78 min (B), purity 99%, MS (m/e) 319 MH$^+$.

7-(2-(4-Fluoro-3-methylphenyl)pyridin-3-yl)-3-(3-methoxyphenyl)imidazo[1,5-a]pyridine (Compound 286). LCMS: rt5.36 min (B), purity 99%, MS (m/e) 410 MH$^+$.

7-(2-(4-Fluoro-3-methylphenyl)pyridin-3-yl)-3-(pyridin-4-yl)imidazo[1,5-a]pyridine (Compound 287). $^1$H NMR (300 MHz, DMSO-d$_6$) δ 8.66 (dt, J=4.4, 2.1 Hz, 1H), 8.33 (dd, J=4.4, 2.0 Hz, 1H), 8.22 (s, 1H), 8.07-7.85 (m, 1H), 7.59-7.38 (m, 5H), 7.19 (ddt, J=7.6, 5.0, 2.4 Hz, 1H), 7.13-6.94 (m, 3H), 6.62 (td, J=5.0, 2.4 Hz, 1H), 6.55-6.35 (m, 1H), 2.21 (s, 3H).LCMS: rt3.36 min (B), purity 99%, MS (m/e) 381 MH$^+$.

7-(2-(4-Fluoro-3-methylphenyl)pyridin-3-yl)-3-(4-methoxyphenyl)imidazo[1,5-a]pyridine (Compound 288). LCMS: rt4.73 min (B), purity 99%, MS (m/e) 410 MH$^+$.

7-(2-(4-Fluoro-3-methylphenyl)pyridin-3-yl)-3-phenylimidazo[1,5-a]pyridine (Compound 289). LCMS: rt 5.09 min (B), purity 95%, MS (m/e) 380 MH$^+$.

3-(7-(2-(4-Fluoro-3-methylphenyl)pyridin-3-yl)imidazo[1,5-a]pyridin-3-yl)aniline (Compound 290). LCMS: rt4.38 min (A), purity 97%, MS (m/e) 395 MH$^+$.

6-(2-(3-Chloro-4-fluorophenyl)pyridin-3-yl)-[1,2,4]triazolo[1,5-a]pyridin-2-amine (Compound 291). $^1$H NMR (300 MHz, DMSO-d$_6$) δ 8.68 (dd, J=4.7, 1.6 Hz, 1H), 8.56 (dt, J=1.8, 0.7 Hz, 1H), 8.00-7.90 (m, 1H), 7.63 (dd, J=7.3, 2.0 Hz, 1H), 7.52 (dd, J=7.8, 4.7 Hz, 1H), 7.33-7.18 (m, 3H), 7.05 (dd, J=9.1, 1.8 Hz, 1H), 6.04 (s, 2H).LCMS: rt5.35 min (B), purity 99%, MS (m/e) 340 MH$^+$.

7-(Benzo[d]thiazol-6-yl)-6-(4-fluoro-3-methylphenyl)-1H-pyrido[2,3-b][1,4]oxazin-2(3H)-one (Compound 292). $^1$H NMR (300 MHz, DMSO-d$_6$) δ 9.37 (s, 1H), 8.05-7.90 (m, 2H), 7.31-7.15 (m, 5H), 4.86 (s, 2H), 2.10 (s, 3H).LCMS: rt7.13 min (A), purity 99%, MS (m/e) 392 MH$^+$.

6-(4-Fluoro-3-methylphenyl)-7-(quinolin-6-yl)-1H-pyrido[2,3-b][1,4]oxazin-2(3H)-one (Compound 293). LCMS: rt5.10 min (A), purity 99%, MS (m/e) 386 MH$^+$.

7-(Benzo[d]thiazol-6-yl)-6-(4-fluoro-3-methylphenyl)-1-methyl-1H-pyrido[2,3-b][1,4]oxazin-2(3H)-one (Compound 294). LCMS: rt 7.83 min (A), purity 99%, MS (m/e) 406 MH$^+$.

7-(Benzo[d]thiazol-6-yl)-6-(4-fluoro-3-methylphenyl)-1-methyl-2,3-dihydro-1H-pyrido[2,3-b][1,4]oxazine (Compound 295). $^1$H NMR (300 MHz, DMSO-d$_6$) δ 9.35 (s, 1H), 8.05 (d, J=1.7 Hz, 1H), 7.92 (d, J=8.4 Hz, 1H), 7.26-7.12 (m, 2H), 7.02 (s, 1H), 6.90-6.68 (m, 2H), 4.41 (t, J=8.9 Hz, 2H), 3.37-3.24 (m, 2H), 2.90 (s, 3H), 2.09 (s, 3H).LCMS: rt7.35 min (A), purity 99%, MS (m/e) 392 MH$^+$.

6-(4-Fluoro-3-methylphenyl)-1-methyl-7-(quinolin-6-yl)-2,3-dihydro-1H-pyrido[2,3-b][1,4]oxazine (Compound 296). LCMS: rt5.41 min (A), purity 99%, MS (m/e) 386 MH$^+$.

7-(2-(3-Chloro-4-fluorophenyl)pyridin-3-yl)isoquinolin-1-amine (Compound 297). LCMS: rt5.11 min (A), purity 99%, MS (m/e) 350 MH$^+$.

7-(2-(4-Fluoro-3-methylphenyl)pyridin-3-yl)isoquinolin-1-amine (Compound 298). $^1$H NMR (300 MHz, DMSO-d$_6$) δ 8.62 (dd, J=4.7, 1.7 Hz, 1H), 8.21 (s, 1H), 7.87 (dd, J=7.8, 1.7 Hz, 1H), 7.73 (d, J=5.8 Hz, 1H), 7.54-7.38 (m, 2H), 7.34 (dd, J=7.5, 2.0 Hz, 1H), 7.10 (dd, J=8.4, 1.7 Hz, 1H), 6.96-6.82 (m, 2H), 6.79 (d, J=5.9 Hz, 1H), 6.71 (s, 2H), 2.08 (s, 3H).LCMS: rt4.38 min (A), purity 97%, MS (m/e) 330 MH$^+$.

7-(2-(3-Fluorophenyl)pyridin-3-yl)isoquinolin-1-amine (Compound 299). LCMS: rt4.78 min (A), purity 98%, MS (m/e) 332 MH$^+$.

6-(4-Fluoro-3-methylphenyl)-7-(1H-indazol-5-yl)-1-methyl-2,3-dihydro-1H-pyrido[2,3-b][1,4]oxazine (Compound 300). LCMS: rt6.80 min (B), purity 96%, MS (m/e) 375 MH$^+$.

5-(2-(3-Chlorophenyl)pyridin-3-yl)thiazolo[5,4-b]pyridin-2-amine (Compound 301). $^1$H NMR (300 MHz, DMSO-d$_6$) δ 8.68 (dd, J=4.7, 1.6 Hz, 1H), 8.02 (dd, J=7.8, 1.6 Hz, 1H), 7.86 (s, 2H), 7.55-7.45 (m, 2H), 7.41-7.37 (m, 1H), 7.34 (ddd, J=7.8, 2.1, 1.1 Hz, 1H), 7.25 (t, J=7.8 Hz, 1H), 7.09 (dt, J=7.7, 1.3 Hz, 1H), 7.00 (dd, J=8.2, 0.8 Hz, 1H).LCMS: rt4.85 min (A), purity 99%, MS (m/e) 339 MH$^+$.

5-(2-(3-Chloro-4-fluorophenyl)pyridin-3-yl)thiazolo[5,4-b]pyridin-2-amine (Compound 302). $^1$H NMR (300 MHz, DMSO-d$_6$) δ 8.68 (dd, J=4.7, 1.6 Hz, 1H), 8.02 (dd, J=7.8, 1.7 Hz, 1H), 7.87 (s, 2H), 7.55-7.45 (m, 3H), 7.28 (t, J=7.8 Hz, 1H), 7.12 (ddd, J=8.6, 4.8, 2.2 Hz, 1H), 7.04 (dd, J=8.3, 0.5 Hz, 1H).LCMS: rt5.26 min (A), purity 95%, MS (m/e) 357 MH$^+$.

5-(2-(4-Fluoro-3-methylphenyl)pyridin-3-yl)thiazolo[5,4-b]pyridine (Compound 303). $^1$H NMR (300 MHz, DMSO-d$_6$) δ 9.55 (d, J=0.9 Hz, 1H), 8.73 (ddd, J=4.8, 1.8, 0.9 Hz, 1H), 8.33 (dd, J=8.5, 0.8 Hz, 1H), 8.08 (ddd, J=7.9, 1.8, 0.9 Hz, 1H), 7.52 (ddd, J=7.8, 4.7, 0.9 Hz, 2H), 7.35 (ddd, J=7.9, 1.8, 0.8 Hz, 1H), 7.28 (dd, J=8.5, 0.9 Hz, 1H), 7.01-6.85 (m, 3H), 2.13 (s, 3H).LCMS: rt5.53 min (A), purity 99%, MS (m/e) 322 MH$^+$.

5-(2-(m-Tolyl)pyridin-3-yl)thiazolo[5,4-b]pyridine (Compound 304). LCMS: rt3.37 min (A), purity 96%, MS (m/e) 304 MH$^+$.

5-(2-(3-Chloro-4-fluorophenyl)pyridin-3-yl)thiazolo[5,4-b]pyridine (Compound 305). $^1$H NMR (300 MHz, DMSO-d$_6$) δ 9.56 (s, 1H), 8.76 (dd, J=4.7, 1.7 Hz, 1H), 8.40 (d, J=8.5 Hz, 1H), 8.12 (dd, J=7.8, 1.7 Hz, 1H), 7.68-7.50 (m, 2H), 7.42 (d, J=8.5 Hz, 1H), 7.25 (t, J=9.0 Hz, 1H), 7.09 (ddd, J=8.7, 4.8, 2.2 Hz, 1H).LCMS: rt6.76 min (A), purity 96%, MS (m/e) 342 MH$^+$.

5-(Benzo[d]thiazol-6-yl)-6-(4-fluoro-3-methylphenyl)-N-(pyridin-3-ylmethyl)pyridin-3-amine (Compound 306). LCMS: rt 4.48 min (A), MS (m/e) 427 MH$^+$. $^1$H NMR (CD$_3$OD, 300 MHz): 9.29 (s, 1H), 8.92 (d, J=2.1 Hz, 1H), 8.79 (d, J=5.7 Hz, 1H), 8.60 (dd, J=7.8, 1.5 Hz, 1H), 8.16 (d, J=2.7 Hz, 1H), 7.03-7.91 (m, 3H), 7.85 (d, J=3.0 Hz, 1H), 7.33 (dd, J=8.4, 1.8 Hz, 1H), 7.21 (dd, J=7.5, 1.8 Hz, 1H), 7.05 (m, 1H), 6.98 (m, 1H), 4.83 (s, 2H), 2.18 (s, 3H).

4-(((6-(4-Fluoro-3-methylphenyl)-5-(quinoxalin-6-yl)pyridin-3-yl)amino)methyl)benzamide (Compound 307). LCMS: rt 4.41 min (A), MS (m/e) 464 MH$^+$.

4-(((6-(4-Fluoro-3-methylphenyl)-5-(quinoxalin-6-yl)pyridin-3-yl)amino)methyl)benzonitrile (Compound 308). LCMS: rt 5.81 min (A), MS (m/e) 446 MH$^+$.

4-(((5-(Benzo[d]thiazol-6-yl)-6-(4-fluoro-3-methylphenyl)pyridin-3-yl)amino)methyl)benzonitrile (Compound 309). LCMS: rt 5.85 min (A), MS (m/e) 451 MH$^+$.

4-((5-(Benzo[d]thiazol-6-yl)-6-(4-fluoro-3-methylphenyl)pyridin-3-yl)amino)benzamide (Compound 310). LCMS: rt 5.53 min (A), MS (m/e) 455 MH$^+$.

5-(Benzo[d]thiazol-6-yl)-6-(4-fluoro-3-methylphenyl)-N-(pyridin-4-yl)pyridin-3-amine (Compound 311). LCMS: rt 4.53 min (A), MS (m/e) 413 MH$^+$.

N-(5-(Benzo[d]thiazol-6-yl)-6-(4-fluoro-3-methylphenyl)pyridin-3-yl)-3-morpholinopropanamide (Compound 312). LCMS: rt 3.76 min (A), MS (m/e) 477 MH$^+$.

N-(5-(Benzo[d]thiazol-6-yl)-6-(4-fluoro-3-methylphenyl)pyridin-3-yl)-4-cyanobenzamide (Compound 313). LCMS: rt 7.59 min (A), MS (m/e) 465 MH$^+$.

N-(5-(Benzo[d]thiazol-6-yl)-6-(4-fluoro-3-methylphenyl)pyridin-3-yl)isonicotinamide (Compound 314). LCMS: rt 6.26 min (A), MS (m/e) 441 MH$^+$.

N-(5-(Benzo[d]thiazol-6-yl)-6-(4-fluoro-3-methylphenyl)pyridin-3-yl)nicotinamide (Compound 315). LCMS: rt 6.28 min (A), MS (m/e) 441 MH$^+$. $^1$H NMR (CD$_3$OD, 300 MHz): 9.24 (s, 1H), 9.15 (dd, J=2.1, 0.9 Hz, 1H), 8.99 (d, J=2.4 Hz, 1H), 8.75 (dd, J=8.4, 1.8 Hz, 1H), 8.39 (m, 2H), 7.98 (m, 2H), 7.67-7.53 (m, 2H), 7.35 (dd, J=8.7, 1.8 Hz, 1H), 7.26 (dd, J=4.5, 1.8 Hz, 1H), 7.02 (m, 1H), 6.84 (m, 1H), 2.13 (s, 3H);

N-(5-(Benzo[d]thiazol-6-yl)-6-(4-fluoro-3-methylphenyl)pyridin-3-yl)butyramide (Compound 316). LCMS: rt 6.72 min (A), MS (m/e) 406 MH$^+$.

N-(5-(Benzo[d]thiazol-6-yl)-6-(4-fluoro-3-methylphenyl)pyridin-3-yl)-4-(pyridin-4-yl)butanamide (Compound 317). LCMS: rt 4.03 min (A), MS (m/e) 483 MH$^+$.

4-(5-(Benzo[d]thiazol-6-yl)-6-(4-fluoro-3-methylphenyl)pyridin-3-yl)benzamide (Compound 318). LCMS: rt 7.15 min (B), MS (m/e) 440 MH$^+$.

6-(2-(4-Fluoro-3-methylphenyl)-5-(4-methylpiperazin-1-yl)pyridin-3-yl)benzo[d]thiazole (Compound 319). LCMS: rt 3.86 min (B), MS (m/e) 419 MH$^+$.

5-(Benzo[d]thiazol-6-yl)-6-(4-fluoro-3-methylphenyl)-N-(3-(4-methylpiperazin-1-yl)propyl)pyridin-3-amine (Compound 320). LCMS: rt 2.72 min (A), MS (m/e) 476 MH$^+$.

5-(Benzo[d]thiazol-6-yl)-N-((6-chloropyridin-3-yl)methyl)-6-(4-fluoro-3-methylphenyl)pyridin-3-amine (Compound 321). LCMS: rt 6.08 min (A), MS (m/e) 461 MH$^+$. $^1$H NMR (CD$_3$OD, 300 MHz): 9.30 (s, 1H), 8.46 (d, J=1.8 Hz, 1H), 8.04-7.98 (m, 3H), 7.92 (dd, J=8.1, 2.7 Hz, 1H), 7.80 (d, J=3.0 Hz, 1H), 7.48 (d, J=8.4 Hz, 1H), 7.32 (dd, J=8.4, 2.1 Hz, 1H), 7.25 (dd, J=7.2, 1.8 Hz, 1H), 7.04 (m, 1H), 6.95 (m, 1H), 4.60 (s, 2H), 2.18 (s, 3H);

N-((1H-Imidazol-5-yl)methyl)-5-(benzo[d]thiazol-6-yl)-6-(4-fluoro-3-methylphenyl)pyridin-3-amine (Compound 322). LCMS: rt 3.47 min (B), MS (m/e) 416 MH$^+$.

5-(Benzo[d]thiazol-6-yl)-N-((2-ethyl-1H-imidazol-5-yl)methyl)-6-(4-fluoro-3-methylphenyl)pyridin-3-amine (Compound 323). LCMS: rt 3.63 min (B), MS (m/e) 444 MH$^+$.

5-(Benzo[d]thiazol-6-yl)-6-(4-fluoro-3-methylphenyl)-N-((6-methoxypyridin-3-yl)methyl)pyridin-3-amine (Compound 324). LCMS: rt 5.46 min (A), MS (m/e) 457 MH$^+$. $^1$H NMR (CD$_3$OD, 300 MHz): 9.24 (s, 1H), 8.16 (d, J=1.8 Hz, 1H), 8.02 (d, J=2.7 Hz, 1H), 7.92 (d, J=8.7 Hz, 1H), 7.86 (d, J=1.5 Hz, 1H), 7.74 (dd, J=8.4, 2.4 Hz, 1H), 7.27 (dd, J=8.4, 1.8 Hz, 1H), 7.12 (m, 2H), 6.92-6.74 (m, 3H), 4.38 (s, 2H), 3.88 (s, 3H), 2.10 (s, 3H);

5-(Benzo[d]thiazol-6-yl)-6-(4-fluoro-3-methylphenyl)-N-((5-methoxypyridin-3-yl)methyl)pyridin-3-amine (Compound 325). LCMS: rt 4.43 min (A), MS (m/e) 457 MH$^+$.

5-(Benzo[d]thiazol-6-yl)-6-(4-fluoro-3-methylphenyl)-N-(thiazol-2-ylmethyl)pyridin-3-amine (Compound 326). LCMS: rt 5.64 min (B), MS (m/e) 433 MH$^+$. $^1$H NMR (CD$_3$OD, 300 MHz): 9.16 (s, 1H), 8.08 (d, J=2.4 Hz, 1H), 7.94 (d, J=8.7 Hz, 1H), 7.81 (m, 1H), 7.74 (d, J=3.0 Hz, 1H), 7.46 (d, J=3.3 Hz, 1H), 7.26 (dd, J=8.4, 1.8 Hz, 1H), 7.15 (dd, J=7.5, 1.8 Hz, 1H), 7.12 (d, J=2.7 Hz, 1H), 6.87 (m, 1H), 6.79 (m, 1H), 4.76 (s, 2H), 2.12 (s, 3H);

5-(Benzo[d]thiazol-6-yl)-6-(4-fluoro-3-methylphenyl)-N-(thiazol-5-ylmethyl)pyridin-3-amine (Compound 327). LCMS: rt 5.34 min (B), MS (m/e) 433 MH$^+$.

N-([2,3'-Bipyridin]-5-ylmethyl)-5-(benzo[d]thiazol-6-yl)-6-(4-fluoro-3-methylphenyl)pyridin-3-amine (Compound 328). LCMS: rt 4.78 min (A), MS (m/e) 504 MH$^+$.

N-((1H-Pyrrolo[2,3-b]pyridin-5-yl)methyl)-5-(benzo[d]thiazol-6-yl)-6-(4-fluoro-3-methylphenyl)pyridin-3-amine (Compound 329). LCMS: rt 4.97 min (B), MS (m/e) 466 MH+.

N-((1H-Pyrrolo[2,3-b]pyridin-3-yl)methyl)-5-(benzo[d]thiazol-6-yl)-6-(4-fluoro-3-methylphenyl)pyridin-3-amine (Compound 330). LCMS: rt 4.74 min (B), MS (m/e) 466 MH+.

5-(Benzo[d]thiazol-6-yl)-6-(4-fluoro-3-methylphenyl)-N-((2-methylpyridin-3-yl)methyl)pyridin-3-amine (Compound 331). LCMS: rt 3.62 min (B), MS (m/e) 441 MH+.

3-(((5-(Benzo[d]thiazol-6-yl)-6-(4-fluoro-3-methylphenyl)pyridin-3-yl)amino)methyl)phenol (Compound 332). LCMS: rt 5.29 min (B), MS (m/e) 442 MH+.

4-(((5-(Benzo[d]thiazol-6-yl)-6-(4-fluoro-3-methylphenyl)pyridin-3-yl)amino)methyl)phenol (Compound 333). LCMS: rt 4.76 min (A), MS (m/e) 442 MH+.

5-(Benzo[d]thiazol-6-yl)-6-(4-fluoro-3-methylphenyl)-N-((6-methylpyridin-3-yl)methyl)pyridin-3-amine (Compound 334). LCMS: rt 3.68 min (B), MS (m/e) 441 MH+.

5-(Benzo[d]thiazol-6-yl)-6-(4-fluoro-3-methylphenyl)-N-((3-methyl-3H-imidazo[4,5-b]pyridin-6-yl)methyl)pyridin-3-amine (Compound 335). LCMS: rt 4.50 min (B), MS (m/e) 481 MH+. $^1$H NMR (CD$_3$OD, 300 MHz): 9.19 (s, 1H), 8.50 (d, J=1.5 Hz, 1H), 8.32 (s, 1H), 8.12 (d, J=1.5 Hz, 1H), 8.06 (d, J=2.7 Hz, 1H), 7.90 (d, J=8.7 Hz, 1H), 7.83 (d, J=1.5 Hz, 1H), 7.23 (dd, J=8.7, 1.8 Hz, 1H), 7.14 (d, J=2.7 Hz, 1H), 7.10 (dd, J=8.7, 1.8 Hz, 1H), 6.87 (m, 1H), 6.78 (m, 1H), 4.61 (s, 2H), 3.90 (s, 3H), 2.08 (s, 3H).

5-(Benzo[d]thiazol-6-yl)-6-(4-fluoro-3-methylphenyl)-N-(quinolin-8-ylmethyl)pyridin-3-amine (Compound 336). LCMS: rt 6.02 min (B), MS (m/e) 477 MH+. $^1$H NMR (CD$_3$OD, 300 MHz): 9.19 (s, 1H), 8.34 (dd, J=8.1, 1.8 Hz, 1H), 8.04 (d, J=2.4 Hz, 1H), 7.85 (m, 3H), 7.14 (d, J=1.2 Hz, 1H), 7.55 (m, 2H), 7.19 (dd, J=8.7, 1.8 Hz, 1H), 7.15 (d, J=2.7 Hz, 1H), 7.10 (dd, J=7.8, 2.1 Hz, 1H), 6.86 (m, 1H), 6.78 (m, 1H), 5.09 (s, 2H), 2.09 (s, 3H);

5-(Benzo[d]thiazol-6-yl)-6-(4-fluoro-3-methylphenyl)-N-(iso quinolin-5-ylmethyl)pyridin-3-amine (Compound 337). LCMS: rt 4.47 min (B), MS (m/e) 477 MH+.

N-(4-(((5-(Benzo[d]thiazol-6-yl)-6-(4-fluoro-3-methylphenyl)pyridin-3-yl)amino)methyl)phenyl)acetamide (Compound 338). LCMS: rt 5.14 min (B), MS (m/e) 483 MH+.

5-(Benzo[d]thiazol-6-yl)-6-(4-fluoro-3-methylphenyl)-N-(quinolin-3-ylmethyl)pyridin-3-amine (Compound 339). LCMS: rt 5.41 min (B), MS (m/e) 477 MH+.

6-(2-(4-Fluoro-3-methylphenyl)pyridin-3-yl)-3-methylquinazolin-4(3H)-one (Compound 340). LCMS: rt 4.70 min (A), MS (m/e) 346 MH+.

3-Methyl-6-(2-(m-tolyl)pyridin-3-yl)quinazolin-4(3H)-one (Compound 341). LCMS: rt 4.08 min (A), MS (m/e) 328 MH+.

6-(2-(3-Cyclopropylphenyl)pyridin-3-yl)-3-methylquinazolin-4 (3H)-one (Compound 342). LCMS: rt 4.69 min (A), MS (m/e) 354 MH+.

3-(5-(Benzo[d]thiazol-6-yl)-6-(4-fluoro-3-methylphenyl) pyridin-3-yl)phenol (Compound 343). LCMS: rt 6.83 min (A), MS (m/e) 413 MH+.

N-(3-(5-(Benzo[d]thiazol-6-yl)-6-(4-fluoro-3-methylphenyl)pyridin-3-yl)phenyl)acetamide (Compound 344). LCMS: rt 6.65 min (A), MS (m/e) 454 MH+.

6-(2-(4-Fluoro-3-methylphenyl)-5-(1H-pyrazol-4-yl)pyridin-3-yl)benzo[d]thiazole (Compound 345). LCMS: rt 5.70 min (A), MS (m/e) 387 MH+.

6-(2-(4-Fluoro-3-methylphenyl)pyridin-3-yl)quinazolin-4(1H)-one (Compound 346). LCMS: rt 3.79 min (A), MS (m/e) 332 MH+.

3-(5-(Benzo[d]thiazol-6-yl)-6-(4-fluoro-3-methylphenyl) pyridin-3-yl)benzenesulfonamide (Compound 347). LCMS: rt 6.93 min (A), MS (m/e) 476 MH+.

7-(2-(4-Fluoro-3-methylphenyl)pyridin-3-yl)quinazolin-4(1H)-one (Compound 348). LCMS: rt 4.45 min (A), MS (m/e) 332 MH+.

7-(2-(m-Tolyl)pyridin-3-yl)quinazolin-4(1H)-one (Compound 349). LCMS: rt 4.08 min (A), MS (m/e) 314 MH+.

7-(2-(3-cyclopropylphenyl)pyridin-3-yl)quinazolin-4(1H)-one (Compound 350). LCMS: rt 4.56 min (A), MS (m/e) 340 MH+.

4-(((5-(Benzo[d]thiazol-6-yl)-6-(4-fluoro-3-methylphenyl)pyridin-3-yl)amino)methyl)-2-methoxyphenol (Compound 351). LCMS: rt 4.52 min (A), MS (m/e) 472 MH+.

2-(5-(((5-(Benzo[d]thiazol-6-yl)-6-(4-fluoro-3-methylphenyl)pyridin-3-yl)amino)methyl)-2-methoxyphenoxy) acetamide (Compound 352). LCMS: rt 4.26 min (A), MS (m/e) 529 MH+. $^1$H NMR (CD$_3$OD, 300 MHz): 9.21 (s, 1H), 8.00 (d, J=2.7 Hz, 1H), 7.91 (d, J=8.4 Hz, 1H), 7.82 (m, 1H), 7.23 (dd, J=8.4, 1.8 Hz, 1H), 7.11-7.04 (m, 4H), 7.05 (d, J=2.7 Hz, 1H), 6.86 (m, 1H), 6.78 (m, 1H), 4.47 (s, 2H), 4.35 (s, 2H), 3.84 (s, 3H), 2.09 (s, 3H).

5-(Benzo[d]thiazol-6-yl)-6-(4-fluoro-3-methylphenyl)-N-(4-morpholinobenzyl)pyridin-3-amine (Compound 353). LCMS: rt 5.03 min (A), MS (m/e) 511 MH+.

5-(Benzo[d]thiazol-6-yl)-6-(4-fluoro-3-methylphenyl)-N-(3-morpholinobenzyl)pyridin-3-amine (Compound 354). LCMS: rt 5.13 min (A), MS (m/e) 511 MH+.

6-(2-(4-Fluoro-3-methylphenyl)-5-(1H-pyrazol-1-yl)pyridin-3-yl)benzo[d]thiazole (Compound 355). LCMS: rt 6.85 min (A), MS (m/e) 387 MH+.

2-(4-(((5-(Benzo[d]thiazol-6-yl)-6-(4-fluoro-3-methylphenyl)pyridin-3-yl)amino)methyl)-2-methoxyphenoxy) ethan-1-ol (Compound 356). LCMS: rt 4.41 min (A), MS (m/e) 516 MH+.

5-(Benzo[d]thiazol-6-yl)-6-(4-fluoro-3-methylphenyl)-N-(4-((tetrahydro-2H-pyran-4-yl)oxy)benzyl)pyridin-3-amine (Compound 357). LCMS: rt 5.51 min (A), MS (m/e) 526 MH+.

5-(Benzo[d]thiazol-6-yl)-6-(4-fluoro-3-methylphenyl)-N-(4-(morpholinomethyl)benzyl)pyridin-3-amine (Compound 358). LCMS: rt 3.05 min (A), MS (m/e) 525 MH+.

4-(((5-(Benzo[d]thiazol-6-yl)-6-(4-fluoro-3-methylphenyl)pyridin-3-yl)amino)methyl)benzenesulfonamide (Compound 359). LCMS: rt 4.34 min (A), MS (m/e) 505 MH+.

N-((2-Ethyl-1H-imidazol-5-yl)methyl)-6-(4-fluoro-3-methylphenyl)-5-(imidazo[1,2-a]pyridin-6-yl)pyridin-3-amine (Compound 360). LCMS: rt 3.56 min (A), MS (m/e) 427 MH+.

6-(2-(m-tolyl)pyridin-3-yl)quinazolin-4(1H)-one (Compound 361). LCMS: rt 4.21 min (B), MS (m/e) 314 MH+.

6-(2-(3-Cyclopropylphenyl)pyridin-3-yl)quinazolin-4 (1H)-one (Compound 362). LCMS: rt 4.84 min (B), MS (m/e) 340 MH+.

6-(2-(4-Fluoro-3-methylphenyl)pyridin-3-yl)quinazoline (Compound 363). LCMS: rt 3.81 min (A), MS (m/e) 316 MH+. $^1$H NMR (CD$_3$OD, 300 MHz): 8.82 (dd, J=5.4, 1.2 Hz, 1H), 8.54 (m, 1H), 8.38 (d, J=2.1 Hz, 1H), 7.98 (dd, J=8.1, 5.7 Hz, 1H), 7.64 (s, 1H), 7.39 (m, 2H), 7.18 (m, 2H), 7.06 (m, 2H), 2.22 (s, 3H).

6-(2-(m-Tolyl)pyridin-3-yl)quinazoline (Compound 364). LCMS: rt 3.46 min (A), MS (m/e) 298 MH+.

6-(2-(3-Cyclopropylphenyl)pyridin-3-yl)quinazoline (Compound 365). LCMS: rt 3.98 min (A), MS (m/e) 324

MH⁺. ¹H NMR (CD₃OD, 300 MHz): 8.78 (dd, J=5.4, 1.5 Hz, 1H), 8.45 (dd, J=7.8, 1.5 Hz, 1H), 8.25 (d, J=2.1 Hz, 1H), 7.93 (dd, J=8.1, 5.7 Hz, 1H), 7.59 (m, 1H), 7.32-7.12 (m, 4H), 7.01 (m, 2H), 1.84 (m, 1H), 0.85 (m, 2H), 0.45 (m, 2H).

4-(((5-(Benzo[d]thiazol-6-yl)-6-(4-fluoro-3-methylphenyl)pyridin-3-yl)amino)methyl)-2,6-dimethoxyphenol (Compound 366). LCMS: rt 5.18 min (B), MS (m/e) 502 MH⁺.

5-(((5-(Benzo[d]thiazol-6-yl)-6-(4-fluoro-3-methylphenyl)pyridin-3-yl)amino)methyl)-2,3-dimethoxyphenol (Compound 367). LCMS: rt 5.34 min (B), MS (m/e) 502 MH⁺. ¹H NMR (CD₃OD, 300 MHz): 9.16 (s, 1H), 8.01 (d, J=2.7 Hz, 1H), 7.90 (d, J=8.4 Hz, 1H), 7.80 (bs, 1H), 7.25 (dd, J=8.4, 1.5 Hz, 1H), 7.13 (dd, J=7.5, 2.1 Hz, 1H), 7.05 (d, J=2.7 Hz, 1H), 7.90 (m, 1H), 6.78 (m, 1H), 6.58 (m, 2H), 4.32 (s, 2H), 3.82 (s, 3H), 3.79 (s, 3H), 2.11 (s, 3H);

4-(((5-(Benzo[d]thiazol-6-yl)-6-(4-fluoro-3-methylphenyl)pyridin-3-yl)amino)methyl)benzene-1,2-diol (Compound 368). LCMS: rt 4.82 min (A), MS (m/e) 458 MH⁺.

4-(((5-(Benzo[d]thiazol-6-yl)-6-(4-fluoro-3-methylphenyl)pyridin-3-yl)amino)methyl)-2-fluorophenol (Compound 369). LCMS: rt 5.48 min (B), MS (m/e) 460 MH⁺.

4-(((5-(Benzo[d]thiazol-6-yl)-6-(4-fluoro-3-methylphenyl)pyridin-3-yl)amino)methyl)-2-(trifluoromethyl)phenol (Compound 370). LCMS: rt 6.32 min (B), MS (m/e) 510 MH⁺.

4-(((5-(Benzo[d]thiazol-6-yl)-6-(4-fluoro-3-methylphenyl)pyridin-3-yl)amino)methyl)-2-(trifluoromethoxy)phenol (Compound 371). LCMS: rt 6.38 min (B), MS (m/e) 526 MH⁺. ¹H NMR (CD₃OD, 300 MHz): 9.19 (s, 1H), 8.01 (d, J=2.7 Hz, 1H), 7.88 (d, J=8.7 Hz, 1H), 7.80 (bs, 1H), 7.61-7.50 (m, 3H), 7.22 (m, 1H), 7.08 (d, J=2.7 Hz, 1H), 7.05-6.95 (m, 2H), 6.75 (m, 1H), 4.33 (s, 3H), 2.08 (s, 3H);

4-(((5-(Benzo[d]thiazol-6-yl)-6-(4-fluoro-3-methylphenyl)pyridin-3-yl)amino)methyl)-2-methylphenol (Compound 372). LCMS: rt 5.70 min (B), MS (m/e) 456 MH⁺.

5-(Benzo[d]thiazol-6-yl)-6-(4-fluoro-3-methylphenyl)-N-(4-(4-methylpiperazin-1-yl)benzyl)pyridin-3-amine (Compound 373). LCMS: rt 3.71 min (B), MS (m/e) 524 MH⁺.

1-(4-(((5-(Benzo[d]thiazol-6-yl)-6-(4-fluoro-3-methylphenyl)pyridin-3-yl)amino)methyl)phenyl)piperidin-4-ol (Compound 374). LCMS: rt 4.19 min (B), MS (m/e) 525 MH⁺.

6-(2-(4-Fluoro-3-methylphenyl)pyridin-3-yl)-4-methoxyquinazoline (Compound 375). LCMS: rt 6.91 min (B), MS (m/e) 346 MH⁺. ¹H NMR (CD₃OD, 300 MHz): 8.66 (dd, J=5.1, 1.5 Hz, 1H), 8.15 (d, J=2.1 Hz, 1H), 8.07 (s, 1H), 7.95 (m, 1H), 7.77 (d, J=8.7 Hz, 1H), 7.59-7.49 (m, 2H), 7.26 (d, J=7.5 Hz, 1H), 7.04 (m, 1H), 6.86 (m, 1H), 4.20 (s, 3H), 2.18 (s, 3H).

4-Methoxy-6-(2-(m-tolyl)pyridin-3-yl)quinazoline (Compound 376). LCMS: rt 6.29 min (B), MS (m/e) 328 MH⁺.

6-(2-(3-Cyclopropylphenyl)pyridin-3-yl)-4-methoxyquinazoline (Compound 377). LCMS: rt 6.94 min (B), MS (m/e) 354 MH⁺. ¹H NMR (CD₃OD, 300 MHz): 8.64 (m, 1H), 8.08 (m, 2H), 7.97 (m, 1H), 7.60-7.48 (m, 3H), 7.16-7.02 (m, 3H), 6.91 (m, 1H), 4.17 (s, 3H), 1.77 (m, 1H), 0.84 (m, 2H), 0.38 (m, 2H).

3-(3-(4-Methoxyquinazolin-6-yl)pyridin-2-yl)phenol (Compound 378). LCMS: rt 3.78 min (A), MS (m/e) 330 MH⁺.

6-(2-(3-Hydroxyphenyl)pyridin-3-yl)-3-methylquinazolin-4(3H)-one (Compound 379). LCMS: rt 3.80 min (B), MS (m/e) 330 MH⁺. ¹H NMR (CD₃OD, 300 MHz): 8.62 (dd, J=4.8, 1.5 Hz, 1H), 8.28 (s, 1H), 8.16 (m, 1H), 7.97 (dd, J=7.5, 1.5 Hz, 1H), 7.54 (m, 3H), 7.05 (m, 1H), 6.72 (m, 3H), 3.57 (s, 3H);

N-(3-(3-(3-Methyl-4-oxo-3,4-dihydroquinazolin-6-yl)pyridin-2-yl)phenyl)acetamide (Compound 380). LCMS: rt 3.84 min (B), MS (m/e) 371 MH⁺.

6-(2-(4-Fluorophenyl)pyridin-3-yl)-3-methylquinazolin-4(3H)-one (Compound 381). LCMS: rt 5.03 min (B), MS (m/e) 332 MH⁺.

3-Methyl-6-(2-(quinolin-8-yl)pyridin-3-yl)quinazolin-4(3H)-one (Compound 382). LCMS: rt 3.50 min (B), MS (m/e) 365 MH⁺.

6-(2-(4-Fluoro-3-methylphenyl)pyridin-3-yl)quinazolin-2-amine (Compound 383). LCMS: rt 4.06 min (B), MS (m/e) 331 MH⁺.

6-(2-(m-Tolyl)pyridin-3-yl)quinazolin-2-amine (Compound 384). LCMS: rt 3.53 min (B), MS (m/e) 313 MH⁺.

4-(6-(2-(4-Fluoro-3-methylphenyl)pyridin-3-yl)quinazolin-4-yl)morpholine (Compound 385). LCMS: rt 4.28 min (A), MS (m/e) 401 MH⁺. ¹H NMR (CD₃OD, 300 MHz): 8.81 (dd, J=5.7, 1.5 Hz, 1H), 8.65 (s, 1H), 8.45 (dd, J=8.1, 1.5 Hz, 1H), 8.24 (dd, J=7.8, 1.5 Hz, 1H), 8.17 (m, 2H), 7.90 (m, 1H), 7.63 (m, 1H), 7.44-7.36 (m, 1H), 7.18 (m, 1H), 7.03 (m, 1H), 3.89 (m, 4H), 3.22 (m, 4H), 2.21 (s, 3H).

4-(6-(2-(m-Tolyl)pyridin-3-yl)quinazolin-4-yl)morpholine (Compound 386). LCMS: rt 3.83 min (A), MS (m/e) 383 MH⁺.

4-(6-(2-(3-Cyclopropylphenyl)pyridin-3-yl)quinazolin-4-yl)morpholine (Compound 387). LCMS: rt 4.26 min (A), MS (m/e) 409 MH⁺.

6-(2-(3-Chloro-4-fluorophenyl)pyridin-3-yl)quinazolin-4(1H)-one (Compound 388). LCMS: rt 5.16 min (A), MS (m/e) 352 MH⁺.

6-(2-(3-Chlorophenyl)pyridin-3-yl)quinazolin-4(1H)-one (Compound 389). LCMS: rt 4.76 min (A), MS (m/e) 334 MH⁺. ¹H NMR (CD₃OD, 300 MHz): 8.75 (dd, J=5.1, 1.5 Hz, 1H), 8.23 (dd, J=8.1, 1.5 Hz, 1H), 8.17 (s, 1H), 8.15 (m, 2H), 7.76 (dd, J=8.1, 5.1 Hz, 1H), 7.62 (m, 1H), 7.45 (m, 1H), 7.37 (m, 1H), 7.36-7.18 (m, 2H).

6-(2-(3-Chloro-4-fluorophenyl)pyridin-3-yl)-3-methylquinazolin-4(3H)-one (Compound 390). LCMS: rt 5.70 min (A), MS (m/e) 366 MH⁺. ¹H NMR (CD₃OD, 300 MHz): 8.75-8.73 (m, 1H), 8.36 (s, 1H), 8.20 (dd, 1H), 8.14 (m, 1H), 7.77-7.72 (m, 1H), 7.63 (m, 2H), 7.55 (dd, 1H), 7.28-7.22 (m, 1H), 7.19 (d, 1H), 3.59 (s, 3H).

6-(2-(3-Chlorophenyl)pyridin-3-yl)-3-methylquinazolin-4(3H)-one (Compound 391). LCMS: rt 5.28 min (A), MS (m/e) 348 MH⁺. ¹H NMR (CD₃OD, 300 MHz): 8.67 (dd, 1H), 8.31 (s, 1H), 8.13 (m, 1H), 8.01 (dd, 1H), 7.58 (m, 3H), 7.38 (m, 1H), 7.28 (m, 1H), 7.23-7.14 (m, 2H), 3.58 (s, 3H).

6-(2-(4-Fluoro-3-methylphenyl)pyridin-3-yl)quinazolin-4-amine (Compound 392). LCMS: rt 2.43 min (A), MS (m/e) 331 MH⁺.

6-(2-(3-Chlorophenyl)pyridin-3-yl)quinazolin-4-amine (Compound 393). LCMS: rt 3.26 min (B), MS (m/e) 333 MH⁺. ¹H NMR (CD₃OD, 300 MHz): 8.65 (dd, J=5.1, 1.8 Hz, 1H), 8.37 (s, 1H), 8.16 (m, 1H), 8.03 (dd, J=7.8, 1.8 Hz, 1H), 7.59 (dd, J=7.8, 1.8 Hz, 2H), 7.31 (m, 1H), 7.23-7.13 (m, 2H).

6-(2-(3-Chloro-4-fluorophenyl)pyridin-3-yl)quinazolin-4-amine (Compound 394). LCMS: rt 3.47 min (B), MS (m/e) 351 MH⁺. ¹H NMR (CD₃OD, 300 MHz): 8.67 (dd, J=4.8, 1.5 Hz, 1H), 8.38 (s, 1H), 8.16 (d, J=1.5 Hz, 1H), 8.01 (dd, J=7.8, 1.5 Hz, 1H), 7.61-7.48 (m, 4H), 7.318-7.06 (m, 2H).

6-(2-(3-Chloro-4-fluorophenyl)pyridin-3-yl)-4-methoxyquinazoline (Compound 395). LCMS: rt 6.42 min (A), MS (m/e) 366 MH⁺.

7-(2-(4-Fluoro-3-methylphenyl)pyridin-3-yl)quinazolin-2-amine (Compound 396). LCMS: rt 4.39 min (B), MS (m/e) 331 MH$^+$. $^1$H NMR (CD$_3$OD, 300 MHz): 9.05 (br, 1H), 8.65 (dd, J=5.1, 1.8 Hz, 1H), 8.65 (dd, J=7.8, 1.8 Hz, 1H), 7.70 (d, J=8.4 Hz, 1H), 7.53 (m, 1H), 7.36 (m, 1H), 7.29 (m, 1H), 7.08-7.02 (m, 2H), 6.87 (m, 1H), 2.15 (s, 3H).

N,N-Diethyl-6-(2-(4-fluoro-3-methylphenyl)pyridin-3-yl)quinazolin-4-amine (Compound 397). LCMS: rt 3.89 min (B), MS (m/e) 387 MH$^+$.

6-(2-(3-Chloro-4-fluorophenyl)pyridin-3-yl)-N,N-diethylquinazolin-4-amine (Compound 398). LCMS: rt 4.22 min (B), MS (m/e) 407 MH$^+$.

3-(3-(4-(Diethylamino)quinazolin-6-yl)pyridin-2-yl)phenol (Compound 399). LCMS: rt 3.05 min (B), MS (m/e) 371 MH$^+$.

6-(2-(4-Fluoro-3-methylphenyl)pyridin-3-yl)-N-isopropylquinazolin-4-amine (Compound 400). LCMS: rt 3.85 min (B), MS (m/e) 373 MH$^+$.

6-(2-(3-Chloro-4-fluorophenyl)pyridin-3-yl)-N-isopropylquinazolin-4-amine (Compound 401). LCMS: rt 4.17 min (B), MS (m/e) 393 MH$^+$.

6-(2-(4-Fluoro-3-methylphenyl)pyridin-3-yl)-N-propylquinazolin-4-amine (Compound 402). LCMS: rt 3.25 min (A), MS (m/e) 373 MH$^+$.

N-Butyl-6-(2-(4-fluoro-3-methylphenyl)pyridin-3-yl)quinazolin-4-amine (Compound 403). LCMS: rt 3.65 min (A), MS (m/e) 387 MH$^+$.

N-Cyclopropyl-6-(2-(4-fluoro-3-methylphenyl)pyridin-3-yl)quinazolin-4-amine (Compound 404). LCMS: rt 3.68 min (B), MS (m/e) 371 MH$^+$.

N-Cyclopentyl-6-(2-(4-fluoro-3-methylphenyl)pyridin-3-yl)quinazolin-4-amine (Compound 405). LCMS: rt 4.30 min (B), MS (m/e) 399 MH$^+$.

4-((6-(2-(4-Fluoro-3-methylphenyl)pyridin-3-yl)quinazolin-4-yl)amino)benzamide (Compound 406). LCMS: rt 3.63 min (A), MS (m/e) 450 MH$^+$.

6-(2-(4-Fluoro-3-methylphenyl)pyridin-3-yl)-N-(4-methoxyphenyl)quinazolin-4-amine (Compound 407). LCMS: rt 4.73 min (B), MS (m/e) 437 MH$^+$.

6-(2-(4-Fluoro-3-methylphenyl)pyridin-3-yl)-N-(4-morpholinophenyl)quinazolin-4-amine (Compound 408). LCMS: rt 4.46 min (B), MS (m/e) 492 MH$^+$.

4-((6-(2-(4-Fluoro-3-methylphenyl)pyridin-3-yl)quinazolin-4-yl)amino)benzonitrile (Compound 409). LCMS: rt 6.52 min (B), MS (m/e) 432 MH$^+$.

3-((6-(2-(4-Fluoro-3-methylphenyl)pyridin-3-yl)quinazolin-4-yl)amino)benzamide (Compound 410). LCMS: rt 4.05 min (B), MS (m/e) 450 MH$^+$.

6-(2-(3-Cyclopropylphenyl)pyridin-3-yl)quinazolin-4-amine (Compound 411). LCMS: rt 3.13 min (B), MS (m/e) 339 MH$^+$. $^1$H NMR (CD$_3$OD, 300 MHz): 8.65 (dd, J=4.8, 1.5 Hz, 1H), 8.37 (s, 1H), 8.13 (d, J=2.1 Hz, 1H), 8.03 (dd, J=7.8, 1.5 Hz, 1H), 7.56-7.51 (m, 2H), 7.41 (dd, J=9.0, 2.1 Hz, 1H), 7.15-7.04 (m, 3H), 6.89 (m, 1H), 1.76 (m, 1H), 0.79 (m, 2H), 0.34 (m, 2H).

3-(2-(3-Chloro-4-fluorophenyl)pyridin-3-yl)-1,8-naphthyridine (Compound 412). LCMS: rt 5.84 min (B), MS (m/e) 114 MH$^+$.

3-(2-(3-Chlorophenyl)pyridin-3-yl)-1,8-naphthyridine (Compound 413). LCMS: rt 5.58 min (B), MS (m/e) 318 MH$^+$.

6-(2-(4-Fluoro-3-methylphenyl)pyridin-3-yl)-N-(2-(pyridin-3-yl)ethyl)quinazolin-4-amine (Compound 414). LCMS: rt 2.82 min (B), MS (m/e) 436 MH$^+$.

6-(2-(4-Fluoro-3-methylphenyl)pyridin-3-yl)-N-(pyridin-4-ylmethyl)quinazolin-4-amine (Compound 415). LCMS: rt 2.78 min (B), MS (m/e) 422 MH$^+$.

6-(2-(4-Fluoro-3-methylphenyl)pyridin-3-yl)-N-(pyridin-3-ylmethyl)quinazolin-4-amine (Compound 416). LCMS: rt 3.03 min (B), MS (m/e) 422 MH$^+$.

3-(2-(4-Fluoro-3-methylphenyl)pyridin-3-yl)-1,8-naphthyridine (Compound 417). LCMS: rt 5.23 min (B), MS (m/e) 316 MH$^+$.

6-(2-(4-Fluoro-3-methylphenyl)pyridin-3-yl)quinoline-2-carbonitrile (Compound 418). LCMS: rt 7.75 min (B), MS (m/e) 340 MH$^+$.

6-(2-(3-Chloro-4-fluorophenyl)pyridin-3-yl)quinoline-2-carbonitrile (Compound 419). LCMS: rt 8.26 min (B), MS (m/e) 360 MH$^+$.

6-(2-(3-Chlorophenyl)pyridin-3-yl)quinoline-2-carbonitrile (Compound 420). LCMS: rt 8.07 min (B), MS (m/e) 342 MH$^+$.

6-(2-(4-Fluoro-3-methylphenyl)pyridin-3-yl)-N-((1-methylpiperidin-4-yl)methyl)quinazolin-4-amine (Compound 421). LCMS: rt 2.32 min (B), MS (m/e) 442 MH$^+$.

6-(2-(4-Fluoro-3-methylphenyl)pyridin-3-yl)-N-(2-(1-methylpiperidin-4-yl)ethyl)quinazolin-4-amine (Compound 422). LCMS: rt 1.97 min (A), MS (m/e) 456 MH$^+$.

N1-(6-(2-(4-Fluoro-3-methylphenyl)pyridin-3-yl)quinazolin-4-yl)-N3,N3-dimethylpropane-1,3-diamine (Compound 423). LCMS: rt 3.55 min (A), MS (m/e) 416 MH$^+$. $^1$H NMR (CD$_3$OD, 300 MHz): 8.79 (s, 1H), 8.67 (dd, J=5.4, 1.5 Hz, 1H), 8.49 (m, 1H), 8.21 (dd, J=7.8, 1.8 Hz, 1H), 7.77 (dd, J=8.1, 5.4 Hz, 1H), 7.66 (m, 2H), 7.37 (m, 1H), 7.09 (m, 1H), 6.94 (m, H), 3.94 (t, J=6.6 Hz, 2H), 3.29 (m, 2H), 2.91 (s, 6H), 2.24 (m, 2H), 2.20 (s, 3H);

6-(2-(4-Fluoro-3-methylphenyl)pyridin-3-yl)-N-(3-morpholinopropyl)quinazolin-4-amine (Compound 424). LCMS: rt 3.61 min (A), MS (m/e) 458 MH$^+$.

4-(2-((6-(2-(4-Fluoro-3-methylphenyl)pyridin-3-yl)quinazolin-4-yl)oxy)ethyl)morpholine (Compound 425). LCMS: rt 3.42 min (B), MS (m/e) 445 MH$^+$.

6-(2-(4-Fluoro-3-methylphenyl)pyridin-3-yl)quinolin-2-amine (Compound 426). LCMS: rt 3.19 min (B), MS (m/e) 330 MH$^+$.

6-(2-(3-Chloro-4-fluorophenyl)pyridin-3-yl)quinolin-2-amine (Compound 427). LCMS: rt 3.72 min (B), MS (m/e) 350 MH$^+$.

6-(2-(3-Chlorophenyl)pyridin-3-yl)quinolin-2-amine (Compound 428). LCMS: rt 3.50 min (B), MS (m/e) 332 MH$^+$.

3-((6-(2-(4-Fluoro-3-methylphenyl)pyridin-3-yl)quinazolin-4-yl)oxy)-N,N-dimethylpropan-1-amine (Compound 429). LCMS: rt 3.47 min (B), MS (m/e) 417 MH$^+$. $^1$H NMR (CD$_3$OD, 300 MHz): 8.74 (s, 1H), 8.66 (dd, J=5.1, 1.5 Hz, 1H), 8.10 (m, 1H), 8.03 (dd, J=7.8, 1.5 Hz, 1H), 7.77 (m, 1H), 7.67 (dd, J=7.8, 5.1 Hz, 1H), 7.56 (m, 2H), 7.27 (m, 1H), 7.06 (m, 1H), 6.88 (m, H), 4.67 (t, J=6.0 Hz, 2H), 2.88 (m, 2H), 2.56 (s, 6H), 2.21 (m, 2H), 2.14 (s, 3H).

2-((6-(2-(4-Fluoro-3-methylphenyl)pyridin-3-yl)quinazolin-4-yl)oxy)acetonitrile (Compound 430). LCMS: rt 6.76 min (B), MS (m/e) 371 MH$^+$.

1-(3-((6-(2-(4-Fluoro-3-methylphenyl)pyridin-3-yl)quinazolin-4-yl)oxy)propyl)pyrrolidin-2-one (Compound 431). LCMS: rt 4.92 min (A), MS (m/e) 457 MH$^+$.

6-(2-(4-Fluoro-3-methylphenyl)pyridin-3-yl)-4-((6-methylpyridin-3-yl)oxy)quinazoline (Compound 432). LCMS: rt 6.58 min (B), MS (m/e) 423 MH$^+$. $^1$H NMR (CD$_3$OD, 300 MHz): 8.69 (s, 1H), 8.67 (dd, J=5.4, 1.8 Hz, 1H), 8.35 (dd, J=7.8, 1.5 Hz, 1H), 8.16 (m, 1H), 8.07 (m, 1H), 7.70 (m, 2H), 7.57 (m, 2H), 7.27-7.02 (m, 3H), 6.89 (m, 1H), 2.41 (s, 3H), 2.18 (s, 3H).

6-(2-(4-Fluoro-3-methylphenyl)pyridin-3-yl)-4-(2-(4-methylpiperazin-1-yl)ethoxy)quinazoline (Compound 433). LCMS: rt 3.45 min (B), MS (m/e) 458 MH⁺.

6-(2-(4-Fluoro-3-methylphenyl)pyridin-3-yl)-4-(3-(4-methylpiperazin-1-yl)propoxy)quinazoline (Compound 434). LCMS: rt 3.42 min (B), MS (m/e) 472 MH⁺.

3-((6-(2-(3-Chloro-4-fluorophenyl)pyridin-3-yl)quinazolin-4-yl)oxy)-N,N-dimethylpropan-1-amine (Compound 435). LCMS: rt 3.83 min (B), MS (m/e) 437 MH⁺. ¹H NMR (CD₃OD, 300 MHz): 8.74 (s, 1H), 8.65 (dd, J=5.4, 1.5 Hz, 1H), 8.10 (m, 2H), 8.03 (dd, J=7.8, 1.5 Hz, 1H), 7.84 (m, 1H), 7.67 (dd, J=7.8, 5.1 Hz, 1H), 7.56 (m, 1H), 7.20 (m, 1H), 7.12 (m, 1H), 4.66 (t, J=6.6 Hz, 2H), 2.77 (m, 2H), 2.46 (s, 6H), 2.14 (m, 2H);

1-(3-((6-(2-(3-Chloro-4-fluorophenyl)pyridin-3-yl)quinazolin-4-yl)oxy)propyl)pyrrolidin-2-one (Compound 436). LCMS: rt 6.60 min (B), MS (m/e) 477 MH⁺.

6-(2-(3-Chloro-4-fluorophenyl)pyridin-3-yl)-4-((6-methylpyridin-3-yl)oxy)quinazoline (Compound 437). LCMS: rt 7.36 min (B), MS (m/e) 443 MH⁺. ¹H NMR (CD₃OD, 300 MHz): 8.70 (s, 1H), 8.67 (dd, J=5.4, 1.5 Hz, 1H), 8.37 (dd, J=7.8, 1.5 Hz, 1H), 8.15 (m, 2H), 8.08 (m, 2H), 7.96 (m, 1H), 7.57 (m, 2H), 7.23-7.06 (m, 3H), 2.41 (s, 3H).

2-((6-(2-(3-Chloro-4-fluorophenyl)pyridin-3-yl)quinazolin-4-yl)oxy)-N,N-diethylethan-1-amine (Compound 438). LCMS: rt 3.89 min (B), MS (m/e) 451 MH⁺. ¹H NMR (CD₃OD, 300 MHz): 8.76 (s, 1H), 8.67 (dd, J=5.1, 1.5 Hz, 1H), 8.11 (dd, J=7.8, 1.8 Hz, 1H), 7.99 (m, 1H), 7.82 (m, 1H), 7.59-7.48 (m, 3H), 7.21-7.05 (m, 2H), 4.76 (t, J=2.4 Hz, 2H), 3.83 (t, J=2.4 Hz, 2H), 2.84 (q, J=7.2 Hz, 4H), 1.30 (t, J=7.2 Hz, 6H).

2-((6-(2-(3-Chloro-4-fluorophenyl)pyridin-3-yl)quinazolin-4-yl)oxy)-N,N-dimethylethan-1-amine (Compound 439). LCMS: rt 3.69 min (B), MS (m/e) 423 MH⁺. ¹H NMR (CD₃OD, 300 MHz): 8.76 (s, 1H), 8.61 (dd, J=5.4, 1.5 Hz, 1H), 8.23 (m, 1H), 8.10 (m, 1H), 8.01 (dd, J=7.8, 1.5 Hz, 1H), 7.86 (m, 1H), 7.65 (dd, J=7.8, 5.1 Hz, 1H), 7.61 (m, 1H), 7.16 (m, 1H), 7.09 (m, 1H), 4.75 (t, J=5.7 Hz, 2H), 3.80 (t, J=5.7 Hz, 2H), 2.78 (s, 6H).

4-((6-(2-(4-Fluoro-3-methylphenyl)pyridin-3-yl)quinazolin-4-yl)oxy)benzonitrile (Compound 440). LCMS: rt 8.03 min (B), MS (m/e) 433 MH⁺.

3-((6-(2-(4-Fluoro-3-methylphenyl)pyridin-3-yl)quinazolin-4-yl)oxy)benzonitrile (Compound 441). LCMS: rt 8.06 min (B), MS (m/e) 433 MH⁺.

6-(2-(4-Fluoro-3-methylphenyl)pyridin-3-yl)-4-(pyridin-3-yloxy)quinazoline (Compound 442). LCMS: rt 6.66 min (B), MS (m/e) 409 MH⁺. ¹H NMR (CD₃OD, 300 MHz): 8.70 (s, 1H), 8.67 (dd, J=4.8, 1.5 Hz, 1H), 8.15 (s, 1H), 8.07 (m, 1H), 7.95 (dd, J=7.5, 1.5 Hz, 1H), 7.86 (m, 1H), 7.62-7.50 (m, 3H), 7.59 (m, 1H), 7.35-7.23 (m, 2H), 7.03 (m, 1H), 6.88 (m, 1H), 2.19 (s, 3H).

6-(2-(4-Fluoro-3-methylphenyl)pyridin-3-yl)-4-(2-(pyrrolidin-1-yl)ethoxy)quinazoline (Compound 443). LCMS: rt 2.87 min (A), MS (m/e) 429 MH⁺. ¹H NMR (CD₃OD, 300 MHz): 8.65 (m, 1H), 8.14 (s, 1H), 7.96 (m, 2H), 7.78 (m, 1H), 7.64-7.50 (m, 2H), 7.27 (m, 1H), 7.04 (m, 1H), 6.87 (m, 1H), 4.78 (t, J=5.4 Hz, 2H), 3.06 (t, J=5.4 Hz, 2H), 3.71 (m, 3H), 2.17 (s, 3H), 2.16 (m, 2H), 1.87 (m, 3H);

4-(3-((6-(2-(4-Fluoro-3-methylphenyl)pyridin-3-yl)quinazolin-4-yl)oxy)phenyl)morpholine (Compound 444). LCMS: rt 8.06 min (B), MS (m/e) 493 MH⁺.

5-(2-((6-(2-(4-Fluoro-3-methylphenyl)pyridin-3-yl)quinazolin-4-yl)oxy)ethyl)-4-methylthiazole (Compound 445). LCMS: rt 7.23 min (B), MS (m/e) 457 MH⁺. ¹H NMR (CD₃OD, 300 MHz): 8.75 (s, 1H), 8.66 (dd, J=5.1, 1.8 Hz, 1H), 8.11 (s, 1H), 8.11 (m, 1H), 7.99 (dd, J=6.9, 1.8 Hz, 1H), 7.77 (s, 1H), 7.57 (m, 2H), 7.27 (m, 1H), 7.04 (m, 1H), 6.88 (m, 1H), 4.78 (t, J=6.0 Hz, 2H), 3.38 (t, J=6.0 Hz, 2H), 2.24 (s, 3H), 2.14 (s, 3H).

6-(2-(4-Fluoro-3-methylphenyl)pyridin-3-yl)-4-(quinolin-6-yloxy)quinazoline (Compound 446). LCMS: rt 5.71 min (A), MS (m/e) 459 MH⁺. ¹H NMR (CD₃OD, 300 MHz): 8.75-8.59 (m, 2H), 8.42 (s, 1H), 8.12 (m, 2H), 7.99 (dd, J=8.1, 1.8 Hz, 1H), 7.88 (m, 1H), 7.76 (s, 1H), 7.59 (m, 2H), 7.43-7.27 (m, 3H), 7.25 (m, 1H), 7.06 (m, 1H), 6.88 (m, 1H), 2.17 (s, 3H).

6-(2-(4-Fluoro-3-methylphenyl)pyridin-3-yl)-4-((1-(pyridin-4-yl)piperidin-4-yl)oxy)quinazoline (Compound 447). LCMS: rt 3.31 min (A), MS (m/e) 492 MH⁺. ¹H NMR (CD₃OD, 300 MHz): 8.74 (s, 1H), 8.67 (dd, J=5.4, 1.8 Hz, 1H), 8.52 (s, 1H), 8.09 (m, 3H), 7.98 (m, 1H), 7.87 (m, 1H), 7.57 (m, 2H), 7.25 (m, 1H), 7.14-7.01 (m, 2H), 6.87 (m, 1H), 3.77 (m, 4H), 3.47 (m, 1H), 2.21 (s, 3H), 1.96 (m, 4H).

6-(2-(3-Chloro-4-fluorophenyl)pyridin-3-yl)quinazolin-4-amine (Compound 448). LCMS: rt 4.46 min (A), MS (m/e) 351 MH⁺. ¹H NMR (DMSO-d₆, 300 MHz): 8.67 (dd, J=4.8, 1.5 Hz, 1H), 8.32 (s, 1H), 8.20 (d, J=2.1 Hz, 1H), 7.91 (dd, J=7.5, 1.8 Hz, 1H), 7.69 (bs, 2H), 7.55-7.46 (m, 3H), 7.36 (dd, J=8.4, 1.8 Hz, 1H), 7.16 (m, 1H), 7.09-7.04 (m, 1H).

6-(2-(5-Chloro-2-fluorophenyl)pyridin-3-yl)quinazolin-4-amine (Compound 449). LCMS: rt 4.51 min (A), MS (m/e) 351 MH⁺. ¹H NMR (CD₃OD, 300 MHz): 8.79 (dd, J=4.8, 1.5 Hz, 1H), 8.67 (s, 1H), 8.34 (d, J=1.5 Hz, 1H), 8.13 (dd, J=7.8, 1.5 Hz, 1H), 7.80 (dd, J=8.7, 1.8 Hz, 1H), 7.71 (m, 2H), 7.64 (dd, J=6.3, 3.0 Hz, 1H), 7.42 (m, 1H), 6.92 (m, 1H).

6-(2-(5-Chloro-2,4-difluorophenyl)pyridin-3-yl)quinazolin-4-amine (Compound 450). LCMS: rt 4.80 min (A), MS (m/e) 369 MH⁺. ¹H NMR (CD₃OD, 300 MHz): 8.79 (dd, J=4.8, 1.5 Hz, 1H), 8.68 (s, 1H), 8.34 (d, J=1.8 Hz, 1H), 8.10 (dd, J=7.2, 1.5 Hz, 1H), 7.83 (dd, J=7.5, 2.1 Hz, 1H), 7.79 (m, 1H), 7.71 (m, 2H), 6.99 (m, 1H).

6-(2-(3-Methoxyphenyl)pyridin-3-yl)quinazolin-4-amine (Compound 451). LCMS: rt 3.26 min (A), MS (m/e) 329 MH⁺. ¹H NMR (CD₃OD, 300 MHz): 8.50 (dd, J=5.4, 1.8 Hz, 1H), 8.68 (s, 1H), 8.43 (m, 2H), 7.94 (dd, J=8.1, 5.4 Hz, 1H), 7.76 (dd, J=8.4, 1.8 Hz, 1H), 7.65 (m, 1H), 7.26 (m, 1H), 7.01 (m, 2H), 6.88 (m, 1H), 3.71 (s, 3H).

6-(2-(3-(Trifluoromethoxy)phenyl)pyridin-3-yl)quinazolin-4-amine (Compound 452). LCMS: rt 4.71 min (A), MS (m/e) 383 MH⁺. ¹H NMR (CD₃OD, 300 MHz): 8.80 (dd, J=5.1, 1.5 Hz, 1H), 8.69 (s, 1H), 8.36 (m, 1H), 8.18 (dd, J=7.8, 1.8 Hz, 1H), 7.77-7.65 (m, 3H), 7.43 (m, 2H), 7.28 (m, 1H), 7.19 (m, 2H).

6-(2-(3,4-Difluorophenyl)pyridin-3-yl)quinazolin-4-amine (Compound 453). LCMS: rt 4.01 min (A), MS (m/e) 335 MH⁺. ¹H NMR (CD₃OD, 300 MHz): 8.76 (dd, J=5.4, 1.5 Hz, 1H), 8.69 (s, 1H), 8.38 (m, 1H), 8.14 (dd, J=7.8, 1.5 Hz, 1H), 7.70-7.65 (m, 2H), 7.35 (m, 2H), 7.18 (m, 1H), 7.09 (m, 1H).

6-(2-(2,5-Difluorophenyl)pyridin-3-yl)quinazolin-4-amine (Compound 454). LCMS: rt 4.11 min (A), MS (m/e) 335 MH⁺. ¹H NMR (CD₃OD, 300 MHz): 8.79 (dd, J=4.8, 1.5 Hz, 1H), 8.67 (s, 1H), 8.33 (d, J=1.8 Hz, 1H), 8.11 (dd, J=7.8, 1.8 Hz, 1H), 7.82 (dd, J=8.4, 1.5 Hz, 1H), 7.79-7.65 (m, 2H), 7.36 (m, 2H), 7.16 (m, 1H), 6.92 (m, 1H).

6-(2-(2,4-Difluorophenyl)pyridin-3-yl)quinazolin-4-amine (Compound 455). LCMS: rt 2.26 min (A), MS (m/e) 335 MH⁺.

3-(3-(4-Aminoquinazolin-6-yl)pyridin-2-yl)phenol (Compound 456). LCMS: rt 2.16 min (A), MS (m/e) 315 MH⁺. ¹H NMR (DMSO-d₆, 300 MHz): 9.31 (s, 1H), 8.68 (dd, J=4.8, 1.5 Hz, 1H), 8.37 (s, 1H), 8.28 (m, 1H), 7.90 (dd, J=7.8, 1.5 Hz, 1H), 7.74 (bs, 2H), 7.51 (dd, J=7.8, 4.5 Hz, 1H), 7.43 (m, 1H), 7.31 (dd, J=8.7, 1.5 Hz, 1H), 7.00 (m, 1H), 6.77 (m, 1H), 6.65-6.62 (m, 2H).

N-(3-(3-(4-Amino quinazolin-6-yl)pyridin-2-yl)phenyl) acetamide (Compound 457). LCMS: rt 2.18 min (A), MS (m/e) 356 MH$^+$.

6-(2-(3-Fluoro-5-methylphenyl)pyridin-3-yl)quinazolin-4-amine (Compound 458). LCMS: rt 2.45 min (A), MS (m/e) 331 MH$^+$.

6-(2-(3-Fluoro-4-methylphenyl)pyridin-3-yl)quinazolin-4-amine (Compound 459). LCMS: rt 2.41 min (A), MS (m/e) 331 MH$^+$.

6-(2-(3-Chloro-5-fluorophenyl)pyridin-3-yl)quinazolin-4-amine (Compound 460). LCMS: rt 2.77 min (A), MS (m/e) 351 MH$^+$.

6-(2-(3-Fluorophenyl)pyridin-3-yl)quinazolin-4-amine (Compound 461). LCMS: rt 2.16 min (A), MS (m/e) 317 MH$^+$. $^1$H NMR (CD$_3$OD, 300 MHz): 8.68 (dd, J=5.1, 1.8 Hz, 1H), 8.37 (s, 1H), 8.15 (m, 1H), 8.01 (dd, J=7.8, 1.5 Hz, 1H), 7.59-7.54 (m, 2H), 7.48 (dd, J=8.4, 1.8 Hz, 1H), 7.22 (m, 1H), 7.12 (m, 1H), 7.03 (m, 1H).

6-(2-(o-Tolyl)pyridin-3-yl)quinazolin-4-amine (Compound 462). LCMS: rt 1.85 min (A), MS (m/e) 313 MH$^+$.

6-(2-(5-Chloro-2-methylphenyl)pyridin-3-yl)quinazolin-4-amine (Compound 463). LCMS: rt 2.58 min (A), MS (m/e) 347 MH$^+$. $^1$H NMR (CD$_3$OD, 300 MHz): 8.68 (dd, J=5.1, 1.8 Hz, 1H), 8.37 (s, 1H), 8.14 (m, 1H), 8.08 (dd, J=7.8, 1.8 Hz, 1H), 7.64 (dd, J=8.1, 5.1 Hz, 1H), 7.52-7.43 (m, 2H), 7.28-7.21 (m, 2H), 7.11 (m, 1H), 1.90 (s, 3H).

6-(2-(3-Chloro-2-methylphenyl)pyridin-3-yl)quinazolin-4-amine (Compound 464). LCMS: rt 2.58 min (A), MS (m/e) 347 MH$^+$.

6-(2-(6-Chloro-2-fluoro-3-methylphenyl)pyridin-3-yl) quinazolin-4-amine (Compound 465). LCMS: rt 2.97 min (A), MS (m/e) 365 MH$^+$.

6-(2-(5-Fluoro-2-methylphenyl)pyridin-3-yl)quinazolin-4-amine (Compound 466). LCMS: rt 2.23 min (A), MS (m/e) 331 MH$^+$.

6-(2-(4-Fluoro-2-methylphenyl)pyridin-3-yl)quinazolin-4-amine (Compound 467). LCMS: rt 2.07 min (A), MS (m/e) 331 MH$^+$.

6-(2-(3-Fluoro-2-methylphenyl)pyridin-3-yl)quinazolin-4-amine (Compound 468). LCMS: rt 2.25 min (A), MS (m/e) 331 MH$^+$.

6-(2-(3,4,5-Trifluorophenyl)pyridin-3-yl)quinazolin-4-amine (Compound 469). LCMS: rt 2.74 min (A), MS (m/e) 353 MH$^+$.

6-(2-(2,3-Dihydro-1H-inden-5-yl)pyridin-3-yl)quinazolin-4-amine (Compound 470). LCMS: rt 2.34 min (A), MS (m/e) 339 MH$^+$.

5-(3-(4-Amino quinazolin-6-yl)pyridin-2-yl)-2,3-dihydro-1H-inden-1-one (Compound 471). LCMS: rt 2.09 min (A), MS (m/e) 353 MH$^+$.

(E)-5-(3-(4-Amino quinazolin-6-yl)pyridin-2-yl)-2,3-dihydro-1H-inden-1-one oxime (Compound 472). LCMS: rt 2.15 min (A), MS (m/e) 367 MH$^+$.

6-(2-(2-Fluoro-5-methoxyphenyl)pyridin-3-yl)quinazolin-4-amine (Compound 473). LCMS: rt 2.32 min (A), MS (m/e) 347 MH$^+$. $^1$H NMR (CD$_3$OD, 300 MHz): 8.69 (dd, J=5.1, 1.8 Hz, 1H), 8.40 (s, 1H), 8.16 (m, 1H), 8.02 (dd, J=7.8, 1.5 Hz, 1H), 7.62 (dd, J=7.8, 5.1 Hz, 1H), 7.54 (m, 2H), 7.03 (m, 1H), 6.91-6.77 (m, 2H), 3.75 (s, 3H).

6-(2-(4-Fluoro-3-methoxyphenyl)pyridin-3-yl)quinazolin-4-amine (Compound 474). LCMS: rt 2.14 min (A), MS (m/e) 347 MH$^+$. $^1$H NMR (CD$_3$OD, 300 MHz): 8.68 (dd, J=4.8, 1.5 Hz, 1H), 8.43 (s, 1H), 8.20 (m, 1H), 8.02 (dd, J=7.8, 1.8 Hz, 1H), 7.60-7.51 (m, 3H), 7.08 (dd, J=8.1, 2.1 Hz, 1H), 6.96 (dd, J=8.7, 11.1 Hz, 1H), 6.83-6.78 (m, 1H), 3.63 (s, 3H).

N-(3-(3-(4-Amino quinazolin-6-yl)pyridin-2-yl)phenyl)-N',N'-dimethylsulfonyldiamine (Compound 475). LCMS: rt 2.12 min (A), MS (m/e) 421 MH$^+$.

6-(2-(4-Fluoro-3-(trifluoromethyl)phenyl)pyridin-3-yl) quinazolin-4-amine (Compound 476). LCMS: rt 3.13 min (A), MS (m/e) 385 MH$^+$.

5-(3-(4-Amino quinazolin-6-yl)pyridin-2-yl)-2-fluorobenzonitrile (Compound 477). LCMS: rt 2.35 min (A), MS (m/e) 342 MH$^+$. $^1$H NMR (CD$_3$OD, 300 MHz): 8.72 (dd, J=4.8, 1.5 Hz, 1H), 8.42 (s, 1H), 8.15 (m, 1H), 8.02 (dd, J=6.0, 1.8 Hz, 1H), 7.64-7.51 (m, 4H), 7.21 (m, 1H).

6-(2-(3-Isopropylphenyl)pyridin-3-yl)quinazolin-4-amine (Compound 478). LCMS: rt 2.70 min (A), MS (m/e) 341 MH$^+$.

6-(2-(3-(Benzyloxy)phenyl)pyridin-3-yl)quinazolin-4-amine (Compound 479). LCMS: rt 3.20 min (A), MS (m/e) 405 MH$^+$.

6-(2-(3-isopropoxyphenyl)pyridin-3-yl)quinazolin-4-amine (Compound 480). LCMS: rt 2.51 min (A), MS (m/e) 357 MH$^+$.

2-(3-(3-(4-Amino quinazolin-6-yl)pyridin-2-yl)phenoxy) acetonitrile (Compound 481). LCMS: rt 2.09 min (A), MS (m/e) 354 MH$^+$.

6-(2-(3-(2-Methoxyethoxy)phenyl)pyridin-3-yl)quinazolin-4-amine (Compound 482). LCMS: rt 2.09 min (A), MS (m/e) 373 MH$^+$.

6-(2-(3-(Cyclopropylmethoxy)phenyl)pyridin-3-yl) quinazolin-4-amine (Compound 483). LCMS: rt 2.70 min (A), MS (m/e) 369 MH$^+$. $^1$H NMR (CD$_3$OD, 300 MHz): 8.65 (dd, J=4.8, 1.5 Hz, 1H), 8.40 (s, 1H), 8.18 (m, 1H), 8.01 (dd, J=7.8, 1.5 Hz, 1H), 7.57-7.51 (m, 2H), 7.46 (dd, J=9.0, 2.1 Hz, 1H), 7.17 (m, 1H), 6.92-6.89 (m, 1H), 6.85-6.78 (m, 2H), 3.53 (d, J=7.2 Hz, 2H), 0.93 (m, 1H), 0.43 (m, 2H), 0.13 (m, 2H).

6-(2-(3-(2,2,2-Trifluoroethoxy)phenyl)pyridin-3-yl) quinazolin-4-amine (Compound 484). LCMS: rt 3.59 min (A), MS (m/e) 387 MH$^+$. $^1$H NMR (CD$_3$OD, 300 MHz): 8.69 (dd, J=4.8, 1.5 Hz, 1H), 8.42 (s, 1H), 8.18 (m, 1H), 8.02 (dd, J=7.8, 1.5 Hz, 1H), 7.59-7.53 (m, 3H), 7.19 (m, 1H), 7.03 (m, 1H), 6.97-6.90 (m, 2H), 3.53 (q, J=7.8 Hz, 2H).

6-(2-(3-Morpholinophenyl)pyridin-3-yl)quinazolin-4-amine (Compound 485). LCMS: rt 2.66 min (A), MS (m/e) 384 MH$^+$.

7-(2-(3-Chloro-4-fluorophenyl)pyridin-3-yl)quinazoline-2,4-diamine (Compound 486). LCMS: rt 2.96 min (A), MS (m/e) 366 MH$^+$.

7-(2-(4-Fluoro-3-methylphenyl)pyridin-3-yl)quinazoline-2,4-diamine (Compound 487). LCMS: rt 2.53 min (A), MS (m/e) 346 MH$^+$.

7-(2-(3-Chlorophenyl)pyridin-3-yl)quinazoline-2,4-diamine (Compound 488). LCMS: rt 2.77 min (A), MS (m/e) 348 MH$^+$.

7-(2-(m-Tolyl)pyridin-3-yl)quinazoline-2,4-diamine (Compound 489). LCMS: rt 2.89 min (B), MS (m/e) 328 MH$^+$.

6-(2-(3-Chloro-4-fluorophenyl)pyridin-3-yl)-N-(pyridin-3-yl)quinazolin-4-amine (Compound 490). LCMS: rt 3.85 min (A), MS (m/e) 428 MH$^+$.

6-(2-(3-Chloro-4-fluorophenyl)pyridin-3-yl)-N-(6-methylpyridin-3-yl)quinazolin-4-amine (Compound 491). LCMS: rt 3.54 min (A), MS (m/e) 442 MH$^+$.

6-(2-(3-Chloro-4-fluorophenyl)pyridin-3-yl)-N-(pyridin-4-yl)quinazolin-4-amine (Compound 492). LCMS: rt 3.42 min (A), MS (m/e) 428 MH$^+$.

3-(3-(4-Amino quinazolin-6-yl)pyridin-2-yl)-5-chlorophenol (Compound 493). LCMS: rt 2.32 min (A), MS (m/e) 349 MH+. 1H NMR (CD3OD, 300 MHz): 8.66 (dd, J=4.8, 1.5 Hz, 1H), 8.42 (s, 1H), 8.21 (m, 1H), 8.03 (dd, J=7.8, 1.5 Hz, 1H), 7.61-7.49 (m, 3H), 6.83 (m, 1H), 6.73 (m, 1H), 6.60 (m, 1H).

3-(3-(4-Aminoquinazolin-6-yl)pyridin-2-yl)-5-fluorophenol (Compound 494). LCMS: rt 1.94 min (A), MS (m/e) 333 MH+. 1H NMR (CD3OD, 300 MHz): 8.65 (dd, J=4.8, 1.5 Hz, 1H), 8.41 (s, 1H), 8.12 (m, 1H), 7.95 (dd, J=7.8, 1.5 Hz, 1H), 7.60-7.45 (m, 3H), 6.58 (m, 1H), 6.53-6.46 (m, 2H).

3-(3-(4-Aminoquinazolin-6-yl)pyridin-2-yl)-5-methylphenol (Compound 495). LCMS: rt 1.69 min (A), MS (m/e) 329 MH+. 1H NMR (CD3OD, 300 MHz): 8.63 (dd, J=4.8, 1.5 Hz, 1H), 8.44 (s, 1H), 8.23 (m, 1H), 8.16 (m, 1H), 8.01 (dd, J=7.8, 1.5 Hz, 1H), 7.56-7.51 (m, 3H), 6.65 (m, 1H), 6.56 (m, 1H), 6.47 (m, 1H), 2.15 (s, 3H).

7-(2-(3-Chloro-4-fluorophenyl)pyridin-3-yl)quinazolin-2-amine (Compound 496). LCMS: rt 2.36 min (A), MS (m/e) 351 MH+. 1H NMR (CD3OD, 300 MHz): 9.06 (bs, 1H), 8.68 (dd, J=4.8, 1.5 Hz, 1H), 7.99 (dd, J=7.8, 1.5 Hz, 1H), 7.75 (d, J=8.1 Hz, 1H), 7.57 (dd, J=7.8, 4.8 Hz, 1H), 7.53 (m, 1H), 7.36 (m, 1H), 7.22-7.17 (m, 1H), 7.11-7.05 (m, 2H).

6-(2-(2-Chlorophenyl)pyridin-3-yl)quinazolin-4-amine (Compound 497). LCMS: rt 2.29 min (A), MS (m/e) 333 MH+.

6-(2-(2,3-Dichlorophenyl)pyridin-3-yl)quinazolin-4-amine (Compound 498). LCMS: rt 2.78 min (A), MS (m/e) 368 MH+.

6-(2-(2-Chloro-4-fluorophenyl)pyridin-3-yl)quinazolin-4-amine (Compound 499). LCMS: rt 2.48 min (A), MS (m/e) 351 MH+.

6-(2-(2,4-Dichlorophenyl)pyridin-3-yl)quinazolin-4-amine (Compound 500). LCMS: rt 3.63 min (B), MS (m/e) 368 MH+.

6-(2-(2,5-Dichlorophenyl)pyridin-3-yl)quinazolin-4-amine (Compound 501). LCMS: rt 3.55 min (B), MS (m/e) 368 MH+. 1H NMR (CD3OD, 300 MHz): 8.69 (dd, J=5.1, 1.5 Hz, 1H), 8.36 (s, 1H), 8.13 (m, 1H), 8.07 (dd, J=7.8, 1.5 Hz, 1H), 7.66 (dd, J=7.8, 5.1 Hz, 1H), 7.56-7.53 (m, 3H), 7.33 (m, 1H), 6.26 (m, 1H).

6-(2-(2,4-Difluoro-5-methoxyphenyl)pyridin-3-yl)quinazolin-4-amine (Compound 502). LCMS: rt 3.21 min (B), MS (m/e) 365 MH+.

6-(2-(2-Chloro-3-fluorophenyl)pyridin-3-yl)quinazolin-4-amine (Compound 503). LCMS: rt 3.27 min (B), MS (m/e) 351 MH+.

6-(2-(2-Chloro-5-fluorophenyl)pyridin-3-yl)quinazolin-4-amine (Compound 504). LCMS: rt 3.23 min (B), MS (m/e) 351 MH+.

6-(2-(2,4-Dichloro-5-fluorophenyl)pyridin-3-yl)quinazolin-4-amine (Compound 505). LCMS: rt 3.79 min (B), MS (m/e) 386 MH+.

6-(2-(3-Chloro-4-fluorophenyl)pyridin-3-yl)quinazoline (Compound 506). LCMS: rt 5.24 min (A), MS (m/e) 336 MH+.

6-(2-(3-Chloro-4-fluorophenyl)pyridin-3-yl)-4-cyclopropylquinazoline (Compound 507). LCMS: rt 7.15 min (A), MS (m/e) 376 MH+.

2-(2-Fluorophenyl)-3,4'-bipyridine (Compound 508). 1H NMR (300 MHz, DMSO-d6): δ 8.74 (dd, J=4.8, 1.7 Hz, 1H), 8.45 (dd, J=4.4, 1.7 Hz, 2H), 7.94 (dd, J=1.7, 7.8 Hz, 1H), 7.58 (dd, J=7.8, 4.8 Hz, 1H), 7.58 (dd, J=7.8, 4.8 Hz, 1H), 7.47 (td, J=7.5, 1.8 Hz, 1H), 7.44-7.34 (m, 1H), 7.23 (td, J=7.5, 1.1 Hz, 1H), 7.15 (dd, J=4.4, 1.7 Hz, 2H), 7.08-7.00 (m, 1H). 19F NMR (282 MHz, DMSO-d6): δ −115.75 (ddd, J=10.4, 7.5, 5.4 Hz). LCMS: rt 4.35 min (A), purity 99%, MS (m/e) 251 (MH+).

5-(Benzo[d]thiazol-6-yl)-6-(4-fluoro-3-methylphenyl)-N-(pyridin-4-ylmethyl)pyridin-3-amine (Compound 509). LCMS: rt 4.46 min (A), MS (m/e) 427 MH+.

4-(2-(2-Fluorophenyl)pyridin-3-yl)quinolone (Compound 510). LCMS: rt 4.08 min (B), purity 99%, MS (m/e) 301 (MH+).

4-(2-(3,4-Difluorophenyl)pyridin-3-yl)quinolone (Compound 511). LCMS: rt 4.82 min (B), purity 99%, MS (m/e) 319 (MH+).

4-(2-(4-Fluoro-3-methylphenyl)pyridin-3-yl)quinoline (Compound 512). LCMS: rt 4.73 min (B), purity 99%, MS (m/e) 315 (MH+).

4-(2-(3-Fluorophenyl)pyridin-3-yl)quinolone (Compound 513). LCMS: rt 4.46 min (B), purity 99%, MS (m/e) 301 (MH+).

4-(2-(4-Fluorophenyl)pyridin-3-yl)quinoline (Compound 514). LCMS: rt 4.34 min (B), purity 99%, MS (m/e) 301 (MH+).

4-(2-(m-Tolyl)pyridin-3-yl)quinoline (Compound 515). LCMS: rt 4.32 min (B), purity 99%, MS (m/e) 297 (MH+).

4-(2-(2-Fluoro-5-methylphenyl)pyridin-3-yl)quinolone (Compound 516). LCMS: rt 6.04 min (B), purity 99%, MS (m/e) 315 (MH+).

5-(6-Methyl-[2,3'-bipyridin]-2'-yl)-1H-indazole (Compound 517). 1H NMR (300 MHz, DMSO-d6): δ 12.97 (s, 1H), 8.63 (dd, J=4.7, 1.7 Hz, 1H), 7.92 (dd, J=9.7, 1.7 Hz, 1H), 7.64 (s, 1H), 7.40 (dd, J=8.0, 4.5 Hz, 2H), 7.37-7.29 (m, 2H), 7.16 (dd, J=8.7, 1.5 Hz, 1H), 7.05 (d, J=7.6 Hz, 1H), 6.73 (d, J=7.8 Hz, 1H), 2.41 (s, 3H). LCMS: rt 2.34 min (B), purity 99%, MS (m/e) 287 (MH+).

2'-(Benzo[d][1,3]dioxol-5-yl)-6-methyl-2,3'-bipyridine (Compound 518). LCMS: rt 2.82 min (B), purity 99%, MS (m/e) 291 (MH+).

6-(6-Methyl-[2,3'-bipyridin]-2'-yl)quinoxaline (Compound 519). LCMS: rt 2.80 min (B), purity 99%, MS (m/e) 299 (MH+).

5-(6-Methyl-[2,3'-bipyridin]-2'-yl)-1,3-dihydro-2H-benzo[d]imidazol-2-one (Compound 520). LCMS: rt 2.01 min (B), purity 99%, MS (m/e) 303 (MH+).

6-(6-Methyl-[2,3'-bipyridin]-2'-yl)-1H-benzo[d]imidazole (Compound 521). 1H NMR (300 MHz, DMSO-d6): δ 12.1 (br s, 1H), 8.68 (dd, J=4.7, 1.7 Hz, 1H), 8.16 (s, 1H), 7.96 (dd, J=7.8, 1.7 Hz, 1H), 7.50-7.37 (ddd, J=15.4, 14.4, 8.8 Hz, 4H), 7.10 (d, J=7.7 Hz, 2H), 6.76 (d, J=7.7 Hz, 1H), 2.47 (s, 3H). LCMS: rt 1.23 min (B), purity 99%, MS (m/e) 287 (MH+).

6-(6-Methyl-[2,3'-bipyridin]-2'-yl)isoquinoline (Compound 522). LCMS: rt 1.93 min (B), purity 99%, MS (m/e) 298 (MH+).

2-(2-(4-Fluoro-3-methylphenyl)pyridin-3-yl)-1,6-naphthyridine (Compound 523). 1H NMR (300 MHz, DMSO-d6): δ 9.35 (d, J=0.9 Hz, 1H), 8.78 (dd, J=4.7, 1.7 Hz, 1H), 8.74 (d, J=5.9 Hz, 1H), 8.38 (dd, J=8.6, 0.9 Hz, 1H), 8.14 (dd, J=7.8, 1.7 Hz, 1H), 7.91 (d, J=5.9 Hz, 1H), 7.57 (dd, J=7.8, 4.7 Hz, 1H), 7.38 (dd, J=7.6, 1.9 Hz, 1H), 7.30 (d, J=8.5 Hz, 1H), 7.01-6.86 (m, 2H), 2.13 (s, 3H). 19F NMR (282 MHz, DMSO-d6): δ −117.88 (d, J=8.1 Hz). LCMS: rt 4.58 min (A), purity 99%, MS (m/e) 316 (MH+).

2-(2-(m-Tolyl)pyridin-3-yl)-1,6-naphthyridine (Compound 524). 1H NMR (300 MHz, DMSO-d6): δ 9.33 (s, 1H), 8.74 (d, J=5.9 Hz, 2H), 8.33 (d, J=8.6 Hz, 1H), 8.14 (d, J=7.7 Hz, 1H), 7.91 (d, J=5.9 Hz, 1H), 7.56 (dd, J=7.7, 4.8 Hz, 1H), 7.26 (d, J=7.8 Hz, 2H), 7.08 (d, J=7.6 Hz, 2H), 6.93 (d, J=6.8 Hz, 1H), 2.18 (s, 3H). LCMS: rt 4.11 min (A), purity 99%, MS (m/e) 298 (MH⁺).

2-(2-(3-Cyclopropylphenyl)pyridin-3-yl)-1,6-naphthyridine (Compound 525). LCMS: rt 4.71 min (A), purity 99%, MS (m/e) 324 (MH⁺).

2'-(4-Fluoro-3-methylphenyl)[3,3'-bipyridin]-6-amine (Compound 526). ¹H NMR (300 MHz, DMSO-d₆): δ 8.60 (dd, J=4.7, 1.6 Hz, 1H), 7.85-7.73 (m, 2H), 7.42 (dd, J=7.8, 4.7 Hz, 1H), 7.35 (d, J=7.8 Hz, 1H), 7.24 (dd, J=8.8, 2.4 Hz, 1H), 7.13-6.95 (m, 2H), 6.66 (br s, 2H), 6.51 (d, J=8.8 Hz, 1H), 2.19 (d, J=1.5 Hz, 3H). ¹⁹F NMR (282 MHz, DMSO-d₆): δ −118.73 (s). LCMS: rt 1.76 min (A), purity 99%, MS (m/e) 280 (MH⁺).

6-(2-(4-Fluoro-3-methylphenyl)pyridin-3-yl)-3-methylimidazo[1,2-a]pyridine (Compound 527). ¹H NMR (300 MHz, DMSO-d₆): δ 8.68 (dd, J=4.7, 1.7 Hz, 1H), 8.28 (dd, J=1.7, 0.9 Hz, 1H), 7.98 (dd, J=7.8, 1.7 Hz, 1H), 7.49 (dd, J=7.8, 4.8 Hz, 1H), 7.45 (app dd, J=8.6 and 0.9 Hz, 1H), 7.38 (d, J=0.9 Hz, 1H), 7.36 (dd, J=8.6, 0.9 Hz, 1H), 7.09-7.05 (m, 1H), 6.97 (dd, J=9.6, 8.6 Hz, 1H), 6.77 (dd, J=9.3, 1.8 Hz, 1H), 2.43 (s, 3H), 2.16 (s, 3H). ¹⁹F NMR (282 MHz, DMSO-d₆): δ −118.43 (ddd, J=10.0, 7.5, 3.8 Hz). LCMS: rt 3.83 min (A), purity 99%, MS (m/e) 318 (MH⁺).

3-Methyl-6-(2-(m-Tolyl)pyridin-3-yl)imidazo[1,2-a]pyridine (Compound 528). LCMS: rt 3.40 min (A), purity 99%, MS (m/e) 300 (MH⁺).

6-(2-(3-Cyclopropylphenyl)pyridin-3-yl)-3-methylimidazo[1,2-a]pyridine (Compound 529). LCMS: rt 3.98 min (A), purity 99%, MS (m/e) 326 (MH⁺).

3-Methyl-6-(2-(3-(trifluoromethyl)phenyl)pyridin-3-yl)imidazo[1,2-a]pyridine (Compound 530). LCMS: rt 4.90 min (A), purity 99%, MS (m/e) 354 (MH⁺).

6-(2-(4-Fluoro-3-methylphenyl)pyridin-3-yl)-2-methylimidazo[1,2-a]pyridine (Compound 531). LCMS: rt 3.86 min (A), purity 99%, MS (m/e) 318 (MH⁺).

2-Methyl-6-(2-(m-tolyl)pyridin-3-yl)imidazo[1,2-a]pyridine (Compound 532). ¹H NMR (300 MHz, DMSO-d₆): δ 8.67 (dd, J=4.7, 1.7 Hz, 1H), 8.43 (dd, J=1.8, 1.0 Hz, 1H), 7.88 (dd, J=7.7, 1.7 Hz, 1H), 7.61 (s, 1H), 7.46 (dd, J=7.8, 4.7 Hz, 1H), 7.31 (d, J=1.2 Hz, 1H), 7.25 (d, J=9.3 Hz, 1H), 7.10-7.08 (app m, 2H), 7.06-7.00 (m, 1H), 6.75 (dd, J=9.3, 1.8 Hz, 1H), 2.30 (s, 3H), 2.22 (s, 3H). LCMS: rt 3.41 min (A), purity 99%, MS (m/e) 300 (MH⁺).

6-(2-(3-Cyclopropylphenyl)pyridin-3-yl)-2-methylimidazo[1,2-a]pyridine (Compound 533). LCMS: rt 3.96 min (A), purity 99%, MS (m/e) 326 (MH⁺).

2-Methyl-6-(2-(3-trifluoromethyl)phenyl)pyridin-3-yl)imidazo[1,2-a]pyridine (Compound 534). LCMS: rt 4.86 min (A), purity 99%, MS (m/e) 354 (MH⁺).

2-(2-(4-Fluoro-3-methylphenyl)pyridin-3-yl)-1,5-naphthyridine (Compound 535). ¹H NMR (300 MHz, DMSO-d₆): δ 9.00 (dd, J=4.2, 1.6 Hz, 1H), 8.80 (dd, J=4.8, 1.6 Hz, 1H), 8.44 (dd, J=8.9, 1.1 Hz, 1H), 8.35-8.17 (m, 2H), 7.81 (dd, J=8.5, 4.2 Hz, 1H), 7.63 (dd, J=7.8, 4.9 Hz, 1H), 7.40 (d, J=8.7 Hz, 2H), 6.96 (d, J=7.9 Hz, 2H), 2.28-1.96 (m, 3H). ¹⁹F NMR (282 MHz, DMSO-d₆): δ −117.43 (dd, J=13.7, 6.5 Hz), −117.43 (dd, J=13.7, 6.5 Hz). LCMS: rt 5.20 min (A), purity 99%, MS (m/e) 316 (MH⁺).

2-(2-(m-Tolyl)pyridin-3-yl)-1,5-naphthyridine (Compound 536). LCMS: rt 4.78 min (A), purity 99%, MS (m/e) 298 (MH⁺).

2-(2-(3-Cyclopropylphenyl)pyridin-3-yl)-1,5-naphthyridine (Compound 537). LCMS: rt 5.30 min (A), purity 99%, MS (m/e) 324 (MH⁺).

2-(2-(3-(Trifluoromethyl)phenyl)pyridin-3-yl)-1,5-naphthyridine (Compound 538). LCMS: rt 5.43 min (A), purity 99%, MS (m/e) 352 (MH⁺).

6-(2-(4-Fluoro-3-methylphenyl)pyridin-3-yl)quinoxaline (Compound 539). LCMS: rt 5.25 min (A), purity 99%, MS (m/e) 316 (MH⁺).

6-(2-(m-Tolyl)pyridin-3-yl)quinoxaline (Compound 540). ¹H NMR (300 MHz, DMSO-d₆): δ 8.93 (s, 2H), 8.78 (dd, J=4.9, 1.6 Hz, 1H), 8.17 (dd, J=7.8, 1.6 Hz, 1H), 8.03 (d, J=2.0 Hz, 1H), 7.96 (d, J=8.7 Hz, 1H), 7.66 (dd, J=7.8, 5.0 Hz, 1H), 7.53 (dd, J=8.7, 2.0 Hz, 1H), 7.31 (d, J=0.5 Hz, 1H), 7.16-7.03 (m, 2H), 6.98 (d, J=7.2 Hz, 1H), 2.19 (s, 3H). LCMS: rt 4.86 min (A), purity 99%, MS (m/e) 298 (MH⁺).

6-(2-(3-Cyclopropylphenyl)pyridin-3-yl)quinoxaline (Compound 541). LCMS: rt 5.35 min (A), purity 99%, MS (m/e) 324 (MH⁺).

6-(2-(3-(Trifluoromethyl)phenyl)pyridin-3-yl)quinoxaline (Compound 542). LCMS: rt 6.61 min (A), purity 99%, MS (m/e) 351 (MH⁺).

4-(6-(2-(4-Fluoro-3-methylphenyl)pyridin-3-yl)imidazo[1,2-a]pyridin-3-yl)morpholine (Compound 543). ¹H NMR (300 MHz, DMSO-d₆): δ 8.67 (dd, J=4.7, 1.7 Hz, 1H), 7.98 (dd, J=7.8, 1.7 Hz, 1H), 7.90 (dd, J=1.7, 1.0 Hz, 1H), 7.50 (dd, J=7.8, 4.7 Hz, 1H), 7.47-7.39 (m, 2H), 7.26 (s, 1H), 7.11-7.04 (m, 1H), 7.00 (d, J=9.6 Hz, 1H), 6.98-6.92 (m, 1H), 3.68 (dd, J=5.5, 3.7 Hz, 4H), 2.81 (dd, J=5.5, 3.7 Hz, 4H), 2.17 (d, J=1.6 Hz, 3H). ¹⁹F NMR (282 MHz, DMSO-d₆): δ −118.33-−118.66 (m). LCMS: rt 4.25 min (A), purity 99%, MS (m/e) 389 (MH⁺).

4-(6-(2-(m-Tolyl)pyridin-3-yl)imidazo[1,2-a]pyridin-3-yl)morpholine (Compound 544). LCMS: rt 3.85 min (A), purity 99%, MS (m/e) 371 (MH⁺).

4-(6-(2-(3-Cyclopropylphenyl)pyridin-3-yl)imidazo[1,2-a]pyridin-3-yl)morpholine (Compound 545). LCMS: rt 4.33 min (A), purity 99%, MS (m/e) 397 (MH⁺).

4-(6-(2-(3-(Trifluoromethyl)phenyl)pyridin-3-yl)imidazo[1,2-a]pyridin-3-yl)morpholine (Compound 546). LCMS: rt 5.15 min (A), purity 99%, MS (m/e) 425 (MH⁺).

4-(6-(2-(4-Fluoro-3-methylphenyl)pyridin-3-yl)quinolin-4-yl)morpholine (Compound 547). LCMS: rt 4.15 min (A), purity 99%, MS (m/e) 400 (MH⁺).

4-(6-(2-(m-Tolyl)pyridin-3-yl)quinolin-4-yl)morpholine (Compound 548). ¹H NMR (300 MHz, DMSO-d₆): δ 8.69 (dd, J=4.7, 1.7 Hz, 1H), 8.65 (d, J=5.0 Hz, 1H), 7.99 (d, J=8.6 Hz, 1H), 7.92 (dd, J=7.8, 1.7 Hz, 1H), 7.75 (dd, J=8.6, 2.0 Hz, 1H), 7.62 (d, J=1.8 Hz, 1H), 7.50 (dd, J=7.8, 4.7 Hz, 1H), 7.31 (s, 1H), 7.09-6.99 (m, 2H), 6.99-6.94 (app m, 1H), 6.91 (d, J=5.1 Hz, 1H), 3.75-3.41 (m, 4H), 2.89-2.62 (m, 4H), 2.19 (s, 3H). LCMS: rt 3.81 min (A), purity 99%, MS (m/e) 381 (MH⁺).

4-(6-(2-(3-Cyclopropylphenyl)pyridin-3-yl)quinolin-4-yl)morpholine (Compound 549). LCMS: rt 4.20 min (A), purity 99%, MS (m/e) 408 (MH⁺).

4-(6-(2-(3-(Trifluoromethyl)phenyl)pyridin-3-yl)quinolin-4-yl)morpholine (Compound 550). LCMS: rt 5.11 min (A), purity 99%, MS (m/e) 436 (MH⁺).

6-(2-(4-Fluoro-3-methylphenyl)pyridin-3-yl)-N,N-dimethylimidazo[1,2-a]pyridin-3-amine (Compound 551). LCMS: rt 4.33 min (A), purity 99%, MS (m/e) 347 (MH⁺).

N,N-Dimethyl-6-(2-(m-tolyl)pyridin-3-yl)imidazo[1,2-a]pyridin-3-amine (Compound 552). LCMS: rt 3.93 min (A), purity 99%, MS (m/e) 329 (MH⁺).

6-(2-(3-Cyclopropylphenyl)pyridin-3-yl)-N,N-dimethylimidazo[1,2-a]pyridin-3-amine (Compound 553). LCMS: rt 4.45 min (A), purity 99%, MS (m/e) 355 (MH⁺).

N,N-Dimethyl-6-(2-(3-(trifluoromethyl)phenyl)pyridin-3-yl)imidazo[1,2-a]pyridin-3-amine (Compound 554). LCMS: rt5.33 min (A), purity 99%, MS (m/e) 383 (MH+).

6-(2-(4-Fluoro-3-methylphenyl)pyridin-3-yl)-3-(trifluoromethyl)imidazo[1,2-a]pyridine (Compound 555). $^1$H NMR (300 MHz, DMSO-d$_6$): δ 8.71 (dd, J=4.8, 1.6 Hz, 1H), 8.29 (s, 1H), 8.17 (d, J=1.0 Hz, 1H), 7.99 (dd, J=7.8, 1.7 Hz, 1H), 7.71 (dd, J=9.4, 0.8 Hz, 1H), 7.52 (dd, J=7.8, 4.8 Hz, 1H), 7.42 (dd, J=7.7, 1.6 Hz, 1H), 7.24 (dd, J=9.4, 1.7 Hz, 1H), 7.06 (ddd, J=7.6, 5.3, 2.3 Hz, 1H), 7.02-6.93 (m, 1H), 2.16 (d, J=1.7 Hz, 3H). $^{19}$F NMR (282 MHz, DMSO-d$_6$): δ −60.01 (s), −118.29 (d, J=5.5 Hz).LCMS: rt5.90 min (A), purity 99%, MS (m/e) 372 (MH+).

6-(2-(3-Cyclopropylphenyl)pyridin-3-yl)-3-(trifluoromethyl)imidazo[1,2-a]pyridine (Compound 556). LCMS: rt5.90 min (A), purity 99%, MS (m/e) 380 (MH+).

6-(2-(4-Fluoro-3-methylphenyl)pyridin-3-yl)imidazo[1,2-a]pyridine-3-carbonitrile (Compound 557). LCMS: rt5.38 min (A), purity 99%, MS (m/e) 329 (MH+).

6-(2-(m-Tolyl)pyridin-3-yl)imidazo[1,2-a]pyridine-3-carbonitrile (Compound 558). $^1$H NMR (300 MHz, DMSO-d$_6$): δ 8.72 (dd, J=4.8, 1.7 Hz, 1H), 8.62 (d, J=0.6 Hz, 1H), 8.44 (s, 1H), 8.05 (dd, J=7.8, 1.6 Hz, 1H), 7.64 (d, J=9.3 Hz, 1H), 7.52 (dd, J=7.8, 4.8 Hz, 1H), 7.34 (s, 1H), 7.16-7.02 (m, 4H), 2.24 (s, 3H). LCMS: rt4.93 min (A), purity 99%, MS (m/e) 311 (MH+).

6-(2-(3-Cyclopropylphenyl)pyridin-3-yl)imidazo[1,2-a]pyridine-3-carbonitrile (Compound 559). LCMS: rt5.48 min (A), purity 99%, MS (m/e) 337 (MH+).

6-(2-(3-(Trifluoromethyl)phenyl)pyridin-3-yl)imidazo[1,2-a]pyridine-3-carbonitrile (Compound 560). LCMS: rt6.66 min (A), purity 99%, MS (m/e) 365 (MH+).

6-(2-(4-Fluoro-3-methylphenyl)pyridin-3-yl)-3-(pyrrolidin-1-yl)imidazo[1,2-a]pyridine (Compound 561). LCMS: rt4.90 min (A), purity 99%, MS (m/e) 373 (MH+).

3-(Pyrrolidin-1-yl)-6-(2-(m-tolyl)pyridin-3-yl)imidazo[1,2-a]pyridine (Compound 562). LCMS: rt4.46 min (A), purity 99%, MS (m/e) 355 (MH+).

6-(2-(3-Cyclopropylphenyl)pyridin-3-yl)-3-(pyrrolidin-1-yl)imidazo[1,2-a]pyridine (Compound 563). LCMS: rt4.93 min (A), purity 99%, MS (m/e) 381 (MH+).

3-(Pyrrolidin-1-yl)-6-(2-(3-(trifluoromethyl)phenyl)pyridin-3-yl)imidazo[1,2-a]pyridine (Compound 564). $^1$H NMR (300 MHz, DMSO-d$_6$): δ 8.73 (dd, J=4.7, 1.6 Hz, 1H), 8.02 (dd, J=7.8, 1.6 Hz, 1H), 7.96-7.87 (m, 1H), 7.81 (s, 1H), 7.63 (d, J=7.7 Hz, 1H), 7.56 (dt, J=7.8, 3.7 Hz, 2H), 7.47 (t, J=7.7 Hz, 1H), 7.38 (dd, J=9.3, 0.8 Hz, 1H), 7.15 (s, 1H), 6.91 (dd, J=9.3, 1.8 Hz, 1H), 2.93 (t, J=6.5 Hz, 4H), 1.96-1.52 (m, 4H). $^{19}$F NMR (282 MHz, DMSO-d$_6$): δ− 61.36 (s).LCMS: rt5.78 min (A), purity 99%, MS (m/e) 409 (MH+).

(6-(2-(4-Fluoro-3-methylphenyl)pyridin-3-yl)imidazo[1,2-a]pyridin-3-yl)methanol (Compound 565). $^1$H NMR (300 MHz, DMSO-d$_6$): δ 8.69 (dd, J=4.7, 1.6 Hz, 1H), 8.46 (s, 1H), 7.96 (dd, J=7.7, 1.6 Hz, 1H), 7.54 (s, 1H), 7.53-7.48 (m, 1H), 7.44 (t, J=8.6 Hz, 2H), 7.11-7.02 (m, 1H), 6.98 (t, J=9.1 Hz, 1H), 6.84 (dd, J=9.3, 1.6 Hz, 1H), 5.26 (s, 1H), 4.78 (s, 2H), 2.17 (s, 3H). $^{19}$F NMR (282 MHz, DMSO-d$_6$): δ −118.29 (s).LCMS: rt3.36 min (A), purity 99%, MS (m/e) 334 (MH+).

(6-(2-(m-Tolyl)pyridin-3-yl)imidazo[1,2-a]pyridin-3-yl)methanol (Compound 566). LCMS: rt2.55 min (A), purity 99%, MS (m/e) 316 (MH+).

(6-(2-(3-Cyclopropylphenyl)pyridin-3-yl)imidazo[1,2-a]pyridin-3-yl)methanol (Compound 567). LCMS: rt3.53 min (A), purity 99%, MS (m/e) 342 (MH+).

(6-(2-(3-(Trifluoromethyl)phenyl)pyridin-3-yl)imidazo[1,2-a]pyridin-3-yl)methanol (Compound 568). LCMS: rt4.38 min (A), purity 99%, MS (m/e) 370 (MH+).

4-((6-(2-(4-Fluoro-3-methylphenyl)pyridin-3-yl)imidazo[1,2-a]pyridin-3-yl)methyl)morpholine (Compound 569). $^1$H NMR (300 MHz, DMSO-d$_6$): δ 8.69 (dd, J=4.7, 1.7 Hz, 1H), 8.33 (dd, J=1.7, 0.9 Hz, 1H), 7.90 (dd, J=7.8, 1.7 Hz, 1H), 7.55-7.46 (m, 3H), 7.43 (dd, J=7.6, 1.6 Hz, 1H), 7.12-7.04 (m, 1H), 7.04-6.93 (m, 2H), 3.72 (s, 2H), 3.49-3.36 (m, 4H), 2.33-2.18 (m, 4H), 2.14 (s, 3H). $^{19}$F NMR (282 MHz, DMSO-d$_6$): δ −118.39 (s, 1H).LCMS: rt3.38 min (A), purity 99%, MS (m/e) 403 (MH+).

4-((6-(2-(m-Tolyl)pyridin-3-yl)imidazo[1,2-a]pyridin-3-yl)methyl)morpholine (Compound 570). LCMS: rt2.65 min (A), purity 99%, MS (m/e) 385 (MH+).

4-((6-(2-(3-Cyclopropylphenyl)pyridin-3-yl)imidazo[1,2-a]pyridin-3-yl)methyl)morpholine (Compound 571). LCMS: rt3.53 min (A), purity 99%, MS (m/e) 411 (MH+)

4-((6-(2-(3-(Trifluoromethyl)phenyl)pyridin-3-yl)imidazo[1,2-a]pyridin-3-yl)methyl)morpholine (Compound 572). LCMS: rt4.15 min (A), purity 99%, MS (m/e) 439 (MH+).

6-(2-(4-Fluoro-3-methylphenyl)pyridin-3-yl)-N-(3,4,5-trimethoxyphenyl)imidazo[1,2-a]pyridine-3-carboxamide (Compound 573). $^1$H NMR (300 MHz, DMSO-d$_6$): δ 10.25 (s, 1H), 9.54 (s, 1H), 8.75 (dd, J=4.8, 1.6 Hz, 1H), 8.67 (s, 1H), 8.05 (dd, J=7.8, 1.6 Hz, 1H), 7.70 (d, J=9.4 Hz, 1H), 7.59 (dd, J=7.8, 4.8 Hz, 1H), 7.47 (dd, J=7.5, 1.6 Hz, 1H), 7.20 (dd, J=9.3, 1.8 Hz, 1H), 7.16 (s, 2H), 7.14-7.06 (m, 1H) 6.93 (m, J=9.1 Hz, 1H), 3.77 (s, 6H), 3.63 (s, 3H), 2.17 (s, 3H). $^{19}$F NMR (282 MHz, DMSO-d$_6$): δ −117.82 (s, 1H).LCMS: rt5.53 min (A), purity 99%, MS (m/e) 513 (MH+).

6-(2-(m-Tolyl)pyridin-3-yl)-N-(3,4,5-trimethoxyphenyl)imidazo[1,2-a]pyridine-3-carboxamide (Compound 574). LCMS: rt5.18 min (A), purity 99%, MS (m/e) 495 (MH+).

6-(2-(3-Cyclopropylphenyl)pyridin-3-yl)-N-(3,4,5-trimethoxyphenyl)imidazo[1,2-a]pyridine-3-carboxamide (Compound 575). LCMS: rt5.55 min (A), purity 99%, MS (m/e) 521 (MH+).

6-(2-(3-(Trifluoromethyl)phenyl)pyridin-3-yl)-N-(3,4,5-trimethoxyphenyl)imidazo[1,2-a]pyridine-3-carboxamide (Compound 576). LCMS: rt6.26 min (A), purity 99%, MS (m/e) 549 (MH+).

6-(2-(4-Fluoro-3-methylphenyl)pyridin-3-yl)-3-(3,4,5-trimethoxyphenyl)imidazo[1,2-a]pyridine (Compound 577). $^1$H NMR (300 MHz, DMSO-d$_6$): δ 8.69 (dd, J=4.7, 1.5 Hz, 1H), 8.61 (s, 1H), 8.04 (d, J=9.3, 1.6 Hz, 1H), 8.01 (s, 1H), 7.68 (d, J=9.3 Hz, 1H), 7.56-7.39 (m, 2H), 7.17 (d, J=9.4 Hz, 1H), 7.09 (ddd, J=7.6, 5.1, 2.3 Hz, 1H), 7.01-6.87 (app m, 3H), 3.82 (s, 6H), 3.76-3.67 (m, 3H), 2.17 (s, 3H). $^{19}$F NMR (282 MHz, DMSO-d$_6$): δ −118.31 (s, 1H).LCMS: rt5.05 min (A), purity 99%, MS (m/e) 470 (MH+).

6-(2-(m-Tolyl)pyridin-3-yl)-3-(3,4,5-trimethoxyphenyl)imidazo[1,2-a]pyridine (Compound 578). LCMS: rt 4.68 min (A), purity 99%, MS (m/e) 452 (MH+).

6-(2-(4-Fluoro-3-methylphenyl)pyridin-3-yl)imidazo[1,2-a]pyridine-3-carboxylic acid (Compound 579). $^1$H NMR (300 MHz, DMSO-d$_6$) δ 13.01 (br s, 1H), 9.21 (dd, J=1.9, 1.0 Hz, 1H), 8.71 (dd, J=4.8, 1.7 Hz, 1H), 8.23 (s, 1H), 7.97 (dd, J=7.8, 1.7 Hz, 1H), 7.65 (dd, J=9.3, 1.0 Hz, 1H), 7.52 (dd, J=7.7, 4.8 Hz, 1H), 7.43 (dd, J=7.7, 2.3 Hz, 1H), 7.14 (dd, J=9.3, 1.9 Hz, 1H), 7.06 (ddd, J=7.8, 5.1, 2.3 Hz, 1H), 6.96 (dd, J=9.7, 8.4 Hz, 1H), 2.16 (s, 3H). LCMS: rt 3.70 min (A), purity 99%, MS (m/e) 348 (MH+).

(6-(2-(4-Fluoro-3-methylphenyl)pyridin-3-yl)imidazo[1,2-a]pyridin-3-yl)(morpholino)methanone (Compound 580). $^1$H NMR (300 MHz, DMSO-d$_6$): δ 8.89-8.83 (app m, 1H), 8.70 (dd, J=4.8, 1.2 Hz, 1H), 8.03 (d, J=0.5 Hz, 1H), 7.94 (dd, J=7.8, 1.2 Hz, 1H), 7.57 (d, J=9.3 Hz, 1H), 7.51 (dd, J=7.6, 5.0 Hz, 1H), 7.44 (d, J=7.8 Hz, 1H), 7.13-7.04 (m, 1H), 7.02-6.95 (m, 2H), 3.71-3.69 (m, 4H), 3.65-3.62 (m, 4H), 2.17 (s, 3H). $^{19}$F NMR (282 MHz, DMSO-$d_6$): δ −118.29 (s, 1H). LCMS: rt4.58 min (A), purity 99%, MS (m/e) 417 (MH$^+$).

(6-(2-(4-Fluoro-3-methylphenyl)pyridin-3-yl)imidazo[1,2-a]pyridin-3-yl)(4-methylpiperazin-1-yl)methanone (Compound 581). LCMS: rt3.41 min (A), purity 99%, MS (m/e) 430 (MH$^+$).

N-(3,4-Dimethoxyphenyl)-6-(2-(4-fluoro-3-methylphenyl)pyridin-3-yl)imidazo[1,2-a]pyridine-3-carboxamide (Compound 582). $^1$H NMR (300 MHz, DMSO-$d_6$): δ 10.32 (s, 1H), 9.58 (dd, J=1.7, 0.9 Hz, 1H), 8.77 (dd, J=4.9, 1.6 Hz, 1H), 8.73 (s, 1H), 8.07 (dd, J=7.8, 1.6 Hz, 1H), 7.76 (dd, J=9.3, 0.9 Hz, 1H), 7.61 (dd, J=7.8, 4.9 Hz, 1H), 7.47 (dd, J=7.5, 1.5 Hz, 1H), 7.41 (d, J=2.4 Hz, 1H), 7.28 (ddd, J=10.3, 9.1, 2.1 Hz, 2H), 7.10 (dd, J=5.2, 2.5 Hz, 1H), 6.97 (dd, J=17.6, 9.1 Hz, 2H), 3.75 (s, 3H), 3.73 (s, 3H), 2.17 (s, 3H). $^{19}$F NMR (282 MHz, DMSO-$d_6$): δ −118.32 (s, 1H). LCMS: rt5.23 min (A), purity 99%, MS (m/e) 483 (MH$^+$).

6-(2-(4-Fluoro-3-methylphenyl)pyridin-3-yl)-N-propylimidazo[1,2-a]pyridine-3-carboxamide (Compound 583). LCMS: rt4.51 min (B), purity 99%, MS (m/e) 389 (MH$^+$).

6-(2-(4-Fluoro-3-methylphenyl)pyridin-3-yl)-N-methylimidazo[1,2-a]pyridine-3-carboxamide (Compound 584). $^1$H NMR (300 MHz, DMSO-$d_6$): δ 9.48 (s, 1H), 8.71 (dd, J=4.8, 1.6 Hz, 1H), 8.48 (app qt, J=4.7 Hz, 1H), 8.26 (s, 1H), 7.93 (dd, J=7.8, 1.7 Hz, 1H), 7.55 (d, J=9.3 Hz, 1H), 7.51 (dd, J=7.8, 4.7 Hz, 1H), 7.42 (d, J=5.4 Hz, 1H), 7.11-7.04 (m, 1H), 7.04-6.91 (m, 2H), 2.79 (d, J=4.6 Hz, 3H), 2.15 (s, 3H). $^{19}$F NMR (282 MHz, DMSO-$d_6$): δ −118.32 (s, 1H). LCMS: rt3.57 min (B), purity 99%, MS (m/e) 361 (MH$^+$).

6-(2-(4-Fluoro-3-methylphenyl)pyridin-3-yl)-N-(2-morpholinoethyl)imidazo[1,2-a]pyridine-3-carboxamide (Compound 585). LCMS: rt2.42 min (B), purity 99%, MS (m/e) 460 (MH$^+$).

1-(6-(2-(4-Fluoro-3-methylphenyl)pyridin-3-yl)imidazo[1,2-a]pyridin-3-yl)ethan-1-one (Compound 586). LCMS: rt4.68 min (A), purity 99%, MS (m/e) 346 (MH$^+$).

1-(6-(2-(m-Tolyl)pyridin-3-yl)imidazo[1,2-a]pyridin-3-yl)ethan-1-one (Compound 587). LCMS: rt4.26 min (A), purity 99%, MS (m/e) 328 (MH$^+$).

1-(6-(2-(3-Cyclopropylphenyl)pyridin-3-yl)imidazo[1,2-a]pyridin-3-yl)ethan-1-one (Compound 588). $^1$H NMR (300 MHz, DMSO-$d_6$): δ 9.44 (dd, J=1.7, 0.8 Hz, 1H), 8.72 (dd, J=4.8, 1.6 Hz, 1H), 8.60 (s, 1H), 7.94 (dd, J=7.7, 1.7 Hz, 1H), 7.69 (dd, J=9.2, 0.7 Hz, 1H), 7.51 (dd, J=7.7, 4.8 Hz, 1H), 7.23 (dd, J=9.2, 1.8 Hz, 1H), 7.16-7.04 (m, 2H), 7.03-6.96 (m, 2H), 2.53 (s, 3H). 1.87-1.66 (m, 1H), 0.89-0.66 (m, 2H), 0.44-0.20 (m, 2H). LCMS: rt 4.81 min (A), purity 99%, MS (m/e) 354 (MH$^+$).

1-(6-(2-(3-(Trifluoromethyl)phenyl)pyridin-3-yl)imidazo[1,2-a]pyridin-3-yl)ethan-1-one (Compound 589). LCMS: rt 5.71 min (A), purity 99%, MS (m/e) 382 (MH$^+$).

6-(2-(4-Fluoro-3-methylphenyl)pyridin-3-yl)-N-(2-(4-methylpiperazin-1-yl)ethyl)imidazo[1,2-a]pyridine-3-carboxamide (Compound 590). LCMS: rt2.89 min (B), purity 99%, MS (m/e) 473 (MH$^+$).

6-(2-(4-Fluoro-3-methylphenyl)pyridin-3-yl)-N-(3-(4-methylpiperazin-1-yl)propyl)imidazo[1,2-a]pyridine-3-carboxamide (Compound 591). LCMS: rt 2.76 min (B), purity 99%, MS (m/e) 487 (MH$^+$).

6-(2-(4-Fluoro-3-methylphenyl)pyridin-3-yl)-N-(1-methylpiperidin-4-yl)imidazo[1,2-a]pyridine-3-carboxamide (Compound 592). $^1$H NMR (300 MHz, DMSO-$d_6$): δ 9.54 (dd, J=1.8, 0.9 Hz, 1H), 8.78 (dd, J=4.8, 1.7 Hz, 1H), 8.43 (s, 1H), 8.34 (d, J=7.6 Hz, 1H), 8.01 (dd, J=7.8, 1.7 Hz, 1H), 7.69-7.54 (m, 2H), 7.50 (dd, J=7.6, 2.0 Hz, 1H), 7.19-6.99 (m, 3H), 3.95-3.70 (m, 1H), 2.85 (d, J=11.7 Hz, 2H), 2.24 (s, 6H), 2.01 (t, J=10.7 Hz, 2H), 1.85 (d, J=9.3 Hz, 2H), 1.76-1.51 (m, 2H). LCMS: rt 3.03 min (B), purity 99%, MS (m/e) 444 (MH$^+$).

6-(2-(4-Fluoro-3-methylphenyl)pyridin-3-yl)-N-(tetrahydro-2H-pyran-4-yl)imidazo[1,2-a]pyridine-3-carboxamide (Compound 593). LCMS: rt 4.78 min (B), purity 99%, MS (m/e) 431 (MH$^+$).

7-(2-(4-Fluoro-3-methylphenyl)pyridin-3-yl)imidazo[1,5-a]pyridine (Compound 594). $^1$H NMR (300 MHz, DMSO-$d_6$): δ 8.65 (dd, J=4.7, 1.6 Hz, 1H), 8.31 (s, 1H), 8.17 (dd, J=7.3, 0.9 Hz, 1H), 7.89 (dd, J=7.6, 1.4 Hz, 1H), 7.55 (s, 1H), 7.46 (dd, J=7.3, 4.7 Hz, 2H), 7.36 (s, 1H), 7.11 (ddd, J=7.8, 5.0, 2.5 Hz, 1H), 7.06-6.94 (m, 1H), 6.20 (d, J=7.3 Hz, 1H), 2.18 (s, 4H). LCMS: rt3.53 min (A), purity 99%, MS (m/e) 304 (MH$^+$).

7-(2-(m-Tolyl)pyridin-3-yl)imidazo[1,5-a]pyridine (Compound 595). LCMS: rt3.01 min (A), purity 99%, MS (m/e) 286 (MH$^+$).

7-(2-(3-Cyclopropylphenyl)pyridin-3-yl)imidazo[1,5-a]pyridine (Compound 596). LCMS: rt3.73 min (A), purity 99%, MS (m/e) 312 (MH$^+$).

7-(2-(3-(Trifluoromethyl)phenyl)pyridin-3-yl)imidazo[1,5-a]pyridine (Compound 597). LCMS: rt4.66 min (A), purity 99%, MS (m/e) 340 (MH$^+$).

rac-1-(6-(2-(4-Fluoro-3-methylphenyl)pyridin-3-yl)imidazo[1,2-a]pyridin-3-yl)ethan-1-ol (Compound 598). $^1$H NMR (300 MHz, DMSO-$d_6$): δ 8.69 (dd, J=4.7, 1.7 Hz, 1H), 8.40 (d, J=0.9 Hz, 1H), 7.95 (dd, J=7.8, 1.7 Hz, 1H), 7.51 (dd, J=7.8, 4.8 Hz, 1H), 7.47-7.37 (m, 3H), 7.12-7.02 (m, 1H), 6.98 (t, J=9.1 Hz, 1H), 6.86 (dd, J=9.3, 1.8 Hz, 1H), 5.33 (br s, 1H), 5.07 (app qt, J=6.5 Hz, 1H), 2.14 (s, 3H), 1.50 (d, J=6.5 Hz, 3H). $^{19}$F NMR (282 MHz, DMSO-$d_6$): δ −118.42 (s). LCMS: rt3.78 min (A), purity 99%, MS (m/e) 348 (MH$^+$).

2-(6-(2-(4-Fluoro-3-methylphenyl)pyridin-3-yl)imidazo[1,2-a]pyridin-3-yl)propan-2-ol (Compound 599). LCMS: rt 4.03 min (A), purity 99%, MS (m/e) 362 (MH$^+$).

6-(2-(3-(Methyl-$d_3$)phenyl)pyridin-3-yl)imidazo[1,2-a]pyridine (Compound 600). LCMS: rt3.35 min (A), purity 99%, MS (m/e) 289 (MH$^+$).

6-(2-(3-(Methyl-$d_3$)phenyl)pyridin-3-yl)imidazo[1,2-a]pyridine-3-carbonitrile (Compound 601). $^1$H NMR (300 MHz, DMSO-$d_6$): δ 8.72 (dd, J=4.8, 1.7 Hz, 1H), 8.62 (dd, J=1.7, 1.0 Hz, 1H), 8.44 (s, 1H), 8.05 (dd, J=7.8, 1.7 Hz, 1H), 7.64 (dd, J=9.3, 0.9 Hz, 1H), 7.52 (dd, J=7.8, 4.8 Hz, 1H), 7.34 (dd, J=2.6, 1.4 Hz, 1H), 7.16-7.01 (m, 4H). LCMS: rt4.96 min (A), purity 99%, MS (m/e) 314 (MH$^+$).

5-(2-(3-(Methyl-d3)phenyl)pyridin-3-yl)pyrazolo[1,5-a]pyrimidine (Compound 602). LCMS: rt5.00 min (A), purity 99%, MS (m/e) 290 (MH$^+$).

6-(2-(3-(Methyl-$d_3$)phenyl)pyridin-3-yl)benzo[d]thiazole (Compound 603). LCMS: rt5.15 min (A), purity 99%, MS (m/e) 306 (MH$^+$).

7-(2-(3-(Methyl-$d_3$)phenyl)pyridin-3-yl)imidazo[1,5-a]pyridine (Compound 604). LCMS: rt3.35 min (A), purity 99%, MS (m/e) 289 (MH$^+$).

6-(2-(3-(Methyl-$d_3$)phenyl)pyridin-3-yl)quinoxaline (Compound 605). $^1$H NMR (300 MHz, DMSO-$d_6$): δ 8.87 (s, 2H), 8.67 (dd, J=4.7, 1.6 Hz, 1H), 8.00-7.93 (m, 2H), 7.89 (d, J=8.7 Hz, 1H), 7.53-7.43 (m, 2H), 7.24 (s, 1H), 6.99 (dt, J=7.5, 4.1 Hz, 2H), 6.90 (ddd, J=5.0, 2.7, 1.5 Hz, 1H). LCMS: rt4.83 min (A), purity 99%, MS (m/e) 301 (MH$^+$).

1-(6-(2-(3-(Methyl-$d_3$)phenyl)pyridin-3-yl)imidazo[1,2-a]pyridin-3-yl)ethan-1-one (Compound 606). LCMS: rt 4.25 min (A), purity 99%, MS (m/e) 331 (MH$^+$).

N-(2-(Dimethylamino)ethyl)-6-(2-(4-fluoro-3-methylphenyl)pyridin-3-yl)imidazo[1,2-a]pyridine-3-carboxamide (Compound 607). LCMS: rt2.62 min (B), purity 99%, MS (m/e) 418 (MH+).

N-(3-(Dimethylamino)propyl)-6-(2-(4-fluoro-3-methylphenyl)pyridin-3-yl)imidazo[1,2-a]pyridine-3-carboxamide (Compound 608). LCMS: rt2.62 min (B), purity 99%, MS (m/e) 432 (MH+).

6-(2-(4-Fluoro-3-methylphenyl)pyridin-3-yl)-N-(3-morpholinopropyl)imidazo[1,2-a]pyridine-3-carboxamide (Compound 609). LCMS: rt2.64 min (B), purity 99%, MS (m/e) 474 (MH+).

6-(2-(4-Fluoro-3-methylphenyl)pyridin-3-yl)-N-(2-(pyrrolidin-1-yl)ethyl)imidazo[1,2-a]pyridine-3-carboxamide (Compound 610). LCMS: rt2.72 min (B), purity 99%, MS (m/e) 444 (MH+).

6-(2-(4-Fluoro-3-methylphenyl)pyridin-3-yl)-N-(3-(piperidin-1-yl)propyl)imidazo[1,2-a]pyridine-3-carboxamide (Compound 611). LCMS: rt2.78 min (B), purity 99%, MS (m/e) 472 (MH+).

6-(2-(4-Fluoro-3-methylphenyl)pyridin-3-yl)-N-(3-(2-oxopyrrolidin-1-yl)propyl)imidazo[1,2-a]pyridine-3-carboxamide (Compound 612). $^1$H NMR (300 MHz, DMSO-$d_6$): δ 9.47 (s, 1H), 8.71 (dd, J=4.7, 1.5 Hz, 1H), 8.51 (t, J=4.9 Hz, 1H), 8.31 (s, 1H), 7.95 (d, J=7.8 Hz, 1H), 7.57 (app d, J=9.5 Hz, 1H), 7.52 (dd, J=7.7, 4.8 Hz, 1H), 7.43 (d, J=7.9 Hz, 1H), 7.05 (d, J=9.2 Hz, 2H), 6.97 (app dd, J=17.6, 9.1 Hz, 1H), 3.34 (t, J=6.8 Hz, 2H), 3.23 (t, J=6.8 Hz, 4H), 2.21 (t, J=8.1 Hz, 2H), 2.16 (s, 3H), 1.99-1.82 (m, 2H), 1.80-1.64 (m, 2H). $^{19}$F NMR (282 MHz, DMSO-$d_6$): δ –118.24 (s). LCMS: rt2.94 min (B), purity 99%, MS (m/e) 472 (MH+).

N-(2,3-Dihydroxypropyl)-6-(2-(4-fluoro-3-methylphenyl)pyridin-3-yl)imidazo[1,2-a]pyridine-3-carboxamide (Compound 613). LCMS: rt4.15 min (A), purity 99%, MS (m/e) 421 (MH+).

(S)-2-((tert-Butoxycarbonyl)amino)-3-(1H-indol-3-yl)propyl 6-(2-(4-fluoro-3-methylphenyl)pyridin-3-yl)imidazo[1,2-a]pyridine-3-carboxylate (Compound 614). $^1$H NMR (300 MHz, DMSO-$d_6$): δ 10.81 (s, 1H), 9.13 (s, 1H), 8.71 (dd, J=4.7, 1.6 Hz, 1H), 8.33 (s, 1H), 7.97 (dd, J=7.7, 1.5 Hz, 1H), 7.66 (d, J=9.3 Hz, 1H), 7.57-7.46 (m, 2H), 7.42 (dd, J=8.1, 1.6 Hz, 1H), 7.31 (d, J=8.0 Hz, 1H), 7.13 (app dd, J=4.1, 1.9 Hz, 2H), 7.04 (app t, J=7.7 Hz, 3H), 6.99-6.90 (m, 2H), 4.29 (dd, J=10.3, 4.9 Hz, 1H), 4.19 (app qt, J=6.9 Hz, 1H), 2.90 (t, J=8.7 Hz, 2H), 2.14 (s, 3H), 1.28 (s, 9H). $^{19}$F NMR (282 MHz, DMSO-$d_6$): δ –118.18 (s). LCMS: rt7.10 min (A), purity 99%, MS (m/e) 620 (MH+).

(S)-2-Amino-3-(1H-indol-3-yl)propyl 6-(2-(4-fluoro-3-methylphenyl)pyridin-3-yl)imidazo[1,2-a]pyridine-3-carboxylate formic acid salt (Compound 615). LCMS: rt5.10 min (A), purity 99%, MS (m/e) 520 (MH+-HCOOH).

6-(2-(4-Fluoro-3-methylphenyl)pyridin-3-yl)-N-(3-sulfamoylphenyl)imidazo[1,2-a]pyridine-3-carboxamide (Compound 616). LCMS: rt 4.05 min (A), purity 99%, MS (m/e) 502 (MH+).

6-(2-(4-Fluoro-3-methylphenyl)pyridin-3-yl)-N-(4-sulfamoylphenyl)imidazo[1,2-a]pyridine-3-carboxamide (Compound 617). LCMS: rt 4.71 min (A), purity 99%, MS (m/e) 502 (MH+).

N-(4-Carbamoylphenyl)-6-(2-(4-fluoro-3-methylphenyl)pyridin-3-yl)imidazo[1,2-a]pyridine-3-carboxamide (Compound 618). LCMS: rt 4.48 min (A), purity 99%, MS (m/e) 466 (MH+).

N-(3-Carbamoylphenyl)-6-(2-(4-fluoro-3-methylphenyl)pyridin-3-yl)imidazo[1,2-a]pyridine-3-carboxamide (Compound 619). $^1$H NMR (300 MHz, DMSO-$d_6$): δ 10.59 (s, 1H), 9.73-9.51 (m, 1H), 8.82 (s, 1H), 8.80-8.72 (m, 1H), 8.24 (s, 1H), 8.09 (d, J=7.8 Hz, 1H), 7.95-7.89 (m, 1H), 7.76 (d, J=9.3 Hz, 1H), 7.63 (dd, J=7.9, 4.7 Hz, 2H), 7.45 (dd, J=16.4, 8.5 Hz, 2H), 7.33-7.24 (m, 1H), 7.12 (dd, J=8.0, 5.4 Hz, 1H), 6.99 (app t, J=9.3 Hz, 1H), 6.95 (br s, 2H), 2.18 (s, 3H). LCMS: rt 4.56 min (A), purity 96%, MS (m/e) 466 (MH+).

(R)-2-Amino-3-(1H-indol-3-yl)propyl 6-(2-(4-fluoro-3-methylphenyl)pyridin-3-yl)imidazo[1,2-a]pyridine-3-carboxylateformic acid salt (Compound 620). $^1$H NMR (300 MHz, DMSO-$d_6$): δ 10.85 (s, 1H), 9.16 (s, 1H), 8.71 (dd, J=4.7, 1.7 Hz, 1H), 7.96 (dd, J=7.6, 1.7 Hz, 1H), 7.67 (d, J=8.9 Hz, 1H), 7.57-7.45 (m, 2H), 7.42 (d, J=8.1 Hz, 1H), 7.32 (d, J=8.0 Hz, 1H), 7.22-7.10 (m, 2H), 7.12-6.98 (m, 2H), 7.00-6.86 (m, 2H), 4.40-3.91 (m, 2H), 3.38-3.33 (m, 1H), 3.02-2.68 (m, 2H), 2.15 (s, 3H). LCMS: rt 5.10 min (A), purity 98%, MS (m/e) 520 (MH+-HCOOH).

6-(2-(3-Fluorophenyl)pyridin-3-yl)imidazo[1,2-a]pyridine-3-carbonitrile (Compound 621). LCMS: rt5.64 min (A), purity 99%, MS (m/e) 315 (MH+).

6-(2-(3,4-Difluorophenyl)pyridin-3-yl)imidazo[1,2-a]pyridine-3-carbonitrile (Compound 622). LCMS: rt6.19 min (A), purity 99%, MS (m/e) 333 (MH+).

6-(2-(2-Fluorophenyl)pyridin-3-yl)imidazo[1,2-a]pyridine-3-carbonitrile (Compound 623). LCMS: rt5.55 min (A), purity 99%, MS (m/e) 333 (MH+).

6-(2-(2-Fluoro-5-methylphenyl)pyridin-3-yl)imidazo[1,2-a]pyridine-3-carbonitrile (Compound 624). LCMS: rt6.02 min (A), purity 99%, MS (m/e) 333 (MH+).

6-(2-(4-Fluorophenyl)pyridin-3-yl)imidazo[1,2-a]pyridine-3-carbonitrile (Compound 625). LCMS: rt5.24 min (A), purity 99%, MS (m/e) 333 (MH+).

6-(2-(3-Methoxyphenyl)pyridin-3-yl)imidazo[1,2-a]pyridine-3-carbonitrile (Compound 626). LCMS: rt4.97 min (A), purity 99%, MS (m/e) 333 (MH+).

6-(2-(3-Cyanophenyl)pyridin-3-yl)imidazo[1,2-a]pyridine-3-carbonitrile (Compound 627). LCMS: rt5.77 min (A), purity 99%, MS (m/e) 333 (MH+).

6-(2-(3-Cyano-4-fluorophenyl)pyridin-3-yl)imidazo[1,2-a]pyridine-3-carbonitrile (Compound 628). LCMS: rt6.29 min (A), purity 99%, MS (m/e) 333 (MH+).

(R)-2-Amino-3-(1H-indol-3-yl)propyl 5-(2-(4-fluoro-3-methylphenyl)pyridin-3-yl)-1H-indazole-1-carboxylate TFA salt (Compound 628). LCMS: rt5.15 min (A), purity 95%, MS (m/e) 520 (MH+-TFA).

5-(2-(4-Fluoro-3-methylphenyl)pyridin-3-yl)-N-(3,4,5-trimethoxyphenyl)-1H-indazole-1-carboxamide (Compound 630). LCMS: rt6.71 min (A), purity 98%, MS (m/e) 513 (MH+).

N-(3,4-Dimethoxybenzyl)-5-(2-(4-fluoro-3-methylphenyl)pyridin-3-yl)-1H-indazole-1-carboxamide (Compound 631). $^1$H NMR (300 MHz, DMSO-$d_6$): δ 8.92 (t, J=6.3 Hz, 1H), 8.66 (dd, J=4.7, 1.7 Hz, 1H), 8.37 (d, J=0.7 Hz, 1H), 8.13 (d, J=8.7 Hz, 1H), 7.86 (dd, J=7.7, 1.7 Hz, 1H), 7.73 (s, 1H), 7.47 (dd, J=7.8, 4.7 Hz, 1H), 7.37 (d, J=8.0 Hz, 1H), 7.28 (dd, J=8.7, 1.7 Hz, 1H), 7.01 (s, 1H), 6.95-6.84 (m, 4H), 4.39 (d, J=6.3 Hz, 2H), 3.72 (s, 3H), 3.70 (s, 3H), 2.12 (s, 3H). $^{19}$F NMR (282 MHz, DMSO-$d_6$): δ –118.67 (d, J=7.8 Hz). LCMS: rt7.05 min (A), purity 99%, MS (m/e) 497 (MH+).

N-(2-(1H-Indol-3-yl)ethyl)-5-(2-(4-fluoro-3-methylphenyl)pyridin-3-yl)-1H-indazole-1-carboxamide (Compound 632). LCMS: rt 6.48 min (A), purity 99%, MS (m/e) 490 (MH+)

N-(2-(Dimethylamino)ethyl)-5-(2-(4-fluoro-3-methylphenyl)pyridin-3-yl)-1H-indazole-1-carboxamide (Compound 633). LCMS: rt 4.16 min (A), purity 98%, MS (m/e) 418 (MH+).

N-(3-(Dimethylamino)propyl)-5-(2-(4-fluoro-3-methylphenyl)pyridin-3-yl)-1H-indazole-1-carboxamide (Compound 634). LCMS: rt 5.30 min (A), purity 98%, MS (m/e) 431 (MH+).

5-(2-(4-Fluoro-3-methylphenyl)pyridin-3-yl)-N-(3-(2-oxopyrrolidin-1-yl)propyl)-1H-indazole-1-carboxamide (Compound 635). LCMS: rt 5.30 min (A), purity 97%, MS (m/e) 472 (MH+).

5-(2-(4-Fluoro-3-methylphenyl)pyridin-3-yl)-N-(2-(pyrrolidin-1-yl)ethyl)-1H-indazole-1-carboxamide (Compound 636). LCMS: rt 4.33 min (A), purity 99%, MS (m/e) 444 (MH+).

5-(2-(4-Fluoro-3-methylphenyl)pyridin-3-yl)-N-(3-(piperidin-1-yl)propyl)-1H-indazole-1-carboxamide (Compound 637). LCMS: rt 4.53 min (A), purity 98%, MS (m/e) 472 (MH+).

5-(2-(4-Fluoro-3-methylphenyl)pyridin-3-yl)-N-(3-morpholinopropyl)-1H-indazole-1-carboxamide (Compound 638). LCMS: rt 4.21 min (A), purity 99%, MS (m/e) 474 (MH+).

N-(2-Amino ethyl)-5-(2-(4-fluoro-3-methylphenyl)pyridin-3-yl)-1H-indazole-1-carboxamide (Compound 639). LCMS: rt 4.00 min (A), purity 99%, MS (m/e) 390 (MH+).

N-(3-Aminopropyl)-5-(2-(4-fluoro-3-methylphenyl)pyridin-3-yl)-1H-indazole-1-carboxamide (Compound 640).LCMS: rt 3.41 min (A), purity 99%, MS (m/e) 404 (MH+).

(S)-2-((tert-Butoxycarbonyl)amino)-3-(1H-indol-3-yl)propyl 6-(2-(4-fluoro-3-methylphenyl)pyridin-3-yl)imidazo[1,5-a]pyridine-3-carboxylate (Compound 641). $^1$H NMR (300 MHz, DMSO-$d_6$): δ 10.82 (s, 1H), 9.17 (s, 1H), 8.71 (d, J=4.7 Hz, 1H), 7.97 (d, J=7.8 Hz, 1H), 7.70 (d, J=9.8 Hz, 2H), 7.60-7.38 (m, 3H), 7.32 (d, J=8.1 Hz, 1H), 7.21-6.86 (m, 6H), 6.75 (d, J=9.3 Hz, 1H), 4.45-4.29 (m, 1H), 4.23 (t, J=9.6 Hz, 1H), 4.13-4.02 (m, 1H), 2.92 (d, J=6.4 Hz, 2H), 2.15 (s, 3H), 1.27 (s, 9H). LCMS: rt 7.41 min (A), purity 96%, MS (m/e) 620 (MH+).

(R)-2-((tert-Butoxycarbonyl)amino)-3-(1H-indol-3-yl)propyl 6-(2-(4-fluoro-3-methylphenyl)pyridin-3-yl)imidazo[1,5-a]pyridine-3-carboxylate (Compound 642). LCMS: rt 7.41 min (A), purity 96%, MS (m/e) 620 (MH+).

(S)-2-((tert-Butoxycarbonyl)amino)-3-(1H-indol-3-yl)propyl 7-(2-(4-fluoro-3-methylphenyl)pyridin-3-yl)imidazo[1,5-a]pyridine-3-carboxylate (Compound 643). $^1$H NMR (300 MHz, DMSO-$d_6$): δ 10.82 (s, 1H), 8.96 (d, J=7.4 Hz, 1H), 8.80-8.63 (m, 1H), 7.94 (d, J=7.8 Hz, 1H), 7.86 (s, 1H), 7.71 (s, 1H), 7.66-7.40 (m, 3H), 7.31 (d, J=7.8 Hz, 1H), 7.15 (s, 1H), 7.00 (ddd, J=12.4, 7.2, 3.1 Hz, 5H), 6.67 (d, J=7.4 Hz, 1H), 4.36 (dd, J=10.7, 4.3 Hz, 1H), 4.28-4.13 (m, 1H), 4.13-4.01 (m, 1H), 2.91 (d, J=6.3 Hz, 2H), 2.17 (s, 3H), 1.28 (s, 9H). $^{19}$F NMR (282 MHz, DMSO-$d_6$): δ −118.08 (s). LCMS: rt 7.36 min (A), purity 99%, MS (m/e) 620 (MH+).

(R)-2-((tert-Butoxycarbonyl)amino)-3-(1H-indol-3-yl)propyl 7-(2-(4-fluoro-3-methylphenyl)pyridin-3-yl)imidazo[1,5-a]pyridine-3-carboxylate (Compound 644). LCMS: rt 7.36 min (A), purity 99%, MS (m/e) 620 (MH+).

(S)-2-Amino-3-(1H-indol-3-yl)propyl 6-(2-(4-fluoro-3-methylphenyl)pyridin-3-yl)imidazo[1,5-a]pyridine-3-carboxylate formic acid salt (Compound 645). LCMS: rt 5.45 min (A), purity 99%, MS (m/e) 520 (MH+-HCOOH).

(R)-2-Amino-3-(1H-indol-3-yl)propyl 6-(2-(4-fluoro-3-methylphenyl)pyridin-3-yl)imidazo[1,5-a]pyridine-3-carboxylate formic acid salt (Compound 646). LCMS: rt 5.45 min (A), purity 99%, MS (m/e) 520 (MH+-HCOOH).

(S)-2-Amino-3-(1H-indol-3-yl)propyl 7-(2-(4-fluoro-3-methylphenyl)pyridin-3-yl)imidazo[1,5-a]pyridine-3-carboxylate formic acid salt (Compound 647). LCMS: rt 5.41 min (A), purity 99%, MS (m/e) 520 (MH+-HCOOH).

(R)-2-Amino-3-(1H-indol-3-yl)propyl 7-(2-(4-fluoro-3-methylphenyl)pyridin-3-yl)imidazo[1,5-a]pyridine-3-carboxylateformic acid salt (Compound 648). LCMS: rt 5.41 min (A), purity 99%, MS (m/e) 520 (MH+-HCOOH).

N-((1R,2R)-2-Aminocyclohexyl)-5-(2-(4-fluoro-3-methylphenyl)pyridin-3-yl)-1H-indazole-1-carboxamide hydrochloride salt (Compound 649). $^1$H NMR (300 MHz, DMSO-$d_6$): δ 8.82 (d, J=5.2 Hz, 1H), 8.71 (s, 1H), 8.49 (d, J=9.0 Hz, 1H), 8.42 (d, J=0.7 Hz, 1H), 8.32 (d, J=7.8 Hz, 1H), 8.16 (d, J=8.8 Hz, 3H), 7.95-7.81 (m, 1H), 7.80 (s, 1H), 7.48 (d, J=6.7 Hz, 1H), 7.33 (dd, J=8.7, 1.6 Hz, 1H), 7.16-6.89 (m, 2H), 3.75-3.52 (m, 2H), 3.46 (dd, J=8.0, 4.0 Hz, 1H), 2.12 (s, 3H), 1.94-1.78 (m, 1H), 1.75-1.55 (m, 3H), 1.50-1.35 (m, 1H), 1.31-1.02 (m, 2H).LCMS: rt 4.63 min (A), purity 92%, MS (m/e) 444 (MH+-HCl).

N-((1S,2S)-2-Amino cyclohexyl)-5-(2-(4-fluoro-3-methylphenyl)pyridin-3-yl)-1H-indazole-1-carboxamide (Compound 650). LCMS: rt 4.58 min (A), purity 94%, MS (m/e) 444 (MH+-HCl).

6-(2-(4-Fluoro-3-methylphenyl)pyridin-3-yl)-N-((1-methylpiperidin-4-yl)methyl)imidazo[1,2-a]pyridine-3-carboxamide (Compound 651). LCMS: rt 3.70 min (A), purity 99%, MS (m/e) 458 (MH+).

6-(2-(4-Fluoro-3-methylphenyl)pyridin-3-yl)-N-(piperidin-4-yl)imidazo[1,2-a]pyridine-3-carboxamide (Compound 652). LCMS: rt 3.56 min (A), purity 98%, MS (m/e) 430 (MH+).

N-(3-(1H-Imidazol-1-yl)propyl)-6-(2-(4-fluoro-3-methylphenyl)pyridin-3-yl)imidazo[1,2-a]pyridine-3-carboxamide (Compound 653). LCMS: rt 3.71 min (A), purity 99%, MS (m/e) 455 (MH+).

6-(2-(4-Fluoro-3-methylphenyl)pyridin-3-yl)-N-(pyridin-4-yl)imidazo[1,2-a]pyridine-3-carboxamide (Compound 654). $^1$H NMR (300 MHz, DMSO-$d_6$): δ 10.50 (s, 1H), 9.44 (s, 1H), 8.73 (d, J=4.7 Hz, 1H), 8.63 (s, 1H), 8.46 (d, J=6.2 Hz, 2H), 7.98 (d, J=7.7 Hz, 1H), 7.73 (d, J=6.3 Hz, 2H), 7.65 (d, J=9.3 Hz, 1H), 7.53 (dd, J=7.8, 4.7 Hz, 1H), 7.45 (d, J=6.9 Hz, 1H), 7.20-7.04 (m, 2H), 7.03-6.90 (m, 1H), 2.17 (s, 3H).LCMS: rt 4.08 min (A), purity 99%, MS (m/e) 424 (MH+).

5-(2-(4-Fluoro-3-methylphenyl)pyridin-3-yl)-N-(1-methylpiperidin-4-yl)pyrazolo[1,5-a]pyridine-3-carboxamide (Compound 655). $^1$H NMR (300 MHz, DMSO-$d_6$): δ 8.71-8.62 (m, 1H), 8.57 (d, J=7.2 Hz, 1H), 8.53 (s, 1H), 8.10 (d, J=2.0 Hz, 1H), 8.05 (d, J=7.2 Hz, 1H), 7.92-7.83 (m, 1H), 7.47 (dd, J=7.8, 4.8 Hz, 1H), 7.39 (d, J=6.0 Hz, 1H), 6.99 (dd, J=5.3, 2.3 Hz, 1H), 6.93 (t, J=9.0 Hz, 1H), 6.57 (dd, J=7.1, 2.0 Hz, 1H), 3.96-3.82 (m, 1H), 3.22-3.11 (m, 2H), 2.80-2.63 (m, 2H), 2.56 (s, 3H), 2.12 (s, 3H), 1.95-1.82 (m, 2H), 1.68-1.65 (m, 2H).LCMS: rt 4.03 min (A), purity 99%, MS (m/e) 444 (MH+).

5-(2-(4-Fluoro-3-methylphenyl)pyridin-3-yl)-N-((1-methylpiperidin-4-yl)methyl)pyrazolo[1,5-a]pyridine-3-carboxamide (Compound 656). LCMS: rt 4.06 min (A), purity 99%, MS (m/e) 458 (MH+).

6-(2-(2-Fluorophenyl)pyridin-3-yl)benzo[d]thiazole (Compound 657). LCMS: rt 5.60 min (A), purity 99%, MS (m/e) 307 (MH+).

6-(2-(3-Fluorophenyl)pyridin-3-yl)benzo[d]thiazole (Compound 658). LCMS: rt 5.65 min (A), purity 99%, MS (m/e) 307 (MH+).

6-(2-(4-Fluorophenyl)pyridin-3-yl)benzo[d]thiazole (Compound 659). LCMS: rt 5.25 min (A), purity 99%, MS (m/e) 307 (MH+).

6-(2-(3,5-Difluorophenyl)pyridin-3-yl)benzo[d]thiazole (Compound 660). LCMS: rt 6.32 min (A), purity 99%, MS (m/e) 325 (MH+).

6-(2-(3,4-Difluorophenyl)pyridin-3-yl)benzo[d]thiazole (Compound 661). LCMS: rt 6.25 min (A), purity 99%, MS (m/e) 325 (MH+).

6-(2-(2,3-Difluorophenyl)pyridin-3-yl)benzo[d]thiazole (Compound 662). LCMS: rt 6.58 min (A), purity 99%, MS (m/e) 325 (MH+).

N-((1R,2R)-2-Aminocyclohexyl)-5-(2-(4-fluoro-3-methylphenyl)pyridin-3-yl)pyrazolo[1,5-a]pyridine-3-carboxamide (Compound 663). LCMS: rt 4.40 min (A), purity 99%, MS (m/e) 444 (MH+).

N-((1S,2S)-2-Amino cyclohexyl)-5-(2-(4-fluoro-3-methylphenyl)pyridin-3-yl)pyrazolo[1,5-a]pyridine-3-carboxamide (Compound 664). LCMS: rt 4.38 min (A), purity 99%, MS (m/e) 444 (MH+).

6-(2-(2,4-Difluorophenyl)pyridin-3-yl)benzo[d]thiazole (Compound 665). LCMS: rt 6.60 min (A), purity 99%, MS (m/e) 325 (MH+).

6-(2-(3,4,5-Trifluorophenyl)pyridin-3-yl)benzo[d]thiazole (Compound 666). LCMS: rt 5.54 min (B), purity 99%, MS (m/e) 343 (MH+).

6-(2-(2-Fluoro-5-methylphenyl)pyridin-3-yl)benzo[d]thiazole (Compound 667). LCMS: rt 5.91 min (A), purity 99%, MS (m/e) 321 (MH+).

6-(2-(3-Chlorophenyl)pyridin-3-yl)benzo[d]thiazole (Compound 668). $^1$H NMR (300 MHz, DMSO-$d_6$): δ 9.39 (s, 1H), 8.72 (dd, J=4.8, 1.7 Hz, 1H), 8.12 (d, J=1.8 Hz, 1H), 8.04-7.88 (m, 2H), 7.55 (dd, J=7.8, 4.8 Hz, 1H), 7.43 (t, J=1.9 Hz, 1H), 7.34-7.28 (m, 1H), 7.26 (dd, J=8.4, 1.8 Hz, 1H), 7.20 (t, J=7.8 Hz, 1H), 7.11 (dt, 17.7, 1.4 Hz, 1H).LCMS: rt 6.20 min (A), purity 99%, MS (m/e) 323 (MH+).

6-(2-(3-Methoxyphenyl)pyridin-3-yl)benzo[d]thiazole (Compound 669). LCMS: rt 5.05 min (A), purity 99%, MS (m/e) 319 (MH+).

3-(3-(Benzo[d]thiazol-6-yl)pyridin-2-yl)benzonitrile (Compound 670). LCMS: rt5.93 min (A), purity 99%, MS (m/e) 314 (MH+).

6-(2-(Benzo[d][1,3]dioxol-5-yl)pyridin-3-yl)benzo[d]thiazole (Compound 671). LCMS: rt 4.78 min (A), purity 99%, MS (m/e) 333 (MH+).

5-(2-(4-Fluoro-3-methylphenyl)pyridin-3-yl)-N-(3-morpholinopropyl)pyrazolo[1,5-a]pyridine-3-carboxamide (Compound 672). LCMS: rt min 2.86 (B), purity 99%, MS (m/e) 474 (MH+)

N-(2-(Dimethylamino)ethyl)-5-(2-(4-fluoro-3-methylphenyl)pyridin-3-yl)pyrazolo[1,5-a]pyridine-3-carboxamide (Compound 673). LCMS: rt 2.72 min (B), purity 99%, MS (m/e) 418 (MH+)

5-(2-(4-Fluoro-3-methylphenyl)pyridin-3-yl)-N-(2-morpholino ethyl)pyrazolo[1,5-a]pyridine-3-carboxamide (Compound 674). LCMS: rt 2.80 min (B), purity 99%, MS (m/e) 460 (MH+)

5-(2-(4-Fluoro-3-methylphenyl)pyridin-3-yl)-N-(3-(pyrrolidin-1-yl)propyl)pyrazolo[1,5-a]pyridine-3-carboxamide (Compound 675). LCMS: rt 2.91 min (B), purity 99%, MS (m/e) 458 (MH+)

5-(2-(4-Fluoro-3-methylphenyl)pyridin-3-yl)-N-(3-(4-methylpiperazin-1-yl)propyl)pyrazolo[1,5-a]pyridine-3-carboxamide (Compound 676). LCMS: rt 2.47 min (B), purity 99%, MS (m/e) 487 (MH+)

Ethyl 5-(2-(4-Fluoro-3-methylphenyl)pyridin-3-yl)pyrazolo[1,5-a]pyridine-3-carboxylate (Compound 677). $^1$H NMR (300 MHz, DMSO-$d_6$): δ 8.76 (dd, J=7.2, 0.9 Hz, 1H), 8.72 (dd, J=4.8, 1.7 Hz, 1H), 8.44 (s, 1H), 7.99 (dd, J=7.8, 1.7 Hz, 1H), 7.94 (dd, J=2.1, 0.9 Hz, 1H), 7.53 (dd, J=7.8, 4.8 Hz, 1H), 7.45 (dd, J=7.7, 1.8 Hz, 1H), 7.10-6.94 (m, 2H), 6.80 (dd, J=7.2, 2.0 Hz, 1H), 4.24 (q, J=7.1 Hz, 2H), 2.17 (s, 3H), 1.26 (t, J=7.1 Hz, 3H). $^{19}$F NMR (282 MHz, DMSO-$d_6$): δ −118.06−−118.13 (m). LCMS: rt 6.51 min (A), purity 96%, MS (m/e) 376 (MH+)

5-(2-(4-Fluoro-3-methylphenyl)pyridin-3-yl)pyrazolo[1,5-a]pyridine-3-carboxylic acid (Compound 678). $^1$H NMR (300 MHz, DMSO-$d_6$): δ 12.47 (s, 1H), 8.76-8.65 (m, 2H), 8.39 (s, 1H), 8.05-7.91 (m, 2H), 7.52 (dd, J=7.8, 4.8 Hz, 1H), 7.45 (dd, J=7.5, 2.2 Hz, 1H), 7.11-6.90 (m, 2H), 6.71 (dd, J=7.2, 2.0 Hz, 1H), 2.17 (s, 3H). $^{19}$F NMR (282 MHz, DMSO-$d_6$): δ −118.05. LCMS: rt 5.01 min (A), purity 97%, MS (m/e) 348 (MH+)

N-((1R,2R)-2-Aminocyclohexyl)-6-(2-(4-fluoro-3-methylphenyl)pyridin-3-yl)imidazo[1,2-a]pyridine-3-carboxamide (Compound 679). $^1$H NMR (300 MHz, DMSO-$d_6$): δ 9.48 (s, 1H), 8.70 (d, J=4.4 Hz, 1H), 8.37 (s, 1H), 8.27-8.13 (m, 1H), 7.93 (dd, J=7.8, 1.4 Hz, 1H), 7.62-7.46 (m, 2H), 7.43 (dd, J=7.8, 2.0 Hz, 1H), 7.12-6.84 (m, 3H), 3.75-3.52 (m, 2H), 3.46 (dd, J=8.0, 4.0 Hz, 1H), 2.12 (s, 3H), 1.94-1.78 (m, 1H), 1.75-1.55 (m, 3H), 1.50-1.35 (m, 1H), 1.31-1.02 (m, 2H).LCMS: rt 4.05 min (A), purity 98%, MS (m/e) 444 (MH+)

N-((1S,2S)-2-Aminocyclohexyl)-6-(2-(4-fluoro-3-methylphenyl)pyridin-3-yl)imidazo[1,2-a]pyridine-3-carboxamide (Compound 680). LCMS: rt 4.00 min (A), purity 98%, MS (m/e) 444 (MH+)

N-(2-Aminoethyl)-6-(2-(4-fluoro-3-methylphenyl)pyridin-3-yl)imidazo[1,2-a]pyridine-3-carboxamide (Compound 681). $^1$H NMR (300 MHz, DMSO-$d_6$): δ 9.48 (s, 1H), 9.04 (t, J=5.6 Hz, 1H), 8.78 (dd, J=4.9, 0.7 Hz, 1H), 8.56 (s, 1H), 8.27-8.13 (m, 3H), 7.93 (dd, J=7.8, 1.4 Hz, 1H), 7.62 (dd, J=7.8, 4.9 Hz, 1H), 7.44 (d, J=7.5 Hz, 1H), 7.35 (dd, J=9.3, 1.1 Hz, 1H), 7.15-7.04 (m, 1H), 6.98 (t, J=9.1 Hz, 1H), 3.54 (q, J=5.9 Hz, 2H), 3.02 (dd, J=11.6, 5.8 Hz, 2H), 2.16 (s, 3H). LCMS: rt 3.48 min (A), purity 98%, MS (m/e) 390 (MH+)

N-(3-Aminopropyl)-6-(2-(4-fluoro-3-methylphenyl)pyridin-3-yl)imidazo[1,2-a]pyridine-3-carboxamide (Compound 682). LCMS: rt 3.53 min (A), purity 98%, MS (m/e) 404 (MH+)

N-(2-Aminoethyl)-5-(2-(4-fluoro-3-methylphenyl)pyridin-3-yl)pyrazolo[1,5-a]pyridine-3-carboxamide (Compound 683). LCMS: rt 3.88 min (A), purity 98%, MS (m/e) 390 (MH+)

N-(3-Aminopropyl)-5-(2-(4-fluoro-3-methylphenyl)pyridin-3-yl)pyrazolo[1,5-a]pyridine-3-carboxamide (Compound 684). LCMS: rt 3.93 min (A), purity 98%, MS (m/e) 404 (MH+)

Methyl 6-(2-(4-fluoro-3-methylphenyl)pyridin-3-yl)imidazo[1,2-a]pyridine-3-carboxylate (Compound 685). $^1$H NMR (300 MHz, DMSO-$d_6$): δ 9.16 (s, 1H), 8.72 (dd, J=4.7, 1.4 Hz, 1H), 8.31 (s, 1H), 7.97 (dd, J=7.7, 1.5 Hz, 1H), 7.68 (d, J=9.2 Hz, 1H), 7.53 (dd, J=7.8, 4.7 Hz, 1H), 7.43 (dd, J=7.6, 1.9 Hz, 1H), 7.18 (dd, J=9.2, 1.6 Hz, 1H), 7.12-7.01 (m, 1H), 6.97 (t, J=9.1 Hz, 1H), 3.87 (s, 3H), 2.16 (s, 3H). LCMS: rt 5.08 min (A), purity 96%, MS (m/e) 362 (MH+).

6-(2-(3-Chloro-4-fluorophenyl)pyridin-3-yl)benzo[d]thiazole (Compound 686). $^1$H NMR (300 MHz, DMSO-$d_6$): δ 9.40 (d, J=0.7 Hz, 1H), 8.70 (dd, J=4.7, 1.6 Hz, 1H), 8.13 (dd, J=1.8, 0.6 Hz, 1H), 7.99 (dd, J=8.4, 0.7 Hz, 1H), 7.93 (dd, J=7.7, 1.7 Hz, 1H), 7.60-7.47 (m, 2H), 7.27 (dd, J=8.5, 1.8 Hz, 1H), 7.22 (d, J=9.3 Hz, 1H), 7.13 (ddd, J=8.6, 4.9, 2.2 Hz, 1H). $^{19}$F NMR (282 MHz, DMSO-$d_6$): δ −117.36 (td, J=8.5, 8.0, 5.0 Hz). LCMS: rt 6.37 min (A), purity 99%, MS (m/e) 341 (MH+)

6-(2-(3-Chloro-4-fluorophenyl)pyridin-3-yl)imidazo[1,2-a]pyridine (Compound 687). LCMS: rt 4.53 min (A), purity 99%, MS (m/e) 324 (MH$^+$)

6-(2-(3-Chloro-4-fluorophenyl)pyridin-3-yl)quinoline (Compound 688). LCMS: rt 5.03 min (A), purity 99%, MS (m/e) 335 (MH$^+$)

6-(2-(3-Chloro-4-fluorophenyl)pyridin-3-yl)imidazo[1,2-a]pyridine-3-carbonitrile (Compound 689). $^1$H NMR (300 MHz, DMSO-d$_6$): δ 8.74 (ddd, J=4.8, 1.7, 0.8 Hz, 1H), 8.69 (dt, J=1.8, 0.9 Hz, 1H), 8.47 (d, J=0.8 Hz, 1H), 8.09 (ddd, J=7.7, 1.7, 0.8 Hz, 1H), 7.76-7.64 (m, 2H), 7.57 (ddd, J=7.8, 4.8, 0.8 Hz, 1H), 7.34-7.25 (m, 2H), 7.13 (ddd, J=9.3, 1.8, 0.8 Hz, 1H). $^{19}$F NMR (282 MHz, DMSO-d$_6$): δ −116.87 (q, J=7.8 Hz). LCMS: rt 6.58 min (A), purity 99%, MS (m/e) 349 (MH$^+$)

6-(2-(3-Chloro-4-fluorophenyl)pyridin-3-yl)quinoxaline (Compound 690). LCMS: rt 6.48 min (A), purity 99%, MS (m/e) 336 (MH$^+$)

2-(2-(3-Chloro-4-fluorophenyl)pyridin-3-yl)-1,5-naphthyridine (Compound 691). LCMS: rt 6.23 min (A), purity 99%, MS (m/e) 336 (MH$^+$).

6-(2-(3-Chloro-4-fluorophenyl)pyridin-3-yl)-[1,2,4]triazolo[1,5-a]pyridine (Compound 692). $^1$H NMR (300 MHz, DMSO-d$_6$): δ 9.05 (dd, J=1.8, 0.9 Hz, 1H), 8.74 (dd, J=4.8, 1.7 Hz, 1H), 8.52 (s, 1H), 8.03 (dd, J=7.8, 1.7 Hz, 1H), 7.73 (dd, J=9.2, 0.9 Hz, 1H), 7.67 (ddd, J=7.3, 1.9, 0.6 Hz, 1H), 7.56 (dd, J=7.8, 4.8 Hz, 1H), 7.32-7.23 (m, 3H). LCMS: rt 5.80 min (A), purity 99%, MS (m/e) 325 (MH$^+$).

6-(2-(2,4,5-Trifluorophenyl)pyridin-3-yl)benzo[d]thiazole (Compound 693). $^1$H NMR (300 MHz, DMSO-d$_6$): δ 9.00 (dd, J=4.3, 1.8 Hz, 1H), 8.85-8.76 (m, 1H), 8.39 (d, J=8.7 Hz, 1H), 8.31 (d, J=8.9 Hz, 1H), 8.18 (ddd, J=7.8, 1.7, 0.6 Hz, 1H), 7.80 (dd, J=8.5, 4.2 Hz, 1H), 7.66-7.56 (m, 2H), 7.53 (d, J=8.7 Hz, 1H), 7.24 (t, J=9.0 Hz, 1H), 7.10 (ddd, J=8.7, 4.9, 2.3 Hz, 1H). $^{19}$F NMR (282 MHz, DMSO-d$_6$): δ −116.93 (td, J=8.1, 5.5 Hz). LCMS: rt 7.16 min (A), purity 99%, MS (m/e) 343 (MH$^+$).

6-(2-(2,4,5-Trifluorophenyl)pyridin-3-yl)imidazo[1,2-a]pyridine (Compound 694). LCMS: rt 4.41 min (A), purity 99%, MS (m/e) 326 (MH$^+$).

6-(2-(2,4,5-Trifluorophenyl)pyridin-3-yl)imidazo[1,2-a]pyridine-3-carbonitrile (Compound 695). LCMS: rt 6.61 min (A), purity 99%, MS (m/e) 351 (MH$^+$).

6-(2-(2,4,5-Trifluorophenyl)pyridin-3-yl)quinoline (Compound 696). LCMS: rt 5.06 min (A), purity 99%, MS (m/e) 337 (MH$^+$).

6-(2-(3-Chlorophenyl)pyridin-3-yl)imidazo[1,2-a]pyridine-3-carbonitrile (Compound 697). $^1$H NMR (300 MHz, DMSO-d$_6$): δ 8.75 (dd, J=4.8, 1.7 Hz, 1H), 8.68 (dd, J=1.8, 1.0 Hz, 1H), 8.46 (s, 1H), 8.09 (dd, J=7.8, 1.7 Hz, 1H) 7.67 (dd, J=9.3, 1.0 Hz, 1H),), 7.58-7.55 (app m, 2H), 7.44-7.30 (m, 1H), 7.25 (appd, J=4.8 Hz, 1H), 7.12 (dd, J=9.3, 1.8 Hz, 1H). LCMS: rt 6.15 min (A), purity 99%, MS (m/e) 331 (MH$^+$).

6-(2-(3-Chlorophenyl)pyridin-3-yl)imidazo[1,2-a]pyridine (Compound 698). LCMS: rt 4.16 min (A), purity 99%, MS (m/e) 306 (MH$^+$).

6-(2-(3-Chlorophenyl)pyridin-3-yl)quinolone (Compound 699). LCMS: rt 4.65 min (A), purity 99%, MS (m/e) 317 (MH$^+$).

6-(2-(4-Fluoro-3-methylphenyl)pyridin-3-yl)-N-(1-isopropylpiperidin-4-yl)imidazo[1,2-a]pyridine-3-carboxamide (Compound 700). $^1$H NMR (300 MHz, DMSO-d$_6$): δ 9.46 (s, 1H), 8.70 (d, J=4.2 Hz, 1H), 8.35 (s, 1H), 8.26 (d, J=8.3 Hz, 1H), 7.93 (d, J=7.8 Hz, 1H), 7.62-7.36 (m, 3H), 7.14-6.84 (m, 3H), 3.77-3.70 (m, 1H), 2.82 (d, J=10.0 Hz, 2H), 2.72 (dt, J=14.0, 7.0 Hz, 1H), 2.15 (s, 4H), 1.81 (d, J=11.4 Hz, 2H), 1.66-1.35 (m, 2H), 0.97 (d, J=6.5 Hz, 6H). LCMS: rt 3.21 min (B), purity 99%, MS (m/e) 472 (MH$^+$)

5-(2-(4-Fluoro-3-methylphenyl)pyridin-3-yl)-N-(1-isopropylpiperidin-4-yl)pyrazolo[1,5-a]pyridine-3-carboxamide (Compound 701). LCMS: rt 3.53 min (B), purity 99%, MS (m/e) 472 (MH$^+$)

6-(2-(4-Fluoro-3-methylphenyl)pyridin-3-yl)-N-(1,2,2,6,6-pentamethylpiperidin-4-yl)imidazo[1,2-a]pyridine-3-carboxamide (Compound 702). LCMS: rt 2.90 min (A), purity 99%, MS (m/e) 500 (MH$^+$).

5-(2-(4-Fluoro-3-methylphenyl)pyridin-3-yl)-N-(1,2,2,6,6-pentamethylpiperidin-4-yl)pyrazolo[1,5-a]pyridine-3-carboxamide (Compound 703). $^1$H NMR (300 MHz, DMSO-d$_6$): δ 8.71 (dd, J=4.9, 1.7 Hz, 1H), 8.59 (d, J=7.3 Hz, 1H), 8.56 (s, 1H), 8.21 (s, 1H), 7.93 (t, J=8.2 Hz, 2H), 7.51 (dd, J=7.8, 4.7 Hz, 1H), 7.44 (d, J=7.6 Hz, 1H), 7.14-6.89 (m, 2H), 6.57 (dd, J=7.3, 2.1 Hz, 1H), 4.37-3.93 (m, 1H), 2.18 (s, 6H), 1.71 (dd, J=12.7, 3.4 Hz, 2H), 1.39 (t, J=12.3 Hz, 2H), 1.08 (s, 6H), 1.02 (s, 6H). LCMS: rt 3.16 min (A), purity 99%, MS (m/e) 500 (MH$^+$).

6-(2-(4-Fluoro-3-methylphenyl)pyridin-3-yl)-N-(3-hydroxypropyl)imidazo[1,2-a]pyridine-3-carboxamide (Compound 704). $^1$H NMR (300 MHz, DMSO-d$_6$): δ 9.48 (dd, J=1.9, 1.0 Hz, 1H), 8.70 (dd, J=4.7, 1.6 Hz, 1H), 8.47 (t, J=5.7 Hz, 1H), 8.31 (s, 1H), 7.93 (dd, J=7.8, 1.6 Hz, 1H), 7.60-7.46 (m, 2H), 7.43 (dd, J=7.9, 1.8 Hz, 1H), 7.13-6.87 (m, 3H), 4.54-4.33 (app m, 1H), 3.46 (q, J=5.8 Hz, 2H), 3.39-3.29 (m, 2H), 2.16 (s, 3H), 1.81-1.55 (m, 2H). $^{19}$F NMR (282 MHz, DMSO-d$_6$): δ −118.29. LCMS: rt 3.95 min (A), purity 99%, MS (m/e) 405 (MH$^+$)

6-(2-(4-Fluoro-3-methylphenyl)pyridin-3-yl)-N-(2-hydroxyethyl)imidazo[1,2-a]pyridine-3-carboxamide (Compound 705). LCMS: rt 3.85 min (A), purity 99%, MS (m/e) 391 (MH$^+$).

5-(2-(4-Fluoro-3-methylphenyl)pyridin-3-yl)-N-(3-hydroxypropyl)pyrazolo[1,5-a]pyridine-3-carboxamide (Compound 706). $^1$H NMR (300 MHz, DMSO-d$_6$): δ 8.71 (ddd, J=4.8, 1.7, 0.6 Hz, 1H), 8.60 (d, J=7.2 Hz, 1H), 8.52 (s, 1H), 8.25-8.07 (m, 2H), 7.94 (dd, J=7.8, 1.7 Hz, 1H), 7.51 (dd, J=7.8, 4.8 Hz, 1H), 7.45 (dd, J=7.5, 1.9 Hz, 1H), 7.06 (ddd, J=7.6, 5.2, 2.3 Hz, 1H), 7.02-6.92 (app m, 1H), 6.57 (dd, J=7.2, 2.0 Hz, 1H), 4.46 (t, J=5.2 Hz, 1H), 3.45 (q, J=6.1 Hz, 2H), 3.28-3.25 (q, J=6.1 Hz, 2H), 2.17 (s, 3H), 1.67 (q, J=6.7 Hz, 2H). $^{19}$F NMR (282 MHz, DMSO-d$_6$): δ −118.29 (s). LCMS: rt 4.50 min (A), purity 99%, MS (m/e) 405 (MH$^+$).

5-(2-(4-Fluoro-3-methylphenyl)pyridin-3-yl)-N-(2-hydroxyethyl)pyrazolo[1,5-a]pyridine-3-carboxamide (Compound 707). LCMS: rt 4.35 min (A), purity 99%, MS (m/e) 391 (MH$^+$).

6-(2-(3-Chlorophenyl)pyridin-3-yl)-N-(1-methylpiperidin-4-yl)imidazo[1,2-a]pyridine-3-carboxamide (Compound 708). $^1$H NMR (300 MHz, DMSO-d$_6$): δ 9.48 (dd, J=1.9, 0.9 Hz, 1H), 8.74 (dd, J=4.8, 1.6 Hz, 1H), 8.36 (s, 1H), 8.27 (d, J=7.8 Hz, 1H), 7.97 (dd, J=7.8, 1.7 Hz, 1H), 7.62-7.52 (m, 2H), 7.49 (ddd, J=2.2, 1.5, 0.7 Hz, 1H), 7.35 (dt, J=7.5, 2.0 Hz, 1H), 7.31-7.14 (m, 2H), 7.05 (ddd, J=9.3, 1.9, 0.6 Hz, 1H), 3.84-3.61 (m, 1H), 2.76 (d, J=12.8 Hz, 2H), 2.15 (s, 3H), 2.04-1.86 (m, 2H), 1.77 (d, J=11.1 Hz, 2H), 1.67-1.45 (m, 2H). LCMS: rt 3.96 min (A), purity 99%, MS (m/e) 446 (MH$^+$).

6-(2-(3-Chloro-4-fluorophenyl)pyridin-3-yl)-N-(1-methylpiperidin-4-yl)imidazo[1,2-a]pyridine-3-carboxamide (Compound 709). LCMS: rt 4.21 min (A), purity 99%, MS (m/e) 464 MH$^+$).

N-(1-Methylpiperidin-4-yl)-6-(2-(2,4,5-Trifluorophenyl)pyridin-3-yl)imidazo[1,2-a]pyridine-3-carboxamide (Compound 710). LCMS: rt 4.10 min (A), purity 99%, MS (m/e) 466 (MH+).

rac-6-(2-(4-Fluoro-3-methylphenyl)pyridin-3-yl)-N-(8-methyl-8-azabicyclo[3.2.1]octan-3-yl)imidazo[1,2-a]pyridine-3-carboxamide (Compound 711). LCMS: rt 2.66 min (B), purity 99%, MS (m/e) 470 (MH+).

exo-6-(2-(4-Fluoro-3-methylphenyl)pyridin-3-yl)-N-(8-methyl-8-azabicyclo[3.2.1]octan-3-yl)imidazo[1,2-a]pyridine-3-carboxamide (Compound 712). LCMS: rt 2.73 min (B), purity 99%, MS (m/e) 470 (MH+).

endo-6-(2-(4-Fluoro-3-methylphenyl)pyridin-3-yl)-N-(8-methyl-8-azabicyclo[3.2.1]octan-3-yl)imidazo[1,2-a]pyridine-3-carboxamide (Compound 713). LCMS: rt 2.67 min (B), purity 99%, MS (m/e) 470 (MH+).

rac-5-(2-(4-Fluoro-3-methylphenyl)pyridin-3-yl)-N-(8-methyl-8-azabicyclo[3.2.1]octan-3-yl)pyrazolo[1,5-a]pyridine-3-carboxamide (Compound 714). LCMS: rt 3.42 min (B), purity 99%, MS (m/e) 470 (MH+).

exo-5-(2-(4-Fluoro-3-methylphenyl)pyridin-3-yl)-N-(8-methyl-8-azabicyclo[3.2.1]octan-3-yl)pyrazolo[1,5-a]pyridine-3-carboxamide (Compound 715). LCMS: rt 3.44 min (B), purity 99%, MS (m/e) 470 (MH+).

endo-5-(2-(4-Fluoro-3-methylphenyl)pyridin-3-yl)-N-(8-methyl-8-azabicyclo[3.2.1]octan-3-yl)pyrazolo[1,5-a]pyridine-3-carboxamide (Compound 716). LCMS: rt 3.46 min (B), purity 99%, MS (m/e) 470 (MH+).

6-(2-(5-Chloro-2-fluorophenyl)pyridin-3-yl)benzo[d]thiazole (Compound 717). $^1$H NMR (300 MHz, DMSO-$d_6$): δ 9.38 (s, 1H), 8.72 (dd, J=4.8, 1.7 Hz, 1H), 8.09 (dd, J=1.8, 0.6 Hz, 1H), 8.02-7.89 (m, 2H), 7.66-7.54 (m, 2H), 7.40 (ddd, J=8.8, 4.3, 2.8 Hz, 1H), 7.27 (dd, J=8.5, 1.8 Hz, 1H), 7.03 (appt, J=8.8 Hz, 1H). $^{19}$F NMR (282 MHz, DMSO-$d_6$): δ −118.29 (s). LCMS: rt 7.31 min (A), purity 99%, MS (m/e) 341 (MH+).

6-(2-(5-Chloro-2,4-difluorophenyl)pyridin-3-yl)benzo[d]thiazole (Compound 718). $^1$H NMR (300 MHz, DMSO-$d_6$): δ 9.38 (d, J=0.6 Hz, 1H), 8.73 (ddd, J=4.8, 1.7, 0.6 Hz, 1H), 8.11 (dd, J=1.8, 0.6 Hz, 1H), 8.03-7.95 (m, 2H), 7.80 (dd, J=8.4, 7.4 Hz, 1H), 7.61 (dd, J=7.8, 4.8 Hz, 1H), 7.33 (app t, J=9.2 Hz, 1H, 7.28 (dd, J=9.1 Hz, 1H), 7.38-7.24 (m, 2H). $^{19}$F NMR (282 MHz, DMSO-$d_6$): δ −111.43 (q, J=8.7 Hz), −111.62 (t, J=8.9 Hz). LCMS: rt7.66 min (A), purity 99%, MS (m/e) 359 (MH+).

6-(2-(5-Chloro-2-fluorophenyl)pyridin-3-yl)imidazo[1,2-a]pyridine-3-carbonitrile (Compound 719). LCMS: rt 6.76 min (A), purity 99%, MS (m/e) 349 (MH+).

6-(2-(5-Chloro-2,4-difluorophenyl)pyridin-3-yl)imidazo[1,2-a]pyridine-3-carbonitrile (Compound 720). LCMS: rt 7.08 min (A), purity 99%, MS (m/e) 367 (MH+).

6-(2-(5-Chloro-2-fluorophenyl)pyridin-3-yl)imidazo[1,2-a]pyridine (Compound 721). LCMS: rt 4.61 min (A), purity 99%, MS (m/e) 324 (MH+).

6-(2-(5-Chloro-2-fluorophenyl)pyridin-3-yl)-N-(1-methylpiperidin-4-yl)imidazo[1,2-a]pyridine-3-carboxamide (Compound 722). LCMS: rt 4.23 min (A), purity 99%, MS (m/e) 464 (MH+).

6-(2-(5-Chloro-2,4-difluorophenyl)pyridin-3-yl)-N-(1-methylpiperidin-4-yl)imidazo[1,2-a]pyridine-3-carboxamide (Compound 723). $^1$H NMR (300 MHz, DMSO-$d_6$): δ 9.39 (s, 1H), 8.75 (dd, J=4.6, 1.4 Hz, 1H), 8.33 (s, 1H), 8.25 (d, J=7.8 Hz, 1H), 8.04 (dd, J=7.8, 1.5 Hz, 1H), 7.83 (t, J=7.8 Hz, 1H), 7.72-7.54 (m, 2H), 7.38 (t, J=9.7 Hz, 1H), 7.20 (dd, J=9.3, 1.6 Hz, 1H), 3.92-3.60 (m, 1H), 2.82 (d, J=13.8 Hz, 2H), 2.21 (s, 3H), 2.03 (t, J=10.9 Hz, 2H), 1.79 (d, J=13.1 Hz, 2H), 1.69-1.40 (m, 2H). $^{19}$F NMR (282 MHz, DMSO-$d_6$): δ −111.36 (q, J=9.1 Hz), −112.11 (q, J=8.7 Hz). LCMS: rt 4.43 min (A), purity 99%, MS (m/e) 482 (MH+).

N-(3-(2-oxopyrrolidin-1-yl)propyl)-6-(2-(m-tolyl)pyridin-3-yl)imidazo[1,2-a]pyridine-3-carboxamide (Compound 724). LCMS: rt 4.08 min (A), purity 99%, MS (m/e) 454 (MH+).

6-(2-(2-Fluoro-5-methylphenyl)pyridin-3-yl)-N-(3-(2-oxopyrrolidin-1-yl)propyl)imidazo[1,2-a]pyridine-3-carboxamide (Compound 725). LCMS: rt 4.58 min (A), purity 99%, MS (m/e) 472 (MH+).

6-(2-(3-Chlorophenyl)pyridin-3-yl)-N-(3-(2-oxopyrrolidin-1-yl)propyl)imidazo[1,2-a]pyridine-3-carboxamide (Compound 726). LCMS: rt 4.73 min (A), purity 99%, MS (m/e) 474 (MH+).

6-(2-(3-Chloro-4-fluorophenyl)pyridin-3-yl)-N-(3-(2-oxopyrrolidin-1-yl)propyl)imidazo[1,2-a]pyridine-3-carboxamide (Compound 727). LCMS: rt 5.00 min (A), purity 99%, MS (m/e) 492 (MH+).

N-(3-(2-oxopyrrolidin-1-yl)propyl)-6-(2-(2,4,5-Trifluorophenyl)pyridin-3-yl)imidazo[1,2-a]pyridine-3-carboxamide (Compound 728). LCMS: rt 4.95 min (A), purity 99%, MS (m/e) 494 (MH+).

6-(2-(5-Chloro-2-fluorophenyl)pyridin-3-yl)-N-(3-(2-oxopyrrolidin-1-yl)propyl)imidazo[1,2-a]pyridine-3-carboxamide (Compound 729). $^1$H NMR (300 MHz, DMSO-$d_6$): δ 9.48 (s, 1H), 8.78 (dd, J=4.8, 1.6 Hz, 1H), 8.63 (t, J=5.5 Hz, 1H), 8.43 (s, 1H), 8.05 (dd, J=7.8, 1.6 Hz, 1H), 7.74 (d, J=9.3 Hz, 1H), 7.70-7.56 (m, 2H), 7.50-7.31 (m, 2H), 7.08 (t, J=9.2 Hz, 1H), 3.34 (t, J=7.0 Hz, 2H), 3.22 (t, J=7.0 Hz, 4H), 2.20 (t, J=8.0 Hz, 2H), 1.91 (p, J=7.5 Hz, 2H), 1.71 (p, J=7.2 Hz, 2H). $^{19}$F NMR (282 MHz, DMSO-$d_6$): δ −117.76 (ddd, J=10.0, 5.9, 4.2 Hz). LCMS: rt5.03 min (A), purity 99%, MS (m/e) 492 (MH+).

6-(2-(5-Chloro-2,4-difluorophenyl)pyridin-3-yl)-N-(3-(2-oxopyrrolidin-1-yl)propyl)imidazo[1,2-a]pyridine-3-carboxamide (Compound 730). LCMS: rt 5.25 min (A), purity 99%, MS (m/e) 510 (MH+).

7-(2-(2-Fluoro-5-methylphenyl)pyridin-3-yl)-[1,2,4]triazolo[1,5-a]pyridine (Compound 731). LCMS: rt 4.85 min (A), purity 99%, MS (m/e) 305 (MH+).

7-(2-(m-Tolyl)pyridin-3-yl)-[1,2,4]triazolo[1,5-a]pyridine (Compound 732). LCMS: rt 4.40 min (A), purity 99%, MS (m/e) 287 (MH+).

7-(2-(3-Chloro-4-fluorophenyl)pyridin-3-yl)-[1,2,4]triazolo[1,5-a]pyridine (Compound 733). LCMS: rt 5.88 min (A), purity 99%, MS (m/e) 325 (MH+).

7-(2-(3-Chlorophenyl)pyridin-3-yl)-[1,2,4]triazolo[1,5-a]pyridine (Compound 734). LCMS: rt 5.43 min (A), purity 99%, MS (m/e) 307 (MH+).

7-(2-(5-Chloro-2,4-difluorophenyl)pyridin-3-yl)-[1,2,4]triazolo[1,5-a]pyridine (Compound 735). LCMS: rt 6.41 min (A), purity 99%, MS (m/e) 343 (MH+).

7-(2-(5-Chloro-2-fluorophenyl)pyridin-3-yl)-[1,2,4]triazolo[1,5-a]pyridine (Compound 736). $^1$H NMR (300 MHz, DMSO-$d_6$): δ 8.88 (dd, J=7.1, 0.9 Hz, 1H), 8.78 (dd, J=4.8, 1.6 Hz, 1H), 8.49 (s, 1H), 8.07 (dd, J=7.9, 1.6 Hz, 1H), 7.74 (dd, J=1.9, 0.9 Hz, 1H), 7.68 (dd, J=6.2, 2.8 Hz, 1H), 7.64 (dd, J=7.9, 4.8 Hz, 1H), 7.46 (ddd, J=8.8, 4.4, 2.8 Hz, 1H), 7.09 (dd, J=9.6, 8.9 Hz, 1H), 6.97 (dd, J=7.1, 1.9 Hz, 1H). LCMS: rt 6.10 min (A), purity 99%, MS (m/e) MH+ 325.

7-(2-(2-Fluoro-5-methylphenyl)pyridin-3-yl)-[1,2,4]triazolo[1,5-a]pyridine (Compound 737). LCMS: rt min (A), purity 99%, MS (m/e) 305 MH+.

6-(2-(4-Fluoro-3-methylphenyl)pyridin-3-yl)pyrido[2,3-b]pyrazine (Compound 738). LCMS: rt 5.06 min (A), purity 99%, MS (m/e) 317 MH+.

6-(2-(3-Chlorophenyl)pyridin-3-yl)pyrido[2,3-b]pyrazine (Compound 739). LCMS: rt 5.63 min (A), purity 99%, MS (m/e) 319 MH$^+$.

6-(2-(3-Chloro-4-fluorophenyl)pyridin-3-yl)pyrido[2,3-b]pyrazine (Compound 740). LCMS: rt 6.06 min (A), purity 99%, MS (m/e) 337 MH$^+$.

6-(2-(2,4,5-Trifluorophenyl)pyridin-3-yl)pyrido[2,3-b]pyrazine (Compound 741). LCMS: rt 6.03 min (A), purity 99%, MS (m/e) 339 MH$^+$.

6-(2-(5-Chloro-2-fluorophenyl)pyridin-3-yl)pyrido[2,3-b]pyrazine (Compound 742). LCMS: rt 6.20 min (A), purity 99%, MS (m/e) 337 MH$^+$.

6-(2-(5-Chloro-2,4-difluorophenyl)pyridin-3-yl)pyrido[2,3-b]pyrazine (Compound 743). LCMS: rt 6.56 min (A), purity 99%, MS (m/e) 355 MH$^+$.

N-((7R,8aS)-5,5-Dimethyloctahydroindolizin-7-yl)-6-(2-(4-fluoro-3-methylphenyl)pyridin-3-yl)imidazo[1,2-a]pyridine-3-carboxamide (Compound 744). LCMS: rt 4.06 min (A), purity 99%, MS (m/e) 498 MH$^+$.

N-((7R,8aS)-5,5-Dimethyloctahydroindolizin-7-yl)-5-(2-(4-difluoro-3-methylphenyl)pyridin-3-yl)pyrazolo[1,5-a]pyridine-3-carboxamide (Compound 745). $^1$H NMR (300 MHz, DMSO-d$_6$): δ 8.71 (dd, J=4.8, 1.7 Hz, 1H), 8.61-8.57 (m, 1H), 8.55 (s, 1H), 8.18 (dd, J=2.1, 0.9 Hz, 1H), 8.02-7.79 (m, 2H), 7.52 (dd, J=7.8, 4.8 Hz, 1H), 7.45 (dd, J=8.0, 2.3 Hz, 1H), 7.13-6.87 (m, 2H), 6.58 (dd, J=7.2, 2.1 Hz, 1H), 4.18-3.89 (m, 1H), 2.84 (td, J=8.5, 3.3 Hz, 1H), 2.44-2.35 (m, 2H), 2.28 (q, J=8.5 Hz, 1H), 2.17 (s, 3H), 1.95 (d, J=11.7 Hz, 1H), 1.87-1.71 (m, 1H), 1.69-1.54 (m, 3H), 1.46-1.26 (m, 2H), 1.08 (s, 3H), 0.95 (s, 3H). $^{19}$F NMR (282 MHz, DMSO-d$_6$): δ −118.10. LCMS: rt 4.45 min (A), purity 99%, MS (m/e) 498 MH$^+$.

6-(2-(3-Chlorophenyl)pyridin-3-yl)-[1,2,4]triazolo[1,5-a]pyridine (Compound 746). LCMS: rt 5.40 min (A), purity 99%, MS (m/e) 307 MH$^+$.

6-(2-(5-Chloro-2-fluorophenyl)pyridin-3-yl)-[1,2,4]triazolo[1,5-a]pyridine (Compound 747). LCMS: rt 6.10 min (A), purity 99%, MS (m/e) 325 MH$^+$.

6-(2-(2-Fluoro-5-methylphenyl)pyridin-3-yl)-[1,2,4]triazolo[1,5-a]pyridine (Compound 748). LCMS: rt 5.21 min (A), purity 99%, MS (m/e) 305 MH$^+$.

6-(2-(5-Chloro-2,4-difluorophenyl)pyridin-3-yl)-[1,2,4]triazolo[1,5-a]pyridine (Compound 749). $^1$H NMR (300 MHz, DMSO-d$_6$): δ 9.01 (dd, J=1.8, 1.0 Hz, 1H), 8.77 (dd, J=4.8, 1.6 Hz, 1H), 8.50 (s, 1H), 8.08 (dd, J=7.8, 1.6 Hz, 1H), 7.86 (dd, J=8.5, 7.4 Hz, 1H), 7.76 (dd, J=9.2, 0.9 Hz, 1H), 7.64 (dd, J=7.8, 4.8 Hz, 1H), 7.41 (dd, J=9.1 Hz, 0.9 Hz, 1H)), 7.37 (app t, J=9.3 Hz, 1H). $^{19}$F NMR (282 MHz, DMSO-d$_6$): δ −111.06 (q, J=9.0 Hz), −111.78 (q, J=8.8 Hz). LCMS: rt 6.43 min (A), purity 99%, MS (m/e) 343 MH$^+$.

2-(5-(2-(4-Fluoro-3-methylphenyl)pyridin-3-yl)-1H-indazol-1-yl)acetamide (Compound 750). $^1$H NMR (300 MHz, DMSO-d$_6$): δ 8.63 (dd, J=4.7, 1.7 Hz, 1H), 8.04 (d, J=1.0 Hz, 1H), 7.84 (dd, J=7.8, 1.8 Hz, 1H), 7.65 (s, 1H), 7.59-7.51 (m, 1H), 7.50-7.43 (m, 2H), 7.38 (dd, J=8.0, 2.2 Hz, 1H), 7.20 (br s, 1H), 7.06 (dd, J=8.7, 1.7 Hz, 1H), 6.99-6.82 (m, 2H), 5.02 (s, 2H), 2.13 (s, 3H). $^{19}$F NMR (282 MHz, DMSO-d$_6$): δ −118.90 (s). LCMS: r 4.33 min (A), purity 99%, MS (m/e) 361 MH$^+$.

2-(5-(2-(4-Fluoro-3-methylphenyl)pyridin-3-yl)-2H-indazol-2-yl)acetamide (Compound 751). $^1$H NMR (300 MHz, DMSO-d$_6$): δ 8.63 (dd, J=4.7, 1.6 Hz, 1H), 8.33 (d, J=0.9 Hz, 1H), 7.83 (dd, J=7.7, 1.7 Hz, 1H), 7.72-7.61 (m, 2H), 7.48-7.43 (m, 2H), 7.43-7.40 (m, 1H), 7.36-7.29 (m, 1H), 6.98 (ddd, J=7.7, 5.2, 2.1 Hz, 1H), 6.93 (d, J=9.4 Hz, 1H), 6.87 (dd, J=8.9, 1.6 Hz, 1H), 5.07 (s, 2H), 2.15 (s, 3H). LCMS: rt 4.18 min (A), purity 99%, MS (m/e) 361 MH$^+$.

2-(6-(2-(4-Fluoro-3-methylphenyl)pyridin-3-yl)-1H-indazol-1-yl)acetamide (Compound 752). $^1$H NMR (300 MHz, DMSO-d$_6$): δ 8.66 (dd, J=4.7, 1.7 Hz, 1H), 8.03 (d, J=0.9 Hz, 1H), 7.84 (dd, J=7.7, 1.7 Hz, 1H), 7.61 (br s, 1H), 7.59 (dd, J=8.3, 0.8 Hz, 1H), 7.47 (dd, J=7.8, 4.7 Hz, 2H), 7.36 (dd, J=7.8, 2.2 Hz, 1H), 7.16 (br s, 1H), 6.97 (ddd, J=7.5, 5.3, 2.1 Hz, 1H), 6.89 (dd, J=9.6, 8.5 Hz, 1H), 6.76 (dd, J=8.3, 1.4 Hz, 1H), 5.01 (s, 2H), 2.21 (s, 3H). LCMS: rt4.55 min (A), purity 99%, MS (m/e) 361 MH$^+$.

2-(6-(2-(3-Chloro-4-fluorophenyl)pyridin-3-yl)-1H-indazol-1-yl)acetamide (Compound 753). LCMS: rt 5.18 min (A), purity 99%, MS (m/e) 381 MH$^+$.

2-(6-(2-(4-Fluoro-3-methylphenyl)pyridin-3-yl)-2H-indazol-2-yl)acetamide (Compound 754). $^1$H NMR (300 MHz, DMSO-d$_6$): δ 8.65 (dd, J=4.8, 1.6 Hz, 1H), 8.30 (s, 1H), 7.87 (dd, J=7.8, 1.7 Hz, 1H), 7.62 (s, 1H), 7.57 (dd, J=8.6, 0.9 Hz, 1H), 7.52 (q, J=1.1 Hz, 1H), 7.51-7.37 (m, 2H), 7.29 (s, 1H), 7.01 (ddd, J=7.8, 5.2, 2.4 Hz, 1H), 6.91 (dd, J=9.7, 8.5 Hz, 1H), 6.68 (dd, J=8.6, 1.5 Hz, 1H), 5.07 (s, 2H), 2.14 (s 3H). LCMS: rt 4.40 min (A), purity 99%, MS (m/e) 361 MH$^+$.

2-(6-(2-(3-Chloro-4-fluorophenyl)pyridin-3-yl)-2H-indazol-2-yl)acetamide (Compound 755). LCMS: rt 5.01 min (A), purity 99%, MS (m/e) 381 MH$^+$.

5-(2-(4-Fluoro-3-methylphenyl)pyridin-3-yl)pyrazolo[1,5-a]pyridine (Compound 756). LCMS: rt 5.58 min (A), purity 99%, MS (m/e) 304 MH$^+$.

5-(2-(m-Tolyl)pyridin-3-yl)pyrazolo[1,5-a]pyridine (Compound 757). LCMS: rt 5.15 min (A), purity 99%, MS (m/e) 286 MH$^+$.

5-(2-(3-Chloro-4-fluorophenyl)pyridin-3-yl)pyrazolo[1,5-a]pyridine (Compound 758). LCMS: rt 6.71 min (A), purity 99%, MS (m/e) 324 MH$^+$.

5-(2-(3-Chlorophenyl)pyridin-3-yl)pyrazolo[1,5-a]pyridine (Compound 759). LCMS: rt 6.28 min (A), purity 99%, MS (m/e) 306 MH$^+$.

5-(2-(5-Chloro-2,4-difluorophenyl)pyridin-3-yl)pyrazolo[1,5-a]pyridine (Compound 760). LCMS: rt 7.48 min (A), purity 99%, MS (m/e) 342 MH$^+$.

5-(2-(5-Chloro-2-fluorophenyl)pyridin-3-yl)pyrazolo[1,5-a]pyridine (Compound 761). $^1$H NMR (300 MHz, DMSO-d$_6$): δ 8.73 (dd, J=4.8, 1.6 Hz, 1H), 8.56 (dt, J=7.2, 1.0 Hz, 1H), 8.01 (dd, J=7.8, 1.7 Hz, 1H), 7.96 (d, J=2.3 Hz, 1H), 7.65-7.57 (m, 2H), 7.56 (dd, J=2.0, 1.0 Hz, 1H), 7.44 (ddd, J=8.8, 4.4, 2.8 Hz, 1H), 7.10 (dd, J=9.6, 8.9 Hz, 1H), 6.60 (dd, J=7.2, 2.0 Hz, 1H), 6.57 (dd, J=2.3, 0.9 Hz, 1H). $^{19}$F NMR (282 MHz, DMSO-d$_6$): δ −117.44 (dt, J=10.1, 5.4 Hz). LCMS: rt 7.13 min (A), purity 99%, MS (m/e) 324 MH$^+$.

1-(6-(2-(3-Chloro-4-fluorophenyl)pyridin-3-yl)imidazo[1,2-a]pyridin-3-yl)ethan-1-one (Compound 762). LCMS: rt 5.58 min (A), purity 99%, MS (m/e) 366 MH$^+$.

1-(6-(2-(3-Chlorophenyl)pyridin-3-yl)imidazo[1,2-a]pyridin-3-yl)ethan-1-one (Compound 763). LCMS: rt 5.21 min (A), purity 99%, MS (m/e) 348 MH$^+$.

6-(2-(3-Chloro-4-fluorophenyl)pyridin-3-yl)-3-methylimidazo[1,2-a]pyridine (Compound 764). LCMS: rt 4.83 min (A), purity 99%, MS (m/e) 338 MH$^+$.

6-(2-(3-Chlorophenyl)pyridin-3-yl)-3-methylimidazo[1,2-a]pyridine (Compound 765). LCMS: rt 4.46 min (A), purity 99%, MS (m/e) 320 MH$^+$.

6-(2-(5-Chloro-2,4-difluorophenyl)pyridin-3-yl)-3-methylimidazo[1,2-a]pyridine (Compound 766). $^1$H NMR (300 MHz, DMSO-d$_6$): δ 8.73 (dd, J=4.8, 1.6 Hz, 1H), 8.20 (dd, J=1.8, 1.0 Hz, 1H), 8.07 (dd, J=7.8, 1.6 Hz, 1H), 7.82 (dd, J=8.4, 7.4 Hz, 1H), 7.61 (dd, J=7.8, 4.8 Hz, 1H), 7.50-7.28 (m, 3H), 6.91 (dd, J=9.3, 1.8 Hz, 1H), 2.37 (s, 3H).). $^{19}$F NMR (282 MHz, DMSO-d$_6$): δ −111.47 (q, J=9.0 Hz), −111.57 (q, J=8.8 Hz). LCMS: rt 5.10 min (A), purity 99%, MS (m/e) 356 MH⁺.

6-(2-(5-Chloro-2-fluorophenyl)pyridin-3-yl)-3-methylimidazo[1,2-a]pyridine (Compound 767). LCMS: rt 4.86 min (A), purity 99%, MS (m/e) 338 MH⁺.

6-(2-(3-Chloro-4-fluorophenyl)pyridin-3-yl)-1-methyl-1H-benzo[d]imidazole (Compound 768). $^1$H NMR (300 MHz, DMSO-d$_6$): δ 8.67 (dd, J=4.7, 1.7 Hz, 1H), 8.18 (s, 1H), 7.91 (dd, J=7.8, 1.7 Hz, 1H), 7.60-7.46 (m, 4H), 7.28-7.09 (m, 2H), 6.90 (dd, J=8.3, 1.7 Hz, 1H), 3.79 (s, 3H).). $^{19}$F NMR (282 MHz, DMSO-d$_6$): δ −117.66 (s). LCMS: rt 4.48 min (A), purity 99%, MS (m/e) 338 MH⁺.

6-(2-(3-Chlorophenyl)pyridin-3-yl)-1-methyl-1H-benzo[d]imidazole (Compound 769). LCMS: rt 4.10 min (A), purity 99%, MS (m/e) 320 MH⁺.

6-(2-(3-Chloro-5-fluorophenyl)pyridin-3-yl)-[1,2,4]triazolo[1,5-a]pyridine (Compound 770). LCMS: rt 6.23 min (A), purity 99%, MS (m/e) 325 MH⁺.

6-(2-(2,5-Dichlorophenyl)pyridin-3-yl)-[1,2,4]triazolo[1,5-a]pyridine (Compound 771). LCMS: rt 6.30 min (A), purity 99%, MS (m/e) 341 MH⁺.

6-(2-(3-Chloro-2-fluorophenyl)pyridin-3-yl)-[1,2,4]triazolo[1,5-a]pyridine (Compound 772). LCMS: rt 5.91 min (A), purity 99%, MS (m/e) 325 MH⁺.

6-(2-(3-Chloro-2-methylphenyl)pyridin-3-yl)-[1,2,4]triazolo[1,5-a]pyridine (Compound 773). LCMS: rt 5.30 min (A), purity 99%, MS (m/e) 321 MH⁺.

6-(2-(5-Chloro-2-methylphenyl)pyridin-3-yl)-[1,2,4]triazolo[1,5-a]pyridine (Compound 774). LCMS: rt 5.75 min (A), purity 99%, MS (m/e) 321 MH⁺.

6-(2-(3-Chloro-5-methylphenyl)pyridin-3-yl)-[1,2,4]triazolo[1,5-a]pyridine (Compound 775). LCMS: rt 5.36 min (A), purity 99%, MS (m/e) 321 MH⁺.

6-(2-(3,5-Dichlorophenyl)pyridin-3-yl)-[1,2,4]triazolo[1,5-a]pyridine (Compound 776). LCMS: rt 6.80 min (A), purity 99%, MS (m/e) 341 MH⁺.

6-(2-(3,4-Dimethylphenyl)pyridin-3-yl)-[1,2,4]triazolo[1,5-a]pyridine (Compound 777). LCMS: rt 4.63 min (A), purity 99%, MS (m/e) 301 MH⁺.

6-(2-(2,4-Dichlorophenyl)pyridin-3-yl)-[1,2,4]triazolo[1,5-a]pyridine (Compound 778). LCMS: rt 6.21 min (A), purity 99%, MS (m/e) 341 MH⁺.

6-(2-(3-Methoxyphenyl)pyridin-3-yl)-[1,2,4]triazolo[1,5-a]pyridine (Compound 779). $^1$H NMR (300 MHz, DMSO-d$_6$): δ 8.99 (dd, J=1.9, 0.9 Hz, 1H), 8.77 (ddd, J=4.9, 1.7, 0.6 Hz, 1H), 8.50 (s, 1H), 8.11 (dt, J=7.8, 1.4 Hz, 1H), 7.70 (dd, J=9.3, 0.9 Hz, 1H), 7.61 (ddd, J=7.9, 4.9, 0.9 Hz, 1H), 7.29 (ddd, J=9.2, 1.8, 0.6 Hz, 1H), 7.23-7.10 (m, 1H), 7.05-6.96 (m, 1H), 6.92-6.83 (m, 2H), 3.62 (s, 3H). LCMS: rt 4.26 min (A), purity 99%, MS (m/e) 303 MH⁺.

6-(2-(3-(Trifluoromethoxy)phenyl)pyridin-3-yl)-[1,2,4]triazolo[1,5-a]pyridine (Compound 780). LCMS: rt 6.23 min (A), purity 99%, MS (m/e) 357 MH⁺.

6-(2-Phenylpyridin-3-yl)-[1,2,4]triazolo[1,5-a]pyridine (Compound 781). LCMS: rt 3.93 min (A), purity 99%, MS (m/e) 273 MH⁺.

6-(2-(3-Chloro-4-fluorophenyl)pyridin-3-yl)-1H-benzo[d]imidazole (Compound 782). $^1$H NMR (300 MHz, DMSO-d$_6$): δ 8.66 (dd, J=4.7, 1.7 Hz, 1H), 8.36 (s, 1H), 7.88 (dd, J=7.8, 1.7 Hz, 1H), 7.60-7.45 (m, 4H), 7.27-7.10 (m, 2H), 7.01 (dd, J=8.4, 1.7 Hz, 1H). $^{19}$F NMR (282 MHz, DMSO-d$_6$): δ −117.47--117.92 (m). LCMS: rt 4.35 min (A), purity 99%, MS (m/e) 324 MH⁺.

6-(2-(5-Chloro-4-fluorophenyl)pyridin-3-yl)-1H-benzo[d]imidazole (Compound 783). LCMS: rt 4.00 min (A), purity 99%, MS (m/e) 306 MH⁺.

6-(2-(5-Chloro-2,4-difluorophenyl)pyridin-3-yl)-1-methyl-1H-benzo[d]imidazole (Compound 784). $^1$H NMR (300 MHz, DMSO-d$_6$): δ 8.68 (dd, J=4.7, 1.7 Hz, 1H), 8.16 (s, 1H), 7.97 (dd, J=7.8, 1.7 Hz, 1H), 7.74 (dd, J=8.4, 7.3 Hz, 1H), 7.58 (dd, J=7.8, 4.8 Hz, 1H), 7.53-7.45 (m, 2H), 7.29 (t, J=9.6 Hz, 1H), 6.92 (dd, J=8.3, 1.7 Hz, 1H), 3.76 (s, 3H). $^{19}$F NMR (282 MHz, DMSO-d$_6$): δ −111.26 (q, J=8.5 Hz), −112.11 (q, J=8.9 Hz). LCMS: rt 5.05 min (A), purity 99%, MS (m/e) 356 MH⁺.

6-(2-(5-Chloro-2-fluorophenyl)pyridin-3-yl)-1-methyl-1H-benzo[d]imidazole (Compound 785). LCMS: rt 4.78 min (A), purity 99%, MS (m/e) 338 MH⁺.

6-(2-(4-Fluoro-3-methylphenyl)pyridin-3-yl)-1H-indazol-3-amine (Compound 786). $^1$H NMR (300 MHz, DMSO-d$_6$): δ 11.33 (s, 1H), 8.63 (dd, J=4.7, 1.7 Hz, 1H), 7.82 (dd, J=7.7, 1.7 Hz, 1H), 7.56 (dd, J=8.3, 0.8 Hz, 1H), 7.43 (dd, J=7.7, 4.7 Hz, 1H), 7.38 (ddd, J=7.5, 2.2, 1.2 Hz, 1H), 7.05 (dd, J=1.4, 0.8 Hz, 1H), 7.02-6.93 (m, 1H), 6.90 (dd, J=9.7, 8.5 Hz, 1H), 6.63 (dd, J=8.3, 1.4 Hz, 1H), 5.27 (s, 2H), 2.13 (s, 3H). LCMS: rt 4.13 min (A), purity 99%, MS (m/e) 319 MH⁺.

6-(2-(4-Fluoro-3-methylphenyl)pyridin-3-yl)-1-methyl-1H-indazol-3-amine (Compound 787). LCMS: rt 4.63 min (A), purity 99%, MS (m/e) 333 MH⁺.

5-(2-(4-Fluoro-3-methylphenyl)pyridin-3-yl)-1H-indazol-3-amine (Compound 788). LCMS: rt 4.05 min (A), purity 99%, MS (m/e) 319 MH⁺.

5-(2-(4-Fluoro-3-methylphenyl)pyridin-3-yl)-1-methyl-1H-indazol-3-amine (Compound 789). LCMS: rt 4.73 min (A), purity 99%, MS (m/e) 333 MH⁺.

(S)-6-(2-(4-Fluoro-3-methylphenyl)pyridin-3-yl)-N-(quinuclidin-3-yl)imidazo[1,2-a]pyridine-3-carboxamide (Compound 790). LCMS: rt 3.81 min (A), purity 99%, MS (m/e) 456 MH⁺.

(R)-6-(2-(4-Fluoro-3-methylphenyl)pyridin-3-yl)-N-(quinuclidin-3-yl)imidazo[1,2-a]pyridine-3-carboxamide (Compound 791). LCMS: rt 3.81 min (A), purity 99%, MS (m/e) 456 MH⁺.

(S)-5-(2-(4-Fluoro-3-methylphenyl)pyridin-3-yl)-N-(quinuclidin-3-yl)pyrazolo[1,5-a]pyridine-3-carboxamide (Compound 792). LCMS: rt 4.23 min (A), purity 99%, MS (m/e) 456 MH⁺.

(R)-5-(2-(4-Fluoro-3-methylphenyl)pyridin-3-yl)-N-(quinuclidin-3-yl)pyrazolo[1,5-a]pyridine-3-carboxamide (Compound 793). LCMS: rt 4.23 min (A), purity 99%, MS (m/e) 456 MH⁺.

6-(2-(4-Fluoro-3-methylphenyl)pyridin-3-yl)benzo[d]isoxazol-3-amine (Compound 794). $^1$H NMR (300 MHz, DMSO-d$_6$): δ 8.67 (dd, J=4.7, 1.7 Hz, 1H), 7.87 (dd, J=7.8, 1.7 Hz, 1H), 7.68 (d, J=8.1 Hz, 1H), 7.47 (dd, J=7.8, 4.7 Hz, 1H), 7.40-7.25 (m, 2H), 7.02-6.82 (m, 3H), 6.35 (s, 2H), 2.13 (s, 3H). $^{19}$F NMR (282 MHz, DMSO-d$_6$): δ −118.64 (app s). LCMS: rt 5.11 min (A), purity 99%, MS (m/e) 320 MH⁺.

5-(2-(4-Fluoro-3-methylphenyl)pyridin-3-yl)benzo[d]isoxazol-3-amine (Compound 795). LCMS: rt 5.11 min (A), purity 99%, MS (m/e) 320 MH⁺.

5-(2-(3-Chloro-4-fluorophenyl)pyridin-3-yl)benzo[d]isoxazol-3-amine (Compound 796). LCMS: rt 5.98 min (A), purity 99%, MS (m/e) 340 MH⁺.

6-(2-(3-Chloro-4-fluorophenyl)pyridin-3-yl)benzo[d]isoxazol-3-amine (Compound 797). LCMS: rt 6.15 min (A), purity 99%, MS (m/e) 340 MH⁺.

6-(2-(3-Chlorophenyl)pyridin-3-yl)benzo[d]isoxazol-3-amine (Compound 798). LCMS: rt 5.76 min (A), purity 99%, MS (m/e) 321 MH⁺.

5-(2-(3-Chlorophenyl)pyridin-3-yl)benzo[d]isoxazol-3-amine (Compound 799). LCMS: rt 5.53 min (A), purity 99%, MS (m/e) 322 MH+.

6-(2-(3-Chloro-4-fluorophenyl)pyridin-3-yl)-1H-indazol-3-amine (Compound 800). LCMS: rt 4.85 min (A), purity 99%, MS (m/e) 339 MH+.

5-(2-(3-Chloro-4-fluorophenyl)pyridin-3-yl)-1H-indazol-3-amine (Compound 801). LCMS: rt 4.63 min (A), purity 99%, MS (m/e) 339 MH+.

6-(2-(4-Fluoro-3-methylphenyl)pyridin-3-yl)-N-((tetrahydro-1H-pyrrolizin-7a(5H)-yl)methyl)imidazo[1,2-a]pyridine-3-carboxamide (Compound 802). LCMS: rt 4.08 min (A), purity 99%, MS (m/e) 470 MH+.

6-(2-(4-Fluoro-3-methylphenyl)pyridin-3-yl)-N-(2-(tetrahydro-1H-pyrrolizin-7a(5H)-yl)ethyl)imidazo[1,2-a]pyridine-3-carboxamide (Compound 803). LCMS: rt 3.98 min (A), purity 99%, MS (m/e) 484 MH+.

5-(2-(4-Fluoro-3-methylphenyl)pyridin-3-yl)-N-((tetrahydro-1H-pyrrolizin-7a(5H)-yl)methyl)pyrazolo[1,5-a]pyridine-3-carboxamide (Compound 804). LCMS: rt 4.53 min (A), purity 99%, MS (m/e) 470 MH+.

5-(2-(4-Fluoro-3-methylphenyl)pyridin-3-yl)-N-(2-(tetrahydro-1H-pyrrolizin-7a(5H)-yl)ethyl)pyrazolo[1,5-a]pyridine-3-carboxamide (Compound 805). LCMS: rt 4.38 min (A), purity 99%, MS (m/e) 484 MH+.

6-(2-(4-Fluoro-3-methylphenyl)pyridin-3-yl)pyrido[2,3-d]pyrimidin-4-amine (Compound 806). $^1$H NMR (300 MHz, DMSO-$d_6$): δ 8.73 (app dd, J=4.8, 1.9 Hz, 2H), 8.53 (app d, J=2.7 Hz, 2H), 8.15 (s, 2H), 7.99 (dd, J=7.8, 1.7 Hz, 1H), 7.56 (dd, J=7.8, 4.8 Hz, 1H), 7.39 (ddt, J=7.7, 2.1, 1.0 Hz, 1H), 6.99-6.93 (m, 2H), 2.16 (s, 3H). $^{19}$F NMR (282 MHz, DMSO-$d_6$): δ −118.12 (dd, J=9.1, 6.4 Hz). LCMS: rt 3.76 min (A), purity 99%, MS (m/e) 332 MH+.

6-(2-(3-Chloro-4-fluorophenyl)pyridin-3-yl)pyrido[2,3-d]pyrimidin-4-amine (Compound 807). LCMS: rt 4.41 min (A), purity 99%, MS (m/e) 352 MH+.

6-(2-(4-Fluoro-3-methylphenyl)pyridin-3-yl)-7-methylimidazo[1,2-a]pyridine (Compound 808). $^1$H NMR (300 MHz, DMSO-$d_6$): δ 8.87 (s, 1H), 8.80 (dd, J=4.8, 1.7 Hz, 1H), 8.21 (dd, J=2.1, 0.7 Hz, 1H), 8.14 (d, J=2.1 Hz, 1H), 7.86 (dd, J=7.7, 1.7 Hz, 1H), 7.77 (q, J=1.0 Hz, 1H), 7.56 (dd, J=7.7, 4.8 Hz, 1H), 7.45 (ddd, J=7.6, 2.4, 1.0 Hz, 1H), 7.06 (ddd, J=7.8, 5.0, 2.3 Hz, 1H), 6.94 (dd, J=9.6, 8.5 Hz, 1H), 2.14 (s, 3H), 1.96 (app s, 3H). $^{19}$F NMR (282 MHz, DMSO-$d_6$): δ −117.60 (app s). LCMS: rt 4.23 min (A), purity 99%, MS (m/e) 318 MH+.

6-(2-(4-Fluoro-3-methylphenyl)pyridin-3-yl)-5-methyl-[1,2,4]triazolo[1,5-a]pyridine (Compound 809). LCMS: rt 5.08 min (A), purity 99%, MS (m/e) 319 MH+.

6-(2-(3-Chloro-4-fluorophenyl)pyridin-3-yl)-5-methyl-[1,2,4]triazolo[1,5-a]pyridine (Compound 810). $^1$H NMR (300 MHz, DMSO-$d_6$): δ 8.78 (dd, J=4.8, 1.7 Hz, 1H), 8.53 (s, 1H), 7.99-7.92 (m, 1H), 7.72 (dd, J=9.2, 0.8 Hz, 1H), 7.64-7.55 (m, 2H), 7.45 (d, J=9.1 Hz, 1H), 7.24 (t, J=8.9 Hz, 1H), 7.16 (ddd, J=8.6, 4.9, 2.1 Hz, 1H), 2.41 (s, 3H). $^{19}$F NMR (282 MHz, DMSO-$d_6$): δ −116.72 (app td, J=8.3, 5.1 Hz). LCMS: rt 6.15 min (A), purity 99%, MS (m/e) 339 MH+.

6-(2-(3-Chlorophenyl)pyridin-3-yl)-5-methyl-[1,2,4]triazolo[1,5-a]pyridine (Compound 811). LCMS: rt 5.71 min (A), purity 99%, MS (m/e) 321 MH+.

6-(2-(5-Chloro-2-fluorophenyl)pyridin-3-yl)-5-methyl-[1,2,4]triazolo[1,5-a]pyridine (Compound 812). LCMS: rt 6.35 min (A), purity 99%, MS (m/e) 339 MH+.

6-(2-(5-Chloro-2,4-difluorophenyl)pyridin-3-yl)-5-methyl-[1,2,4]triazolo[1,5-a]pyridine (Compound 813). LCMS: rt 6.65 min (A), purity 99%, MS (m/e) 357 MH+.

6-(2-(4-Fluoro-3-methylphenyl)pyridin-3-yl)-7-methyl-[1,2,4]triazolo[1,5-a]pyridine (Compound 814). $^1$H NMR (300 MHz, DMSO-$d_6$): δ 8.92 (s, 1H), 8.79 (ddd, J=4.9, 1.7, 0.8 Hz, 1H), 8.47 (d, J=0.9 Hz, 1H), 7.97 (ddd, J=7.7, 1.7, 0.9 Hz, 1H), 7.67 (q, J=1.0 Hz, 1H), 7.60 (ddd, J=7.7, 4.9, 0.9 Hz, 1H), 7.43 (ddd, J=7.6, 2.3, 1.0 Hz, 1H), 7.09 (ddd, J=8.5, 5.1, 2.3 Hz, 1H), 6.97 (dd, J=9.7, 8.6 Hz, 1H), 2.12 (s, 3H), 1.92 (s, 3H). $^{19}$F NMR (282 MHz, DMSO-$d_6$): δ −117.35 (app s). LCMS: rt 5.08 min (A), purity 99%, MS (m/e) 319 MH+.

N-(2-Acetamidoethyl)-6-(2-(4-fluoro-3-methylphenyl)pyridin-3-yl)imidazo[1,2-a]pyridine-3-carboxamide (Compound 815). LCMS: rt 3.93 min (A), purity 99%, MS (m/e) 432 MH+.

N-(3-Acetamidopropyl)-6-(2-(4-fluoro-3-methylphenyl)pyridin-3-yl)imidazo[1,2-a]pyridine-3-carboxamide (Compound 816). LCMS: rt 4.03 min (A), purity 99%, MS (m/e) 446 MH+.

6-(2-(4-Fluoro-3-methylphenyl)pyridin-3-yl)-N-(2-(2-oxooxazolidin-3-yl)ethyl)imidazo[1,2-a]pyridine-3-carboxamide (Compound 817). LCMS: rt 4.16 min (A), purity 99%, MS (m/e) 460 MH+.

6-(2-(5-Chloro-2-fluorophenyl)pyridin-3-yl)quinazolin-4-amine (Compound 818). $^1$H NMR (300 MHz, DMSO-$d_6$): δ 8.73 (dd, J=4.8, 1.6 Hz, 1H), 8.34 (s, 1H), 8.25-8.18 (m, 1H), 8.00 (dd, J=7.8, 1.7 Hz, 1H), 7.83-7.66 (br s, 2H), 7.66-7.56 (m, 2H), 7.48 (d, J=8.6 Hz, 1H), 7.45-7.35 (m, 2H), 7.02 (dd, J=9.6, 8.8 Hz, 1H). $^{19}$F NMR (282 MHz, DMSO-$d_6$): δ −117.11--117.25 (app m). LCMS: rt 4.55 min (A), purity 99%, MS (m/e) 351 MH+.

6-(2-(5-Chloro-2,4-difluorophenyl)pyridin-3-yl)quinazolin-4-amine (Compound 819). $^1$H NMR (300 MHz, DMSO-$d_6$): δ 8.73 (dd, J=4.8, 1.6 Hz, 1H), 8.36 (s, 1H), 8.21 (d, J=1.9 Hz, 1H), 8.01 (dd, J=7.8, 1.7 Hz, 1H), 7.80 (dd, J=8.5, 7.3 Hz, 1H), 7.75 (br s, 2H), 7.63 (dd, J=7.8, 4.8 Hz, 1H), 7.52 (d, J=8.6 Hz, 1H), 7.43 (dd, J=8.6, 1.9 Hz, 1H), 7.31 (t, J=9.7 Hz, 1H). $^{19}$F NMR (282 MHz, DMSO-$d_6$): δ −111.32 (q, J=8.8 Hz), −111.57 (q, J=8.9 Hz). LCMS: rt 4.80 min (A), purity 99%, MS (m/e) 369 MH+.

6-(2-(5-Chloro-2-fluorophenyl)pyridin-3-yl)-4-methoxyquinazoline (Compound 820). $^1$H NMR (300 MHz, DMSO-$d_6$): δ 8.78 (s, 1H), 8.75 (dd, J=4.8, 1.6 Hz, 1H), 8.05 (dd, J=8.6, 1.6 Hz 1H), 8.00 (dd, J=2.1, 0.6 Hz, 1H), 7.79 (dd, J=8.6, 0.6 Hz, 1H), 7.70-7.58 (m, 3H), 7.42 (ddd, J=8.8, 4.4, 2.8 Hz, 1H), 7.03 (dd, J=9.6, 8.9 Hz, 1H), 4.09 (s, 3H). $^{19}$F NMR (282 MHz, DMSO-$d_6$): δ −117.61 (ddd, J=10.1, 6.3, 4.4 Hz). LCMS: rt 6.91 min (A), purity 99%, MS (m/e) 366 MH+.

6-(2-(5-Chloro-2,4-difluorophenyl)pyridin-3-yl)-4-methoxyquinazoline (Compound 821). $^1$H NMR (300 MHz, DMSO-$d_6$): δ 8.79 (s, 1H), 8.75 (dd, J=4.8, 1.6 Hz, 1H), 8.06 (dd, J=7.8, 1.6 Hz, 1H), 8.01 (dd, J=2.1, 0.6 Hz, 1H), 7.86 (d, J=7.4 Hz, 1H), 7.81 (d, J=8.8 Hz, 1H), 7.70-7.57 (m, 2H), 7.32 (t, J=9.7 Hz, 1H), 4.10 (s, 3H). $^{19}$F NMR (282 MHz, DMSO-$d_6$): δ −111.35 (q, J=8.9 Hz), −111.82 (q, J=8.7 Hz). LCMS: rt 7.26 min (A), purity 99%, MS (m/e) 384 MH+.

6-(2-(5-Chloro-2-fluorophenyl)pyridin-3-yl)quinazolin-4(3H)-one (Compound 822). $^1$H NMR (300 MHz, DMSO-$d_6$): δ 12.25 (br, 1H), 8.73 (dd, J=4.8, 1.6 Hz, 1H), 8.08 (s, 1H), 8.00 (dd, J=7.8, 1.5 Hz, 1H), 7.92 (dd, J=1.7, 1.0 Hz, 1H), 7.67-7.53 (m, 4H), 7.42 (ddd, J=8.9, 4.4, 2.8 Hz, 1H), 7.06 (dd, J=9.6, 8.8 Hz, 1H). LCMS: rt 5.53 min (A), purity 99%, MS (m/e) 352 MH+.

6-(2-(5-Chloro-2,4-difluorophenyl)pyridin-3-yl)quinazolin-4(3H)-one (Compound 823). $^1$H NMR (300 MHz, DMSO-$d_6$): δ 12.28 (s, 1H), 8.73 (dd, J=4.8, 1.6 Hz, 1H), 8.08 (s, 1H), 8.01 (dd, J=7.8, 1.6 Hz, 1H), 7.93 (t, J=1.4 Hz, 1H), 7.83 (dd, J=8.5, 7.3 Hz, 1H), 7.63-7.59 (m, 1H), 7.58 (d, J=1.4

Hz, 2H), 7.36 (t, J=9.6 Hz, 1H). $^{19}$F NMR (282 MHz, DMSO-d$_6$): δ −111.43 (q, J=9.0 Hz), −111.78 (q, J=8.7 Hz). LCMS: rt 5.83 min (A), purity 99%, MS (m/e) 370 MH$^+$.

2-(2,3-Dihydro-1H-inden-5-yl)-3,4'-bipyridine (Compound 824). LCMS: rt 4.23 min (A), purity 99%, MS (m/e) 273 MH$^+$.

6-(2-(2,3-Dihydro-1H-inden-5-yl)pyridin-3-yl)-[1,2,4]triazolo[1,5-a]pyridine (Compound 825). $^1$H NMR (300 MHz, DMSO-d$_6$): δ 9.00 (dd, J=1.8, 0.9 Hz, 1H), 8.70 (dd, J=4.8, 1.7 Hz, 1H), 8.50 (s, 1H), 7.97 (dd, J=7.7, 1.7 Hz, 1H), 7.68 (dd, J=9.2, 0.9 Hz, 1H), 7.48 (dd, J=7.8, 4.8 Hz, 1H), 7.35 (d, J=1.5 Hz, 1H), 7.24 (dd, J=9.2, 1.8 Hz, 1H), 7.05 (d, J=7.9 Hz, 1H), 6.99 (dd, J=7.7, 1.6 Hz, 1H), 2.78 (q, J=8.1 Hz, 4H), 1.96 (p, J=7.5 Hz, 2H). LCMS: rt 4.84 min (A), purity 99%, MS (m/e) 313 MH$^+$.

6-(2-(2,3-Dihydro-1H-inden-5-yl)pyridin-3-yl)imidazo[1,2-a]pyridine-3-carbonitrile (Compound 826). LCMS: rt 5.46 min (A), purity 99%, MS (m/e) 337 MH$^+$.

6-(2-(2,3-Dihydro-1H-inden-5-yl)pyridin-3-yl)imidazo[1,2-a]pyridine (Compound 827). LCMS: rt 3.81 min (A), purity 99%, MS (m/e) 312 MH$^+$.

3-(Benzo[d][1,3]dioxol-5-yl)-2-(2,3-dihydro-1H-inden-5-yl)pyridine (Compound 828). LCMS: rt 6.06 min (A), purity 99%, MS (m/e) 316 MH$^+$.

4-(2-(2,3-Dihydro-1H-inden-5-yl)pyridin-3-yl)quinolone (Compound 829). LCMS: rt 5.78 min (A), purity 99%, MS (m/e) 323 MH$^+$.

6-(2-(2,3-Dihydro-1H-inden-5-yl)pyridin-3-yl)benzo[d]thiazole (Compound 830). LCMS: rt 5.68 min (A), purity 99%, MS (m/e) 329 MH$^+$.

6-(2-(2,3-Dihydro-1H-inden-5-yl)pyridin-3-yl)quinoxaline (Compound 831). LCMS: rt 5.39 min (A), purity 99%, MS (m/e) 324 MH$^+$.

5-([3,4'-Bipyridin]-2-yl)-2,3-dihydro-1H-inden-1-one (Compound 832). $^1$H NMR (300 MHz, DMSO-d$_6$): δ 8.76 (dd, J=4.8, 1.7 Hz, 1H), 8.53-8.45 (m, 2H), 7.94 (dd, J=7.8, 1.7 Hz, 1H), 7.63-7.52 (m, 2H), 7.48 (dd, J=8.0, 0.8 Hz, 1H), 7.24-7.16 (m, 3H), 3.09-2.92 (m, 2H), 2.62 (d, J=11.8 Hz, 2H). LCMS: rt 3.61 min (A), purity 99%, MS (m/e) 287 MH$^+$.

2-(3-Methyl-1H-inden-6-yl)-3,4'-bipyridine (Compound 833). MeMgBr [2 mL, 1.4 M solution in toluene/THF (75:25)] was added to a stirring solution of 5-([3,4'-bipyridin]-2-yl)-2,3-dihydro-1H-inden-1-one (175 mg) in THF (4 mL) at −78° C. under argon. The reaction was stirred for 30 min and warmed to room temperature after complete addition of MeMgBr and. After 1 h, the complete consumption of 5-([3,4'-bipyridin]-2-yl)-2,3-dihydro-1H-inden-1-one to 5-([3,4'-bipyridin]-2-yl)-1-methyl-2,3-dihydro-1H-inden-1-ol was observed. Subsequently, the reaction was cooled in ice-bath, quenched with conc. HCl (5 mL) over a period of 30 min. The cooling was removed and allowed the reaction to warm to temperature. After 4 h, the reaction mixture was concentrated, diluted with EtOAc (50 mL) and aq. NaHCO$_3$ solution (15 mL). Aqueous layer was discarded, washed the organic layer with brine, dried over MgSO$_4$, filtered, concentrated and purified by flash column chromatography (Combiflash® companion System® with RediSep® silica gel column 12 g, 30-50-70% EtOAc/hexanes as an eluting solvent) to obtain 2-(3-Methyl-1H-inden-6-yl)-3,4'-bipyridine as an oil. LCMS: rt 4.47 min (A), purity 95%, MS (m/e) 285 (MH$^+$).

rac-5-([3,4'-Bipyridin]-2-yl)-2,3-dihydro-1H-inden-1-ol (Compound 834). Sodium borohydride (21 mg) was added to a stirring solution of 5-([3,4'-bipyridin]-2-yl)-2,3-dihydro-1H-inden-1-one (162 mg) in MeOH (4 mL). The reaction mixture was concentrated and quenched with aq. NH$_4$Cl. The resultant solid was extracted into CH$_2$Cl$_2$ (2×20 mL). Combined organic layers were stirred over MgSO4, filtered and concentrated. Flash chromatographic purification (Combiflash® companion System® with RediSep® silica gel column 12 g, 50-75% EtOAc/hexanes as eluting solvent) provided rac-5-([3,4'-bipyridin]-2-yl)-2,3-dihydro-1H-inden-1-ol (170 mg) as a white solid. $^1$H NMR (300 MHz, DMSO-d$_6$): δ 8.69 (dd, J=4.8, 1.6 Hz, 1H), 8.48 (d, J=6.0 Hz, 2H), 7.85 (dd, J=7.8, 1.7 Hz, 1H), 7.48 (dd, J=7.8, 4.7 Hz, 1H), 7.25-7.11 (m, 4H), 7.00 (dd, J=7.8, 1.5 Hz, 1H), 5.29-5.20 (m, 1H), 5.00 (q, J=6.4 Hz, 1H), 2.81 (ddd, J=16.0, 8.7, 3.9 Hz, 1H), 2.61 (dt, J=15.9, 8.0 Hz, 1H), 2.36-2.21 (m, 1H), 1.74 (dtd, J=12.8, 8.2, 6.3 Hz, 1H). LCMS: rt 2.81 min (A), purity 99%, MS (m/e) 289 (MH$^+$).

(E/Z)-5-([3,4'-bipyridin]-2-yl)-2,3-dihydro-1H-inden-1-one oxime (Compound 835). 5-([3,4'-Bipyridin]-2-yl)-2,3-dihydro-1H-inden-1-one (162 mg), NH$_2$OH.HCl (55 mg) and NaOAc (84 mg) were stirred and heated at 80° C. for 4 h in EtOH (3 mL). The reaction mixture was diluted with water and filtered the solid The solid was washed with water and dried to obtain 130 mg of (E/Z)-5-([3,4'-bipyridin]-2-yl)-2,3-dihydro-1H-inden-1-one oxime as a white solid. $^1$H NMR (300 MHz, DMSO-d$_6$): δ 10.93 (s, 1H), 8.71 (dd, J=4.7, 1.7 Hz, 1H), 8.50-8.45 (m, 2H), 7.88 (dd, J=7.8, 1.7 Hz, 1H), 7.51 (dd, J=7.8, 4.8 Hz, 1H), 7.41-7.33 (m, 2H), 7.23-7.16 (m, 2H), 7.05 (dd, J=7.9, 1.6 Hz, 1H), 2.97-2.83 (m, 2H), 2.76 (ddd, J=9.7, 5.3, 2.1 Hz, 2H). LCMS: rt 3.56 min (A), purity 99%, MS (m/e) 302 MH$^+$.

6-(2-(4-Fluoro-3-methylphenyl)pyridin-3-yl)quinolin-4-amine (Compound 836). LCMS: rt 3.98 min (A), purity 99%, MS (m/e) 330 MH$^+$.

6-(2-(3-Chloro-4-fluorophenyl)pyridin-3-yl)quinolin-4-amine (Compound 837). $^1$H NMR (300 MHz, DMSO-d$_6$): δ 8.72 (dd, J=4.7, 1.7 Hz, 1H), 8.36-8.28 (m, 2H), 7.96 (dd, J=7.8, 1.7 Hz, 1H), 7.73 (d, J=9.9 Hz, 2H), 7.66 (d, J=8.7 Hz, 1H), 7.61-7.54 (m, 2H), 7.38 (dt, J=8.8, 1.6 Hz, 1H), 7.23 (dd, J=9.3, 8.6 Hz, 1H), 7.13 (ddd, J=8.6, 4.8, 2.2 Hz, 1H), 6.64 (dd, J=6.0, 1.3 Hz, 1H). $^{19}$F NMR (282 MHz, DMSO-d$_6$): δ −117.19 (td, J=8.3, 4.9 Hz). LCMS: rt 4.70 min (A), purity 99%, MS (m/e) 350 MH$^+$.

6-(2-(4-Fluoro-3-methylphenyl)pyridin-3-yl)-4-methoxyquinoline (Compound 838). $^1$H NMR (300 MHz, DMSO-d$_6$): δ 8.72 (d, J=5.2 Hz, 1H), 8.68 (dd, J=4.7, 1.7 Hz, 1H), 8.07 (dd, J=2.1, 0.6 Hz, 1H), 7.92 (dd, J=7.7, 1.7 Hz, 1H), 7.77 (dd, J=8.7, 0.6 Hz, 1H), 7.48 (dd, J=7.7, 4.7 Hz, 1H), 7.41-7.36 (m, 1H), 7.33 (dd, J=8.7, 2.1 Hz, 1H), 7.03 (d, J=5.3 Hz, 1H), 6.98-6.84 (m, 2H), 4.01 (s, 3H), 2.12 (s, 3H). $^{19}$F NMR (282 MHz, DMSO-d$_6$): δ −118.46--118.69 (m). LCMS: rt 4.30 min (A), purity 99%, MS (m/e) 345 MH$^+$.

6-(2-(3-Chloro-4-fluorophenyl)pyridin-3-yl)-4-methoxyquinoline (Compound 839). LCMS: rt 5.08 min (A), purity 99%, MS (m/e) 365 MH$^+$.

6-(2-(5-Chloro-2-fluorophenyl)pyridin-3-yl)-4-methoxyquinoline (Compound 840). LCMS: rt 5.28 min (A), purity 99%, MS (m/e) 365 MH$^+$.

6-(2-(3-Chlorophenyl)pyridin-3-yl)-4-methoxyquinoline (Compound 841). LCMS: rt 4.76 min (A), purity 99%, MS (m/e) 347 MH$^+$.

6-(2-(5-Chloro-2,4-difluorophenyl)pyridin-3-yl)-4-methoxyquinoline (Compound 842). LCMS: rt 5.52 min (A), purity 99%, MS (m/e) 383 MH$^+$.

6-(2-(3-Chloro-4-fluorophenyl)pyridin-3-yl)imidazo[1,2-a]pyridine-3-carboxamide (Compound 843). Conc. H$_2$SO$_4$ was added dropwise to stirring TFA at room temperature for 5 min. 6-(2-(3-Chloro-4-fluorophenyl)pyridin-3-yl)imidazo[1,2-a]pyridine-3-carbonitrile (870 mg) was added all at once to the homogenous solution after fuming subsided from acid mixture. Additional TFA and conc. H$_2$SO$_4$ were added successively to the heterogeneous reaction mixture. After 6 h, the reaction mixture was added to ice/water and stirred. The homogeneous solution was basified with aq. NaOH (50%). The resultant heterogeneous slurry was filtered and dried. Subsequently, the white solid was purified by flash chromatography (Combiflash® companion System® with RediSep® silica gel column 24 g, 70% EtOAc/hexanes-3% MeOH/EtOH) to obtain 6-(2-(3-chloro-4-fluorophenyl)pyridin-3-yl)imidazo[1,2-a]pyridine-3-carboxamide (720 mg). $^1$H NMR (300 MHz, DMSO-$d_6$): δ 9.48 (s, 1H), 8.72 (dd, J=4.8, 1.6 Hz, 1H), 8.33 (s, 1H), 7.97 (dd, J=7.8, 1.7 Hz, 2H), 7.64 (d, J=6.8 Hz, 1H), 7.61-7.57 (m, 1H), 7.55 (dd, J=7.9, 4.9 Hz, 1H), 7.52-7.48 (br s, 2H), 7.26 (dd, J=7.7, 1.5 Hz, 1H), 7.10 (dd, J=9.4, 1.9 Hz, 1H). $^{19}$F NMR (282 MHz, DMSO-$d_6$): δ −117.01 (q, J=7.5, 7.1 Hz). LCMS: rt 4.65 min (A), purity 99%, MS (m/e) 367 MH$^+$.

6-(2-(3-Chloro-4-fluorophenyl)pyridin-3-yl)-3-(1H-1,2,4-triazol-5-yl)imidazo[1,2-a]pyridine (Compound 844). 6-(2-(3-Chloro-4-fluorophenyl)pyridin-3-yl)imidazo[1,2-a]pyridine-3-carboxamide (290 mg) and DMF.DMA (5 mL) were heated at 95° C. and stirred in a screw capped vial overnight. The pale yellow homogeneous reaction mixture was cooled to room temperature and concentrated the heterogeneous slurry by rotary evaporator under vacuum. The off-white solid residue was transferred to a screw capped vial, treated with AcOH (3 mL) dropwise for 3 min followed by N$_2$H$_4$.H$_2$O (0.05 mL) and heated for 1 h at 90° C. The homogeneous reaction mixture was concentrated, diluted with ice/water and allowed the resulting suspension warm to room temperature. Upon filtration, the collected solid was neutralized with aq. NaHCO$_3$ and filtered again to obtain 6-(2-(3-chloro-4-fluorophenyl)pyridin-3-yl)-3-(1H-1,2,4-triazol-5-yl)imidazo[1,2-a]pyridine as an off-white solid (220 mg). $^1$H NMR (300 MHz, DMSO-$d_6$): δ 14.03 (br s, 1H), 9.46 (dd, J=1.9, 1.0 Hz, 1H), 8.79-8.70 (m, 1H), 8.70-8.52 (m, 1H), 8.18 (s, 1H), 8.02 (dd, J=7.8, 1.6 Hz, 1H), 7.67 (dd, J=6.2, 1.4 Hz, 1H), 7.61 (dd, J=9.3, 1.0 Hz, 1H), 7.56 (dd, J=7.8, 4.7 Hz, 1H), 7.28 (d, J=0.7 Hz, 1H), 7.27-7.20 (m, 1H), 7.04 (dd, J=9.3, 1.8 Hz, 1H). $^{19}$F NMR (282 MHz, DMSO-$d_6$): δ −114.49--119.56 (m). LCMS: rt 4.70 min (A), purity 99%, MS (m/e) 391 MH$^+$.

6-(2-(3-Chloro-4-fluorophenyl)pyridin-3-yl)-3-(1H-imidazol-2-yl)imidazo[1,2-a]pyridine (Compound 845). Aminoacetaldeyde (0.2 mL, 0.193 g, 1.72 mmol) was added to dry THF (8 mL) under argon and cooled the homogenous solution to −78° C. and stirred for 5 min. n-BuLi (1.2 mL, 1.6 M solution in hexanes, 1.97 mmol) was added dropwise for 10 min and stirred for 30 min. 6-(2-(3-chloro-4-fluorophenyl)pyridin-3-yl)imidazo[1,2-a]pyridine-3-carbonitrile (0.3 g, 0.86 mmol) dissolved in dry THF (5 mL) was added to the above faint yellow homogeneous solution. The red solution was cooled and stirred at 0° C. for 2 h. Subsequently, dark reaction mixture was concentrated under vacuum by rotary evaporator, treated with 6N aq. HCl (15 mL), stirred and heated at 90° C. for 2 h. The reaction mixture was concentrated, neutralized with aq. NaOH and extracted into CH$_2$Cl$_2$. Workup and purification by preparative HPLC provided (6-(2-(3-chloro-4-fluorophenyl)pyridin-3-yl)imidazo[1,2-a]pyridine-3-carbonitrile (120 mg). $^1$H NMR (300 MHz, DMSO-$d_6$): δ 12.70 (s, 1H), 9.73 (s, 1H), 8.73 (dd, J=4.7, 1.5 Hz, 1H), 8.14 (s, 1H), 8.00 (dd, J=7.8, 1.6 Hz, 1H), 7.67 (d, J=6.4 Hz, 1H), 7.62-7.50 (m, 3H), 7.34-7.18 (m, 3H), 7.02 (dd, J=9.3, 1.9 Hz, 1H). $^{19}$F NMR (282 MHz, DMSO-$d_6$): δ −117.11 (q, J=7.3 Hz). LCMS: rt 4.81 min (A), purity 99%, MS (m/e) 390 MH$^+$.

6-(2-(4-Fluoro-3-methylphenyl)pyridin-3-yl)quinoline-4-carboxamide (Compound 846). $^1$H NMR (300 MHz, DMSO-$d_6$): δ 8.99 (d, J=4.4 Hz, 1H), 8.76 (dd, J=5.0, 1.6 Hz, 1H), 8.24 (t, J=2.2 Hz, 2H), 8.09 (dd, J=7.8, 1.6 Hz, 1H), 7.95 (d, J=8.7 Hz, 1H), 7.90 (s, 2H), 7.71-7.58 (m, 2H), 7.44 (ddd, J=11.6, 8.1, 2.0 Hz, 2H), 7.06-6.87 (m, 1H), 2.14 (d, J=1.9 Hz, 3H). $^{19}$F NMR (282 MHz, DMSO-$d_6$): δ −117.44 (s). LCMS: rt 4.11 min (A), purity 99%, MS (m/e) 358 MH$^+$.

6-(2-(3-Chloro-4-fluorophenyl)pyridin-3-yl)quinoline-4-carboxamide (Compound 847). LCMS: rt 4.76 min (A), purity 99%, MS (m/e) 378 MH$^+$.

6-(2-(3-Chlorophenyl)pyridin-3-yl)quinoline-4-carboxamide (Compound 848). LCMS: rt 4.36 min (A), purity 99%, MS (m/e) 360 MH$^+$.

6-(2-(5-Chloro-2-fluorophenyl)pyridin-3-yl)quinoline-4-carboxamide (Compound 849). LCMS: rt 4.86 min (A), purity 99%, MS (m/e) 378 MH$^+$.

6-(2-(5-Chloro-2,4-difluorophenyl)pyridin-3-yl)quinoline-4-carboxamide (Compound 850). LCMS: rt 5.20 min (A), purity 99%, MS (m/e) 396 MH$^+$.

7-(2-(5-Chloro-2-fluorophenyl)pyridin-3-yl)-[1,2,4]triazolo[4,3-a]pyridine (Compound 851). $^1$H NMR (300 MHz, DMSO-$d_6$): δ 9.20 (t, J=0.8 Hz, 1H), 8.76 (ddd, J=4.8, 1.6, 0.6 Hz, 1H), 8.47 (dt, J=7.2, 0.9 Hz, 1H), 8.05 (ddd, J=7.9, 1.7, 0.6 Hz, 1H), 7.70-7.59 (m, 3H), 7.46 (dddd, J=8.9, 4.3, 2.8, 0.6 Hz, 1H), 7.11 (ddd, J=9.5, 8.8, 0.6 Hz, 1H), 6.76 (ddd, J=7.1, 1.6, 0.6 Hz, 1H). $^{19}$F NMR (282 MHz, DMSO-$d_6$): δ −115.57--119.56 (m). LCMS: rt 5.00 min (A), purity 99%, MS (m/e) 325 MH$^+$.

6-(2-(3-Chloro-4-fluorophenyl)pyridin-3-yl)-3-(1H-pyrazol-3-yl)imidazo[1,2-a]pyridine (Compound 852). 1-(6-(2-(3-Chloro-4-fluorophenyl)pyridin-3-yl)imidazo[1,2-a]pyridin-3-yl)ethan-1-one (300 mg) and DMF.DMA (5 mL) were heated at 95° C. and stirred in a screw capped vial overnight. The reaction mixture was concentrated and the semi-solid residue was diluted with Et$_2$O/hexanes (1:1). The solid was filtered and dried. The enamine (75 mg) and the hydrazine (1.2 eq) were heated in a screw capped vial at 100° C. for 12 h. The reaction mixture was concentrated and purified by preparative HPLC. $^1$H NMR (300 MHz, DMSO-$d_6$): δ 13.02 (br s), 9.71 (dd, J=1.8, 1.0 Hz, 1H), 8.79 (dd, J=4.8, 1.6 Hz, 1H), 8.62 (s, 1H), 8.06 (dd, J=7.8, 1.7 Hz, 1H), 8.01 (d, J=2.4 Hz, 1H), 7.89 (dd, J=9.3, 0.9 Hz, 1H), 7.74 (dd, J=7.3, 2.1 Hz, 1H), 7.62 (dd, J=7.8, 4.8 Hz, 1H), 7.50 (dd, J=9.3, 1.7 Hz, 1H), 7.37-7.14 (m, 2H), 6.95 (d, J=2.4 Hz, 1H). $^{19}$F NMR (282 MHz, DMSO-$d_6$): δ −116.76 (q, J=7.3 Hz). LCMS: rt 4.98 min (A), purity 99%, MS (m/e) 390 MH$^+$.

6-(2-(3-Chloro-4-fluorophenyl)pyridin-3-yl)-3-(1-methyl-1H-pyrazol-3-yl)imidazo[1,2-a]pyridine (Compound 853). 6-(2-(3-Chloro-4-fluorophenyl)pyridin-3-yl)-3-(1-methyl-1H-pyrazol-3-yl)imidazo[1,2-a]pyridine was prepared by the reaction of MeNHNH$_2$ and enamine, analogous to the preparation of 6-(2-(3-Chloro-4-fluorophenyl)pyridin-3-yl)-3-(1H-pyrazol-3-yl)imidazo[1,2-a]pyridine. $^1$H NMR (300 MHz, DMSO-$d_6$): δ 8.74 (dd, J=4.8, 1.6 Hz, 1H), 8.43 (dd, J=1.7, 0.9 Hz, 1H), 8.42 (s, 1H), 8.04 (dd, J=7.8, 1.6 Hz, 1H), 7.89 (dd, J=9.4, 0.8 Hz, 1H), 7.73 (dt, J=8.1, 1.1 Hz, 1H), 7.67 (d, J=2.0 Hz, 1H), 7.56 (dd, J=7.8, 4.8 Hz, 1H), 7.51 (dd, J=9.3, 1.6 Hz, 1H), 7.31-7.21 (m, 2H), 6.74 (d, J=2.0 Hz, 1H), 3.82 (s, 3H). $^{19}$F NMR (282 MHz, DMSO-$d_6$): δ −116.76 (q, J=7.3 Hz). LCMS: rt 5.09 min (A), purity 99%, MS (m/e) 404 MH$^+$.

7-(2-(4-Fluoro-3-methylphenyl)-5-methoxypyridin-3-yl)-[1,2,4]triazolo[1,5-a]pyridine (Compound 854). LCMS: rt 5.78 min (A), purity 99%, MS (m/e) 335 MH$^+$.

7-(2-(3-Chlorophenyl)-5-methoxypyridin-3-yl)-[1,2,4]triazolo[1,5-a]pyridine (Compound 855). $^1$H NMR (300 MHz, DMSO-$d_6$): δ 8.85 (dd, J=7.1, 0.9 Hz, 1H), 8.52 (s, 1H), 8.47 (d, J=2.8 Hz, 1H), 7.94-7.89 (m, 1H), 7.62 (d, J=2.8 Hz, 1H), 7.45 (t, J=1.9 Hz, 1H), 7.32 (ddd, J=8.0, 2.2, 1.2 Hz, 1H), 7.22 (t, J=7.8 Hz, 1H), 7.12 (dt, J=7.7, 1.4 Hz, 1H), 6.85 (dd, J=7.1, 1.9 Hz, 1H), 3.94 (s, 3H). LCMS: rt 6.40 min (A), purity 99%, MS (m/e) 337 MH+.

7-(2-(3-Chloro-4-fluorophenyl)-5-methoxypyridin-3-yl)-[1,2,4]triazolo[1,5-a]pyridine (Compound 856). LCMS: rt 6.75 min (A), purity 99%, MS (m/e) 355 MH+.

7-(2-(5-Chloro-2,4-difluorophenyl)-5-methoxypyridin-3-yl)-[1,2,4]triazolo[1,5-a]pyridine (Compound 857). LCMS: rt 6.71 min (A), purity 99%, MS (m/e) 373 MH+.

7-(2-(5-Chloro-2-fluorophenyl)-5-methoxypyridin-3-yl)-[1,2,4]triazolo[1,5-a]pyridine (Compound 858). LCMS: rt 6.71 min (A), purity 99%, MS (m/e) 355 MH+.

7-(2-(3-(Difluoro-13-methyl)-12-fluoranyl)phenyl)-5-methoxypyridin-3-yl)-[1,2,4]triazolo[1,5-a]pyridine (Compound 859). LCMS: rt 7.05 min (A), purity 99%, MS (m/e) 372 MH+.

7-(2-(3-Chloro-4-fluorophenyl)-5-fluoropyridin-3-yl)-[1,2,4]triazolo[1,5-a]pyridine (Compound 860). $^1$H NMR (300 MHz, DMSO-d$_6$): δ 8.87 (dd, J=7.0, 0.9 Hz, 1H), 8.77 (d, J=2.8 Hz, 1H), 8.53 (s, 1H), 8.07 (dd, J=9.3, 2.8 Hz, 1H), 7.93 (dd, J=1.9, 0.9 Hz, 1H), 7.64 (dd, J=7.3, 2.2 Hz, 1H), 7.28 (dd, J=9.3, 8.6 Hz, 1H), 7.19 (ddd, J=8.6, 4.9, 2.2 Hz, 1H), 6.88 (dd, J=7.1, 1.9 Hz, 1H). $^{19}$F NMR (282 MHz, DMSO-d$_6$): δ −116.71 (ddd, J=9.4, 7.3, 4.8 Hz), −129.02 (d, J=9.2 Hz). LCMS: rt 7.28 min (A), purity 99%, MS (m/e) 343 MH+.

7-(2-(5-Chloro-2,4-difluorophenyl)-5-fluoropyridin-3-yl)-[1,2,4]triazolo[1,5-a]pyridine (Compound 861). LCMS: rt 7.30 min (A), purity 99%, MS (m/e) 361 MH+.

7-(2-(5-Chloro-2-fluorophenyl)-5-fluoropyridin-3-yl)-[1,2,4]triazolo[1,5-a]pyridine (Compound 862). LCMS: rt 7.08 min (A), purity 99%, MS (m/e) 343 MH+.

7-(2-(3-((Difluoro-13-methyl)-12-fluoranyl)phenyl)-5-fluoropyridin-3-yl)-[1,2,4]triazolo[1,5-a]pyridine (Compound 863). LCMS: rt 7.55 min (A), purity 99%, MS (m/e) 370 MH+.

7-(2-(3-Chloro-4-fluorophenyl)-5-methylpyridin-3-yl)-[1,2,4]triazolo[1,5-a]pyridine (Compound 864). $^1$H NMR (300 MHz, DMSO-d$_6$): δ 8.85 (dd, J=7.0, 0.9 Hz, 1H), 8.60 (d, J=1.8 Hz, 1H), 8.52 (s, 1H), 7.90 (s, 1H), 7.86 (s, 1H), 7.65 (dd, J=7.3, 2.1 Hz, 1H), 7.27 (t, J=8.9 Hz, 1H), 7.19 (ddd, J=8.5, 4.9, 2.2 Hz, 1H), 6.85 (dd, J=7.1, 1.8 Hz, 1H), 2.42 (s, 3H). $^{19}$F NMR (282 MHz, DMSO-d$_6$): δ −116.87 (dd, J=7.6, 3.3 Hz). LCMS: rt 5.86 min (A), purity 99%, MS (m/e) 339 MH+.

7-(2-(5-Chloro-2,4-difluorophenyl)-5-methylpyridin-3-yl)-[1,2,4]triazolo[1,5-a]pyridine (Compound 865). LCMS: rt 6.65 min (A), purity 99%, MS (m/e) 357 MH+.

7-(2-(5-Chloro-2-fluorophenyl)-5-methylpyridin-3-yl)-[1,2,4]triazolo[1,5-a]pyridine (Compound 866). LCMS: rt 6.25 min (A), purity 99%, MS (m/e) 339 MH+.

7-(2-(3-((Difluoro-13-methyl)-12-fluoranyl)phenyl)-5-methylpyridin-3-yl)-[1,2,4]triazolo[1,5-a]pyridine (Compound 867). LCMS: rt 6.26 min (A), purity 99%, MS (m/e) 356 MH+.

7-(2-(3-Chlorophenyl)-5-methylpyridin-3-yl)-[1,2,4]triazolo[1,5-a]pyridine (Compound 868). LCMS: rt 5.30 min (A), purity 99%, MS (m/e) 321 MH+.

6-(2-(2,5-Dichlorophenyl)pyridin-3-yl)benzo[d]thiazole (Compound 869). $^1$H NMR (300 MHz, DMSO-d$_6$): δ 9.37 (s, 1H), 8.70 (dd, J=4.8, 1.6 Hz, 1H), 8.05 (dd, J=1.8, 0.6 Hz, 1H), 7.99 (dd, J=7.8, 1.6 Hz, 1H), 7.94 (dd, J=8.4, 0.6 Hz, 1H), 7.60 (dd, J=7.8, 4.8 Hz, 1H), 7.54 (dd, J=2.5, 0.6 Hz, 1H), 7.39 (dd, J=8.6, 2.4 Hz, 1H), 7.34 (dd, J=8.6, 0.6 Hz, 1H), 7.26 (dd, J=8.5, 1.8 Hz, 1H). LCMS: rt 7.38 min (A), purity 99%, MS (m/e) 356 MH+.

6-(2-(2,5-Dichlorophenyl)pyridin-3-yl)-1-methyl-1H-benzo[d]imidazole (Compound 870). $^1$H NMR (300 MHz, DMSO-d$_6$): δ 8.67 (dd, J=4.8, 1.6 Hz, 1H), 8.33 (s, 1H), 7.98 (dd, J=7.8, 1.6 Hz, 1H), 7.59 (dd, J=7.9, 4.7 Hz, 1H), 7.54-7.48 (m, 3H), 7.41-7.30 (m, 2H), 6.99 (dd, J=8.4, 1.7 Hz, 1H), 3.75 (s, 3H). LCMS: rt 4.81 min (A), purity 99%, MS (m/e) 354 MH+.

6-(2-(2,5-Dichlorophenyl)pyridin-3-yl)-1H-benzo[d]imidazole (Compound 871). LCMS: rt 4.61 min (A), purity 99%, MS (m/e) 340 MH+.

6-(2-(2,5-Dichlorophenyl)pyridin-3-yl)imidazo[1,2-a]pyridine (Compound 872). LCMS: rt 4.70 min (A), purity 99%, MS (m/e) 340 MH+.

7-(2-(2,5-Dichlorophenyl)pyridin-3-yl)-[1,2,4]triazolo[1,5-a]pyridine (Compound 873). LCMS: rt 6.21 min (A), purity 99%, MS (m/e) 341 MH+.

7-(2-(2,4,5-Trifluorophenyl)pyridin-3-yl)-[1,2,4]triazolo[1,5-a]pyridine (Compound 874). 17LCMS: rt 5.88 min (A), purity 99%, MS (m/e) 327 MH+.

7-(2-(3,4,5-Trifluorophenyl)pyridin-3-yl)-[1,2,4]triazolo[1,5-a]pyridine (Compound 875). LCMS: rt 6.15 min (A), purity 99%, MS (m/e) 327 MH+.

7-(2-(2-Chloro-5-methylphenyl)pyridin-3-yl)-[1,2,4]triazolo[1,5-a]pyridine (Compound 876). LCMS: rt 6.40 min (A), purity 99%, MS (m/e) 321 MH+.

7-(2-(4,5-Difluoro-2-methylphenyl)pyridin-3-yl)-[1,2,4]triazolo[1,5-a]pyridine (Compound 877). LCMS: rt 5.31 min (A), purity 99%, MS (m/e) 323 MH+.

7-(2-(2-Methyl-5-(trifluoromethyl)phenyl)pyridin-3-yl)-[1,2,4]triazolo[1,5-a]pyridine (Compound 878). LCMS: rt 6.18 min (A), purity 99%, MS (m/e) 355 MH+.

7-(2-(3-(Trifluoromethyl)phenyl)pyridin-3-yl)-[1,2,4]triazolo[1,5-a]pyridine (Compound 879). LCMS: rt 6.20 min (A), purity 99%, MS (m/e) 341 MH+.

7-(2-(3-Methoxyphenyl)pyridin-3-yl)-[1,2,4]triazolo[1,5-a]pyridine (Compound 880). $^1$H NMR (300 MHz, DMSO-d$_6$): δ 8.87-8.74 (m, 2H), 8.51 (d, J=1.3 Hz, 1H), 8.15 (dd, J=7.8, 1.6 Hz, 1H), 7.84 (dd, J=2.1, 1.1 Hz, 1H), 7.67 (dd, J=7.8, 5.0 Hz, 1H), 7.18 (t, J=7.9 Hz, 1H), 7.02 (dt, J=2.8, 1.5 Hz, 1H), 6.95-6.80 (m, 3H), 3.62 (s, 3H). LCMS: rt 4.28 min (A), purity 99%, MS (m/e) 303 MH+.

7-(2-(5-Chloro-2-methoxyphenyl)pyridin-3-yl)-[1,2,4]triazolo[1,5-a]pyridine (Compound 881). LCMS: rt 4.98 min (A), purity 99%, MS (m/e) 337 MH+.

7-(2-(3-(Trifluoromethoxy)phenyl)pyridin-3-yl)-[1,2,4]triazolo[1,5-a]pyridine (Compound 882). LCMS: rt 6.28 min (A), purity 99%, MS (m/e) 357 MH+.

7-(2-(3-(Difluoromethoxy)phenyl)pyridin-3-yl)-[1,2,4]triazolo[1,5-a]pyridine (Compound 883). $^1$H NMR (300 MHz, DMSO-d$_6$): δ 8.83 (dd, J=7.0, 1.0 Hz, 1H), 8.78 (dd, J=4.8, 1.6 Hz, 1H), 8.51 (s, 1H), 8.09 (dd, J=7.8, 1.6 Hz, 1H), 7.84 (dd, J=2.0, 1.0 Hz, 1H), 7.62 (ddd, J=7.8, 4.8, 0.8 Hz, 1H), 7.32 (t, J=7.6 Hz, 1H), 7.24-7.07 (m, 4H), 6.85 (dd, J=7.1, 1.9 Hz, 1H). $^{19}$F NMR (282 MHz, DMSO-d$_6$): δ −82.56 (d, J=73.8 Hz). LCMS: rt 5.36 min (A), purity 99%, MS (m/e) 339 MH+.

7-(2-(2-Fluoro-5-(trifluoromethoxy)phenyl)pyridin-3-yl)-[1,2,4]triazolo[1,5-a]pyridine (Compound 884). LCMS: rt 6.83 min (A), purity 99%, MS (m/e) 375 MH+.

6-(2-(3-Chloro-4-fluorophenyl)pyridin-3-yl)-N-(2,2,6,6-tetramethylpiperidin-4-yl-1-oxy)quinazolin-4-amine (Compound 885). 4-Chloro-6-(2-(3-chloro-4-fluorophenyl)pyridin-3-yl)quinazoline (75 mg), EtOH, 4-amino-2,2,6,6-tetramethyl-1-piperidinyloxy and i-Pr$_2$NEt were added successively to a screw capped vial, stirred and heated at 90° C. for 3 days. The reaction mixture was concentrated and purified by preparative HPLC to obtain pale pink solid. LCMS: rt 5.85 min (A), purity 99%, MS (m/e) 505 MH+.

6-(2-(3-Chloro-4-fluorophenyl)pyridin-3-yl)-N-methylquinazolin-4-amine (Compound 886). 4-Chloro-6-(2-(3-chloro-4-fluorophenyl)pyridin-3-yl)quinazoline (75 mg), 2M MeNH$_2$ in THF (2 mL) and i-PrOH (3 mL) were heated and stirred in a screw capped vial for 12 h at 65° C. The heterogeneous reaction mixture was cooled and filtered. The solid on the funnel was washed with water and dried to obtain 6-(2-(3-chloro-4-fluorophenyl)pyridin-3-yl)-N-methylquinazolin-4-amine (53 mg) as a white solid. $^1$H NMR (300 MHz, DMSO-d$_6$): δ 8.72 (dd, J=4.7, 1.7 Hz, 1H), 8.47 (s, 1H), 8.31 (q, J=4.7 Hz, 1H), 8.25 (d, J=1.9 Hz, 1H), 7.95 (dd, J=7.8, 1.7 Hz, 1H), 7.61-7.50 (m, 3H), 7.36 (dd, J=8.6, 1.9 Hz, 1H), 7.24 (t, J=8.9 Hz, 1H), 7.13 (ddd, J=8.6, 4.8, 2.2 Hz, 1H), 2.98 (d, J=4.4 Hz, 3H). $^{19}$F NMR (282 MHz, DMSO-d$_6$): δ −117.17 (td, J=8.6, 5.1 Hz). LCMS: rt 4.68 min (A), purity 99%, MS (m/e) 365 MH$^+$.

7-(2-(3-Chloro-4-fluorophenyl)pyridin-3-yl)-1-methylquinoxalin-2(1H)-one (Compound 887). $^1$H NMR (300 MHz, DMSO-d$_6$): δ 8.73 (dd, J=4.8, 1.6 Hz, 1H), 8.30-8.18 (m, 1H), 8.01 (dt, J=7.8, 1.4 Hz, 1H), 7.71 (d, J=8.3 Hz, 1H), 7.62 (dt, J=7.3, 1.5 Hz, 1H), 7.60-7.51 (m, 2H), 7.25 (t, J=8.9 Hz, 1H), 7.16 (ddd, J=8.4, 4.8, 2.1 Hz, 1H), 7.07 (dd, J=8.3, 1.7 Hz, 1H), 3.53 (s, 3H). $^{19}$F NMR (282 MHz, DMSO-d$_6$): δ −117.11 (td, J=8.6, 5.1 Hz). LCMS: rt 6.26 min (A), purity 99%, MS (m/e) 366 MH$^+$.

7-(2-(4-Fluoro-3-methylphenyl)pyridin-3-yl)-1-methylquinoxalin-2(1H)-one (Compound 888). LCMS: rt 5.16 min (A), purity 99%, MS (m/e) 346 MH$^+$.

7-(2-(5-Chloro-2-fluorophenyl)pyridin-3-yl)-1-methylquinoxalin-2(1H)-one (Compound 889). LCMS: rt 6.66 min (A), purity 99%, MS (m/e) 366 MH$^+$.

7-(2-(3-Chloro-4-fluorophenyl)pyridin-3-yl)quinoxalin-2(1H)-one (Compound 890). LCMS: rt 5.63 min (A), purity 99%, MS (m/e) 352 MH$^+$.

7-(2-(4-Fluoro-3-methylphenyl)pyridin-3-yl)quinoxalin-2(1H)-one (Compound 891). LCMS: rt 4.73 min (A), purity 99%, MS (m/e) 332 MH$^+$.

7-(2-(5-Chloro-2-fluorophenyl)pyridin-3-yl)quinoxalin-2(1H)-one (Compound 892). $^1$H NMR (300 MHz, DMSO-d$_6$): δ 12.35 (s, 1H), 8.69 (dd, J=4.8, 1.6 Hz, 1H), 8.08 (s, 1H), 7.90 (dd, J=7.9, 1.6 Hz, 1H), 7.64 (d, J=8.8 Hz, 1H), 7.60-7.46 (m, 2H), 7.46-7.30 (m, 1H), 7.15-6.92 (m, 3H). $^{19}$F NMR (282 MHz, DMSO-d$_6$): δ −117.11--117.91 (m). LCMS: rt 5.93 min (A), purity 99%, MS (m/e) 352 MH$^+$.

7-(2-(3-Chloro-4-fluorophenyl)pyridin-3-yl)-2H-benzo[e][1,2,4]thiadiazine 1,1-dioxide (Compound 893). LCMS: rt 5.53 min (A), purity 99%, MS (m/e) 388 MH$^+$.

7-(2-(4-Fluoro-3-methylphenyl)pyridin-3-yl)-2H-benzo[e][1,2,4]thiadiazine 1,1-dioxide (Compound 894). LCMS: rt 4.50 min (A), purity 97%, MS (m/e) 368 MH$^+$.

7-(2-(5-Chloro-2-fluorophenyl)pyridin-3-yl)-2H-benzo[e][1,2,4]thiadiazine 1,1-dioxide (Compound 895). $^1$H NMR (300 MHz, DMSO-d$_6$): δ 12.35 (s, 1H), 8.69 (dd, J=4.8, 1.6 Hz, 1H), 8.08 (s, 1H), 7.90 (dd, J=7.9, 1.6 Hz, 1H), 7.64 (d, J=8.8 Hz, 1H), 7.60-7.50 (m, 2H), 7.39 (ddd, J=8.7, 4.4, 2.9 Hz, 1H), 7.11-6.91 (m, 3H). $^{19}$F NMR (282 MHz, DMSO-d$_6$): δ −117.44--117.69 (m). LCMS: rt 5.86 min (A), purity 97%, MS (m/e) 388 MH$^+$.

5-(2-(3-Cyclopropyl-4-fluorophenyl)pyridin-3-yl)pyrazolo[1,5-a]pyrimidine (Compound 896). LCMS: rt 6.03 min (A), MS (m/e) 331 MH$^+$.

Ethyl 5-(2-(4-fluoro-3-methylphenyl)pyridin-3-yl)pyrazolo[1,5-a]pyrimidine-3-carboxylate (Compound 897). $^1$H NMR (300 MHz, DMSO-d$_6$) δ 8.86 (ddd, J=4.8, 1.7, 0.6 Hz, 1H), 8.81 (dd, J=4.4, 0.6 Hz, 1H), 8.44 (s, 1H), 8.12 (ddd, J=7.8, 1.7, 0.6 Hz, 1H), 7.61 (dd, J=7.7, 4.7 Hz, 1H), 7.38- 7.25 (m, 2H), 6.94-6.85 (m, 2H), 4.27 (q, J=7.0 Hz, 2H), 2.08 (s, 3H), 1.29 (t, J=7.0 Hz, 3H). LCMS: rt6.88 min (A), purity 99%, MS (m/e) 376 MH$^+$.

Ethyl 5-(2-(3-Chloro-4-fluorophenyl)pyridin-3-yl)pyrazolo[1,5-a]pyrimidine-3-carboxylate (Compound 898). $^1$H NMR (300 MHz, DMSO-d$_6$) δ 9.15 (d, J=7.2 Hz, 1H), 8.82 (dd, J=4.7, 1.7 Hz, 1H), 8.62 (s, 1H), 8.21 (dd, J=7.8, 1.7 Hz, 1H), 7.73 (dd, J=7.3, 2.2 Hz, 1H), 7.64 (dd, J=7.9, 4.8 Hz, 1H), 7.28 (t, J=8.9 Hz, 1H), 7.23-7.16 (m, 1H), 7.00 (d, J=7.3 Hz, 1H), 4.25 (q, J=7.1 Hz, 2H), 1.97 (s, 1H), 1.27 (t, J=7.1 Hz, 3H). LCMS: rt 7.38 min (A), purity 95%, MS (m/e) 397 MH$^+$.

5-(2-(3-Chloro-4-fluorophenyl)pyridin-3-yl)-N-(1-methylpiperidin-4-yl)pyrazolo[1,5-a]pyrimidine-3-carboxamide (Compound 899). $^1$H NMR (300 MHz, DMSO-d$_6$) δ 9.25 (d, J=7.3 Hz, 1H), 8.83 (dd, J=4.8, 1.7 Hz, 1H), 8.55 (s, 1H), 8.27 (dd, J=7.9, 1.7 Hz, 1H), 7.76 (dd, J=7.2, 2.2 Hz, 1H), 7.66 (dd, J=7.8, 4.8 Hz, 1H), 7.58 (d, J=7.7 Hz, 1H), 7.28 (t, J=8.9 Hz, 1H), 7.12 (d, J=7.3 Hz, 1H), 3.86-3.66 (m, 1H), 2.67 (d, J=11.7 Hz, 2H), 2.21-2.14 (m, 5H), 1.77 (d, J=13.1 Hz, 2H), 1.52-1.33 (m, 2H). LCMS: rt 3.48 min (B), purity 97%, MS (m/e) 465 MH$^+$.

5-(2-(3-Chloro-4-fluorophenyl)pyridin-3-yl)pyrazolo[1,5-a]pyrimidine-3-carbonitrile (Compound 900). $^1$H NMR (300 MHz, DMSO-d$_6$) δ 9.21 (dd, J=7.3, 2.6 Hz, 1H), 8.89-8.77 (m, 2H), 8.31-8.17 (m, 1H), 7.79-7.71 (m, 1H), 7.69-7.59 (m, 1H), 7.29 (t, J=8.9 Hz, 1H), 7.24-7.14 (m, 1H), 7.04 (dd, J=7.3, 2.7 Hz, 1H). LCMS: rt7.05 min (B), purity 99%, MS (m/e) 350 MH$^+$.

5-(2-(4-Fluoro-3-methylphenyl)pyridin-3-yl)pyrazolo[1,5-a]pyrimidine-3-carbonitrile (Compound 901). $^1$H NMR (300 MHz, DMSO-d$_6$) δ 9.15 (d, J=7.3 Hz, 1H), 8.86-8.76 (m, 2H), 8.21 (dd, J=7.9, 1.7 Hz, 1H), 7.66-7.53 (m, 3H), 7.06-6.98 (m, 1H), 6.87 (d, J=7.3 Hz, 1H), 2.20 (s, 3H). LCMS: rt6.80 min (B), purity 99%, MS (m/e) 330 MH$^+$ 4-(2-(4-Fluoro-3-methylphenyl)pyridin-3-yl)-2-methoxypyrimidine (Compound 902). $^1$H NMR (300 MHz, DMSO-d$_6$): δ 8.74 (dd, J=4.8, 1.7 Hz, 1H), 8.48 (d, J=5.1 Hz, 1H), 8.08 (dd, J=7.8, 1.7 Hz, 1H), 7.54 (dd, J=7.8, 4.8 Hz, 1H), 7.34 (dd, J=7.6, 2.1 Hz, 0H), 7.11-6.98 (m, 2H), 6.90 (d, J=5.1 Hz, 1H), 3.77 (s, 3H), 2.18 (app d, J=2.1 Hz, 2H). $^{19}$F NMR (282 MHz, DMSO-d$_6$): δ −118.09 (q, J=8.0, 7.5 Hz). LCMS: rt5.04 min (B), purity 99%, MS (m/e) 296 (MH$^+$).

4-(2-(4-Fluoro-3-methylphenyl)pyridin-3-yl)-N-(3,4,5-trimethoxyphenyl)pyrimidin-2-amine (Compound 903). $^1$H NMR (300 MHz, DMSO-d$_6$): δ 9.58 (s, 1H), 8.73 (dd, J=4.7, 1.7 Hz, 1H), 8.31 (d, J=5.1 Hz, 1H), 8.16-8.08 (m, 1H), 7.53 (dd, J=7.8, 4.7 Hz, 1H), 7.42 (dd, J=7.0, 2.3 Hz, 1H), 7.19 (s, 2H), 7.13-6.99 (m, 2H), 6.45 (d, J=5.0 Hz, 1H), 3.70 (s, 6H), 3.59 (s, 3H), 2.19 (s, 3H). $^{19}$F NMR (282 MHz, DMSO-d$_6$): δ −117.92 (d, J=7.5 Hz). LCMS: rt6.14 min (B), purity 99%, MS (m/e) 447 (MH$^+$).

4-(2-(4-Fluoro-3-methylphenyl)pyridin-3-yl)-N-(4-morpholinophenyl)pyrimidin-2-amine (Compound 904). LCMS: rt5.17 min (A), purity 99%, MS (m/e) 442 (MH$^+$).

4-(2-(4-Fluoro-3-methylphenyl)pyridin-3-yl)-N-(3-morpholinophenyl)pyrimidin-2-amine (Compound 905). LCMS: rt5.90 min (A), purity 99%, MS (m/e) 442 (MH$^+$).

4-((4-(2-(4-Fluoro-3-methylphenyl)pyridin-3-yl)pyrimidin-2-yl)amino)benzenesulfonamide (Compound 906). LCMS: rt5.43 min (A), purity 99%, MS (m/e) 436 (MH$^+$).

3-((4-(2-(4-Fluoro-3-methylphenyl)pyridin-3-yl)pyrimidin-2-yl)amino)benzenesulfonamide (Compound 907). $^1$H NMR (300 MHz, DMSO-d$_6$): δ 10.02 (s, 1H), 8.75 (dd, J=4.8, 1.7 Hz, 1H), 8.42 (d, J=5.1 Hz, 1H), 8.22 (s, 1H), 8.11 (dd, J=7.8, 1.7 Hz, 1H), 7.65 (dt, J=6.4, 2.5 Hz, 1H), 7.54 (dd, J=7.8, 4.8 Hz, 1H), 7.44 (dd, J=7.3, 2.2 Hz, 1H), 7.40-7.31

(m, 2H), 7.27 (s, 2H), 7.17-6.95 (m, 2H), 6.67 (d, J=5.1 Hz, 1H), 2.20 (s, 3H). $^{19}$F NMR (282 MHz, DMSO-d$_6$): δ −117.92. LCMS:rt 5.58 min (A), purity 99%, MS (m/e) 436 (MH$^+$).

4-(2-(4-Fluoro-3-methylphenyl)pyridin-3-yl)-N-(4-(piperazin-1-yl)phenyl)pyrimidin-2-amine (Compound 908). LCMS: rt4.73 min (A), purity 99%, MS (m/e) 441 (MH$^+$).

4-(2-(4-Fluoro-3-methylphenyl)pyridin-3-yl)-N-(6-(piperazin-1-yl)pyridin-3-yl)pyrimidin-2-amine (Compound 909). LCMS: rt4.60 min (A), purity 99%, MS (m/e) 442 (MH$^+$).

5-(2-(4-Fluoro-3-methylphenyl)pyridin-3-yl)pyrazolo[1,5-a]pyrimidine (Compound 910). LCMS: rt5.41 min (A), purity 99%, MS (m/e) 305 (MH$^+$).

5-(2-(m-Tolyl)pyridin-3-yl)pyrazolo[1,5-a]pyrimidine (Compound 911). $^1$H NMR (300 MHz, DMSO-d$_6$): δ 8.90 (dd, J=7.3, 0.9 Hz, 1H), 8.76 (dd, J=4.7, 1.7 Hz, 1H), 8.22 (d, J=2.3 Hz, 1H), 8.12 (dd, J=7.8, 1.7 Hz, 1H), 7.54 (dd, J=7.8, 4.8 Hz, 1H), 7.33 (s, 1H), 7.15 (dd, J=3.9, 1.5 Hz, 2H), 7.01 (dd, J=5.1, 1.5 Hz, 1H), 6.75 (dd, J=2.3, 0.9 Hz, 1H), 6.53 (d, J=7.3 Hz, 1H), 2.25 (s, 3H).LCMS: rt4.90 min (A), purity 99%, MS (m/e) 287 (MH$^+$).

5-(2-(3-Cyclopropylphenyl)pyridin-3-yl)pyrazolo[1,5-a]pyrimidine (Compound 912). LCMS: rt5.51 min (A), purity 99%, MS (m/e) 313 (MH$^+$).

5-(2-(3-(Trifluoromethyl)phenyl)pyridin-3-yl)pyrazolo[1,5-a]pyrimidine. (Compound 913). LCMS: rt6.71 min (A), purity 99%, MS (m/e) 341 (MH$^+$).

5-(2-(3-Chloro-4-fluorophenyl)pyridin-3-yl)pyrazolo[1,5-a]pyrimidine (Compound 914). $^1$H NMR (300 MHz, DMSO-d$_6$): δ 9.00 (d, J=7.2 Hz, 1H), 8.79 (dd, J=4.8, 1.7 Hz, 1H), 8.23 (d, J=2.4 Hz, 1H), 8.15 (dd, J=7.8, 1.7 Hz, 1H), 7.68 (dd, J=7.4, 2.1 Hz, 1H), 7.59 (dd, J=7.9, 4.9 Hz, 1H), 7.32 (t, J=8.9 Hz, 1H), 7.25-7.10 (m, 1H), 6.73 (d, J=7.1 Hz, 2H). $^{19}$F NMR (282 MHz, DMSO-d$_6$): δ −116.52-−116.67 (m). LCMS: rt 6.68 min (A), purity 99%, MS (m/e) 325 (MH$^+$).

5-(2-(2,4,5-Trifluorophenyl)pyridin-3-yl)pyrazolo[1,5-a]pyrimidine (Compound 915). LCMS: rt 6.66 min (A), purity 99%, MS (m/e) 327 (MH$^+$).

5-(2-(3-Chlorophenyl)pyridin-3-yl)pyrazolo[1,5-a]pyrimidine (Compound 916). $^1$H NMR (300 MHz, DMSO-d$_6$): δ 8.98 (dd, J=7.3, 0.9 Hz, 1H), 8.79 (dd, J=4.8, 1.7 Hz, 1H), 8.23 (d, J=2.4 Hz, 1H), 8.15 (dd, J=7.8, 1.7 Hz, 1H), 7.64-7.54 (m, 2H), 7.41 (ddd, J=8.0, 2.2, 1.1 Hz, 1H), 7.29 (t, J=7.8 Hz, 1H), 7.16 (dt, J=7.7, 1.4 Hz, 1H), 6.74 (dd, J=2.4, 0.9 Hz, 1H), 6.69 (d, J=7.3 Hz, 1H).LCMS: rt 4.16 min (A), purity 99%, MS (m/e) 307 (MH$^+$).

5-(2-(5-Chloro-2-fluorophenyl)pyridin-3-yl)pyrazolo[1,5-a]pyrimidine (Compound 917). LCMS: rt 6.86 min (A), purity 99%, MS (m/e) 325 (MH$^+$).

5-(2-(5-Chloro-2,4-difluorophenyl)pyridin-3-yl)pyrazolo[1,5-a]pyrimidine (Compound 918). LCMS: rt 7.18 min (A), purity 99%, MS (m/e) 343 (MH$^+$).

4-(2-(4-Fluoro-3-methylphenyl)pyridin-3-yl)pyrimidin-2-amine (Compound 919). $^1$H NMR (300 MHz, DMSO-d$_6$): δ 8.69 (dd, J=4.7, 1.7 Hz, 1H), 8.07 (d, J=5.0 Hz, 1H), 7.93 (dd, J=7.8, 1.7 Hz, 1H), 7.47 (dd, J=7.8, 4.8 Hz, 1H), 7.38 (dd, J=7.4, 1.6 Hz, 1H), 7.18-6.95 (m, 2H), 6.70 (s, 2H), 6.20 (d, J=5.0 Hz, 1H), 2.19 (s, 3H). $^{19}$F NMR (282 MHz, DMSO-d$_6$): δ −118.16 (q, J=7.7 Hz).LCMS: rt4.40 min (A), purity 99%, MS (m/e) 281 MH$^+$.

5-(2-(2,5-Dichlorophenyl)pyridin-3-yl)pyrazolo[1,5-a]pyrimidine (Compound 920). LCMS: rt 7.06 min (A), purity 99%, MS (m/e) 342 (MH$^+$).

5-(2-(3-(Difluoromethoxy)phenyl)pyridin-3-yl)pyrazolo[1,5-a]pyrimidine (Compound 921). $^1$H NMR (300 MHz, DMSO-d$_6$): δ 8.95 (dd, J=7.3, 0.9 Hz, 1H), 8.80 (dd, J=4.7, 1.7 Hz, 1H), 8.22 (s, 1H), 8.14 (dd, J=7.8, 1.7 Hz, 1H), 7.59 (dd, J=7.8, 4.8 Hz, 1H), 7.43-7.28 (m, 1H), 7.21 (t, J=2.1 Hz, 1H), 7.19-7.11 (m, 3H), 6.73 (dd, J=2.3, 0.9 Hz, 1H), 6.64 (d, J=7.3 Hz, 1H). $^{19}$F NMR (282 MHz, DMSO-d$_6$): δ −82.40 (d, J=73.8 Hz). LCMS: rt.4.95 min (B), purity 99%, MS (m/e) 338 MH$^+$.

6-(2-(4-Fluoro-3-methylphenyl)pyridin-3-yl)-[1,2,4]triazolo[1,5-a]pyrimidine (Compound 922). LCMS: rt4.60 min (A), purity 99%, MS (m/e) 306 (MH$^+$).

6-(2-(m-Tolyl)pyridin-3-yl)-[1,2,4]triazolo[1,5-a]pyrimidine (Compound 923). LCMS: rt4.13 min (A), purity 99%, MS (m/e) 288 (MH$^+$).

6-(2-(3-Cyclopropylphenyl)pyridin-3-yl)-[1,2,4]triazolo[1,5-a]pyrimidine (Compound 924). LCMS: rt4.81 min (A), purity 99%, MS (m/e) 314 (MH$^+$).

6-(2-(3-(Trifluoromethyl)phenyl)pyridin-3-yl)-[1,2,4]triazolo[1,5-a]pyrimidine (Compound 925). LCMS: rt5.95 min (A), purity 99%, MS (m/e) 342 (MH$^+$).

6-(2-(4-Fluoro-3-methylphenyl)pyridin-3-yl)imidazo[1,2-a]pyrimidine (Compound 926). LCMS: rt3.75 min (A), purity 99%, MS (m/e) 305 (MH$^+$).

6-(2-(m-Tolyl)pyridin-3-yl)imidazo[1,2-a]pyrimidine (Compound 927). LCMS: rt3.25 min (A), purity 99%, MS (m/e) 287 (MH$^+$).

6-(2-(3-Cyclopropylphenyl)pyridin-3-yl)imidazo[1,2-a]pyrimidine (Compound 928). LCMS: rt3.96 min (A), purity 99%, MS (m/e) 313 (MH$^+$).

6-(2-(3-(Trifluoromethyl)phenyl)pyridin-3-yl)imidazo[1,2-a]pyrimidine (Compound 929). LCMS: rt4.73 min (A), purity 99%, MS (m/e) 341 (MH$^+$).

6-(2-(3-Chloro-4-fluorophenyl)pyridin-3-yl)-7-methylimidazo[1,2-a]pyridine (Compound 930). LCMS: rt 4.90 min (A), purity 99%, MS (m/e) 338 MH$^+$.

6-(2-(3-Chlorophenyl)pyridin-3-yl)-7-methylimidazo[1,2-a]pyridine (Compound 931). $^1$H NMR (300 MHz, DMSO-d$_6$): δ 8.87 (d, J=0.8 Hz, 1H), 8.84 (dd, J=4.8, 1.7 Hz, 1H), 8.22 (d, J=2.2 Hz, 1H), 8.14 (d, J=2.1 Hz, 1H), 7.90 (dd, J=7.7, 1.7 Hz, 1H), 7.80 (s, 1H), 7.61 (dd, J=7.8, 4.8 Hz, 1H), 7.53 (t, J=1.9 Hz, 1H), 7.36 (dt, J=7.6, 2.0 Hz, 1H), 7.23 (t, J=7.7 Hz, 1H), 7.18 (dt, J=7.8, 1.6 Hz, 1H), 2.00 (s, 3H). LCMS: rt 4.58 min (A), purity 99%, MS (m/e) 320 MH$^+$.

6-(2-(5-Chloro-2-fluorophenyl)pyridin-3-yl)-7-methylimidazo[1,2-a]pyridine (Compound 932). LCMS: rt 4.86 min (A), purity 99%, MS (m/e) 338 MH$^+$.

6-(2-(5-Chloro-2,4-difluorophenyl)pyridin-3-yl)-7-methylimidazo[1,2-a]pyridine (Compound 933). LCMS: rt 5.11 min (A), purity 99%, MS (m/e) 356 MH$^+$.

6-(2-(4-Fluoro-3-methylphenyl)pyridin-3-yl)imidazo[1,2-b]pyridazine (Compound 934). LCMS: rt 4.61 min (A), purity 99%, MS (m/e) 305 MH$^+$.

6-(2-(3-Chloro-4-fluorophenyl)pyridin-3-yl)imidazo[1,2-b]pyridazine (Compound 935). $^1$H NMR (300 MHz, DMSO-d$_6$): δ 8.76 (dd, J=4.8, 1.7 Hz, 1H), 8.26 (dt, J=1.2, 0.6 Hz, 1H), 8.08 (ddd, J=7.8, 1.7, 0.5 Hz, 1H), 7.97 (dt, J=9.4, 0.6 Hz, 1H), 7.76 (dd, J=1.2, 0.5 Hz, 1H), 7.62 (dd, J=7.3, 2.3 Hz, 1H), 7.56 (ddd, J=7.8, 4.8, 0.5 Hz, 1H), 7.25 (dd, J=9.3, 8.6 Hz, 1H), 7.14 (dddd, J=8.6, 4.8, 2.2, 0.5 Hz, 1H), 6.89 (dd, J=9.5, 0.5 Hz, 1H). $^{19}$F NMR (282 MHz, DMSO-d$_6$): δ −116.49 (td, J=8.3, 4.9 Hz). LCMS: rt5.13 min (A), purity 99%, MS (m/e) 325 MH$^+$.

6-(2-(3-Chlorophenyl)pyridin-3-yl)imidazo[1,2-b]pyridazine (Compound 936). LCMS: rt4.83 min (A), purity 99%, MS (m/e) 307 MH$^+$.

6-(2-(5-Chloro-2-fluorophenyl)pyridin-3-yl)imidazo[1,2-b]pyridazine (Compound 937). LCMS: rt5.03 min (A), purity 99%, MS (m/e) 325 MH$^+$.

6-(2-(5-Chloro-2,4-difluorophenyl)pyridin-3-yl)imidazo[1,2-b]pyridazine (Compound 938). LCMS: rt5.28 min (A), purity 99%, MS (m/e) 343 MH+.

8-Fluoro-6-(2-(4-fluoro-3-methylphenyl)pyridin-3-yl)-[1,2,4]triazolo[1,5-a]pyridine (Compound 939). LCMS: rt5.45 min (A), purity 99%, MS (m/e) 323 MH+.

6-(2-(3-Chloro-4-fluorophenyl)pyridin-3-yl)-8-fluoro-[1,2,4]triazolo[1,5-a]pyridine (Compound 940). $^1$H NMR (300 MHz, DMSO-$d_6$): δ 8.95 (t, J=1.0 Hz, 1H), 8.75 (ddd, J=4.8, 1.7, 0.6 Hz, 1H), 8.61 (d, J=0.6 Hz, 1H), 8.04 (ddd, J=7.8, 1.7, 0.6 Hz, 1H), 7.70 (ddd, J=7.3, 1.9, 0.6 Hz, 1H), 7.58 (ddd, J=7.8, 4.8, 0.6 Hz, 1H), 7.42 (ddd, J=11.1, 1.4, 0.6 Hz, 1H), 7.35-7.17 (m, 2H). $^{19}$F NMR (282 MHz, DMSO-$d_6$): δ −116.75 (td, J=8.1, 5.6 Hz), −130.02 (d, J=11.2 Hz).LCMS: rt6.55 min (A), purity 99%, MS (m/e) 343 MH+.

6-(2-(3-Chlorophenyl)pyridin-3-yl)-8-fluoro-[1,2,4]triazolo[1,5-a]pyridine (Compound 941). LCMS: rt6.13 min (A), purity 99%, MS (m/e) 325 MH+.

6-(2-(5-Chloro-2-fluorophenyl)pyridin-3-yl)-8-fluoro-[1,2,4]triazolo[1,5-a]pyridine (Compound 942). LCMS: rt 6.75 min (A), purity 99%, MS (m/e) 343 MH+.

7-Chloro-6-(2-(4-fluoro-3-methylphenyl)pyridin-3-yl)imidazo[1,2-a]pyridine (Compound 943). LCMS: rt 4.56 min (A), purity 99%, MS (m/e) 338 MH+.

7-Chloro-6-(2-(3-chloro-4-fluorophenyl)pyridin-3-yl)imidazo[1,2-a]pyridine (Compound 944). $^1$H NMR (300 MHz, DMSO-$d_6$): δ 8.99 (d, J=0.8 Hz, 1H), 8.82 (dd, J=4.8, 1.7 Hz, 1H), 8.19 (dd, J=1.8, 0.8 Hz, 1H), 8.08 (t, J=0.8 Hz, 1H), 8.04 (t, J=1.4 Hz, 1H), 7.92 (dd, J=7.8, 1.7 Hz, 1H), 7.73-7.67 (m, 1H), 7.66-7.56 (m, 1H), 7.26 (app d, J=1.3 Hz, 1H), 7.24 (app q, J=1.0 Hz, 1H). $^{19}$F NMR (282 MHz, DMSO-$d_6$): δ −116.57 (q, J=7.0 Hz). LCMS: rt 5.20 min (A), purity 99%, MS (m/e) 359 MH+.

7-Chloro-6-(2-(3-chlorophenyl)pyridin-3-yl)imidazo[1,2-a]pyridine (Compound 945). LCMS: rt 4.91 min (A), purity 99%, MS (m/e) 341 MH+.

7-Chloro-6-(2-(5-chloro-2-fluorophenyl)pyridin-3-yl)imidazo[1,2-a]pyridine (Compound 946). LCMS: rt5.03 min (A), purity 99%, MS (m/e) 359 MH+.

6-(2-(4-Fluoro-3-methylphenyl)pyridin-3-yl)imidazo[1,2-b]pyridazine-3-carbonitrile (Compound 947). $^1$H NMR (300 MHz, DMSO-$d_6$): δ 8.78 (ddd, J=4.8, 1.7, 0.8 Hz, 1H), 8.55 (s, 1H), 8.15 (dd, J=9.5, 0.9 Hz, 1H), 8.10 (ddd, J=7.8, 1.7, 0.8 Hz, 1H), 7.59-7.52 (m, 2H), 7.41 (dd, J=7.7, 2.2 Hz, 1H), 7.08 (dd, J=9.5, 0.9 Hz, 1H), 6.95 (dd, J=9.6, 8.5 Hz, 1H), 2.13 (s, 3H). $^{19}$F NMR (282 MHz, DMSO-$d_6$): δ −117.44 (s). LCMS: rt 5.34 min (B), purity 99%, MS (m/e) 330 MH+.

6-(2-(3-Chloro-4-fluorophenyl)pyridin-3-yl)imidazo[1,2-b]pyridazine-3-carbonitrile (Compound 948). LCMS: rt 5.59 min (B), purity 99%, MS (m/e) 350 MH+.

6-(2-(3-Chlorophenyl)pyridin-3-yl)imidazo[1,2-b]pyridazine-3-carbonitrile (Compound 949). LCMS: rt 5.43 min (B), purity 99%, MS (m/e) 332 MH+.

6-(2-(5-Chloro-2-fluorophenyl)pyridin-3-yl)imidazo[1,2-b]pyridazine-3-carbonitrile (Compound 950). LCMS: rt 5.34 min (B), purity 99%, MS (m/e) 350 MH+.

6-(2-(5-Chloro-2,4-difluorophenyl)pyridin-3-yl)imidazo[1,2-b]pyridazine-3-carbonitrile (Compound 951). LCMS: rt 5.56 min (B), purity 99%, MS (m/e) 368 MH+.

6-(2-(4-Fluoro-3-methylphenyl)pyridin-3-yl)-[1,2,4]triazolo[1,5-b]pyridazine (Compound 952). LCMS: rt 5.68 min (A), purity 99%, MS (m/e) 306 MH+.

6-(2-(3-Chloro-4-fluorophenyl)pyridin-3-yl)-[1,2,4]triazolo[1,5-b]pyridazine (Compound 953). $^1$H NMR (300 MHz, DMSO-$d_6$): δ 8.84 (dd, J=4.8, 1.7 Hz, 1H), 8.70 (s, 1H), 8.34 (d, J=9.3 Hz, 1H), 8.19 (dd, J=7.8, 1.7 Hz, 1H), 7.71 (dd, J=7.2, 2.1 Hz, 1H), 7.65 (dd, J=7.8, 4.8 Hz, 1H), 7.39 (d, J=9.4 Hz, 1H), 7.28 (dd, J=9.3, 8.5 Hz, 1H), 7.19 (ddd, J=8.6, 4.8, 2.2 Hz, 1H). $^{19}$F NMR (282 MHz, DMSO-$d_6$): δ −116.26 (ddd, J=9.3, 7.3, 4.7 Hz). LCMS: rt 6.50 min (A), purity 99%, MS (m/e) 326 MH+.

6-(2-(3-Chlorophenyl)pyridin-3-yl)-[1,2,4]triazolo[1,5-b]pyridazine (Compound 954). LCMS: rt 6.15 min (A), purity 99%, MS (m/e) 308 MH+.

6-(2-(5-Chloro-2-fluorophenyl)pyridin-3-yl)-[1,2,4]triazolo[1,5-b]pyridazine (Compound 955). LCMS: rt 6.46 min (A), purity 99%, MS (m/e) 326 MH+.

6-(2-(5-Chloro-2,4-difluorophenyl)pyridin-3-yl)-[1,2,4]triazolo[1,5-b]pyridazine (Compound 956). LCMS: rt 6.85 min (A), purity 99%, MS (m/e) 344 MH+.

7-(2-(3-Chloro-4-fluorophenyl)pyridin-3-yl)-2-methyl-2H-benzo[e][1,2,4]thiadiazine 1,1-dioxide (Compound 957). LCMS: rt 5.91 min (A), purity 97%, MS (m/e) 402 MH+.

7-(2-(4-Fluoro-3-methylphenyl)pyridin-3-yl)-2-methyl-2H-benzo[e][1,2,4]thiadiazine 1,1-dioxide (Compound 958). $^1$H NMR (300 MHz, DMSO-$d_6$): δ 8.71 (dd, J=4.8, 1.6 Hz, 1H), 8.05 (s, 1H), 7.97 (dd, J=7.8, 1.6 Hz, 1H), 7.68 (d, J=2.1 Hz, 1H), 7.61-7.50 (m, 2H), 7.44 (d, J=8.8 Hz, 1H), 7.37 (ddt, J=7.5, 1.9, 0.8 Hz, 1H), 7.06-6.94 (m, 2H), 3.59 (s, 3H), 2.17 (s, 3H). $^{19}$F NMR (282 MHz, DMSO-$d_6$): δ −117.82 (app s). LCMS: rt4.85 min (A), purity 98%, MS (m/e) 382 MH+.

7-(2-(5-Chloro-2-fluorophenyl)pyridin-3-yl)-2-methyl-2H-benzo[e][1,2,4]thiadiazine 1,1-dioxide (Compound 959). LCMS: rt6.31 min (A), purity 98%, MS (m/e) 402 MH+.

6-(2-(3-Chloro-4-fluorophenyl)pyridin-3-yl)pyrido[3,2-d]pyrimidin-4(3H)-one (Compound 960). $^1$H NMR (300 MHz, DMSO-$d_6$): δ 12.60 (s, 1H), 8.77 (app ddd, J=4.8, 1.7, 0.6 Hz, 1H), 8.16 (s, 1H), 8.10 (app ddd, J=7.8, 1.8, 0.7 Hz, 1H), 7.94 (dd, J=8.6, 0.7 Hz, 1H), 7.65-7.55 (m, 2H), 7.48 (dd, J=8.5, 0.6 Hz, 1H), 7.27 (app t, J=9.0 Hz, 1H), 7.16-7.03 (m, 1H). $^{19}$F NMR (282 MHz, DMSO-$d_6$): δ −116.85 (app td, J=9.0, 8.5, 4.9 Hz).LCMS: rt4.73 min (A), purity 99%, MS (m/e) 353 MH+.

6-(2-(3-(Difluoromethoxy)phenyl)pyridin-3-yl)benzo[d]thiazole (Compound 961). LCMS: rt5.67 min (A), purity 97%, MS (m/e) 355 MH+.

6-(2-(3-(Difluoromethoxy)phenyl)pyridin-3-yl)quinoxaline (Compound 962). LCMS: rt5.23 min (B), purity 96%, MS (m/e) 350 MH+.

6-(2-(3-(Difluoromethoxy)phenyl)pyridin-3-yl)-1-methyl-1H-benzo[d]imidazole (Compound 963). LCMS: rt2.89 min (B), purity 99%, MS (m/e) 352 MH+.

6-(2-(3-Chloro-4-fluorophenyl)pyridin-3-yl)pyrido[3,2-d]pyrimidin-4-amine (Compound 964). $^1$H NMR (300 MHz, DMSO-$d_6$): δ 8.77 (dd, J=4.7, 1.7 Hz, 1H), 8.40 (s, 1H), 8.27 (dd, J=7.8, 1.7 Hz, 1H), 7.94 (app d, J=8.7 Hz, 2H), 7.69-7.54 (m, 3H), 7.52 (d, J=8.7 Hz, 1H), 7.27 (dd, J=9.3, 8.6 Hz, 1H), 7.11 (ddd, J=8.6, 4.7, 2.2 Hz, 1H). $^{19}$F NMR (282 MHz, DMSO-$d_6$): δ −116.92 (ddd, J=9.3, 7.3, 4.7 Hz).LCMS: rt4.61 min (A), purity 99%, MS (m/e) 352 MH+.

5-(2-(3-Chloro-2,4-difluorophenyl)pyridin-3-yl)pyrazolo[1,5-a]pyrimidine (Compound 965). $^1$H NMR (300 MHz, DMSO-$d_6$): δ 9.05 (dd, J=7.3, 1.0 Hz, 1H), 8.82 (dd, J=4.8, 1.7 Hz, 1H), 8.27 (dd, J=7.9, 1.6 Hz, 1H), 8.21 (d, J=2.3 Hz, 1H), 7.67 (dd, J=7.8, 4.7 Hz, 1H), 7.55 (td, J=8.5, 6.3 Hz, 1H), 7.39 (td, J=8.8, 1.6 Hz, 1H), 6.89 (dd, J=7.3, 1.0 Hz, 1H), 6.62 (dd, J=2.3, 0.9 Hz, 1H). $^{19}$F NMR (282 MHz, DMSO-$d_6$): δ −113.03 (ddd, J=9.3, 6.3, 3.6 Hz), −115.55 (dd, J=9.1, 3.3 Hz).LCMS: rt5.27 min (B), purity 99%, MS (m/e) 343 MH+.

6-(2-(3-Chloro-2,4-difluorophenyl)pyridin-3-yl)quinoxaline (Compound 966). LCMS: rt5.63 min (B), purity 99%, MS (m/e) 354 MH+.

6-(2-(3-Chloro-2,4-difluorophenyl)pyridin-3-yl)-1-methyl-1H-benzo[d]imidazole (Compound 967). LCMS: rt3.37 min (B), purity 99%, MS (m/e) 356 MH+.

6-(2-(3-chloro-4-fluorophenyl)pyridin-3-yl)-4-methoxypyrido[3,2-d]pyrimidine (Compound 968). $^1$H NMR (300 MHz, DMSO-$d_6$): δ 8.86 (s, 1H), 8.80 (dd, J=4.7, 1.7 Hz, 1H), 8.17 (d, J=8.8 Hz, 1H), 8.17 (d, J=8.8, 1.7 Hz, 1H), 7.77-7.46 (m, 3H), 7.22 (app t, J=9.2 Hz, 1H), 7.07 (ddd, J=8.6, 4.7, 2.2 Hz, 1H), 4.15 (s, 3H). $^{19}$F NMR (282 MHz, DMSO-$d_6$): δ −116.74 (ddd, J=9.2, 7.2, 4.7 Hz).

6-(2-(3-Chloro-4-fluorophenyl)pyridin-3-yl)-7-methyl-[1,2,4]triazolo[1,5-a]pyridine (Compound 969). LCMS: rt 6.15 min (A), purity 99%, MS (m/e) 339 MH+.

6-(2-(3-Chlorophenyl)pyridin-3-yl)-7-methyl-[1,2,4]triazolo[1,5-a]pyridine (Compound 970). LCMS: rt 5.71 min (A), purity 99%, MS (m/e) 321 MH+.

6-(2-(5-Chloro-2-fluorophenyl)pyridin-3-yl)-7-methyl-[1,2,4]triazolo[1,5-a]pyridine (Compound 971). LCMS: rt 6.20 min (A), purity 99%, MS (m/e) 339 MH+.

6-(2-(5-Chloro-2,4-difluorophenyl)pyridin-3-yl)-7-methyl-[1,2,4]triazolo[1,5-a]pyridine (Compound 972). LCMS: rt 6.50 min (A), purity 99%, MS (m/e) 357 MH+.

4-(6-Methyl-[2,3'-bipyridin]-2'-yl)quinoline (Compound 973). LCMS: rt 2.80 min (B), purity 99%, MS (m/e) 298 (MH+).

6-(2-(3-Chloro-2,4-difluorophenyl)pyridin-3-yl)benzo[d]thiazole) (Compound 974). LCMS: rt6.11 min (B), purity 99%, MS (m/e) 359 MH+.

Example 82

The following additional 2-chloro-3-(hetero)arylpyridine compounds were prepared substantially as described herein.

2-Chloro-3,4'-bipyridine

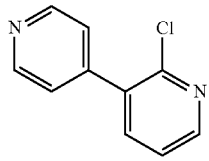 [SMILES: Clc1ncccc1-c1ccncc1]

$^1$H NMR (300 MHz, DMSO-$d_6$): δ 8.68 (d, J=5.7 Hz, 2H), 8.49 (dd, J=4.8, 1.9 Hz, 1H), 7.94 (dd, J=7.6, 1.9 Hz, 1H), 7.56 (dd, J=7.6, 4.8 Hz, 1H), 7.52 (d, J=5.7 Hz, 2H).

4-(2-Chloropyridin-3-yl)quinoline

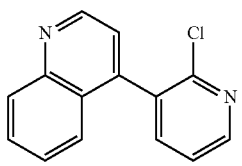 [SMILES: Clc1ncccc1-c1ccnc2ccccc12]

$^1$H NMR (300 MHz, DMSO-$d_6$): δ 9.01 (d, J=4.4 Hz, 1H), 8.60 (dd, J=4.8, 1.9 Hz, 1H), 8.13 (d, J=8.5 Hz, 1H), 7.98 (dd, J=7.5, 1.9 Hz, 1H), 7.81 (ddd, J=8.4, 6.9, 1.4 Hz, 1H), 7.64 (dd, J=7.5, 4.8 Hz, 1H), 7.58 (dd, J=6.9, 1.3 Hz, 1H), 7.51 (d, J=4.4 Hz, 1H), 7.42 (dd, J=8.1, 1.1 Hz, 1H).

2'-Chloro-6-methyl-2,3'-bipyridine

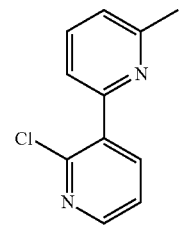

$^1$H NMR (300 MHz, DMSO-$d_6$): δ 8.46 (dd, J=4.8, 2.0 Hz, 1H), 7.99 (dd, J=7.6, 1.9 Hz, 1H), 7.80 (t, J=7.8 Hz, 1H), 7.58-7.47 (m, 2H), 7.31 (d, J=7.9 Hz, 1H), 2.52 (s, 3H).

2-(2-Chloropyridin-3-yl)-1,6-naphthyridine

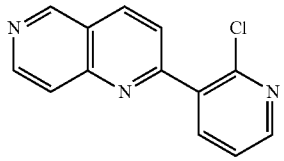 [SMILES: Clc1ncccc1-c1ccc2cnccc2n1]

$^1$H NMR (300 MHz, DMSO-$d_6$): δ 9.48 (d, J=0.9 Hz, 1H), 8.79 (d, J=6.0 Hz, 1H), 8.71 (dd, J=8.6, 0.8 Hz, 1H), 8.57 (ddd, J=4.8, 2.0, 0.7 Hz, 1H), 8.16 (ddd, J=7.6, 1.9, 0.7 Hz, 1H), 8.03 (dd, J=8.5, 0.6 Hz, 1H), 7.96 (d, J=5.9 Hz, 1H), 7.63 (ddd, J=7.6, 4.8, 0.7 Hz, 1H).

2'-Chloro-[3,3'-bipyridin]-6-amine

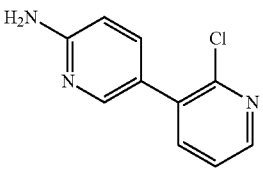 [SMILES: Nc1ccc(-c2cccnc2Cl)cn1]

¹H NMR (300 MHz, DMSO-d₆): δ 8.34 (dd, J=4.8, 1.7 Hz, 1H), 7.99 (d, J=2.6 Hz, 1H), 7.83 (dd, J=7.6, 1.8 Hz, 1H), 7.52 (dd, J=8.6, 2.5 Hz, 1H), 7.46 (dd, J=7.6, 4.7 Hz, 1H), 6.51 (d, J=8.6 Hz, 1H), 6.20 (s, 2H).

6-(2-Chloropyridin-3-yl)-3-methylimidazo[1,2-a]pyridine

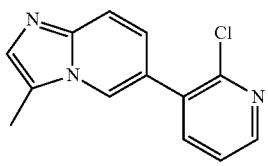 [SMILES: Cc1cnc2ccc(-c3cccnc3Cl)cn12]

¹H NMR (300 MHz, DMSO-d₆): δ 8.47 (dd, J=5.2, 1.9 Hz, 1H), 8.40 (s, 1H), 8.07-7.97 (m, 1H), 7.61 (d, J=9.3 Hz, 1H), 7.56 (dd, J=7.8, 4.6 Hz, 1H), 7.42 (s, 1H), 7.33 (dd, J=9.3, 1.6 Hz, 1H), 2.46 (s, 3H).

6-(2-Chloropyridin-3-yl)-2-methylimidazo[1,2-a]pyridine

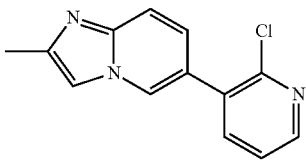 [SMILES: Cc1cn2cc(-c3cccnc3Cl)ccc2n1]

¹H NMR (300 MHz, DMSO-d₆): δ 8.63 (dd, J=1.9, 1.0 Hz, 1H), 8.46 (dd, J=4.8, 1.9 Hz, 1H), 7.97 (dd, J=7.6, 1.9 Hz, 1H), 7.71 (s, 1H), 7.59-7.44 (m, 2H), 7.27 (dd, J=9.3, 1.8 Hz, 1H), 2.34 (s, 3H).

2-(2-Chloropyridin-3-yl)-1,5-naphthyridine

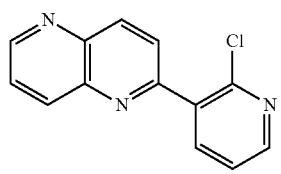 [SMILES: Clc1ncccc1-c1ccc2ncccc2n1]

¹H NMR (300 MHz, DMSO-d₆): δ 9.06 (dd, J=4.2, 1.7 Hz, 1H), 8.60-8.52 (m, 2H), 8.49 (dd, J=8.6, 0.9 Hz, 1H), 8.17 (dd, J=7.6, 2.0 Hz, 1H), 8.12 (dd, J=8.7, 0.6 Hz, 1H), 7.85 (dd, J=8.5, 4.2 Hz, 1H), 7.63 (dd, J=7.6, 4.8 Hz, 1H).

6-(2-Chloropyridin-3-yl)quinoxaline

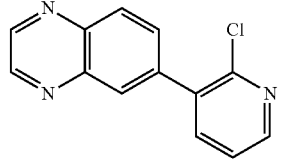 [SMILES: Clc1ncccc1-c1ccc2nccnc2c1]

¹H NMR (300 MHz, DMSO-d₆): δ 9.01 (s, 2H), 8.51 (dd, J=4.7, 1.9 Hz, 1H), 8.25-8.14 (m, 2H), 8.07 (dd, J=7.6, 1.9 Hz, 1H), 7.99 (dd, J=8.7, 1.9 Hz, 1H), 7.59 (dd, J=7.5, 4.8 Hz, 1H).

4-(6-(2-Chloropyridin-3-yl)imidazo[1,2-a]pyridin-3-yl)morpholine

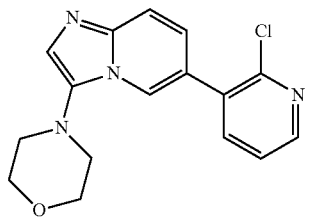 [SMILES: Clc1ncccc1-c1ccc2ncc(N3CCOCC3)n2c1]

¹H NMR (300 MHz, DMSO-d₆): δ 8.47 (dd, J=4.8, 1.9 Hz, 1H), 8.28 (dd, J=1.8, 1.0 Hz, 1H), 8.02 (dd, J=7.5, 1.9 Hz, 1H), 7.61-7.51 (m, 2H), 7.35 (s, 1H), 7.27 (dd, J=9.3, 1.8 Hz, 1H), 3.97-3.47 (m, 4H), 3.13-2.71 (m, 4H).

4-(6-(2-Chloropyridin-3-yl)quinolin-4-yl)morpholine

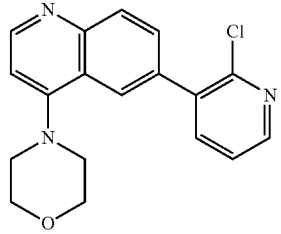 [SMILES: Clc1ncccc1-c1ccc2nccc(N3CCOCC3)c2c1]

¹H NMR (300 MHz, DMSO-d₆): δ 8.75 (d, J=5.0 Hz, 1H), 8.47 (dd, J=4.7, 1.9 Hz, 1H), 8.11 (d, J=2.1 Hz, 1H), 8.07-7.95

(m, 2H), 7.79 (dd, J=8.7, 2.0 Hz, 1H), 7.57 (dd, J=7.6, 4.8 Hz, 1H), 7.05 (d, J=5.0 Hz, 1H), 3.85-3.82 (m, 4H), 3.25-3.12 (m, 4H).

6-(2-Chloropyridin-3-yl)-[1,2,4]triazolo[1,5-a]pyrimidine

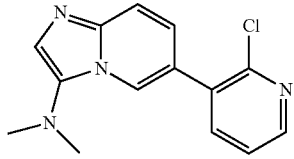 [SMILES: CN(C)c1cnc2ccc(-c3cccnc3Cl)cn12]

¹H NMR (300 MHz, DMSO-d₆): δ 9.70 (d, J=2.4 Hz, 1H), 9.07 (dd, J=2.4 Hz, 1H), 8.77 (s, 1H), 8.55 (dd, J=4.8, 2.0 Hz, 1H), 8.12 (dd, J=7.6, 1.9 Hz, 1H), 7.63 (dd, J=7.6, 4.8 Hz, 1H).

6-(2-Chloropyridin-3-yl)-N,N-dimethylimidazo[1,2-a]pyridin-3-amine

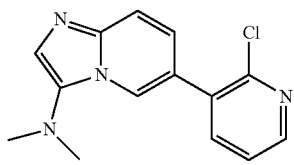 [SMILES: CN(C)c1cnc2ccc(-c3cccnc3Cl)cn12]

¹H NMR (300 MHz, DMSO-d₆): δ 8.46 (dd, J=4.7, 1.9 Hz, 1H), 8.19 (dd, J=1.8, 1.0 Hz, 1H), 8.03 (dd, J=7.5, 1.9 Hz, 1H), 7.60-7.49 (m, 2H), 7.29 (s, 1H), 7.26 (dd, J=9.4, 1.8 Hz, 1H), 2.75 (s, 6H).

5-(2-Chloropyridin-3-yl)pyrazolo[1,5-a]pyrimidine

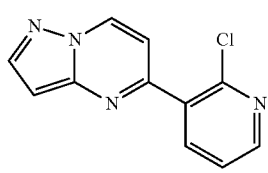 [SMILES: Clc1ncccc1-c1ccn2nccc2n1]

¹H NMR (300 MHz, DMSO-d₆): δ 9.24 (dd, J=7.3, 0.9 Hz, 1H), 8.55 (dd, J=4.8, 2.0 Hz, 1H), 8.30 (d, J=2.4 Hz, 1H), 8.14 (dd, J=7.6, 2.0 Hz, 1H), 7.61 (dd, J=7.6, 4.8 Hz, 1H), 7.37 (d, J=7.3 Hz, 1H), 6.82 (d, J=2.4 Hz, 1H).

6-(2-Chloropyridin-3-yl)-3-(trifluoromethyl)imidazo[1,2-a]pyridine

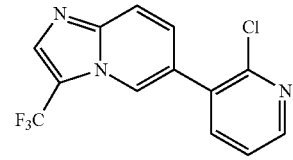 [SMILES: FC(F)(F)c1cnc2ccc(-c3cccnc3Cl)cn12]

¹H NMR (300 MHz, DMSO-d₆): δ 8.65 (s, 1H), 8.50 (dd, J=4.8, 1.9 Hz, 1H), 8.26 (s, 1H), 8.04 (dd, J=7.6, 1.9 Hz, 1H), 7.91 (d, J=9.6 Hz, 1H), 7.67 (d, J=9.4 Hz, 1H), 7.57 (dd, J=7.6, 4.8 Hz, 1H). ¹⁹F NMR (282 MHz, DMSO-d₆) δ −59.81 (s).

6-(2-Chloropyridin-3-yl)imidazo[1,2-a]pyridine-3-carbonitrile

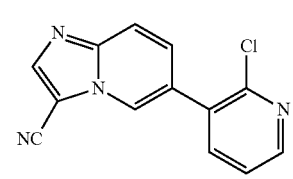 [SMILES: N#Cc1cnc2ccc(-c3cccnc3Cl)cn12]

¹H NMR (300 MHz, DMSO-d₆): δ 8.82 (d, J=1.9 Hz), 8.54-8.45 (m, 2H), 8.07 (dd, J=7.6, 1.9 Hz, 1H), 7.94 (d, J=9.3 Hz, 1H), 7.75 (dd, J=9.3, 1.7 Hz, 1H), 7.58 (dd, J=7.6, 4.8 Hz, 1H).

6-(2-Chloropyridin-3-yl)imidazo[1,2-a]pyrimidine

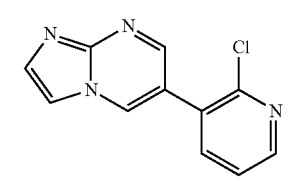 [SMILES: Clc1ncccc1-c1cnc2nccn2c1]

611

$^1$H NMR (300 MHz, DMSO-d$_6$): δ 9.20 (dd, J=2.5, 0.8 Hz, 1H), 8.66 (d, J=2.5 Hz, 1H), 8.51 (dd, J=4.8, 1.9 Hz, 1H), 8.08 (dd, J=7.5, 1.9 Hz, 1H), 7.97 (s, 1H), 7.80 (s, 1H), 7.60 (dd, J=7.6, 4.8 Hz, 1H).

6-(2-Chloropyridin-3-yl)-3-(pyrrolidin-1-yl)imidazo[1,2-a]pyridine

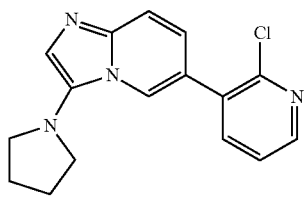 [SMILES: Clc1ncccc1-c1ccc2ncc(N3CCCC3)n2c1]

$^1$H NMR (300 MHz, DMSO-d$_6$): δ 8.46 (dd, J=4.8, 1.9 Hz, 1H), 8.25 (d, J=1.7 Hz, 1H), 8.01 (dd, J=7.6, 1.9 Hz, 1H), 7.54 (dd, J=5.1, 2.5 Hz, 1H), 7.51 (d, J=0.6 Hz, 1H), 7.25 (s, 1H), 7.21 (dd, J=9.3, 1.8 Hz, 1H), 3.16 (t, J=4.3 Hz, 4H), 2.00-1.82 (m, 4H).

(6-(2-Chloropyridin-3-yl)imidazo[1,2-a]pyridin-3-yl)methanol

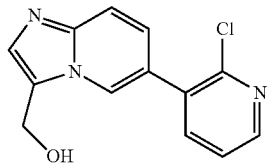 [SMILES: OCc1cnc2ccc(-c3cccnc3Cl)cn12]

$^1$H NMR (300 MHz, DMSO-d$_6$): δ 8.51 (d, J=1.7 Hz, 1H), 8.48 (dd, J=4.8, 1.9 Hz, 1H), 8.01 (dd, J=7.6, 1.9 Hz, 1H), 7.66 (d, J=9.3 Hz, 1H), 7.61-7.53 (m, 2H), 7.40 (dd, J=9.4, 1.8 Hz, 1H), 5.24 (t, J=5.5 Hz, 1H), 4.82 (d, J=5.5 Hz, 2H).

4-((6-(2-Chloropyridin-3-yl)imidazo[1,2-a]pyridin-3-yl)methyl)morpholine

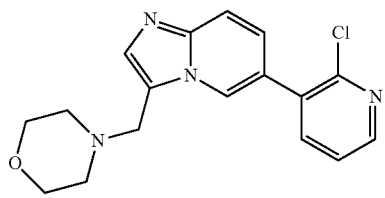 [SMILES: Clc1ncccc1-c1ccc2ncc(CN3CCOCC3)n2c1]

$^1$H NMR (300 MHz, DMSO-d$_6$): δ 8.65 (d, J=1.7 Hz, 1H), 8.48 (dd, J=4.8, 1.9 Hz, 1H), 8.00 (dd, J=7.6, 1.9 Hz, 1H),

612

7.65 (d, J=9.3 Hz, 1H), 7.62-7.54 (m, 2H), 7.37 (dd, J=9.3, 1.8 Hz, 1H), 3.84 (s, 2H), 3.59-3.32 (m, 4H), 2.41-2.29 (m, 4H).

6-(2-Chloropyridin-3-yl)-N-(3,4,5-trimethoxyphenyl)imidazo[1,2-a]pyridine-3-carboxamide

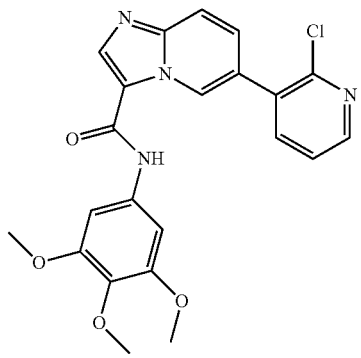 [SMILES: COc1cc(NC(=O)c2cnc3ccc(-c4cccnc4Cl)cn23)cc(OC)c1OC]

$^1$H NMR (300 MHz, DMSO-d$_6$): δ 10.17 (s, 1H), 9.55 (dd, J=1.9, 1.0 Hz, 1H), 8.63 (s, 1H), 8.51 (dd, J=4.8, 1.9 Hz, 1H), 8.06 (dd, J=7.6, 1.9 Hz, 1H), 7.87 (dd, J=9.3, 1.0 Hz, 1H), 7.65 (dd, J=9.3, 1.8 Hz, 1H), 7.59 (dd, J=7.6, 4.8 Hz, 1H), 7.16 (s, 2H), 3.76 (s, 6H), 3.63 (s, 3H).

6-(2-Chloropyridin-3-yl)-3-(3,4,5-trimethoxyphenyl)imidazo[1,2-a]pyridine

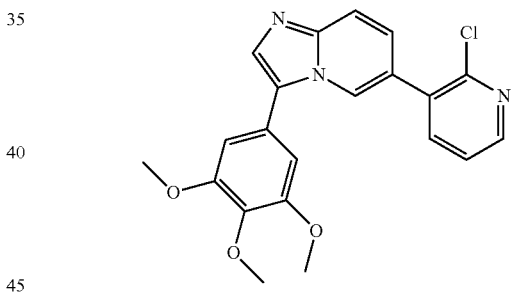

$^1$H NMR (300 MHz, DMSO-d$_6$): δ 8.68 (d, J=1.6 Hz, 1H), 8.44 (dd, J=4.8, 1.9 Hz, 1H), 8.04 (dd, J=7.6, 1.9 Hz, 1H), 7.81 (d, J=0.8 Hz, 1H), 7.74 (d, J=9.3 Hz, 1H), 7.59-7.45 (m, 1H), 7.41 (dd, J=9.3, 1.7 Hz, 1H), 6.95 (s, 2H), 3.83 (s, 6H), 3.70 (s, 3H).

1-(6-(2-Chloropyridin-3-yl)imidazo[1,2-a]pyridin-3-yl)ethan-1-one

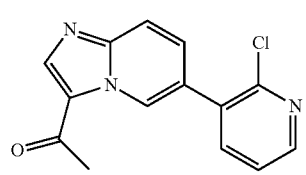 [SMILES: CC(=O)c1cnc2ccc(-c3cccnc3Cl)cn12]

$^1$H NMR (300 MHz, DMSO-d$_6$): δ 9.61 (d, J=1.8 Hz, 1H), 8.69 (s, 1H), 8.51 (dd, J=4.7, 1.9 Hz, 1H), 8.04 (dd, J=7.6, 1.9

Hz, 1H), 7.94 (d, J=9.2 Hz, 1H), 7.77 (dd, J=9.2, 1.9 Hz, 1H), 7.59 (dd, J=7.6, 4.7 Hz, 1H), 2.58 (s, 3H).

7-(2-Chloropyridin-3-yl)imidazo[1,5-a]pyridine

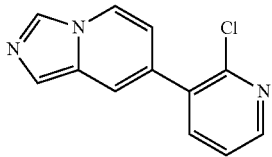 [SMILES: Clc1ncccc1-c1ccn2cncc2c1]

¹H NMR (300 MHz, DMSO-d₆): δ 8.50-8.33 (m, 2H), 7.95 (d, J=6.9 Hz, 1H), 7.67 (s, 1H), 7.52 (dd, J=7.6, 4.7 Hz, 1H), 7.45 (s, 1H), 6.78 (d, J=7.3 Hz, 1H).

Ethyl 5-(2-chloropyridin-3-yl)pyrazolo[1,5-a]pyridine-3-carboxylate

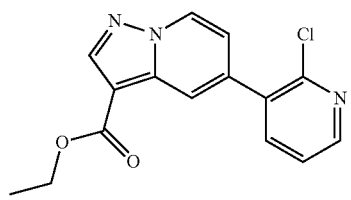 [SMILES: CCOC(=O)c1cnn2ccc(-c3cccnc3Cl)cc12]

¹H NMR (300 MHz, DMSO-d₆): δ 8.98 (dd, J=7.2, 0.9 Hz, 1H), 8.59-8.32 (m, 2H), 8.12 (dd, J=2.1, 1.0 Hz, 1H), 8.05 (dd, J=7.6, 1.8 Hz, 1H), 7.59 (dd, J=7.6, 4.8 Hz, 1H), 7.29 (dd, J=7.1, 2.0 Hz, 1H), 4.29 (q, J=7.1 Hz, 2H), 1.30 (t, J=7.0 Hz, 3H).

Methyl 6-(2-chloropyridin-3-yl)imidazo[1,2-a]pyridine-3-carboxylate

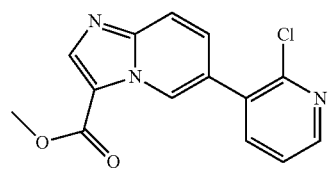 [SMILES: COC(=O)c1cnc2ccc(-c3cccnc3Cl)cn12]

¹H NMR (300 MHz, DMSO-d₆): δ 9.30 (d, J=1.6 Hz, 1H), 8.52 (dd, J=4.8, 1.9 Hz, 1H), 8.38 (s, 1H), 8.05 (dd, J=7.6, 1.9

Hz, 1H), 7.93 (d, J=9.4 Hz, 1H), 7.72 (dd, J=9.2, 1.6 Hz, 1H), 7.59 (dd, J=7.4, 4.7 Hz, 1H), 3.88 (s, 3H).

6-(2-Chloropyridin-3-yl)-N-(3-(2-oxopyrrolidin-1-yl)propyl)imidazo[1,2-a]pyridine-3-carboxamide

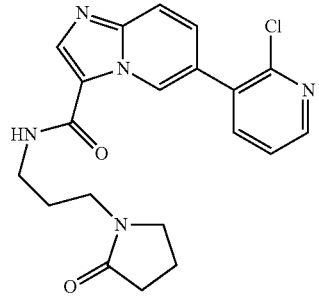 [SMILES: O=C(NCCCN1CCCC1=O)c1cnc2ccc(-c3cccnc3Cl)cn12]

¹H NMR (300 MHz, DMSO-d₆): δ 9.55 (dd, J=1.9, 0.9 Hz, 1H), 8.54 (t, J=5.7 Hz, 1H), 8.50 (dd, J=4.8, 1.9 Hz, 1H), 8.36 (s, 1H), 8.03 (dd, J=7.6, 1.9 Hz, 1H), 7.81 (d, J=9.4 Hz, 1H), 7.58 (dd, J=9.4, 2.0 Hz, 2H), 3.33 (t, J=6.9 Hz, 2H), 3.23 (t, J=7.0 Hz, 4H), 2.19 (t, J=8.0 Hz, 2H), 1.91 (dq, J=15.0, 7.5 Hz, 2H), 1.71 (p, J=7.2 Hz, 2H).

7-(2-Chloropyridin-3-yl)-[1,2,4]triazolo[1,5-a]pyridine

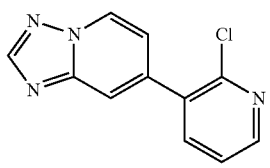 [SMILES: Clc1ncccc1-c1ccn2ncnc2c1]

¹H NMR (300 MHz, DMSO-d₆): δ 9.06 (d, J=6.5 Hz, 1H), 8.58 (s, 1H), 8.51 (dd, J=4.8, 1.9 Hz, 1H), 8.03 (dd, J=7.6, 1.9 Hz, 1H), 7.99 (s, 1H), 7.58 (dd, J=7.6, 4.8 Hz, 1H), 7.34 (dd, J=7.1, 1.8 Hz, 1H).

6-(2-Chloropyridin-3-yl)pyrido[2,3-b]pyrazine

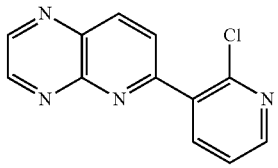 [SMILES: Clc1ncccc1-c1ccc2nccnc2n1]

¹H NMR (300 MHz, DMSO-d₆): δ 9.20 (d, J=1.6 Hz, 1H), 9.12 (d, J=1.6 Hz, 1H), 8.70 (d, J=8.6 Hz, 1H), 8.59 (dd,

J=4.8, 1.9 Hz, 1H), 8.25 (d, J=8.6 Hz, 1H), 8.21 (dd, J=7.6, 1.9 Hz, 1H), 7.65 (dd, J=7.6, 4.8 Hz, 1H).

5-(2-Chloropyridin-3-yl)pyrazolo[1,5-a]pyridine

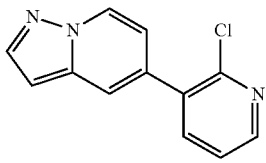 [SMILES: Clc1ncccc1-c1ccn2nccc2c1]

¹H NMR (300 MHz, DMSO-d₆): δ 8.76 (dd, J=7.2, 0.9 Hz, 1H), 8.47 (dd, J=4.8, 1.9 Hz, 1H), 8.06 (d, J=2.2 Hz, 1H), 7.99 (dd, J=7.6, 1.9 Hz, 1H), 7.81 (dd, J=1.9, 0.9 Hz, 1H), 7.55 (dd, J=7.6, 4.8 Hz, 1H), 6.99 (dd, J=7.2, 2.0 Hz, 1H), 6.70 (dd, J=2.2, 0.9 Hz, 1H).

4-(2-Chloropyridin-3-yl)-2-fluorobenzonitrile

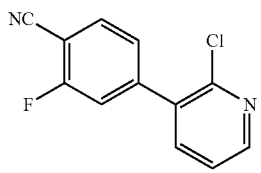 [SMILES: N#Cc1ccc(-c2cccnc2Cl)cc1F]

¹H NMR (300 MHz, DMSO-d₆): δ 8.50 (dd, J=4.8, 1.9 Hz, 1H), 8.05 (dd, J=8.0, 7.0 Hz, 1H), 7.95 (dd, J=7.6, 1.9 Hz, 1H), 7.76 (dd, J=10.4, 1.5 Hz, 1H), 7.62-7.51 (m, 2H). ¹⁹F NMR (282 MHz, DMSO-d₆): δ −108.27 (dd, J=10.5, 7.0 Hz).

5-(2-Chloropyridin-3-yl)-2-fluorobenzonitrile

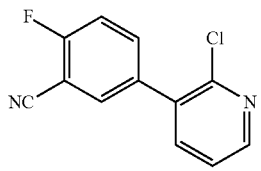 [SMILES: N#Cc1cc(-c2cccnc2Cl)ccc1F]

¹H NMR (300 MHz, DMSO-d₆): δ 8.47 (dd, J=4.8, 1.9 Hz, 1H), 8.11 (dd, J=6.2, 2.2 Hz, 1H), 7.97-7.94 (m, 1H), 7.94-7.90 (m, 1H), 7.65 (t, J=9.1 Hz, 1H), 7.55 (dd, J=7.6, 4.8 Hz, 1H). ¹⁹F NMR (282 MHz, DMSO-d₆): δ −109.00 (dt, J=9.4, 5.7 Hz).

6-(2-Chloropyridin-3-yl)pyrido[2,3-d]pyrimidin-4-amine

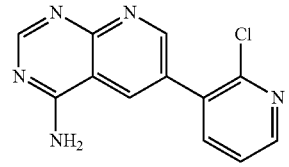 [SMILES: Nc1ncnc2ncc(-c3cccnc3Cl)cc12]

¹H NMR (300 MHz, DMSO-d₆): δ 9.09 (d, J=2.4 Hz, 1H), 8.83 (d, J=2.4 Hz, 1H), 8.56 (s, 1H), 8.52 (dd, J=4.8, 1.9 Hz, 1H), 8.17 (br s, 2H), 8.07 (dd, J=7.6, 1.9 Hz, 1H), 7.62 (dd, J=7.6, 4.8 Hz, 1H).

6-(2-Chloropyridin-3-yl)-7-methylimidazo[1,2-a]pyridine

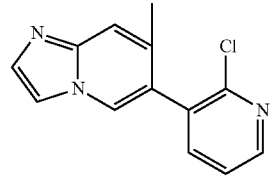 [SMILES: Cc1cc2nccn2cc1-c1cccnc1Cl]

¹H NMR (300 MHz, DMSO-d₆): δ 8.50 (dd, J=4.8, 2.0 Hz, 1H), 8.49 (s, 1H), 7.93 (dd, J=7.5, 2.0 Hz, 1H), 7.85 (d, J=0.9 Hz, 1H), 7.58-7.53 (m, 2H), 7.52 (app s 1H), 2.06 (d, J=0.9 Hz, 3H).

6-(2-Chloropyridin-3-yl)-5-methyl-[1,2,4]triazolo[1,5-a]pyridine

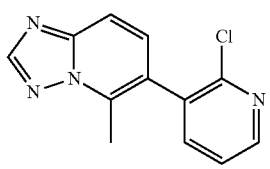 [SMILES: Cc1c(-c2cccnc2Cl)ccc2ncnn12]

¹H NMR (300 MHz, DMSO-d₆): δ 8.59 (s, 1H), 8.53 (dd, J=4.8, 1.9 Hz, 1H), 7.99 (dd, J=7.6, 1.9 Hz, 1H), 7.83 (d, J=9.1 Hz, 1H), 7.62-7.56 (m, 2H), 2.53 (s, 3H).

6-(2-Chloropyridin-3-yl)-7-methyl-[1,2,4]triazolo[1,5-a]pyridine

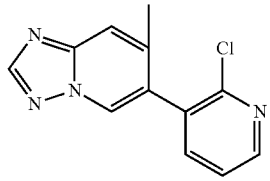 [SMILES: Cc1cc2ncnn2cc1-c1cccnc1Cl]

¹H NMR (300 MHz, DMSO-d₆): δ 8.97 (s, 1H), 8.53 (dd, J=4.8, 1.9 Hz, 1H), 8.48 (s, 1H), 7.97 (dd, J=7.5, 1.9 Hz, 1H), 7.83 (s, 1H), 7.58 (dd, J=7.5, 4.8 Hz, 1H), 2.15 (s, 3H).

6-(2-Chloropyridin-3-yl)imidazo[1,2-b]pyridazine

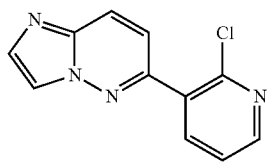 [SMILES: Clc1ncccc1-c1ccc2nccn2n1]

¹H NMR (300 MHz, DMSO-d₆): δ 8.58 (dd, J=4.8, 1.9 Hz, 1H), 8.38 (d, J=0.8 Hz, 1H), 8.25 (d, J=9.4 Hz, 1H), 8.13 (dd, J=7.6, 1.9 Hz, 1H), 7.87 (d, J=0.8 Hz, 1H), 7.62 (dd, J=7.6, 4.8 Hz, 1H), 7.50 (d, J=9.4 Hz, 1H).

6-(2-Chloropyridin-3-yl)-8-fluoro-[1,2,4]triazolo[1,5-a]pyridine

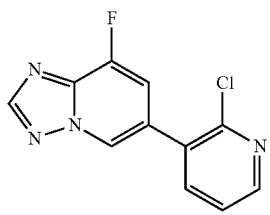 [SMILES: Fc1cc(-c2cccnc2Cl)cn2ncnc12]

¹H NMR (300 MHz, DMSO-d₆): δ 9.14 (d, J=1.4 Hz, 1H), 8.67 (s, 1H), 8.51 (dd, J=4.8, 1.9 Hz, 1H), 8.05 (dd, J=7.6, 1.9 Hz, 1H), 7.90 (dd, J=11.1, 1.4 Hz, 1H), 7.58 (dd, J=7.6, 4.8 Hz, 1H). ¹⁹F NMR (282 MHz, DMSO-d₆): δ −129.92 (d, J=11.2 Hz).

7-Chloro-6-(2-chloropyridin-3-yl)imidazo[1,2-a]pyridine

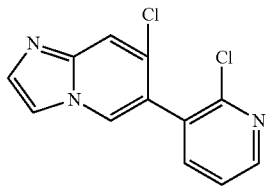 [SMILES: Clc1cc2nccn2cc1-c1cccnc1Cl]

¹H NMR (300 MHz, DMSO-d₆): δ 8.76 (s, 1H), 8.53 (dd, J=4.8, 1.9 Hz, 1H), 8.03-7.95 (m, 2H), 7.67 (d, J=1.2 Hz, 1H), 7.58 (dd, J=7.5, 4.8 Hz, 1H).

6-(2-Chloropyridin-3-yl)quinolin-4-amine

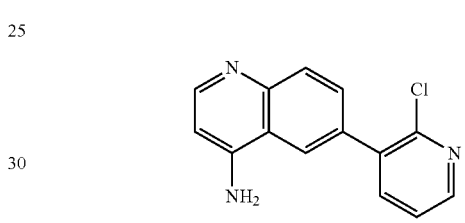

¹H NMR (300 MHz, DMSO-d₆): δ 8.46 (d, J=4.3 Hz, 1H), 8.33 (d, J=5.2 Hz, 1H), 8.24 (s, 1H), 7.97 (d, J=7.2 Hz, 1H), 7.81 (d, J=9.0 Hz, 1H), 7.69 (d, J=9.6 Hz, 1H), 7.56 (dd, J=7.4, 4.9 Hz, 1H), 6.85 (br s, 2H), 6.56 (d, J=5.0 Hz, 1H).

6-(2-Chloropyridin-3-yl)-4-methoxyquinoline

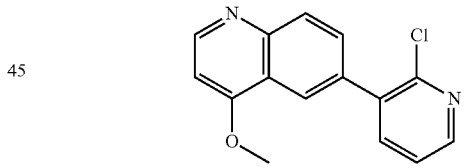

¹H NMR (300 MHz, DMSO-d₆): δ 8.79 (d, J=5.3 Hz, 1H), 8.47 (dd, J=4.8, 1.7 Hz, 1H), 8.17 (d, J=2.1 Hz, 1H), 8.06-7.94 (m, 2H), 7.83 (dd, J=8.7, 2.1 Hz, 1H), 7.55 (dd, J=7.6, 4.8 Hz, 1H), 7.08 (d, J=5.2 Hz, 1H), 4.04 (s, 3H).

6-(2-Chloropyridin-3-yl)quinoline-4-carboxamide

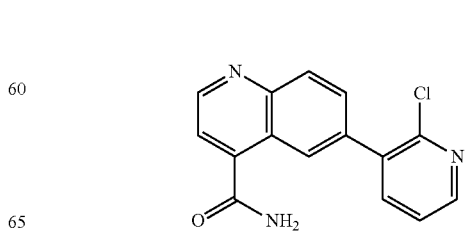

619

$^1$H NMR (300 MHz, DMSO-d$_6$): δ 9.02 (d, J=4.3 Hz, 1H), 8.49 (dd, J=4.7, 1.8 Hz, 1H), 8.29 (d, J=1.8 Hz, 2H), 8.16 (d, J=8.7 Hz, 1H), 8.00 (dd, J=7.5, 1.8 Hz, 1H), 7.92 (dd, J=8.7, 2.0 Hz, 2H), 7.63 (d, J=4.3 Hz, 1H), 7.58 (dd, J=7.6, 4.8 Hz, 1H).

6-(2-Chloropyridin-3-yl)imidazo[1,2-b]pyridazine-3-carbonitrile

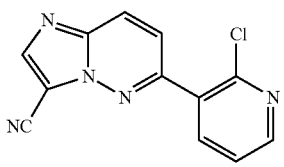 [SMILES: N#Cc1cnc2ccc(-c3cccnc3Cl)nn12]

$^1$H NMR (300 MHz, DMSO-d$_6$): δ 8.67 (s, 1H), 8.62 (dd, J=4.8, 1.9 Hz, 1H), 8.52 (d, J=9.5 Hz, 1H), 8.17 (dd, J=7.6, 1.9 Hz, 1H), 7.90 (d, J=9.5 Hz, 1H), 7.67 (dd, J=7.6, 4.8 Hz, 1H).

6-(2-Chloropyridin-3-yl)-[1,2,4]triazolo[1,5-b]pyridazine

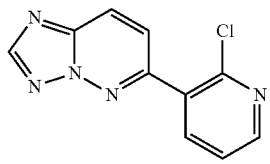 [SMILES: Clc1ncccc1-c1ccc2ncnn2n1]

$^1$H NMR (300 MHz, DMSO-d$_6$): δ 8.77 (s, 1H), 8.61 (d, J=4.8, 1.9 Hz, 1H), 8.59 (d, J=9.4 Hz, 1H), 8.19 (dd, J=7.6, 1.9 Hz, 1H), 8.01 (d, J=9.4 Hz, 1H), 7.66 (dd, J=7.6, 4.8 Hz, 1H).

7-(2-Chloro-5-methoxypyridin-3-yl)-[1,2,4]triazolo[1,5-a]pyridine

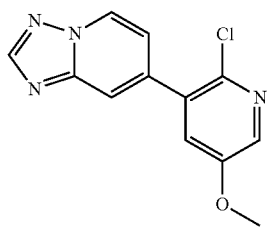 [SMILES: COc1cnc(Cl)c(-c2ccn3ncnc3c2)c1]

620

$^1$H NMR (300 MHz, DMSO-d$_6$): δ 9.06 (dd, J=7.1, 0.9 Hz, 1H), 8.58 (s, 1H), 8.23 (d, J=3.0 Hz, 1H), 8.02 (d, J=1.9 Hz, 1H), 7.67 (d, J=3.0 Hz, 1H), 7.36 (dd, J=7.1, 1.9 Hz, 1H), 3.89 (s, 3H).

7-(2-Chloro-5-fluoropyridin-3-yl)-[1,2,4]triazolo[1,5-a]pyridine

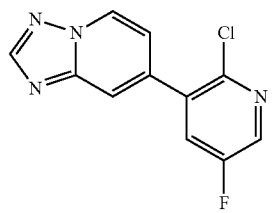 [SMILES: Fc1cnc(Cl)c(-c2ccn3ncnc3c2)c1]

$^1$H NMR (300 MHz, DMSO-d$_6$): δ 9.09 (dd, J=7.1, 0.9 Hz, 1H), 8.60 (s, 1H), 8.59 (d, J=3.0 Hz, 1H), 8.13 (dd, J=8.6, 3.0 Hz, 1H), 8.05 (dd, J=1.8, 0.9 Hz, 1H), 7.38 (dd, J=7.1, 1.8 Hz, 2H).

7-(2-Chloro-5-methylpyridin-3-yl)-[1,2,4]triazolo[1,5-a]pyridine

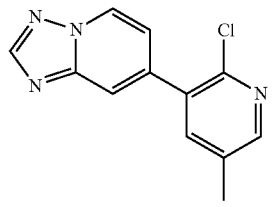 [SMILES: Cc1cnc(Cl)c(-c2ccn3ncnc3c2)c1]

$^1$H NMR (300 MHz, DMSO-d$_6$): δ 9.05 (d, J=8.0 Hz, 1H), 8.57 (s, 1H), 8.34 (d, J=2.3 Hz, 1H), 7.97 (d, J=1.8 Hz, 1H), 7.88 (d, J=2.3 Hz, 1H), 7.33 (dd, J=7.1, 1.9 Hz, 1H), 2.35 (s, 3H).

7-(2-Chloropyridin-3-yl)-1-methylquinoxalin-2(1H)-one

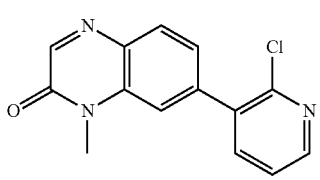 [SMILES: Cn1c(=O)cnc2ccc(-c3cccnc3Cl)cc21]

$^1$H NMR (300 MHz, DMSO-d$_6$): δ 8.49 (dd, J=4.8, 1.9 Hz, 1H), 8.27 (s, 1H), 8.00 (dd, J=7.6, 1.9 Hz, 1H), 7.91 (d, J=8.2

Hz, 1H), 7.68 (d, J=1.7 Hz, 1H), 7.58 (dd, J=7.6, 4.8 Hz, 1H), 7.50 (dd, J=8.2, 1.8 Hz, 1H), 3.62 (s, 4H).

7-(2-Chloropyridin-3-yl)quinoxalin-2(1H)-one

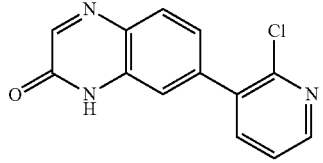 [SMILES: O=c1cnc2ccc(-c3cccnc3Cl)cc2[nH]1]

¹H NMR (300 MHz, DMSO-d₆): δ 12.51 (s, 1H), 8.48 (dd, J=4.7, 1.9 Hz, 1H), 8.21 (s, 1H), 7.94 (dd, J=7.6, 1.9 Hz, 1H), 7.87 (d, J=8.3 Hz, 1H), 7.56 (dd, J=7.6, 4.7 Hz, 1H), 7.42-7.33 (m, 2H).

7-(2-Chloropyridin-3-yl)-2H-benzo[e][1,2,4]thiadiazine 1,1-dioxide

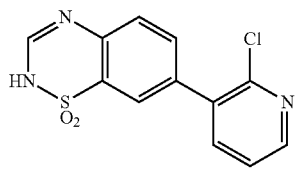 [SMILES: O=S1(=O)NC=Nc2ccc(-c3cccnc3Cl)cc21]

¹H NMR (300 MHz, DMSO-d₆): δ 12.47 (s, 1H), 8.45 (dd, J=4.8, 1.9 Hz, 1H), 8.03 (s, 1H), 7.93 (dd, J=7.6, 1.9 Hz, 1H), 7.88 (d, J=1.9 Hz, 1H), 7.80 (dd, J=8.5, 2.0 Hz, 1H), 7.53 (dd, J=7.6, 4.8 Hz, 1H), 7.43 (d, J=8.5 Hz, 1H).

7-(2-Chloropyridin-3-yl)-2-methyl-2H-benzo[e][1,2,4]thiadiazine 1,1-dioxide

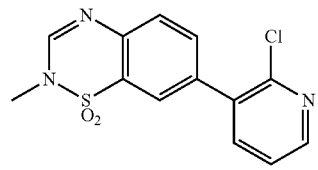 [SMILES: CN1C=Nc2ccc(-c3cccnc3Cl)cc2S1(=O)=O]

¹H NMR (300 MHz, DMSO-d₆): δ 8.47 (dd, J=4.8, 1.9 Hz, 1H), 8.12 (s, 1H), 7.96-7.94 (m, 2H), 7.90 (d, J=2.1 Hz, 1H), 7.61 (d, J=8.8 Hz, 1H), 7.55 (dd, J=7.6, 4.8 Hz, 1H), 3.66 (s, 3H).

Ethyl 5-(2-chloropyridin-3-yl)pyrazolo[1,5-a]pyrimidine-3-carboxylate

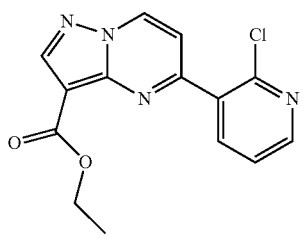 [SMILES: CCOC(=O)c1cnn2ccc(-c3cccnc3Cl)nc12]

¹H NMR (300 MHz, DMSO-d₆): δ 9.40 (d, J=7.3 Hz, 1H), 8.69 (s, 1H), 8.64-8.50 (m, 1H), 8.17 (dd, J=7.7, 1.9 Hz, 1H), 7.76-7.58 (m, 2H), 4.27 (q, J=7.1 Hz, 2H), 1.29 (t, J=7.1 Hz, 3H).

5-(2-Chloropyridin-3-yl)pyrazolo[1,5-a]pyrimidine-3-carbonitrile

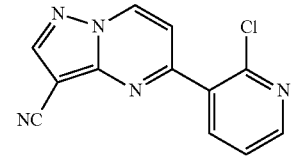 [SMILES: N#Cc1cnn2ccc(-c3cccnc3Cl)nc12]

¹H NMR (300 MHz, DMSO-d₆): δ 9.50 (dd, J=7.2, 0.9 Hz, 1H), 8.90 (s, 1H), 8.60 (dd, J=4.7, 1.9 Hz, 1H), 8.20 (dd, J=7.6, 1.9 Hz, 1H), 7.75 (d, J=7.2 Hz, 1H), 7.65 (dd, J=7.6, 4.8 Hz, 1H).

N-(2'-chloro-[3,3'-bipyridin]-6-yl)acetamide

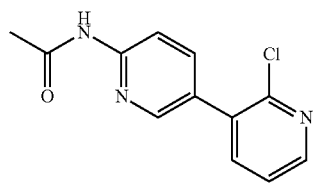 [SMILES: CC(=O)Nc1ccc(-c2cccnc2Cl)cn1]

$^1$H NMR (300 MHz, DMSO-d$_6$) δ 10.64 (s, 1H), 8.44 (dd, J=4.7, 1.9 Hz, 1H), 8.40 (d, J=2.5 Hz, 1H), 8.16 (d, J=8.7 Hz, 1H), 8.02-7.84 (m, 2H), 7.53 (dd, J=7.6, 4.8 Hz, 1H), 2.11 (s, 3H).

5-(2-Chloropyridin-3-yl)thiazolo[5,4-b]pyridin-2-amine

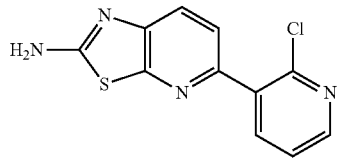 [SMILES: Nc1nc2ccc(-c3cccnc3Cl)nc2s1]

$^1$H NMR (300 MHz, DMSO-d$_6$): δ 8.44 (dd, J=4.7, 1.9 Hz, 1H), 8.04 (dd, J=7.6, 1.9 Hz, 1H), 7.94 (s, 2H), 7.70 (d, J=8.3 Hz, 1H), 7.59 (d, J=8.3 Hz, 1H), 7.52 (dd, J=7.6, 4.7 Hz, 1H).

5-(2-Chloropyridin-3-yl)thiazolo[5,4-b]pyridine

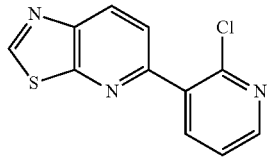 [SMILES: Clc1ncccc1-c1ccc2ncsc2n1]

$^1$H NMR (300 MHz, DMSO-d$_6$): δ 9.63 (s, 1H), 8.61 (d, J=8.5 Hz, 1H), 8.53 (dd, J=4.7, 1.9 Hz, 1H), 8.12 (dd, J=7.6, 1.9 Hz, 1H), 7.94 (d, J=8.5 Hz, 1H), 7.59 (dd, J=7.6, 4.8 Hz, 1H).

Example 83

2-(6-(2-Chloropyridin-3-yl)-1H-indazol-1-yl)acetamide and 2-(6-(2-chloropyridin-3-yl)-2H-indazol-2-yl)acetamide can be prepared as shown in Scheme 33, and as described below:

Scheme 33

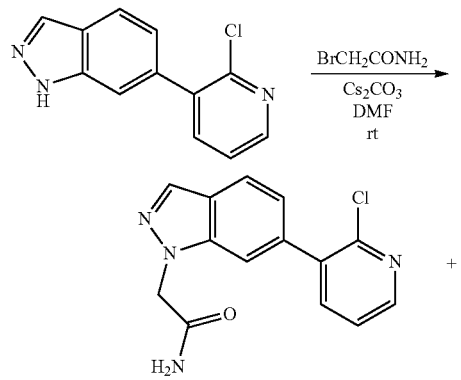

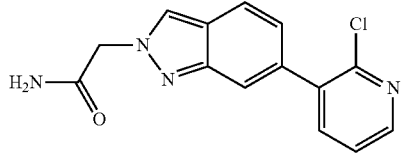

6-(2-Chloropyridin-3-yl)-1H-indazole (0.6 g, 2.6 mmol), 2-bromoacetamide (0.5 g, 3.4 mmol) and Cs$_2$CO$_3$ (1.3 g, 3.9 mmol) in dry DMF (2.5 mL) was stirred under argon in a screw capped vial at room temperature. The reaction mixture was diluted with water after 2 days and the resultant solid was collected by filtration. Individual alkylated indazole regio-isomers were isolated by from the solid by purification (Combiflash® companion System® with RediSep® silica gel column 24 g and 30-50-75% EtOAC/hexanes as an eluting solvent). 2-(6-(2-chloropyridin-3-yl)-1H-indazol-1-yl)acetamide (fast eluted N1-regio-isomer: $^1$H NMR (300 MHz, DMSO-d$_6$): δ 8.45 (dd, J=4.7, 1.9 Hz, 1H), 8.12 (s, 1H), 7.91 (dd, J=7.6, 1.9 Hz, 1H), 7.84 (d, J=8.3 Hz, 1H), 7.71 (s, 1H), 7.54 (dd, J=7.6, 4.7 Hz, 2H), 7.23 (dd, J=8.3, 1.4 Hz, 2H), 5.08 (s, 2H). 2-(6-(2-Chloropyridin-3-yl)-2H-indazol-2-yl)acetamide (late eluted N2-regio-isomer: $^1$H NMR (300 MHz, DMSO-d$_6$): δ 8.43 (dd, J=4.7, 1.9 Hz, 1H), 8.40 (d, J=0.8 Hz, 1H), 7.91 (dd, J=7.5, 1.9 Hz, 1H), 7.80 (dd, J=8.6, 0.8 Hz, 1H), 7.74-7.61 (m, 2H), 7.52 (dd, J=7.6, 4.8 Hz, 1H), 7.35 (s, 1H), 7.10 (dd, J=8.6, 1.4 Hz, 1H), 5.12 (s, 2H).

Example 84

6-Bromo-3-methylimidazo[1,2-a]pyridine can be prepared as shown in Scheme 34, and as described below:

Scheme 34

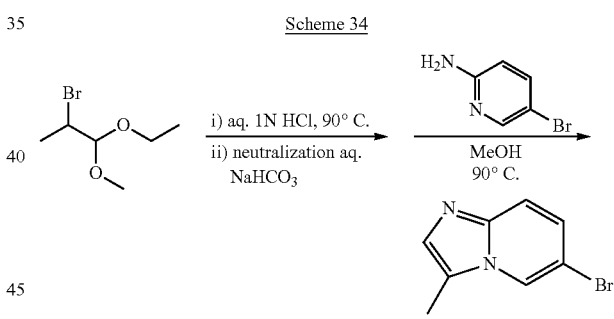

2-Bromo-1,1-diethoxypropane (5g) was added to a stirring solution of aq. 1N HCl (15 mL) and heated at 90° C. for 1 h. The clear reaction mixture was cooled to room temperature and treated with solid NaHCO$_3$ till pH 7.0. 2-amino-5-bromopyridine (1.8 G) and MeOH (25 mL) were transferred successively to the above reaction mixture and heated at 90° C. After 8 h, the reaction mixture was concentrated under vacuum by rotary evaporator. The resulting solid concentrate was stirred in CH$_2$Cl$_2$/water (200 mL/75 ml). Organic layer was separated, dried over MgSO$_4$, filtered and concentrated. The crude concentrate was stirred in EtOAc (30 mL) and the solid was collected by filtration to obtain 6-bromo-3-methylimidazo[1,2-a]pyridine as a tan solid (1.6 g). $^1$H NMR (300 MHz, DMSO-d$_6$): δ 8.55 (s, 1H), 7.50 (d, J=9.5 Hz, 1H), 7.37 (s, 1H), 7.28 (d, J=9.5 Hz, 1H), 2.44 (s, 3H).

Example 85

6-Iodo-2-methylimidazo[1,2-a]pyridine can be prepared as shown in Scheme 35, and as described below:

Scheme 35

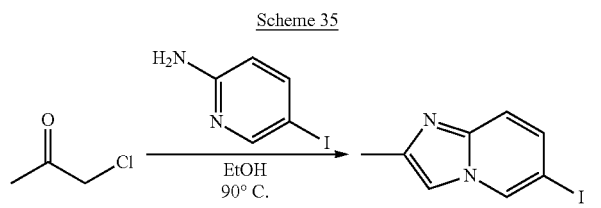

Chloroacetone (3 mL) was added to a stirring solution of 2-amino-5-iodopyridine (2g) in EtOH (20 mL) and heated to reflux. The reaction progress (50% of unreacted 2-amino-5-iodopyridine) was analyzed after 12 h by LC/MS and TLC. Additional amount of chloroacetone (3 mL) was transferred to the reaction mixture and heated for additional 8 h to observe the >90% consumption of 2-amino-5-iodopyridine. The reaction mixture was cooled and concentrated to dryness. The crude residue was diluted with EtOAc (130 mL)/water (50 mL) and neutralized with 5% aq. NaOH (25 mL). Organic layer from the biphasic solution was separated and the aqueous phase was partitioned again with EtOAc (70 mL). Combined organic layers were dried over MgSO$_4$, filtered and concentrated. The crude brown residue was purified by Combiflash® companion System® with RediSep® silica gel column [(80g), 50-75-100% EtOAC/hexanes as an eluting solvent gradient. The product fractions were concentrated to provide 2.2 g of 6-iodo-2-methylimidazo[1,2-a]pyridine (1.8 g) as an off-brown solid. $^1$H NMR (300 MHz, DMSO-d$_6$) δ 8.81 (dd, J=1.7, 1.0 Hz, 1H), 7.62-7.55 (app s, 1H), 7.31 (dd, J=9.4, 1.7 Hz, 1H), 7.25 (dd, J=9.3, 0.8 Hz, 1H), 2.29 (s, 3H). See Helvetica Chimica Acta, 90(12), 2349-2367 (2007).

Example 86

6-Iodo-2-methylimidazo[1,2-a]pyridine

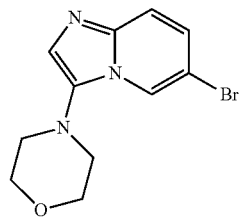 [SMILES: Brc1ccc2ncc(N3CCOCC3)n2c1]

6-Iodo-2-methylimidazo[1,2-a]pyridine can be prepared via the procedures described in J. Med. Chem., 54(7), 2455-66 (2011). $^1$H NMR (300 MHz, DMSO-d$_6$) δ 8.38 (dd, J=1.9, 0.9 Hz, 1H), 7.47 (dd, J=9.5, 0.8 Hz, 1H), 7.33 (s, 1H), 7.26 (dd, J=9.5, 2.0 Hz, 1H), 3.78-3.75 (m 4H), 3.07-2.80 (m, 5H).

Example 87

4-(6-Bromoquinolin-4-yl)morpholine can be prepared as shown in Scheme 36, and as described below:

Scheme 36

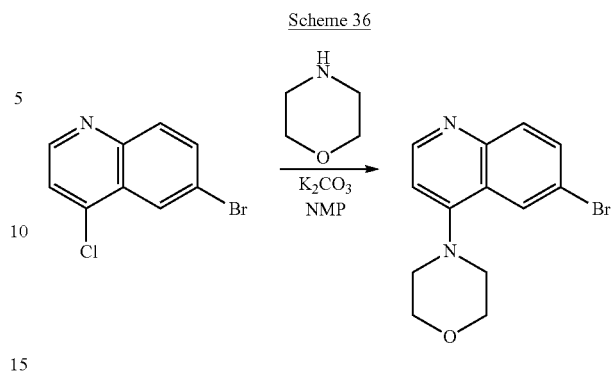

6-Bromo-4-chloroquinoline (1.0 G, 4.1 mmol), morpholine (0.468 g, 5.3 mmol) and K$_2$CO$_3$ (1.0 G, 7.2 mmol) in NMP (5 mL) were heated at 100° C. for 12 h. The reaction mixture was cooled to room temperature, diluted with water (20 mL) and the product was extracted into EtOAc/hexanes (140 mL/60 mL). The organic layer was washed with water (75 mL) and brine (20 mL) successively, dried over MgSO$_4$ and filtered. The filtrate was concentrated and purified by flash column chromatography (Combiflash® companion System® with RediSep® silica gel column 40 g and 30-70% EtOAC/hexanes as an eluting solvent]. The product fractions were concentrated to provide 4-(6-bromoquinolin-4-yl)morpholine (700 mg) as a white solid. $^1$H NMR (300 MHz, DMSO-d$_6$) δ 8.73 (d, J=5.0 Hz, 1H), 8.13 (d, J=2.2 Hz, 1H), 7.90 (d, J=8.9 Hz, 1H), 7.81 (dd, J=9.0, 2.2 Hz, 1H), 7.06 (d, J=5.0 Hz, 1H), 3.87-3.84 (m, 4H), 3.18-3.02 (m, 4H).

Example 88

6-Bromo-3-(trifluoromethyl)imidazo[1,2-a]pyridine can be prepared as shown in Scheme 37, and as described below:

Scheme 37

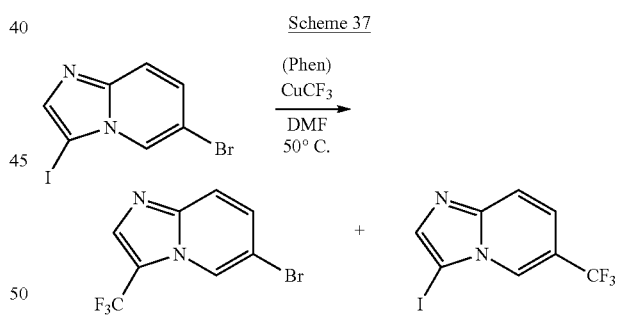

A screw capped vial (20 mL) containing a stir bar was charged with 6-bromo-3-iodoimidazo[1,2-a]pyridine (0.27 g) followed by dry DMF (4 mL) and (Phen)CuCF$_3$ sequentially. The capped vial containing initial dark reaction mixture was stirred at 50° C. The reaction mixture changed colors as it progressed from pink to off-yellow and off-green at the end of the reaction. The progress was monitored intermittently by LC/MS. After 48 h, the reaction mixture was diluted with EtOAc/CH$_2$Cl$_2$ (1:1, 50 mL) and filtered through a pad of Celite®/Fluorosil® and washed the pad with additional amount of EtOAc/CH$_2$Cl$_2$ (1:1, 50 mL). The filtrate was concentrated by rotary evaporator under vacuum to dryness. The crude concentrate was diluted with water, sonicated for 10 min and filtered. The collected solid was suction dried to provide the desired 6-bromo-3-(trifluoromethyl)imidazo[1, 2-a]pyridine along with 3-iodo-6-(trifluoromethyl)imidazo [1,2-a]pyridine (12:1) which can be used in the subsequent coupling with no further purification. See *Hartwig Angew. Int. Ed. Eng.* 2011, 50, 3793-3794.

Example 89

6-Bromoimidazo[1,2-a]pyridine-3-carbonitrile can be prepared as shown in Scheme 38:

Scheme 38

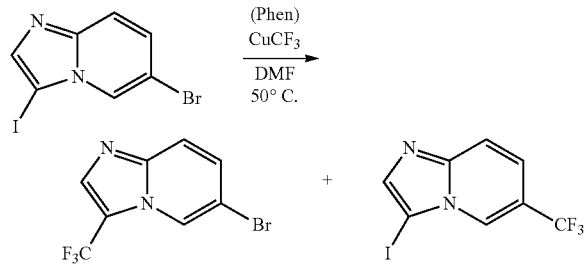

See *J. Med. Chem.*, 54(7), 2455-66 (2011).

Example 90

4-(6-Bromoimidazo[1,2-a]pyridin-3-yl)morpholine

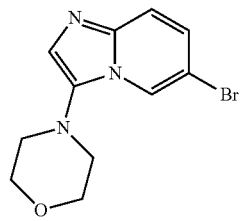 [SMILES: Brc1ccc2ncc(N3CCOCC3)n2c1]

4-(6-Bromoimidazo[1,2-a]pyridin-3-yl)morpholine can be prepared as described in *J. Med. Chem.*, 54(7), 2455-66 (2011). $^1$H NMR (300 MHz, DMSO-$d_6$) δ 8.38 (dd, J=1.9, 0.9 Hz, 1H), 7.47 (dd, J=9.5, 0.8 Hz, 1H), 7.33 (s, 1H), 7.26 (dd, J=9.5, 2.0 Hz, 1H), 3.78-3.75 (m 4H), 3.07-2.80 (m, 5H).

Example 91

4-(6-Bromo-3-(pyrrolidin-1-yl)imidazo[1,2-a]pyridine

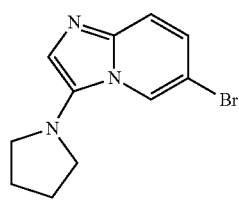 [SMILES: Brc1ccc2ncc(N3CCCC3)n2c1]

4-(6-Bromo-3-(pyrrolidin-1-yl)imidazo[1,2-a]pyridine can be prepared as described in *J. Med. Chem.*, 54(7), 2455-66 (2011).

Example 92

6-Bromoimidazo[1,2-a]pyridine-3-carbonitrile can be prepared as shown in Scheme 39:

Scheme 39

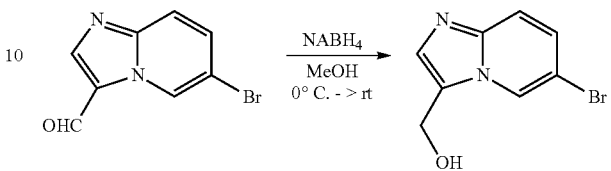

Stirring solution of 6-bromoimidazo[1,2-a]pyridine-3-carbaldehyde [see Bioorg. Med. Chem. Let. 15(17), 5837-5844; 2007; Int'l Pat. App. Pub. no, 2011/055320] (1.5 g, 6.6 mmol) in MeOH (20 mL) was cooled to 0° C. and NaBH$_4$ (0.50 g, 13.2 mmol) was added in portions for a period of 20 min. Cooling was removed after 1 h and allowed to stir for 3 h. The reaction mixture was quenched with water and concentrated by rotary evaporator to dryness. Subsequently, the solid concentrate was diluted with water and collected on the Buchner funnel by suction filtration. The solid was suction dried to obtain (6-bromoimidazo[1,2-a]pyridin-3-yl)methanol as a pale yellow crystalline solid (0.83 g). $^1$H NMR (300 MHz, DMSO-$d_6$) δ 8.63 (dd, J=2.0, 0.9 Hz, 1H), 7.55 (dd, J=9.5, 0.9 Hz, 1H), 7.52 (s, 1H), 7.36 (dd, J=9.5, 2.0 Hz, 1H), 5.27 (t, J=5.4 Hz, 1H), 4.79 (d, J=5.3 Hz, 2H). See *J. Med. Chem.*, 54(7), 2455-66 (2011).

Example 93

4-((6-Bromoimidazo[1,2-a]pyridin-3-yl)methyl)morpholine can be prepared as shown in Scheme 40:

Scheme 40

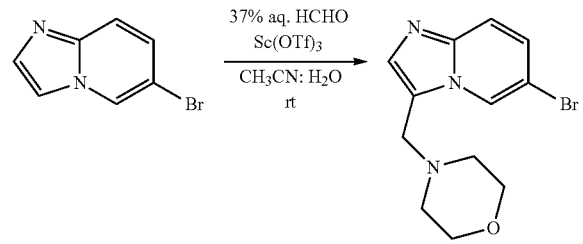

Morpholine (1.91 g, 22 mmol) and 37% aq. formaldehyde (5 mL, 60 mmol) in acetonitrile:water (6:1, mL) was stirred for 15 min at room temperature. 6-bromoimidazo[1,2-a]pyridine (3.94 g, 20 mmol) and Sc(OTf)$_3$ were added sequentially to the above solution and stirred for 36 h at room temperature to observe the complete consumption of 6-bromoimidazo[1,2-a]pyridine. The reaction mixture was concentrated, diluted with aq.K$_2$CO$_3$ (150 mL) and stirred the suspension for 25 min. The solid was collected by filtration and dried on the funnel to obtain 44(6-bromoimidazo[1,2-a]pyridin-3-yl)methyl)morpholine (3.9 g). $^1$H NMR (300 MHz, DMSO-$d_6$) δ 8.69 (d, J=1.7 Hz, 1H), 7.54 (d, J=9.6 Hz, 1H), 7.51 (s, 1H), 7.34 (dd, J=9.5, 1.7 Hz, 1H), 3.81 (s, 2H), 3.64-3.39 (m, 3H), 2.43-2.26 (m, 3H). See U.S. Pat. App. Pub. no. 2005/0054701.

Example 94

46-Bromo-N-(3,4,5-trimethoxyphenyl)imidazo[1,2-a]pyridine-3-carboxamide can be prepared as shown in Scheme 41:

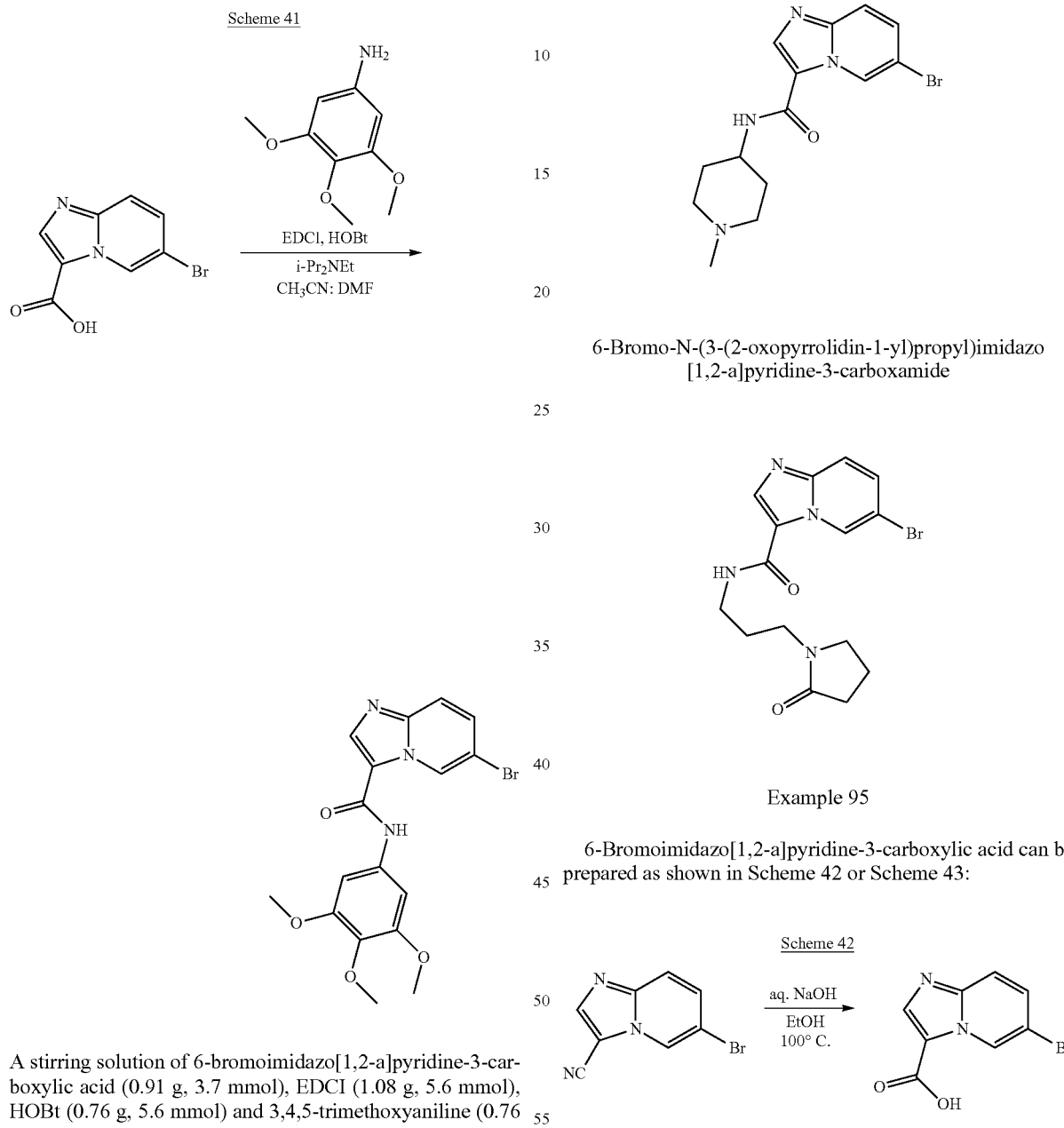

A stirring solution of 6-bromoimidazo[1,2-a]pyridine-3-carboxylic acid (0.91 g, 3.7 mmol), EDCI (1.08 g, 5.6 mmol), HOBt (0.76 g, 5.6 mmol) and 3,4,5-trimethoxyaniline (0.76 g, 4.1 mmol) in acetonitrile/DMF (8/3 mL) under argon was added i-Pr$_2$NEt (2.00 g, 2.6 ml), 15.4 mmol) drop wise for 5 min at room temperature. The resulting off-brown homogeneous reaction mixture was continued to stir at room temperature for 18 h. Subsequently, the heterogeneous reaction mixture was diluted with water and the solid was collected by filtration. The solid was suction dried on funnel to obtain 6-bromo-N-(3,4,5-trimethoxyphenyl)imidazo[1,2-a]pyridine-3-carboxamide (1.1 g) as a white solid. $^1$H NMR (300 MHz, DMSO-d$_6$) δ 10.17 (s, 1H), 9.64 (s, 1H), 8.56 (d, J=1.1 Hz, 1H), 7.75 (d, J=9.7 Hz, 1H), 7.64 (dd, J=9.5, 1.9 Hz, 1H), 7.15 (s, 2H), 3.78 (s, 6H), 3.63 (s, 3H).

Similarly, the following compounds can be prepared:

6-Bromo-N-(1-methylpiperidin-4-yl)imidazo[1,2-a]pyridine-3-carboxamide

6-Bromo-N-(3-(2-oxopyrrolidin-1-yl)propyl)imidazo[1,2-a]pyridine-3-carboxamide

Example 95

6-Bromoimidazo[1,2-a]pyridine-3-carboxylic acid can be prepared as shown in Scheme 42 or Scheme 43:

A stirring solution of 6-bromoimidazo[1,2-a]pyridine-3-carbonitrile [JMC 54(7). 2455-2466; 2011] (1.0 g), EtOH (10 mL) and aq. NaOH (1.0 g, 10 mL) was heated at 100° C. After 12 h, the reaction mixture was cooled and concentrated to dryness by rotary evaporator under reduced pressure. Subsequently, the crude solid was diluted with water, cooled in ice-bath and acidified with conc. HCl till pH 4 while stirring. The resulting suspension was suction filtered and the solid was dried overnight. Subsequently, the collected solid was further dried over P$_2$O$_5$ under high vacuum to obtain 6-bromoimidazo[1,2-a]pyridine-3-carboxylic acid (0.91 g) as a white solid. $^1$H NMR (300 MHz, DMSO-d$_6$) δ 13.27 (s, 1H), 9.36 (s, 1H), 8.24 (s, 1H), 7.77 (d, J=9.5 Hz, 1H), 7.67 (d, J=9.5, 1.7 Hz, 1H).

Scheme 43

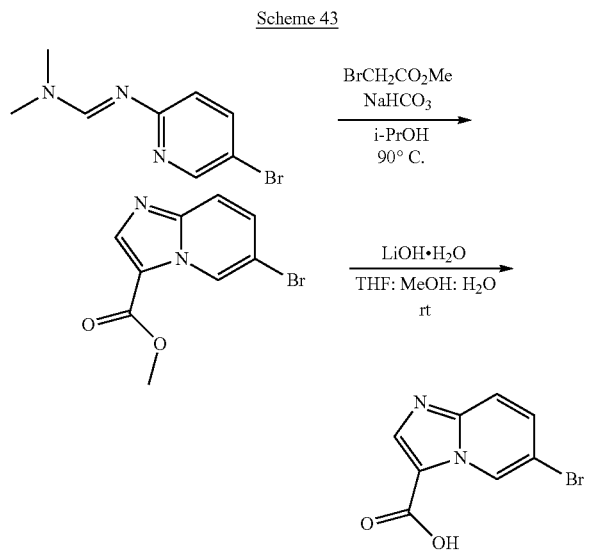

Reaction mixture containing N'-(5-bromopyridin-2-yl)-N,N-dimethylformimidamide (6.5 g, 28.5 mmol), methyl 2-bromoacetate (5.6 g, 3.5 mL, 37.0 mmol) and NaHCO$_3$ (4.1 g, 48.8 mmol) in i-PrOH (60 mL) was heated at 90° C. under nitrogen. The heating was stopped after 12 h and cooled the dense heterogeneous reaction mixture to room temperature. The reaction mixture was concentrated and diluted with water. The resultant slurry was collected by suction filtration and obtained methyl 6-bromoimidazo[1,2-a]pyridine-3-carboxylate (6.9 g) as a tan white solid upon drying. $^1$H NMR (300 MHz, DMSO-d$_6$): δ 9.31 (d, J=1.8 Hz, 1H), 8.31 (s, 1H), 7.80 (d, J=9.5 Hz, 1H), 7.71 (dd, J=9.5, 1.6 Hz, 1H), 3.88 (s, 4H). Ester hydrolysis was done by stirring a solution of methyl 6-bromoimidazo[1,2-a]pyridine-3-carboxylate (2.5 g), LiOH.H$_2$O (1.2 g) in THF/MeOH/H$_2$O (1/1/1, 75 mL) at room temperature. Reaction mixture was concentrated upon complete hydrolysis of ester to corresponding acid, diluted with water/ice and acidified with 2N. aq HCl until pH 6. The resulting solid was filtered, suction dried followed by drying under P$_2$O$_5$ under vacuum to obtain 6-bromoimidazo[1,2-a]pyridine-3-carboxylic acid (2.2 g) as a white solid. $^1$H NMR (300 MHz, DMSO-d$_6$) δ 13.27 (s, 1H), 9.36 (s, 1H), 8.24 (s, 1H), 7.77 (d, J=9.5 Hz, 1H), 7.67 (d, J=9.5, 1.7 Hz, 1H).

Example 96

6-Bromo-3-(3,4,5-trimethoxyphenyl)imidazo[1,2-a]pyridine can be prepared as shown in Scheme 44:

Scheme 44

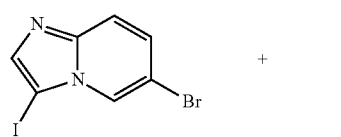

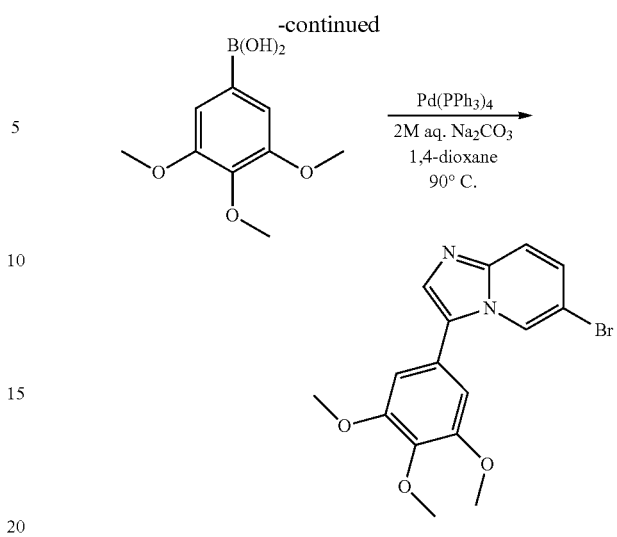

A reaction flask was charged with 6-bromo-3-iodoimidazo[1,2-a]pyridine (2.0 g, 6.2 mmol), (3,4,5-trimethoxyphenyl)boronic acid (1.44 g, 6.8 mmol), 2M. aq. Na$_2$CO$_3$ (8 mL, 16 mmol), 1,4-dioxane (50 mL) and a stir bar. The contents were degassed by vacuum and back filled with argon in three times while stirring. Subsequently, catalyst Pd(PPh$_3$)$_4$ (0.35 g, 0.30 mmol) was added to the reaction contents, repeated degassing cycles and heated at 90° C. for 12 h. Reaction mixture was cooled and filtered the biphasic reaction mixture through Celite® and concentrated the filtrate. The crude solid residue was partitioned between CH$_2$Cl$_2$(150 mL)/water (50 mL). The organic layer was separated, dried over MgSO$_4$, filtered and concentrated. The crude concentrate (2.2 g) was subjected to purification by flash column chromatography (Combiflash® companion System® with RediSep® silica gel column 40 g, 30-60% EtOAC/hexanes as an eluting solvent) to obtain 6-bromo-3-(3,4,5-trimethoxyphenyl)imidazo[1,2-a] pyridine as a white solid (1.0 g).

Example 97

1-(6-Bromoimidazo[1,2-a]pyridin-3-yl)ethan-1-one can be prepared as shown in Scheme 45:

Scheme 45

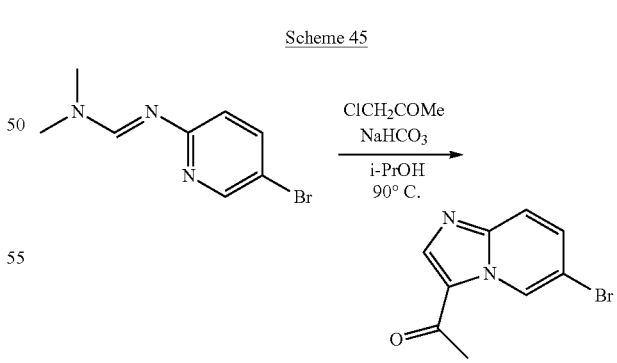

(E)-N'-(5-Bromopyridin-2-yl)-N,N-dimethylformimidamide (2.0 g, 8.8 mmol), 1-chloropropan-2-one (1.2 mL, 1.4 g, 15 mmol), NaHCO$_3$ (1.3 g, 15.5 mmol) in 2-propanol (30 mL) were heated at 90° C. under nitrogen for 12 h. The dark reaction mixture was cooled and the dense heterogeneous suspension was diluted with water. The solid was collected by filtration, washed with water and dried to obtain 1.0 g of 1-(6-bromoimidazo[1,2-a]pyridin-3-yl)ethan-1-one. $^1$H NMR (300 MHz, DMSO-d$_6$) δ 9.62 (d, J=1.9 Hz, 1H), 8.61 (s, 1H), 7.81 (d, J=9.5 Hz, 1H), 7.75 (dd, J=9.5, 1.9 Hz, 1H), 2.55 (s, 3H). See Bioorg. Med. Chem. Lett. 15(1), 403-412 (2007); Int'l Pat. App. Pub, no. 2009/158011.

Example 98

7-Bromoimidazo[1,5-a]pyridine

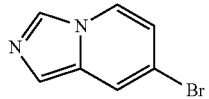

7-Bromoimidazo[1,5-a]pyridine can be prepared as described in Int'l Pat. App. Pub. no. 2005090304.

Example 99

1-(6-Bromoimidazo[1,2-a]pyridin-3-yl)ethan-1-one can be prepared as shown in Scheme 46:

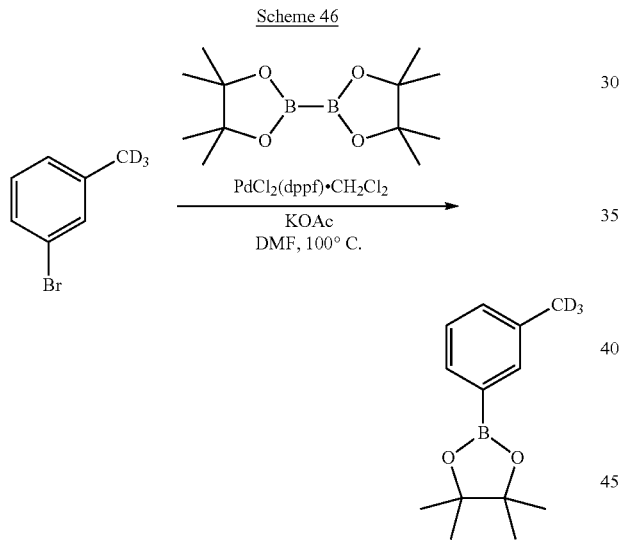

A reaction flask was charged with 1-bromo-3-(methyl-d$_3$) benzene (2.0 g, 11.5 mmol), bis(pinacolato)diboron (5.8 g, 23 mmol) and KOAc (2.25 g, 23 mmol), DMF (20 mL) and a stir bar. The contents were degassed by vacuum and back filled with argon three times while stirring. Subsequently, catalyst PdCl$_2$ (dppf)·CH$_2$Cl$_2$ (0.85 g, 1.15 mmol) was added to the reaction contents, repeated degassing cycles and heated at 100° C. for 12 h. Reaction mixture was cooled and filtered the reaction mixture through Celite®. The filtrate cake was washed with EtOAc (30 mL) and the filtrate was partitioned between EtOAc (150 mL)/water (40 mL). Organic layer was separated and the aqueous layer was extracted with additional EtOAc. Combined organic layers were stirred over MgSO$_4$/Celite®/Fluorosil® and filtered. The filtrate was concentrated and purified by flash column chromatography (Combiflash® companion System® with RediSep® silica gel column 80 g, 10-20% EtOAC/hexanes as elutant) to obtain 4,4,5,5-tetramethyl-2-(3-(methyl-d$_3$)phenyl)-1,3,2-dioxaborolaneas a semi solid (2.85 g) and used in the boronate coupling with no further purification.

Example 100

Triazolopyrimidines can be prepared using the protocol of Scheme 47, described as in Huntsman, E and Balsells, J., Eur. J. Org. Chem. 2005, (17), 3761-3765:

Scheme 47

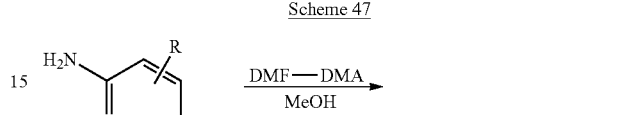

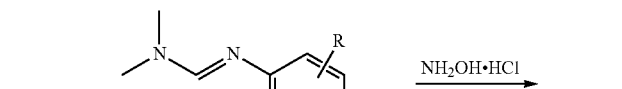

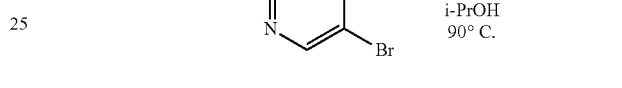

The following compounds were made:

6-Bromo-5-methyl-[1,2,4]triazolo[1,5-a]pyridine

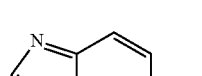

$^1$H NMR (300 MHz, DMSO-d$_6$) δ 8.52 (s, 1H), 7.83 (d, J=9.4 Hz, 1H), 7.69 (d, J=9.4 Hz, 1H), 2.84 (s, 3H).

6-Bromo-7-methyl-[1,2,4]triazolo[1,5-a]pyridine

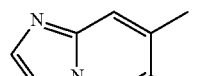

¹H NMR (300 MHz, DMSO-d₆) δ 9.36 (s, 1H), 8.44 (s, 1H), 7.86 (s, 1H), 2.45 (s, 3H).

6-Bromo-8-fluoro-[1,2,4]triazolo[1,5-a]pyridine

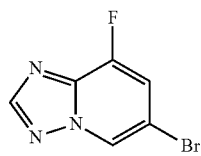 [SMILES: Fc1cc(Br)cn2ncnc12]

¹H NMR (300 MHz, DMSO-d₆) δ 9.32 (app dd, J=1.5, 0.7 Hz, 1H), 8.59 (s, 1H), 7.98 (dd, J=9.9, 1.5 Hz, 1H). ¹⁹F NMR (282 MHz, DMSO-d₆) δ −127.85 (d, J=9.9 Hz).

Example 101

6-Bromoimidazo[1,2-b]pyridazine-3-carbonitrile can be prepared as shown in Scheme 48:

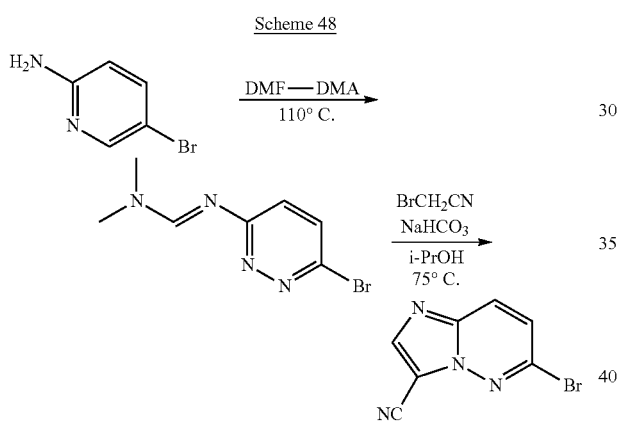

Example 102

(E)-N'-(6-Bromopyridazin-3-yl)-N,N-dimethylformimidamide

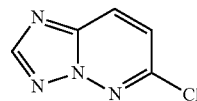

3-Amino-6-bromopyridazine (5.0 g, 28.7 mmol) was heated and stirred with dimethylformamide dimethylacetal (5.36 g, 6.0 mL, 45.0 mmol) under nitrogen at 110° C. for 3 h. The brown homogeneous reaction mixture was cooled to room temperature. The resulting heterogeneous slurry was stirred in EtOAc/hexanes (1:1, 75 mL) and filtered. The filtered solid was suction dried to obtain apparently (E)-N'-(6-bromopyridazin-3-yl)-N,N-dimethylformimidamide (4.9 g) as a pale pink crystalline solid. ¹H NMR (300 MHz, DMSO-d₆) δ 8.45 (s, 1H), 7.64 (d, J=9.1 Hz, 1H), 7.03 (d, J=9.1 Hz, 1H), 3.11 (s, 3H), 3.00 (s, 3H).

Example 103

6-Bromoimidazo[1,2-b]pyridazine-3-carbonitrile

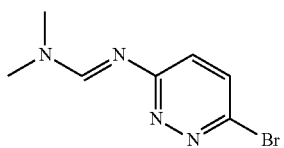

(E)-N'-(6-Bromopyridazin-3-yl)-N,N-dimethylformimidamide (2.5 g, 10.9 mmol), bromoacetonitrile (3.92 g, 32.7 mmol) and NaHCO₃ (1.8 g, 21.8 mmol) in i-PrOH (15 mL) were heated at 75° C. for 8 h while stirring the contents. Subsequently, the dark reaction mixture was diluted with water and the resulting solid was collected by filtration. The solid was purified by flash chromatography (Combiflash® companion System® with RediSep® silica gel column 40 g and 15-30-50% EtOAC/hexanes as an eluting solvent) to obtain 1.3 g of 6-bromoimidazo[1,2-b]pyridazine-3-carbonitrile. ¹H NMR (300 MHz, DMSO-d₆) δ 8.58 (s, 1H), 8.33 (d, J=9.5 Hz, 1H), 7.77 (d, J=9.5 Hz, 1H).

Example 104

6-Chloro-[1,2,4]triazolo[1,5-b]pyridazine

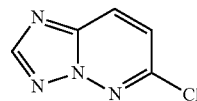

(6-Chloro-[1,2,4]triazolo[1,5-b]pyridazine can be prepared as described in J. Het. Chem., 12(1), 107-110 (1975).

Example 105

Bromopyrido[2,3-d]pyrimidin-4-amine can prepared as shown in Scheme 49, and as described below:

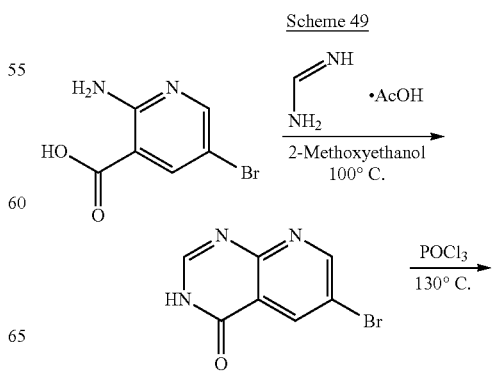

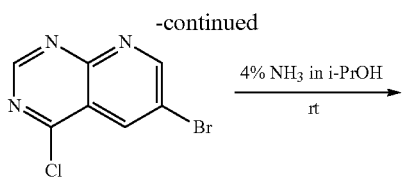

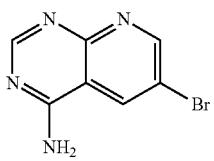

6-Bromopyrido[2,3-d]pyrimidin-4(3H)-one

2-Amino-5-bromonictoinic acid (2g) and formamidine acetate (3.0 g) were heated at 120° C. in 2-methoxyethanol (15 ml) for 36 h under argon. The heterogeneous reaction mixture was diluted with water and filtered. The solid was suction dried to obtain 1.7 g of 6-bromopyrido[2,3-d]pyrimidin-4(3H)-one. $^1$H NMR (300 MHz, DMSO-d$_6$) δ 12.70 (s, 1H), 9.01 (d, J=2.6 Hz, 1H), 8.59 (d, J=2.6 Hz, 1H), 8.33 (s, 1H).

6-Bromo-4-chloropyrido[2,3-d]pyrimidine

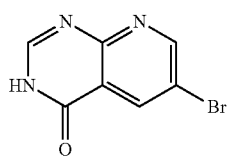 [SMILES: O=c1[nH]cnc2ncc(Br)cc12]

6-Bromopyrido[2,3-d]pyrimidin-4(3H)-one (3.0 g) and POCl$_3$ (15 mL) were heated at 130° C. under nitrogen for 3 h. The homogeneous dark solution was concentrated under reduced pressure and diluted with EtOAc (150 mL). The heterogeneous brown slurry was poured onto mixture of ice/aq. NaHCO$_3$ and allowed the mixture warm to room temperature. The heterogeneous brown mixture was further diluted with EtOAc (75 mL) and separated the organic layer. The organic layer was partitioned with aq. NaCl, separated, stirred with MgSO$_4$ and filtered through a pad of Celite® and silica gel. The pale yellow filtrate was concentrated and the crude solid was stirred in 50% EA/hexanes. 6-Bromo-4-chloropyrido[2,3-d]pyrimidine was obtained as a pale yellow crystalline solid (1.8 g, purity: 95%) upon filtration.

6-Bromopyrido[2,3-d]pyrimidin-4-amine

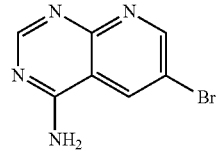

6-Bromo-4-chloropyrido[2,3-d]pyrimidine (1.0 g) and 4% NH$_3$ in i-PrOH (25 mL) were stirred in a sealed tube at room temperature overnight. The pale brown heterogeneous slurry was concentrated, diluted with water and filtered. The brown solid thus collected was suction dried to obtain 6-bromopyrido[2,3-d]pyrimidin-4-amine (1.3 g, purity: 97%). $^1$H NMR (300 MHz, DMSO-d$_6$) δ 9.09 (d, J=2.5 Hz, 1H), 9.01 (d, J=2.5 Hz, 1H), 8.52 (s, 1H), 8.31 (br s, 2H).

Biological Example 1

AlphaScreen® SureFire® SMAD3 (p-Ser423/425) Assay

The p-SMAD-3 (Ser423/425) SureFire® assay has been designed to measure the phosphorylation of endogenous cellular p-SMAD-3 (Ser423/425) in cell lysates and is a system for the screening of both modulators of receptor activation (e.g. agonists and antagonists) as well as agents acting intracellularly, such as small molecule inhibitors of upstream events. The assay will measure p-SMAD-3 (Ser423/425) activation by either cloned or endogenous receptors, and can be applied to primary cells.

P-SMAD-3 (Ser423/425) SureFire® Assay Protocols

Step A: Preparation of Buffers

1× Lysis buffer: 1 ml of 5× Lysis buffer was diluted with 4 ml of sterile water. After dilution, excess 1× Lysis buffer can be frozen and thawed up to 5 times without loss in activity.

Activation buffer: The buffer was warmed slowly to 37° C. and gently mixed to re-suspend. Activation buffer can be stored at room temperature with no loss in activity.

Reaction buffer: The buffer was kept at 4° C. while in use.

AlphaScreen® Protein A IgG Kit: The kit was stored at 4° C. in the dark.

Reaction buffer+Activation buffer+AlphaScreen® Acceptor beads: Reaction buffer (40 parts), Activation Buffer (10 parts) and Acceptor beads (1 part) were mixed and the mixture was stored at room temperature and used the same day. Mixture was added to 384-well plates; excess mixture was discarded.

Dilution buffer+AlphaScreen® Donor beads: Dilution buffer (20 parts) and Donor beads (1 part) were mixed and the mixture was stored at room temperature and used the same day. Excess mixture was discarded.

Assay control samples: After reconstitution in 250 μl of water, lysates were at −20° C. in single use aliquots.

Step B: Preparation of Samples and Cells 96-well Assay Protocol for 293FT and RMS13 adherent cells can be carried out manually or in high throughput with liquid handling robots.

The cells (80 μL, of cells for 96 well plates) were plated in collagen coated tissue culture plates in RPMI or FreeStyle medium (Invitrogen) and incubated overnight. For manual analysis, 6 plates for GDF8, 6 plates for TGFβ, and optionally 6 plates for Alk5ca (ALK5 constitutively active) were used.

The compound dilution plates were prepared as follows: 12 µL of DMSO was transferred into first column of 96-well plate, and 16 µL of DMSO was transferred into columns 2-12 of the 96-well plate. 12 µL of compound solution was transferred into first column of the DMSO-containing 96-well plate. Three-fold dilution was performed up to column 10 of the DMSO-containing 96-well plate.

Step C: Treatment and Analysis

The plate containing cells were treated with compounds for about 10 minutes, and then ligand was added. GDF8 or TGFb was added to plates to stimulate. 293FL cells were stimulated for 90 minutes at 37° C.; and RMS13 cells were stimulated for 60 minutes at 37° C. The medium was then removed from the cells, and 1× Lysis Buffer (about 25 µL) was added and the plate was gently agitated on plate shaker for 5-10 minutes.

The lysate (5 µL) was then placed into 384-well shallow plates avoiding the generation of bubbles. To this, the Reaction Buffer+Activation Buffer+AlphaScreen® Acceptor beads mixture (5 µL) was added. The plate was sealed with adhesive cover and shielded from light (e.g., with metal foil), and agitated gently on plate shaker for 2 hours at room temperature.

Dilution buffer+AlphaScreen® Donor beads (2 µL) was then added, and the plate was intubated on the plate shaker for an additional 1½ hours. After completion, the plate was read on Synergy-4 or Enspire plate reader, using AlphaScreen® pSMAD3® settings.

Representative results for inhibition of GDF8 signaling are shown in Table 2:

| Cmpd # | GDF pSMAD (MPC11) µM |
|---|---|
| 1 | 1.654 |
| 2 | --* |
| 3 | 1.296 |
| 4 | ---- |
| 5 | ---- |
| 6 | 18.65 |
| 7 | 23.11 |
| 8 | 5.349 |
| 9 | 5.135 |
| 10 | 0.5349 |
| 11 | 0.5945 |
| 12 | 18.89 |
| 13 | ---- |
| 14 | ---- |
| 15 | 0.0649 |
| 16 | 6.34 |
| 17 | 0.3358 |
| 18 | 0.1419 |
| 19 | 0.083 |
| 20 | 0.1037 |
| 21 | 1.917 |
| 22 | 1.414 |
| 23 | 2.245 |
| 24 | 0.6713 |
| 25 | 0.6123 |
| 26 | 0.8118 |
| 27 | 0.4527 |
| 28 | 1.754 |
| 29 | 1.446 |
| 30 | 3.704 |
| 31 | 1.899 |
| 32 | 2.796 |
| 33 | 5007 |
| 34 | 8.832 |
| 35 | 10.78 |
| 36 | 19.71 |
| 37 | 18.1 |
| 38 | 3.227 |
| 39 | 14.33 |
| 40 | 18.47 |
| 41 | 3.136 |
| 42 | 10.49 |
| 43 | 1.621 |
| 44 | ---- |
| 45 | ---- |
| 46 | 1.73 |
| 47 | 8.229 |
| 48 | 8.379 |
| 49 | ---- |
| 50 | ---- |
| 51 | 5.441 |
| 52 | 1.398 |
| 53 | 13.37 |
| 54 | ---- |
| 55 | ---- |
| 61 | 3.882 |
| 62 | 0.8036 |
| 63 | 0.1415 |
| 64 | 0.8396 |
| 65 | 2.238 |
| 66 | 1.784 |
| 67 | 1.807 |
| 68 | 0.1865 |
| 69 | 5005 |
| 70 | 5.703 |
| 71 | 7.012 |
| 72 | 5014 |
| 73 | 0.4969 |
| 74 | ---- |
| 75 | 3.468 |
| 76 | 1.815 |
| 77 | 3.65 |
| 78 | 0.3157 |
| 79 | 0.2636 |
| 80 | 6.333 |
| 81 | ---- |
| 82 | ---- |
| 83 | -- |
| 84 | -- |
| 85 | -- |
| 86 | -- |
| 87 | -- |
| 88 | -- |
| 89 | 2.551 |
| 90 | 2.612 |
| 91 | 3.028 |
| 92 | -- |
| 93 | 4.835 |
| 94 | -- |
| 95 | -- |
| 96 | -- |
| 97 | -- |
| 98 | 10.34 |
| 99 | 0.8936 |
| 100 | 6.034 |
| 101 | 11.24 |
| 102 | 0.3408 |
| 103 | -- |
| 104 | -- |
| 105 | -- |
| 106 | -- |
| 107 | -- |
| 108 | -- |
| 109 | 17.19 |
| 110 | -- |
| 111 | -- |
| 112 | 0.2733 |
| 113 | -- |
| 114 | -- |
| 115 | -- |
| 116 | 0.0326 |
| 117 | 0.1786 |
| 118 | 3.785 |
| 119 | -- |

| Cmpd # | GDF pSMAD (MPC11) μM |
|---|---|
| 120 | 0.3635 |
| 121 | 5.348 |
| 122 | 4.037 |
| 123 | -- |
| 124 | 0.5478 |
| 125 | -- |
| 126 | -- |
| 127 | -- |
| 128 | -- |
| 129 | -- |
| 130 | -- |
| 131 | -- |
| 132 | -- |
| 133 | -- |
| 134 | -- |
| 135 | -- |
| 136 | -- |
| 137 | 22.83 |
| 138 | 4.331 |
| 139 | 3.371 |
| 140 | 2.886 |
| 141 | 18.57 |
| 142 | 1.192 |
| 143 | 12.16 |
| 144 | 9.39 |
| 145 | 1.127 |
| 146 | 0.6209 |
| 147 | -- |
| 148 | -- |
| 149 | 0.6418 |
| 150 | 0.2085 |
| 151 | 0.678 |
| 152 | 0.0487 |
| 153 | 0.4504 |
| 154 | 1.306 |
| 155 | 0.2236 |
| 156 | 1.789 |
| 157 | 1.564 |
| 158 | 1.859 |
| 159 | 0.1304 |
| 160 | 0.0843 |
| 161 | 9.101 |
| 162 | 5.664 |
| 163 | -- |
| 164 | -- |
| 165 | 0.2646 |
| 166 | 0.1093 |
| 167 | 17.46 |
| 168 | -- |
| 169 | -- |
| 170 | 1.959 |
| 171 | -- |
| 172 | 0.1874 |
| 173 | 1.827 |
| 174 | 1.176 |
| 175 | 0.1181 |
| 176 | 0.057 |
| 177 | 0.3629 |
| 178 | 0.187 |
| 179 | 0.3368 |
| 180 | 0.4224 |
| 181 | 0.5391 |
| 182 | -- |
| 183 | -- |
| 184 | 12.92 |
| 185 | 8.86 |
| 186 | 0.2996 |
| 187 | 0.2282 |
| 188 | -- |
| 189 | -- |
| 190 | 1.551 |
| 191 | 0.6629 |
| 192 | 0.3473 |
| 193 | 0.2432 |
| 194 | 0.1494 |
| 195 | 9.52 |
| 196 | -- |
| 197 | 0.3588 |
| 198 | 0.44 |
| 199 | 1.164 |
| 200 | 0.2601 |
| 201 | -- |
| 207 | 2.039 |
| 208 | 1.146 |
| 209 | 18.25 |
| 210 | 12.72 |
| 211 | 0.1979 |
| 212 | 18.39 |
| 213 | 4.437 |
| 214 | 2.642 |
| 215 | 15.67 |
| 216 | 0.7365 |
| 217 | 0.8413 |
| 218 | 0.4459 |
| 219 | 6.766 |
| 220 | 8.62 |
| 221 | -- |
| 222 | 5.623 |
| 223 | 0.7071 |
| 224 | 0.6209 |
| 225 | 9.457 |
| 226 | 10.04 |
| 227 | -- |
| 228 | 9.762 |
| 229 | -- |
| 230 | 10.77 |
| 231 | 10.81 |
| 232 | 10.64 |
| 233 | 6.691 |
| 234 | -- |
| 235 | -- |
| 236 | -- |
| 237 | -- |
| 238 | -- |
| 239 | 0.2662 |
| 240 | 7.454 |
| 241 | 4.056 |
| 242 | -- |
| 243 | 11.89 |
| 244 | 0.7979 |
| 245 | 1.257 |
| 246 | 1.29 |
| 247 | 3.197 |
| 248 | 5007 |
| 249 | 8.832 |
| 250 | 10.46 |
| 251 | 17.81 |
| 252 | 12.65 |
| 253 | 12.38 |
| 254 | 0.3904 |
| 255 | -- |
| 256 | -- |
| 257 | 1.84 |
| 258 | 1.267 |
| 259 | 5007 |
| 260 | -- |
| 261 | -- |
| 262 | -- |
| 263 | -- |
| 264 | 9.152 |
| 265 | 8.122 |
| 266 | 4.535 |
| 267 | 6.757 |
| 268 | 14.41 |
| 269 | 1.383 |
| 270 | -- |
| 271 | 4.444 |
| 272 | 3.401 |
| 273 | 9.786 |
| 274 | 14.77 |
| 275 | 2.948 |
| 276 | -- |

| Cmpd # | GDF pSMAD (MPC11) µM | Cmpd # | GDF pSMAD (MPC11) µM |
|---|---|---|---|
| 277 | 1.671 | 353 | 0.6888 |
| 278 | 2.226 | 354 | 1.27 |
| 279 | -- | 355 | -- |
| 280 | -- | 356 | 0.9646 |
| 281 | 1.304 | 357 | -- |
| 282 | 19.38 | 358 | 0.8629 |
| 283 | 17.72 | 359 | 0.5243 |
| 284 | -- | 360 | 5.669 |
| 285 | -- | 361 | 0.2296 |
| 286 | 11.96 | 362 | 0.1051 |
| 287 | 3.03 | 363 | 0.9033 |
| 288 | -- | 364 | 0.3383 |
| 289 | -- | 365 | 0.1653 |
| 290 | -- | 366 | 0.2258 |
| 291 | 1.231 | 367 | 0.2799 |
| 292 | 1.739 | 368 | 0.1894 |
| 293 | 5.541 | 369 | 0.1933 |
| 294 | -- | 370 | 0.4111 |
| 295 | -- | 371 | 0.7368 |
| 296 | -- | 372 | 0.3387 |
| 297 | 2.26 | 373 | 1.2 |
| 298 | 0.9992 | 374 | 0.4949 |
| 299 | 1.2 | 375 | 0.1524 |
| 300 | 12.79 | 376 | 0.276 |
| 301 | 0.3451 | 377 | 0.1724 |
| 302 | 0.7949 | 378 | 0.5583 |
| 303 | 0.0947 | 379 | 0.3954 |
| 304 | 0.0853 | 380 | 18.51 |
| 305 | 0.1751 | 381 | 2.607 |
| 306 | 0.1294 | 382 | 14.8 |
| 307 | 2.222 | 383 | 16.74 |
| 308 | 4.809 | 384 | 7.792 |
| 309 | 1.475 | 385 | 2.557 |
| 310 | 1.143 | 386 | 2.004 |
| 311 | 4.719 | 387 | 1.279 |
| 312 | 7.538 | 388 | 0.5469 |
| 313 | 5009 | 389 | 0.1871 |
| 314 | 5.345 | 390 | 0.5164 |
| 315 | 0.7489 | 391 | 0.2278 |
| 316 | 6.389 | 392 | 0.1274 |
| 317 | 5.5 | 393 | 0.07 |
| 318 | 1.305 | 394 | 0.1191 |
| 319 | 10.63 | 395 | 0.9586 |
| 320 | 2.993 | 396 | 0.2083 |
| 321 | 0.6792 | 397 | 9.407 |
| 322 | 0.2531 | 398 | 3341 |
| 323 | 0.327 | 399 | 4.653 |
| 324 | 0.4612 | 400 | 5.806 |
| 325 | 0.1865 | 401 | 5.891 |
| 326 | 0.1983 | 402 | 5000 |
| 327 | 0.3234 | 403 | 1.666 |
| 328 | 2.497 | 404 | 1.029 |
| 329 | 0.8032 | 405 | 10.69 |
| 330 | 0.4565 | 406 | 2.794 |
| 331 | 1.329 | 407 | 2.467 |
| 332 | 0.3115 | 408 | 0.6732 |
| 333 | 0.3764 | 409 | 7.954 |
| 334 | 0.3727 | 410 | 4.13 |
| 335 | 0.306 | 411 | 0.0725 |
| 336 | 0.7635 | 412 | -- |
| 337 | 0.4792 | 413 | -- |
| 338 | 0.1639 | 414 | 3.334 |
| 339 | 0.5903 | 415 | 11.8 |
| 340 | 0.4637 | 416 | 4.858 |
| 341 | 0.2595 | 417 | -- |
| 342 | 0.1058 | 418 | -- |
| 343 | 2.644 | 419 | -- |
| 344 | -- | 420 | -- |
| 345 | 4.83 | 421 | 1.401 |
| 346 | 0.1933 | 422 | 1.275 |
| 347 | 1.493 | 423 | 0.6277 |
| 348 | 1.303 | 424 | 2.426 |
| 349 | 1.009 | 425 | 0.5369 |
| 350 | 0.3473 | 426 | -- |
| 351 | 0.2151 | 427 | -- |
| 352 | 0.3069 | 428 | -- |

| Cmpd # | GDF pSMAD (MPC11) μM |
|---|---|
| 429 | 0.3842 |
| 430 | 0.4748 |
| 431 | 0.3736 |
| 432 | 0.5131 |
| 433 | 0.2851 |
| 434 | 1.491 |
| 435 | 0.608 |
| 436 | 1.18 |
| 437 | 0.7391 |
| 438 | 0.9588 |
| 439 | 0.7381 |
| 440 | 1.863 |
| 441 | 1.156 |
| 442 | 0.3659 |
| 443 | 0.429 |
| 444 | 1.081 |
| 445 | 0.5146 |
| 446 | 0.3975 |
| 447 | 0.7534 |
| 448 | 0.1368 |
| 449 | 0.0686 |
| 450 | 0.1358 |
| 451 | 0.1151 |
| 452 | 0.2231 |
| 453 | 0.8161 |
| 454 | 0.9262 |
| 455 | 1.163 |
| 456 | 0.2988 |
| 457 | 5005 |
| 458 | 3333 |
| 459 | 11.48 |
| 460 | 0.1291 |
| 461 | 0.5511 |
| 462 | 18.41 |
| 463 | 0.2966 |
| 464 | 3.96 |
| 465 | 10.26 |
| 466 | 7.583 |
| 467 | 12.19 |
| 468 | 7.824 |
| 469 | 1.58 |
| 470 | 21.11 |
| 471 | -- |
| 472 | -- |
| 473 | 0.2925 |
| 474 | 0.4292 |
| 475 | -- |
| 476 | 2.756 |
| 477 | 0.4919 |
| 478 | 6.604 |
| 479 | -- |
| 480 | 1.213 |
| 481 | 1.285 |
| 482 | 1.698 |
| 483 | 0.8197 |
| 484 | 0.1606 |
| 485 | -- |
| 486 | -- |
| 487 | -- |
| 488 | -- |
| 489 | -- |
| 490 | 6.51 |
| 491 | 9.218 |
| 492 | 3.729 |
| 493 | 0.9379 |
| 494 | 0.1069 |
| 495 | 0.2471 |
| 496 | 0.7833 |
| 497 | 9.222 |
| 498 | 1.197 |
| 499 | 6.521 |
| 500 | -- |
| 501 | 0.3552 |
| 502 | 0.5629 |
| 503 | 4.816 |
| 504 | 4.96 |

| Cmpd # | GDF pSMAD (MPC11) μM |
|---|---|
| 505 | -- |
| 506 | 1.832 |
| 507 | 3.365 |
| 508 | -- |
| 509 | 0.2652 |
| 510 | -- |
| 511 | -- |
| 512 | -- |
| 513 | -- |
| 514 | -- |
| 515 | -- |
| 516 | -- |
| 517 | 1.166 |
| 518 | -- |
| 519 | -- |
| 520 | -- |
| 521 | 8.061 |
| 522 | -- |
| 523 | 5006 |
| 524 | 5007 |
| 525 | -- |
| 526 | |
| 527 | 0.1369 |
| 528 | 0.1751 |
| 529 | 0.3228 |
| 530 | 0.6247 |
| 531 | 11.23 |
| 532 | 17.67 |
| 533 | 6.118 |
| 534 | 18 |
| 535 | 0.5038 |
| 536 | 0.4043 |
| 537 | 0.1106 |
| 538 | 0.4739 |
| 539 | 0.6993 |
| 540 | 0.4264 |
| 541 | 0.2497 |
| 542 | 1.717 |
| 543 | -- |
| 544 | -- |
| 545 | -- |
| 546 | -- |
| 547 | -- |
| 548 | 16.4 |
| 549 | 5.006 |
| 550 | -- |
| 551 | 4.883 |
| 552 | 4.058 |
| 553 | 3.241 |
| 554 | 4.683 |
| 555 | 0.1564 |
| 556 | 0.3633 |
| 557 | 0.4389 |
| 558 | 0.1875 |
| 559 | 0.1616 |
| 560 | 2.477 |
| 561 | 10.96 |
| 562 | 9.784 |
| 563 | 5.199 |
| 564 | 18.35 |
| 565 | 0.406 |
| 566 | 0.342 |
| 567 | 0.2253 |
| 568 | 0.6745 |
| 569 | 5.414 |
| 570 | 5.903 |
| 571 | 7.312 |
| 572 | -- |
| 573 | 1.214 |
| 574 | 0.8526 |
| 575 | 1.166 |
| 576 | 3.691 |
| 577 | 2.257 |
| 578 | 2.229 |
| 579 | 12.38 |
| 580 | 8.455 |

| Cmpd # | GDF pSMAD (MPC11) μM | Cmpd # | GDF pSMAD (MPC11) μM |
|---|---|---|---|
| 581 | 6.308 | 657 | 3.488 |
| 582 | 0.4936 | 658 | 1.501 |
| 583 | 0.5178 | 659 | 2.007 |
| 584 | 0.0962 | 660 | 2.243 |
| 585 | 0.5103 | 661 | 1.842 |
| 586 | 0.6169 | 662 | 9.637 |
| 587 | 0.3662 | 663 | 8.093 |
| 588 | 0.3164 | 664 | 1.382 |
| 589 | 1.223 | 665 | 2.36 |
| 590 | 0.5137 | 666 | 3.973 |
| 591 | 0.3331 | 667 | 0.2261 |
| 592 | 0.2046 | 668 | 0.3134 |
| 593 | 1.859 | 669 | 0.4992 |
| 594 | 0.5704 | 670 | 0.3666 |
| 595 | 1.159 | 671 | -- |
| 596 | 0.2038 | 672 | 0.2727 |
| 597 | 0.8369 | 673 | 0.3747 |
| 598 | 2.046 | 674 | 0.2109 |
| 599 | 3.883 | 675 | 0.2268 |
| 600 | 0.1788 | 676 | 0.2668 |
| 601 | 0.1409 | 677 | 0.5621 |
| 602 | 0.0681 | 678 | 2.472 |
| 603 | 0.1093 | 679 | 10.82 |
| 604 | 8.522 | 680 | 2.133 |
| 605 | 7.936 | 681 | 0.2881 |
| 606 | 1.439 | 682 | 0.5389 |
| 607 | 0.7054 | 683 | 0.2336 |
| 608 | 0.3258 | 684 | 0.5928 |
| 609 | 0.3188 | 685 | 0.1499 |
| 610 | 0.6479 | 686 | 0.2054 |
| 611 | 0.1141 | 687 | 0.1722 |
| 612 | 0.408 | 688 | 1.263 |
| 613 | 0.6236 | 689 | 0.5163 |
| 614 | 5.558 | 690 | 0.4136 |
| 615 | 2.129 | 691 | 0.4468 |
| 616 | 2.185 | 692 | 0.4361 |
| 617 | 10.8 | 693 | 0.5073 |
| 618 | 1.12 | 694 | 0.7936 |
| 619 | 0.5439 | 695 | 1.517 |
| 620 |  | 696 | 2.106 |
| 621 | 3.926 | 697 | 0.4147 |
| 622 | 3.63 | 698 | 0.145 |
| 623 | 6.867 | 699 | 2.301 |
| 624 | 0.1605 | 700 | 0.1376 |
| 625 | 7.793 | 701 | 0.1671 |
| 626 | 0.3457 | 702 | 0.8818 |
| 627 | 1.255 | 703 | 0.2081 |
| 628 | 1.707 | 704 | 0.2805 |
| 629 | 0.1318 | 705 | 0.1217 |
| 630 | 4.152 | 706 | 0.2275 |
| 631 | -- | 707 | 0.2215 |
| 632 | -- | 708 | 0.2659 |
| 633 | 11.34 | 709 | 0.2523 |
| 634 | 14.75 | 710 | 1.218 |
| 635 | -- | 711 | 9.278 |
| 636 | 8.691 | 712 | 4.057 |
| 637 | -- | 713 | 10.2 |
| 638 | -- | 714 | 5.662 |
| 639 | 10.56 | 715 | 2.03 |
| 640 | 19.18 | 716 | 5.026 |
| 641 |  | 717 | 0.2169 |
| 642 |  | 718 | 0.3141 |
| 643 |  | 719 | 0.4018 |
| 644 |  | 720 | 0.8217 |
| 645 |  | 721 | 0.4398 |
| 646 |  | 722 | 0.0639 |
| 647 |  | 723 | 0.1017 |
| 648 |  | 724 | 0.5366 |
| 649 |  | 725 | 0.4645 |
| 650 |  | 726 | 0.5654 |
| 651 | 1.18 | 727 | 0.8864 |
| 652 | 3.777 | 728 | 5.062 |
| 653 | 1.037 | 729 | 0.2864 |
| 654 | 0.5532 | 730 | 0.5898 |
| 655 | 0.2453 | 731 | 0.5061 |
| 656 | 0.5499 | 732 | 0.2577 |

| Cmpd # | GDF pSMAD (MPC11) μM |
|---|---|
| 733 | 1.273 |
| 734 | 0.6942 |
| 735 | 0.6762 |
| 736 | 0.2507 |
| 737 | 0.2596 |
| 738 | 1.376 |
| 739 | 2.318 |
| 740 | 9.499 |
| 741 | 10.01 |
| 742 | 1.825 |
| 743 | 0.6383 |
| 744 | 0.9677 |
| 745 | 0.3663 |
| 746 | 0.5661 |
| 747 | 0.2844 |
| 748 | 0.4473 |
| 749 | 0.2982 |
| 750 | -- |
| 751 | -- |
| 752 | -- |
| 753 | -- |
| 754 | -- |
| 755 | -- |
| 756 | 0.3644 |
| 757 | 0.1274 |
| 758 | 0.4264 |
| 759 | 0.1747 |
| 760 | 0.2742 |
| 761 | 0.1312 |
| 762 | 1.188 |
| 763 | 0.5199 |
| 764 | 0.2751 |
| 765 | 0.096 |
| 766 | 0.1048 |
| 767 | 0.2267 |
| 768 | 0.3267 |
| 769 | 0.1533 |
| 770 | 1.309 |
| 771 | 1.107 |
| 772 | 4.949 |
| 773 | 8.48 |
| 774 | -- |
| 775 | 3.961 |
| 776 | -- |
| 777 | -- |
| 778 | -- |
| 779 | 0.7609 |
| 780 | 0.7298 |
| 781 | 5.864 |
| 782 | 0.3324 |
| 783 | 0.2309 |
| 784 | 0.1252 |
| 785 | 0.1103 |
| 786 | 0.3404 |
| 787 | -- |
| 788 | 4.042 |
| 789 | -- |
| 790 | 4.991 |
| 791 | 5.372 |
| 792 | 2.433 |
| 793 | 2.082 |
| 794 | 1.798 |
| 795 | 8.105 |
| 796 | 14 |
| 797 | 3.813 |
| 798 | 2.615 |
| 799 | 14.64 |
| 800 | 0.8792 |
| 801 | -- |
| 802 | 5.828 |
| 803 | 2.262 |
| 804 | 10.11 |
| 805 | 0.9533 |
| 806 | -- |
| 807 | 5008 |
| 808 | 1.537 |

| Cmpd # | GDF pSMAD (MPC11) μM |
|---|---|
| 809 | 4 |
| 810 | 5.784 |
| 811 | 2.924 |
| 812 | 2.142 |
| 813 | 2.43 |
| 814 | -- |
| 815 | 0.9414 |
| 816 | 1.609 |
| 817 | 0.5839 |
| 818 | 0.0774 |
| 819 | 0.1192 |
| 820 | 3.062 |
| 821 | 2.161 |
| 822 | 0.1272 |
| 823 | 0.2137 |
| 824 | -- |
| 825 | -- |
| 826 | -- |
| 827 | -- |
| 828 | -- |
| 829 | -- |
| 830 | -- |
| 831 | -- |
| 832 | -- |
| 833 | -- |
| 834 | -- |
| 835 | -- |
| 836 | 5.937 |
| 837 | 4.861 |
| 838 | -- |
| 839 | -- |
| 840 | 8.142 |
| 841 | 7.644 |
| 842 | 17.37 |
| 843 | 0.0213 |
| 844 | 0.0324 |
| 845 | 0.0588 |
| 846 | 14.28 |
| 847 | -- |
| 848 | 11.12 |
| 849 | 18.08 |
| 850 | 20.7 |
| 851 | -- |
| 852 | 0.2074 |
| 853 | 0.8812 |
| 854 | 4.666 |
| 855 | 3.442 |
| 856 | 5.585 |
| 857 | 1.854 |
| 858 | 2.367 |
| 859 | 3.7 |
| 860 | 9.985 |
| 861 | 4.006 |
| 862 | 1.836 |
| 863 | 5.894 |
| 864 | 1.54 |
| 865 | 0.6077 |
| 866 | 0.2506 |
| 867 | 0.752 |
| 868 | 0.4041 |
| 869 | 0.6883 |
| 870 | 0.557 |
| 871 | 1.828 |
| 872 | 0.7755 |
| 873 | 1.193 |
| 874 | 6.466 |
| 875 | 12.41 |
| 876 | 2.374 |
| 877 | -- |
| 878 | 10.22 |
| 879 | 1.477 |
| 880 | 0.8077 |
| 881 | -- |
| 882 | 1.124 |
| 883 | 0.5124 |
| 884 | 0.9974 |

651

-continued

| Cmpd # | GDF pSMAD (MPC11) μM |
|---|---|
| 885 | -- |
| 886 | 0.2526 |
| 887 | 1.746 |
| 888 | 4.054 |
| 889 | 1.519 |
| 890 | 1.296 |
| 891 | 0.6324 |
| 892 | 0.426 |
| 896 | 0.0936 |
| 897 | -- |
| 898 | 0.7137 |
| 899 | 2.144 |
| 900 | 2.346 |
| 901 | 1.065 |
| 902 | -- |
| 903 | 2.584 |
| 904 | 9.071 |
| 905 | 1.489 |
| 906 | 3.339 |
| 907 | 0.1635 |
| 908 | -- |
| 909 | -- |
| 910 | 0.0972 |
| 911 | 0.0939 |
| 912 | 0.112 |
| 913 | 0.6611 |
| 914 | 0.126 |
| 915 | 0.5578 |
| 916 | 0.1035 |
| 917 | 0.1804 |
| 918 | 0.2063 |
| 919 | -- |
| 920 | 0.272 |
| 921 | 0.0706 |
| 922 | -- |
| 923 | -- |
| 924 | -- |
| 925 | -- |
| 926 | -- |
| 927 | -- |
| 928 | -- |
| 929 | -- |
| 930 | -- |
| 931 | -- |
| 932 | -- |
| 933 | -- |
| 934 | 0.4097 |
| 935 | 0.1918 |
| 936 | 0.2281 |
| 937 | 0.2072 |
| 938 | 0.2419 |
| 939 | -- |
| 940 | -- |
| 941 | -- |
| 942 | -- |
| 943 | -- |
| 944 | -- |
| 945 | -- |
| 946 | -- |
| 947 | 0.4288 |
| 948 | 0.9508 |
| 949 | 0.3754 |
| 950 | 0.129 |
| 951 | 0.5429 |
| 952 | 0.3911 |
| 953 | 0.6607 |
| 954 | 0.4381 |
| 955 | 0.2901 |
| 956 | 0.4211 |
| 957 | -- |
| 958 | -- |
| 959 | -- |
| 960 | 1.685 |
| 961 | 0.129 |
| 962 | 0.622 |
| 963 | 0.1751 |

652

-continued

| Cmpd # | GDF pSMAD (MPC11) μM |
|---|---|
| 964 | 0.2315 |
| 965 | 5.188 |
| 966 | -- |
| 967 | 1.44 |

*The notation "--" indicates that the compound was tested but did not have measurable activity in this assay.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:
1. A compound of the formula

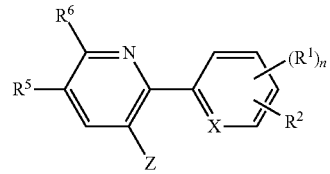

or a pharmaceutically acceptable salt thereof, wherein
X is C(H);
$R^1$ is hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^{10}$, or —$C_{1-6}$alkyl-$R^{10}$,
$R^2$ is halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^{10}$, or —$C_{1-6}$alkyl-$R^{10}$,
wherein
$R^{10}$ is —OR, —SR, —$NR^aR^a$, —C(O)R, —C(O)OR, —C(O)$NR^aR^a$, —S(O)$_2NR^aR^a$, —OC(O)R, —N(R)C(O)R, —OC(O)OR, —O(CH$_2$)$_m$C(O)$NR^aR^a$, —N(R)C(O)OR, —N(R)C(O)$NR^aR^a$, —N(R)S(O)$_2NR^aR^a$ or —N(R)S(O)$_2$R;
or when $R^1$ and $R^2$ are attached to adjacent carbon atoms they are optionally taken together with the atoms to which they are attached to form a 5- or 6-membered ring optionally substituted with one or two groups that are each independently halogen, oxo, oxime, imino, $C_{1-6}$alkyl, $C_{1-6}$haloalkyl, or —$R^{10}$;
each $R^a$ is independently R or, two $R^a$ together with the nitrogen atom to which they are attached form a 3-8 membered heterocyclyl group, optionally including 1-4 additional heteroatoms selected from O, N and S and optionally substituted with 1-4 R groups;
each $R^b$ is independently halogen, cyano, oxo, $C_{1-6}$alkyl, $C_{1-6}$haloalkyl, or —OR;
m is 0, 1 or 2;
n is 1, 2, 3 or 4;
$R^5$ is hydrogen, halogen, $C_{1-6}$alkyl, —$OR^{50}$, —$NR^{50}R^{50}$, —N($R^{50}$)C(O)$R^{50}$, or —N($R^{50}$)S(O)$_2R^{50}$, wherein each $R^{50}$ is independently hydrogen or $C_{1-6}$alkyl;
$R^6$ is hydrogen, halogen, $C_{1-6}$alkyl, —$OR^{60}$, —$NR^{60}R^{60}$, —N($R^{60}$)C(O)$R^{60}$, or —N($R^{60}$)S(O)$_2R^{60}$, wherein each $R^{60}$ is independently hydrogen or $C_{1-6}$alkyl;

Z is a fused bicyclic ring of the formula,

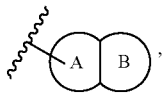

wherein
ring A is a phenyl or 5- or 6-membered heteroaryl,
ring B is a 5- or 6-membered heterocyclyl or 5- or 6-membered heteroaryl;
wherein
Z is optionally substituted by one or two groups that are each independently halogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl($C_{1-6}$alkyl), —$R^Z$, or —$C_{1-6}$alkyl-$R^z$, wherein the $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), and heteroaryl($C_{1-6}$alkyl) are each optionally substituted by one or two groups that are each independently halogen, $C_{1-6}$alkyl, or —$R^Z$;

and $R^Z$ is cyano, —$CF_3$, —OR, —SR, —$NR^aR^a$, —C(O)R, —C(O)OR, —C(O)$NR^aR^a$, —$S(O)_2NR^aR^a$, —$S(O)_2R^0$, —OC(O)R, —N(R)C(O)R, —OC(O)OR, —OC(O)$NR^aR^a$, —N(R)C(O)OR, —N(R)C(O)$NR^aR^a$, —N(R)$S(O)_2$R, or —$OP(O)(OR)_2$;

wherein each R is independently hydrogen, $C_{1-6}$alkyl, $C_{1-6}$haloalkyl, $C_{3-8}$cycloalkyl, heterocyclyl, aryl, heteroaryl, heteroaryl(heteroaryl)-, heterocyclyl(aryl)-, heteroaryl(heterocyclyl)-, $C_{3-8}$cycloalkyl($C_{1-6}$alkyl), heterocyclyl($C_{1-6}$alkyl), aryl($C_{1-6}$alkyl), or heteroaryl($C_{1-6}$alkyl), each optionally substituted by 1-5 groups that are each independently $R^b$, —$OR^0$, —$SR^0$, —$N(R^0)_2$, —$C(O)R^0$, —$C(O)OR^0$, —$C(O)N(R^0)_2$, —$S(O)_2N(R^0)_2$, —$OC(O)R^0$, —$N(R^0)C(O)R^0$, —$OC(O)OR^0$, —$O(CH_2)_mC(O)N(R^0)_2$, —$N(R^0)C(O)OR^0$, —$N(R^0)C(O)N(R^0)_2$, or —$N(R^0)S(O)_2R^0$ and each $R^0$ is independently hydrogen, $C_{1-6}$haloalkyl, $C_{1-6}$alkyl optionally substituted with 1-3 $R^b$, $C_{3-8}$cycloalkyl optionally substituted with one or two $R^b$ or, alternatively two $R^0$ together with a nitrogen atom to which they are bound form a 3-8 membered heterocyclyl group, optionally including 1-4 additional heteroatoms selected from O, N and S and optionally substituted with 0-3 $R^b$ and R groups.

2. The compound or pharmaceutically acceptable salt of claim 1 of the formula,

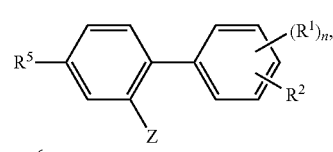

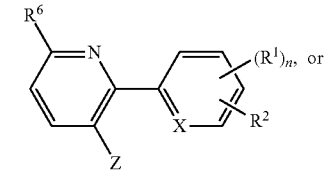

3. The compound or pharmaceutically acceptable salt of claim 1 of the formula,

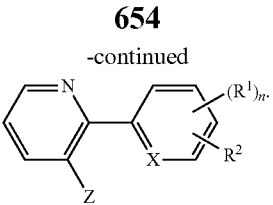

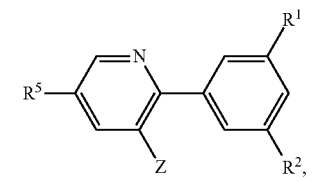

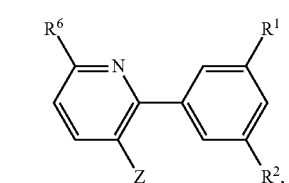

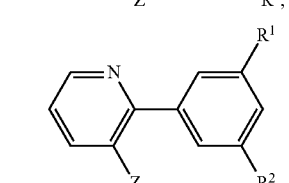

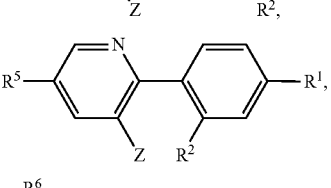

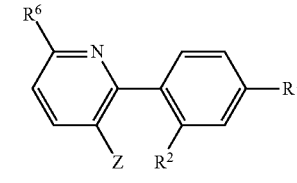

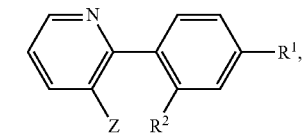

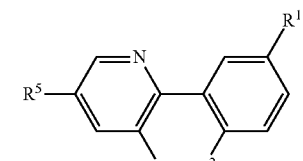

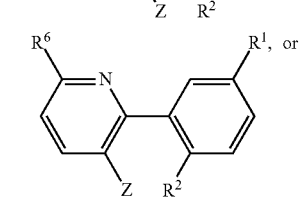

-continued

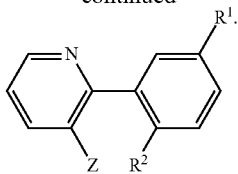

4. The compound or pharmaceutically acceptable salt of claim 1 of the formula

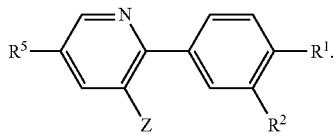

5. The compound or pharmaceutically acceptable salt of claim 1 of the formula

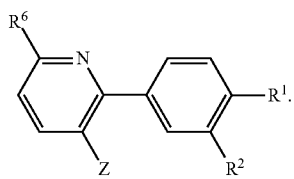

6. The compound or pharmaceutically acceptable salt of claim 1 of the formula

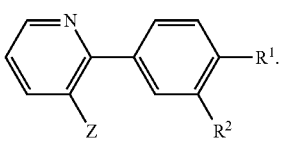

7. The compound or pharmaceutically acceptable salt of claim 1, wherein $R^1$ is hydrogen, halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, —$R^{10}$, or —$C_{1-6}$alkyl-$R^{10}$, $R^2$ is halogen, cyano, nitro, $C_{1-6}$alkyl, $C_{1-6}$haloalkyl, $C_{3-8}$cycloalkyl, $C_{3-8}$cycloalkenyl, heterocyclyl, aryl, heteroaryl, -$R^{10}$, or -$C_{1-6}$alkyl-$R^{10}$, wherein $R^{10}$ is —OR, —SR, —NR$_2$, —C(O)R, —C(O)OR, —C(O)NR$_2$, —S(O)$_2$NR$_2$, —OC(O)R, —N(R)C(O)R, —OC(O)OR, —OC(O)NR$_2$, —N(R)C(O)OR, —N(R)C(O)NR$_2$, or —N(R)S(O)$_2$R.

8. The compound or pharmaceutically acceptable salt of claim 1, wherein $R^1$ is hydrogen, halogen, or $C_{1-6}$alkyl, and $R^2$ is halogen, or $C_{1-6}$alkyl.

9. The compound or pharmaceutically acceptable salt of claim 1, wherein $R^1$ is fluoro and $R^2$ is methyl.

10. The compound or pharmaceutically acceptable salt of claim 1 of the formula

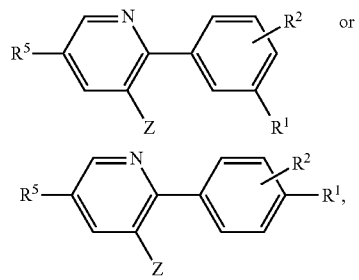

provided $R^1$ is not H.

11. The compound or pharmaceutically acceptable salt of claim 1 of the formula,

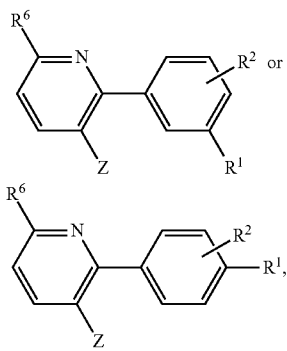

provided $R^1$ is not H.

12. The compound or pharmaceutically acceptable salt of claim 1 of the formula,

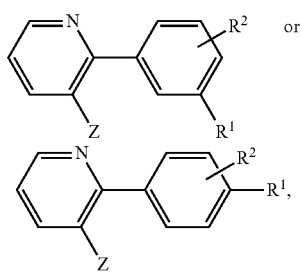

provided $R^1$ is not H.

13. The compound or pharmaceutically acceptable salt of claim 1, wherein $R^1$ is hydrogen, halogen, cyano, nitro, $C_{1-8}$alkyl, $C_{1-8}$haloalkyl, $C_{3-8}$cycloalkyl, $C_{3-8}$cycloalkenyl, heterocyclyl, aryl, heteroaryl, —$R^{10}$, or —$C_{1-6}$alkyl-$R^{10}$, wherein $R^{10}$ is —OR, —SR, —NR$_2$, —C(O)R, —C(O)OR, —C(O)NR$_2$, —S(O)$_2$NR$_2$, —OC(O)R, —N(R)C(O)R, —OC(O)OR, —OC(O)NR$_2$, —N(R)C(O)OR, —N(R)C(O)NR$_2$, or —N(R)S(O)$_2$R.

14. The compound or pharmaceutically acceptable salt of claim 1, wherein $R^1$ is halogen or $C_{1-6}$alkyl.

15. The compound or pharmaceutically acceptable salt of claim 1, wherein Z is of the formula,

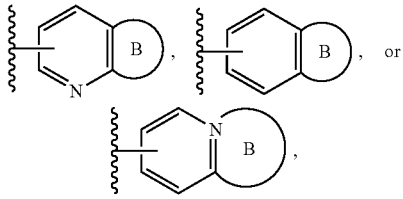

wherein
each is optionally substituted by one or two groups that are each independently halogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl($C_{1-6}$alkyl), —$R^z$, or —$C_{1-6}$alkyl-$R^z$, wherein the $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), and heteroaryl($C_{1-6}$alkyl) are each optionally substituted by one or two groups that are each independently $C_{1-6}$alkyl or —$R^z$.

16. The compound or pharmaceutically acceptable salt of claim 1, wherein Z is of the formula,

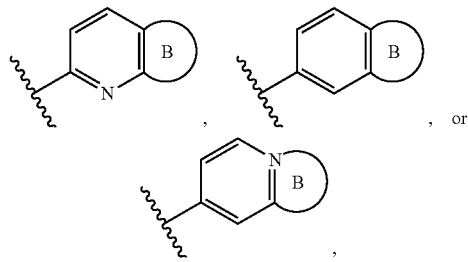

wherein each is optionally substituted by one or two groups that are each independently halogen, $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), heteroaryl($C_{1-6}$alkyl), —$R^z$, or —$C_{1-6}$alkyl-$R^z$, wherein the $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), and heteroaryl($C_{1-6}$alkyl) are each optionally substituted by one or two groups that are each independently $C_{1-6}$alkyl or —$R^z$.

17. The compound or pharmaceutically acceptable salt of claim 1, wherein Z is

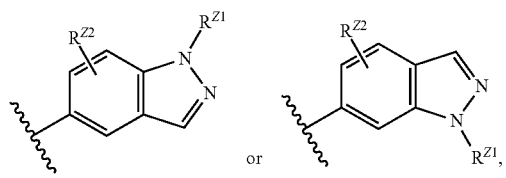

wherein $R^{z1}$ is hydrogen, $C_{1-6}$alkyl, $C_{1-6}$haloalkyl, or —$C_{1-6}$alkyl-$R^z$; and $R^{z2}$ is hydrogen, halogen, or $C_{1-6}$alkyl.

18. The compound or pharmaceutically acceptable salt of claim 1, wherein Z is

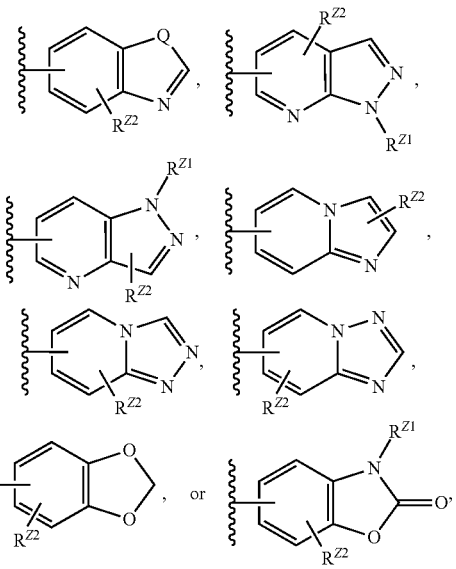

wherein
Q is —O—, —S—, or —N($R^{z1}$)—; and
$R^{z1}$ is hydrogen, $C_{1-6}$alkyl, $C_{1-6}$haloalkyl, or —$C_{1-6}$alkyl-$R^z$; and
$R^{z2}$ is hydrogen, halogen, or $C_{1-6}$alkyl.

19. The compound of claim 1 according to the formula,

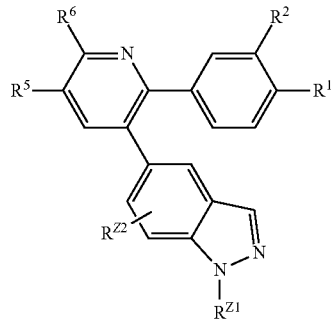

or a pharmaceutically acceptable salt thereof, wherein
$R^1$ is hydrogen, halogen, cyano, nitro, $C_{1-6}$alkyl, $C_{1-6}$haloalkyl, $C_{-8}$cycloalkyl, $C_{3-8}$cycloalkenyl, heterocyclyl, aryl, heteroaryl, —$R^{10}$, or —$C_{1-6}$alkyl-$R^{10}$, wherein $R^{10}$ is —OR, —SR, —$NR_2$, —C(O)R, —C(O)OR, —C(O)$NR_2$, —S(O)$_2NR_2$, —OC(O)R, —N(R)C(O)R, —OC(O)OR, —OC(O)$NR_2$, —N(R)C(O)OR, —N(R)C(O)$NR_2$, or —N(R)S(O)$_2$R;

$R^2$ is halogen, cyano, nitro, $C_{1-6}$alkyl, $C_{1-6}$haloalkyl, $C_{3-8}$cycloalkyl, $C_{3-8}$cycoalkenyl, heterocyclyl, aryl, heteroaryl, —$R^{10}$, or —$C_{1-6}$alkyl-$R^{10}$, wherein $R^{10}$ is —OR, —SR, —$NR_2$, —C(O)R, —C(O)OR, —C(O)$NR_2$, —S(O)$_2NR_2$, —OC(O)R, —N(R)C(O)R, —OC(O)OR, —OC(O)$NR_2$, —N(R)C(O)OR, —N(R)C(O)$NR_2$, or —N(R)S(O)$_2$R;

$R^5$ is hydrogen, halogen, $C_{1-6}$alkyl, —$OR^{50}$, —$NR^{50}R^{50}$, —$N(R^{50})C(O)R^{50}$, or —$N(R^{50})S(O)_2R^{50}$, wherein each $R^{50}$ is independently hydrogen or $C_{1-6}$alkyl;

$R^6$ is hydrogen, halogen, $C_{1-6}$alkyl, —$OR^{60}$, —$NR^{60}R^{60}$, —$N(R^{60})C(O)R^{60}$, or —$N(R^{60})S(O)_2R^{60}$, wherein each $R^{60}$ is independently hydrogen or $C_{1-6}$alkyl;

$R^{Z1}$ is hydrogen, $C_{1-6}$alkyl, $C_{1-6}$haloalkyl, $C_{3-8}$cycloalkyl, helerocyclyl, aryl, heteroaryl, $C_{3-8}$cycloalkyl($C_{1-6}$ alkyl), heterocyclyl($C_{1-6}$alkyl), aryl($C_{1-6}$alkyl), heleroaryl($C_{1-6}$alkyl), —$R^{Z3}$, —$C_{1-6}$alkyl-$R^{Z3}$ or —$C_{1-6}$ alkyl-$R^{Z4}$, wherein the $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), and heteroaryl($C_{1-6}$alkyl) are each optionally substituted by one or two groups that are each independently halogen, $C_{1-6}$alkyl, —$R^{Z3}$, or —$R^{Z4}$, wherein $R^{Z3}$ is —C(O)R, —C(O)OR, —C(O)NR$_2$, or —S(O)$_2$NR$_2$; and $R^{Z4}$ is —OR, —SR, —NR$_2$, —OC(O)R, —N(R)C(O)R, —OC(O)OR, —OC(O)NR$_2$, —N(R)C(O)OR, N(R)C(O)NR$_2$, —N(R)S(O)$_2$R, or —OP(O)(OR)$_2$;

$R^{Z2}$ is hydrogen, halogen, or $C_{1-6}$alkyl; and and each R is independently hydrogen or $C_{1-6}$alkyl, $C_{1-6}$haloalkyl, $C_{3-8}$cycloalkyl, heterocyclyl, aryl, heteroaryl, $C_{3-8}$cycloalkyl($C_{1-6}$alkyl), heterocyclyl($C_{1-6}$alkyl), aryl($C_{1-6}$alkyl), or heteroaryl($C_{1-6}$alkyl), each optionally substituted by one or two groups that are each independently —OR$^O$, —SR$^O$, —N(R$^O$)$_2$, —C(O)R$^O$, —C(O)OR$^O$, —C(O)N(R$^O$)$_2$, —S(O)$_2$N(R$^O$)$_2$, —OC(O)R$^O$, —N(R$^O$)C(O)R$^O$, —OC(O)OR$^O$, —OC(O)N(R$^O$)$_2$, —N(R$^O$)C(O)OR$^O$, —N(R$^O$)C(O)N(R$^O$)$_2$, or —N(R$^O$)S(O)$_2$R$^O$, wherein each R$^O$ independently hydrogen or $C_{1-6}$alkyl.

20. A pharmaceutical composition comprising a compound or pharmaccutically acceptable salt according to claim 1 and a pharmaceutically acceptable carrier, excipient, or diluent.

21. A method for inhibiting GDF-8 in a cell, the method comprising contacting the cell with an effective amount of a compound or pharmaceutically acceptable salt according to claim 1.

\* \* \* \* \*